(12) United States Patent
Shvartsbart et al.

(10) Patent No.: US 11,773,102 B2
(45) Date of Patent: *Oct. 3, 2023

(54) HETEROCYCLIC COMPOUNDS AS PI3K-γ INHIBITORS

(71) Applicant: Incyte Corporation, Wilmington, DE (US)

(72) Inventors: Artem Shvartsbart, Kennett Square, PA (US); Stacey Shepard, Wilmington, DE (US); Andrew P. Combs, Kennett Square, PA (US); Lixin Shao, Wilmington, DE (US); Nikoo Falahatpisheh, Wilmington, DE (US); Ge Zou, Greenville, DE (US); Andrew W. Buesking, Wilmington, DE (US); Richard B. Sparks, Hockessin, DE (US); Eddy W. Yue, Landenberg, PA (US); Ravi Kumar Jalluri, Avondale, PA (US)

(73) Assignee: Incyte Corporation, Wilmington, DE (US)

(*) Notice: Subject to any disclaimer, the term of this patent is extended or adjusted under 35 U.S.C. 154(b) by 8 days.

This patent is subject to a terminal disclaimer.

(21) Appl. No.: 17/356,984

(22) Filed: Jun. 24, 2021

(65) Prior Publication Data
US 2023/0009843 A1 Jan. 12, 2023

Related U.S. Application Data

(60) Continuation of application No. 16/589,523, filed on Oct. 1, 2019, now Pat. No. 11,091,491, which is a division of application No. 16/045,358, filed on Jul. 25, 2018, now Pat. No. 10,472,368, which is a continuation of application No. 15/343,375, filed on Nov. 4, 2016, now Pat. No. 10,065,963.

(60) Provisional application No. 62/252,050, filed on Nov. 6, 2015.

(51) Int. Cl.
| | |
|---|---|
| A61P 35/00 | (2006.01) |
| A61K 31/519 | (2006.01) |
| A61P 17/06 | (2006.01) |
| A61P 35/02 | (2006.01) |
| A61P 37/06 | (2006.01) |
| A61P 35/04 | (2006.01) |
| A61P 19/02 | (2006.01) |
| C07D 487/04 | (2006.01) |
| C07D 519/00 | (2006.01) |

(52) U.S. Cl.
CPC .......... *C07D 487/04* (2013.01); *A61K 31/519* (2013.01); *A61P 17/06* (2018.01); *A61P 19/02* (2018.01); *A61P 35/00* (2018.01); *A61P 35/02* (2018.01); *A61P 35/04* (2018.01); *A61P 37/06* (2018.01); *C07D 519/00* (2013.01)

(58) Field of Classification Search
CPC .......................... C07D 487/04; C07D 519/00
See application file for complete search history.

(56) References Cited

U.S. PATENT DOCUMENTS

| | | | |
|---|---|---|---|
| 4,269,846 | A | 5/1981 | Huang et al. |
| 5,521,184 | A | 5/1996 | Zimmermann |
| 7,186,832 | B2 | 3/2007 | Sun |
| 7,511,145 | B2 | 3/2009 | Schmitz et al. |
| 8,680,108 | B2 | 3/2014 | Li et al. |
| 8,759,359 | B2 | 6/2014 | Combs et al. |
| 8,940,752 | B2 | 1/2015 | Li et al. |
| 9,062,055 | B2 | 6/2015 | Li et al. |
| 9,096,600 | B2 | 8/2015 | Li et al. |
| 9,108,984 | B2 | 8/2015 | Combs et al. |
| 9,126,948 | B2 | 9/2015 | Combs et al. |
| 9,193,721 | B2 | 11/2015 | Combs et al. |
| 9,199,982 | B2 | 12/2015 | Li et al. |

(Continued)

FOREIGN PATENT DOCUMENTS

| | | |
|---|---|---|
| EP | 2044051 | 1/2010 |
| JP | 2015-512940 | 4/2015 |

(Continued)

OTHER PUBLICATIONS

U.S. Appl. No. 60/578,491, Ren, filed Jun. 10, 2004.

(Continued)

*Primary Examiner* — Susanna Moore
(74) *Attorney, Agent, or Firm* — Fish & Richardson P.C.

(57) ABSTRACT

This application relates to compounds of Formula (I):

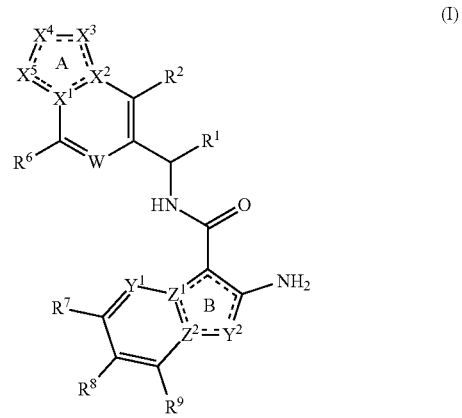

or pharmaceutically acceptable salts or stereoisomers thereof, which are inhibitors of PI3K-γ which are useful for the treatment of disorders such as autoimmune diseases, cancer, cardiovascular diseases, and neurodegenerative diseases.

27 Claims, No Drawings

(56) References Cited

U.S. PATENT DOCUMENTS

| | | |
|---|---|---|
| 9,586,949 B2 | 3/2017 | Zou et al. |
| 10,022,387 B2 | 7/2018 | Zou et al. |
| 10,065,963 B2 | 9/2018 | Shvartsbart et al. |
| 10,138,248 B2 | 11/2018 | Buesking et al. |
| 10,472,368 B2 | 11/2019 | Shvartsbart et al. |
| 10,479,795 B2 | 11/2019 | Buesking et al. |
| 10,596,184 B2 | 3/2020 | Zou et al. |
| 10,975,088 B2 | 4/2021 | Buesking et al. |
| 11,091,491 B2 | 8/2021 | Shvartsbart et al. |
| 11,352,340 B2 | 6/2022 | Sparks et al. |
| 2008/0019915 A1 | 1/2008 | Hadida-Ruah et al. |
| 2010/0298334 A1 | 11/2010 | Rodgers et al. |
| 2011/0015212 A1 | 1/2011 | Li et al. |
| 2011/0059951 A1 | 3/2011 | Rodgers et al. |
| 2011/0183985 A1 | 7/2011 | Li et al. |
| 2011/0224190 A1 | 9/2011 | Huang et al. |
| 2012/0149681 A1 | 6/2012 | Rodgers et al. |
| 2012/0149682 A1 | 6/2012 | Rodgers et al. |
| 2012/0157430 A1 | 6/2012 | Li et al. |
| 2012/0238564 A1 | 9/2012 | Luk et al. |
| 2013/0018034 A1 | 1/2013 | Yao et al. |
| 2013/0045963 A1 | 2/2013 | Rodgers et al. |
| 2013/0059835 A1 | 3/2013 | Li et al. |
| 2013/0261101 A1 | 10/2013 | Combs et al. |
| 2014/0005166 A1 | 1/2014 | Rodgers et al. |
| 2014/0121198 A1 | 5/2014 | Li et al. |
| 2014/0249132 A1 | 9/2014 | Li et al. |
| 2014/0275127 A1 | 9/2014 | Combs et al. |
| 2014/0343030 A1 | 11/2014 | Li et al. |
| 2015/0284390 A1 | 10/2015 | Li et al. |
| 2015/0361650 A1 | 12/2015 | Li et al. |
| 2016/0000795 A1 | 1/2016 | Scherle et al. |
| 2016/0022685 A1 | 1/2016 | Li et al. |
| 2016/0024117 A1 | 1/2016 | Li et al. |
| 2017/0129899 A1 | 5/2017 | Shvartsbart et al. |
| 2017/0190649 A1 | 7/2017 | Sparks et al. |
| 2018/0009816 A1 | 1/2018 | Buesking et al. |
| 2019/0060331 A1 | 2/2019 | Zou et al. |
| 2019/0062336 A1 | 2/2019 | Shvartsbart et al. |
| 2019/0119287 A1 | 4/2019 | Buesking et al. |
| 2019/0359592 A1 | 11/2019 | Sparks et al. |
| 2020/0031837 A1 | 1/2020 | Shvartsbart et al. |
| 2020/0102315 A1 | 4/2020 | Buesking et al. |
| 2022/0227736 A1 | 7/2022 | Sparks et al. |
| 2022/0251087 A1 | 8/2022 | Buesking et al. |

FOREIGN PATENT DOCUMENTS

| | | |
|---|---|---|
| WO | WO 00/09495 | 2/2000 |
| WO | WO 00/053595 | 9/2000 |
| WO | WO 01/014402 | 3/2001 |
| WO | WO 01/064655 | 9/2001 |
| WO | WO 01/85724 | 11/2001 |
| WO | WO 2002/000196 | 1/2002 |
| WO | WO 03/024967 | 3/2003 |
| WO | WO 03/035065 | 5/2003 |
| WO | WO 03/035644 | 5/2003 |
| WO | WO 03/037347 | 5/2003 |
| WO | WO 03/068225 | 8/2003 |
| WO | WO 03/099771 | 12/2003 |
| WO | WO 04/005281 | 1/2004 |
| WO | WO 04/046120 | 6/2004 |
| WO | WO 04/056786 | 7/2004 |
| WO | WO 04/080980 | 9/2004 |
| WO | WO 2004/078943 | 9/2004 |
| WO | WO 2005/012288 | 2/2005 |
| WO | WO 05/028444 | 3/2005 |
| WO | WO 2005/118580 | 12/2005 |
| WO | WO 2006/056399 | 6/2006 |
| WO | WO 2007/019416 | 2/2007 |
| WO | WO 2007/019417 | 2/2007 |
| WO | WO 2007/028051 | 3/2007 |
| WO | WO 2009/005551 | 1/2009 |
| WO | WO 2009/016118 | 2/2009 |
| WO | WO 2009/024585 | 2/2009 |
| WO | WO 2009/079011 | 6/2009 |
| WO | WO 2009/123776 | 10/2009 |
| WO | WO 2009/133127 | 11/2009 |
| WO | WO 2009/158118 | 12/2009 |
| WO | WO 2010/051245 | 5/2010 |
| WO | WO 2010/061903 | 6/2010 |
| WO | WO 2010/069684 | 6/2010 |
| WO | WO 2010/135014 | 11/2010 |
| WO | WO 2011/099832 | 8/2011 |
| WO | WO 2011/123609 | 10/2011 |
| WO | WO 2011/149856 | 12/2011 |
| WO | WO 2011/149874 | 12/2011 |
| WO | WO 2012/051410 | 4/2012 |
| WO | WO 2012/074126 | 6/2012 |
| WO | WO 2012/143796 | 10/2012 |
| WO | WO 2012/170867 | 12/2012 |
| WO | WO 2013/129674 | 9/2013 |
| WO | WO 2013/154878 | 10/2013 |
| WO | WO 2013/180193 | 12/2013 |
| WO | WO 2014/009295 | 1/2014 |
| WO | WO 2014/149207 | 9/2014 |
| WO | WO 2014/153529 | 9/2014 |
| WO | WO 2014/182954 | 11/2014 |
| WO | WO 2015/008872 | 1/2015 |
| WO | WO 2015/051241 | 4/2015 |
| WO | WO 2015/154878 | 10/2015 |
| WO | WO 2016/044342 | 3/2016 |
| WO | WO 2016/054491 | 4/2016 |
| WO | WO 2016/075130 | 5/2016 |

OTHER PUBLICATIONS

Ameriks and Venable, "Small Molecule Inhibitors of Phosphoinositide 3-Kinase (PI3K) δ and γ," Curr Topics Med Chem., 2009, 9:738-753.

Bala et al., "Highly efficient water-mediated approach to access benzazoles: metal catalyst and base-free synthesis of 2-substituted benzimidazoles, benzoxazoles, and benzothiazoles," Molecular Diversity, Mar. 2015, 19(2):263-272.

Barber et al., "Class IB-Phosphatidylinositol 3-Kinase (PI3K) Deficiency Ameliorates IA-PI3K-Induces Systemic Lupus but Not T Cell Invasion," J Immunol., 2006, 176:589-593.

Barber et al., "PI3Kgamma inhibition blocks glomerulonephritis and extends lifespan in a mouse model of systemic lupus," Nat Med., Sep. 2005, 11(9):933-5.

Berge, Journal of Pharmaceutical Science, 66, 2 (1977).

Berod et al., "PI3Kγ deficiency delays the onset of experimental autoimmune encephalomyelitis and ameliorates its clinical outcome," Eur J Immunol, Mar. 2011, 41(3):833-44.

Blom et al., "Optimizing Preparative LC/MS Configurations and Methods for Parallel Synthesis Purification," J. Comb. Chem., 2003, 5:670-683.

Blom et al., "Preparative LC-MS Purification: Improved Compound-Specific Method Optimization," J. Comb. Chem., 2004, 6:874-883.

Blom, "Two-Pump at-Column-Dilution Configuration for Preparative Liquid Chromatography-Mass Spectrometry," J. Comb. Chem., 2002, 4:295-301.

Brock et al., "Roles of G beta gamma in membrane recruitment and activation of p110 gamma/p101 phosphoinositide 3-kinase gamma," J Cell Biol, Jan. 2003, 160(1):89-99.

Camps et al., "Blockade of PI3Kγ suppresses joint inflammation and damage in mouse models of rheumatoid arthritis," Nature Medicine, Sep. 2005, 11(9):936-943.

Cantley, "The phosphoinositide 3-kinase pathway," Science, May 2002, 296(5573):1655-7.

Carter et al., "Prioritization of driver mutations in pancreatic cancer using cancer-specific high-throughput annotation of somatic mutations (CHASM)," Cancer Biol Ther, Sep. 2010, 10(6):582-7.

Collier et al., "Discovery of Highly Isoform Selective Thiazolopiperidine Inhibitors of Phosphoinositide 3-Kinase γ," Journal of Medicinal Chemistry, 2015, 58:5684-5688.

Collier et al., "Structural Basis for Isoform Selectivity in a Class of Benzothiazole Inhibitors of Phosphoinositide 3-Kinase [gamma]," Journal of Medicinal Chemistry, Jan. 2015, 58(1):517-521.

(56) References Cited

OTHER PUBLICATIONS

Comerford et al., "PI3Kγ drives priming and survival of autoreactive CD4(+) T cells during experimental autoimmune encephalomyelitis," PLoS One, 2012, 7(9):e45095.
Cossy et al., "Formation of optically active 3-hydroxypiperidines," Tetrahedron Letters, Jan. 23, 1995, 36(4):549-552.
Cushing et al., "PI3Kδ and PI3Kγ as Targets for Autoimmune and Inflammatory Diseases," Journal of Medicinal Chemistry, 2012, 55:8559-8581.
Database Registry [online], Chemical Abstracts Service, Columbus, OH, US; Aug. 2012, CAS client services:XP002755356, Database accession No. 1391828-67-3.
Database Registry [online], Chemical Abstracts Service, Columbus, OH, US; Dec. 2011, Chemical Catalog; Supplier:Ukrorgsyntez ltd.:XP002755357, Database accession No. 1347088-14-5.
Database Registry [online], Chemical Abstracts Service, Columbus, OH, US; Dec. 2012, Chemical Catalog; Supplier:Aurora Fine Chemicals:XP002755355, Database accession No. 1411464-90-8.
Database Registry [online], Chemical Abstracts Service, Columbus, OH, US; Feb. 2014, Chemical Catalog; Supplier: Aurora Fine Chemicals:XP002755346, Database accession No. 1554931-95-1.
Database Registry [online], Chemical Abstracts Service, Columbus, OH, US; Feb. 2014, Chemical Catalog; Supplier:Aurora Fine Chemicals:XP002755347, Database accession No. 1540856-06-1.
Database Registry [online], Chemical Abstracts Service, Columbus, OH, US; Feb. 2014, Chemical Catalog; Supplier:Aurora Fine Chemicals:XP002755349, Database accession No. 1538237-68-1.
Database Registry [online], Chemical Abstracts Service, Columbus, OH, US; Feb. 2014, Chemical Catalog; Supplier:Aurora Fine Chemicals:XP002755350, Database accession No. 1536955-67-5.
Database Registry [online], Chemical Abstracts Service, Columbus, OH, US; Jan. 2014, Chemical Catalog; Supplier:Aurora Fine Chemicals:XP002755351, Database accession No. 1528719-88-1.
Database Registry [online], Chemical Abstracts Service, Columbus, OH, US; Jan. 2014, Chemical Catalog; Supplier:Aurora Fine Chemicals:XP002755352, Database accession No. 1526778-80-2.
Database Registry [online], Chemical Abstracts Service, Columbus, OH, US; Jan. 2014, Chemical Catalog; Supplier:Aurora Fine Chemicals:XP002755353, Database accession No. 1522493-70-4.
Database Registry [online], Chemical Abstracts Service, Columbus, OH, US; Jan. 2014, Chemical Catalog; Supplier:Aurora Fine Chemicals:XP002755354, Database accession No. 1520181-20-7.
Database Registry [online], Chemical Abstracts Service, Columbus, OH, US; Oct. 2005, Chemical Library; Supplier:interchim:XP002755358, Database accession No. 866138-38-7.
Database Registry [online], Chemical Abstracts Service, Columbus, OH, US; Oct. 2005, Chemical Library; Supplier:interchim:XP002755359, Database accession No. 864939-76-4.
Database Registry [online], Chemical Abstracts Service, Columbus, Ohio, US, Feb. 2010, Chemical Catalog; Supplier:Aurora Fine Chemicals:XP002755348, Database accession No. 1540777-22-7.
Database Registry [online], Chemical Abstracts Service, Columbus, OH, US, May 29, 2015, Chemical Catalog; Supplier:Aurora Fine Chemicals:XP002755360, Database Accession No. 1715195-44-0.
Database Registry [online], Chemical Abstracts Service, Columbus, OH, US, Jun. 1, 2015, Chemical Catalog; Supplier:Aurora Fine Chemicals:XP002755361, Database Accession No. 1770353-29-1.
Database Registry [online], Chemical Abstracts Service, Columbus, OH, US, Jun. 4, 2015, Chemical Catalog; Supplier:Aurora Fine Chemicals:XP002755362, Database Accession No. 1773443-64-3.
Dorwald et al., "Side reactions in Organic Synthesis," Wiley: VCH Weinheinn Preface, 2005, pp. 1-15, Chapter 8, pp. 279-308.
Doukas et al., "Aerosolized phosphoinositide 3-kinase gamma/delta inhibitor TG100-115 [3-[2,4-diamino-6-(3-hydroxyphenyl)pteridin-7-yl]phenol] as a therapeutic candidate for asthma and chronic obstructive pulmonary disease," J Pharmacol Exp Ther, Mar. 2009, 328(3):758-65.

Doukas et al., "Phosphoinositide 3-kinase gamma/delta inhibition limits infarct size after myocardial ischemia/reperfusion injury," Proc Natl Acad Sci USA, Dec. 2006, 103(52):19866-71.
El Khoury et al., "Ccr2 deficiency impairs microglial accumulation and accelerates progression of Alzheimer-like disease," Nat Med, Apr. 2007, 13(4):432-8.
Elger et al., "Novel alpha-amino-3-hydroxy-5-methyl-4-isoxazole propionate (AMPA) receptor antagonists of 2,3-benzodiazepine type: chemical synthesis, in vitro characterization, and in vivo prevention of acute neurodegeneration," J. Med. Chem., Jul. 2005, 48(14):4618-4627.
European Office Action in European Application No. 16805238.9, dated Mar. 27, 2020, 5 pages.
European Search Report in European Application No. 20187907.9, dated Jan. 20, 2021, 6 pages.
Falasca and Maffucci, "Targeting p110gamma in gastrointestinal cancers: attack on multiple fronts," Frontiers in Physiology, 2014, 5:1-10.
Giri et al., "Mechanism of amyloid peptide induced CCR5 expression in monocytes and its inhibition by siRNA for Egr-1," Am J Physiol Cell Physiol, Aug. 2005, 289(2):C264-76.
Gonzalez-Garcia et al., "Phosphatidylinositol 3-Kinase Inhibition Ameliorates Inflammation and Tumor Growth in a Model of Colitis-Associated Cancer," Gastroenterology, 2010, 138:1373-1384.
Hanahan and Weinberg, "Hallmarks of Cancer: The Next Generation," Cell, 2011, 144:646-674.
Hayer et al., "PI3Kgamma regulates cartilage damage in chronic inflammatory arthritis," FASEB J, Dec. 2009, 23(12):4288-98.
International Search Report and Written Opinion in International Application No. PCT/US2016/017073, dated Apr. 15, 2016, 21 pages.
International Search Report and Written Opinion in International Application No. PCT/US2016/060468, dated Jan. 25, 2017, 14 pages.
International Search Report and Written Opinion in International Application No. PCT/US2017/038955, dated Aug. 8, 2017, 15 pages.
International Search Report and Written Opinion in International Application No. PCT/US2017/012135, dated May 19, 2017, 17 pages.
International Preliminary Report on Patentability in International Application No. PCT/US2017/038955, dated Dec. 25, 2018, 8 pages.
International Preliminary Report on Patentability in International Application No. PCT/US2016/017073, dated Aug. 15, 2017, 11 pages.
International Preliminary Report on Patentability in International Application No. PCT/US2016/060468, dated May 8, 2018, 9 pages.
International Preliminary Report on Patentability in International Application No. PCT/US2017/012135, dated Jul. 19, 2018, 10 pages.
Japanese Office Action in Japanese Application No. 2018-523015, dated Oct. 20, 2020, 7 pages.
Jimenez et al., "The p85 regulatory subunit controls sequential activation of phosphoinositide 3-kinase by Tyr kinases and Ras," J Biol Chem, Nov. 2002, 277(44):41556-62.
Kaneda et al., "Abstract 3650:PI3-kinase gamma controls the macrophage M1-M2 switch, thereby promoting tumor immunosuppression and progression," Cancer Res., Oct. 2014, 74(Suppl 19), 2 pages.
Kumar et al., "Discovery and optimization of a new class of pyruvate kinase inhibitors as potential therapeutics for the treatment of methicillin-resistant *Staphylococcus aureus* infections," Bioorganic & Medicinal Chemistry, Jan. 2014, 22(5):1708-1725.
Laffargue et al., "Phosphoinositide 3-kinase gamma is an essential amplifier of mast cell function," Immunity, Mar. 2002, 16(3):441-51.
Li et al., "PI3Kγ inhibition alleviates symptoms and increases axon number in experimental autoimmune encephalomyelitis mice," Neuroscience, Dec. 2013, 253:89-99.
Liu et al., "Discovery of Novel Small Molecule Mer Kinase Inhibitors for the Treatment of Pediatric Acute Lymphoblastic Leukemia," ACS Med. Chem. Lett., Feb. 9, 2012, 3(2):129-134.

(56) References Cited

OTHER PUBLICATIONS

Lupia et al., "Ablation of phosphoinositide 3-kinase-gmma reduces the severity of acute pancreatitis," Am J Pathol, Dec. 2004, 165(6):2003-11.

Mamedov et al., "Acid-catalyzed rearrangement of 3-(beta-2-aminostyryl)quinoxalin-2(1H)ones-a new and efficient method for the synthesis of 2-benzimidazol-2-ylquinolines," Tetrahedron Letters, Dec. 2010, 51(50):6503-6506.

Martin et al., "PI3Kγ mediates Kaposi's sarcoma-associated herpesvirus vGPCR-induced sarcomagenesis," Cancer Cell, Jun. 2011, 19(6):805-13.

Mejdrova et al., "Highly selective Phosphatidylinositol 4-Kinase III[beta] Inhibitors and Structural Insight into Their Mode of Action," Journal of Medicinal Chemistry, May 2015, 58(9):3767-3793.

Passos et al., "Involvement of phosphoinositide 3-kinase gamma in the neuro-inflammatory response and cognitive impairments induced by beta-amyloid 1-40 peptide in mice," Brain Behav Immun, Mar. 2010, 24(3):493-501.

Park et al., "Homogenous proximity tyrosine kinase assays: scintillation proximity assay versus homogenous time-resolved fluorescence," Anal. Biochem., Apr. 1999, 269(1):94-104.

Pinho et al., "Phosphoinositide-3 kinases critically regulate the recruitment and survival of eosinophils in vivo: importance for the resolution of allergic inflammation," J Leukoc Biol, May 2005, 77(5):800-10.

Pomel et al., "Furan-2-ylmethylene thiazolidinediones as novel, potent, and selective inhibitors of phosphoinositide 3-kinase gamma," J. Med. Chem., Jun. 2006, 49(13):3857-71.

Prete et al., "Defective dendritic cell migration and activation of adaptive immunity in PI3Kgamma-deficient mice," EMBO J, Sep. 2004, 23(17):3505-15.

Randis et al., "Role of PI3Kdelta and PI3Kgamma in inflammatory arthritis and tissue localization of neutrophils," Eur J Immunol, May 2008, 38(5):1215-24.

Remington's Pharmaceutical Sciences, 17th ed., Mack Publishing Company, Easton, Pa., 1985, p. 1418.

Rodrigues et al., "Absence of PI3Kgamma leads to increased leukocyte apoptosis and diminished severity of experimental autoimmune encephalomyelitis," J Neuroimmunol, May 2010, 222(1-2)90-4.

Rommel et al., "PI3Kδ and PI3Kγ:partners in crime in inflammation in rheumatoid arthritis and beyond?" Nature Rev Immunol., 2007, 7:191-201.

Ruckle et al., "PI3Kgamma inhibition: towards an 'aspirin of the 21st century'?" Nat Rev Drug Discov, Nov. 2006, 5(11):903-18.

Schmid et al., "Receptor tyrosine kinases and TLR/IL1Rs unexpectedly activate myeloid cell PI3Kγ, a single convergent point promoting tumor inflammation and progression," Cancer Cell, Jun. 2011, 19(6):715-27.

Schmidt et al., Cancer Res. 2012, 72 (Suppl 1:Abstract, 411).

Subramaniam et al., "Targeting nonclassical oncogenes for therapy in T-ALL," Cancer Cell, Apr. 2012, 21(4):459-72.

Taiwan Office Action in Taiwan Application No. 105136055, dated Aug. 8, 2020, 14 pages.

T. W. Greene and P. G. M. Wuts, Protective Groups in Organic Synthesis, 3rd Ed., Wiley & Sons, Inc., New York (1999), 799 pages.

Thomas et al., "Airway inflammation: chemokine-induced neutrophilia and the class I phosphoinositide 3-kinases," Eur J Immunol, Apr. 2005, 35(4):1283-91.

Vaillard et al., "Synthesis of 6-substituted 2-pyrrolyl and Indolyl Benzoxazoles by Intramolecular O-Arylation in Photostimulated Reactions," The Journal of Organic Chemistry, Feb. 2012, 77(3):1507-1519.

Vanhaesebroeck et al., "Signalling by PI3K isoforms: insights from gene-targeted mice," Trends Biochem Sci, Apr. 2005, 30(4):194-204.

Vecchione et al., "Protection from angiotensin II-mediated vasculotoxic and hypertensive response in mice lacking PI3Kgamma," J Exp Med, Apr. 2005, 201(8):1217-28.

Venable et al., "Phosphoinositide 3-Kinase Gamma (PI3K[gamma]) Inhibitors for the Treatment of Inflammation and Autoimmune Disease," Recent Patents on Inflammation & Allergy Drug Discovery, Jan. 2010, 4(1):1-15.

European Office Action in European Application No. 20187907.9, dated Jun. 27, 2022, 3 pages.

European Search Report in European Application No. 22162035.4, dated Jul. 27, 2022, 9 pages.

Cheung et al., "Future therapeutic targets in rheumatoid arthritis?" Semin Immunopathol., 2017, 39:487-500.

Campa et al., "Inhalation of the prodrug PI3K inhibitor CL27c improves lung function in asthma and fibrosis," Nature Communications, 2018, 9:5232.

Chamcheu et al., "Dual Inhibition of PI3K/Akt and mTOR by the Dietary Antioxidant, Delphinidin, Ameliorates Psoriatic Features In Vitro and in an Imiquimod-Induced Psoriasis-Like Disease in Mice," Antioxidants Redox Signaling, 2017, 26(2):49-69.

Jacot et al., "Potential Therapeutic Roles for Inhibition of the PI3K/Akt/mTOR Pathway in the Pathophysiology of Diabetic Retinopathy," J Ophthalmology, 2011, ID:589813.

HETEROCYCLIC COMPOUNDS AS PI3K-γ INHIBITORS

CROSS REFERENCE TO RELATED APPLICATIONS

This application is a continuation of U.S. application Ser. No. 16/589,523, filed Oct. 1, 2019, which is a divisional of U.S. application Ser. No. 16/045,358, filed Jul. 25, 2018, which is a continuation of U.S. application Ser. No. 15/343,375, filed Nov. 4, 2016, which claims the benefit of U.S. Ser. No. 62/252,050, filed Nov. 6, 2015, the disclosure of which is incorporated herein by reference in its entirety.

FIELD OF THE INVENTION

The present invention provides heterocyclic compounds that modulate the activity of phosphoinositide 3-kinases-gamma (PI3Kγ) and are useful in the treatment of diseases related to the activity of PI3Kγ including, for example, autoimmune diseases, cancer, cardiovascular diseases, and neurodegenerative diseases.

BACKGROUND

The phosphoinositide 3-kinases (PI3Ks) belong to a large family of lipid signaling kinases that phosphorylate phosphoinositides at the D3 position of the inositol ring (Cantley, Science, 2002, 296(5573):1655-7). PI3Ks are divided into three classes (class I, II, and III) according to their structure, regulation and substrate specificity. Class I PI3Ks, which include PI3Kα, PI3Kβ, PI3Kγ, and PI3Kδ, are a family of dual specificity lipid and protein kinases that catalyze the phosphorylation of phosphatidylinosito-4,5-bisphosphate ($PIP_2$) giving rise to phosphatidylinosito-3,4,5-trisphosphate ($PIP_3$). $PIP_3$ functions as a second messenger that controls a number of cellular processes, including growth, survival, adhesion and migration. All four class I PI3K isoforms exist as heterodimers composed of a catalytic subunit (p110) and a tightly associated regulatory subunit that controls their expression, activation, and subcellular localization. PI3Kα, PI3Kβ, and PI3Kδ associate with a regulatory subunit known as p85 and are activated by growth factors and cytokines through a tyrosine kinase-dependent mechanism (Jimenez, et al., J Biol Chem., 2002, 277(44):41556-62) whereas PI3Kγ associates with two regulatory subunits (p101 and p84) and its activation is driven by the activation of G-protein-coupled receptors (Brock, et al., J Cell Biol., 2003, 160(1):89-99). PI3Kα, and PI3Kβ are ubiquitously expressed. In contrast, PI3Kγ and PI3Kδ are predominantly expressed in leukocytes (Vanhaesebroeck, et al., Trends Biochem Sci., 2005, 30(4):194-204).

Expression of PI3Kγ is mainly restricted to hematopoietic system, although it can be also detected at lower level in endothelium, heart and brain. PI3Kγ knock-out or kinase dead knock in mice are normal and fertile and do not present any overt adverse phenotypes. Analysis at the cellular level indicates that PI3Kγ is required for GPCR ligand-induced PtdINs (3,4,5)P3 production, chemotaxis and respiratory burst in neutrophils. PI3Kγ-null macrophages and dendritic cell exhibit reduced migration towards various chemoattractants. T-cells deficient in PI3Kγ show impaired cytokine production in response to anti-CD3 or Con A stimulation. PI3Kγ working downstream of adenosine A3A receptor is critical for sustained degranulation of mast cells induced by FCεRI cross-linking with IgE. PI3Kγ is also essential for survival of eosinophils (Ruckle et al., *Nat. Rev. Drug Discovery*, 2006, 5, 903-918)

Given its unique expression pattern and cellular functions, the potential role of PI3Kγ in various autoimmune and inflammatory disease models has been investigated with genetic and pharmacological tools. In asthma and allergy models, PI3Kγ$^{-/-}$ mice or mice treated with PI3Kγ inhibitor showed a defective capacity to mount contact hypersensitivity and delayed-type hypersensitivity reactions. In these models, PI3Kγ was shown to be important for recruitment of neutrophils and eosinopohils to airways and degranulation of mast cells (see e.g. Laffargue et al., *Immunity*, 2002, 16, 441-451; Prete et al., *The EMBO Journal*, 2004, 23, 3505-3515; Pinho et al., *L. Leukocyte Biology*, 2005, 77, 800-810; Thomas et al., *Eur. J. Immunol.* 2005, 35, 1283-1291; Doukas et al., *J. Pharmacol. Exp Ther.* 2009, 328, 758-765).

In two different acute pancreatitis models, genetic ablation of PI3Kγ significantly reduced the extent of acinar cell injury/necrosis and neutrophil infiltration without any impact on secretive function of isolated pancreatic acini (Lupia et al., *Am. J. Pathology*, 2004, 165, 2003-2011). PI3Kγ$^{-/-}$ mice were largely protected in four different models of rheumatoid arthritis (CIA, α-CII-IA, K/BxN serum transfer and TNF transgenic) and PI3Kγ inhibition suppressed the progression of joint inflammation and damage in the CIA and α-CII-IA models (see e.g., Camps et al., *Nat. Medicine*, 2005, 11, 939-943; Randis et al., *Eur. J. Immunol*, 2008, 38, 1215-1224; Hayer et al., *FASB J.*, 2009, 4288-4298). In the MRL-lpr mouse model of human systemic lupus erythematous, inhibition of PI3Kγ reduced glomerulonephritis and prolonged life span (Barber et al., *Nat. Medicine*, 2005, 9, 933-935).

There is evidence suggesting that chronic inflammation due to infiltration by myeloid-derived cells is a key component in the progression of neurodegeneration diseases, such as Alzheimer's disease (AD) (Giri et al., Am. J. Physiol. Cell Physiol., 2005, 289, C264-C276; El Khoury et al., Nat. Med., 2007, 13, 432-438). In line with this suggestion, PI3Kγ inhibition was shown to attenuate Aβ(1-40)-induced accumulation of activated astrocytes and microglia in the hippocampus and prevent the peptide-induced congnitive deficits and synaptic dysfunction in a mouse model of AD (Passos et al., Brain Behav. Immun. 2010, 24, 493-501). PI3Kγ deficiency or inhibition also was shown to delay onset and alleviate symptoms in experimental autoimmune encephalomyelitis in mice, a mouse model of human multiple sclerosis, which is another form of neurodegeneration disease (see e.g., Rodrigues et al., *J. Neuroimmunol.* 2010, 222, 90-94; Berod et al., *Euro. J. Immunol.* 2011, 41, 833-844; Comerford et al., *PLOS one*, 2012, 7, e45095; Li et al., *Neuroscience*, 2013, 253, 89-99).

Chronic inflammation has been formally recognized as one of the hallmarks for many different types of cancers. Accordingly, selective anti-inflammatory drugs represent a novel class of anti-cancer therapies (Hanahan and Weinberg, Cell, 2011, 144, 646-674). Since PI3Kγ is reported to mediate various inflammatory processes, its role as an immune oncology target has also been investigated. A recent study reported that PI3Kγ deficiency suppressed tumor growth in the syngeneic models of lung cancer, pancreatic cancer and melanoma (LLC, PAN02 and B16). PI3Kγ deficiency or inhibition also inhibited tumor growth in a spontaneous breast cancer model (Schmid et al., Cancer Cell, 2011, 19, 715-727). A further study reported that PI3Kγ deficiency could ameliorate inflammation and tumor growth in mice having colitis-associated colon cancer, (Gonzalez-Garcia et al., Gastroenterology, 2010, 138, 1373-1384). Detailed mechanistic analysis indicates that tumor infiltration by CD11b+ myeloid cells can cause protumorigenic inflammation at tumor sites and PI3Kγ in the myeloid cells is critical in mediating signaling of various chemoattractants in bring the cells to the tumor (Schmid et al., Cancer Cell, 2011, 19, 715-727). Other studies suggest that PI3Kγ is also required for differentiation of naïve myeloid cells into M2 macrophges at tumor sites. M2 macrophages promote tumor growth and progression by secreting immunosuppressive factors such arginase 1, which depletes the tumor microenvironment of arginine, thereby promoting T-cell death and NK cell inhibition (Schmidt et al., Cancer Res. 2012, 72 (Suppl 1: Abstract, 411; Kaneda et al., Cancer Res., 74 (Suppl 19: Abstact 3650)).

In addition to its potential role in promoting protumorigenic microenvironment, PI3Kγ may play a direct role in cancer cells. PI3Kγ is reported to be required for signaling from the Kaposi's sarcoma-associated herpevirus encoded vGPCR oncogene and tumor growth in a mouse model of sarcoma (Martin et al., Cancer Cell, 2011, 19, 805-813). PI3Kγ was also suggested to be required for growth of T-ALL (Subramanjam et al., Cancer Cell, 2012, 21, 459-472), PDAC and HCC cells (Falasca and Maffucci, Frontiers in Physiology, 2014, 5, 1-10). Moreover, in a survey of driver mutations in pancreatic cancer, PI3Kγ gene was found to contain second highest scoring predicted driven mutation (R839C) among the set of genes not previously identified as a driver in pancreatic cancer (Carter et al., Cancer Biol. Ther. 2010, 10, 582-587).

Finally, PI3Kγ deficiency also has been reported to offer protection to experimental animals in different cardiovascular disease models. For examples, lack of PI3Kγ would reduce angiotension-evoked smooth muscle contraction and, therefore, protect mice from angiotension-induced hypertension (Vecchione et al., J. Exp. Med. 2005, 201, 1217-1228). In rigorous animal myocardial infarction models, PI3Kγ inhibition provided potent cardioprotection, reducing infarct development and preserving myocardial function (Doukas et al., Proc. Natl. Acad. Sci. USA, 2006, 103, 19866-19871).

For these reasons, there is a need to develop new PI3Kγ inhibitors that can be used for the treatment of diseases such as cancer, autoimmune disorders, and inflammatory and cardiac diseases. This application is directed to this need and others.

SUMMARY

The present invention related to, inter alia, compounds of Formula (I):

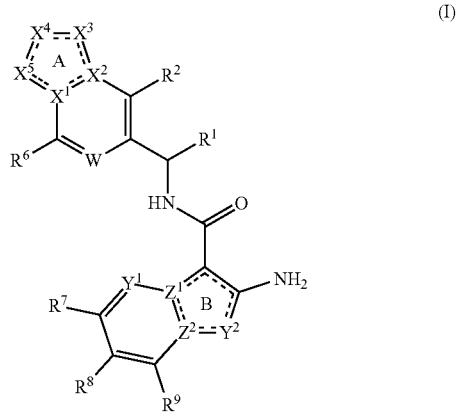

or pharmaceutically acceptable salts, wherein constituent members are defined herein.

The present invention further provides pharmaceutical compositions comprising a compound of Formula I, or a pharmaceutically acceptable salt thereof, and a pharmaceutically acceptable carrier.

The present invention further provides methods of inhibiting an activity of PI3Kγ kinase comprising contacting the kinase with a compound of Formula I, or a pharmaceutically acceptable salt thereof.

The present invention further provides methods of treating a disease or a disorder associated with abnormal PI3Kγ kinase expression or activity in a patient by administering to a patient a therapeutically effective amount of a compound of Formula I, or a pharmaceutically acceptable salt thereof.

The present invention further provides a compound of Formula I, or a pharmaceutically acceptable salt thereof, for use in any of the methods described herein.

The present invention further provides use of a compound of Formula I, or a pharmaceutically acceptable salt thereof, for the preparation of a medicament for use in any of the methods described herein.

DETAILED DESCRIPTION

Compounds

The present application provides, inter alia, a compound of Formula I:

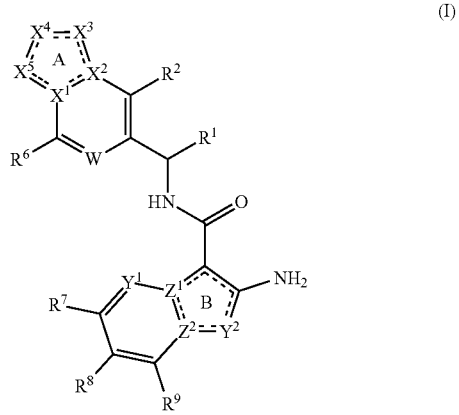

or a pharmaceutically acceptable salt thereof; wherein:
$X^1$ and $X^2$ are each independently C or N, provided $X^1$ and $X^2$ are not simultaneously N;
$X^3$ is N, $NR^{3a}$, or $CR^3$;
$X^4$ is N, $NR^{4a}$, or $CR^4$;
$X^5$ is N, $NR^{5a}$, or $CR^5$;
W is CH or N;
$Y^1$ is N or $CR^{10}$;
$Y^2$ is N or $CR^{11}$;
one of $Z^1$ and $Z^2$ is N, the other of $Z^1$ and $Z^2$ is C;
----- is a single bond or a double bond to maintain ring A and ring B being aromatic;
$R^1$ is H, $C_{1-6}$ alkyl, $C_{2-6}$ alkenyl, $C_{2-6}$ alkynyl, $C_{1-6}$ haloalkyl, $C_{3-6}$ cycloalkyl or 4-10 membered heterocycloalkyl, wherein $C_{1-6}$ alkyl, $C_{2-6}$ alkenyl, $C_{2-6}$ alkynyl, $C_{1-6}$ haloalkyl, $C_{3-6}$ cycloalkyl, and 4-10 membered heterocycloalkyl are each optionally substituted with 1, 2 or 3 independently seleted $R^j$ substituents;
$R^2$ is $OR^{13}$, $C_{3-6}$ cycloalkyl, 4-10 membered heterocycloalkyl, $C_{6-10}$ aryl, or 5-10 membered heteroaryl, wherein the $C_{3-6}$ cycloalkyl, 4-10 membered heterocycloalkyl, $C_{6-10}$ aryl, and 5-10 membered heteroaryl of $R^2$ are each optionally substituted with 1, 2, 3, 4, or 5 independently selected $R^j$ substituents;
$R^3$, $R^4$, $R^5$ and $R^6$ are each independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, $NO_2$, $OR^a$, $SR^a$, $NHOR^a$, $C(O)R^a$, $C(O)NR^aR^a$, $C(O)OR^a$, $OC(O)R^a$, $OC(O)NR^aR^a$, $NHR^a$, $NR^aR^a$, $NR^aC(O)R^a$, $NR^aC(O)OR^a$, $NR^aC(O)NR^aR^a$, $C(=NR^a)R^a$, $C(=NR^a)NR^aR^a$, $NR^aC(=NR^a)NR^aR^a$, $NR^aS(O)R^a$, $NR^aS(O)_2R^a$, $NR^aS(O)_2NR^aR^a$, $S(O)R^a$, $S(O)NR^aR^a$, $S(O)_2R^a$, and $S(O)_2NR^aR^a$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^3$, $R^4$, $R^5$, and $R^6$ are each optionally substituted with 1, 2, 3, or 4 independently selected $R^b$ substituents;
$R^{3a}$, $R^{4a}$, and $R^{5a}$ are each independently selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, $C(O)R^a$, $C(O)NR^aR^a$, $C(O)OR^a$, $C(=NR^a)R^a$, $C(=NR^a)NR^aR^a$, $S(O)R^a$, $S(O)NR^aR^a$, $S(O)_2R^a$, and $S(O)_2NR^aR^a$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^{3a}$, $R^{4a}$, and $R^{5a}$ are each optionally substituted with 1, 2, 3, or 4 independently selected $R^b$ substituents;
$R^7$ is selected from H, halo, CN, —OH, —C(O)O($C_{1-4}$ alkyl), —C(O)$NH_2$, —C(O)NH($C_{1-4}$ alkyl), —C(O)N($C_{1-4}$ alkyl)$_2$, ($C_{1-4}$ alkyl)C(O)NH—, ($C_{1-4}$ alkyl)C(O)—, $C_{1-4}$ alkylthio, —NH($C_{1-4}$ alkyl), —N($C_{1-4}$ alkyl)$_2$, $C_{1-4}$ alkyl, $C_{1-4}$ alkoxy, $C_{1-4}$ haloalkyl, $C_{1-4}$ haloalkoxy, —$SO_2$($C_{1-4}$ alkyl), —$SO_2NH$($C_{1-4}$ alkyl), —$SO_2N$($C_{1-4}$ alkyl)$_2$, ($C_{1-4}$ alkyl)$SO_2NH$—, 4-10 membered heterocycloalkyl, and 5-10 membered heteroaryl, wherein the —C(O)O($C_{1-4}$ alkyl), —C(O)NH($C_{1-4}$ alkyl), —C(O)N($C_{1-4}$ alkyl)$_2$, ($C_{1-4}$ alkyl)C(O)NH—, ($C_{1-4}$ alkyl)C(O)—, $C_{1-4}$ alkylthio, —NH($C_{1-4}$ alkyl), —N($C_{1-4}$ alkyl)$_2$, $C_{1-6}$ alkyl, $C_{1-6}$ alkoxy, $C_{1-6}$ haloalkyl, $C_{1-6}$ haloalkoxy, —$SO_2$($C_{1-4}$ alkyl), —$SO_2NH$($C_{1-4}$ alkyl), —$SO_2N$($C_{1-4}$ alkyl)$_2$, ($C_{1-4}$ alkyl)$SO_2NH$—, 4-10 membered heterocycloalkyl, and 5-10 membered heteroaryl groups of $R^7$ are each optionally substituted with 1 or 2 independently selected $R^q$ substituents $R^8$, $R^9$, $R^{10}$ and $R^{11}$ are each independently H, halo, CN, —OH, —C(O)O($C_{1-4}$ alkyl), —C(O)$NH_2$, —C(O)NH($C_{1-4}$ alkyl), —C(O)N($C_{1-4}$ alkyl)$_2$, ($C_{1-4}$ alkyl)C(O)NH—, ($C_{1-4}$ alkyl)C(O)—, $C_{1-4}$ alkylthio, —NH($C_{1-4}$ alkyl), —N($C_{1-4}$ alkyl)$_2$, $C_{1-4}$ alkyl, $C_{1-4}$ alkoxy, $C_{1-4}$ haloalkyl, $C_{1-4}$ haloalkoxy, —$SO_2$($C_{1-4}$ alkyl), —$SO_2NH$($C_{1-4}$ alkyl), —$SO_2N$($C_{1-4}$ alkyl)$_2$, and ($C_{1-4}$ alkyl)$SO_2NH$—, wherein the —C(O)O($C_{1-4}$ alkyl), —C(O)NH($C_{1-4}$ alkyl), —C(O)N($C_{1-4}$ alkyl)$_2$, ($C_{1-4}$ alkyl)C(O)NH—, ($C_{1-4}$ alkyl)C(O)—, $C_{1-4}$ alkylthio, —NH($C_{1-4}$ alkyl), —N($C_{1-4}$ alkyl)$_2$, $C_{1-6}$ alkyl, $C_{1-6}$ alkoxy, $C_{1-6}$ haloalkyl, $C_{1-6}$ haloalkoxy, —$SO_2$($C_{1-4}$ alkyl), —$SO_2NH$($C_{1-4}$ alkyl), —$SO_2N$($C_{1-4}$ alkyl)$_2$ and ($C_{1-4}$ alkyl)$SO_2NH$— groups of $R^8$, $R^9$, $R^{10}$ and $R^{11}$ are each optionally substituted with 1 or 2 independently selected $R^q$ substituents;
each $R^{12}$ is an independently selected $C_{1-6}$ alkyl group;
$R^{13}$ is H or $C_{1-6}$ alkyl optionally substituted with 1, 2 or 3 independently selected $R^q$ substituents;
each $R^a$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^a$ are each optionally substituted with 1, 2, 3, 4, or 5 independently selected $R^d$ substituents;
or any two $R^a$ substituents together with the nitrogen atom to which they are attached form a 4-, 5-, 6-, 7-, 8-, 9- or 10-membered heterocycloalkyl group optionally substituted with 1, 2 or 3 $R^b$ substituents;
each $R^b$ is independently selected from halo, $C_{1-4}$ alkyl, $C_{1-4}$ haloalkyl, $C_{1-4}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, OH, $NH_2$, $NO_2$, $NHOR^c$, $OR^c$, $SR^c$, $C(O)R^c$, $C(O)NR^cR^c$, $C(O)OR^c$, $OC(O)R^c$, $OC(O)NR^cR^c$, $C(=NR^c)NR^cR^c$, $NR^cC(=NR^c)NR^cR^c$, $NHR^c$, $NR^cR^c$, $NR^cC(O)R^c$, $NR^cC(O)OR^c$, $NR^cC(O)NR^cR^c$, $NR^cS(O)R^c$, $NR^cS(O)_2R^c$, $NR^cS(O)_2NR^cR^c$, $S(O)R^c$, $S(O)NR^cR^c$, $S(O)_2R^c$ and $S(O)_2NR^cR^c$; wherein the $C_{1-4}$ alkyl, $C_{1-4}$ haloalkyl, $C_{1-4}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^b$ are each further optionally substituted with 1, 2, or 3 independently selected $R^d$ substituents;

each $R^c$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^c$ are each optionally substituted with 1, 2, 3, 4, or 5 independently selected W substituents;

or any two $R^c$ substituents together with the nitrogen atom to which they are attached form a 4-, 5-, 6-, or 7-membered heterocycloalkyl group optionally substituted with 1, 2, or 3 independently selected $R^h$ substituents;

each $R^d$ is independently selected from halo, $C_{1-4}$ alkyl, $C_{1-4}$ haloalkyl, $C_{3-10}$ cycloalkyl, 4-10 membered heterocycloalkyl, CN, $NH_2$, $NHOR^e$, $OR^e$, $SR^e$, $C(O)R^e$, $C(O)NR^eR^e$, $C(O)OR^e$, $OC(O)R^e$, $OC(O)NR^eR^e$, $NHR^e$, $NR^eR^e$, $NR^eC(O)R^e$, $NR^eC(O)NR^eR^e$, $NR^eC(O)OR^e$, $C(=NR^e)NR^eR^e$, $NR^eC(=NR^e)NR^eR^e$, $S(O)R^e$, $S(O)NR^eR^e$, $S(O)_2R^e$, $NR^eS(O)_2R^e$, $NR^eS(O)_2NR^eR^e$, and $S(O)_2NR^eR^e$, wherein the $C_{1-4}$ alkyl, $C_{3-10}$ cycloalkyl and 4-10 membered heterocycloalkyl of $R^d$ are each further optionally substituted with 1, 2, or 3 independently selected $R^q$ substituents;

each $R^f$ is independently selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, halo, CN, $NHOR^g$, $OR^g$, $SR^g$, $C(O)R^g$, $C(O)NR^gR^g$, $C(O)OR^g$, $OC(O)R^g$, $OC(O)NR^gR^g$, $NHR^g$, $NR^gR^g$, $NR^gC(O)R^g$, $NR^gC(O)NR^gR^g$, $NR^gC(O)OR^g$, $C(=NR^g)NR^gR^g$, $NR^gC(=NR^g)NR^gR^g$, $S(O)R^g$, $S(O)NR^gR^g$, $S(O)_2R^g$, $NR^gS(O)_2R^g$, $NR^gS(O)_2NR^gR^g$, and $S(O)_2NR^gR^g$; wherein the $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^f$ are each optionally substituted with 1, 2, 3, 4, or 5 independently selected $R^n$ substituents;

each $R^g$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^g$ are each optionally substituted with 1, 2, or 3 independently selected $R^p$ substituents;

each $R^h$ is selected from $C_{1-6}$ alkyl, $C_{3-10}$ cycloalkyl, 4-7 membered heterocycloalkyl, $C_{6-10}$ aryl, 5-6 membered heteroaryl, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl-, $C_{1-6}$ haloalkyl, $C_{2-6}$ alkenyl, $C_{2-6}$ alkynyl, halo, CN, $OR^i$, $SR^i$, $NHOR^i$, $C(O)R^i$, $C(O)NR^iR^i$, $C(O)OR^i$, $OC(O)R^i$, $OC(O)NR^iR^i$, $NHR^i$, $NR^iR^i$, $NR^iC(O)R^i$, $NR^iC(O)NR^iR^i$, $NR^iC(O)OR^i$, $C(=NR^i)NR^iR^i$, $NR^iC(=NR^i)NR^iR^i$, $S(O)R^i$, $S(O)NR^iR^i$, $S(O)_2R^i$, $NR^iS(O)_2R^i$, $NR^iS(O)_2NR^iR^i$, and $S(O)_2NR^iR^i$, wherein the $C_{1-6}$ alkyl, $C_{3-10}$ cycloalkyl, 4-7 membered heterocycloalkyl, $C_{6-10}$ aryl, 5-6 membered heteroaryl, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl- of $R^h$ are each further optionally substituted with 1, 2, or 3 independently selected $R^j$ substituents;

or two $R^h$ groups attached to the same carbon atom of the 4- to 10-membered heterocycloalkyl taken together with the carbon atom to which they attach form a $C_{3-6}$ cycloalkyl or 4- to 6-membered heterocycloalkyl having 1-2 heteroatoms as ring members selected from O, N or S;

each $R^j$ substituent is independently selected from $C_{3-6}$ cycloalkyl, $C_{6-10}$ aryl, 5 or 6-membered heteroaryl, $C_{2-4}$ alkenyl, $C_{2-4}$ alkynyl, halo, $C_{1-4}$ alkyl, $C_{1-4}$ haloalkyl, CN, $NHOR^k$, $OR^k$, $SR^k$, $C(O)R^k$, $C(O)NR^kR^k$, $C(O)OR^k$, $OC(O)R^k$, $OC(O)NR^kR^k$, $NHR^k$, $NR^kR^k$, $NR^kC(O)R^k$, $NR^kC(O)NR^kR^k$, $NR^kC(O)OR^k$, $C(=NR^k)NR^kR^k$, $NR^kC(=NR^k)NR^kR^k$, $S(O)R^k$, $S(O)NR^kR^k$, $S(O)_2R^k$, $NR^kS(O)_2R^k$, $NR^kS(O)_2NR^kR^k$, and $S(O)_2NR^kR^k$;

each $R^n$ is independently selected from $C_{1-4}$ alkyl, $C_{1-4}$ haloalkyl, halo, CN, $R^o$, $NHOR^o$, $OR^o$, $SR^o$, $C(O)R^o$, $C(O)NR^oR^o$, $C(O)OR^o$, $OC(O)R^o$, $OC(O)NR^oR^o$, $NHR^o$, $NR^oR^o$, $NR^oC(O)R^o$, $NR^oC(O)NR^oR^o$, $NR^oC(O)OR^o$, $C(=NR^o)NR^oR^o$, $NR^oC(=NR^o)NR^oR^o$, $S(O)R^o$, $S(O)NR^oR^o$, $S(O)_2R^o$, $NR^oS(O)_2R^o$, $NR^oS(O)_2NR^oR^o$, and $S(O)_2NR^oR^o$; and each $R^e$, $R^i$, $R^k$, $R^o$ or $R^p$ is independently selected from H, $C_{1-4}$ alkyl, $C_{1-4}$ haloalkyl, $C_{2-4}$ alkenyl, $C_{2-4}$ alkynyl, $C_{3-6}$ cycloalkyl, $C_{6-10}$ aryl, and 5 or 6-membered heteroaryl; wherein the $C_{1-4}$ alkyl, $C_{1-4}$ haloalkyl, $C_{2-4}$ alkenyl, $C_{2-4}$ alkynyl, $C_{3-6}$ cycloalkyl, $C_{6-10}$ aryl, 5 or 6-membered heteroaryl of $R^e$, $R^i$, $R^k$, $R^o$ or $R^p$ are each optionally substituted with 1, 2 or 3 independently selected $R^q$ substituents;

or any two $R^e$ substituents together with the nitrogen atom to which they are attached form a 4-, 5-, 6-, or 7-membered heterocycloalkyl group optionally substituted with 1, 2, or 3 independently selected $R^h$ substituents;

or any two $R^g$ substituents together with the nitrogen atom to which they are attached form a 4-, 5-, 6-, or 7-membered heterocycloalkyl group optionally substituted with 1, 2, or 3 independently selected $R^h$ substituents;

or any two $R^i$ substituents together with the nitrogen atom to which they are attached form a 4-, 5-, 6-, or 7-membered heterocycloalkyl group optionally substituted with 1, 2, or 3 independently selected $R^h$ substituents;

or any two $R^k$ substituents together with the nitrogen atom to which they are attached form a 4-, 5-, 6-, or 7-membered heterocycloalkyl group optionally substituted with 1, 2, or 3 independently selected $R^h$ substituents;

or any two $R^o$ substituents together with the nitrogen atom to which they are attached form a 4-, 5-, 6-, or 7-membered heterocycloalkyl group optionally substituted with 1, 2, or 3 independently selected $R^h$ substituents; and each $R^q$ is independently selected from OH, CN, —COOH, $NH_2$, halo, $C_{1-4}$ alkyl, $C_{1-4}$ alkoxy, $C_{1-4}$ alkylthio, phenyl, 5-6 membered heteroaryl, $C_{3-6}$ cycloalkyl, $NHR^{12}$, $NR^{12}R^{12}$, and $C_{1-4}$ haloalkoxy, wherein the $C_{1-4}$ alkyl, phenyl and 5-6 membered heteroaryl of $R^q$ are each optionally substituted with OH, CN, —COOH, $NH_2$, $C_{1-4}$ alkoxy, $C_{3-10}$ cycloalkyl, and 4-6 membered heterocycloalkyl.

In some embodiments:

$X^1$ and $X^2$ are each independently C or N, provided $X^1$ and $X^2$ are not simultaneously N;

$X^3$ is N, $NR^{3a}$, or $CR^3$;

$X^4$ is N, $NR^{4a}$, or $CR^4$;

$X^5$ is N, $NR^{5a}$, or $CR^5$;

W is CH or N;

$Y^1$ is N or $CR^{10}$;

$Y^2$ is N or $CR^{11}$;

one of $Z^1$ and $Z^2$ is N, the other of $Z^1$ and $Z^2$ is C;

----- is a single bond or a double bond to maintain ring A and ring B being aromatic;

$R^1$ is H, $C_{1-6}$ alkyl, $C_{2-6}$ alkenyl, $C_{2-6}$ alkynyl, $C_{1-6}$ haloalkyl, $C_{3-6}$ cycloalkyl or 4-10 membered heterocycloalkyl, wherein $C_{1-6}$ alkyl, $C_{2-6}$ alkenyl, $C_{2-6}$ alkynyl, $C_{1-6}$ haloalkyl, $C_{3-6}$ cycloalkyl, and 4-10 membered heterocycloalkyl are each optionally substituted with 1, 2 or 3 independently seleted $R^j$ substituents;

$R^2$ is $OR^{13}$, $C_{3-6}$ cycloalkyl, 4-10 membered heterocycloalkyl, $C_{6-10}$ aryl, or 5-10 membered heteroaryl, wherein the $C_{3-6}$ cycloalkyl, 4-10 membered heterocycloalkyl, $C_{6-10}$ aryl, and 5-10 membered heteroaryl of $R^2$ are each optionally substituted with 1, 2, 3, 4, or 5 independently selected substituents;

$R^3$, $R^4$, $R^5$ and $R^6$ are each independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, $NO_2$, $OR^a$, $SR^a$, $NHOR^a$, $C(O)R^a$, $C(O)NR^aR^a$, $C(O)OR^a$, $OC(O)R^a$, $OC(O)NR^aR^a$, $NHR^a$, $NR^aR^a$, $NR^aC(O)R^a$, $NR^aC(O)OR^a$, $NR^aC(O)NR^aR^a$, $C(=NR^a)R^a$, $C(=NR^a)NR^aR^a$, $NR^aC(=NR^a)NR^aR^a$, $NR^aS(O)R^a$, $NR^aS(O)_2R^a$, $NR^aS(O)_2NR^aR^a$, $S(O)R^a$, $S(O)NR^aR^a$, $S(O)_2R^a$, and $S(O)_2NR^aR^a$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^3$, $R^4$, $R^5$, and $R^6$ are each optionally substituted with 1, 2, 3, or 4 independently selected $R^b$ substituents;

$R^{3a}$, $R^{4a}$, and $R^{5a}$ are each independently selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, $C(O)R^a$, $C(O)NR^aR^a$, $C(O)OR^a$, $C(=NR^a)R^a$, $C(=NR^a)NR^aR^a$, $S(O)R^a$, $S(O)NR^aR^a$, $S(O)_2R^a$, and $S(O)_2NR^aR^a$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^{3a}$, $R^{4a}$ and $R^{5a}$ are each optionally substituted with 1, 2, 3, or 4 independently selected $R^b$ substituents;

$R^7$, $R^8$, $R^9$, $R^{10}$ and $R^{11}$ are each independently H, halo, CN, —OH, —C(O)O($C_{1-4}$ alkyl), —C(O)$NH_2$, —C(O)NH($C_{1-4}$ alkyl), —C(O)N($C_{1-4}$ alkyl)$_2$, ($C_{1-4}$ alkyl)C(O)NH—, ($C_{1-4}$ alkyl)C(O)—, $C_{1-4}$ alkylthio, —NH($C_{1-4}$ alkyl), —N($C_{1-4}$ alkyl)$_2$, $C_{1-4}$ alkyl, $C_{1-4}$ alkoxy, $C_{1-4}$ haloalkyl, $C_{1-4}$ haloalkoxy, —$SO_2$($C_{1-4}$ alkyl), —$SO_2$NH($C_{1-4}$ alkyl), —$SO_2$N($C_{1-4}$ alkyl)$_2$, and ($C_{1-4}$ alkyl)$SO_2$NH—, wherein the —C(O)O($C_{1-4}$ alkyl), —C(O)NH($C_{1-4}$ alkyl), —C(O)N($C_{1-4}$ alkyl)$_2$, ($C_{1-4}$ alkyl)C(O)NH—, ($C_{1-4}$ alkyl)C(O)—, $C_{1-4}$ alkylthio, —NH($C_{1-4}$ alkyl), —N($C_{1-4}$ alkyl)$_2$, $C_{1-6}$ alkyl, $C_{1-6}$ alkoxy, $C_{1-6}$ haloalkyl, $C_{1-6}$ haloalkoxy, —$SO_2$($C_{1-4}$ alkyl), —$SO_2$NH($C_{1-4}$ alkyl), —$SO_2$N($C_{1-4}$alkyl)$_2$ and ($C_{1-4}$ alkyl)$SO_2$NH— groups of $R^7$, $R^8$, $R^9$, $R^{10}$ and $R^{11}$ are each optionally substituted with 1 or 2 independently selected $R^q$ substituents;

each $R^{12}$ is an independently selected $C_{1-6}$ alkyl group;

$R^{13}$ is H or $C_{1-6}$ alkyl optionally substituted with 1, 2 or 3 independently selected $R^q$ substituents;

each $R^a$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^a$ are each optionally substituted with 1, 2, 3, 4, or 5 independently selected $R^d$ substituents;

or any two $R^a$ substituents together with the nitrogen atom to which they are attached form a 4-, 5-, 6-, 7-, 8-, 9- or 10-membered heterocycloalkyl group optionally substituted with 1, 2 or 3 $R^h$ substituents;

each $R^b$ is independently selected from halo, $C_{1-4}$ alkyl, $C_{1-4}$ haloalkyl, $C_{1-4}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, OH, $NH_2$, $NO_2$, $NHOR^c$, $OR^c$, $C(O)R^c$, $C(O)NR^cR^c$, $C(O)OR^c$, $OC(O)R^c$, $OC(O)NR^cR^c$, $C(=NR^c)NR^cR^c$, $NR^c$ $C(=NR^c)NR^cR^c$, $NHR^c$, $NR^cR^c$, $NR^c$ $C(O)R^c$, $NR^c$ $C(O)OR^c$, $NR^cC(O)NR^cR^c$, $NR^cS(O)R^c$, $NR^cS(O)_2R^c$, $NR^cS(O)_2NR^cR^c$, $S(O)R^c$, $S(O)NR^cR^c$, $S(O)_2R^c$ and $S(O)_2NR^cR^c$; wherein the $C_{1-4}$ alkyl, $C_{1-4}$ haloalkyl, $C_{1-4}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^b$ are each further optionally substituted with 1, 2, or 3 independently selected $R^d$ substituents;

each $R^c$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^c$ are each optionally substituted with 1, 2, 3, 4, or 5 independently selected $R^f$ substituents;

or any two $R^c$ substituents together with the nitrogen atom to which they are attached form a 4-, 5-, 6-, or 7-membered heterocycloalkyl group optionally substituted with 1, 2, or 3 independently selected $R^h$ substituents;

each $R^d$ is independently selected from halo, $C_{1-4}$ alkyl, $C_{1-4}$ haloalkyl, $C_{3-10}$ cycloalkyl, 4-10 membered heterocycloalkyl, CN, $NH_2$, $NHOR^e$, $OR^e$, $SR^e$, $C(O)R^e$, $C(O)NR^eR^e$, $C(O)OR^e$, $OC(O)R^e$, $OC(O)NR^eR^e$, $NHR^e$, $NR^eR^e$, $NR^eC(O)R^e$, $NR^eC(O)NR^eR^e$, $NR^eC(O)OR^e$, $C(=NR^e)NR^eR^e$, $NR^eC(=NR^e)NR^eR^e$, $S(O)R^e$, $S(O)NR^eR^e$, $S(O)_2R^e$, $NR^eS(O)_2R^e$, $NR^eS(O)_2NR^eR^e$, and $S(O)_2NR^eR^e$, wherein the $C_{1-4}$ alkyl, $C_{3-10}$ cycloalkyl and 4-10 membered heterocycloalkyl of $R^d$ are each further optionally substituted with 1, 2, or 3 independently selected $R^q$ substituents;

each $R^f$ is independently selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, halo, CN, $NHOR^g$, $OR^g$, $SR^g$, $C(O)R^g$, $C(O)NR^gR^g$, $C(O)OR^g$, $OC(O)R^g$, $OC(O)NR^gR^g$, $NHR^g$, $NR^gR^g$, $NR^gC(O)R^g$, $NR^gC(O)NR^gR^g$, $NR^gC(O)OR^g$, $C(=NR^g)NR^gR^g$, $NR^gC(=NR^gNR^gR^g$, $S(O)R^g$, $S(O)NR^gR^g$, $S(O)_2R^g$, $NR^gS(O)_2R^g$, $NR^gS(O)_2NR^gR^g$, and $S(O)_2NR^gR^g$; wherein the $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^f$ are each optionally substituted with 1, 2, 3, 4, or 5 independently selected $R^a$ substituents;

each $R^g$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^g$ are each optionally substituted with 1, 2, or 3 independently selected $R^p$ substituents;

each $R^h$ is selected from $C_{1-6}$ alkyl, $C_{3-10}$ cycloalkyl, 4-7 membered heterocycloalkyl, $C_{6-10}$ aryl, 5-6 membered heteroaryl, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$alkyl-, $C_{1-6}$ haloalkyl, $C_{2-6}$ alkenyl, $C_{2-6}$ alkynyl, halo, CN, $OR^i$, $SR^i$, $NHOR^i$, $C(O)R^i$, $C(O)NR^iR^i$, $C(O)OR^i$, $OC(O)R^i$, $OC(O)NR^iR^i$, $NHR^i$, $NR^iR^i$, $NR^i$, $C(O)R^i$, $NR^iC(O)NR^iR^i$, $NR^iC(O)OR^i$, $C(=NR^i)NR^iR^i$, $NR^iC(=NR^i)NR^iR^i$, $S(O)R^i$, $S(O)NR^iR^i$, $S(O)_2R^i$, $NR^iS(O)_2R^i$, $NR^iS(O)_2NR^iR^i$, and $S(O)_2NR^iR^i$, wherein the $C_{1-6}$ alkyl, $C_{3-10}$ cycloalkyl, 4-7 membered heterocycloalkyl, $C_{6-10}$ aryl, 5-6 membered heteroaryl, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl- of $R^h$ are each further optionally substituted with 1, 2, or 3 independently selected IV substituents;

or two $R^h$ groups attached to the same carbon atom of the 4- to 10-membered heterocycloalkyl taken together with the carbon atom to which they attach form a $C_{3-6}$ cycloalkyl or 4- to 6-membered heterocycloalkyl having 1-2 heteroatoms as ring members selected from O, N or S;

each $R^j$ substituent is independently selected from $C_{3-6}$ cycloalkyl, $C_{6-10}$ aryl, 5 or 6-membered heteroaryl, $C_{2-4}$ alkenyl, $C_{2-4}$ alkynyl, halo, $C_{1-4}$ alkyl, $C_{1-4}$ haloalkyl, CN, $NHOR^k$, $OR^k$, $SR^k$, $C(O)R^k$, $C(O)NR^kR^k$, $C(O)OR^k$, $OC(O)R^k$, $OC(O)NR^kR^k$, $NHR^k$, $NR^kR^k$, $NR^kC(O)R^k$, $NR^kC(O)NR^kR^k$, $NR^kC(O)OR^k$, $C(=NR^k)NR^kR^k$, $NR^kC(=NR^k)NR^kR^k$, $S(O)R^k$, $S(O)NR^kR^k$, $S(O)_2R^k$, $NR^kS(O)_2R^k$, $NR^kS(O)_2NR^kR^k$, and $S(O)_2NR^kR^k$;

each $R^n$ is independently selected from $C_{1-4}$ alkyl, $C_{1-4}$ haloalkyl, halo, CN, $R^o$, $NHOR^o$, $OR^o$, $SR^o$, $C(O)R^o$, $C(O)NR^oR^o$, $C(O)OR^o$, $OC(O)R^o$, $OC(O)NR^oR^o$, $NHR^o$, $NR^oR^o$, $NR^oC(O)R^o$, $NR^oC(O)NR^oR^o$, $NR^oC(O)OR^o$, $C(=NR^o)NR^oR^o$, $NR^oC(=NR^oNR^oR^o$, $S(O)R^o$, $S(O)NR^oR^o$, $S(O)_2R^o$, $NR^oS(O)_2R^o$, $NR^oS(O)_2NR^oR^o$, and $S(O)_2NR^oR^o$; and each $R^e$, $R^i$, $R^k$, $R^o$ or $R^p$ is independently selected from H, $C_{1-4}$ alkyl, $C_{1-4}$ haloalkyl, $C_{2-4}$ alkenyl, $C_{2-4}$ alkynyl, $C_{3-6}$ cycloalkyl, $C_{6-10}$ aryl, and 5 or 6-membered heteroaryl; wherein the $C_{1-4}$ alkyl, $C_{1-4}$ haloalkyl, $C_{2-4}$ alkenyl, $C_{2-4}$ alkynyl, $C_{3-6}$ cycloalkyl, $C_{6-10}$ aryl, 5 or 6-membered heteroaryl of $R^e$, $R^i$, $R^k$, $R^o$ or $R^p$ are each optionally substituted with 1, 2 or 3 independently selected $R^q$ substituents;

or any two $R^e$ substituents together with the nitrogen atom to which they are attached form a 4-, 5-, 6-, or 7-membered heterocycloalkyl group optionally substituted with 1, 2, or 3 independently selected $R^h$ substituents;

or any two $R^g$ substituents together with the nitrogen atom to which they are attached form a 4-, 5-, 6-, or 7-membered heterocycloalkyl group optionally substituted with 1, 2, or 3 independently selected $R^h$ substituents;

or any two $R^i$ substituents together with the nitrogen atom to which they are attached form a 4-, 5-, 6-, or 7-membered heterocycloalkyl group optionally substituted with 1, 2, or 3 independently selected $R^h$ substituents;

or any two $R^k$ substituents together with the nitrogen atom to which they are attached form a 4-, 5-, 6-, or 7-membered heterocycloalkyl group optionally substituted with 1, 2, or 3 independently selected $R^h$ substituents;

or any two $R^o$ substituents together with the nitrogen atom to which they are attached form a 4-, 5-, 6-, or 7-membered heterocycloalkyl group optionally substituted with 1, 2, or 3 independently selected $R^h$ substituents; and each $R^q$ is independently selected from OH, CN, —COOH, $NH_2$, halo, $C_{1-4}$ alkyl, $C_{1-4}$ alkoxy, $C_{1-4}$ alkylthio, phenyl, 5-6 membered heteroaryl, $C_{3-6}$ cycloalkyl, $NHR^{12}$, $NR^{12}R^{12}$, and $C_{1-4}$ haloalkoxy, wherein the $C_{1-4}$ alkyl, phenyl and 5-6 membered heteroaryl of $R^q$ are each optionally substituted with OH, CN, —COOH, $NH_2$, $C_{1-4}$ alkoxy, $C_{3-10}$ cycloalkyl, and 4-6 membered heterocycloalkyl.

In some embodiments, $X^1$ is C; and $X^2$ is C.
In some embodiments, $X^1$ is N; and $X^2$ is C.
In some embodiments, $X^1$ is C; and $X^2$ is N.
In some embodiments, $X^3$ is N.
In some embodiments, $X^3$ is $NR^{3a}$.
In some embodiments, $X^3$ is $CR^3$.
In some embodiments, $X^4$ is N.
In some embodiments, $X^4$ is $NR^{4a}$.

In some embodiments, $X^4$ is $CR^4$.
In some embodiments, $X^5$ is N.
In some embodiments, $X^5$ is $NR^{5a}$.
In some embodiments, $X^5$ is $CR^5$.
In some embodiments, W is CH.
In some embodiments, W is N.
In some embodiments, W is CH; $X^1$ is C; $X^2$ is N; $X^3$ is $CR^3$; $X^4$ is N; and $X^5$ is $CR^5$.
In some embodiments, W is CH; $X^1$ is C; $X^2$ is C; $X^3$ is $NR^{3a}$; $X^4$ is N; and $X^5$ is $CR^5$.
In some embodiments, W is CH; $X^1$ is C; $X^2$ is C; $X^3$ is N; $X^4$ is $NR^{4a}$; and $X^5$ is $CR^5$.
In some embodiments, $Y^1$ is N.
In some embodiments, $Y^2$ is N.
In some embodiments, $Z^1$ is C; and $Z^2$ is N.
In some embodiments:

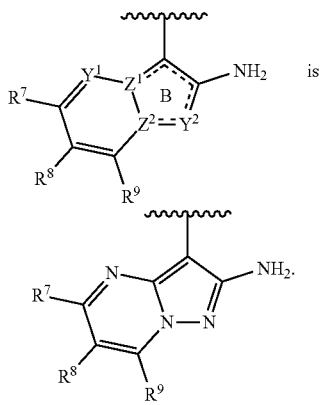

In some embodiments:

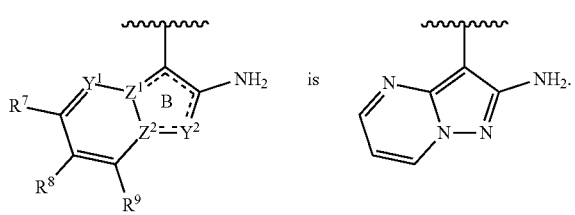

In some embodiments:

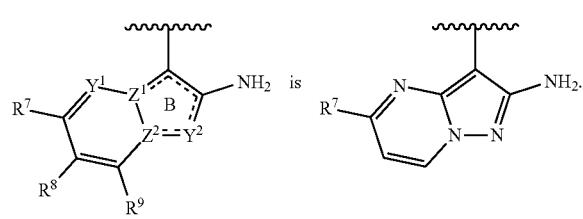

In some embodiments, $R^1$ is H, $C_{3-6}$ cycloalkyl, $C_{1-6}$ haloalkyl or $C_{1-6}$ alkyl.
In some embodiments, $R^1$ is H or $C_{1-6}$ alkyl.
In some embodiments, $R^1$ is $C_{1-6}$ alkyl.
In some embodiments, $R^1$ is methyl, ethyl or 1-propyl.
In some embodiments, $R^1$ is methyl.
In some embodiments, $R^2$ is $OR^{13}$, $C_{6-10}$ aryl, 5-10 membered heterocycloalkyl, or 5-10 membered heteroaryl; wherein said $C_{6-10}$ aryl, 5-10 membered heterocycloalkyl, and 5-10 membered heteroaryl of $R^2$ are each optionally substituted with 1, 2, 3, 4, or 5 independently selected $R^j$ substituents.

In some embodiments, $R^2$ is $OR^{13}$, $C_{6-10}$ aryl, or 5-10 membered heteroaryl; wherein said $C_{6-10}$ aryl or 5-10 membered heteroaryl of $R^2$ are each optionally substituted with 1, 2, 3, 4, or 5 independently selected R substituents.

In some embodiments, $R^2$ is $OR^{13}$ or $C_{6-10}$ aryl; wherein said $C_{6-10}$ aryl of $R^2$ is optionally substituted with 1, 2, or 3 independently selected $R^j$ substituents.

In some embodiments, $R^2$ is $C_{1-6}$ alkoxy, phenyl, or monocyclic 5-6 membered heteroaryl; wherein said $C_{6-10}$ aryl or monocyclic 5-6 membered heteroaryl of $R^2$ are each optionally substituted with 1, 2, or 3 independently selected $R^j$ substituents.

In some embodiments, $R^2$ is $C_{1-6}$ alkoxy or phenyl, wherein said phenyl of $R^2$ is optionally substituted with 1, 2, or 3 independently selected $R^j$ substituents.

In some embodiments, $R^2$ is $C_{1-6}$ alkoxy, phenyl, 5-6 membered heterocycloalkyl, or monocyclic 5-6 membered heteroaryl; wherein said $C_{6-10}$ aryl, 5-6 membered heterocycloalkyl, monocyclic 5-6 membered heteroaryl of $R^2$ are each optionally substituted with 1, 2, or 3 independently selected $R^j$ substituents.

In some embodiments, $R^2$ is 5-6 membered heterocycloalkyl which is optionally substituted with 1, 2, or 3 independently selected $R^j$ substituents.

In some embodiments, $R^2$ is 1,1-dioxidothiomorpholin-4-yl optionally substituted with 1 or 2 independently selected $R^j$ substituents.

In some embodiments, $R^2$ is ethoxy, 1,1-dioxidothiomorpholino optionally substituted with 1 or 2 $C_{1-4}$ independently selected alkyl substituents, or phenyl optionally substituted with halo.

In some embodiments, $R^2$ is ethoxy or phenyl optionally substituted with halo.

In some embodiments, $R^2$ is 1,1-dioxidothiomorpholino optionally substituted with 1 or 2 independently selected $C_{1-4}$ alkyl substituents.

In some embodiments, $R^2$ is 2-methyl-1,1-dioxidothiomorpholino.

In some embodiments, each $R^j$ is independently selected from halo, CN, $C_{1-4}$ alkyl, $C_{1-4}$ haloalkyl, $C_{2-4}$ alkenyl, $C_{2-4}$ alkynyl, $NHOR^k$, $OR^k$, $C(O)R^k$, $C(O)NR^kR^k$, $C(O)OR^k$, $OC(O)R^k$, $OC(O)NR^kR^k$, $NHR^k$, $NR^kR^k$, $NR^kC(O)R^k$, $S(O)_2R^k$, $NR^kS(O)_2R^k$, and $S(O)_2NR^kR^k$.

In some embodiments, each $R^k$ is independently selected from H, $C_{1-4}$ alkyl, and $C_{1-4}$ haloalkyl.

In some embodiments, each R is independently selected from halo, CN, $C_{1-4}$ alkyl, $C_{1-4}$ haloalkyl, $C_{1-4}$ alkoxy, $C_{1-4}$ haloalkoxy, amino, $C_{1-4}$ alkylamino, and di($C_{1-4}$ alkyl)amino.

In some embodiments, each $R^j$ is independently $C_{1-4}$ alkyl or halo.

In some embodiments, each $R^j$ is independently $C_{1-4}$ alkyl.

In some embodiments, each $R^j$ is independently methyl.
In some embodiments, each $R^j$ is independently halo.
In some embodiments, $R^2$ is ethoxy, phenyl, or 3-fluorophenyl.

In some embodiments, $R^{3a}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-; wherein the $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl- of $R^{3a}$ are each optionally substituted by 1, 2, 3, or 4 independently selected $R^b$ substituents.

In some embodiments, $R^{3a}$ is H, $C_{1-6}$ alkyl, $C_{2-6}$ alkynyl, $C_{3-7}$ cycloalkyl, phenyl-$C_{1-4}$ alkyl-, (5-6 membered heteroaryl)-$C_{1-4}$ alkyl, and (4-6 membered heterocycloalkyl)-$C_{1-4}$ alkyl; wherein said $C_{1-6}$ alkyl, $C_{2-6}$ alkynyl, $C_{3-7}$ cycloalkyl, phenyl-$C_{1-4}$ alkyl-, (5-6 membered heteroaryl)-$C_{1-4}$ alkyl, and (4-6 membered heterocycloalkyl)-$C_{1-4}$ alkyl of $R^{3a}$ are each optionally substituted by 1, 2, 3, or 4 independently selected $R^b$ substituents. In some embodiments, each $R^b$ is independently selected from halo, $C_{1-4}$ alkyl, $C_{1-4}$ haloalkyl, CN, OH, $NH_2$, $NHOR^c$, $OR^c$, $C(O)R^c$, $C(O)NR^cR^c$, $C(O)OR^c$, $OC(O)R^c$, $OC(O)NR^cR^c$, $NHR^c$, $NHR^c$, $NR^cR^c$, $NR^cC(O)R^c$, $NR^c(O)OR^c$, $NR^cS(O)R^c$, $NR^cS(O)_2R^c$, $S(O)_2R^c$ and $S(O)_2NR^cR^c$. In some embodiments, each $R^b$ is independently selected from $C_{1-4}$ alkyl, OH, $OR^c$, CN, $C(O)NR^cR^c$, and $NR^cR^c$. In some embodiments, each $R^c$ is independently selected from H and $C_{1-6}$ alkyl.

In some embodiments, $R^{3a}$ is H, methyl, isopropyl, isobutyl, —$CH_2C\equiv CCH_3$, —$CH_2CH_2OH$, —$CH_2CH_2OCH_3$, —$CH_2CN$, —$CH_2CH_2NH_2$, —$CH_2C(O)NH_2$, benzyl, cyclobutyl, —$CH_2$-(1-methyl-1H-pyrazol-3-yl), or —$CH_2CH_2$-(morpholin-4-yl).

In some embodiments, $R^3$ is H, halo, CN, $C_{1-6}$ alkyl, or $C_{1-6}$ haloalkyl.

In some embodiments, $R^3$ is H or $C_{1-6}$ alkyl.

In some embodiments, $R^3$ is H, methyl, or ethyl.

In some embodiments, $R^{4a}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-; wherein the $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl- of $R^{4a}$ are each optionally substituted by 1, 2, 3, or 4 independently selected $R^b$ substituents.

In some embodiments, $R^{4a}$ is selected from H, $C_{1-6}$ alkyl, $C_{2-6}$ alkynyl, $C_{3-10}$ cycloalkyl, phenyl-$C_{1-4}$ alkyl-, and (5-6 membered heteroaryl)-$C_{1-4}$ alkyl-, wherein said $C_{1-6}$ alkyl, $C_{1-6}$ alkynyl, $C_{3-10}$ cycloalkyl, phenyl-$C_{1-4}$ alkyl-, and (5-6 membered heteroaryl)-$C_{1-4}$ alkyl- of $R^{4a}$ are each optionally substituted by 1, 2, 3, or 4 independently selected $R^b$ substituents.

In some embodiments, $R^{4a}$ is selected from H, $C_{1-6}$ alkyl, $C_{2-6}$ alkynyl, $C_{3-10}$ cycloalkyl, $C_{6-10}$ aryl-$C_{1-4}$ alkyl-, and (5-10 membered heteroaryl)-$C_{1-4}$ alkyl-, wherein said $C_{1-6}$ alkyl and (4-10 membered heteroaryl)-$C_{1-4}$ alkyl- of $R^{4a}$ are each optionally substituted by 1, 2, 3, or 4 independently selected $R^b$ substituents.

In some embodiments, each $R^b$ is independently selected from halo, $C_{1-4}$ alkyl, $C_{1-4}$ haloalkyl, CN, OH, $NH_2$, $NHOR^c$, $OR^c$, $C(O)R^c$, $C(O)NR^cR^c$, $C(O)OR^c$, $OC(O)R^c$, $OC(O)NR^cR^c$, $NHR^cC$, $NR^cR^c$, $NR^c(O)R^c$, $NR^cC(O)OR^c$, $NR^cS(O)R^c$, $NR^cS(O)_2R^c$, $S(O)_2R^c$ and $S(O)_2NR^cR^c$. In some embodiments, each $R^b$ is independently selected from $C_{1-4}$ alkyl, OH, $OR^c$, CN, $NR^cR^c$, and $C(O)NR^cR^c$. In some embodiments, each $R^c$ is independently H or $C_{1-6}$ alkyl; or any two $R^c$ substituents together with the nitrogen atom to which they are attached form a 4-, 5-, 6-, or 7-membered heterocycloalkyl group optionally substituted with 1, 2, or 3 independently selected $R^h$ substituents.

In some embodiments, $R^{4a}$ is H, methyl, ethyl, isopropyl, isobutyl, —$CH_2C\equiv CCH_3$, —$CH_2CH_2OH$, —$CH_2CH_2OCH_3$, —$CH_2CN$, —$CH_2CH_2NH_2$, cyclobutyl, benzyl, —$CH_2C(O)NH_2$, —$CH_2$-(1-methyl-1H-pyrazol-3-yl), or —$CH_2C(O)$-(morpholin-4-yl).

In some embodiments, $R^4$ is selected from H, halo, CN, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-; wherein the $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl- of $R^4$ are each optionally substituted by 1, 2, 3, or 4 independently selected $R^b$ substituents.

In some embodiments, $R^4$ is selected from H, halo, CN, $C_{1-6}$ alkyl, $C_{2-6}$ alkynyl, $C_{3-10}$ cycloalkyl, phenyl-$C_{1-4}$ alkyl-, and (5-6 membered heteroaryl)-$C_{1-4}$ alkyl-, wherein said $C_{1-6}$ alkyl, $C_{1-6}$ alkynyl, $C_{3-10}$ cycloalkyl, phenyl-$C_{1-4}$ alkyl-, and (5-6 membered heteroaryl)-$C_{1-4}$ alkyl- of $R^4$ are each optionally substituted by 1, 2, 3, or 4 independently selected $R^b$ substituents.

In some embodiments, $R^4$ is H, halo, CN, $C_{1-6}$ alkyl, or $C_{1-6}$ haloalkyl.

In some embodiments, $R^4$ is H or $C_{1-6}$ alkyl.

In some embodiments, $R^5$ is H, halo, $C_{1-6}$ alkyl, or $C_{1-6}$ haloalkyl.

In some embodiments, $R^5$ is H, halo, or $C_{1-6}$ alkyl.

In some embodiments, $R^5$ is H, bromo, chloro, fluoro, methyl, ethyl, n-propyl, or isopropyl.

In some embodiments, $R^5$ is H, bromo, or methyl.

In some embodiments, $R^6$ is H, halo, CN, $C_{1-6}$ alkyl, or $C_{1-6}$ haloalkyl.

In some embodiments, $R^6$ is halo, CN, or $C_{1-6}$ alkyl.

In some embodiments, $R^6$ is selected from chloro, CN, and methyl.

In some embodiments, $R^7$ is H, 4-10 membered heterocycloalkyl, or 5-10 membered heteroaryl, wherein the 4-10 membered heterocycloalkyl and 5-10 membered heteroaryl are each optionally substituted with 1 or 2 independently selected $R^q$ substituents.

In some embodiments, $R^7$ is H, 5-6 membered heterocycloalkyl, or 5-6 membered heteroaryl, wherein the 5-6 membered heterocycloalkyl and 5-6 membered heteroaryl are each optionally substituted with 1 or 2 independently selected $R^q$ substituents.

In some embodiments, $R^7$ is H, piperidinyl, or pyridyl, wherein the piperidinyl and pyridyl groups are each optionally substituted with 1 or 2 independently selected $R^q$ substituents.

In some embodiments, $R^7$ is H, piperidinyl, or pyridyl, wherein the piperidinyl and pyridyl groups are each optionally substituted with 1 or 2 groups independently selected from $C_{1-4}$ alkyl and $C_{1-4}$ alkoxy, wherein the $C_{1-4}$ alkyl group is optionally substituted by OH.

In some embodiments, $R^7$ is H, piperidin-1-yl, or pyridin-3-yl, wherein the piperidin-1-yl and piperidin-3-yl groups are each optionally substituted with 1 or 2 groups independently selected from $C_{1-4}$ alkyl and $C_{1-4}$ alkoxy, wherein the $C_{1-4}$ alkyl group is optionally substituted by OH.

In some embodiments, $R^7$, $R^8$, and $R^9$ are each H.

In some embodiments:

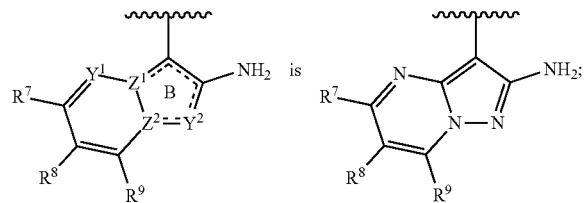

$R^1$ is H or $C_{1-6}$ alkyl;
$R^2$ is 5-6 membered heterocycloalkyl optionally substituted with 1, 2 or 3 independently selected $R^j$ substituents;
each $R^j$ is independently selected from halo, CN, $C_{1-4}$ alkyl, $C_{1-4}$ haloalkyl, $C_{2-4}$ alkenyl, $C_{2-4}$ alkynyl, $NHOR^k$, $OR^k$, $C(O)R^k$, $C(O)NR^kR^k$, $C(O)OR^k$, $OC(O)R^k$, $OC(O)NR^kR^k$, $NHR^k$, $NR^kR^k$, $NR^kC(O)R^k$, $S(O)_2R^k$, $NR^kS(O)_2R^k$, and $S(O)_2NR^kR^k$;
$R^{3a}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-; wherein the $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl- of $R^{3a}$ are each optionally substituted by 1, 2, 3, or 4 independently selected $R^b$ substituents;
$R^{4a}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-; wherein the $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl- of $R^{4a}$ are each optionally substituted by 1, 2, 3, or 4 independently selected $R^b$ substituents;
$R^3$ is H or $C_{1-6}$ alkyl;
$R^4$ is H or $C_{1-6}$ alkyl;
$R^5$ is H, halo, $C_{1-6}$ alkyl, or $C_{1-6}$ haloalkyl;
$R^{5a}$ is H or $C_{1-6}$ alkyl;
$R^6$ is H, halo, CN, $C_{1-6}$ alkyl, or $C_{1-6}$ haloalkyl; and
$R^7$ is H, halo, CN, $C_{1-6}$ alkyl, or $C_{1-6}$ haloalkyl.

In some embodiments:

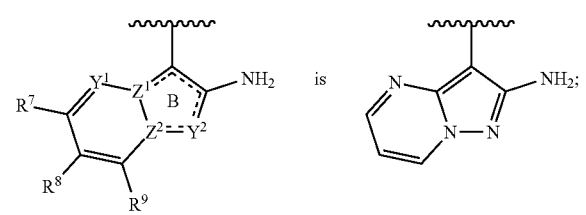

$R^1$ is $C_{1-6}$ alkyl;
$R^2$ is 5-6 membered heterocycloalkyl, wherein said 5-6 membered heterocycloalkyl of $R^2$ is optionally substituted with 1 or 2 independently selected R substituents;
each R is independently $C_{1-4}$ alkyl;
$R^{3a}$ is H, $C_{1-6}$ alkyl, $C_{2-6}$ alkynyl, $C_{3-7}$ cycloalkyl, phenyl-$C_{1-4}$ alkyl-, (5-6 membered heteroaryl)-$C_{1-4}$ alkyl, and (4-6 membered heterocycloalkyl)-$C_{1-4}$ alkyl; wherein said $C_{1-6}$ alkyl, $C_{3-7}$ cycloalkyl, phenyl-$C_{1-4}$ alkyl-, (5-6 membered heteroaryl)-$C_{1-4}$ alkyl, and (4-6 membered heterocycloalkyl)-$C_{1-4}$ alkyl of $R^{3a}$ are each optionally substituted by 1, 2, 3, or 4 independently selected $R^b$ substituents;
$R^{4a}$ is selected from H, $C_{1-6}$ alkyl, $C_{2-6}$ alkynyl, $C_{3-7}$ cycloalkyl, phenyl-$C_{1-4}$ alkyl-, and (5-6 membered heteroaryl)-$C_{1-4}$ alkyl-; wherein said $C_{1-6}$ alkyl and (5-6 membered heteroaryl)-$C_{1-4}$ alkyl- of $R^{4a}$ are each optionally substituted by 1, 2, 3, or 4 independently selected $R^b$ substituents;
$R^3$ is H or $C_{1-6}$ alkyl;
$R^4$ is H or $C_{1-6}$ alkyl;
$R^{5a}$ is H or $C_{1-6}$ alkyl;
$R^5$ is H, halo, or $C_{1-6}$ alkyl;
$R^6$ is halo, CN, or $C_{1-6}$ alkyl;
each $R^b$ is independently selected from $C_{1-4}$ alkyl, OH, $OR^c$, CN, and $NR^cR^c$, and $C(O)NR^cR^c$; and
each $R^c$ is independently H or $C_{1-6}$ alkyl;
or any two $R^c$ substituents together with the nitrogen atom to which they are attached form a 4-, 5-, 6-, or 7-membered heterocycloalkyl group optionally substituted with 1, 2, or 3 independently selected $R^h$ substituents.

In some embodiments:

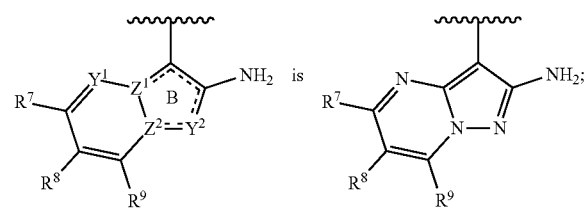

$R^1$ is H or $C_{1-6}$ alkyl;
$R^2$ is $OR^{13}$, $C_{6-10}$ aryl, or 5-10 membered heteroaryl; wherein said $C_{6-10}$ aryl or 5-10 membered heteroaryl of $R^2$ are each optionally substituted with 1, 2, 3, 4, or 5 independently selected $R^j$ substituents;
each $R^j$ is independently selected from halo, CN, $C_{1-4}$ alkyl, $C_{1-4}$ haloalkyl, $C_{2-4}$ alkenyl, $C_{2-4}$ alkynyl, $NHOR^k$, $OR^k$, $C(O)R^k$, $C(O)NR^kR^k$, $C(O)OR^k$, $OC(O)R^k$, $OC(O)NR^kR^k$, $NHR^k$, $NR^kR^k$, $NR^kC(O)R^k$, $S(O)_2R^k$, $NR^kS(O)_2R^k$, and $S(O)_2NR^kR^k$;
$R^{3a}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-GA alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-; wherein the $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl- of $R^{3a}$ are each optionally substituted by 1, 2, 3, or 4 independently selected $R^b$ substituents;

$R^{4a}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-; wherein the $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl- of $R^{4a}$ are each optionally substituted by 1, 2, 3, or 4 independently selected $R^b$ substituents;

$R^3$ is H or $C_{1-6}$ alkyl;

$R^4$ is H or $C_{1-6}$ alkyl;

$R^5$ is H, halo, $C_{1-6}$ alkyl, or $C_{1-6}$ haloalkyl;

$R^{5a}$ is H or $C_{1-6}$ alkyl;

$R^6$ is H, halo, CN, $C_{1-6}$ alkyl, or $C_{1-6}$ haloalkyl; and $R^7$ is H, halo, CN, $C_{1-6}$ alkyl, or $C_{1-6}$ haloalkyl.

In some embodiments:

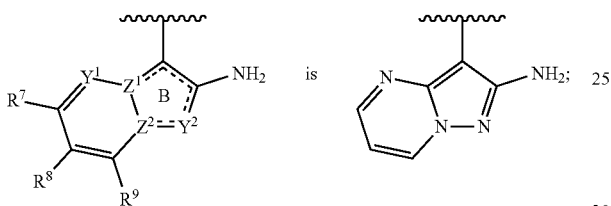

$R^1$ is $C_{1-6}$ alkyl;

$R^2$ is $C_{1-6}$ alkoxy, phenyl, or monocyclic 5-6 membered heteroaryl; wherein said $C_{6-10}$ aryl or monocyclic 5-6 membered heteroaryl of $R^2$ are each optionally substituted with 1, 2, or 3 independently selected $R^j$ substituents;

each $R^j$ is independently selected from halo, CN, $C_{1-4}$ alkyl, $C_{1-4}$ haloalkyl, $C_{2-4}$ alkenyl, $C_{2-4}$ alkynyl, $NHOR^k$, $OR^k$, $C(O)R^k$, $C(O)NR^kR^k$, $C(O)OR^k$, $OC(O)R^k$, $OC(O)NR^kR^k$, $NHR^k$, $NR^kR^k$, $NR^kC(O)R^k$, $S(O)_2R^k$, $NR^kS(O)_2R^k$, and $S(O)_2NR^kR^k$;

each $R^k$ is independently selected from H, $C_{1-4}$ alkyl, and $C_{1-4}$ haloalkyl;

$R^{3a}$ is H, $C_{1-6}$ alkyl, $C_{2-6}$ alkynyl, $C_{3-7}$ cycloalkyl, phenyl-$C_{1-4}$ alkyl-, (5-6 membered heteroaryl)-$C_{1-4}$ alkyl, and (4-6 membered heterocycloalkyl)-$C_{1-4}$ alkyl; wherein said $C_{1-6}$ alkyl, $C_{2-6}$ alkynyl, $C_{3-7}$ cycloalkyl, phenyl-$C_{1-4}$ alkyl-, (5-6 membered heteroaryl)-$C_{1-4}$ alkyl, and (4-6 membered heterocycloalkyl)-$C_{1-4}$ alkyl of $R^{3a}$ are each optionally substituted by 1, 2, 3, or 4 independently selected $R^b$ substituents;

each $R^b$ is independently selected from halo, $C_{1-4}$ alkyl, $C_{1-4}$ haloalkyl, CN, OH, $NH_2$, $NHOR^c$, $OR^c$, $C(O)R^c$, $C(O)NR^cR^c$, $C(O)OR^c$, $OC(O)R^c$, $OC(O)NR^cR^c$, $NHR^c$, $NR^cR^c$, $NR^c C(O)R^c$, $NR^c C(O)OR^c$, $NR^cS(O)R^c$, $NR^cS(O)_2R^c$, $S(O)_2 12C$ and $S(O)_2NR^cR^c$;

$R^{4a}$ is selected from H, $C_{1-6}$ alkyl, $C_{2-6}$ alkynyl, $C_{3-7}$ cycloalkyl, phenyl-$C_{1-4}$ alkyl-, and (5-6 membered heteroaryl)-$C_{1-4}$ alkyl-; wherein said $C_{1-6}$ alkyl, $C_{1-6}$ alkynyl, $C_{3-7}$ cycloalkyl, phenyl-$C_{1-4}$ alkyl-, and (5-6 membered heteroaryl)-$C_{1-4}$ alkyl- of $R^{4a}$ are each optionally substituted by 1, 2, 3, or 4 independently selected $R^b$ substituents;

$R^3$ is H or $C_{1-6}$ alkyl;

$R^4$ is H or $C_{1-6}$ alkyl;

$R^{5a}$ is H or $C_{1-6}$ alkyl;

$R^5$ is H, halo, or $C_{1-6}$ alkyl;

$R^6$ is halo, CN, or $C_{1-6}$ alkyl; and each $R^c$ is independently H or $C_{1-6}$ alkyl;

or any two $R^c$ substituents together with the nitrogen atom to which they are attached form a 4-, 5-, 6-, or 7-membered heterocycloalkyl group optionally substituted with 1, 2, or 3 independently selected $R^h$ substituents.

In some embodiments:

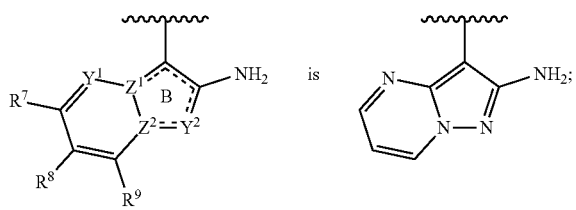

$R^1$ is $C_{1-6}$ alkyl;

$R^2$ is $C_{1-6}$ alkoxy or phenyl, wherein said phenyl of $R^2$ is optionally substituted with 1, 2, or 3 independently selected R substituents;

each $R^j$ is independently selected from halo, CN, $C_{1-4}$ alkyl, $C_{1-4}$ haloalkyl, $C_{1-4}$ alkoxy, $C_{1-4}$ haloalkoxy, amino, $C_{1-4}$ alkylamino, and di($C_{1-4}$alkyl)amino;

$R^{3a}$ is H, $C_{1-6}$ alkyl, $C_{2-6}$ alkynyl, $C_{3-7}$ cycloalkyl, phenyl-$C_{1-4}$ alkyl-, (5-6 membered heteroaryl)-$C_{1-4}$ alkyl, and (4-6 membered heterocycloalkyl)-$C_{1-4}$ alkyl; wherein said $C_{1-6}$ alkyl, $C_{2-6}$ alkynyl, $C_{3-7}$ cycloalkyl, phenyl-$C_{1-4}$ alkyl-, (5-6 membered heteroaryl)-$C_{1-4}$ alkyl, and (4-6 membered heterocycloalkyl)-$C_{1-4}$ alkyl of $R^{3a}$ are each optionally substituted by 1, 2, 3, or 4 independently selected $R^b$ substituents;

$R^{4a}$ is selected from H, $C_{1-6}$ alkyl, $C_{2-6}$ alkynyl, $C_{3-7}$ cycloalkyl, phenyl-$C_{1-4}$ alkyl-, and (5-6 membered heteroaryl)-$C_{1-4}$ alkyl-; wherein said $C_{1-6}$ alkyl and (5-6 membered heteroaryl)-$C_{1-4}$ alkyl- of $R^{4a}$ are each optionally substituted by 1, 2, 3, or 4 independently selected $R^b$ substituents;

$R^3$ is H or $C_{1-6}$ alkyl;

$R^4$ is H or $C_{1-6}$ alkyl;

$R^{5a}$ is H or $C_{1-6}$ alkyl;

$R^5$ is H, halo, or $C_{1-6}$ alkyl;

$R^6$ is halo, CN, or $C_{1-6}$ alkyl;

each $R^b$ is independently selected from $C_{1-4}$ alkyl, OH, $OR^c$, CN, and $NR^cR^c$, and $C(O)NR^cR^c$; and each $R^c$ is independently H or $C_{1-6}$ alkyl;

or any two $R^c$ substituents together with the nitrogen atom to which they are attached form a 4-, 5-, 6-, or 7-membered heterocycloalkyl group optionally substituted with 1, 2, or 3 independently selected $R^h$ substituents.

In some embodiments:

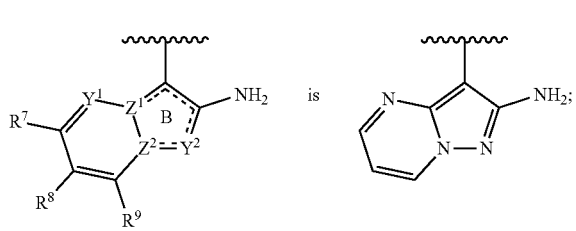

$R^1$ is $C_{1-6}$ alkyl;

$R^2$ is $C_{1-6}$ alkoxy or phenyl, wherein said phenyl of $R^2$ is optionally substituted with 1, 2, or 3 independently selected R substituents;

each $R^j$ is independently halo;

$R^{3a}$ is H, $C_{1-6}$ alkyl, $C_{2-6}$ alkynyl, $C_{3-7}$ cycloalkyl, phenyl-$C_{1-4}$ alkyl-, (5-6 membered heteroaryl)-$C_{1-4}$ alkyl, and (4-6 membered heterocycloalkyl)-$C_{1-4}$ alkyl; wherein said $C_{1-6}$ alkyl, $C_{2-6}$ alkynyl, $C_{3-7}$ cycloalkyl, phenyl-$C_{1-4}$ alkyl-, (5-6 membered heteroaryl)-$C_{1-4}$ alkyl, and (4-6 membered heterocycloalkyl)-$C_{1-4}$ alkyl of $R^{3a}$ are each optionally substituted by 1, 2, 3, or 4 independently selected $R^b$ substituents;

$R^{4a}$ is selected from H, $C_{1-6}$ alkyl, $C_{2-6}$ alkynyl, $C_{3-7}$ cycloalkyl, phenyl-$C_{1-4}$ alkyl-, and (5-6 membered heteroaryl)-$C_{1-4}$ alkyl-; wherein said $C_{1-6}$ alkyl and (5-6 membered heteroaryl)-$C_{1-4}$ alkyl- of $R^{4a}$ are each optionally substituted by 1, 2, 3, or 4 independently selected $R^b$ substituents;

$R^3$ is H or $C_{1-6}$ alkyl;

$R^4$ is H or $C_{1-6}$ alkyl;

$R^{5a}$ is H or $C_{1-6}$ alkyl;

$R^5$ is H, halo, or $C_{1-6}$ alkyl;

$R^6$ is halo, CN, or $C_{1-6}$ alkyl;

each $R^b$ is independently selected from $C_{1-4}$ alkyl, OH, $OR^c$, CN, and $NR^cR^c$, and $C(O)NR^cR^c$; and each $R^c$ is independently H or $C_{1-6}$ alkyl;

or any two $R^c$ substituents together with the nitrogen atom to which they are attached form a 4-, 5-, 6-, or 7-membered heterocycloalkyl group optionally substituted with 1, 2, or 3 independently selected $R^h$ substituents.

In some embodiments:

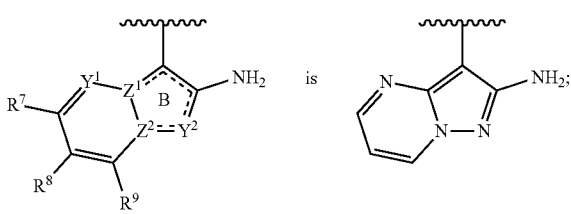

is $R^1$ is methyl;

$R^2$ is ethoxy, phenyl, or 3-fluorophenyl;

each $R^j$ is independently halo;

$R^{3a}$ is H, methyl, isopropyl, isobutyl, —CH$_2$C≡CCH$_3$, —CH$_2$CH$_2$OH, —CH$_2$CH$_2$OCH$_3$, —CH$_2$CN, —CH$_2$CH$_2$NH$_2$, —CH$_2$C(O)NH$_2$, benzyl, cyclobutyl, —CH$_2$-(1-methyl-1H-pyrazol-3-yl), or —CH$_2$CH$_2$—(morpholin-4-yl);

$R^3$ is H or methyl;

$R^{4a}$ is H, methyl, ethyl, isopropyl, isobutyl, —CH$_2$C≡CCH$_3$, —CH$_2$CH$_2$OH, —CH$_2$CH$_2$OCH$_3$, —CH$_2$CN, —CH$_2$CH$_2$NH$_2$, cyclobutyl, benzyl, —CH$_2$C(O)NH$_2$, —CH$_2$-(1-methyl-1H-pyrazol-3-yl), or —CH$_2$C(O)-(morpholin-4-yl);

$R^5$ is H, bromo, or methyl; and $R^6$ is chloro, CN, or methyl.

In some embodiments, the compound is a compound of Formula X, XI, or XII:

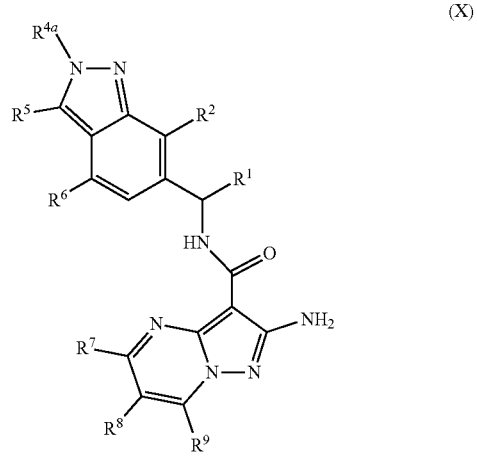

(X)

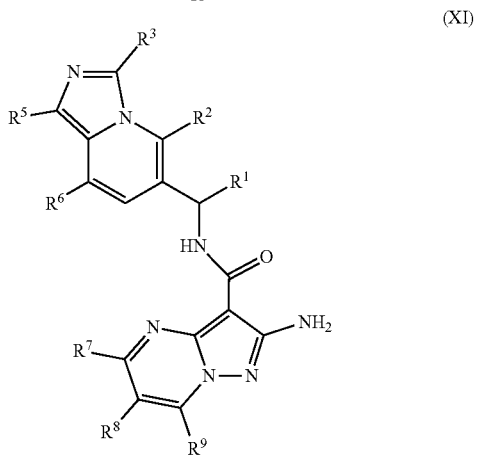

(XI)

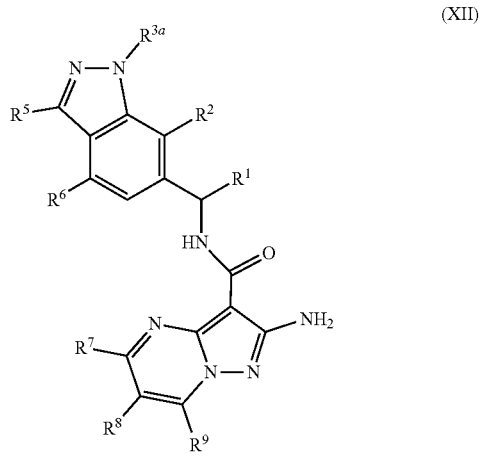

(XII)

or a pharmaceutically acceptable salt thereof, wherein:

$R^1$ is $C_{1-6}$ alkyl;

$R^2$ is $C_{1-6}$ alkoxy, phenyl, monocyclic 5-6 membered heterocycloalkyl, monocyclic 5-6 membered heteroaryl; wherein said $C_{6-10}$ aryl, monocyclic 5-6 membered heterocycloalkyl, and monocyclic 5-6 membered heteroaryl of $R^2$ are each optionally substituted with 1, 2, or 3 independently selected IV substituents;

each $R^j$ is independently selected from halo, CN, $C_{1-4}$ alkyl, $C_{1-4}$ haloalkyl, $C_{2-4}$ alkenyl, $C_{2-4}$ alkynyl, NHOR$^k$, OR$^k$, C(O)R$^k$, C(O)NR$^k$R$^k$, C(O)OR$^k$, OC(O)R$^k$, OC(O)NR$^k$R$^k$, NHR$^k$, NR$^k$R$^k$, NR$^k$C(O)R$^k$, S(O)$_2$R$^k$, NR$^k$S(O)$_2$R$^k$, and S(O)$_2$NR$^k$R$^k$;

each R$^k$ is independently selected from H, C$_{1-4}$ alkyl, and C$_{1-4}$ haloalkyl;

R$^3$ is H or C$^{1-6}$ alkyl;

R$^{3a}$ is H, C$_{1-6}$ alkyl, C$_{2-6}$ alkynyl, C$_{3-7}$ cycloalkyl, phenyl-C$_{1-4}$ alkyl-, (5-6 membered heteroaryl)-C$_{1-4}$ alkyl, and (4-6 membered heterocycloalkyl)-C$_{1-4}$ alkyl; wherein said C$_{1-6}$ alkyl, C$_{2-6}$ alkynyl, C$_{3-7}$ cycloalkyl, phenyl-C$_{1-4}$ alkyl-, (5-6 membered heteroaryl)-C$_{1-4}$ alkyl, and (4-6 membered heterocycloalkyl)-C$_{1-4}$ alkyl of R$^{3a}$ are each optionally substituted by 1, 2, 3, or 4 independently selected R$^b$ substituents;

each R$^b$ is independently selected from halo, C$_{1-4}$ alkyl, C$_{1-4}$ haloalkyl, CN, OH, NH$_2$, NHOR$^c$, OR$^c$, C(O)R$^c$, C(O)NR$^c$R$^c$, C(O)OR$^c$, OC(O)R$^c$, OC(O)NR$^c$R$^c$, NHR$^c$, NR$^c$R$^c$, NR$^c$C(O)R$^c$, NR$^c$(O)OR$^c$, NR$^c$S(O)R$^c$, NR$^c$S(O)$_2$R$^c$, S(O)$_2$R$^c$ and S(O)$_2$NR$^c$R$^c$;

R$^{4a}$ is selected from H, C$_{1-6}$ alkyl, C$_{2-6}$ alkynyl, C$_{3-7}$ cycloalkyl, phenyl-C$_{1-4}$ alkyl-, and (5-6 membered heteroaryl)-C$_{1-4}$ alkyl-; wherein said C$_{1-6}$ alkyl, C$_{1-6}$ alkynyl, C$_{3-7}$ cycloalkyl, phenyl-C$_{1-4}$ alkyl-, and (5-6 membered heteroaryl)-C$_{1-4}$ alkyl- of R$^{4a}$ are each optionally substituted by 1, 2, 3, or 4 independently selected R$^b$ substituents;

R$^3$ is H or C$_{1-6}$ alkyl;

R$^4$ is H or C$_{1-6}$ alkyl;

R$^{5a}$ is H or C$_{1-6}$ alkyl;

R$^5$ is H, halo, or C$_{1-6}$ alkyl;

R$^6$ is halo, CN, or C$_{1-6}$ alkyl;

R$^7$, R$^8$, R$^9$ are each H; and each R$^c$ is independently H or C$_{1-6}$ alkyl;

or any two R$^c$ substituents together with the nitrogen atom to which they are attached form a 4-, 5-, 6-, or 7-membered heterocycloalkyl group optionally substituted with 1, 2, or 3 independently selected R$^h$ substituents.

In some embodiments, the compound is a compound of Formula X, XI, or XII:

(X)

(XI)

(XII)

or a pharmaceutically acceptable salt thereof, wherein:

R$^1$ is C$_{1-6}$ alkyl;

R$^2$ is C$_{1-6}$ alkoxy, phenyl, 5-6 membered monocyclic heterocycloalkyl, or monocyclic 5-6 membered heteroaryl; wherein said C$_{6-10}$ aryl or monocyclic 5-6 membered heteroaryl of R$^2$ are each optionally substituted with 1, 2, or 3 independently selected R$^j$ substituents;

each R$^j$ is independently selected from halo, CN, C$_{1-4}$ alkyl, C$_{1-4}$ haloalkyl, C$_{2-4}$ alkenyl, C$_{2-4}$ alkynyl, NHOR$^k$, OR$^k$, C(O)R$^k$, C(O)NR$^k$R$^k$, C(O)OR$^k$, OC(O)R$^k$, OC(O)NR$^k$R$^k$, NHR$^k$, NR$^k$R$^k$, NR$^k$C(O)R$^k$, S(O)$_2$R$^k$, NR$^k$S(O)$_2$R$^k$, and S(O)$_2$NR$^k$R$^k$;

each R$^k$ is independently selected from H, C$_{1-4}$ alkyl, and C$_{1-4}$ haloalkyl;

R$^3$ is H or C$^{1-6}$ alkyl;

R$^{3a}$ is H, C$_{1-6}$ alkyl, C$_{2-6}$ alkynyl, C$_{3-7}$ cycloalkyl, phenyl-C$_{1-4}$ alkyl-, (5-6 membered heteroaryl)-C$_{1-4}$ alkyl, and (4-6 membered heterocycloalkyl)-C$_{1-4}$ alkyl; wherein said C$_{1-6}$ alkyl, C$_{2-6}$ alkynyl, C$_{3-7}$ cycloalkyl, phenyl-C$_{1-4}$ alkyl-, (5-6 membered heteroaryl)-C$_{1-4}$ alkyl, and (4-6 membered heterocycloalkyl)-C$_{1-4}$ alkyl of R$^{3a}$ are each optionally substituted by 1, 2, 3, or 4 independently selected R$^b$ substituents;

each R$^b$ is independently selected from halo, C$_{1-4}$ alkyl, C$_{1-4}$ haloalkyl, CN, OH, NH$_2$, NHOR$^c$, OR$^c$, C(O)R$^c$, C(O)NR$^c$R$^c$, C(O)OR$^c$, OC(O)R$^c$, OC(O)NR$^c$R$^c$, NHR$^c$, NR$^c$R$^c$, NR$^c$ C(O)R$^c$, NR$^c$ C(O)OR$^c$, NR$^c$S(O)R$^c$, NR$^c$S(O)$_2$R$^c$, S(O)$_2$R$^c$ and S(O)$_2$NR$^c$R$^c$;

$R^{4a}$ is selected from H, $C_{1-6}$ alkyl, $C_{2-6}$ alkynyl, $C_{3-7}$ cycloalkyl, phenyl-$C_{1-4}$ alkyl-, and (5-6 membered heteroaryl)-$C_{1-4}$ alkyl-; wherein said $C_{1-6}$ alkyl, $C_{1-6}$ alkynyl, $C_{3-7}$ cycloalkyl, phenyl-$C_{1-4}$ alkyl-, and (5-6 membered heteroaryl)-$C_{1-4}$ alkyl- of $R^{4a}$ are each optionally substituted by 1, 2, 3, or 4 independently selected $R^h$ substituents;

$R^3$ is H or $C_{1-6}$ alkyl;

$R^4$ is H or $C_{1-6}$ alkyl;

$R^{5a}$ is H or $C_{1-6}$ alkyl;

$R^5$ is H, halo, or $C_{1-6}$ alkyl;

$R^6$ is halo, CN, or $C_{1-6}$ alkyl;

$R^7$, $R^8$, $R^9$ are each H; and each $R^c$ is independently H or $C_{1-6}$ alkyl;

or any two $R^c$ substituents together with the nitrogen atom to which they are attached form a 4-, 5-, 6-, or 7-membered heterocycloalkyl group optionally substituted with 1, 2, or 3 independently selected $R^h$ substituents.

In some embodiments, the compound is a compound of Formula X, XI, or XII:

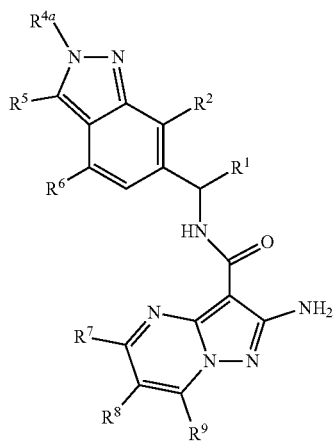

(X)

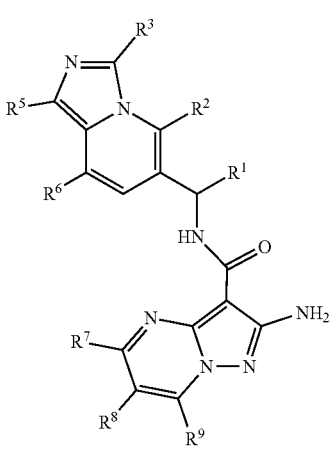

(XI)

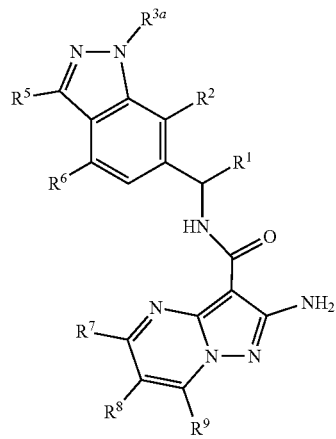

(XII)

or a pharmaceutically acceptable salt thereof, wherein:

$R^1$ is $C_{1-6}$ alkyl;

$R^2$ is $C_{1-6}$ alkoxy, phenyl, or monocyclic 5-6 membered heteroaryl; wherein said $C_{6-10}$ aryl or monocyclic 5-6 membered heteroaryl of $R^2$ are each optionally substituted with 1, 2, or 3 independently selected $R^j$ substituents;

each $R^j$ is independently selected from halo, CN, $C_{1-4}$ alkyl, $C_{1-4}$ haloalkyl, $C_{2-4}$ alkenyl, $C_{2-4}$ alkynyl, $NHOR^k$, $OR^k$, $C(O)R^k$, $C(O)NR^kR^k$, $C(O)OR^k$, $OC(O)R^k$, $OC(O)NR^kR^k$, $NHR^k$, $NR^kR^k$, $NR^kC(O)R^k$, $S(O)_2R^k$, $NR^kS(O)_2R^k$, and $S(O)_2NR^kR^k$;

each $R^k$ is independently selected from H, $C_{1-4}$ alkyl, and $C_{1-4}$ haloalkyl;

$R^3$ is H or $C^{1-6}$ alkyl;

$R^{3a}$ is H, $C_{1-6}$ alkyl, $C_{2-6}$ alkynyl, $C_{3-7}$ cycloalkyl, phenyl-$C_{1-4}$ alkyl-, (5-6 membered heteroaryl)-$C_{1-4}$ alkyl, and (4-6 membered heterocycloalkyl)-$C_{1-4}$ alkyl; wherein said $C_{1-6}$ alkyl, $C_{2-6}$ alkynyl, $C_{3-7}$ cycloalkyl, phenyl-$C_{1-4}$ alkyl-, (5-6 membered heteroaryl)-$C_{1-4}$ alkyl, and (4-6 membered heterocycloalkyl)-$C_{1-4}$ alkyl of $R^{3a}$ are each optionally substituted by 1, 2, 3, or 4 independently selected $R^b$ substituents;

each $R^b$ is independently selected from halo, $C_{1-4}$ alkyl, $C_{1-4}$ haloalkyl, CN, OH, $NH_2$, $NHOR^c$, $OR^c$, $C(O)R^c$, $C(O)NR^cR^c$, $C(O)OR^c$, $OC(O)R^c$, $OC(O)NR^cR^c$, $NHR^c$, $NR^cR^c$, $NR^cC(O)R^c$, $NR^cC(O)OR^c$, $NR^cS(O)R^c$, $NR^cS(O)_2R^c$, $S(O)_2R^c$ and $S(O)_2NR^cR^c$;

$R^{4a}$ is selected from H, $C_{1-6}$ alkyl, $C_{2-6}$ alkynyl, $C_{3-7}$ cycloalkyl, phenyl-$C_{1-4}$ alkyl-, and (5-6 membered heteroaryl)-$C_{1-4}$ alkyl-; wherein said $C_{1-6}$ alkyl, $C_{1-6}$ alkynyl, $C_{3-7}$ cycloalkyl, phenyl-$C_{1-4}$ alkyl-, and (5-6 membered heteroaryl)-$C_{1-4}$ alkyl- of $R^{4a}$ are each optionally substituted by 1, 2, 3, or 4 independently selected $R^b$ substituents;

$R^3$ is H or $C_{1-6}$ alkyl;

$R^4$ is H or $C_{1-6}$ alkyl;

$R^{5a}$ is H or $C_{1-6}$ alkyl;

$R^5$ is H, halo, or $C_{1-6}$ alkyl;

$R^6$ is halo, CN, or $C_{1-6}$ alkyl;

$R^7$, $R^8$, $R^9$ are each H; and each $R^c$ is independently H or $C_{1-6}$ alkyl;

or any two W substituents together with the nitrogen atom to which they are attached form a 4-, 5-, 6-, or 7-membered heterocycloalkyl group optionally substituted with 1, 2, or 3 independently selected $R^h$ substituents.

In some embodiments, the compound is a compound of Formula X, XI, or XII:

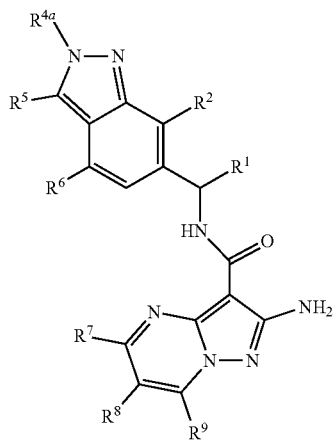

(X)

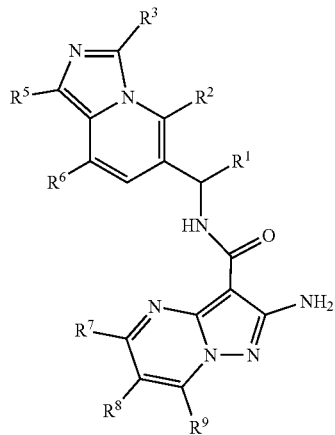

(XI)

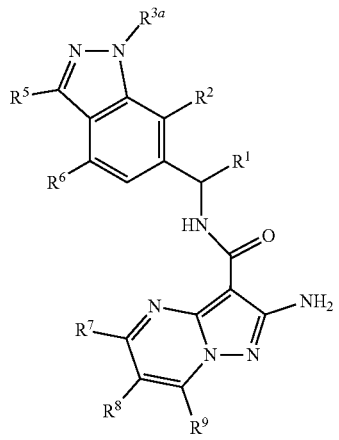

(XII)

or a pharmaceutically acceptable salt thereof, wherein:

$R^1$ is $C_{1-6}$ alkyl;

$R^2$ is $C_{1-6}$ alkoxy or phenyl, wherein said phenyl of $R^2$ is optionally substituted with 1, 2, or 3 independently selected $R^j$ substituents;

each $R^j$ is independently selected from halo, CN, $C_{1-4}$ alkyl, $C_{1-4}$ haloalkyl, $C_{1-4}$ alkoxy, $C_{1-4}$ haloalkoxy, amino, $C_{1-4}$ alkylamino, and di($C_{1-4}$alkyl)amino;

$R^3$ is H or $C_{1-6}$ alkyl;

$R^{3a}$ is H, $C_{1-6}$ alkyl, $C_{2-6}$ alkynyl, $C_{3-7}$ cycloalkyl, phenyl-$C_{1-4}$ alkyl-, (5-6 membered heteroaryl)-$C_{1-4}$ alkyl, and (4-6 membered heterocycloalkyl)-$C_{1-4}$ alkyl; wherein said $C_{1-6}$ alkyl, $C_{2-6}$ alkynyl, $C_{3-7}$ cycloalkyl, phenyl-$C_{1-4}$ alkyl-, (5-6 membered heteroaryl)-$C_{1-4}$ alkyl, and (4-6 membered heterocycloalkyl)-$C_{1-4}$ alkyl of $R^{3a}$ are each optionally substituted by 1, 2, 3, or 4 independently selected $R^b$ substituents;

$R^{4a}$ is selected from H, $C_{1-6}$ alkyl, $C_{2-6}$ alkynyl, $C_{3-7}$ cycloalkyl, phenyl-$C_{1-4}$ alkyl-, and (5-6 membered heteroaryl)-$C_{1-4}$ alkyl-; wherein said $C_{1-6}$ alkyl and (5-6 membered heteroaryl)-$C_{1-4}$ alkyl- of $R^{4a}$ are each optionally substituted by 1, 2, 3, or 4 independently selected $R^b$ substituents;

$R^3$ is H or $C_{1-6}$ alkyl;

$R^4$ is H or $C_{1-6}$ alkyl;

$R^{5a}$ is H or $C_{1-6}$ alkyl;

$R^5$ is H, halo, or $C_{1-6}$ alkyl;

$R^6$ is halo, CN, or $C_{1-6}$ alkyl;

$R^7$, $R^8$, $R^9$ are each H;

each $R^b$ is independently selected from $C_{1-4}$ alkyl, OH, $OR^c$, CN, and $NR^cR^c$, and $C(O)NR^cR^c$; and each $R^c$ is independently H or $C_{1-6}$ alkyl;

or any two $R^c$ substituents together with the nitrogen atom to which they are attached form a 4-, 5-, 6-, or 7-membered heterocycloalkyl group optionally substituted with 1, 2, or 3 independently selected $R^h$ substituents.

In some embodiments, the compound is a compound of Formula X, XI, or XII:

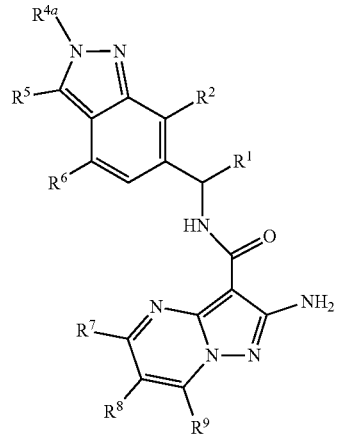

(X)

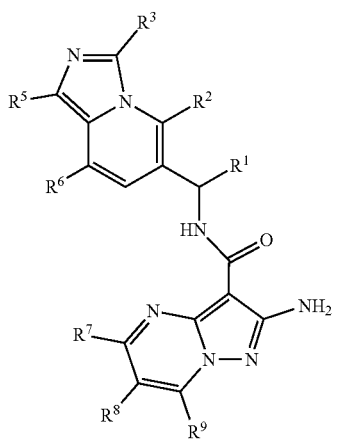

(XI)

-continued

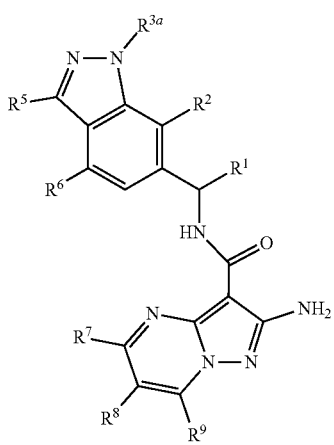

(XII)

or a pharmaceutically acceptable salt thereof, wherein:

$R^1$ is $C_{1-6}$ alkyl;

$R^2$ is $C_{1-6}$ alkoxy or phenyl, wherein said phenyl of $R^2$ is optionally substituted with 1, 2, or 3 independently selected IV substituents;

each $R^j$ is independently halo;

$R^3$ is H or $C_{1-6}$ alkyl;

$R^{3a}$ is H, $C_{1-6}$ alkyl, $C_{2-6}$ alkynyl, $C_{3-7}$ cycloalkyl, phenyl-$C_{1-4}$ alkyl-, (5-6 membered heteroaryl)-$C_{1-4}$ alkyl, and (4-6 membered heterocycloalkyl)-$C_{1-4}$ alkyl; wherein said $C_{1-6}$ alkyl, $C_{2-6}$ alkynyl, $C_{3-7}$ cycloalkyl, phenyl-$C_{1-4}$ alkyl-, (5-6 membered heteroaryl)-$C_{1-4}$ alkyl, and (4-6 membered heterocycloalkyl)-$C_{1-4}$ alkyl of $R^{3a}$ are each optionally substituted by 1, 2, 3, or 4 independently selected $R^b$ substituents;

$R^{4a}$ is selected from H, $C_{1-6}$ alkyl, $C_{2-6}$ alkynyl, $C_{3-7}$ cycloalkyl, phenyl-$C_{1-4}$ alkyl-, and (5-6 membered heteroaryl)-$C_{1-4}$ alkyl-; wherein said $C_{1-6}$ alkyl and (5-6 membered heteroaryl)-$C_{1-4}$ alkyl- of $R^{4a}$ are each optionally substituted by 1, 2, 3, or 4 independently selected $R^b$ substituents;

$R^3$ is H or $C_{1-6}$ alkyl;

$R^4$ is H or $C_{1-6}$ alkyl;

$R^{5a}$ is H or $C_{1-6}$ alkyl;

$R^5$ is H, halo, or $C_{1-6}$ alkyl;

$R^6$ is halo, CN, or $C_{1-6}$ alkyl;

$R^7$, $R^8$, $R^9$ are each H;

each $R^b$ is independently selected from $C_{1-4}$ alkyl, OH, $OR^c$, CN, and $NR^cR^c$, and $C(O)NR^cR^c$; and each $R^c$ is independently H or $C_{1-6}$ alkyl;

or any two $R^c$ substituents together with the nitrogen atom to which they are attached form a 4-, 5-, 6-, or 7-membered heterocycloalkyl group optionally substituted with 1, 2, or 3 independently selected $R^h$ substituents.

In some embodiments, the compound is a compound of Formula X, XI, or XII:

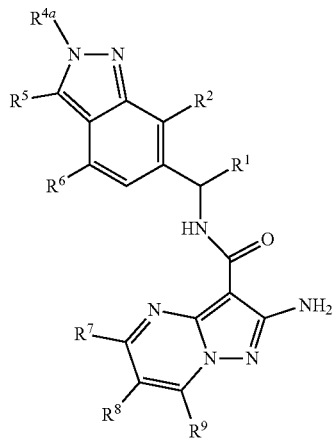

(X)

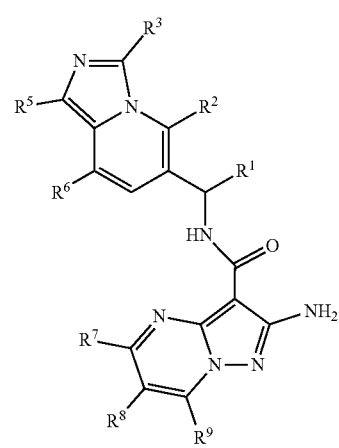

(XI)

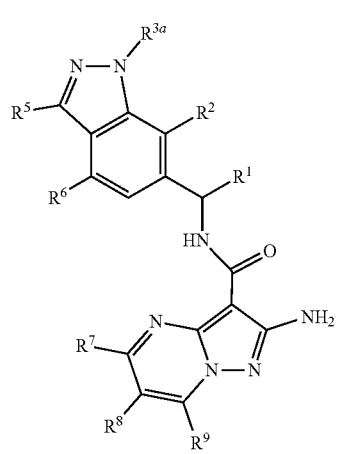

(XII)

or a pharmaceutically acceptable salt thereof, wherein:

$R^1$ is methyl;

$R^2$ is ethoxy, phenyl, 3-fluorophenyl, or 2-methyl-1,1-dioxidothiomorpholino; each $R^j$ is independently halo;

$R^3$ is H or methyl;

$R^{3a}$ is H, methyl, isopropyl, isobutyl, —$CH_2C\equiv CCH_3$, —$CH_2CH_2OH$, —$CH_2CH_2OCH_3$, —$CH_2CN$, —$CH_2CH_2NH_2$, —$CH_2C(O)NH_2$, benzyl, cyclobutyl, —$CH_2$-(1-methyl-1H-pyrazol-3-yl), or —$CH_2CH_2$-(morpholin-4-yl);

R$^{4a}$ is H, methyl, ethyl, isopropyl, isobutyl, —CH$_2$C≡CH$_3$, —CH$_2$CH$_2$OH, —CH$_2$CH$_2$OCH$_3$, —CH$_2$CN, —CH$_2$CH$_2$NH$_2$, cyclobutyl, benzyl, —CH$_2$C(O)NH$_2$, —CH$_2$-(1-methyl-1H-pyrazol-3-yl), or —CH$_2$C(O)-(morpholin-4-yl);

R$^5$ is H, bromo, or methyl;

R$^6$ is chloro, CN, or methyl; and

R$^7$, R$^8$, and R$^9$ are each H.

In some embodiments, the compound is a compound of Formula X, XI, or XII:

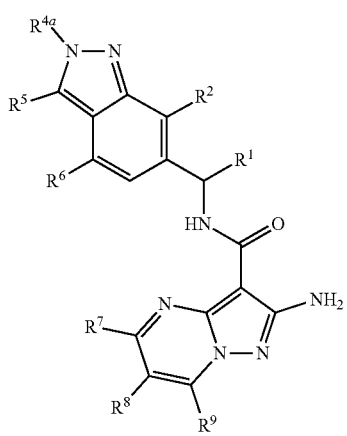

(X)

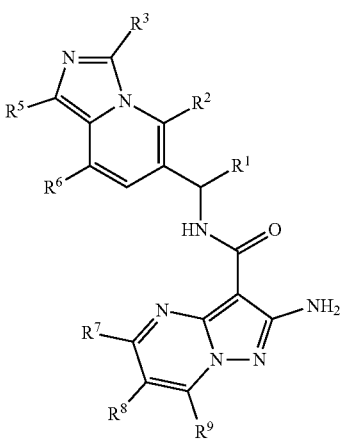

(XI)

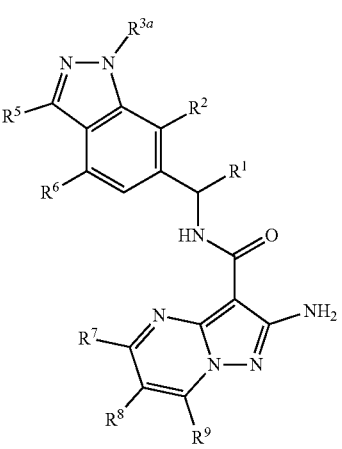

(XII)

or a pharmaceutically acceptable salt thereof, wherein:

R$^1$ is methyl;

R$^2$ is ethoxy, phenyl, or 3-fluorophenyl;

each R$^j$ is independently halo;

R$^3$ is H or methyl;

R$^{3a}$ is H, methyl, isopropyl, isobutyl, —CH$_2$C≡CCH$_3$, —CH$_2$CH$_2$OH, —CH$_2$CH$_2$OCH$_3$, —CH$_2$CN, —CH$_2$CH$_2$NH$_2$, —CH$_2$C(O)NH$_2$, benzyl, cyclobutyl, —CH$_2$-(1-methyl-1H-pyrazol-3-yl), or —CH$_2$CH$_2$-(morpholin-4-yl);

R$^{4a}$ is H, methyl, ethyl, isopropyl, isobutyl, —CH$_2$C≡CCH$_3$, —CH$_2$CH$_2$OH, —CH$_2$CH$_2$OCH$_3$, —CH$_2$CN, —CH$_2$CH$_2$NH$_2$, cyclobutyl, benzyl, —CH$_2$C(O)NH$_2$, —CH$_2$-(1-methyl-1H-pyrazol-3-yl), or —CH$_2$C(O)-(morpholin-4-yl);

R$^5$ is H, bromo, or methyl;

R$^6$ is chloro, CN, or methyl; and

R$^7$, R$^8$, and R$^9$ are each H.

In some embodiments, the compound is a compound of Formula (II):

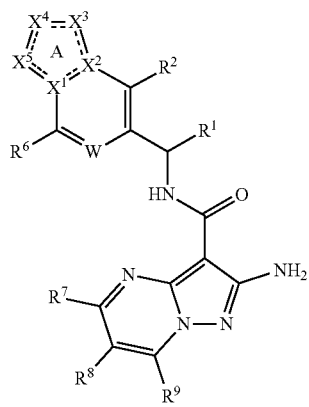

(II)

or a pharmaceutically acceptable salt thereof.

In some embodiments, the compound is a compound of Formula (III):

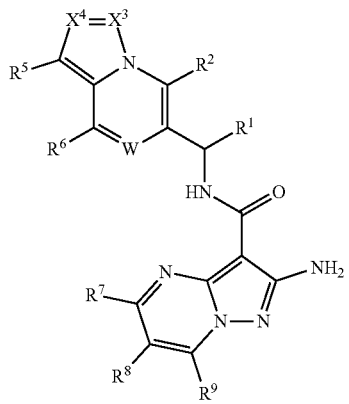

(III)

or a pharmaceutically acceptable salt thereof.

In some embodiments, the compound is a compound of Formula (IV):

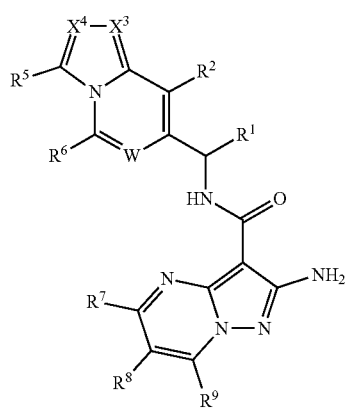

(IV)

or a pharmaceutically acceptable salt or stereoisomer thereof.

In some embodiments, the compound is a compound of Formula (V):

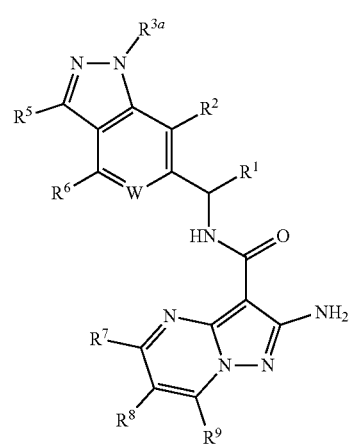

(V)

or a pharmaceutically acceptable salt thereof.

In some embodiments, the compound is a compound of Formula (VI):

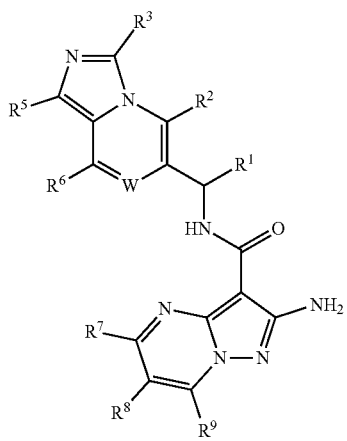

(VI)

or a pharmaceutically acceptable salt thereof.

In some embodiments, the compound is a compound of Formula (VII):

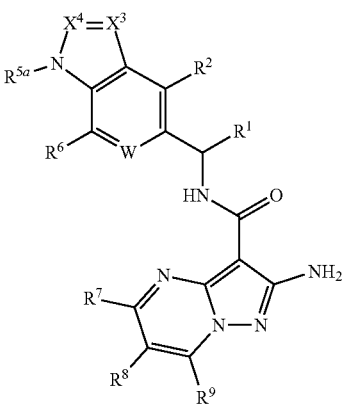

(VII)

or a pharmaceutically acceptable salt thereof.

In some embodiments, the compound is a compound of Formula (VIII):

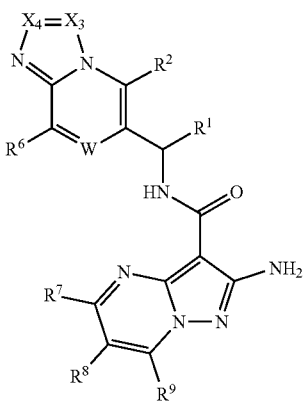

(VIII)

or a pharmaceutically acceptable salt thereof.

In some embodiments, the compound is a compound of Formula (IX):

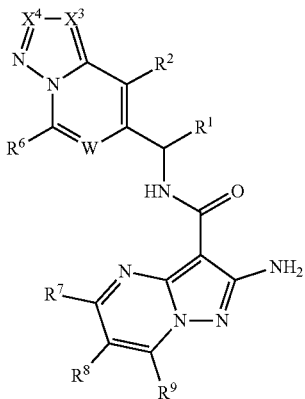

(IX)

or a pharmaceutically acceptable salt thereof.

In some embodiments, the compound is a compound of Formula (X):

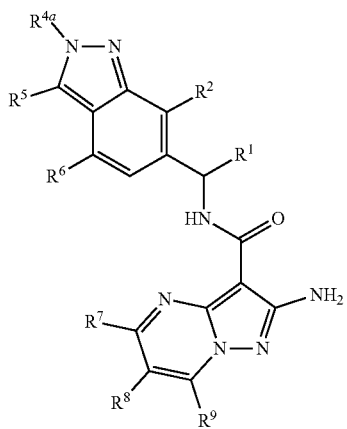

(X)

or a pharmaceutically acceptable salt thereof.

In some embodiments, the compound is a compound of Formula (X), or a pharmaceutically acceptable salt thereof, wherein $R^{4a}$ is H, $C_{1-6}$ alkyl, $C_{2-6}$ alkynyl, benzyl, cyanomethyl, 2-methoxyethyl, 2-hydroxyethyl, cyclobutyl, cyclopentyl, 2-amino-2-oxoethyl, N,N-dimethyl-2-amino-2-oxoethyl, (1-methyl-1H-pyrazol-3-yl)methyl, 2-morpholinoethyl, 2-morpholino-2-oxoethyl or 2-aminoethyl.

In some embodiments, the compound is a compound of Formula (X), or a pharmaceutically acceptable salt thereof, wherein $R^2$ is ethoxy or phenyl optionally substituted with halo.

In some embodiments, the compound is a compound of Formula (X), or a pharmaceutically acceptable salt thereof, wherein $R^1$ is methyl.

In some embodiments, the compound is a compound of Formula (X), or a pharmaceutically acceptable salt thereof, wherein $R^5$ is H, Br or methyl.

In some embodiments, the compound is a compound of Formula (X), or a pharmaceutically acceptable salt thereof, wherein $R^6$ is methyl, CN or Cl.

In some embodiments, the compound is a compound of Formula (X), or a pharmaceutically acceptable salt thereof, wherein $R^7$, $R^8$ and $R^9$ are each H.

In some embodiments, the compound is a compound of Formula (XI):

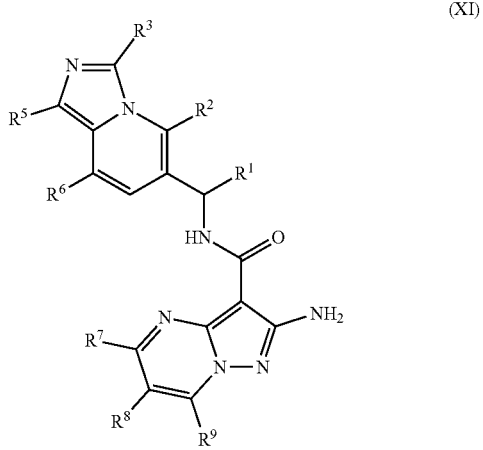

(XI)

or a pharmaceutically acceptable salt thereof.

In some embodiments, the compound is a compound of Formula (XI), or a pharmaceutically acceptable salt thereof, wherein $R^{4a}$ is H, $C_{1-6}$ alkyl, $C_{2-6}$ alkynyl, benzyl, cyanomethyl, 2-methoxyethyl, 2-hydroxyethyl, cyclobutyl, cyclopentyl, 2-amino-2-oxoethyl, N,N-dimethyl-2-amino-2-oxoethyl, (1-methyl-1H-pyrazol-3-yl)methyl, 2-morpholinoethyl, 2-morpholino-2-oxoethyl or 2-aminoethyl.

In some embodiments, the compound is a compound of Formula (XI), or a pharmaceutically acceptable salt thereof, wherein $R^2$ is ethoxy, 1,1-dioxidothiomorpholino optionally substituted with 1 or 2 independently selected $C_{1-4}$ alkyl substituents, or phenyl optionally substituted with halo.

In some embodiments, the compound is a compound of Formula (XI), or a pharmaceutically acceptable salt thereof, wherein $R^2$ is ethoxy or phenyl optionally substituted with halo.

In some embodiments, the compound is a compound of Formula (XI), or a pharmaceutically acceptable salt thereof, wherein $R^1$ is methyl.

In some embodiments, the compound is a compound of Formula (XI), or a pharmaceutically acceptable salt thereof, wherein $R^5$ is H, Br or methyl.

In some embodiments, the compound is a compound of Formula (XI), or a pharmaceutically acceptable salt thereof, wherein $R^6$ is methyl, CN or Cl.

In some embodiments, the compound is a compound of Formula (XI), or a pharmaceutically acceptable salt thereof, wherein $R^7$ is H, piperidin-1-yl, or pyridin-3-yl optionally substituted by $C_{1-4}$ alkyl or $C_{1-4}$ alkoxy, wherein the $C_{1-4}$ alkyl group is substituted by OH.

In some embodiments, the compound is a compound of Formula (XI), or a pharmaceutically acceptable salt thereof, wherein $R^7$, $R^8$ and $R^9$ are each H.

In some embodiments, the compound is a compound of Formula (XII):

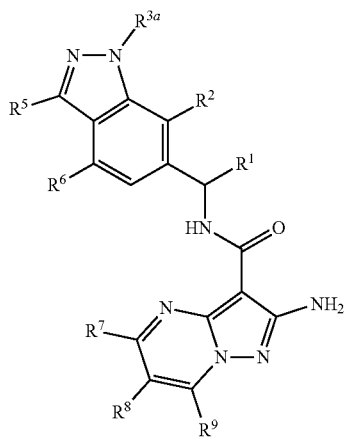

(XII)

or a pharmaceutically acceptable salt thereof.

In some embodiments, the compound is 2-amino-N—((S)-1-(8-chloro-5-((R)-2-methyl-1,1-dioxidothiomorpholino)imidazo[1,5-a]pyridin-6-yl)ethyl)pyrazolo[1,5-a]pyrimidine-3-carboxamide, or a pharmaceutically acceptable salt thereof.

In some embodiments, the compound is 2-amino-N—((S)-1-(8-chloro-5-((S)-2-methyl-1,1-dioxidothiomorpholino)imidazo[1,5-a]pyridin-6-yl)ethyl)pyrazolo[1,5-a]pyrimidine-3-carboxamide, or a pharmaceutically acceptable salt thereof.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. The substituents are independently selected, and substitution may be at any chemically accessible position. As used herein, the term "substituted" means that a hydrogen atom is removed and replaced by a substituent. A single divalent substituent, e.g., oxo, can replace two hydrogen atoms. It is to be understood that substitution at a given atom is limited by valency.

Throughout the definitions, the term "C$_{n-m}$" indicates a range which includes the endpoints, wherein n and m are integers and indicate the number of carbons. Examples include C$_{1-4}$, C$_{1-6}$, and the like.

As used herein, the term "C$_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, "C$_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "C$_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

As used herein, the term "C$_{n-m}$ alkylene", employed alone or in combination with other terms, refers to a divalent alkyl linking group having n to m carbons. Examples of alkylene groups include, but are not limited to, ethan-1,1-diyl, ethan-1,2-diyl, propan-1,1,-diyl, propan-1,3-diyl, propan-1,2-diyl, butan-1,4-diyl, butan-1,3-diyl, butan-1,2-diyl, 2-methyl-propan-1,3-diyl, and the like. In some embodiments, the alkylene moiety contains 2 to 6, 2 to 4, 2 to 3, 1 to 6, 1 to 4, or 1 to 2 carbon atoms.

As used herein, the term "C$_{n-m}$ alkoxy", employed alone or in combination with other terms, refers to a group of formula —O-alkyl, wherein the alkyl group has n to m carbons. Example alkoxy groups include, but are not limited to, methoxy, ethoxy, propoxy (e.g., n-propoxy and isopropoxy), butoxy (e.g., n-butoxy and tert-butoxy), and the like. In some embodiments, the alkyl group has 1 to 6, 1 to 4, or 1 to 3 carbon atoms.

As used herein, the term "C$_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms. Examples of alkylamino groups include, but are not limited to, N-methylamino, N-ethylamino, N-propylamino (e.g., N-(n-propyl)amino and N-isopropylamino), N-butylamino (e.g., N-(n-butyl)amino and N-(tert-butyl)amino), and the like.

As used herein, the term "amino" refers to a group of formula —NH$_2$.

As used herein, the term "aryl," employed alone or in combination with other terms, refers to an aromatic hydrocarbon group, which may be monocyclic or polycyclic (e.g., having 2, 3 or 4 fused rings). The term "C$_{n-m}$ aryl" refers to an aryl group having from n to m ring carbon atoms. Aryl groups include, e.g., phenyl, naphthyl, anthracenyl, phenanthrenyl, indanyl, indenyl, and the like. In some embodiments, aryl groups have from 6 to 10 carbon atoms. In some embodiments, the aryl group is phenyl or naphthyl.

As used herein, the term "di(C$_{n-m}$-alkyl)amino" refers to a group of formula —N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, "halo" refers to F, Cl, Br, or I. In some embodiments, a halo is F, Cl, or Br.

As used herein, "C$_{n-m}$ haloalkoxy" refers to a group of formula —O-haloalkyl having n to m carbon atoms. An example haloalkoxy group is OCF$_3$. In some embodiments, the haloalkoxy group is fluorinated only. In some embodiments, the alkyl group has 1 to 6, 1 to 4, or 1 to 3 carbon atoms.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms.

As used herein, "cycloalkyl" refers to non-aromatic cyclic hydrocarbons including cyclized alkyl and/or alkenyl groups. Cycloalkyl groups can include mono- or polycyclic (e.g., having 2, 3 or 4 fused rings) groups and spirocycles. Ring-forming carbon atoms of a cycloalkyl group can be optionally substituted by oxo or sulfido (e.g., C(O) or C(S)). Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring. Cycloalkyl groups can have 3, 4, 5, 6, 7, 8, 9, or 10 ring-forming carbons ($C_{3-10}$). In some embodiments, the cycloalkyl is a $C_{3-10}$ monocyclic or bicyclic cyclocalkyl. In some embodiments, the cycloalkyl is a $C_{3-7}$ monocyclic cyclocalkyl. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, and the like. In some embodiments, cycloalkyl is cyclopropyl, cyclobutyl, cyclopentyl, or cyclohexyl.

As used herein, "heteroaryl" refers to a monocyclic or polycyclic aromatic heterocycle having at least one heteroatom ring member selected from sulfur, oxygen, and nitrogen. In some embodiments, the heteroaryl ring has 1, 2, 3, or 4 heteroatom ring members independently selected from nitrogen, sulfur and oxygen. In some embodiments, any ring-forming N in a heteroaryl moiety can be an N-oxide. In some embodiments, the heteroaryl is a 5-10 membered monocyclic or bicyclic heteroaryl having 1, 2, 3 or 4 heteroatom ring members independently selected from nitrogen, sulfur and oxygen. In some embodiments, the heteroaryl is a 5-6 monocyclic heteroaryl having 1 or 2 heteroatom ring members independently selected from nitrogen, sulfur and oxygen. In some embodiments, the heteroaryl is a five-membered or six-membered heteroaryl ring. A five-membered heteroaryl ring is a heteroaryl with a ring having five ring atoms wherein one or more (e.g., 1, 2, or 3) ring atoms are independently selected from N, O, and S. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. A six-membered heteroaryl ring is a heteroaryl with a ring having six ring atoms wherein one or more (e.g., 1, 2, or 3) ring atoms are independently selected from N, O, and S. Exemplary six-membered ring heteroaryls are pyridyl, pyrazinyl, pyrimidinyl, triazinyl and pyridazinyl.

As used herein, "heterocycloalkyl" refers to non-aromatic monocyclic or polycyclic heterocycles having one or more ring-forming heteroatoms selected from O, N, or S. Included in heterocycloalkyl are monocyclic 4-, 5-, 6-, 7-, 8-, 9- or 10-membered heterocycloalkyl groups. Heterocycloalkyl groups can also include spirocycles. Example heterocycloalkyl groups include pyrrolidin-2-one, 1,3-isoxazolidin-2-one, pyranyl, tetrahydropuran, oxetanyl, azetidinyl, morpholino, thiomorpholino, 1,1-dioxidothiomorpholin-4-yl, 1,2,3,6-tetrahydropyridin-4-yl, 1,1-dioxido-1,4-thiazepan-4-yl, 1,1-dioxido-1,2,5-thiadiazepan-5-yl, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by oxo or sulfido (e.g., C(O), S(O), C(S), or S(O)$_2$, etc.). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the cycloalkyl ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl is a monocyclic 4-6 membered heterocycloalkyl having 1 or 2 heteroatoms independently selected from nitrogen, oxygen, or sulfur and having one or more oxidized ring members. In some embodiments, the heterocycloalkyl is a monocyclic or bicyclic 4-10 membered heterocycloalkyl having 1, 2, 3, or 4 heteroatoms independently selected from nitrogen, oxygen, or sulfur and having one or more oxidized ring members. In some embodiments, the heterocycloalkyl is a monocyclic or bicyclic 4-10 membered heterocycloalkyl having 1, 2, 3, or 4 heteroatoms independently selected from nitrogen, oxygen, or sulfur and having one or more ring members selected from C(O), S(O), C(S), S(O)$_2$, and S(NH)(O). In some embodiments, the heterocycloalkyl is a monocyclic or bicyclic 4-10 membered heterocycloalkyl having 1, 2, 3, or 4 heteroatoms independently selected from nitrogen, oxygen, or sulfur and having one or more ring members selected from S(O)$_2$ and S(NH)(O).

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

As used herein, the term "oxo" refers to an oxygen atom as a divalent substituent, forming a carbonyl group when attached to a carbon (e.g., C=O), or attached to a heteroatom forming a sulfoxide or sulfone group.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. In some embodiments, the compound has the (R)-configuration. In some embodiments, the compound has the (S)-configuration.

Formulas (I)-(XII) herein include stereoisomers of the compounds. In some embodiments, the carbon atom to which $R^1$ is attached is in the (R)-configuration. In some embodiments, the carbon atom to which $R^1$ is attached is in the (S)-configuration.

Resolution of racemic mixtures of compounds can be carried out by any of numerous methods known in the art. An example method includes fractional recrystallizaion using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms here a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

All compounds, and pharmaceutically acceptable salts thereof, can be found together with other substances such as water and solvents (e.g. hydrates and solvates) or can be isolated.

In some embodiments, preparation of compounds can involve the addition of acids or bases to affect, for example, catalysis of a desired reaction or formation of salt forms such as acid addition salts.

Example acids can be inorganic or organic acids and include, but are not limited to, strong and weak acids. Some example acids include hydrochloric acid, hydrobromic acid, sulfuric acid, phosphoric acid, p-toluenesulfonic acid, 4-nitrobenzoic acid, methanesulfonic acid, benzenesulfonic acid, trifluoroacetic acid, and nitric acid. Some weak acids include, but are not limited to acetic acid, propionic acid, butanoic acid, benzoic acid, tartaric acid, pentanoic acid, hexanoic acid, heptanoic acid, octanoic acid, nonanoic acid, and decanoic acid.

Example bases include lithium hydroxide, sodium hydroxide, potassium hydroxide, lithium carbonate, sodium carbonate, potassium carbonate, and sodium bicarbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include lithium, sodium, and potassium salts of methyl, ethyl, n-propyl, iso-propyl, n-butyl, tert-butyl, trimethylsilyl and cyclohexyl substituted amides.

In some embodiments, the compounds provided herein, or salts thereof, are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

Compounds of the invention can also include all isotopes of atoms occurring in the intermediates or final compounds. Isotopes include those atoms having the same atomic number but different mass numbers. For example, isotopes of hydrogen include tritium and deuterium. One or more constituent atoms of the compounds of the invention can be replaced or substituted with isotopes of the atoms in natural or non-natural abundance. In some embodiments, the compound includes at least one deuterium atom. For example, one or more hydrogen atoms in a compound of the present disclosure can be replaced or substituted by deuterium. In some embodiments, the compound includes two or more deuterium atoms. In some embodiments, the compound includes 1, 2, 3, 4, 5, 6, 7, 8, 9, 10, 11 or 12 deuterium atoms. Synthetic methods for including isotopes into organic compounds are known in the art.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

Synthesis

As will be appreciated, the compounds provided herein, including salts and stereoisomers thereof, can be prepared using known organic synthesis techniques and can be synthesized according to any of numerous possible synthetic routes.

Compounds of Formula I can be prepared from amines 1-1 as shown in Scheme 1. Amine 1-1 can be coupled with an optionally protected (e.g., P=Boc) carboxylic acid such as 1-2 by various methods (e.g., treatment with a coupling reagent, such as N,N,N',N'-tetramethyl-O-(7-azabenzotriazol-1-yl)uronium hexafluorophosphate in the presence of base, such as diisopropylethylamine). After coupling, optionally chosen protecting groups can be removed under conditions suitable for their removal, that are also compatible with the functionality present in the resulting compounds of Formula I.

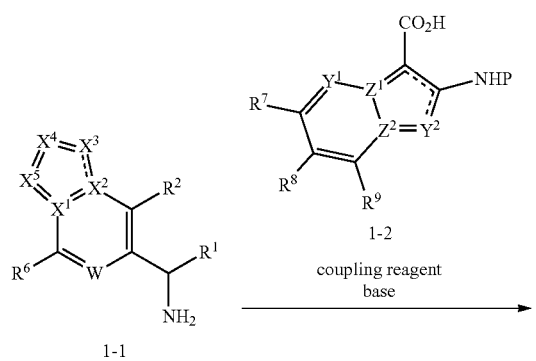

Scheme 1.

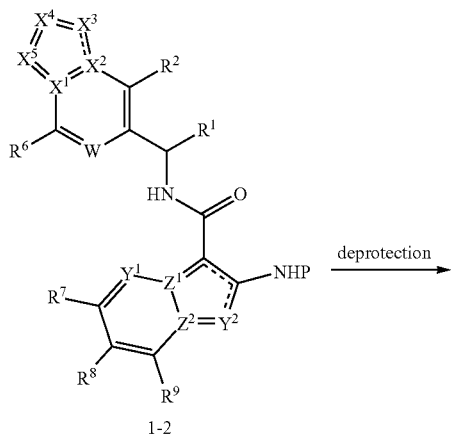

-continued

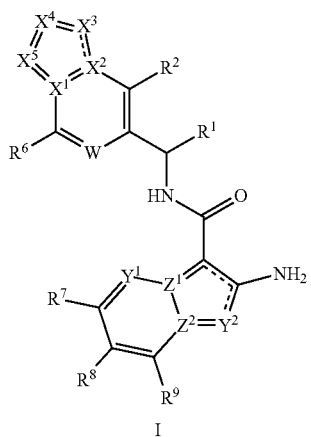

Amines 1-1 can be prepared from ketones 2-1 by various methods, as illustrated in Scheme 2. For example, one method (A) involves imine formation with a source of ammonia (e.g. solution of ammonia in an alcohol, or an ammonium salt such as ammonium acetate), which may be facilitated by the introduction of a Lewis acid (e.g. titanium (IV) ethoxide or titanium tetraisopropoxide). The imine can be reduced using a reducing agent (e.g. NaBH$_4$ or NaCNBH$_3$), to furnish amines 1-1. Alternatively, the method of Ellman (B), can be used to furnish amine 1-1 in enantiomerically enriched form. This would be performed, for example, by condensation of ketones 2-1 with a tert-butanesulfinamide (chiral, if desired) in the presence of Lewis acid (e.g., titanium tetraethoxide), followed by reduction of the tert-butanesulfinyl ketimine (e.g. using L-Selectride®), and removal of the tert-butyl sulfinyl group with acid (e.g., 4 N HCl in dioxane). As an alternative to reductive amination, a sequence of transformations (C) can be used to furnish amine 1-1, which include reduction of the ketone to the alcohol (e.g. using NaBH$_4$), conversion of the resulting alcohol to a leaving group (e.g., reacting with MsCl in the presence of base, such as triethylamine), displacement of the leaving group with sodium azide, followed by reduction of the azide to an amine (e.g., via hydrogenation or Staudinger reduction).

Scheme 2.

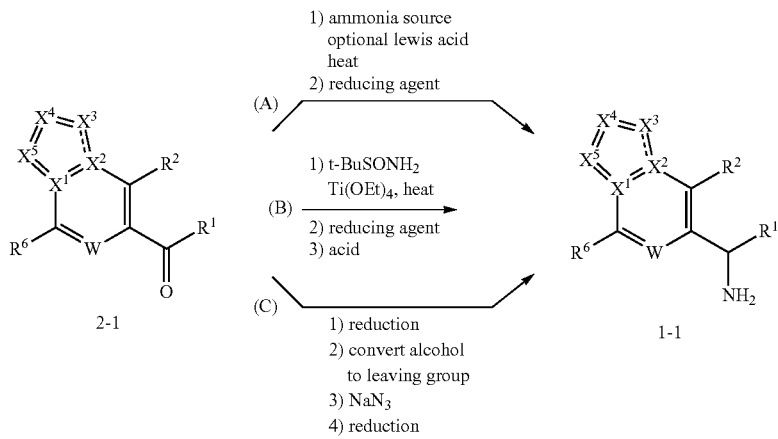

As shown in Scheme 3, ketones 2-1 can be prepared from esters 3-1 via sequential hydrolysis (e.g. treatment with a hydroxide base, such as NaOH), Weinreb amide formation (e.g. by coupling the acid with N,O-dimethylhydroxylamine using a coupling agent such as EDCI and HOBt in the presence of a tertiary amine base, such as triethylamine or diisopropylethylamine), and treatment of the Weinreb amide with a Grignard reagent, $R^1$—MgX, to afford ketone 2-1.

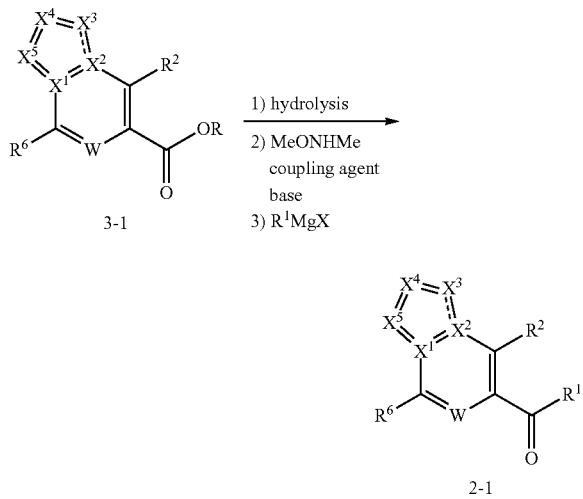

Compounds of Formula I wherein W=CH, $X^1$=C, $X^2$=C, $X^3$=N or $NR^{3a}$, $X^4$=N or $NR^{4a}$, $X^5$=$CR^5$ can be prepared as shown in Scheme 4. Nitro-containing starting materials 4-1 can be converted to the corresponding triflate 4-2 by several methods (e.g., by treatment with trifluoromethanesulfonic anhydride and a base, such as triethylamine). The substituent $R^2$ can be introduced by a coupling of 4-2 with $R^2$-M, where M is a boronic acid, boronic ester, or an appropriately substituted metal such as $Sn(Bu)_4$ or Zn, under standard Suzuki conditions (e.g., in the presence of a palladium catalyst, such as tetrakis(triphenylphosphine)palladium(0) or bis(triphenylphosphine)palladium(II) chloride and a base (e.g., a bicarbonate or carbonate base, or CsF)) or standard Stille conditions (e.g., in the presence of a palladium(0) catalyst, such as tetrakis(triphenylphosphine)palladium(0)) or standard Negishi conditions (e.g., in the presence of a palladium catalyst, such as tetrakis(triphenylphosphine)palladium(0) or [1,1'-bis(diphenylphosphino)ferrocene]dichloropalladium (II)), to give derivative 4-3. The nitro group of intermediate 4-3 can be converted to the primary amine by reduction (e.g. hydrogenation over a Pt or Pd catalyst, Fe/HCl, or $LiAlH_4$). Intermediate 4-4 can then be converted to the indazole via diazotization of the amine and cyclization employing an alkyl nitrite (e.g., amyl nitrite) in warm AcOH. If desired, the halogen present in 4-5 can serve as a handle for installation of substituent $R^6$, via coupling with $R^6$-M, where M is a boronic acid, boronic ester, or an appropriately substituted metal such as $Sn(Bu)_4$ or Zn, under standard Suzuki conditions (e.g., in the presence of a palladium catalyst, such as tetrakis(triphenylphosphine)palladium(0) or bis(triphenylphosphine)palladium(II) chloride and a base (e.g., a bicarbonate or carbonate base, or CsF)) or standard Stille conditions (e.g., in the presence of a palladium(0) catalyst, such as tetrakis(triphenylphosphine)palladium(0)) or standard Negishi conditions (e.g., in the presence of a palladium catalyst, such as tetrakis(triphenylphosphine)palladium(0) or [1,1'-bis(diphenylphosphino)ferrocene]dichloropalladium (II)), to give derivative 4-6. The indazole nitrogens of 4-6 can be alkylated either by treatment with a base and an electrophile, such as an alkyl halide (e.g. $K_2CO_3$ and MeI), or via Mitsunobu conditions ($PPh_3$, DEAD) employing a suitable alcohol, to give 4-7 as a mixture of N1 and N2 substituted indazoles. The ketone in 4-7 can be converted to an amine by various methods as shown in Scheme 2 to furnish amine 4-8. Amine 4-8 can be coupled with an optionally protected carboxylic acid such as 1-2 (from Scheme 1) by various methods as shown in Scheme 1. After coupling, any chosen protecting groups can be removed under conditions suitable for their removal, that are also compatible with the functionality present in the resulting compounds of the Formula I. It will be recognized by one skilled in the art that the order of steps in Scheme 4 can be changed in consideration of compatibility of functional groups present in the intermediates.

Scheme 4.

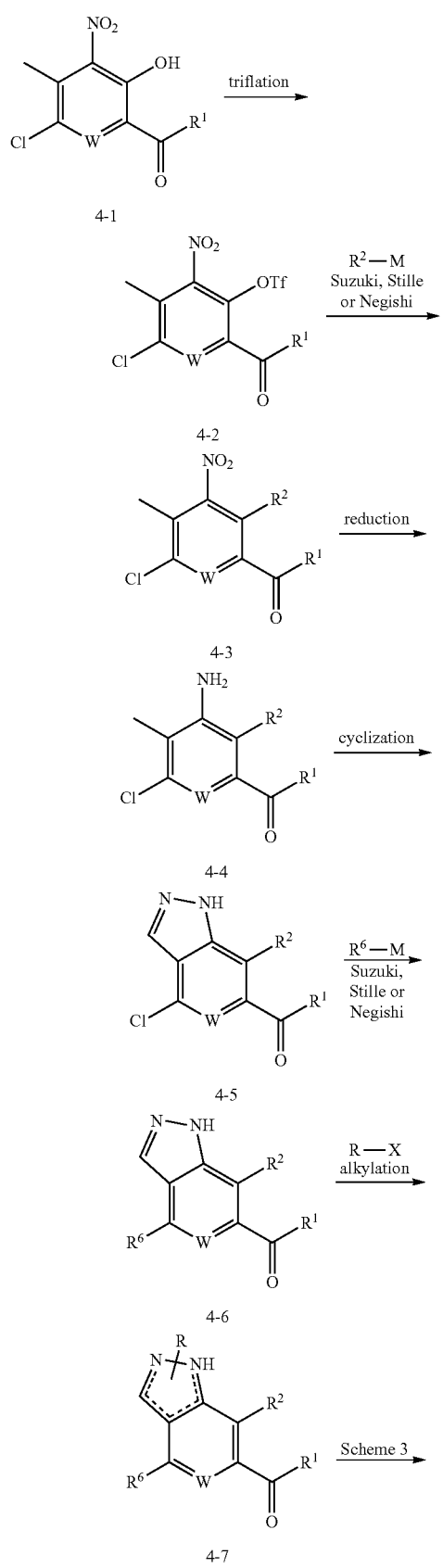

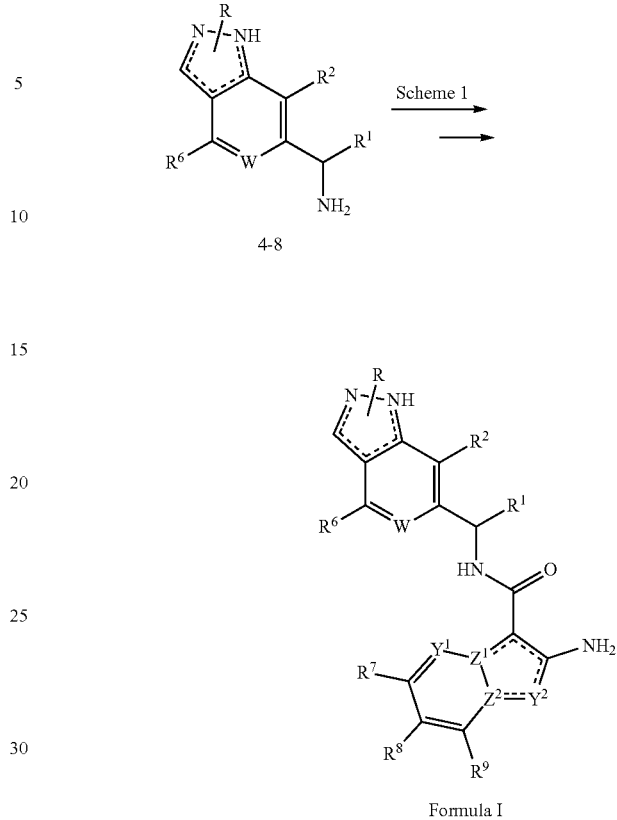

Alkoxy derivatives of the compounds of Formula I, where $R^2=OR^{13}$ can be prepared as shown in Scheme 5. Alkylation of the hydroxyl group in 4-1 employing a base and an electrophile such as an alkyl halide (e.g. $K_2CO_3$ and MeI) provides alkoxy intermediates 5-1, which can be converted to compounds of Formula I employing the synthetic methodologies described in Schemes 1 and 2. It will be recognized by one skilled in the art that the order of steps in Scheme 5 can be changed in consideration of the compatibility of functional groups present in the intermediates.

Scheme 5.

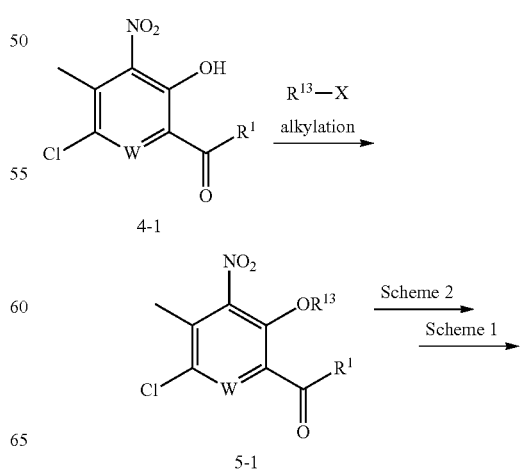

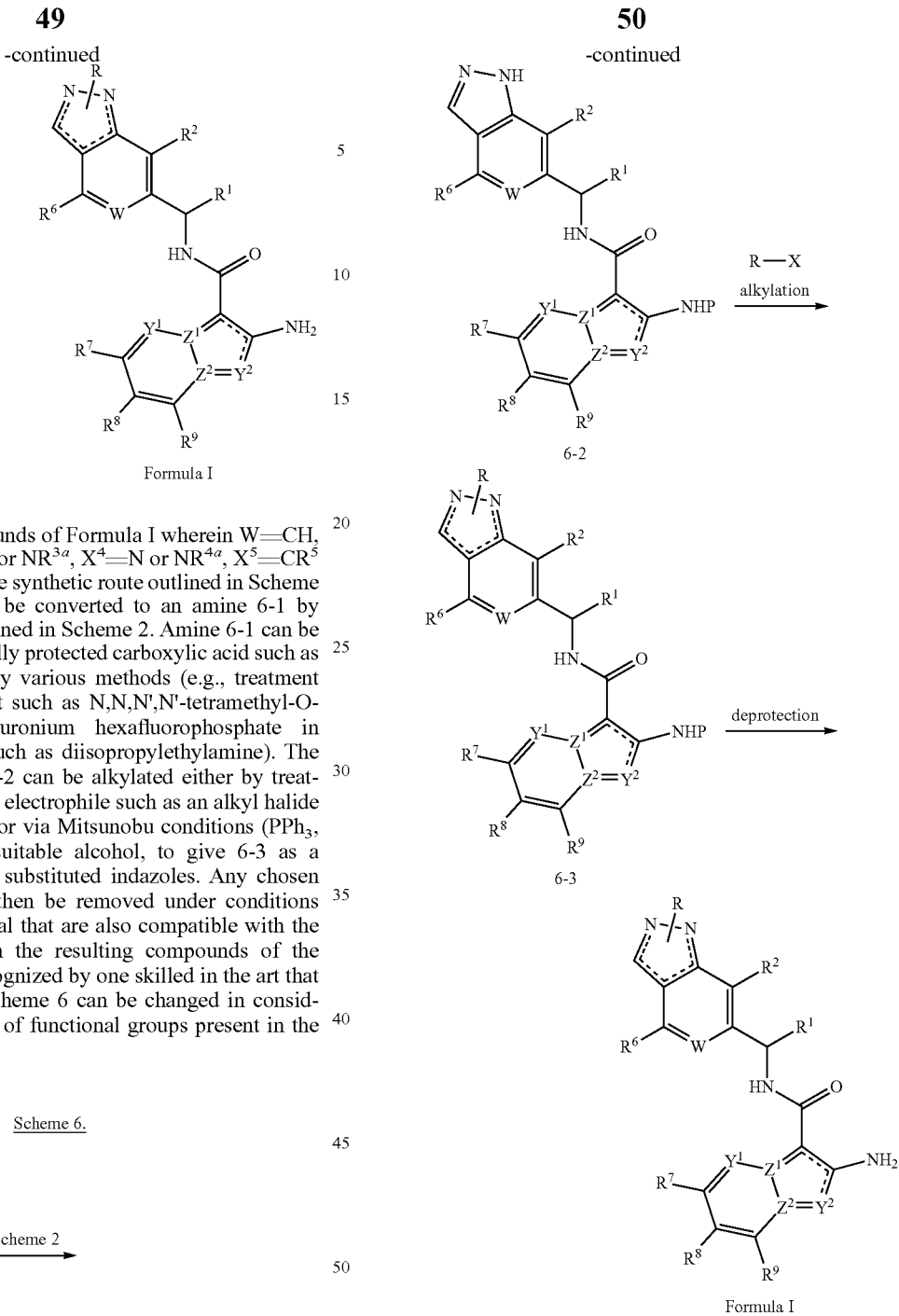

Alternatively, compounds of Formula I wherein W=CH, $X^1$=C, $X^2$=C, $X^3$=N or $NR^{3a}$, $X^4$=N or $NR^{4a}$, $X^5$=$CR^5$ can be synthesized by the synthetic route outlined in Scheme 6. The ketone 4-6 can be converted to an amine 6-1 by various methods as outlined in Scheme 2. Amine 6-1 can be coupled with an optionally protected carboxylic acid such as 1-2 (from Scheme 1) by various methods (e.g., treatment with a coupling reagent such as N,N,N',N'-tetramethyl-O-(7-azabenzotriazol-1-yl)uronium hexafluorophosphate in the presence of base, such as diisopropylethylamine). The indazole nitrogens of 6-2 can be alkylated either by treatment with a base and an electrophile such as an alkyl halide (e.g. $K_2CO_3$ and MeI), or via Mitsunobu conditions ($PPh_3$, DEAD) employing a suitable alcohol, to give 6-3 as a mixture of N1 and N2 substituted indazoles. Any chosen protecting groups can then be removed under conditions suitable for their removal that are also compatible with the functionality present in the resulting compounds of the invention. It will be recognized by one skilled in the art that the order of steps in Scheme 6 can be changed in consideration of compatibility of functional groups present in the intermediates.

Compounds of Formula I wherein $X^1$=C, $X^2$=C, $X^3$=N or $NR^{3a}$, $X^4$=N or $NR^{4a}$, $X^5$=$CR^5$ can also be prepared by the synthetic route described in Scheme 7. Halogenation of heterocycle 4-6 with reagents such as $I_2$, $Br_2$, N-bromosuccinimide, or N-iodosuccinimide can furnish intermediate 7-1, which can serve as a substrate for introduction of substituent $R^5$, via coupling with $R^5$-M, where M is a boronic acid, boronic ester, or an appropriately substituted metal such as $Sn(Bu)_4$ or Zn, under standard Suzuki conditions (e.g., in the presence of a palladium catalyst, such as tetrakis(triphenylphosphine)palladium(0) or bis(triphenylphosphine)palladium(II) chloride and a base (e.g., a bicarbonate or carbonate base, or CsF)) or standard Stille conditions (e.g., in the presence of a palladium(0) catalyst, such as tetrakis(triphenylphosphine)palladium(0)) or standard Negishi conditions (e.g., in the presence of a palladium catalyst, such as tetrakis(triphenylphosphine)palladium(0) or [1,1'-bis(diphenylphosphino)ferrocene]dichloropalladium (II)), to yield intermediate 7-2. The ketone 7-2 can be converted to an amine 7-3 by various methods as illustrated in Scheme 2. Amine 7-3 can be coupled with an optionally protected carboxylic acid such as 1-2 (from Scheme 1) by various methods (e.g., treatment with a coupling reagent such as N,N,N',N'-tetramethyl-O-(7-azabenzotriazol-1-yl) uronium hexafluorophosphate in the presence of base, such as diisopropylethylamine) to provide 7-4. The indazole nitrogens in 7-4 can optionally be alkylated either by treatment with a base and an electrophile, such as an alkyl halide (e.g. $K_2CO_3$ and MeI), or via Mitsunobu conditions ($PPh_3$, DEAD) employing a suitable alcohol, to give a mixture of N1 and N2 substituted indazoles. Any chosen protecting groups can then be removed under conditions known by ones skilled in the art, that are also compatible with the functionality present in the resulting compounds of the invention. It will be recognized by one skilled in the art that the order of steps in Scheme 7 can be changed in consideration of compatibility of functional groups present in the intermediates.

Scheme 7.

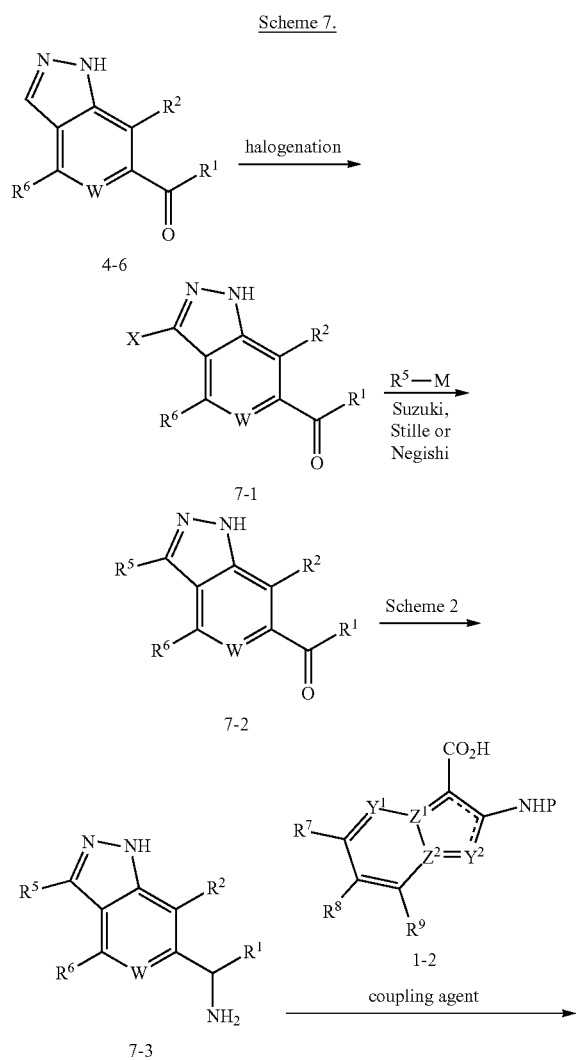

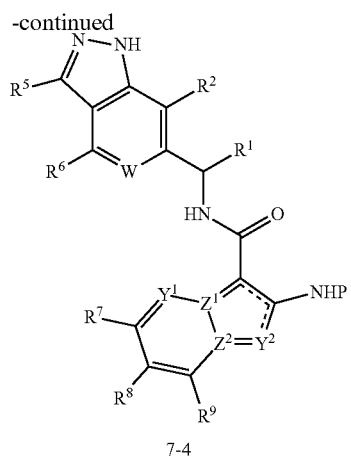

Compounds of Formula I, wherein W=CH, $Z^1$=C, $Z^2$=N, $X^3$=N, $X^4$=$CR^4$, $X^5$=$CR^5$ can be synthesized as shown in Scheme 8. Accordingly, a carboxylic acid of formula 8-1 can be reacted to form an ester by various methods, such as conversion of the carboxylic acid to the acid chloride by reaction with $COCl_2$ and DMF in a suitable solvent such as DCM, followed by reaction of the acid chloride with a suitable alcohol. The substituent $R^2$ can subsequently be introduced by coupling with $R^2$-M, where M is a boronic acid, boronic ester, or an appropriately substituted metal such as $Sn(Bu)_4$ or Zn, under standard Suzuki conditions (e.g., in the presence of a palladium catalyst, such as tetrakis(triphenylphosphine)palladium(0) or bis(triphenylphosphine)palladium(II) chloride and a base (e.g., a bicarbonate or carbonate base, or CsF)) or standard Stille conditions (e.g., in the presence of a palladium(0) catalyst, such as tetrakis(triphenylphosphine)palladium(0)) or standard Negishi conditions (e.g., in the presence of a palladium catalyst, such as tetrakis(triphenylphosphine)palladium(0) or [1,1'-bis(diphenylphosphino)ferrocene]dichloropalladium (II)), to give derivative 8-2. Compound 8-2 can then be aminated with an electrophilic amination reagent (e.g., 2-[(aminooxy)sulfonyl]-1,3,5-trimethylbenzene) to form a N-amino derivative of formula 8-3. Compound 8-3 could then be reacted with a suitable acetylene 8-4 to form a heterocycle of formula 8-5. Compound 8-5 could then be selectively decarboxylated (e.g., acid deprotection of R=t-buyl with trifluoroacetic acid followed by decarboxylation) to form a heterocycle of formula 8-6, which can be halogenated (e.g., X=Cl, Br, I using agents such as an N-halosuccinimide) to give compounds of formula 8-7. If desired, the halogen present in 8-7 can serve as a handle for installation of substituent $R^5$, via coupling with $R^5$-M, where M is a boronic acid, boronic ester, or an appropriately substituted metal such as $Sn(Bu)_4$ or Zn, under standard Suzuki conditions (e.g., in the presence of a palladium catalyst, such as tetrakis(triphenylphosphine)palladium(0) or bis(triphenylphosphine)palladium(II) chloride and a base (e.g., a bicarbonate or carbonate base, or CsF)) or standard Stille conditions (e.g., in the presence of a palladium(0) catalyst, such as tetrakis(triphenylphosphine)palladium(0)) or standard Negishi conditions (e.g., in the presence of a palladium catalyst, such as tetrakis(triphenylphosphine)palladium(0) or [1,1'-bis(diphenylphosphino)ferrocene]dichloropalladium (II)), to give derivative 8-8. Formation of ketone 8-9 from ester 8-8 can be achieved by several methods such as those described in Scheme 3. Intermediates of the formula 8-9 can be converted to compounds of Formula I via conversion to an amine via methods outlined in Scheme 2, followed by coupling and deprotection as outlined in Scheme 1. It will be recognized by one skilled in the art that the order of steps in Scheme 8 can be changed in consideration of compatibility of functional groups present in the intermediates.

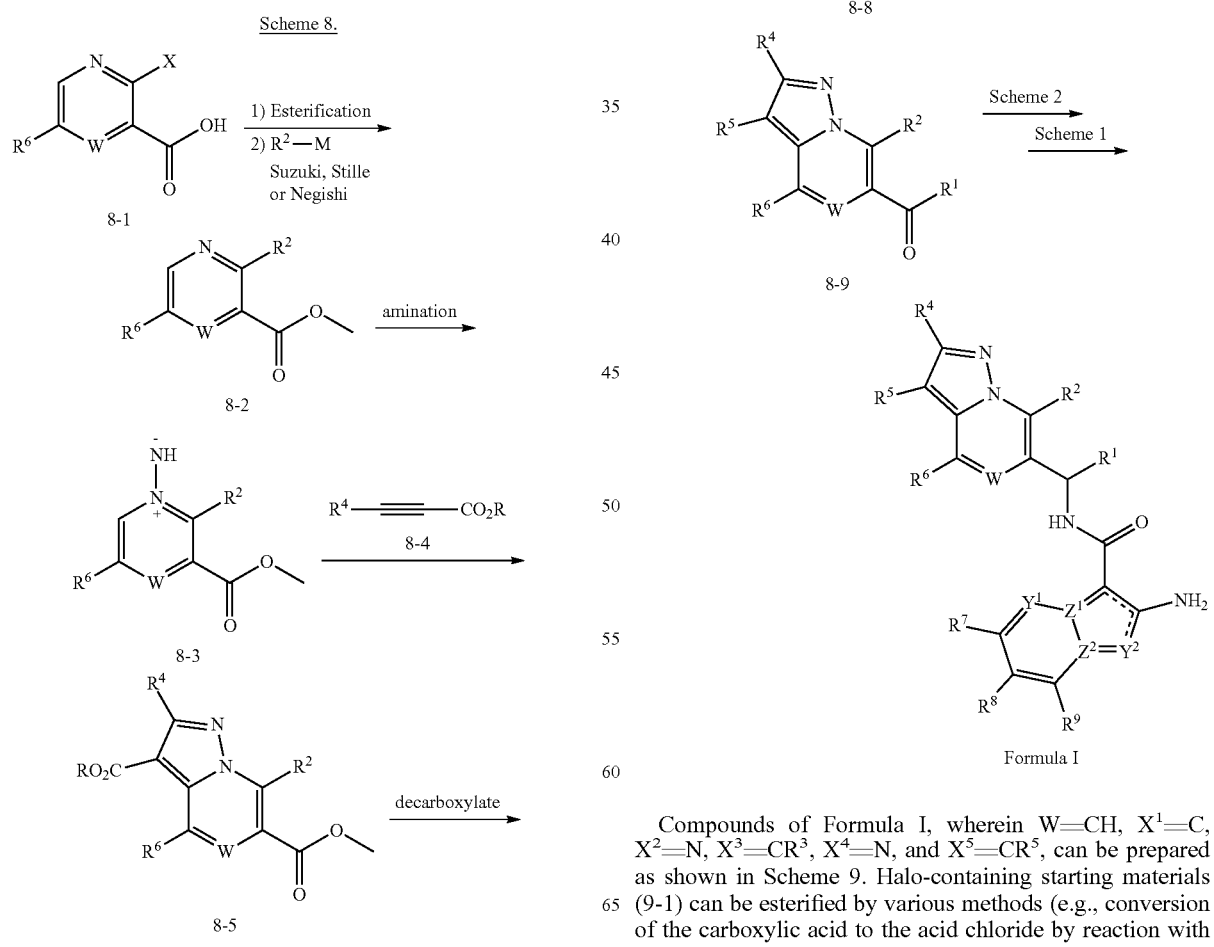

Compounds of Formula I, wherein W=CH, $X^1$=C, $X^2$=N, $X^3$=$CR^3$, $X^4$=N, and $X^5$=$CR^5$, can be prepared as shown in Scheme 9. Halo-containing starting materials (9-1) can be esterified by various methods (e.g., conversion of the carboxylic acid to the acid chloride by reaction with $COCl_2$ and DMF in a suitable solvent such as DCM, followed by reaction of the acid chloride with a suitable alcohol, such as EtOH). The ester intermediate can then be treated with an oxidizing reagent (e.g., a peroxide reagent such as the combination of $H_2O_2$/TFA) to form the heterocyclic N-oxide, and subsequently be converted to the nitrile derivative 9-2 (e.g., by heating with trimethylsilylcyanide and base). The substituent $R^2$ can be introduced by a coupling of 9-2 with $R^2$-M, where M is a boronic acid, boronic ester, or an appropriately substituted metal such as $Sn(Bu)_4$ or Zn, under standard Suzuki conditions (e.g., in the presence of a palladium catalyst, such as tetrakis(triphenylphosphine)palladium(0) or bis(triphenylphosphine)palladium(II) chloride and a base (e.g., a bicarbonate or carbonate base, or CsF)) or standard Stille conditions (e.g., in the presence of a palladium(0) catalyst, such as tetrakis(triphenylphosphine)palladium(0)) or standard Negishi conditions (e.g., in the presence of a palladium catalyst, such as tetrakis(triphenylphosphine)palladium(0) or [1,1'-bis(diphenylphosphino)ferrocene]dichloropalladium (II)), to give derivative 9-3. The nitrile of intermediate 9-3 can be converted to an aminomethyl group by reduction (e.g. using $H_2$ and a catalyst, such as Raney® Ni or Pd on carbon). Following reduction, the aminomethyl group can be acylated (e.g. by reacting with $R^3$—CO-LG, wherein CO-LG is a suitable activated carbonyl group (e.g., an acid chloride (LG=Cl) or anhydride (LG=O—(CO)R), or carboxylic acid in combination with a coupling agent (e.g., BOP, HATU, or EDCI/HOBt) and a base (e.g., diisopropylethylamine)). The acylated intermediate can be cyclized to form the bicyclic intermediate 9-4 under cyclo-dehydrating conditions (e.g. by heating in $POCl_3$ or by treatment with $P_2O_5$, $SOCl_2$ or with acid). Formation of ketone 9-5 from ester 9-4 can proceed as illustrated in Scheme 3. If desired, the halogen present in 9-5 (i.e., group X) can serve as a handle for installation of substituent $R^6$, via coupling with $R^6$-M, where M is a boronic acid, boronic ester, or an appropriately substituted metal such as $Sn(Bu)_4$ or Zn, under standard Suzuki conditions (e.g., in the presence of a palladium catalyst, such as tetrakis(triphenylphosphine)palladium(0) or bis(triphenylphosphine)palladium(II) chloride and a base (e.g., a bicarbonate or carbonate base, or CsF)) or standard Stille conditions (e.g., in the presence of a palladium(0) catalyst, such as tetrakis(triphenylphosphine)palladium(0)) or standard Negishi conditions (e.g., in the presence of a palladium catalyst, such as tetrakis(triphenylphosphine)palladium(0) or [1,1'-bis(diphenylphosphino)ferrocene]dichloropalladium (II)), to give derivative 9-6. If desired, treatment of 9-6 with a halogenating reagent (e.g. $I_2$, $Br_2$, N-chlorosuccinimide N-bromosuccinimide, or N-iodosuccinimide) can furnish intermediate 9-7 (wherein X=Cl, Br, I), which can be substituted with $R^5$, via coupling with $R^5$-M, where M is a boronic acid, boronic ester, or an appropriately substituted metal such as $Sn(Bu)_4$ or Zn, under standard Suzuki conditions (e.g., in the presence of a palladium catalyst, such as tetrakis(triphenylphosphine)palladium(0) or bis(triphenylphosphine)palladium(II) chloride and a base (e.g., a bicarbonate or carbonate base, or CsF)) or standard Stille conditions (e.g., in the presence of a palladium(0) catalyst, such as tetrakis(triphenylphosphine)palladium(0)) or standard Negishi conditions (e.g., in the presence of a palladium catalyst, such as tetrakis(triphenylphosphine)palladium(0) or [1,1'-bis(diphenylphosphino)ferrocene]dichloropalladium (II)), to yield intermediate ketone 9-8. Ketone 9-8 can be treated with one of the conditions of Scheme 2 to provide an amine that can be converted to compounds of the invention 9-9 according to Scheme 1. It will be recognized by one skilled in the art that the order of steps in Scheme 9 can be changed in consideration of compatibility of functional groups present in the intermediates.

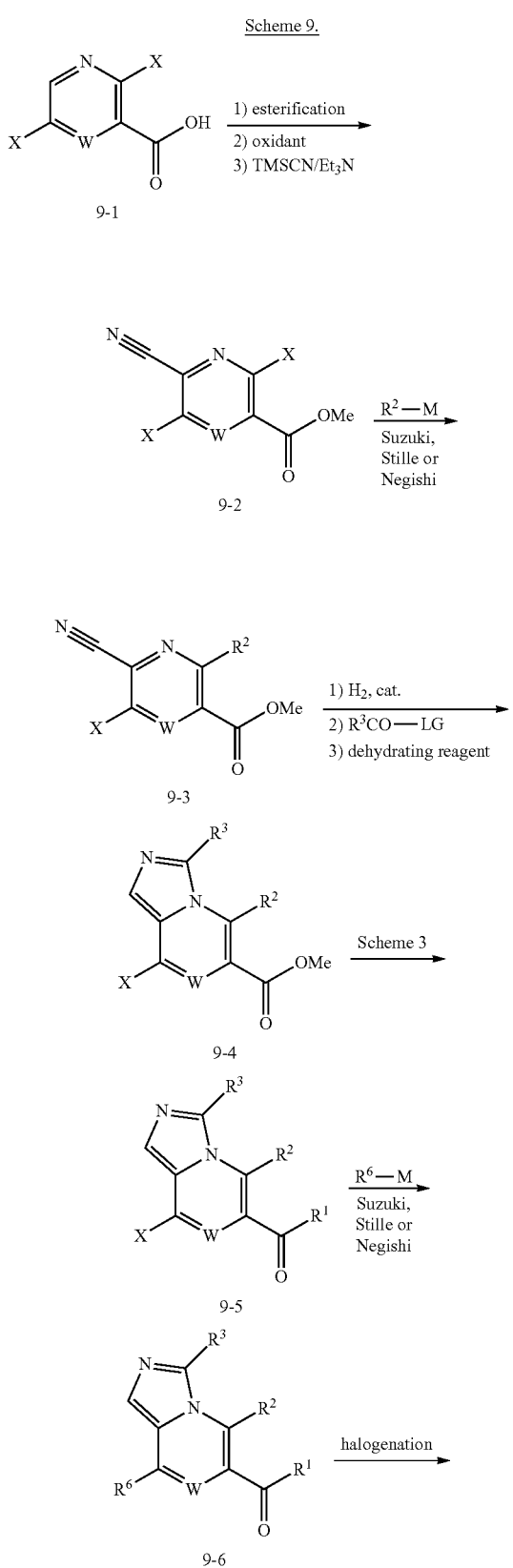

Scheme 9.

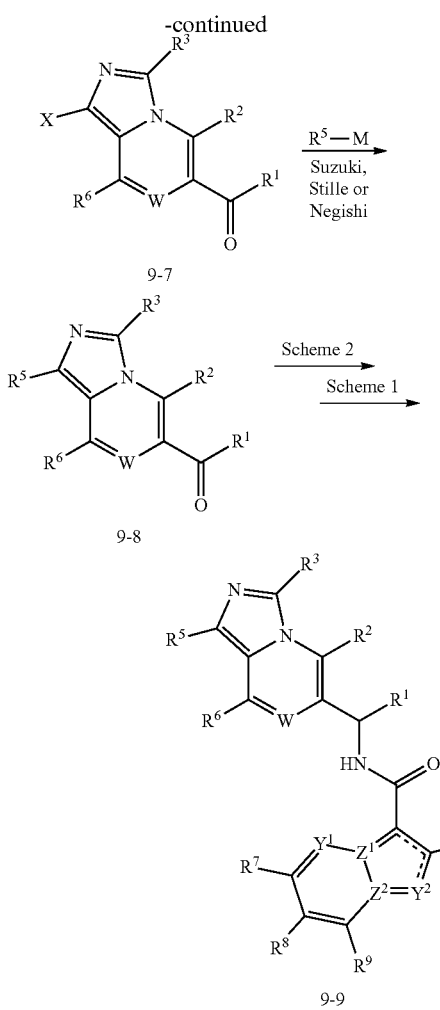

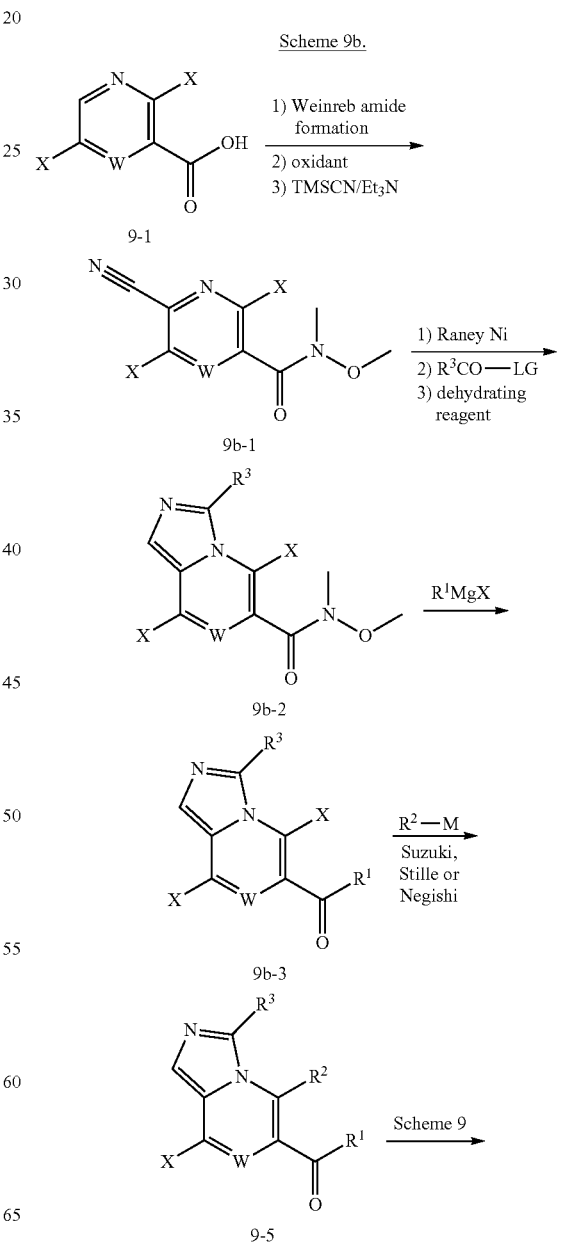

undergo reaction with a Grignard reagent R¹MgX to afford ketone 9b-3. The substituent R² can be introduced by a coupling of 9b-3 with R²-M, where M is a boronic acid, boronic ester, or an appropriately substituted metal such as Sn(Bu)$_4$ or Zn, under standard Suzuki conditions (e.g., in the presence of a palladium catalyst, such as tetrakis(triphenylphosphine)palladium(0) or bis(triphenylphosphine)palladium(II) chloride and a base (e.g., a bicarbonate or carbonate base, or CsF)) or standard Stille conditions (e.g., in the presence of a palladium(0) catalyst, such as tetrakis (triphenylphosphine)palladium(0)) or standard Negishi conditions (e.g., in the presence of a palladium catalyst, such as tetrakis(triphenylphosphine)palladium(0) or [1,1'-bis(diphenylphosphino)ferrocene]dichloropalladium (II)), to give derivative 9-5. Intermediates 9-5 can be transformed to further functionalized compounds of Formula I by the methods outlined in Scheme 9.

Compounds of Formula I, wherein W=CH, X¹=C, X²=N, X³=CR³, X⁴=N, and X⁵=CR⁵, can also be prepared as shown in Scheme 9b. This changing of the order of steps of Scheme 9 enables R² to be introduced at a later stage in the synthesis and can provide for introduction of R² with sensitive functional groups. Halo-containing starting materials 9-1 can be converted to the Weinreb amide 9b-1 (e.g., by reaction with MeONHMe in the presence of a suitable coupling reagent such as EDCI and in the presence of HOBt and a suitable base, such as Hunig's base). The amide intermediate 9b-1 can then be treated with an oxidizing reagent (e.g., a peroxide reagent such as the combination of H$_2$O$_2$/TFA) to form the heterocyclic N-oxide, and subsequently be converted to the nitrile derivative 9b-1 (e.g., by heating with trimethylsilylcyanide and base). The nitrile of intermediate 9b-1 can be converted to an aminomethyl group by reduction (e.g. Raney® Ni in formic acid). Following reduction, the aminomethyl group can be acylated (e.g. by reacting with R³—CO-LG, wherein CO-LG is a suitable activated carbonyl group (e.g., an acid chloride (LG=CO or anhydride (LG=O—(CO)R), or carboxylic acid in combination with a coupling agent (e.g., BOP, HATU, or EDCI/HOBt) and a base (e.g., diisopropylethylamine)). The acylated intermediate can be cyclized to form the bicyclic intermediate 9b-2 under cyclo-dehydrating conditions (e.g. by heating in POCl$_3$ or by treatment with P$_2$O$_5$, SOCl$_2$ or with acid). The Weinreb amide of intermediate 9b-2 can

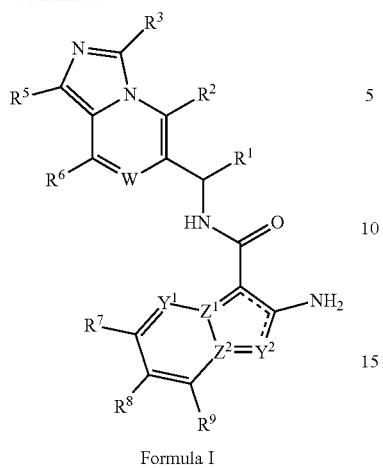

Formula I

Compounds of Formula I, wherein W=CH, X$^1$=C, X$^2$=N, X$^3$=CR$^3$, X$^4$=N, X$^5$=CR$^5$, and R$^2$=NR$^{10}$R$^{11}$ can be prepared by modification of Scheme 9 shown in Scheme 9c. Intermediate 9-2 can be heated in the presence of an amine (R$^{10}$R$^{11}$NH) and in the presence of a suitable base (e.g. cesium carbonate or Hunig's base) in a suitable solvent (e.g. acetonitrile) to provide intermediates 9c-1. The imidazole ring can be annealed to provide intermediate 9c-2, which can be elaborated to ketone 9c-3, which can be functionalized to afford 9c-4, 9c-5 and 9c-6, and finally elaborated to compounds of Formula I using methods previously outlined in Scheme 9.

Scheme 9c.

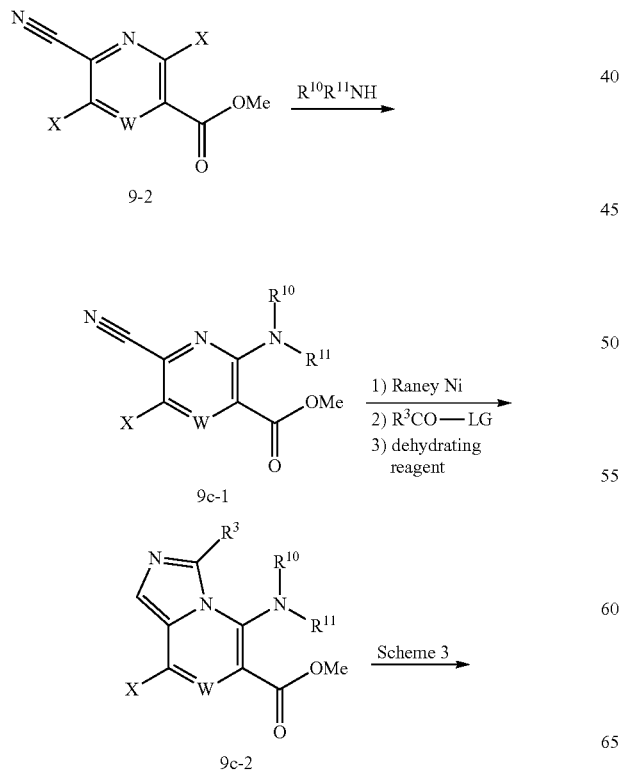

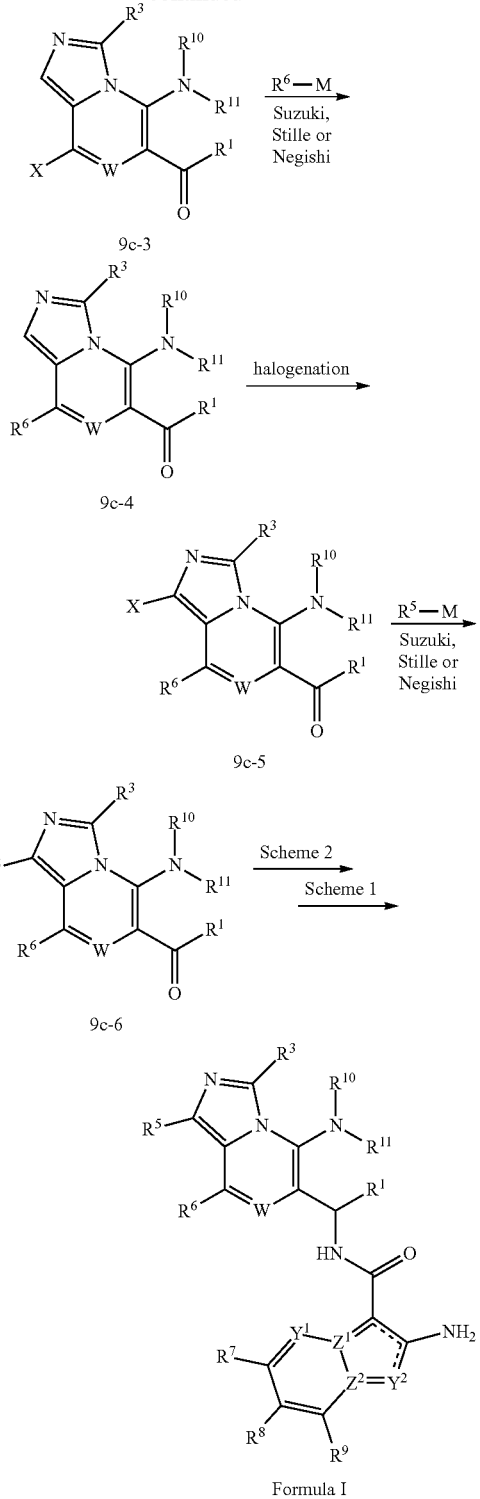

Formula I

As an alternative to early introduction of the amine as shown in Scheme 9c, it is occasionally preferable to introduce it at a later stage as shown in Scheme 9d. Thus, compounds of Formula I, wherein W=CH, X$^1$=C, X$^2$=N, X$^3$=CR$^3$, X$^4$=N, X$^5$=CR$^5$, and R$^2$=NR$^{10}$R$^{11}$ can be prepared by heating (e.g., at temperatures ranging from 70 to 170° C.) the intermediate 9b-3 with an amine (R$^{10}$R$^{11}$NH) in the presence of a suitable base (e.g. cesium carbonate or Hunig's base) in a suitable solvent (e.g. acetonitrile) to provide intermediate 9c-3. Intermediate ketone 9c-3 can be further functionalized and elaborated to compounds of Formula I using methods already described for Scheme 9 and Scheme 9c.

Scheme 9d.

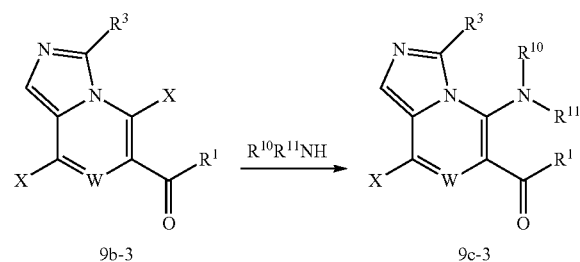

Amine-containing intermediates suitable for synthesis of compounds of Formula I, wherein W=CH, $X^1$=C, $X^2$=N, $X^3$=CR$^3$, $X^4$=N, $X^5$=CR$^5$, and $R^2$=NR$^{10}$R$^{11}$ can be prepared as shown in Scheme 9e. The reaction of Weinreb amide 9b-2 with an amine ($R^{10}R^{11}$NH) in the presence of a suitable base (e.g. cesium carbonate or Hunig's base) in a suitable solvent (e.g. acetonitrile) furnishes adduct 9e-1, which is very flexible for further transformations. Intermediate Weinreb amide 9e-1 can undergo reaction with Grignard reagents $R^1$MgX to afford ketones of type 9e-2 that can be treated according to the methods of Scheme 2 to afford amines 9e-5 which, in turn, can be converted to compounds of Formula I as outlined in Scheme 1. Alternatively, Weinreb amide 9e-1 can be reduced by a suitable reducing agent (e.g. diisobutylaluminum hydride) to afford aldehyde 9e-3. Aldehyde 9e-3 can either be converted to amine 9e-4 by one of the methods of Scheme 2, or converted to amine 9e-5 by condensation with tert-butylsulfinamide (chiral, if desired) in the presence of lewis acid (e.g. titanium isopropoxide), followed by reaction of the tert-butanesulfinyl aldimine with a Grignard reagent $R^1$MgX, and removal of the tert-butyl sulfinyl group with acid (e.g. 4N HCl in dioxane). Amines 9e-4 and 9e-5 serve as useful intermediates for further functionalization and elaboration to compounds of Formula I according to methods outlined in Scheme 9. It will be recognized by one skilled in the art that substituents at $R^5$ and $R^6$ can be introduced on many of the intermediates at various stages in Scheme 9d and Scheme 9e, according to the compatibility of functional groups with the subsequent steps to be performed.

Scheme 9e.

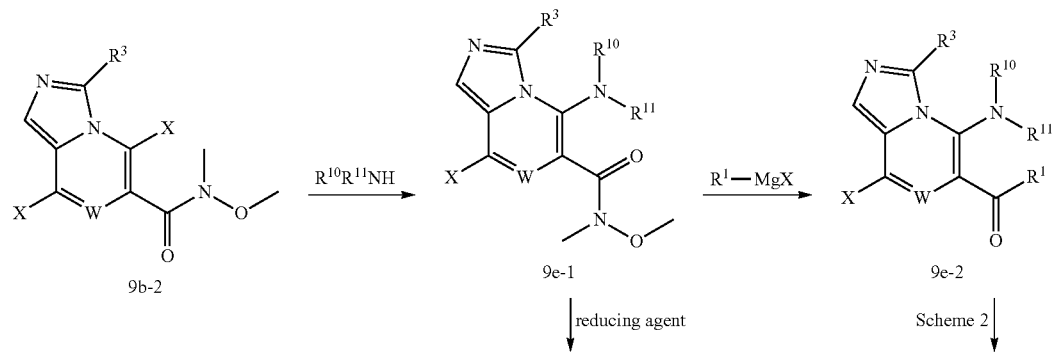

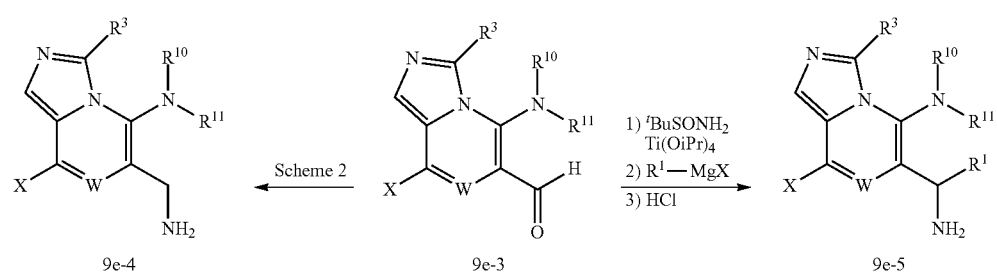

Compounds of Formula I, wherein W=CH, X¹=C, X²=N, X³=CR³, X⁴=CR⁴ and X⁵=N, can be prepared as shown in Scheme 10. An amino heterocycle, such as 10-1, can be halogenated according to a procedure as found in US 2008-0019915, involving protection of the amino moiety with a suitable protecting group (e.g., phthalimide), formation of the N-oxide using a suitable oxidant (e.g., m-CPBA), and rearrangement to the halo-derivative by treatment of the N-oxide with a suitable reagent (e.g., PDX$_3$, RCOX, RSO$_2$X), which upon deprotection would furnish intermediates 10-2 (wherein X=Cl, Br, I). Halo-containing intermediate 10-2 can serve as a substrate for introduction of substituent R². Substituent R² can be introduced, for example, via cross-coupling with R²-M, where M is a boronic acid, boronic ester, or an appropriately substituted metal such as Sn(Bu)$_4$ or Zn, under standard Suzuki conditions (e.g., in the presence of a palladium catalyst, such as tetrakis(triphenylphosphine)palladium(0) or bis(triphenylphosphine)palladium(II) chloride and a base (e.g., a bicarbonate or carbonate base, or CsF)) or standard Stille conditions (e.g., in the presence of a palladium(0) catalyst, such as tetrakis(triphenylphosphine)palladium(0)) or standard Negishi conditions (e.g., in the presence of a palladium catalyst, such as tetrakis(triphenylphosphine)palladium(0) or [1,1'-bis(diphenylphosphino)ferrocene]dichloropalladium (II)), to yield intermediate 10-3. Alternatively, R² can be installed via nucleophilic aromatic substitution of the halogen of 10-2 with amines, for example, to provide 10-3 where R² is an amine. Halogenation of 10-3 using a halogenating reagent (e.g. I$_2$, Br$_2$, N-chlorosuccinimide N-bromosuccinimide, or N-iodosuccinimide) can furnish intermediate 10-4 (wherein X=Cl, Br, I). Formation of bicyclic intermediates 10-6 can proceed by treatment of amino heterocycles 10-4 with α-halo carbonyl intermediates 10-5 (wherein X=Cl, Br), usually with heating and in the presence of a suitable base (e.g., Na$_2$CO$_3$). Alternatively, the intermediate 10-5 may be in the form of the acetal or ketal, in which case reaction of such intermediate with 10-4 may include acid rather than base (e.g., p-toluenesulfonic acid). Conversion of the ester in 10-6 to the ketone 10-7 can be performed as described in Scheme 3. If desired, the halogen in 10-7 can be used as a handle for the introduction of R⁶ via coupling with M-R⁶, where M is a boronic acid, boronic ester, or an appropriately substituted metal such as Sn(Bu)$_4$ or Zn, under standard Suzuki conditions (e.g., in the presence of a palladium catalyst, such as tetrakis(triphenylphosphine)palladium(0) or bis(triphenylphosphine)palladium(II) chloride and a base (e.g., a bicarbonate or carbonate base, or CsF)) or standard Stille conditions (e.g., in the presence of a palladium(0) catalyst, such as tetrakis(triphenylphosphine) palladium(0)) or standard Negishi conditions (e.g., in the presence of a palladium catalyst, such as tetrakis(triphenylphosphine)palladium(0) or [1,1'-bis(diphenylphosphino)ferrocene]dichloropalladium (II)), to yield intermediate 10-8. Ketone 10-8 can be treated with one of the conditions of Scheme 2 to provide an amine that can be converted to compounds of the invention 10-9 according to Scheme 1. It will be recognized by one skilled in the art that the order of steps in Scheme 10 can be changed in consideration of compatibility of functional groups present in the intermediates.

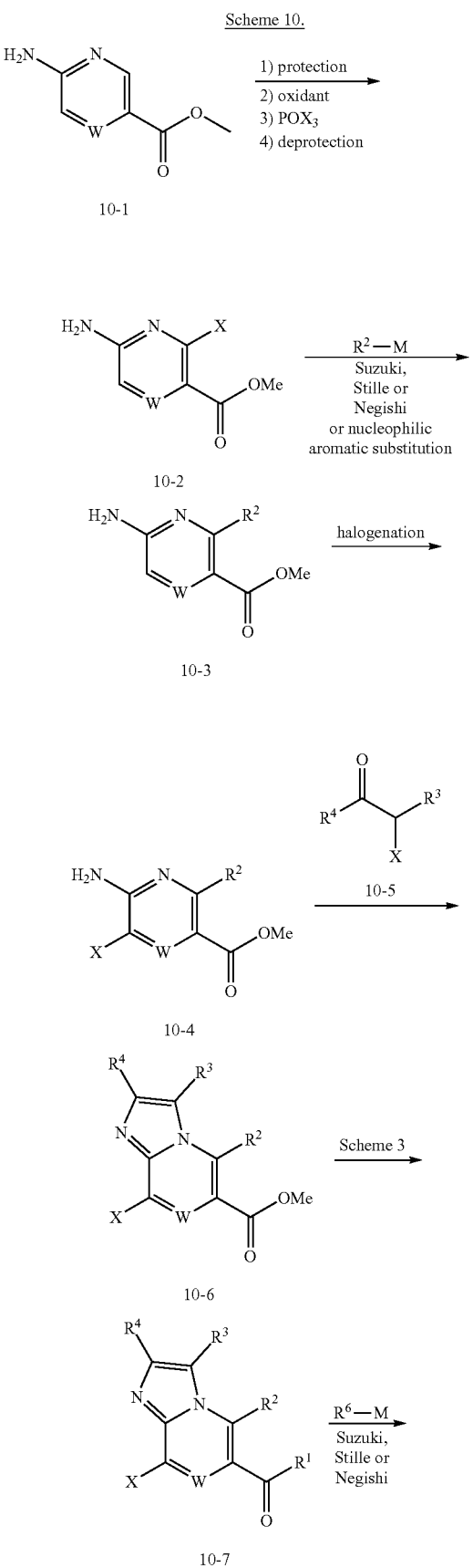

Scheme 10.

-continued

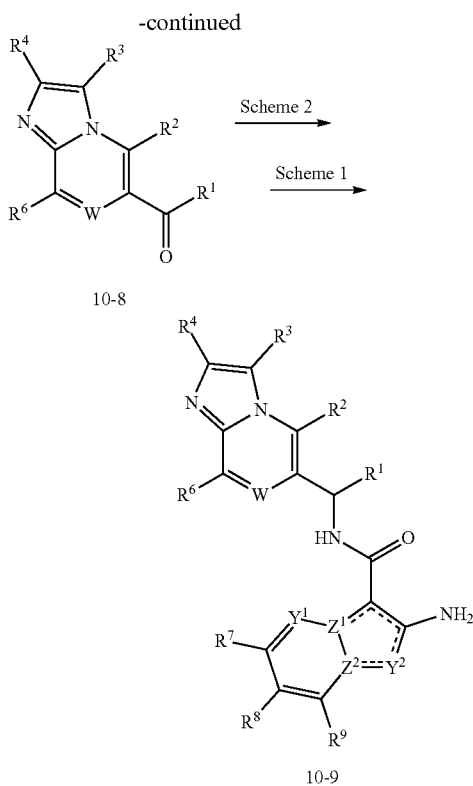

Compounds of Formula I, wherein W=CH, $X^1$=C, $X^2$=N, $X^3$=CR$^3$, $X^4$=N and $X^5$=N, can be prepared as shown in Scheme 11. Heteroaryl starting materials 11-1 can be coupled with R$^2$-M, where M is a boronic acid, boronic ester, or an appropriately substituted metal, such as Sn(Bu)$_4$ or Zn, under standard Suzuki conditions (e.g., in the presence of a palladium catalyst, such as tetrakis(triphenylphosphine)palladium(0) or bis(triphenylphosphine)palladium(II) chloride and a base (e.g., a bicarbonate or carbonate base, or CsF)) or standard Stille conditions (e.g., in the presence of a palladium(0) catalyst, such as tetrakis(triphenylphosphine) palladium(0)) or standard Negishi conditions (e.g., in the presence of a palladium catalyst, such as tetrakis(triphenylphosphine)palladium(0) or [1,1'-bis(diphenylphosphino)ferrocene]dichloropalladium (II)), to yield intermediates 11-2. Formation of the N-oxide using a suitable oxidant (e.g., m-CPBA), and rearrangement to the halo-derivative by treatment of the N-oxide with a suitable reagent (e.g., POX$_3$, RCOX, RSO$_2$X), can furnish intermediate 11-3 (wherein X=Cl, Br). Nucleophilic aromatic substitution of the halide (i.e., group X) in intermediate 11-3 with hydrazine can afford intermediate 11-4. Acylation of 11-4 with 11-5, wherein CO-LG is a suitable carbonyl group (e.g., an acid chloride (LG=Cl) or anhydride (LG=O—(CO)R), or carboxylic acid in combination with a coupling agent (e.g., BOP, HATU, or EDO/HOBO and a base (e.g., diisopropylethylamine)) can provide an acylhydrazide intermediate 11-6. Direct conversion of halide 11-3 to acylhydrazide intermediates 11-6 is also possible by displacement of the halide of 11-3 directly with an acyl hydrazide (e.g., R$^3$(CO)NHNH$_2$). A palladium-catalyzed cross coupling of an acyl hydrazide (e.g., R$^3$(CO)NHNH$_2$) with heteroaryl halide 11-3 (e.g., as described in *Org. Lett.* 2010, 12(4), p.792-795; using Pd$_2$(dba)$_3$, Josiphos, NaHCO$_3$ in DMF at elevated temperature) can also provide 11-6 directly from intermediate 11-3. The intermediate 11-6 can be cyclized to form bicyclic intermediate 11-7 under cyclo-dehydrating conditions (e.g. by heating in POCl$_3$ or by treatment with P$_2$O$_5$, SOCl$_2$ or with acid). Alternatively, hydrazine containing intermediate 11-4 can be heated with orthoesters (e.g., trimethylorthoformate, triethylorthoacetate, or R$^3$C(OR)$_3$), often under acid catalysis (e.g., p-toluenesulfonic acid) to furnish 11-7 directly. If desired, R$^6$ can be introduced into the compound 11-7 via cross-coupling with R$^6$-M, where M is a boronic acid, boronic ester, or an appropriately substituted metal such as Sn(Bu)$_4$ or Zn, under standard Suzuki conditions (e.g., in the presence of a palladium catalyst, such as tetrakis(triphenylphosphine)palladium(0) or bis(triphenylphosphine)palladium(II) chloride and a base (e.g., a bicarbonate or carbonate base, or CsF)) or standard Stille conditions (e.g., in the presence of a palladium(0) catalyst, such as tetrakis(triphenylphosphine)palladium(0)) or standard Negishi conditions (e.g., in the presence of a palladium catalyst, such as tetrakis(triphenylphosphine)palladium(0) or [1,1'-bis(diphenylphosphino)ferrocene]dichloropalladium (II)), to afford intermediate 11-8. Conversion of the ester 11-8 to the ketone 11-9 can be performed as described in Scheme 3. Ketone 11-9 can be treated with one of the conditions of Scheme 2 to provide an amine that can be converted to compounds of the invention 11-10 according to Scheme 1. It will be recognized by one skilled in the art that the order of steps in Scheme 11 can be changed in consideration of compatibility of functional groups present in the intermediates.

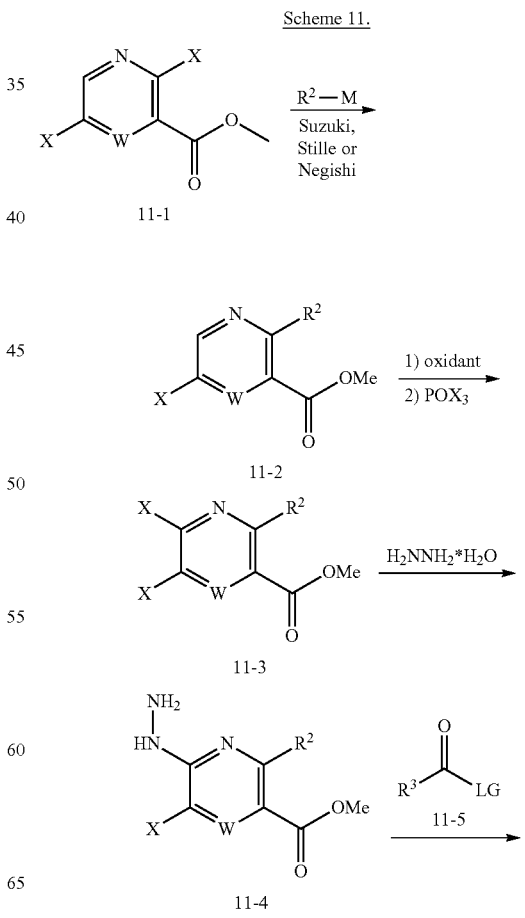

67
-continued

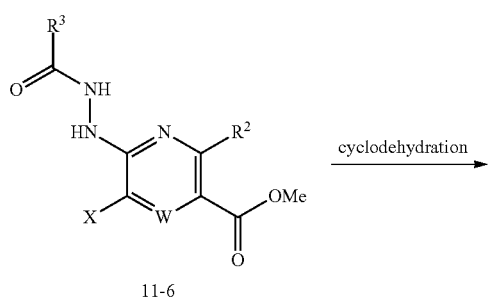

11-6 cyclodehydration →

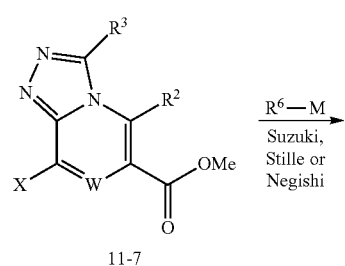

11-7

R⁶—M
Suzuki,
Stille or
Negishi
→

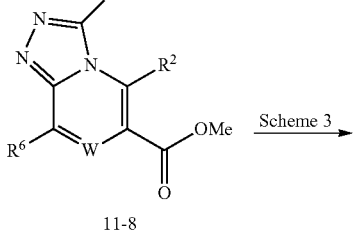

11-8

Scheme 3 →

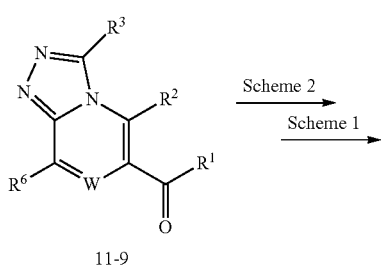

11-9

Scheme 2
Scheme 1
→

68
-continued

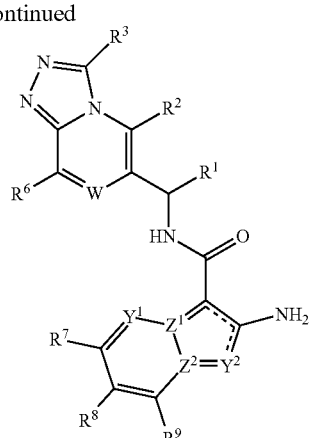

11-10

Compounds of Formula I, wherein $Z^1$=C, $Z^2$=N, $X^3$=N, $X^4$=CR$^4$, $X^5$=CR$^5$ can also be synthesized as shown in Scheme 12. Heteroaryl starting materials 12-1 can be aminated with an electrophilic amination reagent such as 2-[(aminooxy)sulfonyl]-1,3,5-trimethylbenzene, to form a N-amino heterocycle of formula 12-2. Compound 12-2 is then reacted with a suitable acetylene 12-3 to form a heterocycle of formula 12-4. Halogenation (e.g., NCS) then affords intermediates 12-5, which can undergo cross coupling with tributylstannyl vinyl ethers under standard Stille conditions (e.g., in the presence of a palladium(0) catalyst, such as tetrakis(triphenylphosphine)palladium(0), in addition to a base such as CsF) to furnish intermediates 12-7 after hydrolysis. Nucleophilic aromatic substitution with ammonia, followed by halogenation then affords 12-9. Sandmeyer reaction (e.g., NaNO₂, HCl, AcOH) provides compounds of formula 12-10, which can be decarboxylated (e.g., hydrolysis with aq. HCl followed by decarboxylation) to give intermediates 12-11. Halogenation (e.g., NCS) or cyanation (e.g., treatment with ClSO₂NCO followed by DMF) affords compounds of formula 12-12. One method for introduction of R² is via selective cross-coupling with R²-M, where M is a boronic acid, boronic ester, or an appropriately substituted metal such as Sn(Bu)₄ or Zn, under standard Suzuki conditions (e.g., in the presence of a palladium catalyst, such as tetrakis(triphenylphosphine)palladium(0) or bis(triphenylphosphine)palladium(II) chloride and a base (e.g., a bicarbonate or carbonate base, or CsF)) or standard Stille conditions (e.g., in the presence of a palladium(0) catalyst, such as tetrakis(triphenylphosphine)palladium(0)) or standard Negishi conditions (e.g., in the presence of a palladium catalyst, such as tetrakis(triphenylphosphine)palladium(0) or [1,1'-bis(diphenylphosphino)ferrocene]dichloropalladium (II)), to yield intermediates 12-13. Ketones 12-13 can be treated with one of the conditions of Scheme 2 to provide an amine that can be converted to compounds of the invention 12-14 according to Scheme 1. Alternatively, NR₂ can be installed via nucleophilic aromatic substitution of the halogen of 12-12 with amines. Intermediates 12-15 can be treated with one of the conditions of Scheme 2 to provide an amine that can be converted to compounds of the invention 12-16 according to Scheme 1.

Scheme 12
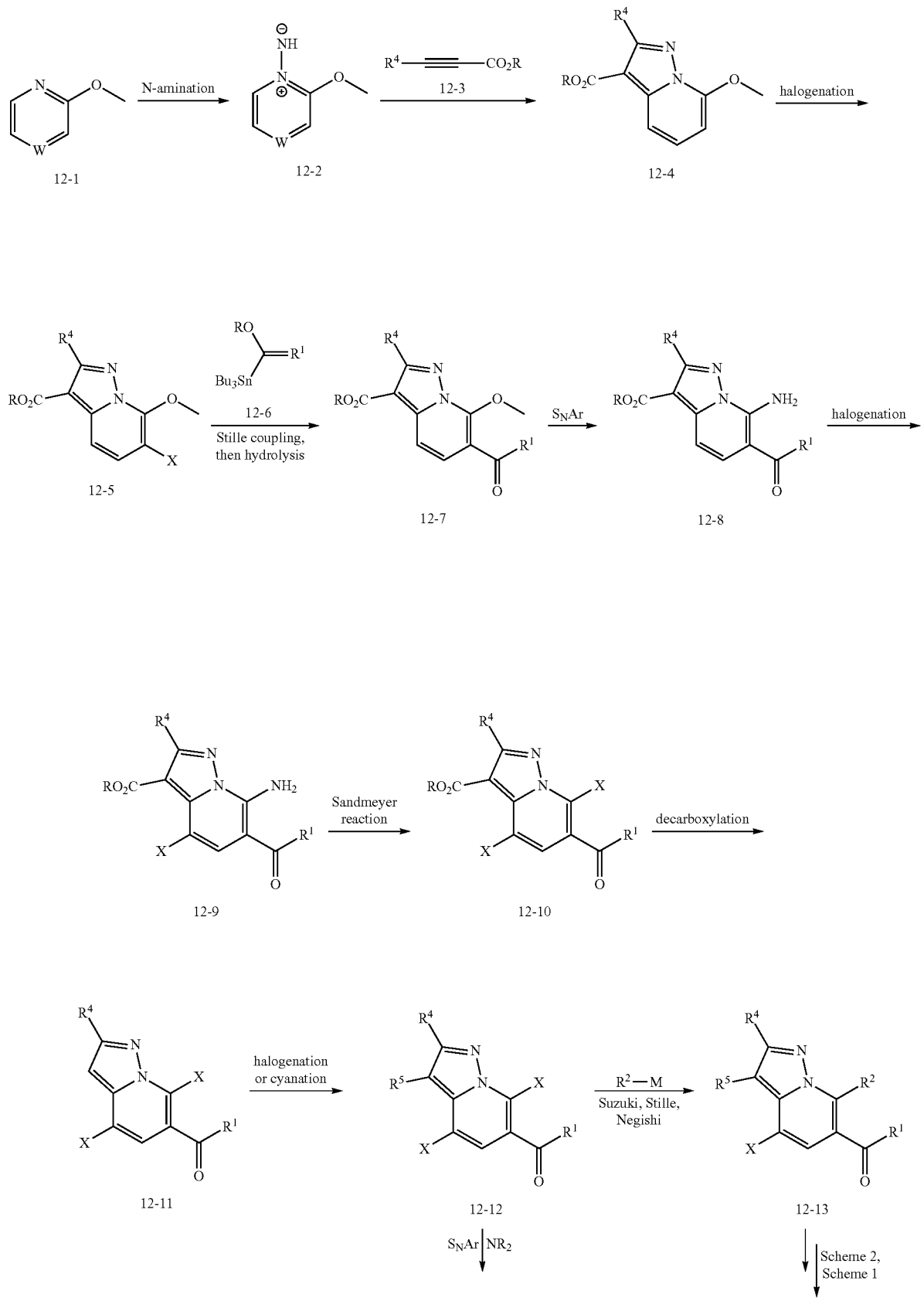

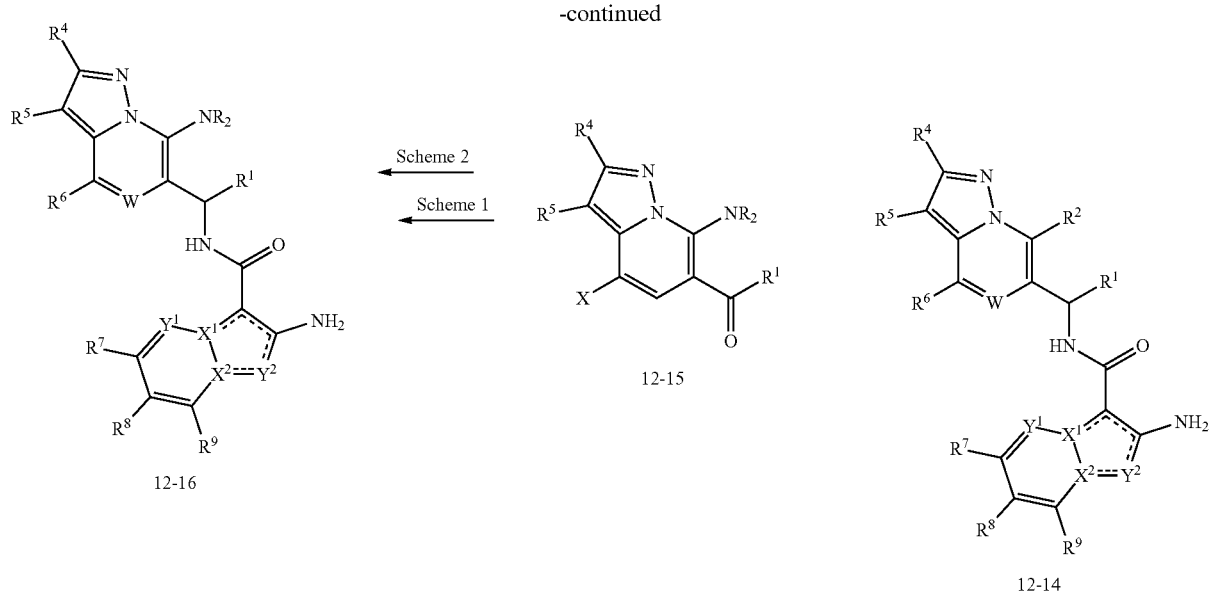

Compounds of the Formula I wherein W=C—H, $Z^1$=C, $Z^2$=N, $X^3$=N, $X^4$=N, $X^5$=$CR^5$ can be prepared as shown in Scheme 13. Heteroaryl starting materials 13-1 can be coupled with $R^2$-M, where M is a boronic acid, boronic ester, or an appropriately substituted metal such as Sn(Bu)$_4$ or Zn, under standard Suzuki conditions (e.g., in the presence of a palladium catalyst, such as tetrakis(triphenylphosphine)palladium(0) or bis(triphenylphosphine)palladium(II) chloride and a base (e.g., a bicarbonate or carbonate base, or CsF)) or standard Stille conditions (e.g., in the presence of a palladium(0) catalyst, such as tetrakis(triphenylphosphine)palladium(0)) or standard Negishi conditions (e.g., in the presence of a palladium catalyst, such as tetrakis(triphenylphosphine)palladium(0) or [1,1'-bis(diphenylphosphino)ferrocene]dichloropalladium (II)), to yield intermediates 13-2. Formation of the N-oxide using a suitable oxidant (e.g., m-CPBA), and rearrangement to the halo-derivative by treatment of the N-oxide with a suitable reagent (e.g., PDX$_3$, RCOX, RSO$_2$X), would furnish intermediate 13-3 (wherein X=Cl, Br). Cross coupling with a vinyl metal species 13-4 such as vinyltributylstannane, followed by oxidative cleavage of the olefin (e.g., OsO$_4$, NaIO$_4$) would afford aldehyde 13-5. Formation of the hydrazide gives 13-6, and oxidative cyclization with a suitable reagent such as MnO$_2$ or PhI(OAc)$_2$ then affords triazole 13-7. The halogen can optionally be cross coupled with $R^6$-M to provide intermediates 13-8. Selective deprotonation of the triazole ring with a strong base such as LiTMP and reaction with an electrophilic halogen source (e.g., I$_2$) would afford 13-9. The halogen can optionally be cross coupled with $R^5$-M to give compounds 13-10. Conversion of the ester in 13-10 to the ketone 13-11 can be performed as described in Scheme 3. Ketones 13-11 can be treated with one of the conditions of Scheme 2 to provide an amine that can be converted to compounds of the invention 13-12 according to Scheme 1.

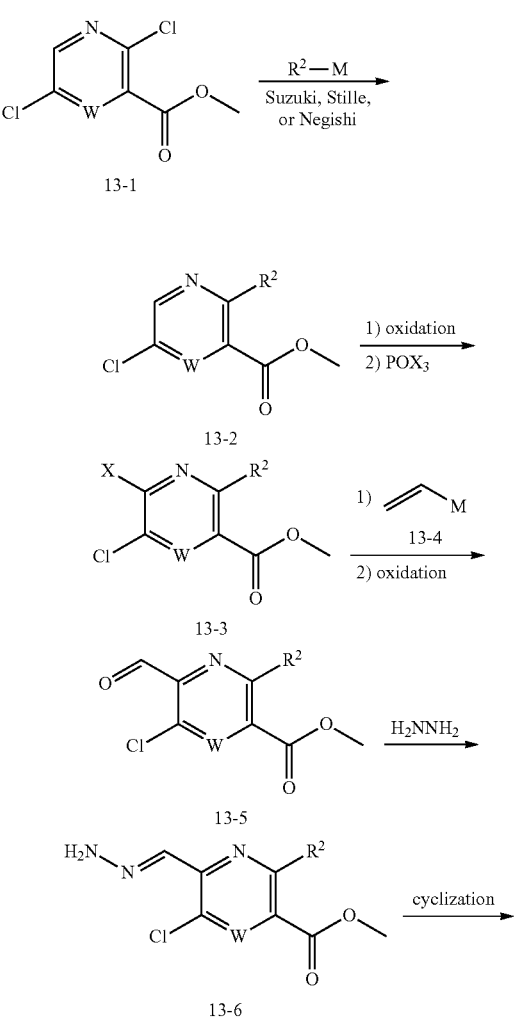

Scheme 13.

-continued

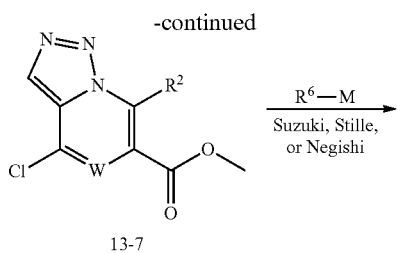

13-7

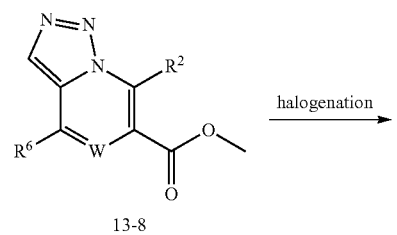

13-8

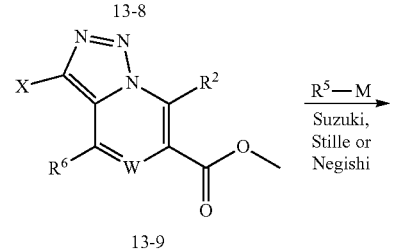

13-9

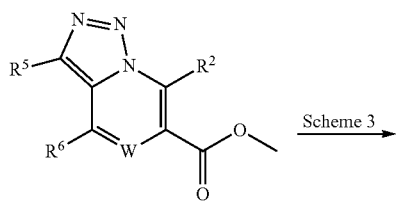

13-10

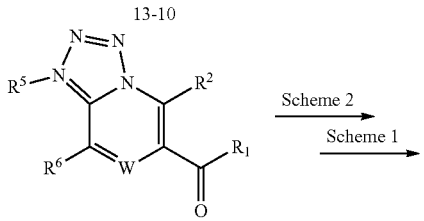

13-12

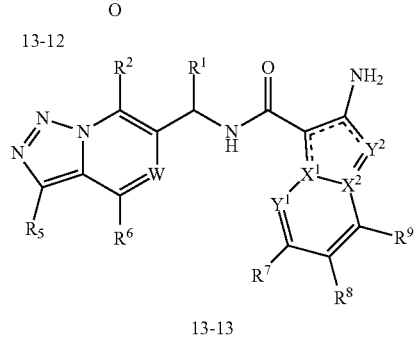

13-13

Compounds of the Formula I wherein W═C—H, $Z^1$═C, $Z^2$═N, $X^3$═N, $X^4$═N, $X^5$═CR$^5$ can be prepared as shown in Scheme 14. Nitro-containing starting materials 1-1 can be reduced to the aniline 1-2. Cyclization of 1-2 with a reagent such as amyl nitrite can give indazole 1-3. Demethylation of 1-3 using BBr$_3$ or a strong acid can give the phenol 1-4.

Phenol 1-4 can be converted to the triflate 1-5 under standard conditions with triflic anhydride. Protection of the indazole nitrogens can be accomplished to give 1-6 along with its regioisomer. Displacement of the triflate with an appropriate amine can give 1-7. The ketone in 1-7 can be converted to an amine by various methods as shown in Scheme 3 to furnish amine 1-8. Amine 1-8 can be coupled with an optionally protected carboxylic acid such as 1-2 (Scheme 1) by various methods as shown in Scheme 1. After coupling, any chosen protecting groups can be removed under conditions suitable for their removal, that are also compatible with the functionality present in the resulting compounds of the Formula I. It will be recognized by one skilled in the art that the order of steps in Scheme 14 can be changed in consideration of compatibility of functional groups present in the intermediates.

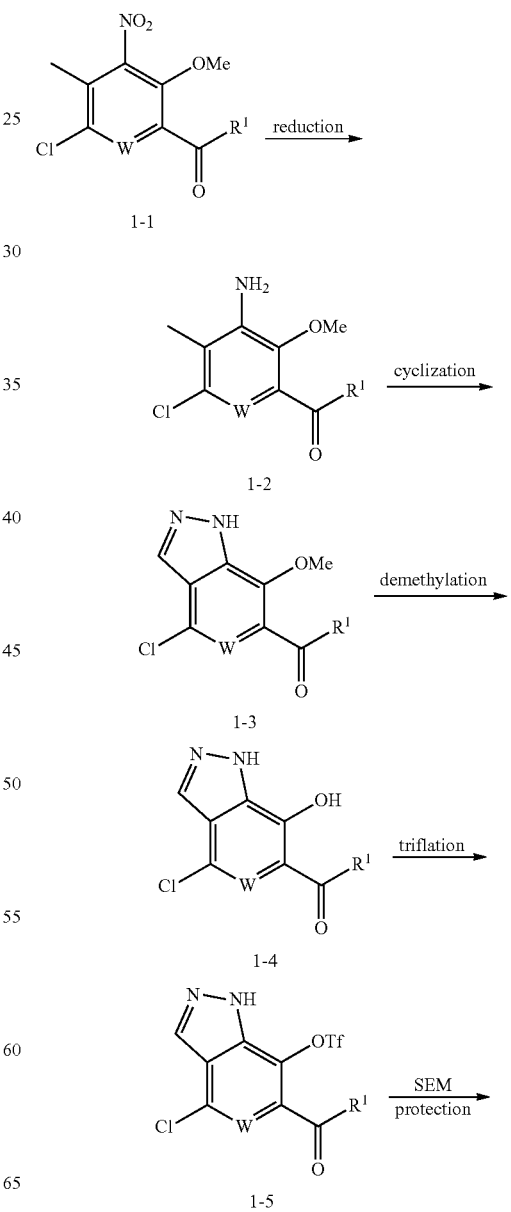

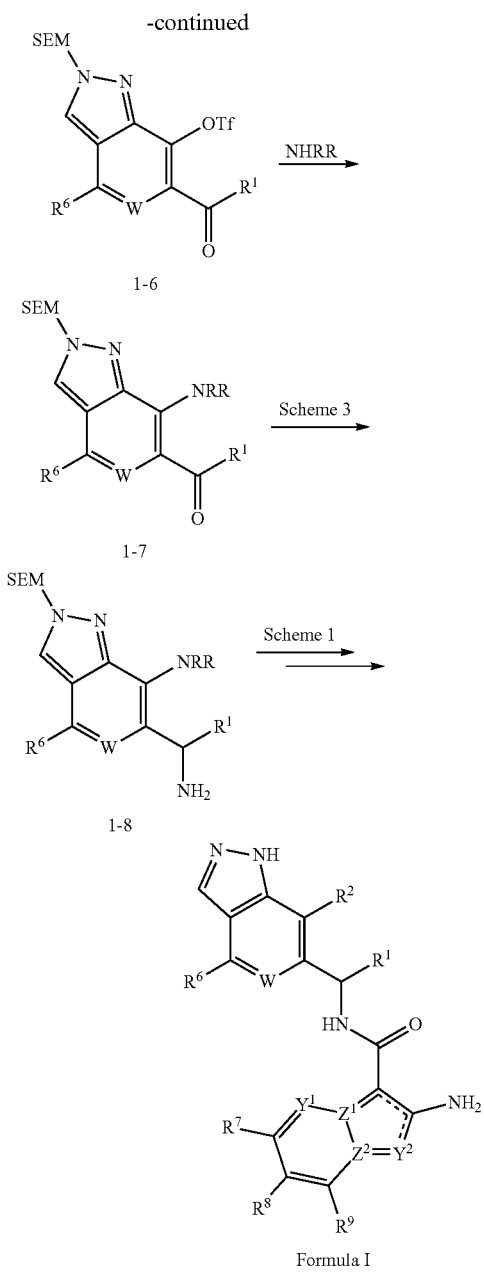

Formula I

The reactions for preparing compounds described herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, (e.g., temperatures which can range from the solvent's freezing temperature to the solvent's boiling temperature). A given reaction can be carried out in one solvent or a mixture of more than one solvent. Depending on the particular reaction step, suitable solvents for a particular reaction step can be selected by the skilled artisan.

The expressions, "ambient temperature" and "room temperature" or "rt" as used herein, are understood in the art, and refer generally to a temperature, e.g. a reaction temperature, that is about the temperature of the room in which the reaction is carried out, for example, a temperature from about 20° C. to about 30° C.

Preparation of compounds described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3$^{rd}$ Ed., Wiley & Sons, Inc., New York (1999).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) and normal phase silica chromatography.

Methods of Use

The compounds, salts or stereoisomers thereof described herein inhibit activity of PI3Kγ kinase. Accordingly, the compounds, salts or stereoisomers described herein can be used in methods of inhibiting PI3Kγ kinase by contacting the kinase with any one or more of the compounds, salts, or compositions described herein. In some embodiments, the compounds or salts can be used in methods of inhibiting activity of PI3Kγ in an individual in need of said inhibition by administering a inhibiting amount of a compound or salt of described herein. In some embodiments, modulating is inhibiting. In some embodiments, the contacting is in vivo. In some embodiments, the contacting is ex vivo.

In some embodiments, the PI3Kγ includes a mutation. A mutation can be a replacement of one amino acid for another, or a deletion of one or more amino acids. In such embodiments, the mutation can be present in the kinase domain of the PI3Kγ.

In some embodiments, the compound or salt further inhibits PI3Kδ.

The compounds or salts described herein can be selective. By "selective" is meant that the compound binds to or inhibits PI3Kγ with greater affinity or potency, respectively, compared to at least one other kinase. In some embodiments, the compounds of the invention are selective inhibitors of PI3Kγ over PI3Kδ, PI3Kα, and PI3Kβ. In some embodiments, the compounds of the invention are selective inhibitors of PI3Kγ over PI3Kα and PI3Kγ. In some embodiments, selectivity can be at least about 2-fold, 3-fold, 5-fold, 10-fold, at or 20-fold over PI3Kδ as measured by the assays described herein. In some embodiments, selectivity can be tested at the $K_m$ ATP concentration of each enzyme. In some embodiments, the selectivity of compounds of the invention can be determined by cellular assays associated with particular PI3K kinase activity.

Another aspect of the present invention pertains to methods of treating a kinase PI3Kγ-associated disease or disorder in an individual (e.g., patient) by administering to the individual in need of such treatment a therapeutically effective amount or dose of one or more compounds of the present invention or a pharmaceutical composition thereof. A PI3Kγ-associated disease or disorder can include any disease, disorder or condition that is directly or indirectly linked to expression or activity of the PI3Kγ, including overexpression and/or abnormal activity levels.

In some embodiments, the disease or disorder is an autoimmune disease or disorder, cancer, cardiovascular disease, or neurodegenerative disease.

In some embodiments, the disease or disorder is lung cancer (e.g., non-small cell lung cancer), melanoma, pancreatic cancer, breast cancer, prostate cancer, liver cancer, color cancer, endometrial cancer, bladder cancer, skin cancer, cancer of the uterus, renal cancer, gastric cancer, or sarcoma. In some embodiments, the sarcoma is Askin's tumor, sarcoma botryoides, chondrosarcoma, Ewing's sarcoma, malignant hemangioendothelioma, malignant schwannoma, osteosarcoma, alveolar soft part sarcoma, angiosarcoma, cystosarcoma phyllodes, dermatofibrosarcoma protuberans, desmoid tumor, desmoplastic small round cell tumor, epithelioid sarcoma, extraskeletal chondrosarcoma, extraskeletal osteosarcoma, fibrosarcoma, gastrointestinal stromal tumor (GIST), hemangiopericytoma, hemangiosarcoma, Kaposi's sarcoma, leiomyosarcoma, liposarcoma, lymphangiosarcoma, lymphosarcoma, malignant peripheral nerve sheath tumor (MPNST), neurofibrosarcoma, rhabdomyosarcoma, synovial sarcoma, or undifferentiated pleomorphic sarcoma.

In some embodiments, the disease or disorder is acute myeloid leukemia (e.g., acute monocytic leukemia), small lymphocyctic lymphoma, chronic lymphocytic leukemia (CLL), chronic myelogenous leukemia (CML), multiple myeloma, T-cell actute lymphoblasic leukemia (T-ALL), cutaneous T-cell lymphoma, large granular lymphocytic leukemia, mature (peripheral) t-cell neoplasm (PTCL), anaplastic large cell lymphoma (ALCL), or lymphoblastic lymphoma. In some embodiments, the mature (peripheral) t-cell neoplasm (PTCL) is T-cell prolymphocytic leukemia, T-cell granular lymphocytic leukemia, aggressive NK-cell leukemia, mycosis fungoides/Sezary syndrome, naplastic large cell lymphoma (T-cell type), enteropathy type T-cell lymphoma, adult T-cell leukemia/lymphoma, or angioimmunoblastic T-cell lymphoma In some embodiments, the anaplastic large cell lymphoma (ALCL) is systemic ALCL or primary cutaneous ALCL.

In some embodiments, the disease or disorder is Burkitt's lymphoma, acute myeloblastic leukemia, chronic myeloid leukemia, non-Hodgkin's lymphoma, Hodgkin's lymphoma, hairy cell leukemia, Mantle cell lymphoma, small lymphocytic lymphoma, follicular lymphoma, lymphoplasmacytic lymphoma, extranodal marginal zone lymphoma, Waldenstrom's macroglobulinemia, prolymphocytic leukemia, acute lymphoblastic leukemia, myelofibrosis, mucosa-associated lymphatic tissue (MALT) lymphoma, mediastinal (thymic) large B-cell lymphoma, lymphomatoid granulomatosis, splenic marginal zone lymphoma, primary effusion lymphoma, intravascular large B-cell lymphoma, plasma cell leukemia, extramedullary plasmacytoma, smouldering myeloma (aka asymptomatic myeloma), monoclonal gammopathy of undetermined significance (MGUS), or diffuse large B cell lymphoma.

In some embodiments, the non-Hodgkin's lymphoma (NHL) is relapsed NHL, refractory NHL, recurrent follicular NHL, indolent NHL (iNHL), or aggressive NHL (aNHL).

In some embodiments, the diffuse large B cell lymphoma is activated B-cell like (ABC) diffuse large B cell lymphoma, or germinal center B cell (GCB) diffuse large B cell lymphoma.

In some embodiments, the Burkitt's lymphoma is endemic Burkitt's lymphoma, sporadic Burkitt's lymphoma, or Burkitt's-like lymphoma In some embodiments, the disease or disorder is rheumatoid arthritis, multiple sclerosis, systemic lupus erythematous, asthma, allergy, pancreatitis, psoriasis, anaphylaxis, glomerulonephritis, inflammatory bowel disease (e.g., Crohn's disease and ulcerative colitis), thrombosis, meningitis, encephalitis, diabetic retinopathy, benign prostatic hypertrophy, myasthenia gravis, Sjögren's syndrome, osteoarthritis, restenosis, or atherosclerosis.

In some embodiments, disease or disorder is heart hypertropy, cardiac myocyte dysfunction, chronic obstructive pulmonary disease (COPD), elevated blood pressure, ischemia, ischemia-reperfusion, vasoconstriction, anemia (e.g., hemolytic anemia, aplastic anemia, or pure red cell anemia), bacterial infection, viral infection, graft rejection, kidney disease, anaphylactic shock fibrosis, skeletal muscle atrophy, skeletal muscle hypertrophy, angiogenesis, sepsis, graft rejection, glomerulosclerosis, progressive renal fibrosis, idiopathic thrombocytopenic purpura (ITP), autoimmune hemolytic anemia, vasculitis, systemic lupus erythematosus, lupus nephritis, pemphigus, or membranous nephropathy.

In some embodiments, the disease or disorder is Alzheimer's disease, central nervous system trauma, or stroke.

In some embodiments, the idiopathic thrombocytopenic purpura (ITP) is relapsed ITP or refractory ITP.

In some embodiments, the vasculitis is Behcet's disease, Cogan's syndrome, giant cell arteritis, polymyalgia rheumatica (PMR), Takayasu's arteritis, Buerger's disease (thromboangiitis obliterans), central nervous system vasculitis, Kawasaki disease, polyarteritis nodosa, Churg-Strauss syndrome, mixed cryoglobulinemia vasculitis (essential or hepatitis C virus (HCV)-induced), Henoch-Schönlein purpura (HSP), hypersensitivity vasculitis, microscopic polyangiitis, Wegener's granulomatosis, or anti-neutrophil cytoplasm antibody associated (ANCA) systemic vasculitis (AASV).

The present invention further provides a compound described herein, or a pharmaceutically acceptable salt thereof, for use in any of the methods described herein.

The present invention further provides use of a compound described herein, or a pharmaceutically acceptable salt thereof, for the preparation of a medicament for use in any of the methods described herein.

As used herein, the term "contacting" refers to the bringing together of indicated moieties in an in vitro system or an in vivo system. For example, "contacting" a PI3K with a compound of the invention includes the administration of a compound of the present invention to an individual or patient, such as a human, having a PI3K, as well as, for example, introducing a compound of the invention into a sample containing a cellular or purified preparation containing the PI3K.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" can refer to one or more of (1) inhibiting the disease; for example, inhibiting a disease, condition or disorder in an individual who is experiencing or displaying the pathology or symptomatology of the disease, condition or disorder (i.e., arresting further development of the pathology and/or symptomatology); and (2) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

Combination Therapies

One or more additional pharmaceutical agents such as, for example, chemotherapeutics, anti-inflammatory agents, steroids, immunosuppressants, immune-oncology agents, metabolic enzyme inhibitors, chemokine receptor inhibitors, and phosphatase inhibitors, as well as Bcr-Abl, Flt-3, EGFR, HER2, JAK, c-MET, VEGFR, PDGFR, cKit, IGF-1R, RAF and FAK kinase inhibitors such as, for example, those described in WO 2006/056399. Other agents such as therapeutic antibodies can be used in combination with the compounds of the present invention for treatment of PI3K-associated diseases, disorders or conditions. The one or more additional pharmaceutical agents can be administered to a patient simultaneously or sequentially.

In some embodiments, the compounds of the present disclosure can be combined with one or more inhibitors of the following kinases for the treatment of cancer: Akt1, Akt2, Akt3, TGF-βR, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, CSFIR, KIT, FLK-II, KDR/FLK-1, FLK-4, flt-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf. In some embodiments, the compounds of the present disclosure can be combined with one or more of the following inhibitors for the treatment of cancer or infections. Non-limiting examples of inhibitors that can be combined with the compounds of the present disclosure for treatment of cancer and infections include an FGFR inhibitor (FGFR1, FGFR2, FGFR3 or FGFR4, e.g., INCB54828, INCB62079 and INCB63904), a JAK inhibitor (JAK1 and/or JAK2, e.g., ruxolitinib, baricitinib or INCB39110), an IDO inhibitor (e.g., epacadostat and NLG919), an LSD1 inhibitor (e.g., INCB59872 and INCB60003), a TDO inhibitor, a PI3K-delta inhibitor (e.g., INCB50797 and INCB50465), a Pim inhibitor, a CSF1R inhibitor, a TAM receptor tyrosine kinases (Tyro-3, Axl, and Mer), an angiogenesis inhibitor, an interleukin receptor inhibitor, bromo and extra terminal family members inhibitors (for example, bromodomain inhibitors or BET inhibitors such as INCB54329 and INCB57643) and an adenosine receptor antagonist or combinations thereof.

In some embodiments, the compound or salt described herein is administered with a PI3Kδ inhibitor. In some embodiments, the compound or salt described herein is administered with a JAK inhibitor. In some embodiments, the compound or salt described herein is administered with a JAK1 or JAK2 inhibitor (e.g., baricitinib or ruxolitinib). In some embodiments, the compound or salt described herein is administered with a JAK1 inhibitor. In some embodiments, the compound or salt described herein is administered with a JAK1 inhibitor, which is selective over JAK2.

Example antibodies for use in combination therapy include but are not limited to Trastuzumab (e.g. anti-HER2), Ranibizumab (e.g. anti-VEGF-A), Bevacizumab (trade name Avastin, e.g. anti-VEGF, Panitumumab (e.g. anti-EGFR), Cetuximab (e.g. anti-EGFR), Rituxan (anti-CD20) and antibodies directed to c-MET.

One or more of the following agents may be used in combination with the compounds of the present invention and are presented as a non limiting list: a cytostatic agent, cisplatin, doxorubicin, taxotere, taxol, etoposide, irinotecan, camptostar, topotecan, paclitaxel, docetaxel, epothilones, tamoxifen, 5-fluorouracil, methoxtrexate, temozolomide, cyclophosphamide, SCH 66336, R115777, L778,123, BMS 214662, Iressa, Tarceva, antibodies to EGFR, Gleevec™, intron, ara-C, adriamycin, cytoxan, gemcitabine, Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, ELOXATIN™, Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17.alpha.-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, herceptin, Bexxar, Velcade, Zevalin, Trisenox, Xeloda, Vinorelbine, Porfimer, Erbitux, Liposomal, Thiotepa, Altretamine, Melphalan, Trastuzumab, Lerozole, Fulvestrant, Exemestane, Fulvestrant, Ifosfomide, Rituximab, C225, Campath, Clofarabine, cladribine, aphidicolon, rituxan, sunitinib, dasatinib, tezacitabine, Smll, fludarabine, pentostatin, triapine, didox, trimidox, amidox, 3-AP, and MDL-101,731.

Additional examples of chemotherapeutics include proteosome inhibitors (e.g., bortezomib), thalidomide, revlimid, and DNA-damaging agents such as melphalan, doxorubicin, cyclophosphamide, vincristine, etoposide, carmustine, and the like.

Example steroids include corticosteroids such as dexamethasone or prednisone.

Example Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491.

Example suitable Flt-3 inhibitors include compounds, and their pharmaceutically acceptable salts, as disclosed in WO 03/037347, WO 03/099771, and WO 04/046120.

Example suitable RAF inhibitors include compounds, and their pharmaceutically acceptable salts, as disclosed in WO 00/09495 and WO 05/028444.

Example suitable FAK inhibitors include compounds, and their pharmaceutically acceptable salts, as disclosed in WO 04/080980, WO 04/056786, WO 03/024967, WO 01/064655, WO 00/053595, and WO 01/014402.

In some embodiments, the compounds of the invention can be used in combination with one or more other kinase inhibitors including imatinib, particularly for treating patients resistant to imatinib or other kinase inhibitors.

In some embodiments, the compounds of the invention can be used in combination with a chemotherapeutic in the treatment of cancer, and may improve the treatment response as compared to the response to the chemotherapeutic agent alone, without exacerbation of its toxic effects. In some embodiments, the compounds of the invention can be used in combination with a chemotherapeutic provided herein. For example, additional pharmaceutical agents used in the treatment of multiple myeloma, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, RAF and FAK kinase inhibitors. Additive or synergistic effects are desirable outcomes of combining a PI3K inhibitor of the present invention with an additional agent.

In some embodiments, PI3Kγ inhibitors provided herein can be used in combination with one or more immune checkpoint inhibitors for the treatment of cancer as described herein. In one embodiment, the combination with one or more immune checkpoint inhibitors as described herein can be used for the treatment of melanoma. Exemplary immune checkpoint inhibitors include inhibitors against immune checkpoint molecules such as CD27, CD28, CD40, CD122, OX40, GITR, CD137, ICOS, A2AR, B7-H3, B7-H4, BTLA, CTLA-4, LAG3, TIM3, VISTA, PD-1, PD-L1 and PD-L2. In some embodiments, the compounds provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is a small molecule PD-1 inhibitor or a small molecule PD-L1 inhibitor.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), pidilizumab, SHR-1210, or AMP-224. In some embodiments, the anti-PD-1 monoclonal antibody is nivolumab or pembrolizumab. In some embodiments, the anti-PD1 antibody is pembrolizumab.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A or MEDI4736.

In some embodiments, the inhibitor of an immune checkpoint molecule is an inhibitor of CTLA-4, e.g., an anti-CTLA-4 antibody. In some embodiments, the anti-CTLA-4 antibody is ipilimumab.

In some embodiments, the inhibitor of an immune checkpoint molecule is an inhibitor of LAG3, e.g., an anti-LAG3 antibody. In some embodiments, the anti-LAG3 antibody is BMS-986016.

In some embodiments, the compounds of the invention can be used in combination with one or more metabolic enzyme inhibitors. In some embodiments, the metabolic enzyme inhibitor is an inhibitor of IDO1, TDO, or arginase. Examples of IDOL inhibitors include epacadostat and NGL919.

In some embodiments, the compounds of the invention can be used in combination with an inhibitor of JAK or PI3Kδ.

In some embodiments, the JAK inhibitor is selective for JAK1 and JAK1 over JAK3 and TYK2. In some embodiments, the JAK inhibitor is selective for JAK1 over JAK2, JAK3, and TYK2. In some embodiments, the JAK inhibitor inhibit JAK1 preferentially over JAK2 (e.g., have a JAK1/JAK2 $IC_{50}$ ratio >1). In some embodiments, the JAK inhibitor is about 10-fold more selective for JAK1 over JAK2.

In some embodiments, the JAK inhibitor is 3-cyclopentyl-3-[4-(7H-pyrrolo[2,3-d]pyrimidin-4-yl)-1H-pyrazol-1-yl]propanenitrile. In some embodiments, the JAK inhibitor is (3R)-3-cyclopentyl-3-[4-(7H-pyrrolo[2,3-d]pyrimidin-4-yl)-1H-pyrazol-1-yl]propanenitrile (ruxolitinib; also known as INCB018424). Ruxolitinib has an $IC_{50}$ of less than 10 nM at 1 mM ATP (assay D) at JAK1 and JAK2. 3-Cyclopentyl-3-[4-(7H-pyrrolo[2,3-d]pyrimidin-4-yl)-1H-pyrazol-1-yl]propanenitrile and ruxolitinib can be made by the procedure described in U.S. Pat. No. 7,598,257 (Example 67), filed Dec. 12, 2006, which is incorporated herein by reference in its entirety. In some embodiments, the inhibitor of JAK1 and/or JAK2 is (3R)-3-cyclopentyl-3-[4-(7H-pyrrolo[2,3-d]pyrimidin-4-yl)-1H-pyrazol-1-yl]propanenitrile phosphoric acid salt. In some embodiments, the inhibitor of JAK1 and/or JAK2 is 2-(3-(4-(7H-pyrrolo[2,3-d]pyrimidin-4-yl)-1H-pyrazol-1-yl)-1-(ethylsulfonyl)azetidin-3-yl)acetonitrile (baricitinib; also known as INCB028050).

In some embodiments, the JAK inhibitor is a compound of Table A, or a pharmaceutically acceptable salt thereof. The compounds in Table 1 are selective JAK1 inhibitors (selective over JAK2, JAK3, and TYK2). The $IC_{50}$s obtained by the method of Assay D at 1 mM ATP.

TABLE A

| # | Prep. | Name | Structure | JAK1 $IC_{50}$ (nM) | JAK2/ JAK1 |
|---|---|---|---|---|---|
| 1 | US 2014/012 1198 | ((2R,5S)-5-{2-[(1R)-1-hydroxy-ethyl]-1H-imidazo[4,5-d]-thieno[3,2-b]-pyridin-1-yl}-tetrahydro-2H-pyran-2-yl)-acetonitrile | 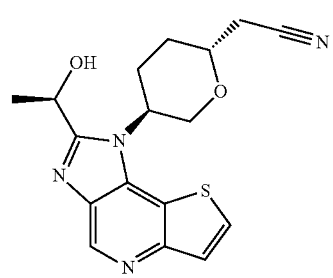 [SMILES: C[C@@H](O)c1nc2cnc3ccsc3c2n1[C@H]1CC[C@H](CC#N)OC1] | ++ | >10 |

TABLE A-continued

| # | Prep. | Name | Structure | JAK1 IC$_{50}$ (nM) | JAK2/JAK1 |
|---|---|---|---|---|---|
| 2 | US 2014/0343030 | 4-[3-(cyanomethyl)-3-(3',5'-dimethyl-1H,1'H-4,4'-bi-pyrazol-1-yl)-azetidin-1-yl]-2,5-difluoro-N-[(1S)-2,2,2-trifluoro-1-methylethyl]-benzamide | 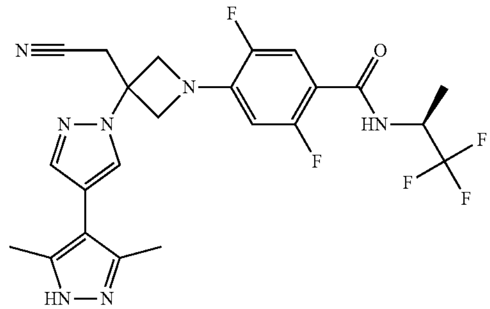 [SMILES: Cc1n[nH]c(C)c1-c1cnn(C2(CC#N)CN(c3cc(F)c(C(=O)N[C@@H](C)C(F)(F)F)cc3F)C2)c1] | +++ | >10 |
| 3 | US 2010/0298334 (Example 2)$^a$ | 3-[1-(6-chloro-pyridin-2-yl)-pyrrolidin-3-yl]-3-[4-(7H-pyrrolo[2,3-d]-pyrimidin-4-yl)-1H-pyrazol-1-yl]propanenitrile | 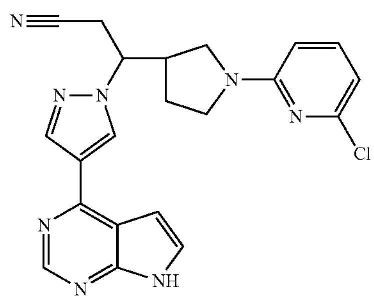 [SMILES: N#CCC(C1CCN(c2cccc(Cl)n2)C1)n1cc(-c2ncnc3[nH]ccc23)cn1] | + | >10 |
| 4 | US 2010/0298334 (Example 13c) | 3-(1-[1,3]-oxazolo[5,4-b]pyridin-2-ylpyrrolidin-3-yl)-3-[4-(7H-pyrrolo[2,3-d]-pyrimidin-4-yl)-1H-pyrazol-1-yl]propanenitrile | 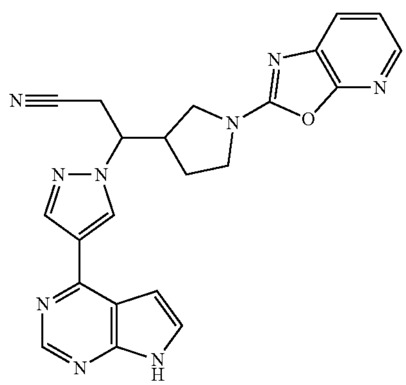 [SMILES: N#CCC(C1CCN(c2nc3cccnc3o2)C1)n1cc(-c2ncnc3[nH]ccc23)cn1] | + | >10 |
| 5 | US 2011/0059951 (Example 12) | 4-[(4-{3-cyano-2-[4-(7H-pyrrolo-[2,3-d]pyrimidin-4-yl)-1H-pyrazol-1-yl]propyl}-piperazin-1-yl)-carbonyl]-3-fluorobenzonitrile | 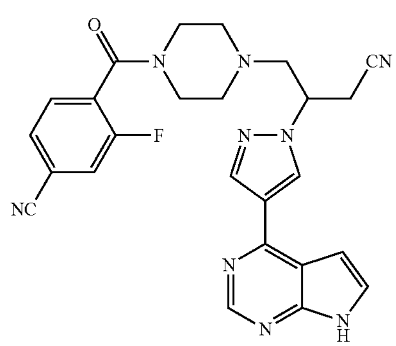 [SMILES: N#CCC(CN1CCN(C(=O)c2ccc(C#N)cc2F)CC1)n1cc(-c2ncnc3[nH]ccc23)cn1] | + | >10 |

TABLE A-continued

| # | Prep. | Name | Structure | JAK1 IC$_{50}$ (nM) | JAK2/ JAK1 |
|---|---|---|---|---|---|
| 6 | US 2011/ 0059951 (Example 13) | 4-[(4-{3-cyano-2-[3-(7H-pyrrolo-[2,3-d]pyrimidin-4-yl)-1H-pyrrol-1-yl]propyl}-piperazin-1-yl)-carbonyl]-3-fluorobenzonitrile | 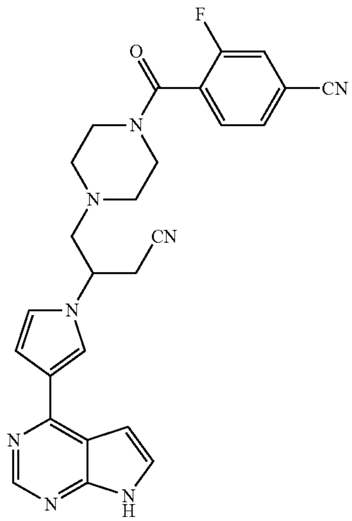 [SMILES: N#CCC(CN1CCN(C(=O)c2ccc(C#N)cc2F)CC1)n1ccc(-c2ncnc3[nH]ccc23)c1] | + | >10 |
| 7 | US 2011/ 0224190 (Example 1) | {1-{1-[3-Fluoro-2-(trifluoromethyl)isonicotinoyl]-piperidin-4-yl}-3-[4-(7H-pyrrolo[2,3-d]-pyrimidin-4-yl)-1H-pyrazol-1-yl]azetidin-3-yl}acetonitrile | 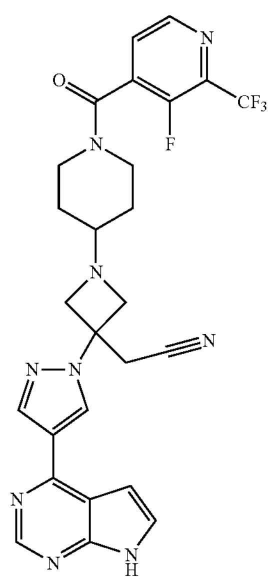 [SMILES: N#CCC1(n2cc(-c3ncnc4[nH]ccc34)cn2)CN(C2CCN(C(=O)c3ccnc(C(F)(F)F)c3F)CC2)C1] | + | >10 |

TABLE A-continued
| # | Prep. | Name | Structure | JAK1 IC$_{50}$ (nM) | JAK2/ JAK1 |
|---|---|---|---|---|---|
| 8 | US 2011/ 0224190 (Example 154) | 4-{3-(Cyano-methyl)-3-[4-(7H-pyrrolo[2,3-d]pyrimidin-4-yl)-1H-pyrazol-1-yl]azetidin-1-yl}-N-[4-fluoro-2-(trifluoro-methyl)phenyl]-piperidine-1-carboxamide | 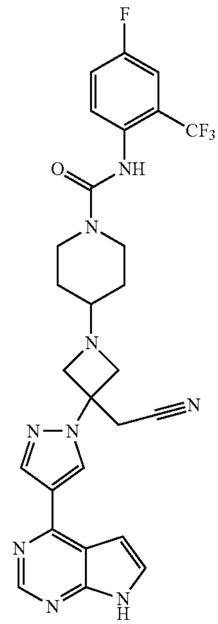 [SMILES: N#CCC1(n2cc(-c3ncnc4[nH]ccc34)cn2)CN(C2CCN(C(=O)Nc3ccc(F)cc3C(F)(F)F)CC2)C1] | + | >10 |
| 9 | US 2011/ 0224190 (Example 85) | [3-[4-(7H-pyrrolo[2,3-d]-pyrimidin-4-yl)-1H-pyrazol-1-yl]-1-(1-{[2-(trifluoromethyl)-pyrimidin-4-yl]-carbonyl}piperi-din-4-yl)azetidin-3-yl]acetonitrile | 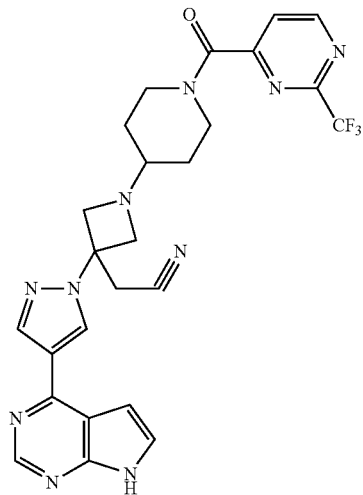 [SMILES: N#CCC1(n2cc(-c3ncnc4[nH]ccc34)cn2)CN(C2CCN(C(=O)c3ccnc(C(F)(F)F)n3)CC2)C1] | + | >10 |

TABLE A-continued

| # | Prep. | Name | Structure | JAK1 IC$_{50}$ (nM) | JAK2/JAK1 |
|---|---|---|---|---|---|
| 10 | US 2012/0149681 (Example 7b) | [trans-1-[4-(7H-pyrrolo[2,3-d]-pyrimidin-4-yl)-1H-pyrazol-1-yl]-3-(4-{[2-(trifluoromethyl)-pyrimidin-4-yl]-carbonyl}piperazin-1-yl)cyclobutyl]acetonitrile | 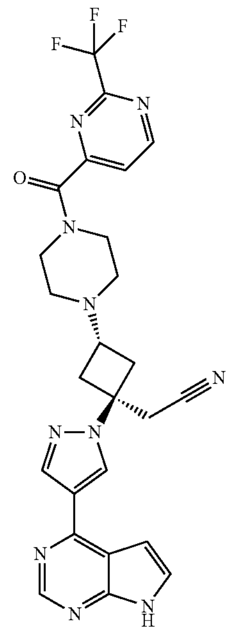 [SMILES: N#CC[C@]1(n2cc(-c3ncnc4[nH]ccc34)cn2)C[C@H](N2CCN(C(=O)c3ccnc(C(F)(F)F)n3)CC2)C1] | + | >10 |
| 11 | US 2012/0149681 (Example 157) | {trans-3-(4-{[4-[(3-hydroxy-azetidin-1-yl-[methyl]-6-(trifluoromethyl)-pyridin-2-yl]-oxy}piperidin-1-yl)-1-[4-(7H-pyrrolo[2,3-d]-pyrimidin-4-yl)-1H-pyrazol-1-yl]cyclobutyl}-acetonitrile | 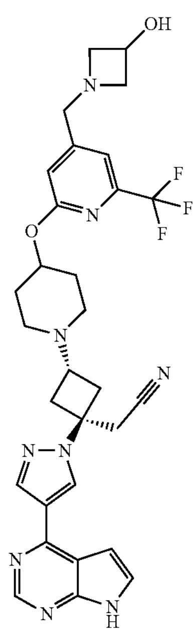 [SMILES: N#CC[C@]1(n2cc(-c3ncnc4[nH]ccc34)cn2)C[C@H](N2CCC(Oc3cc(CN4CC(O)C4)cc(C(F)(F)F)n3)CC2)C1] | + | >10 |

TABLE A-continued

| # | Prep. | Name | Structure | JAK1 IC$_{50}$ (nM) | JAK2/ JAK1 |
|---|---|---|---|---|---|
| 12 | US 2012/ 0149681 (Example 161) | {trans-3-(4-{[4-{[(2S)-2-(hydroxymethyl)-pyrrolidin-1-yl]-methyl}-6-(trifluoromethyl)-pyridin-2-yl]-oxy}piperidin-1-yl)-1-[4-(7H-pyrrolo[2,3-d]-pyrimidin-4-yl)-1H-pyrazol-1-yl]cyclobutyl}-acetonitrile | 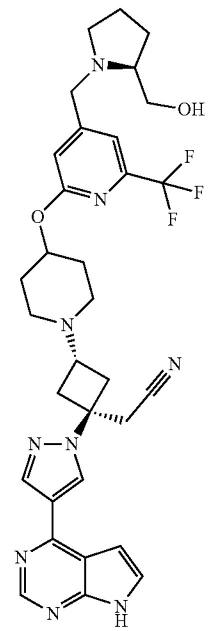 [SMILES: N#CC[C@]1(n2cc(-c3ncnc4[nH]ccc34)cn2)C[C@H](N2CCC(Oc3cc(CN4CCC[C@H]4CO)cc(C(F)(F)F)n3)CC2)C1] | + | >10 |
| 13 | US 2012/ 0149681 (Example 162) | {trans-3-(4-{[4-{[(2R)-2-(hydroxymethyl)-pyrrolidin-1-yl]-methyl}-6-(tri-fluoromethyl)-pyridin-2-yl]-oxy}piperidin-1-yl)-1-[4-(7H-pyrrolo[2,3-d]-pyrimidin-4-yl)-1H-pyrazol-1-yl]cyclobutyl}-acetonitrile | 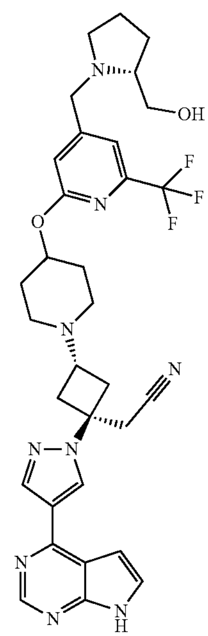 [SMILES: N#CC[C@]1(n2cc(-c3ncnc4[nH]ccc34)cn2)C[C@H](N2CCC(Oc3cc(CN4CCC[C@@H]4CO)cc(C(F)(F)F)n3)CC2)C1] | + | >10 |
| 14 | US 2012/ 0149682 (Example 20)[b] | 4-(4-{3-[(dimeth-ylamino)methyl]-5-fluorophenoxy}-piperidin-1-yl)-3-[4-(7H-pyrrolo-[2,3-d]pyrimidin-4-yl)-1H-pyrazol-1-yl]butanenitrile | 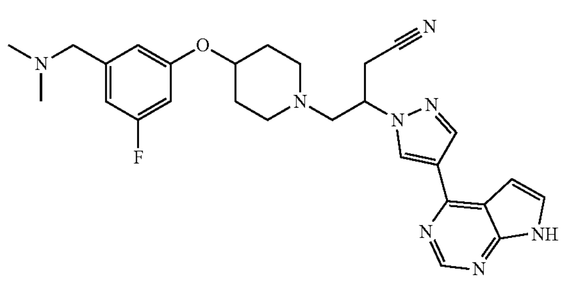 [SMILES: CN(C)Cc1cc(F)cc(OC2CCN(CC(CC#N)n3cc(-c4ncnc5[nH]ccc45)cn3)CC2)c1] | + | >10 |

TABLE A-continued

| # | Prep. | Name | Structure | JAK1 IC$_{50}$ (nM) | JAK2/JAK1 |
|---|---|---|---|---|---|
| 15 | US 2013/0018034 (Example 18) | 5-{3-(cyanomethyl)-3-[4-(7H-pyrrolo[2,3-d]pyrimidin-4-yl)-1H-pyrazol-1-yl]azetidin-1-yl}-N-isopropylpyrazine-2-carboxamide | 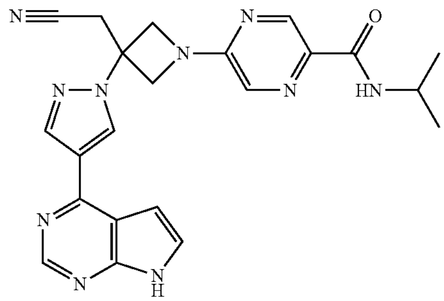 [SMILES: CC(C)NC(=O)c1cnc(N2CC(CC#N)(n3cc(-c4ncnc5[nH]ccc45)cn3)C2)cn1] | + | >10 |
| 16 | US 2013/0018034 (Example 28) | 4-{3-(cyanomethyl)-3-[4-(7H-pyrrolo[2,3-d]pyrimidin-4-yl)-1H-pyrazol-1-yl]azetidin-1-yl}-2,5-difluoro-N-[(1S)-2,2,2-trifluoro-1-methylethyl]-benzamide | 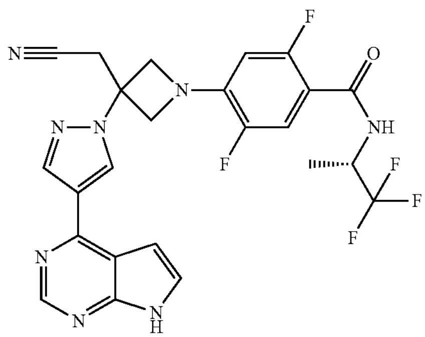 [SMILES: C[C@H](NC(=O)c1cc(F)c(N2CC(CC#N)(n3cc(-c4ncnc5[nH]ccc45)cn3)C2)cc1F)C(F)(F)F] | + | >10 |
| 17 | US 2013/0018034 (Example 34) | 5-{3-(cyanomethyl)-3-[4-(1H-pyrrolo[2,3-b]pyridin-4-yl)-1H-pyrazol-1-yl]-azetidin-1-yl}-N-isopropylpyrazine-2-carboxamide | 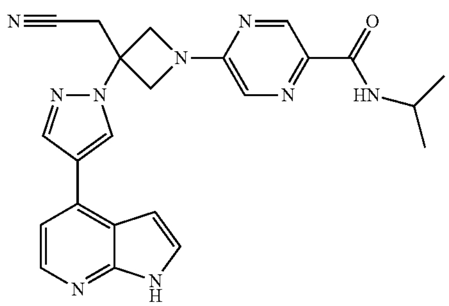 [SMILES: CC(C)NC(=O)c1cnc(N2CC(CC#N)(n3cc(-c4ccnc5[nH]ccc45)cn3)C2)cn1] | + | >10 |
| 18 | US 2013/0045963 (Example 45) | {1-(cis-4-{[6-(2-hydroxyethyl)-2-(trifluoromethyl)-pyrimidin-4-yl)-oxy}cyclohexyl)-3-[4-(7H-pyrrolo-[2,3-d]pyrimidin-4-yl)-1H-pyrazol-1-yl]azetidin-3-yl}acetonitrile | 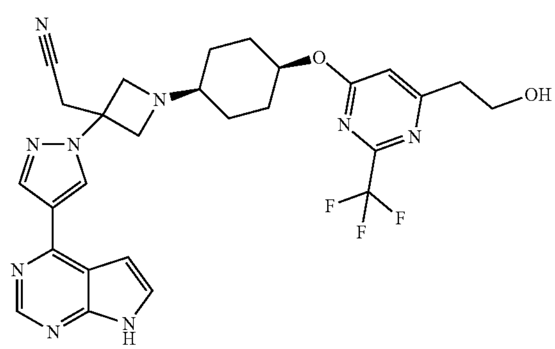 [SMILES: N#CCC1(n2cc(-c3ncnc4[nH]ccc34)cn2)CN([C@H]2CC[C@@H](Oc3cc(CCO)nc(C(F)(F)F)n3)CC2)C1] | + | >10 |

TABLE A-continued

| # | Prep. | Name | Structure | JAK1 IC$_{50}$ (nM) | JAK2/ JAK1 |
|---|---|---|---|---|---|
| 19 | US 2013/ 0045963 (Example 65) | {1-(cis-4-{[4-[(ethylamino)-methyl]-6-(tri-fluoromethyl)-pyridin-2-yl]-oxy}cyclohexyl)-3-[4-(7H-pyrrolo-[2,3-d]pyrimidin-4-yl)-1H-pyrazol-1-yl]azetidin-3-yl}acetonitrile | 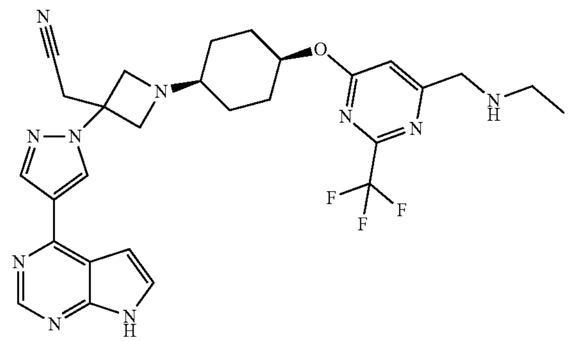 [SMILES: CCNCc1cc(O[C@H]2CC[C@@H](N3CC(CC#N)(n4cc(-c5ncnc6[nH]ccc56)cn4)C3)CC2)nc(C(F)(F)F)n1] | + | >10 |
| 20 | US 2013/ 0045963 (Example 69) | {1-{cis-4-{[4-(1-hydroxy-1-methylethyl)-6-(tri-fluoromethyl)-pyridin-2-yl]-oxy}cyclohexyl)-3-[4-(7H-pyrrolo-[2,3-d]pyrimidin-4-yl)-1H-pyrazol-1-yl]azetidin-3-yl}acetonitrile | 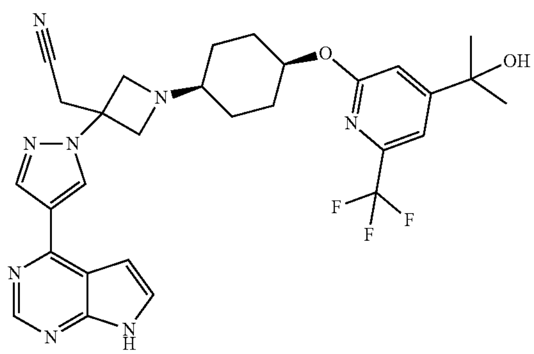 [SMILES: CC(C)(O)c1cc(O[C@H]2CC[C@@H](N3CC(CC#N)(n4cc(-c5ncnc6[nH]ccc56)cn4)C3)CC2)nc(C(F)(F)F)c1] | + | >10 |
| 21 | US 2013/ 0045963 (Example 95) | {1-(cis-4-{[4-{(3R)-3-hydroxy-pyrrolidin-1-yl]-methyl}-6-(tri-fluoromethyl)-pyridin-2-yl]-oxy}cyclohexyl)-3-[4-(7H-pyrrolo-[2,3-d]pyrimidin-4-yl)-1H-pyrazol-1-yl]azetidin-3-yl}acetonitrile | 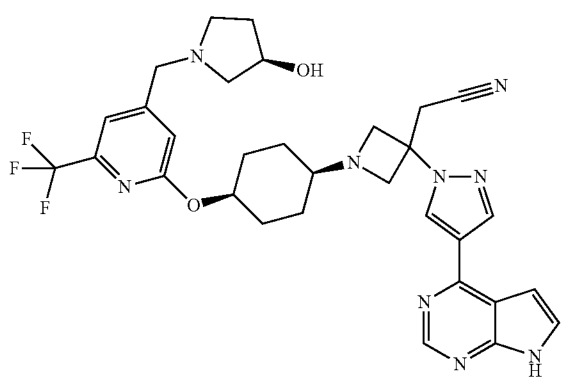 [SMILES: N#CCC1(n2cc(-c3ncnc4[nH]ccc34)cn2)CN([C@H]2CC[C@@H](Oc3cc(CN4CC[C@@H](O)C4)cc(C(F)(F)F)n3)CC2)C1] | + | >10 |
| 22 | US 2013/ 0045963 (Example 95) | {1-(cis-4-{[4-{[(3S)-3-hydroxy-pyrrolidin-1-yl]methyl}-6-(trifluoromethyl)-pyridin-2-yl]oxy}-cyclohexyl)-3-[4-(7H-pyrrolo[2,3-d]pyrimidin-4-yl)-1H-pyrazol-1-yl]-azetidin-3-yl}-acetonitrile | 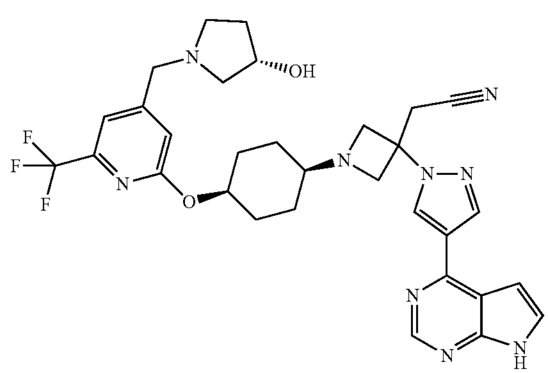 [SMILES: N#CCC1(n2cc(-c3ncnc4[nH]ccc34)cn2)CN([C@H]2CC[C@@H](Oc3cc(CN4CC[C@H](O)C4)cc(C(F)(F)F)n3)CC2)C1] | + | >10 |

TABLE A-continued

| # | Prep. | Name | Structure | JAK1 IC$_{50}$ (nM) | JAK2/JAK1 |
|---|---|---|---|---|---|
| 23 | US 2014/0005166 (Example 1) | {trans-3-(4-{[4-({[(1S)-2-hydroxy-1-methylethyl]amino}-methyl)-6-(trifluoromethyl)-pyridin-2-yl]-oxy}piperidin-1-yl)-1-[4-(7H-pyrrolo-[2,3-d]-pyrimidin-4-yl)-1H-pyrazol-1-yl]cyclobutyl}-acetonitrile | 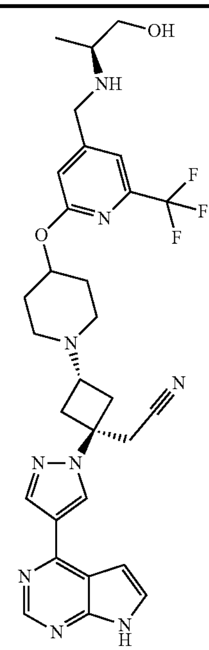 | + | >10 |
| 24 | US 2014/0005166 (Example 14) | {trans-3-(4-{[4-({[(2R)-2-hydroxypropyl]-amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}-acetonitrile | 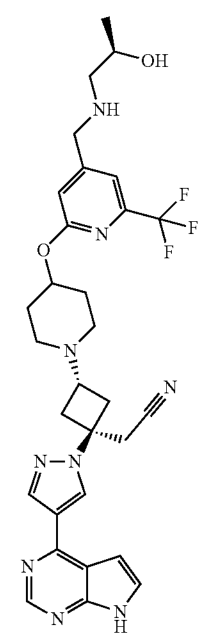 [SMILES: C[C@@H](O)CNCc1cc(OC2CCN([C@H]3C[C@](CC#N)(n4cc(-c5ncnc6[nH]ccc56)cn4)C3)CC2)nc(C(F)(F)F)c1] | + | >10 |

TABLE A-continued

| # | Prep. | Name | Structure | JAK1 IC$_{50}$ (nM) | JAK2/ JAK1 |
|---|---|---|---|---|---|
| 25 | US 2014/ 0005166 (Example 15) | {trans-3-(4-{[4-({[(2S)-2-hydroxypropyl]-amino}methyl)-6-(trifluoro-methyl)pyridin-2-yl]oxy}piperi-din-1-yl)-1-[4-(7H-pyrrolo-[2,3-d]pyrimidin-4-yl)-1H-pyrazol-1-yl]cyclobutyl}-acetonitrile | 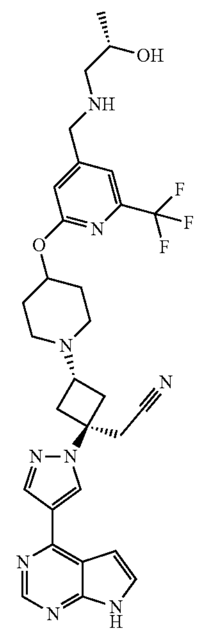 [SMILES: C[C@H](O)CNCc1cc(OC2CCN([C@H]3C[C@](CC#N)(n4cc(-c5ncnc6[nH]ccc56)cn4)C3)CC2)nc(C(F)(F)F)c1] | + | >10 |
| 26 | US 2014/ 0005166 (Example 20) | {trans-3-(4-{[4-(2-hydroxyethyl)-6-(trifluoro-methyl)pyridin-2-yl]oxy}piperidin-1-yl)-1-[4-(7H-pyrrolo[2,3-d]-pyrimidin-4-yl)-1H-pyrazol-1-yl]cyclobutyl}-acetonitrile | 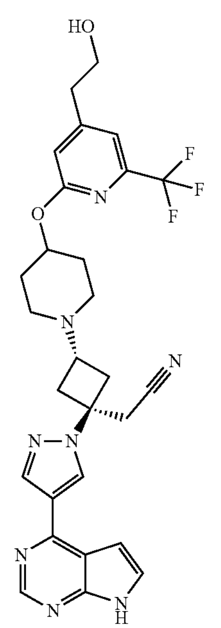 [SMILES: N#CC[C@]1(n2cc(-c3ncnc4[nH]ccc34)cn2)C[C@H](N2CCC(Oc3cc(CCO)cc(C(F)(F)F)n3)CC2)C1] | + | >10 |

+ means <10 nM (see Example D for assay conditions)

++ means ≤100 nM (see Example D for assay conditions)

+++ means ≤300 nM (see Examle D for assay conditions)

[a] Data for enantiomer 1

[b] Data for enantiomer 2

The PI3Kδ inhibitor can be selective. By "selective" is meant that the compound binds to or inhibits a kinase with greater affinity or potency, respectively, compared to at least one other kinase. In some embodiments, the PI3Kδ inhibitor is a selective inhibitors of PI3Kδ (e.g., over PI3Kα, PI3Kβ and PI3Kγ). In some embodiments, selectivity can be at least about 2-fold, 5-fold, 10-fold, at least about 20-fold, at least about 50-fold, at least about 100-fold, at least about 200-fold, at least about 500-fold or at least about 1000-fold. Selectivity can be measured by methods routine in the art. In some embodiments, selectivity can be tested at the $K_m$ ATP concentration of each enzyme. In some embodiments, the selectivity of compounds described herein can be determined by cellular assays associated with particular PI3K kinase activity.

In some embodiments, the inhibitor of PI3Kδ is a compound shown in Table B. The compounds of Table B have been tested in Assay C and shown to be inhibitors of PI3Kδ with the $IC_{50}$s in Table B.

TABLE B

| # | Prep. | Name | Structure | PI3Kδ $IC_{50}$ (nM) |
|---|---|---|---|---|
| 27 | US 2011/0015212 (Example 10) | 7-(1-(9H-purin-6-yl-amino)ethyl)-6-(3-fluorophenyl)-3-methyl-5H-thiazolo-[3,2-a]pyrimidin-5-one | 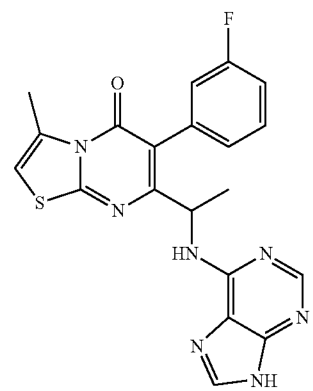 [SMILES: Cc1csc2nc(C(C)Nc3ncnc4[nH]cnc34)c(-c3cccc(F)c3)c(=O)n12] | + |
| 28 | US 2011/0015212 (Example 15) | (S)-7-(1-(9H-purin-6-ylamino)ethyl)-6-(3-fluorophenyl)-3-methyl-5H-thiazolo-[3,2-a]pyrimidin-5-one | 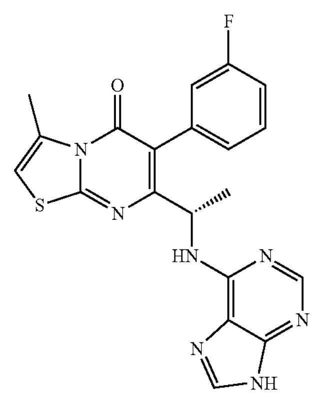 [SMILES: Cc1csc2nc([C@H](C)Nc3ncnc4[nH]cnc34)c(-c3cccc(F)c3)c(=O)n12] | + |
| 29 | US 2013/0059835 (Example 269) | 4-[1-(4-amino-3-methyl-1H-pyrazolo-[3,4-d]-pyrimidin-1-yl)-ethyl]-6-chloro-2-{1-[(2S)-2-hydroxy-propyl]azetidin-3-yl}-3-methoxy-benzonitrile | 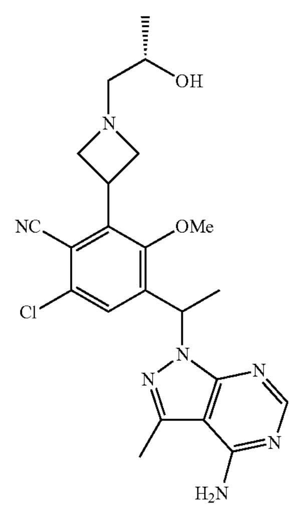 [SMILES: COc1c(C(C)n2nc(C)c3c(N)ncnc32)cc(Cl)c(C#N)c1C1CN(C[C@H](C)O)C1] | + |

TABLE B-continued

| # | Prep. | Name | Structure | PI3Kδ IC$_{50}$ (nM) |
|---|---|---|---|---|
| 30 | US 2013/ 0039833 (Example 268) | 4-[1-(4-amino-3-methyl-1H-pyrazolo[3,4-d]-pyrimidin-1-yl)-ethyl]-6-chloro-2-[1-(2-hydroxyethyl)-azetidin-3-yl]-3-methoxybenzonitrile | 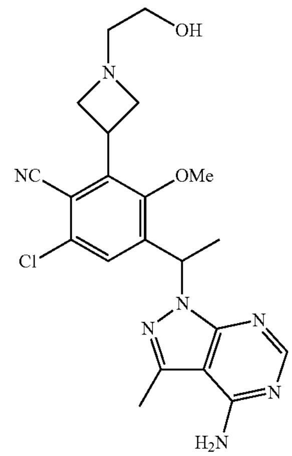 [SMILES: COc1c(C(C)n2nc(C)c3c(N)ncnc32)cc(Cl)c(C#N)c1C1CN(CCO)C1] | + |
| 31 | US 2013/ 0059835 (Example 314) | 5-{3-[1-(4-amino-3-methyl-1H-pyrazolo[3,4-d]-pyrimidin-1-yl)ethyl-6-cyano-2-ethoxy-5-methylphenyl}-N,N-dimethylpyridine-2-carboxamide | 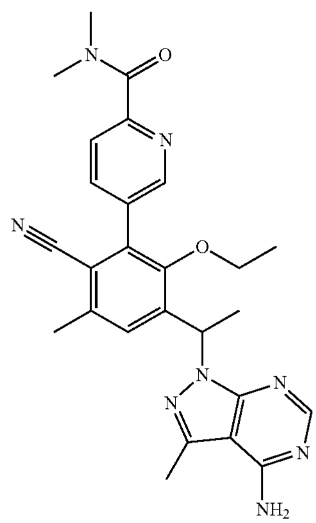 [SMILES: CCOc1c(C(C)n2nc(C)c3c(N)ncnc32)cc(C)c(C#N)c1-c1ccc(C(=O)N(C)C)nc1] | + |
| 32a, 32b, 32c, 32d (four diastereomers)) Compound 32a, 32b, 32c, and 32d are Examples 345, 346, 347, and 348 respectively | US 2013/ 0059835 (Example 345-348 | 4-{3-[1-(4-amino-3-methyl-1H-pyrazolo[3,4-d]-pyrimidin-1-yl)-ethyl]-5-chloro-2-ethoxy-6-fluoro-phenyl}pyrrolidin-2-one | | 32a (++), 32b (+) 32c (+) 32d (+++) |

TABLE B-continued

| # | Prep. | Name | Structure | PI3Kδ IC$_{50}$ (nM) |
|---|---|---|---|---|
| 33 | US 2011/0183985 (Example 17-single enantiomer) | N-{1-[5-chloro-8-(3-fluorophenyl)-cinnolin-7-yl]ethyl}-9H-purin-6-amine | 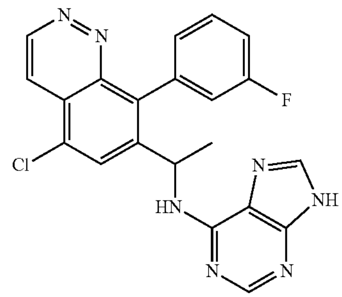 [SMILES: CC(Nc1ncnc2[nH]cnc12)c1cc(Cl)c2ccnnc2c1-c1cccc(F)c1] | + |
| 34 | US 2012/0157430 | 4-chloro-3'-fluoro-3-methyl-6-[1-(9H-purin-6-ylamino)-ethyl]biphenyl-2-carbonitrile | 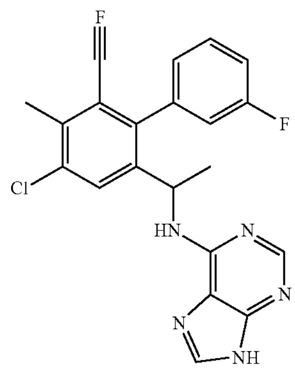 | +++ |

+ means <50 nM
++ means 50 nM to 200 nM
+++ means 50 nM to 100 nM

In some embodiments, the inhibitor of PI3Kδ is selected from:
(S)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one;
(R)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one;
(S)-4-(3-((R)-1-(4-amino-3-methyl-1H-pyrazolo[3,4-d]pyrimidin-1-yl)ethyl)-5-chloro-2-ethoxy-6-fluorophenyl)pyrrolidin-2-one;
(R)-4-(3-((R)-1-(4-amino-3-methyl-1H-pyrazolo[3,4-d]pyrimidin-1-yl)ethyl)-5-chloro-2-ethoxy-6-fluorophenyl)pyrrolidin-2-one;
N-{(1S)-1-[5-chloro-8-(3-fluorophenyl)cinnolin-7-yl]ethyl}-9H-purin-6-amine;
and pharmaceutically acceptable salts of any of the aforementioned.

In some embodiments, the inhibitor of PI3Kδ is selected from:
4-[(R)-1-(4-amino-3-methyl-1H-pyrazolo[3,4-d]pyrimidin-1-yl)ethyl]-6-chloro-2-{1-[(2S)-2-hydroxypropyl]azetidin-3-yl}-3-methoxybenzonitrile;
4-[1(R)-(4-amino-3-methyl-1H-pyrazolo[3,4-d]pyrimidin-1-yl)ethyl]-6-chloro-2-[1-(2-hydroxyethyl)azetidin-3-yl]-3-methoxybenzonitrile;
5-{3-[1(R)-(4-amino-3-methyl-1H-pyrazolo[3,4-d]pyrimidin-1-yl)ethyl]-6-cyano-2-ethoxy-5-methylphenyl}-N,N-dimethylpyridine-2-carboxamide;
4-[(S)-1-(4-amino-3-methyl-1H-pyrazolo[3,4-d]pyrimidin-1-yl)ethyl]-6-chloro-2-{1-[(2S)-2-hydroxypropyl]azetidin-3-yl}-3-methoxybenzonitrile;
4-[1(S)-(4-amino-3-methyl-1H-pyrazolo-[3,4-d]pyrimidin-1-yl)ethyl]-6-chloro-2-[1-(2-hydroxyethyl)azetidin-3-yl]-3-methoxybenzonitrile;
5-{3-[1(S)-(4-amino-3-methyl-1H-pyrazolo[3,4-d]pyrimidin-1-yl)ethyl]-6-cyano-2-ethoxy-5-methylphenyl}-N,N-dimethylpyridine-2-carboxamide;
and pharmaceutically acceptable salts of any of the aforementioned.

In some embodiments, PI3Kγ inhibitors provided herein can be administered in combination with an inhibitor of JAK1 and/or JAK2 or an inhibitor of PI3Kδ.

The agents can be combined with the present compound in a single or continuous dosage form, or the agents can be administered simultaneously or sequentially as separate dosage forms.

In some embodiments, a corticosteroid such as dexamethasone is administered to a patient in combination with the compounds of the invention where the dexamethasone is administered intermittently as opposed to continuously.

In some further embodiments, combinations of the compounds of the invention with other therapeutic agents can be administered to a patient prior to, during, and/or after a bone marrow transplant or stem cell transplant.

Pharmaceutical Formulations and Dosage Forms

When employed as pharmaceuticals, the compounds of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the invention or a pharmaceutically acceptable salt thereof, in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions of the invention contain from about 5 to about 50 mg of the active ingredient. One having ordinary skill in the art will appreciate that this embodies compositions containing about 5 to about 10, about 10 to about 15, about 15 to about 20, about 20 to about 25, about 25 to about 30, about 30 to about 35, about 35 to about 40, about 40 to about 45, or about 45 to about 50 mg of the active ingredient.

In some embodiments, the compositions of the invention contain from about 50 to about 500 mg of the active ingredient. One having ordinary skill in the art will appreciate that this embodies compositions containing about 50 to about 100, about 100 to about 150, about 150 to about 200, about 200 to about 250, about 250 to about 300, about 350 to about 400, or about 450 to about 500 mg of the active ingredient.

In some embodiments, the compositions of the invention contain from about 500 to about 1000 mg of the active ingredient. One having ordinary skill in the art will appreciate that this embodies compositions containing about 500 to about 550, about 550 to about 600, about 600 to about 650, about 650 to about 700, about 700 to about 750, about 750 to about 800, about 800 to about 850, about 850 to about 900, about 900 to about 950, or about 950 to about 1000 mg of the active ingredient.

Similar dosages may be used of the compounds described herein in the methods and uses of the invention.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g. glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the invention. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the invention can further include one or more additional pharmaceutical agents such as a chemotherapeutic, steroid, anti-inflammatory compound, or immunosuppressant, examples of which are listed herein.

Labeled Compounds and Assay Methods

Another aspect of the present invention relates to labeled compounds of the invention (radio-labeled, fluorescent-labeled, etc.) that would be useful not only in imaging techniques but also in assays, both in vitro and in vivo, for localizing and quantitating PI3K in tissue samples, including human, and for identifying PI3K ligands by inhibition binding of a labeled compound. Accordingly, the present invention includes PI3K assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled compounds will depend on the specific application of that radio-labeled compound. For example, for in vitro PI3K labeling and competition assays, compounds that incorporate $^3$H, $^{14}$C, $^{82}$Br, $^{125}$I, $^{131}$I, $^{35}$S or will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is understood that a "radio-labeled" or "labeled compound" is a compound that has incorporated at least one radionuclide. In some embodiments the radionuclide is selected from the group consisting of $^3$H, $^{14}$C, $^{125}$I, $^{35}$S and $^{82}$Br.

The present invention can further include synthetic methods for incorporating radio-isotopes into compounds of the invention. Synthetic methods for incorporating radio-isotopes into organic compounds are well known in the art, and an ordinary skill in the art will readily recognize the methods applicable for the compounds of invention.

A labeled compound of the invention can be used in a screening assay to identify/evaluate compounds. For example, a newly synthesized or identified compound (i.e., test compound) which is labeled can be evaluated for its ability to bind a PI3K by monitoring its concentration variation when contacting with the PI3K, through tracking of the labeling. For example, a test compound (labeled) can be evaluated for its ability to reduce binding of another compound which is known to bind to a PI3K (i.e., standard compound). Accordingly, the ability of a test compound to compete with the standard compound for binding to the PI3K directly correlates to its binding affinity. Conversely, in some other screening assays, the standard compound is labeled and test compounds are unlabeled.

Accordingly, the concentration of the labeled standard compound is monitored in order to evaluate the competition between the standard compound and the test compound, and the relative binding affinity of the test compound is thus ascertained.

Kits

The present invention also includes pharmaceutical kits useful, for example, in the treatment or prevention of PI3K-associated diseases or disorders, such as cancer, which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to be $PI3K_7$ inhibitors according to at least one assay described herein.

EXAMPLES

Preparatory LC-MS purifications of some of the compounds prepared were performed on Waters mass directed fractionation systems. The basic equipment setup, protocols, and control software for the operation of these systems have been described in detail in the literature (see e.g. "Two-Pump At Column Dilution Configuration for Preparative LC-MS", K. Blom, *J. Combi. Chem.*, 4, 295 (2002); "Optimizing Preparative LC-MS Configurations and Methods for Parallel Synthesis Purification", K. Blom, R. Sparks, J. Doughty, G. Everlof, T. Hague, A. Combs, *J. Combi. Chem.*, 5, 670 (2003); and "Preparative LC-MS Purification: Improved Compound Specific Method Optimization", K. Blom, B. Glass, R. Sparks, A. Combs, *J. Combi. Chem.*, 6, 874-883 (2004)). The compounds separated were typically subjected to analytical liquid chromatography mass spectrometry (LCMS) for purity analysis under the following conditions: Instrument; Agilent 1100 series, LC/MSD, Column: Waters Sunfire™ $C_{18}$ 5 μm, 2.1×50 mm, Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 μm, 19×100 mm column, eluting with mobile phase A: 0.1% TFA (trifluoroacetic acid) in water and mobile phase B: acetonitrile; the flow rate was 30 mL/minute, the separating gradient was optimized for each compound using the Compound Specific Method Optimization protocol as described in the literature (see e.g. "Preparative LCMS Purification: Improved Compound Specific Method Optimization", K. Blom, B. Glass, R. Sparks, A. Combs, *J. Comb. Chem.*, 6, 874-883 (2004)). Typically, the flow rate used with the 30×100 mm column was 60 mL/minute.

pH=10 purifications: Waters XBridge $C_{18}$ 5 μm, 19×100 mm column, eluting with mobile phase A: 0.15% $NH_4OH$ in water and mobile phase B: acetonitrile; the flow rate was 30 mL/minute, the separating gradient was optimized for each compound using the Compound Specific Method Optimization protocol as described in the literature (see e.g. "Preparative LCMS Purification: Improved Compound Specific Method Optimization", K. Blom, B. Glass, R. Sparks, A. Combs, *J. Comb. Chem.*, 6, 874-883 (2004)). Typically, the flow rate used with 30×100 mm column was 60 mL/minute.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Example 1. 2-amino-N-[1-(4-chloro-7-ethoxy-2-methyl-2H-indazol-6-yl)ethyl]pyrazolo[1,5-a]pyrimidine-3-carboxamide trifluoroacetate

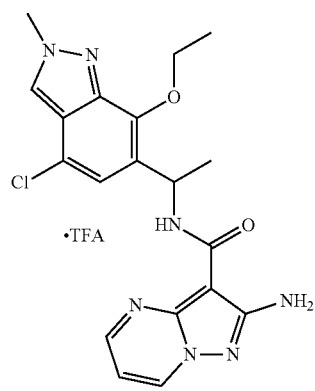 [SMILES: CCOc1c(C(C)NC(=O)c2c(N)nn3cccnc23)cc(Cl)c2cn(C)nc12]

Step 1. 1-(5-chloro-2-ethoxy-4-methyl-3-nitrophenyl)ethanone

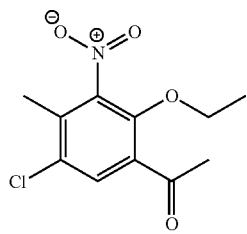 [SMILES: CCOc1c(C(C)=O)cc(Cl)c(C)c1[N+](=O)[O-]]

To a solution of 1-(5-chloro-2-hydroxy-4-methyl-3-nitrophenyl)ethanone (1.0 g, 4.4 mmol, from Oakwood) in DMF (10 mL) was added potassium carbonate (1.2 g, 8.7 mmol) and iodoethane (0.52 mL, 6.5 mmol), and the reaction mixture was heated to 60° C. for 1.5 h. After cooling to room temperature, the reaction mixture was partitioned between water (30 mL) and EtOAc (30 mL), and the layers were separated. The aqueous layer was extracted with EtOAc (20 mL), and the combined organic layers were dried over MgSO$_4$, filtered, and concentrated. The residue was purified by flash chromatography on silica gel (0-20% EtOAc/hexanes) to afford the title compound (1.07 g, 95%) as a colorless oil. LCMS calculated for $C_{11}H_{13}ClNO_4(M+H)^+$: m/z=258.0; found: 258.0.

Step 2. 1-(3-amino-5-chloro-2-ethoxy-4-methylphenyl)ethanone

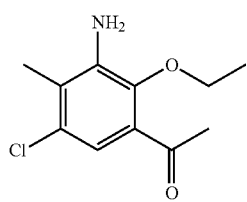

To a solution of 1-(5-chloro-2-ethoxy-4-methyl-3-nitrophenyl)ethanone (1.0 g, 3.9 mmol) in MeOH (10 mL) was added Pt/C (5 wt %, 200 mg, 0.04 mmol). The atmosphere was replaced with hydrogen and the reaction mixture was stirred under balloon pressure of hydrogen overnight. The reaction mixture was filtered through a pad of celite, which was washed with additional MeOH (20 mL), and the volatiles were evaporated. The residue was purified by flash chromatography on silica gel (0-20% EtOAc/hexanes) to afford the product as a white solid (630 mg, 71%). LCMS calculated for $C_{11}H_{15}ClNO_2(M+H)^+$: m/z=228.1; found: 228.1.

Step 3. 1-(4-chloro-7-ethoxy-1H-indazol-6-yl)ethanone

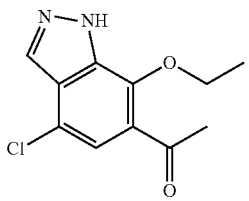 [SMILES: CCOc1c(C(C)=O)cc(Cl)c2cn[nH]c12]

To a solution of 1-(3-amino-5-chloro-2-ethoxy-4-methylphenyl)ethanone (630 mg, 2.8 mmol) in AcOH (17 mL) was added amyl nitrite (0.41 mL, 3.0 mmol) dropwise at room temperature. After stirring for 0.5 h, a precipitate was observed, and the reaction mixture was heated to 110° C. for 1 h. The solution was cooled to room temperature and the volatiles were evaporated. The residue was azeotroped with toluene (50 mL) to remove any remaining AcOH. The resulting orange solid (630 mg, 95%) was dried under high vacuum overnight and used without purification. LCMS calculated for $C_{11}H_{12}ClN_2O_2(M+H)^+$: m/z=239.1; found: 239.1.

Step 4. 1-(4-chloro-7-ethoxy-2-methyl-2H-indazol-6-yl)ethanone

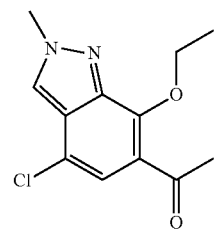 [SMILES: CCOc1c(C(C)=O)cc(Cl)c2cn(C)nc12]

To a solution of 1-(4-chloro-7-ethoxy-1H-indazol-6-yl)ethanone (30.0 mg, 0.126 mmol) in dry EtOAc (1 mL) was added trimethyloxonium tetrafluoroborate (24 mg, 0.16 mmol) at room temperature. The suspension was heated to 40° C. until complete dissolution, and the resulting solution was stirred at room temperature for 3 h. The solution was diluted with EtOAc (10 mL) and washed with saturated NaHCO$_3$ (5 mL). The organic layer was dried over MgSO$_4$, filtered, and concentrated, and the resulting solid was purified by flash chromatography (0-30% EtOAc/hexanes) to afford the title compound as a white solid (27.1 mg, 85%). LCMS calculated for $C_{12}H_{14}ClN_2O_2$ (M+H)$^+$: m/z=253.1; found: 253.1.

Step 5. 1-(4-chloro-7-ethoxy-2-methyl-2H-indazol-6-yl)ethanamine

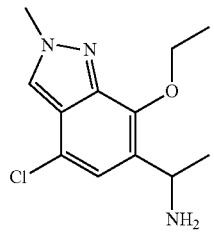 [SMILES: CCOc1c(C(C)N)cc(Cl)c2cn(C)nc12]

A solution of 1-(4-chloro-7-ethoxy-2-methyl-2H-indazol-6-yl)ethanone (27.1 mg, 0.107 mmol) and ammonium acetate (120 mg, 1.6 mmol) in MeCN (1 mL) and MeOH (1 mL) was heated at 65° C. for 0.5 h. The solution was cooled to room temperature, and sodium cyanoborohydride (17 mg, 0.27 mmol) was added. The reaction mixture was heated to 65° C. overnight. The solution was cooled to room temperature, diluted with EtOAc (10 mL), and quenched with sat. NaHCO$_3$ (5 mL). The layers were separated and the aqueous layer was extracted with EtOAc (10 mL). The combined organic layers were dried over MgSO$_4$, filtered, and concentrated, and the product was used without purification (theoretical yield assumed). LCMS calculated for C$_{12}$H$_{14}$ClN$_2$O (M−NH$_2$)$^+$: m/z=237.1; found: 237.1.

Step 6. tert-butyl 3-(1-(4-chloro-7-ethoxy-2-methyl-2H-indazol-6-yl)ethylcarbamoyl)pyrazolo[1,5-a]pyrimidin-2-ylcarbamate

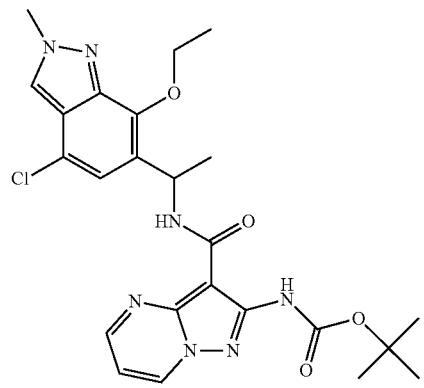 [SMILES: CCOc1c(C(C)NC(=O)c2c(NC(=O)OC(C)(C)C)nn3cccnc23)cc(Cl)c2cn(C)nc12]

To a vial containing 1-(4-chloro-7-ethoxy-2-methyl-2H-indazol-6-yl)ethanamine (27.2 mg, 0.107 mmol, from Example 1, Step 5), 2-[(tert-butoxycarbonyl)amino]pyrazolo[1,5-a]pyrimidine-3-carboxylic acid (39 mg, 0.14 mmol, from J&W Pharmlab), and N,N,N',N'-tetramethyl-O-(7-azabenzotriazol-1-yl)uronium hexafluorophosphate (53 mg, 0.14 mmol) was added DMF (2 mL), followed by dropwise addition of N,N-diisopropylethylamine (0.037 mL, 0.21 mmol) at room temperature. After stirring for 1 h, the reaction mixture was diluted with EtOAc (10 mL) and quenched with water (5 mL). The layers were separated, and the organic layer was dried over MgSO$_4$, filtered, and concentrated. The product was used without purification (theoretical yield assumed). LCMS calculated for C$_{24}$H$_{29}$ClN$_7$O$_4$(M+H)$^+$: m/z=514.2; found: 514.2.

Step 7. 2-amino-N-[1-(4-chloro-7-ethoxy-2-methyl-2H-indazol-6-yl)ethyl]pyrazolo[1,5-a]pyrimidine-3-carboxamide trifluoroacetate The tert-butyl 3-(1-(4-chloro-7-ethoxy-2-methyl-2H-indazol-6-yl)ethylcarbamoyl)pyrazolo[1,5-a]pyrimidin-2-ylcarbamate (54 mg, 0.107 mmol, from Example 1, Step 6) was taken up in CH$_2$Cl$_2$ (2 mL), and trifluoroacetic acid (0.6 mL, 7 mmol) was added at room temperature. After 1 h, the volatiles were evaporated. The residue was dissolved in MeOH and purified by preparative HPLC (C-18 column eluting with a water:acetonitrile gradient buffered at pH 2 with 0.1% trifluoroacetic acid) to give the title compound as a white solid. $^1$H NMR (600 MHz, DMSO-d6) δ 8.91 (dd, J=6.7, 1.6 Hz, 1H), 8.55 (dd, J=4.5, 1.7 Hz, 1H), 8.44 (s, 1H), 8.27 (d, J=8.1 Hz, 1H), 7.03 (s, 1H), 6.99 (dd, J=6.7, 4.5 Hz, 1H), 5.51 (p, J=7.0 Hz, 1H), 4.70-4.59 (m, 2H), 4.19 (s, 3H), 1.50 (d, J=7.0 Hz, 3H), 1.41 (t, J=7.0 Hz, 3H); LCMS calculated for C$_{19}$H$_{20}$ClN$_7$O$_2$Na (M+Na)$^+$: m/z=436.1; found: 436.1.

Example 2. 2-amino-N-[1-(4-chloro-7-ethoxy-2-ethyl-2H-indazol-6-yl)ethyl]pyrazolo[1,5-a]pyrimidine-3-carboxamide trifluoroacetate

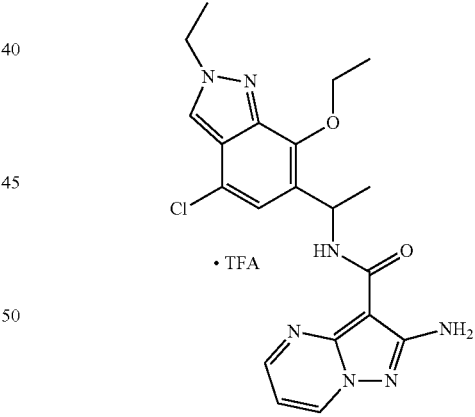

This compound was synthesized according to the procedure described for Example 1, substituting triethyloxonium tetrafluoroborate instead of trimethyloxonium tetrafluoroborate in Step 4. $^1$H NMR (600 MHz, DMSO-d6) δ 8.91 (dd, J=6.7, 1.6 Hz, 1H), 8.55 (dd, J=4.5, 1.7 Hz, 1H), 8.48 (s, 1H), 8.28 (d, J=8.1 Hz, 1H), 7.03 (s, 1H), 6.99 (dd, J=6.7, 4.5 Hz, 1H), 5.50 (p, J=7.0 Hz, 1H), 4.69 (dq, J=9.6, 7.0 Hz, 1H), 4.63 (dq, J=9.6, 7.2 Hz, 1H), 4.47 (q, J=7.3 Hz, 2H), 1.51 (t, J=7.2 Hz, 3H), 1.50 (d, J=7.2 Hz, 3H), 1.41 (t, J=7.0 Hz, 3H); LCMS calculated for C$_{20}$H$_{22}$ClN$_7$O$_2$ (M+Na)$^+$: m/z=450.1; found: 450.1.

Examples 3a & 3b. 2-amino-N-[1-(4-chloro-7-ethoxy-1H-indazol-6-yl)ethyl]pyrazolo[1,5-a]pyrimidine-3-carboxamide trifluoroacetate (Single Enantiomers Isolated)

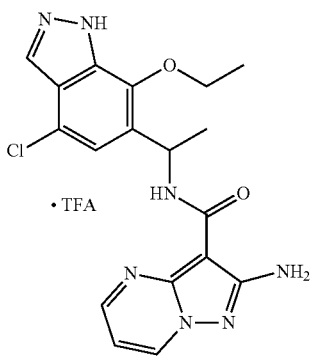 [SMILES: CCOc1c(C(C)NC(=O)c2c(N)nn3cccnc23)cc(Cl)c2cn[nH]c12]

Step 1.
1-(4-chloro-7-ethoxy-1H-indazol-6-yl)ethanamine

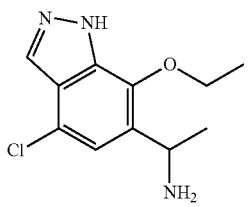 [SMILES: CCOc1c(C(C)N)cc(Cl)c2cn[nH]c12]

This compound was synthesized according to the procedure described in Example 1, Step 5, starting from 1-(4-chloro-7-ethoxy-2-methyl-2H-indazol-6-yl)ethanone (450 mg, 1.9 mmol, from Example 1, Step 3). LCMS calculated for $C_{11}H_{10}ClN_1O$ $(M-NH_2)^+$: m/z=223.1; found: 223.1.

Step 2. tert-butyl 3-(1-(4-chloro-7-ethoxy-1H-indazol-6-yl)ethylcarbamoyl)pyrazolo[1,5-a]pyrimidin-2-ylcarbamate

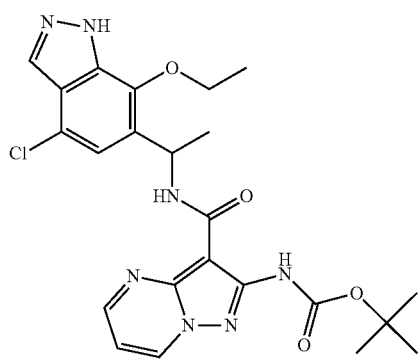 [SMILES: CCOc1c(C(C)NC(=O)c2c(NC(=O)OC(C)(C)C)nn3cccnc23)cc(Cl)c2cn[nH]c12]

This compound was synthesized according to the procedure described in Example 1, Step 6, starting with 1-(4-chloro-7-ethoxy-1H-indazol-6-yl)ethanamine (prepared in the previous step). The product was purified by flash chromatography (0-100% EtOAc/hexanes) to afford the racemic title compound as an off white solid (560 mg, 59%). LCMS calculated for $C_{23}H_{27}ClN_7O_4(M+H)^+$: m/z=500.2; found: 500.2. A fraction of this material (120 mg) was separated by chiral HPLC (Chiral Technologies Chiralcel AD-H, 5 μm, 20×250 mm, eluting with 20% EtOH/hexanes, 18 mL/min) to afford enantiomer 1 (first to elute, retention time 8.4 min; 30 mg) and enantiomer 2 (second to elute, retention time 11.2 min; 30 mg).

Step 3. 2-amino-N-[1-(4-chloro-7-ethoxy-1H-indazol-6-yl)ethyl]pyrazolo[1,5-a]pyrimidine-3-carboxamide trifluoroacetate (Single Enantiomers Isolated)

After removal of solvent in vacuo, each enantiomer from Example 3, Step 2 was deprotected separately by stirring with TFA (0.5 mL) in $CH_2Cl_2$ (2 mL) for 0.5 h. The volatiles were removed in vacuo to afford the title compound as single enantiomers, which did not require purification.

Enantiomer 1 (Example 3a): $^1H$ NMR (600 MHz, DMSO-d6) δ 8.92 (dd, J=6.7, 1.6 Hz, 1H), 8.56 (dd, J=4.5, 1.6 Hz, 1H), 8.19 (d, J=7.7 Hz, 1H), 8.11 (s, 1H), 7.13 (s, 1H), 7.01 (dd, J=6.7, 4.5 Hz, 1H), 5.55 (p, J=7.0 Hz, 1H), 4.29 (d, J=6.7 Hz, 2H), 1.52 (d, J=7.0 Hz, 3H), 1.46 (t, J=7.0 Hz, 3H). LCMS calculated for $C_{18}H_{18}ClN_7O_2(M+H)^+$: m/z=400.1; found: 400.2. Enantiomer 2 (Example 3b): LCMS calculated for $C_{18}H_{18}ClN_7O_2(M+H)^+$: m/z=400.1; found: 400.2.

Example 4. 2-amino-N-[1-(4-chloro-7-ethoxy-1-methyl-1H-indazol-6-yl)ethyl]pyrazolo[1,5-a]pyrimidine-3-carboxamide trifluoroacetate

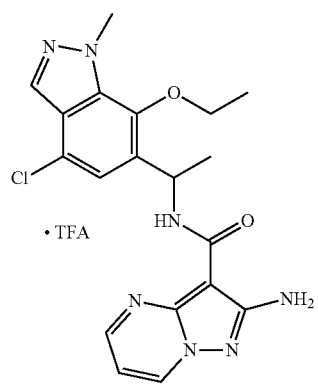 [SMILES: CCOc1c(C(C)NC(=O)c2c(N)nn3cccnc23)cc(Cl)c2cnn(C)c12]

Step 1. tert-butyl 3-(1-(4-chloro-7-ethoxy-1-methyl-1H-indazol-6-yl)ethylcarbamoyl)pyrazolo[1,5-a]pyrimidin-2-ylcarbamate & tert-butyl 3-(1-(4-chloro-7-ethoxy-2-methyl-2H-indazol-6-yl)ethylcarbamoyl)pyrazolo[1,5-a]pyrimidin-2-ylcarbamate

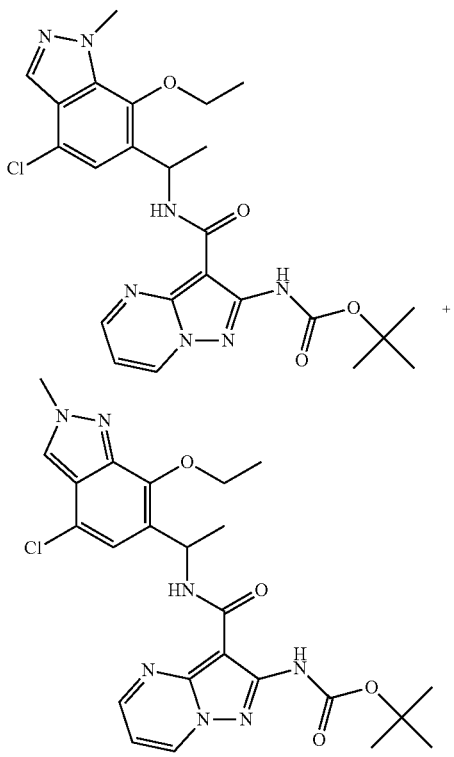

To a solution of tert-butyl [3-({[1-(4-chloro-7-ethoxy-1H-indazol-6-yl)ethyl]amino}carbonyl)pyrazolo[1,5-a]pyrimidin-2-yl]carbamate (30 mg, 0.06 mmol, from Example 3, Step 2) in DMF (0.5 mL) was added potassium carbonate (16 mg, 0.12 mmol), followed by methyl iodide (6 μL, 0.09 mmol) and the reaction mixture was heated to 60° C. for 3 h. After cooling to room temperature, the reaction mixture was diluted with EtOAc (10 mL) and washed with water (5 mL). The organic layer was dried over MgSO$_4$, filtered and concentrated, and the product was used without purification. The title compounds were obtained in approximately a 1:1 ratio. LCMS calculated for $C_{24}H_{29}ClN_7O_4(M+H)^+$: m/z=514.2; found: 514.1.

Step 2. 2-amino-N-[1-(4-chloro-7-ethoxy-1-methyl-1H-indazol-6-yl)ethyl]pyrazolo[1,5-a]pyrimidine-3-carboxamide trifluoroacetate & 2-amino-N-(1-(4-chloro-7-ethoxy-2-methyl-2H-indazol-6-yl)ethyl)pyrazolo[1,5-a]pyrimidine-3-carboxamide trifluoroacetate The deprotection was performed as described in Example 1, Step 7. Along with the desired indazole N1 regioisomer, the N2 regioisomer was also obtained in a ~1:1 ratio. The residue was dissolved in MeOH and purified by preparative HPLC (C-18 column eluting with a water:acetonitrile gradient [37.4-57.4% acetonitrile] buffered at pH 2 with 0.1% trifluoroacetic acid). The title compounds were separable and each was obtained as a white solid. N1 isomer (Example 4): Retention time=5.9 min. LCMS calculated for $C_{19}H_{21}ClN_7O_2(M+H)^+$: m/z=414.1; found: 414.1. N2 isomer (Example 1): Retention time=4.9 min.

Examples 5-13 were synthesized via an alkylation with the appropriate alkyl halide and subsequent deprotection as described for Example 4. In each case, the alkylation step afforded a varying mixture of N1 and N2 indazole regioisomers. These isomers were separable by preparative HPLC after deprotection, unless otherwise noted. The N1 regioisomers prepared and the corresponding data are listed in Table 1. The N2 regioisomers prepared and the corresponding data are listed in Table 2.

TABLE 1

| Ex. No. | Name | R = | LCMS | $^1$H NMR |
|---|---|---|---|---|
| 5 | 2-amino-N-{1-[4-chloro-7-ethoxy-1-(2-methoxyethyl)-1H-indazol-6-yl]ethyl}pyrazolo[1,5-a]pyrimidine-3-carboxamide trifluoroacetate | | Calculated for $C_{21}H_{25}ClN_7O_3$ $(M + H)^+$: m/z = 458.2; found: 458.2 | |

TABLE 1-continued

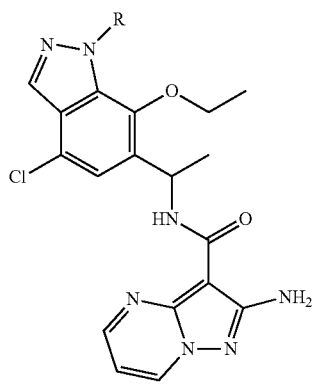

| Ex. No. | Name | R = | LCMS | ¹H NMR |
|---|---|---|---|---|
| 6 | 2-amino-N-(1-(4-chloro-7-ethoxy-1-(2-hydroxy-ethyl)-1H-indazol-6-yl)ethyl)pyrazolo[1,5-a]pyrimidine-3-carbox-amide trifluoroacetate | 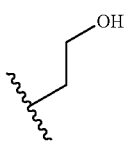 [SMILES: *CCO] | Calculated for $C_{20}H_{23}ClN_7O_3$ $(M + H)^+$: m/z = 444.2; found: 444.2 | |
| 7 | 2-amino-N-(1-(4-chloro-1-cyanomethyl)-7-ethoxy-1H-indazol-6-yl)ethyl)pyrazolo[1,5-a]pyrimidine-3-carbox-amide trifluoroacetate |  | Calculated for $C_{20}H_{20}ClN_8O_2$ $(M + H)^+$: m/z = 439.1; found: 439.2 | 1H NMR (600 MHz, DMSO-$d_6$) δ 8.93 (dd, J = 6.7, 1.6 Hz, 1H), 8.57 (dd, J = 4.5, 1.6 Hz, 1H), 8.28 (s, 1H), 8.17 (d, J = 7.2 Hz, 1H), 7.31 (s, 1H), 7.02 (dd, J = 6.7, 4.5 Hz, 1H), 5.84-5.69 (m, 2H), 5.53 (p, J = 6.9 Hz, 1H), 4.46-4.32 (m, 1H), 4.12 (dq, J = 9.2, 7.0 Hz, 1H), 1.54 (t, J = 6.8 Hz, 6H). |
| 8 | 2-amino-N-(1-(1-benzyl-4-chloro-7-ethoxy-1H-indazol-6-yl)ethyl)-pyrazolo[1,5-a]pyrimidine-3-carboxamide trifluoroacetate | 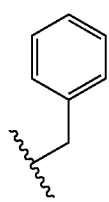 [SMILES: *Cc1ccccc1] | Calculated for $C_{25}H_{25}ClN_7O_2$ $(M + H)^+$: m/z = 490.2; found: 490.2 | |
| 9 | 2-amino-N-(1-(4-chloro-7-ethoxy-1-isobutyl-1H-indazol-6-yl)ethyl)-pyrazolo[1,5-a]pyrimidine-3-carboxamide trifluoroacetate | 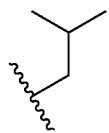 [SMILES: *CC(C)C] | Calculated for $C_{22}H_{27}ClN_7O_2$ $(M + H)^+$: m/z = 456.2; found: 456.2 | |
| 10 | 2-amino-N-(1-(4-chloro-1-cyclobutyl-7-ethoxy-1H-indazol-6-yl)ethyl)-pyrazolo[1,5-a]pyrimidine-3-carboxamide trifluoroacetate | 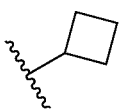 | Calculated for $C_{22}H_{25}ClN_7O_2$ $(M + H)^+$: m/z = 454.2; found: 454.2 | |
| 11 | 2-amino-N-(1-(4-chloro-7-ethoxy-1-isopropyl-1H-indazol-6-yl)ethyl)-pyrazolo[1,5-a]pyrimidine-3-carboxamide trifluoroacetate | 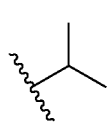 [SMILES: *C(C)C] | Calculated for $C_{21}H_{25}ClN_7O_2$ $(M + H)^+$: m/z = 442.2; found: 442.1 | |

TABLE 2

| Ex. No. | Name | R = | LCMS | ¹H NMR |
|---|---|---|---|---|
| 5a | 2-amino-N-(1-(4-chloro-7-ethoxy-2-(2-methoxy-ethyl)-2H-indazol-6-yl)-ethyl)pyrazolo[1,5-a]-pyrimidine-3-carbox-amide trifluoroacetate | methoxyethyl | Calculated for C₂₁H₂₅ClN₇O₃ (M + H)⁺: m/z = 458.2; found: 458.2 | ¹H NMR (600 MHz, DMSO-d6) δ 8.91 (dd, J = 6.7, 1.6 Hz, 1H), 8.55 (dd, J = 4.5, 1.6 Hz, 1H), 8.44 (s, 1H), 8.28 (d, J = 8.0 Hz, 1H), 7.04 (s, 1H), 6.99 (dd, J = 6.7, 4.5 Hz, 1H), 5.50 (p, J = 7.0 Hz, 1H), 4.71-4.62 (m, 2H), 4.61 (dd, J = 6.4, 4.0 Hz, 2H), 3.83 (t, J = 10.2, 5.4 Hz, 2H), 3.23 (s, 3H), 1.51 (d, J = 7.0 Hz, 3H), 1.41 (t, J = 7.0 Hz, 3H). |
| 6a | 2-amino-N-(1-(4-chloro-7-ethoxy-2-(2-hydroxy-ethyl)-2H-indazol-6-yl)ethyl)pyrazolo[1,5-a]pyrimidine-3-carbox-amide trifluoroacetate | hydroxyethyl | Calculated for C₂₀H₂₃ClN₇O₃ (M + H)⁺: m/z = 444.2; found: 444.2 | ¹H NMR (600 MHz, DMSO-d6) δ 8.91 (dd, J = 6.7, 1.6 Hz, 1H), 8.55 (dd, J = 4.5, 1.6 Hz, 1H), 8.42 (s, 1H), 8.27 (d, J = 8.1 Hz, 1H), 7.03 (s, 1H), 6.99 (dd, J = 6.7, 4.5 Hz, 1H), 5.50 (p, J = 7.0 Hz, 1H), 4.69 (dq, J = 9.6, 7.0 Hz, 1H), 4.63 (dq, J = 9.6, 7.0 Hz, 1H), 4.48 (t, J = 5.4 Hz, 2H), 3.87 (t, J = 5.4 Hz, 2H), 1.50 (d, J = 7.0 Hz, 3H), 1.41 (t, J = 7.0 Hz, 3H). |
| 7a | 2-amino-N-(1-(4-chloro-2-(cyanomethyl)-7-ethoxy-2H-indazol-6-yl)ethyl)pyrazolo[1,5-a]pyrimidine-3-carbox-amide trifluoroacetate | cyanomethyl | Calculated for C₂₀H₂₀ClN₈O₂ (M + H)⁺: m/z = 439.1; found: 439.2 | |
| 8a | 2-amino-N-(1-(2-benzyl-4-chloro-7-ethoxy-2H-indazol-6-yl)ethyl)-pyrazolo[1,5-a]pyrimidine-3-carboxamide trifluoroacetate | benzyl | Calculated for C₂₅H₂₅ClN₇O₂ (M + H)⁺: m/z = 490.2; found: 490.2 | ¹H NMR (600 MHz, DMSO-d6) δ 8.91 (dd, J = 6.7, 1.6 Hz, 1H), 8.60 (s, 1H), 8.54 (dd, J = 4.5, 1.6 Hz, 1H), 8.27 (d, J = 8.0 Hz, 1H), 7.39-7.28 (m, 5H), 7.05 (s, 1H), 6.99 (dd, J = 6.7, 4.5 Hz, 1H), 5.68 (s, 2H), 5.49 (p, J = 7.0 Hz, 1H), 4.66 (dq, J = 9.8, 7.1 Hz, 1H), 4.63-4.58 (m, 1H), 1.49 (d, J = 7.0 Hz, 3H), 1.39 (t, J = 7.0 Hz, 3H). |
| 9a | 2-amino-N-(1-(4-chloro-7-ethoxy-2-isobutyl-2H-indazol-6-yl)ethyl)-pyrazolo[1,5-a]pyrimidine-3-carboxamide trifluoroacetate | isobutyl | Calculated for C₂₂H₂₇ClN₇O₂ (M + H)⁺: m/z = 456.2; found: 456.2 | ¹H NMR (600 MHz, DMSO-d6) δ 8.91(dd, J = 6.7, 1.6 Hz, 1H), 8.55 (dd, J = 4.5, 1.6 Hz, 1H), 8.45 (s, 1H), 8.28 (d, J = 8.1 Hz, 1H), 7.03 (s, 1H), 6.99 (dd, J = 6.7, 4.5 Hz, 1H), 5.50 (p, J = 7.0 Hz, 1H), 4.68 (dq, J = 9.6, 7.0 Hz, 1H), 4.63 (dq, J = 9.6, 7.0 Hz, 1H), 4.25 (d, |

TABLE 2-continued

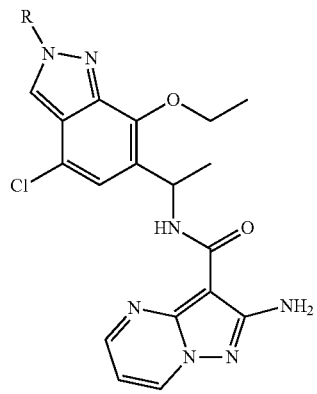

| Ex. No. | Name | R = | LCMS | 1H NMR |
|---|---|---|---|---|
| | | | | J = 7.2 Hz, 2H), 2.29 (hept, J = 6.8 Hz, 1H), 1.51 (d, J = 7.0 Hz, 3H), 1.41 (t, J = 7.0 Hz, 3H), 0.87 (dd, J = 6.7, 3.7 Hz, 6H). |
| 10a | 2-amino-N-(1-(4-chloro-2-cyclobutyl-7-ethoxy-2H-indazol-6-yl)ethyl)-pyrazolo[1,5-a]pyrimidine-3-carboxamide trifluoroacetate | cyclobutyl | Calculated for C22H25ClN7O2 (M + H)+: m/z = 454.2; found: 454.2 | 1H NMR (600 MHz, DMSO-d6) δ 8.91 (dd, J = 6.7, 1.6 Hz, 1H), 8.55 (dd, J = 4.5, 1.7 Hz, 1H), 8.53 (s, 1H), 7.04 (s, 1H), 6.99 (dd, J = 6.7, 4.5 Hz, 1H), 5.50 (p, J = 7.0 Hz, 1H), 5.22-5.14 (m, 1H), 4.72 (dq, J = 9.6, 7.0 Hz, 1H), 4.65 (dq, J = 9.7, 7.0 Hz, 1H), 2.67-2.59 (m, 2H), 2.49 (m, 3H), 1.91-1.83 (m, 3H), 1.50 (d, J = 7.0 Hz, 3H), 1.43 (t, J = 7.0 Hz, 3H). |
| 11a | 2-amino-N-(1-(4-chloro-7-ethoxy-2-isopropyl-2H-indazol-6-yl)ethyl)-pyrazolo[1,5-a]pyrimidine-3-carboxamide trifluoroacetate | isopropyl | Calculated for C21H25ClN7O2 (M + H)+: m/z = 442.2; found: 442.1 | 1H NMR (600 MHz, DMSO-d6) δ 8.91 (dd, J = 6.7, 1.6 Hz, 1H), 8.55 (dd, J = 4.5, 1.6 Hz, 1H), 8.49 (s, 1H), 8.28 (d, J = 8.1 Hz, 1H), 7.03 (s, 1H), 6.99 (dd, J = 6.7, 4.5 Hz, 1H), 5.50 (p, J = 7.0 Hz, 1H), 4.85 (hept, J = 6.7 Hz, 1H), 4.71 (dq, J = 9.6, 7.0 Hz, 1H), 4.64 (dq, J = 9.6, 7.0 Hz, 1H), 1.56 (d, J = 6.7 Hz, 6H), 1.50 (d, J = 7.0 Hz, 3H), 1.42 (t, J = 7.0 Hz, 3H). |
| 12 | 2-amino-N-(1-(2-(2-amino-2-oxoethyl)-4-chloro-7-ethoxy-2H-indazol-6-yl)ethyl)-pyrazolo[1,5-a]pyrimidine-3-carboxamide trifluoroacetate isolated as an inseparable 3:1 mixture of N2:N1 regioisomers; NMR data reported is for N2 isomer (major) | H2N-C(=O)-CH2- | Calculated for C20H22ClN8O3 (M + H)+: m/z = 457.1; found: 457.2 | 1H NMR (600 MHz, DMSO-d6) δ 8.91 (dd, J = 6.7, 1.6 Hz, 1H), 8.55 (dd, J = 4.5, 1.6 Hz, 1H), 8.43 (s, 1H), 8.27 (d, J = 8.0 Hz, 1H), 7.66 (s, 1H), 7.38 (s, 1H), 7.05 (s, 1H), 6.99 (dd, J = 6.7, 4.5 Hz, 1H), 5.51 (m, 1H), 5.13 (s, 2H), 4.65 (dq, J = 9.6, 7.1 Hz, 1H), 4.60 (dq, J = 9.5, 7.1 Hz, 1H), 1.51 (t, J = 7.0 Hz, 3H), 1.40 (t, J = 7.0 Hz, 3H). |
| 13 | 2-amino-N-(1-(2-(but-2-ynyl)-4-chloro-7-ethoxy-2H-indazol-6-yl)ethyl)-pyrazolo[1,5-a]pyrimidine-3-carboxamide trifluoroacetate isolated as an inseparable 3:1 mixture of N2:N1 regioisomers: | but-2-ynyl | Calculated for C22H23ClN7O2 (M + H)+: m/z = 452.2; found: 452.2 | 1H NMR (600 MHz, DMSO-d6) δ 8.90 (dd, J = 6.7, 1.6 Hz, 1H), 8.54 (dd, J = 4.5, 1.6 Hz, 1H), 8.49 (s, 1H), 8.28 (d, J = 8.0 Hz, 1H), 7.07 (s, 1H), 6.99 (dd, J = 6.7, 4.5 Hz, 1H), 5.51 (p, J = 7.0 Hz, 1H), 5.33 (q, J = 2.3 Hz, 2H), 4.67 (dq, J = 9.6, 7.0 Hz, 1H), 4.62 (dq, 9.6, |

TABLE 2-continued

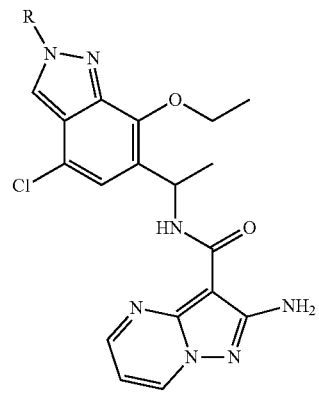

| Ex. No. | Name | R = | LCMS | ¹H NMR |
|---|---|---|---|---|
| | NMR data reported is for N2 isomer (major) | | | 7.0 Hz, 1H), 1.86 (t, J = 2.5 Hz, 3H), 1.51 (d, J = 7.0 Hz, 3H), 1.42 (t, J = 7.0 Hz, 3H). |

Example 14. 2-amino-N-(1-(4-chloro-7-phenyl-1H-indazol-6-yl)ethyl)pyrazolo[1,5-a]pyrimidine-3-carboxamide trifluoroacetate

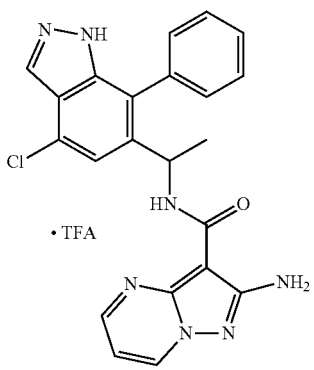 [SMILES: CC(NC(=O)c1c(N)nn2cccnc12)c1cc(Cl)c2cn[nH]c2c1-c1ccccc1]

Step 1. 6-acetyl-4-chloro-3-methyl-2-nitrophenyl trifluoromethanesulfonate

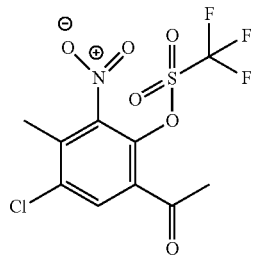 [SMILES: CC(=O)c1cc(Cl)c(C)c([N+](=O)[O-])c1OS(=O)(=O)C(F)(F)F]

Trifluoromethanesulfonic anhydride (1M/CH$_2$Cl$_2$, 13 mL, 13 mmol) was added to a solution of 1-(5-chloro-2-hydroxy-4-methyl-3-nitrophenyl)ethanone (2.0 g, 8.7 mmol, from Oakwood) and triethylamine (2.4 mL, 17 mmol) in THF (20 mL) at −78° C. The solution was allowed to warm to room temperature and stirred for 0.5 h. The reaction mixture was diluted with EtOAc (30 mL) and quenched with sat. NaHCO$_3$ (20 mL). The layers were separated and the organic layer was washed with sat. NaCl (20 mL), dried over MgSO$_4$, filtered, and concentrated. The residue was purified by flash chromatography on silica gel (0-15% EtOAc/hexanes) to afford the product as an orange oil (3.2 g, 100%). LCMS calculated for C$_{10}$H$_8$ClF$_3$NO$_6$S (M+H)$^+$: m/z=362.0; found: 361.8.

Step 2.
1-(4-chloro-5-methyl-6-nitrobiphenyl-2-yl)ethanone

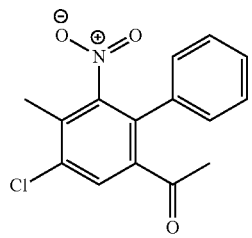 [SMILES: CC(=O)c1cc(Cl)c(C)c([N+](=O)[O-])c1-c1ccccc1]

To a solution of 6-acetyl-4-chloro-3-methyl-2-nitrophenyl trifluoromethanesulfonate (3.2 g, 8.8 mmol) in toluene (20 mL) was added a solution of sodium bicarbonate (1.4 g, 17 mmol) in water (20 mL), followed by phenylboronic acid (1.2 g, 10.0 mmol) and tetrakis(triphenylphosphine)palladium(0) (0.48 g, 0.41 mmol). Nitrogen was bubbled through the solution for 5 min, and the reaction mixture was heated at 80° C. (bath temp) for 2 h. The reaction mixture was diluted with EtOAc (30 mL), the layers were separated and the organic layer was washed with saturated NaCl (20 mL), dried over MgSO$_4$, filtered, and concentrated. The residue was purified by flash chromatography on silica gel (0-10% EtOAc/hexanes) to afford the title compound as a white solid (2.3 g, 88%). LCMS calculated for C$_1$H$_{13}$ClNO$_3$(M+H)$^+$: m/z=290.1; found: 290.0.

Step 3.
1-(6-amino-4-chloro-5-methylbiphenyl-2-yl)ethanone

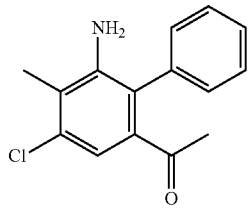 [SMILES: CC(=O)c1cc(Cl)c(C)c(N)c1-c1ccccc1]

This compound was synthesized according to the procedure described in Example 1, Step 2, starting from 1-(4-chloro-5-methyl-6-nitrobiphenyl-2-yl)ethanone (2.25 g, 7.77 mmol). The crude product was purified by flash chromatography on silica gel (0-20% EtOAc/hexanes) to afford the title compound as a white solid (1.57 g, 78%). LCMS calculated for $C_{15}H_{15}ClNO$ $(M+H)^+$: m/z=260.1; found: 260.0.

Step 4.
1-(4-chloro-7-phenyl-1H-indazol-6-yl)ethanone

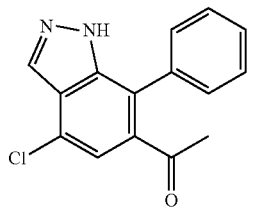 [SMILES: CC(=O)c1cc(Cl)c2cn[nH]c2c1-c1ccccc1]

This compound was synthesized according to the procedure described in Example 1, Step 3, starting from 1-(6-amino-4-chloro-5-methylbiphenyl-2-yl)ethanone (1.57 g, 6.04 mmol). The product was obtained as an orange solid (1.64 g, 100%). LCMS calculated for $C_{15}H_{12}ClN_2O$ $(M+H)^+$: m/z=271.1; found: 271.0.

Step 5.
1-(4-chloro-7-phenyl-1H-indazol-6-yl)ethanamine

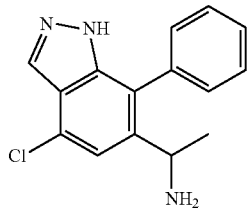 [SMILES: CC(N)c1cc(Cl)c2cn[nH]c2c1-c1ccccc1]

This compound was synthesized according to the procedure described in Example 1, Step 5, starting from 1-(4-chloro-7-phenyl-1H-indazol-6-yl)ethanone (591 mg, 2.18 mmol). The product was used without purification (theoretical yield assumed). LCMS calculated for $C_{15}H_{12}ClN_2$ $(M-NH_2)^+$: m/z=255.1; found: 255.1.

Step 6. tert-butyl 3-(1-(4-chloro-7-phenyl-1H-indazol-6-yl)ethylcarbamoyl)pyrazolo[1,5-a]pyrimidin-2-ylcarbamate

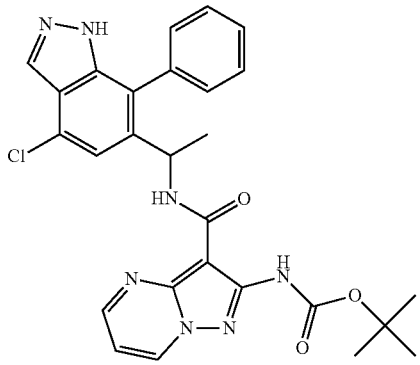 [SMILES: CC(NC(=O)c1c(NC(=O)OC(C)(C)C)nn2cccnc12)c1cc(Cl)c2cn[nH]c2c1-c1ccccc1]

This compound was synthesized according to the general procedure described in Example 1, Step 6, starting from 1-(4-chloro-7-phenyl-1H-indazol-6-yl)ethanamine (593 mg, 2.18 mmol). The product was purified by flash chromatography on silica gel (0-60% EtOAc/hexanes) to afford the title compound as an off white solid (562 mg, 48%). LCMS calculated for $C_{27}H_{26}ClN_7O_3(M+H)^+$: m/z=532.2; found: 532.2.

Step 7. 2-amino-N-(1-(4-chloro-7-phenyl-1H-indazol-6-yl)ethyl)pyrazolo[1,5-a]pyrimidine-3-carboxamide trifluoroacetate The deprotection was performed as described in Example 1, Step 7, starting from tert-butyl 3-(1-(4-chloro-7-phenyl-1H-indazol-6-yl)ethylcarbamoyl)pyrazolo[1,5-a]pyrimidin-2-ylcarbamate (10 mg, 0.020 mmol). The residue was dissolved in MeOH and purified by preparative HPLC (C-18 column eluting with a water:acetonitrile gradient buffered at pH 2 with 0.1% trifluoroacetic acid) to give the title compound as a white solid. LCMS calculated for $C_{22}H_{19}ClN_7O$ $(M+H)^+$: m/z=432.1; found: 432.1.

Examples 15 & 16. 2-amino-N-(1-(4-chloro-1-methyl-7-phenyl-1H-indazol-6-yl)ethyl)pyrazolo[1,5-a]pyrimidine-3-carboxamide trifluoroacetate & 2-amino-N-(1-(4-chloro-2-methyl-7-phenyl-2H-indazol-6-yl)ethyl)pyrazolo[1,5-a]pyrimidine-3-carboxamide trifluoroacetate

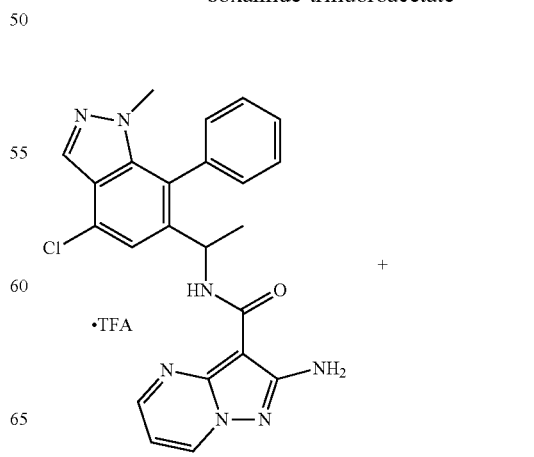

-continued

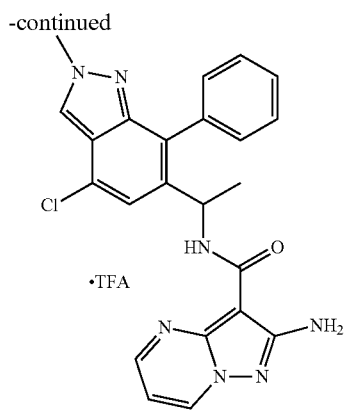

Step 1. tert-butyl 3-(1-(4-chloro-1-methyl-7-phenyl-1H-indazol-6-yl)ethylcarbamoyl)pyrazolo[1,5-a]pyrimidin-2-ylcarbamate & tert-butyl 3-(1-(4-chloro-2-methyl-7-phenyl-2H-indazol-6-yl)ethylcarbamoyl)pyrazolo[1,5-a]pyrimidin-2-ylcarbamate

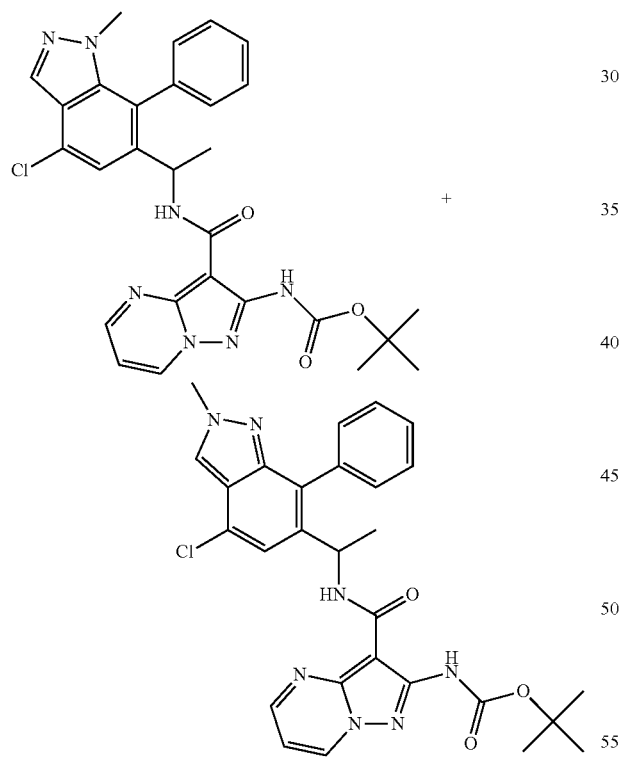

This compound was synthesized according the procedure described in Example 4, Step 1, starting with tert-butyl 3-(1-(4-chloro-7-phenyl-1H-indazol-6-yl)ethylcarbamoyl)pyrazolo[1,5-a]pyrimidin-2-ylcarbamate (30 mg, 0.060 mmol, from Example 14, Step 6). The title compounds were obtained in ~1:1.5 of N2:N1 regioisomers. The products were used without purification (theoretical yield assumed). Peak 1: LCMS calculated for $C_{28}H_{29}ClN_7O_3$ (M+H)$^+$: m/z=546.2; found 546.2. Peak 2: LCMS calculated for $C_{28}H_{29}ClN_7O_3$ (M+H)$^+$: m/z=546.2; found 546.3.

Step 2. 2-amino-N-(1-(4-chloro-1-methyl-7-phenyl-1H-indazol-6-yl)ethyl)pyrazolo[1,5-a]pyrimidine-3-carboxamide trifluoroacetate & 2-amino-N-(1-(4-chloro-2-methyl-7-phenyl-2H-indazol-6-yl)ethyl)pyrazolo[1,5-a]pyrimidine-3-carboxamide trifluoroacetate The deprotection was performed as described in Example 1, Step 7, starting from a 1:1.5 mixture of tert-butyl 3-(1-(4-chloro-1-methyl-7-phenyl-1H-indazol-6-yl)ethylcarbamoyl)pyrazolo[1,5-a]pyrimidin-2-ylcarbamate and tert-butyl 3-(1-(4-chloro-2-methyl-7-phenyl-2H-indazol-6-yl)ethylcarbamoyl)pyrazolo[1,5-a]pyrimidin-2-ylcarbamate (32.7 mg, 0.060 mmol). The residue was dissolved in MeOH and purified by preparative HPLC (C-18 column eluting with a water:acetonitrile gradient [38.5-58.5% acetonitrile] buffered at pH 2 with 0.1% trifluoroacetic acid). The title compounds were separable and each was obtained as a white solid. Peak 1 (Example 16): Retention time=5.6 min. LCMS calculated for $C_{23}H_{21}ClN_7O$ (M+H)$^+$: m/z=446.1; found: 446.2. Peak 2 (Example 15): Retention time=7.0 min. $^1$H NMR (600 MHz, DMSO-d6) δ 8.91 (dd, J=6.7, 1.6 Hz, 1H), 8.56 (dd, J=4.5, 1.6 Hz, 1H), 8.47 (s, 1H), 8.10 (d, J=6.8 Hz, 1H), 7.56-7.45 (m, 4H), 7.45-7.40 (m, 1H), 7.24 (s, 1H), 7.00 (dd, J=6.7, 4.5 Hz, 1H), 5.16 (p, J=6.9 Hz, 1H), 4.11 (s, 3H), 1.38 (d, J=6.9 Hz, 3H); LCMS calculated for $C_{23}H_{21}ClN_7O$ (M+H)$^+$: m/z=446.1; found: 446.2. LCMS calculated for $C_{23}H_{21}ClN_7O$ (M+H)$^+$: m/z=446.1; found: 446.2.

Examples 17 & 18. 2-amino-N-(1-(4-chloro-1-((1-methyl-1H-pyrazol-3-yl)methyl)-7-phenyl-1H-indazol-6-yl)ethyl)pyrazolo[1,5-a]pyrimidine-3-carboxamide trifluoroacetate & 2-amino-N-(1-(4-chloro-2-((1-methyl-1H-pyrazol-3-yl)methyl)-7-phenyl-2H-indazol-6-yl)ethyl)pyrazolo[1,5-a]pyrimidine-3-carboxamide trifluoroacetate

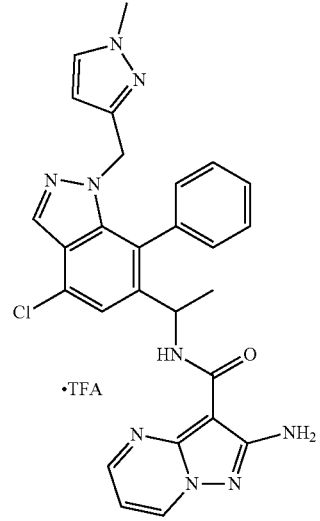

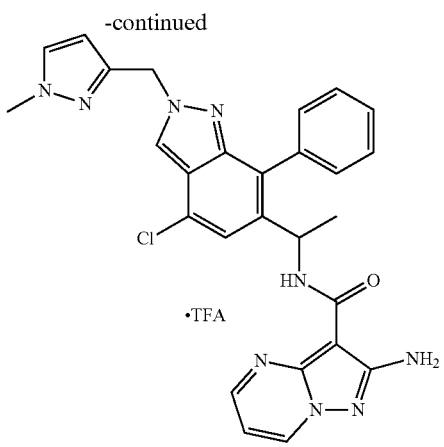

These compounds were synthesized according to the procedure described for Example 15, utilizing 3-(chloromethyl)-1-methyl-1H-pyrazole (from Maybridge) instead of methyl iodide. The residue was dissolved in MeOH and purified by preparative HPLC (C-18 column eluting with a water:acetonitrile gradient [36.4-56.4% acetonitrile] buffered at pH 2 with 0.1% trifluoroacetic acid). The title compounds were separable and each was obtained as a white solid. Peak 1 (Example 18): Retention time=5.4 min. $^1$H NMR (500 MHz, DMSO-d6) δ 8.89 (dd, J=6.7, 1.6 Hz, 1H), 8.53 (dd, J=4.5, 1.6 Hz, 1H), 8.42 (s, 1H), 8.07 (d, J=6.7 Hz, 1H), 7.69 (s, 1H), 7.54-7.45 (m, 4H), 7.45-7.40 (m, 2H), 7.22 (s, 1H), 6.98 (dd, J=6.7, 4.5 Hz, 1H), 5.42 (s, 2H), 5.13 (p, J=6.9 Hz, 1H), 3.76 (s, 3H), 1.36 (d, J=6.9 Hz, 3H). LCMS calculated for $C_{27}H_{25}ClN_9O$ (M+H)$^+$: m/z=526.2; found: 526.2. LCMS calculated for $C_{27}H_{25}ClN_9O$ (M+H)$^+$: m/z=526.2; found: 526.2. Peak 2 (Example 17): Retention time=6.2 min. LCMS calculated for $C_{27}H_{25}ClN_9O$ (M+H)$^+$: m/z=526.2; found: 526.2.

Example 19. 2-amino-N-(1-(4-chloro-1-(2-morpholinoethyl)-7-phenyl-1H-indazol-6-yl)ethyl)pyrazolo[1,5-a]pyrimidine-3-carboxamide

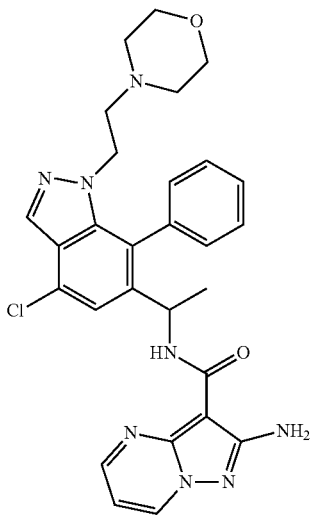 [SMILES: CC(NC(=O)c1c(N)nn2cccnc12)c1cc(Cl)c2cnn(CCN3CCOCC3)c2c1-c1ccccc1]

This compound was synthesized according to the procedure described for Example 15, utilizing 4-(2-bromoethyl)morpholine instead of methyl iodide. The residue was dissolved in MeOH and purified by preparative HPLC (C-18 column eluting with a water:acetonitrile gradient buffered at pH 10 with 0.1% ammonium hydroxide) to give the title compound as a white solid. $^1$H NMR (600 MHz, DMSO-d6) δ 8.92 (dd, J=6.7, 1.6 Hz, 1H), 8.57 (dd, J=4.5, 1.6 Hz, 1H), 8.17 (s, 1H), 8.12 (d, J=6.6 Hz, 1H), 7.67-7.63 (m, 1H), 7.63-7.59 (m, 1H), 7.59-7.53 (m, 2H), 7.49-7.46 (m, 1H), 7.32 (s, 1H), 7.01 (dd, J=6.7, 4.5 Hz, 1H), 6.41 (s, 2H), 4.85 (p, J=6.8 Hz, 1H), 3.81-3.64 (m, 2H), 3.47-3.39 (m, 4H), 2.41-2.32 (m, 2H), 2.13-2.04 (m, 4H), 1.35 (d, J=7.0 Hz, 3H); LCMS calculated for $C_{28}H_{30}ClN_8O_2$ (M+H)$^+$: m/z=545.2; found: 545.2.

Example 20. 2-amino-N-(1-(4-chloro-2-(2-morpholino-2-oxoethyl)-7-phenyl-2H-indazol-6-yl)ethyl)pyrazolo[1,5-a]pyrimidine-3-carboxamide

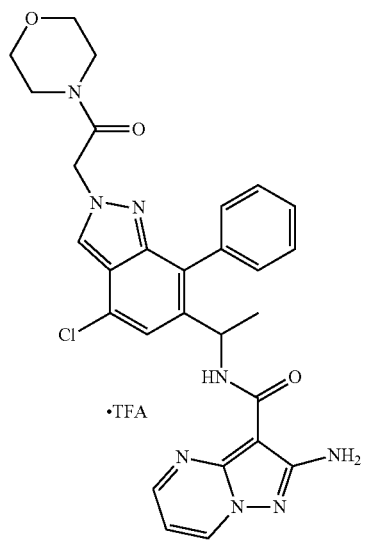 [SMILES: CC(NC(=O)c1c(N)nn2cccnc12)c1cc(Cl)c2cn(CC(=O)N3CCOCC3)nc2c1-c1ccccc1]

This compound was synthesized according to the procedure described for Example 15, utilizing 2-chloro-1-morpholinoethanone instead of methyl iodide. The residue was dissolved in MeOH and purified by preparative HPLC (C-18 column eluting with a water:acetonitrile gradient buffered at pH 10 with 0.1% ammonium hydroxide) to give the title compound as a white solid. $^1$H NMR (500 MHz, DMSO-d6) δ 8.89 (dd, J=6.7, 1.6 Hz, 1H), 8.55 (dd, J=4.5, 1.6 Hz, 1H), 8.39 (s, 1H), 8.09 (d, J=6.7 Hz, 1H), 7.55-7.43 (m, 4H), 7.43-7.36 (m, 1H), 7.24 (s, 1H), 6.98 (dd, J=6.7, 4.5 Hz, 1H), 6.39 (s, 2H), 5.45 (s, 2H), 5.12 (p, J=6.9 Hz, 1H), 3.61-3.57 (m, 2H), 3.57-3.53 (m, 2H), 3.50-3.46 (m, 2H), 3.43-3.39 (m, 2H), 1.38 (d, J=6.9 Hz, 3H); LCMS calculated for $C_{28}H_{28}ClN_8O_3$ (M+H)$^+$: m/z=559.2; found: 559.2.

Example 21 & 22. 2-amino-N-(1-(2-(2-aminoethyl)-4-chloro-7-phenyl-2H-indazol-6-yl)ethyl)pyrazolo[1,5-a]pyrimidine-3-carboxamide trifluoroacetate & 2-amino-N-(1-(1-(2-aminoethyl)-4-chloro-7-phenyl-1H-indazol-6-yl)ethyl)pyrazolo[1,5-a]pyrimidine-3-carboxamide trifluoroacetate Step 1. tert-butyl 3-(1-(4-chloro-2-(2-(1,3-dioxoisoindolin-2-yl)ethyl)-7-phenyl-2H-indazol-6-yl)ethylcarbamoyl)pyrazolo[1,5-a]pyrimidin-2-ylcarbamate & tert-butyl 3-(1-(4-chloro-1-(2-(1,3-dioxoisoindolin-2-yl)ethyl)-7-phenyl-1H-indazol-6-yl)ethylcarbamoyl)pyrazolo[1,5-a]pyrimidin-2-ylcarbamate

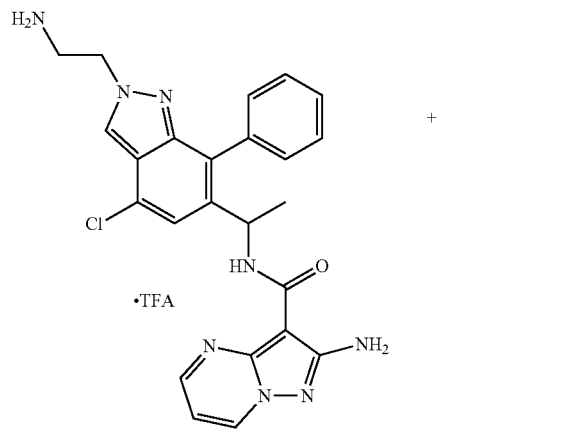

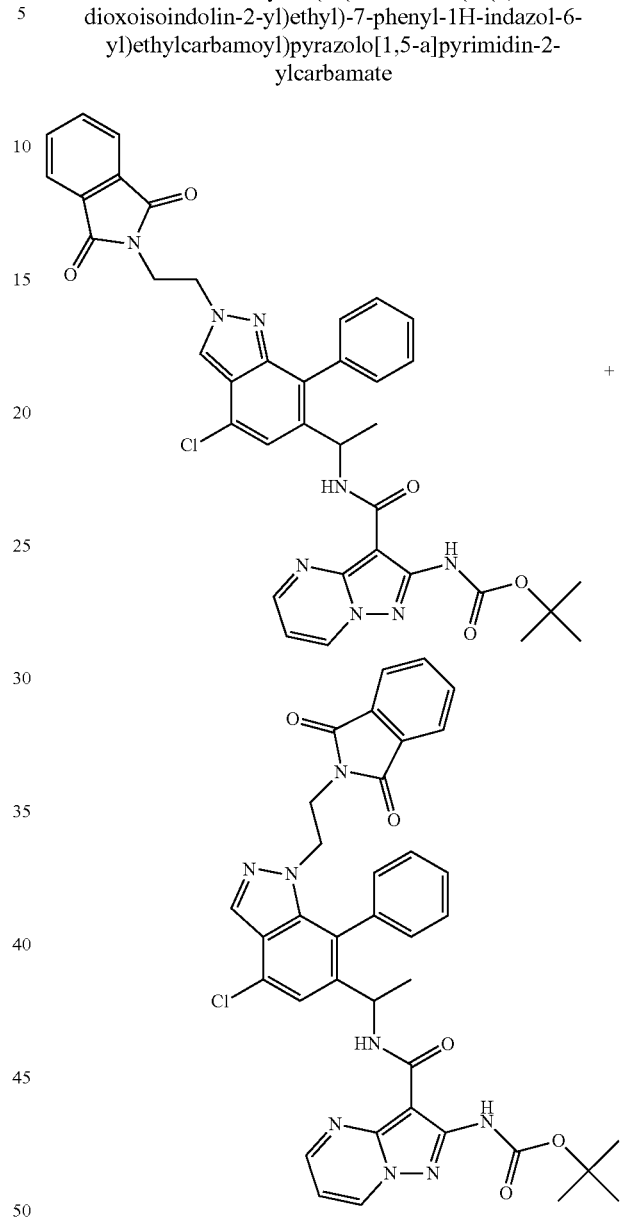

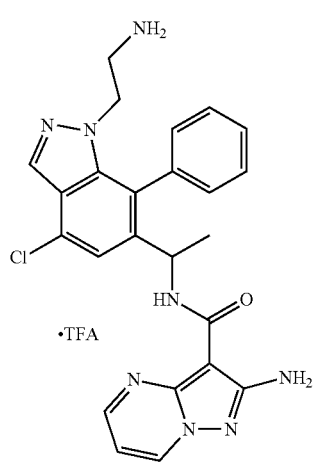

To a solution of tert-butyl 3-(1-(4-chloro-7-phenyl-1H-indazol-6-yl)ethylcarbamoyl)pyrazolo[1,5-a]pyrimidin-2-ylcarbamate (30 mg, 0.06 mmol, from Example 14, Step 6) in DMF (0.5 mL) was added potassium carbonate (23 mg, 0.17 mmol), followed by N-(2-bromoethyl)phthalimide (43 mg, 0.17 mmol) and the reaction mixture was heated to 80° C. overnight. After cooling to room temperature, the reaction mixture was diluted with EtOAc (10 mL) and washed with water (5 mL). The organic layer was dried over MgSO$_4$, filtered, and concentrated. The title compounds, which were obtained in ~1:1 ratio, were used without purification (theoretical yield assumed). Peak 1: LCMS calculated for $C_{37}H_{33}ClN_8O_5$ (M+H)$^+$: m/z=705.2; found: 705.2. Peak 2: LCMS calculated for $C_{37}H_{33}ClN_8O_5$ (M+H)$^+$: m/z=705.2; found: 705.2.

Step 2. 2-amino-N-(1-(4-chloro-2-(2-(1,3-dioxoi-soindolin-2-yl)ethyl)-7-phenyl-2H-indazol-6-yl)ethyl)pyrazolo[1,5-a]pyrimidine-3-carboxamide & 2-amino-N-(1-(4-chloro-1-(2-(1,3-dioxoisoindolin-2-yl)ethyl)-7-phenyl-1H-indazol-6-yl)ethyl)pyrazolo[1,5-a]pyrimidine-3-carboxamide

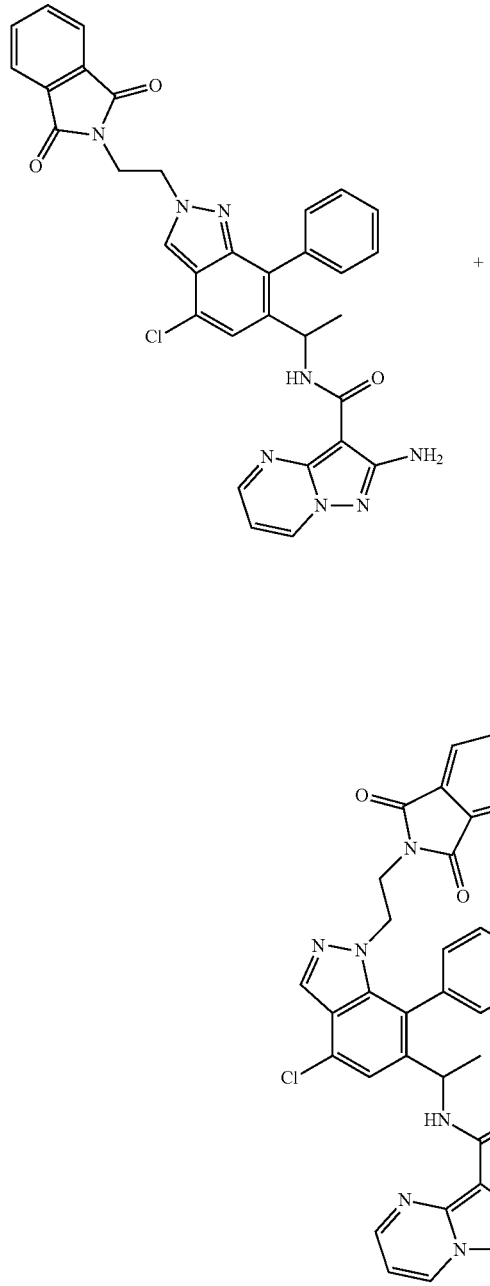

The mixture of products from the previous step (42 mg, 0.060 mmol, ~1.5:1 mixture with the N1 substituted isomer) was dissolved in CH$_2$Cl$_2$ (2 mL) and trifluoroacetic acid (0.5 mL, 6 mmol) was added at room temperature. After 0.5 h, the volatiles were removed in vacuo and the residue was used without purification (theoretical yield assumed). Peak 1: LCMS calculated for C$_{32}$H$_{26}$ClN$_8$O$_3$ (M+H)$^+$: m/z=605.2; found: 605.2. Peak 2: LCMS calculated for C$_{32}$H$_{26}$ClN$_8$O$_3$ (M+H)$^+$: m/z=605.2; found: 605.2.

Step 3. 2-amino-N-(1-(2-(2-aminoethyl)-4-chloro-7-phenyl-2H-indazol-6-yl)ethyl)pyrazolo[1,5-a]pyrimidine-3-carboxamide trifluoroacetate & 2-amino-N-(1-(1-(2-aminoethyl)-4-chloro-7-phenyl-1H-indazol-6-yl)ethyl)pyrazolo[1,5-a]pyrimidine-3-carboxamide trifluoroacetate The mixture of products from the previous step (36 mg, 0.06 mmol) was taken up in MeOH (2 mL) and treated with hydrazine (90 µL, 3 mmol) at room temperature. After 2 h, the volatiles were evaporated and the residue was partitioned between water (10 mL) and EtOAc (10 mL). The layers were separated, and the organic layer was dried over MgSO$_4$, filtered, and concentrated. The residue was dissolved in MeOH and purified by preparative HPLC (C-18 column eluting with a water:acetonitrile gradient [23-43% acetonitrile] buffered at pH 2 with 0.1% trifluoroacetic acid). The title compounds were separable, and each was obtained as a white solid. Peak 1 (Example 21): Retention time=4.43. LCMS calculated for C$_{24}$H$_{24}$ClN$_8$O (M+H)$^+$: m/z=475.2; found: 475.2. Peak 2 (Example 22): Retention time=4.67. LCMS calculated for C$_{24}$H$_{24}$ClN$_8$O (M+H)$^+$: m/z=475.2; found: 475.2.

Example 23. 2-amino-N-(1-(3-bromo-4-chloro-7-phenyl-1H-indazol-6-yl)ethyl)pyrazolo[1,5-a]pyrimidine-3-carboxamide trifluoroacetate

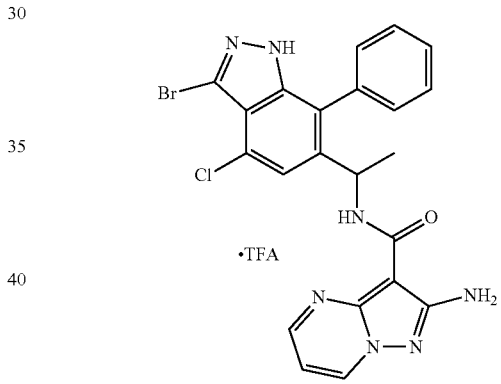

Step 1. 1-(3-bromo-4-chloro-7-phenyl-1H-indazol-6-yl)ethanone

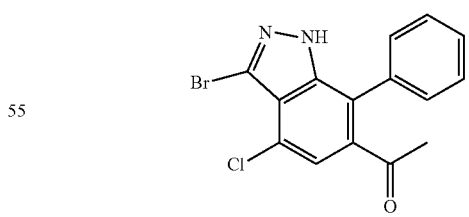

To a solution of 1-(4-chloro-7-phenyl-1H-indazol-6-yl)ethanone (39 mg, 0.14 mmol, from Example 14, Step 4) in DMF (2 mL) was added N-bromosuccinimide (31 mg, 0.17 mmol) at room temperature. After stirring for 2 h, the reaction mixture was quenched with saturated NaHCO$_3$ (5 mL) and extracted with EtOAc (10 mL). The layers were separated, and the organic layer was dried over MgSO$_4$, filtered, and concentrated. The residue was purified by flash chromatography on silica gel (0-35% EtOAc/hexanes) to afford the title compound as an orange solid (47 mg, 93%). LCMS calculated for $C_{15}H_{11}BrClN_2O$ (M+H)$^+$: m/z=349.0; found: 348.9.

Step 2. 1-(3-bromo-4-chloro-7-phenyl-1H-indazol-6-yl)ethanamine

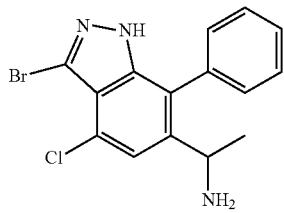 [SMILES: CC(N)c1cc(Cl)c2c(Br)n[nH]c2c1-c1ccccc1]

To a solution of 1-(3-bromo-4-chloro-7-phenyl-1H-indazol-6-yl)ethanone (30.0 mg, 0.0858 mmol) in ammonia (2M/EtOH, 2 mL) was added titanium tetraisopropoxide (51 µL, 0.17 mmol) and the reaction mixture was heated at 60° C. overnight. The resulting solution was cooled to room temperature, then 0° C., and sodium borohydride (9.7 mg, 0.26 mmol) was added. After stirring for 0.5 h, the reaction mixture was quenched with 1M NH$_4$OH, filtered, and the filtrate was washed with EtOAc (20 mL). The organic layer was washed with water (10 mL) and brine (10 mL), dried over MgSO$_4$, filtered, and concentrated. The product was used without purification (theoretical yield assumed). LCMS calculated for $C_{15}H_{11}BrClN_2(M-NH_2)^+$: m/z=333.0; found: 333.0.

Step 3. tert-butyl 3-(1-(3-bromo-4-chloro-7-phenyl-1H-indazol-6-yl)ethylcarbamoyl)pyrazolo[1,5-a]pyrimidin-2-ylcarbamate

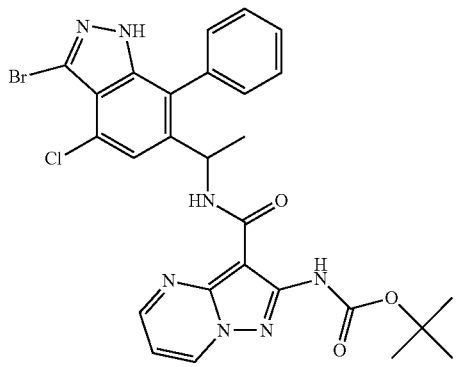 [SMILES: CC(NC(=O)c1c(NC(=O)OC(C)(C)C)nn2cccnc12)c1cc(Cl)c2c(Br)n[nH]c2c1-c1ccccc1]

This compound was synthesized according to the procedure described in Example 1, Step 6, starting from 1-(3-bromo-4-chloro-7-phenyl-1H-indazol-6-yl)ethanamine (30 mg, 0.086 mmol). The product was used without purification (theoretical yield assumed). LCMS calculated for $C_{27}H_{25}BrClN_7O_3(M+H)^+$: m/z=610.1; found: 610.1.

Step 4. 2-amino-N-(1-(3-bromo-4-chloro-7-phenyl-1H-indazol-6-yl)ethyl)pyrazolo[1,5-a]pyrimidine-3-carboxamide trifluoroacetate The deprotection was performed as described in Example 1, Step 7, starting from tert-butyl 3-(1-(3-bromo-4-chloro-7-phenyl-1H-indazol-6-yl)ethylcarbamoyl)pyrazolo[1,5-a]pyrimidin-2-ylcarbamate (52 mg, 0.086 mmol). The residue was dissolved in MeOH and purified by preparative HPLC (C-18 column eluting with a water:acetonitrile gradient buffered at pH 2 with 0.1% trifluoroacetic acid) to give the title compound as a white solid. LCMS calculated for $C_{22}H_{18}BrClN_7O$ (M+H)$^+$: m/z=510.0; found: 510.0.

Example 24. 2-amino-N-(1-(4-chloro-3-methyl-7-phenyl-1H-indazol-6-yl)ethyl)pyrazolo[1,5-a]pyrimidine-3-carboxamide trifluoroacetate

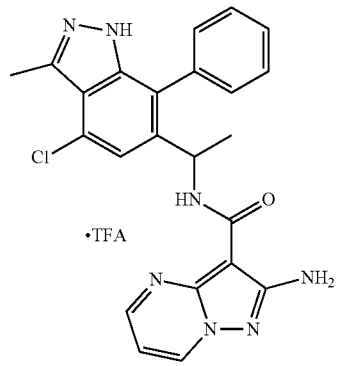 [SMILES: Cc1n[nH]c2c(-c3ccccc3)c(C(C)NC(=O)c3c(N)nn4cccnc34)cc(Cl)c12]

Step 1. 1-(4-chloro-3-methyl-7-phenyl-1H-indazol-6-yl)ethanone

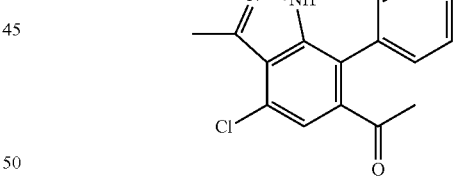

To a solution of 1-(3-bromo-4-chloro-7-phenyl-1H-indazol-6-yl)ethanone (30.0 mg, 0.0858 mmol, from Example 23, Step 1) and [1,1'-bis(diphenylphosphino)ferrocene]dichloropalladium (II) (6.3 mg, 0.0086 mmol) in dioxane (1 mL) was added 1.0 M dimethylzinc in heptane (90.1 µL, 0.0901 mmol) dropwise at room temperature, and the reaction mixture was heated to reflux for 2 h. LCMS indicated 50% conversion so an additional 0.5 equiv. dimethylzinc was added and heating was continued for an additional 1 h. The reaction mixture was filtered and the volatiles were evaporated in vacuo. The residue was purified by flash chromatography on silica gel (0-35% EtOAc/hexanes) to afford the title compound as a colorless oil (7 mg, 29%). LCMS calculated for $C_{16}H_{14}ClN_2O$ (M+H)$^+$: m/z=285.1; found: 285.1.

Step 2. 1-(4-chloro-3-methyl-7-phenyl-1H-indazol-6-yl)ethanamine

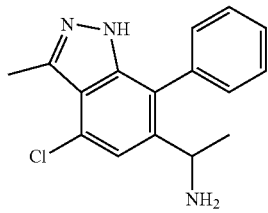 [SMILES: Cc1n[nH]c2c(-c3ccccc3)c(C(C)N)cc(Cl)c12]

This compound was synthesized according to the procedure described in Example 23, Step 2, starting from 1-(4-chloro-3-methyl-7-phenyl-1H-indazol-6-yl)ethanone (7 mg, 0.024 mmol). The product was used without purification (theoretical yield assumed). LCMS calculated for $C_{16}H_{14}ClN_2$ $(M-NH_2)^+$: m/z=269.1; found: 269.0.

Step 3. tert-butyl 3-(1-(4-chloro-3-methyl-7-phenyl-1H-indazol-6-yl)ethylcarbamoyl)pyrazolo[1,5-a]pyrimidin-2-ylcarbamate

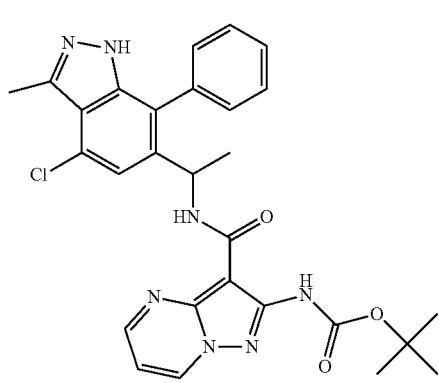 [SMILES: Cc1n[nH]c2c(-c3ccccc3)c(C(C)NC(=O)c3c(NC(=O)OC(C)(C)C)nn4cccnc34)cc(Cl)c12]

This compound was synthesized according to the procedure described in Example 1, Step 6, starting from 1-(4-chloro-3-methyl-7-phenyl-1H-indazol-6-yl)ethanamine (7 mg, 0.024 mmol). The product was used without purification (theoretical yield assumed). LCMS calculated for $C_{28}H_{29}ClN_7O_3$ $(M+H)^+$: m/z=546.2; found: 546.2.

Step 4. 2-amino-N-(1-(4-chloro-3-methyl-7-phenyl-1H-indazol-6-yl)ethyl)pyrazolo[1,5-a]pyrimidine-3-carboxamide trifluoroacetate The deprotection was performed as described in Example 1, Step 7, starting from tert-butyl 3-(1-(4-chloro-3-methyl-7-phenyl-1H-indazol-6-yl)ethylcarbamoyl)pyrazolo[1,5-a]pyrimidin-2-ylcarbamate (13 mg, 0.024 mmol). The residue was dissolved in MeOH and purified by preparative HPLC (C-18 column eluting with a water:acetonitrile gradient buffered at pH 2 with 0.1% trifluoroacetic acid) to give the title compound as a white solid. LCMS calculated for $C_{23}H_{21}ClN_7O$ $(M+H)^+$: m/z=446.1; found: 446.1.

Example 25. 2-amino-N-(1-(3,4-dimethyl-7-phenyl-1H-indazol-6-yl)ethyl)pyrazolo[1,5-a]pyrimidine-3-carboxamide trifluoroacetate

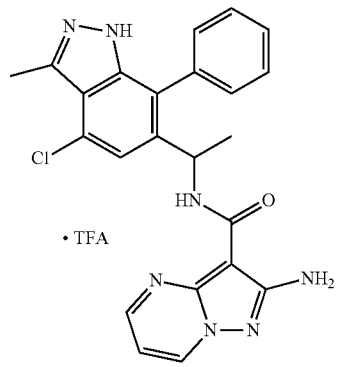 [SMILES: Cc1n[nH]c2c(-c3ccccc3)c(C(C)NC(=O)c3c(N)nn4cccnc34)cc(Cl)c12]

Step 1. 1-(3,4-dimethyl-7-phenyl-1H-indazol-6-yl)ethanone

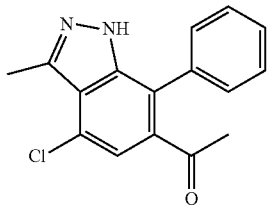 [SMILES: CC(=O)c1cc(Cl)c2c(C)n[nH]c2c1-c1ccccc1]

To a solution of 1-(3-bromo-4-chloro-7-phenyl-1H-indazol-6-yl)ethanone (20.0 mg, 0.0857 mmol, from Example 23, Step 1) and [1,1'-bis(diphenylphosphino)ferrocene]dichloropalladium (II) (4.2 mg, 0.0057 mmol) in dioxane (1 mL) was added 1.0 M dimethylzinc in heptane (110 µL, 0.11 mmol) dropwise at room temperature, and the reaction mixture was heated to reflux for 4 h. The reaction mixture was filtered and the volatiles were evaporated in vacuo. The residue was purified by flash chromatography on silica gel (0-35% EtOAc/hexanes) to afford the title compound as a colorless oil (10 mg, 67%). LCMS calculated for $C_{17}H_{17}N_2O$ $(M+H)^+$: m/z=265.1; found: 265.1.

Steps 2-4. 2-amino-N-(1-(3,4-dimethyl-7-phenyl-1H-indazol-6-yl)ethyl)pyrazolo[1,5-a]pyrimidine-3-carboxamide trifluoroacetate This compound was synthesized starting from 1-(3,4-dimethyl-7-phenyl-1H-indazol-6-yl)ethanone (10 mg, 0.038 mmol) following the procedure described for Example 24, steps 2-4. The residue was dissolved in MeOH and purified by preparative HPLC (C-18 column eluting with a water:acetonitrile gradient buffered at pH 2 with 0.1% trifluoroacetic acid) to give the title compound as a white solid. LCMS calculated for $C_{24}H_{24}N_7O$ $(M+H)^+$: m/z=426.2; found: 426.3.

Example 26. 2-Amino-N-{1-[8-chloro-5-(3-fluoro-phenyl)-3-methylimidazo[1,5-a]pyridin-6-yl]ethyl}pyrazolo[1,5-a]pyrimidine-3-carboxamide trifluoroacetate salt (Mixture of Diastereomers Prepared)

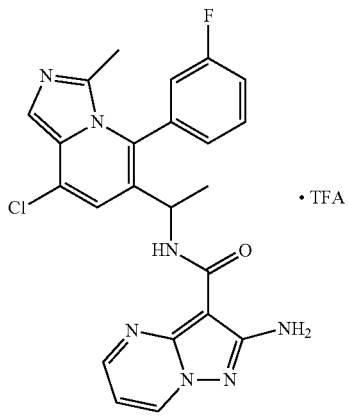 [SMILES: Cc1ncc2c(Cl)cc(C(C)NC(=O)c3c(N)nn4cccnc34)c(-c3cccc(F)c3)n12]

Step 1. Methyl 2,5-dichloronicotinate

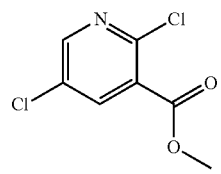

A solution of 2,5-dichloronicotinic acid (20.0 g, 104 mmol, OChem) in DCM (520 mL) was treated with oxalyl chloride (26. mL, 310 mmol) followed by DMF (0.015 mL, 0.19 mmol). The reaction was stirred overnight. The reaction mixture was then concentrated in vacuo. The acid chloride was diluted with DCM (200 mL), cooled to 0° C. and treated with MeOH (110 mL). After stirring for 30 minutes, solvents were removed in vacuo. The crude residue was dissolved in DCM and washed sequentially with saturated NaHCO₃ solution, water, and saturated NaCl solution. The organic layer was dried over Na₂SO₄, filtered, and concentrated to afford a white crystalline solid that was used without further purification. Yield: 18.8 g, 90%. LCMS calculated for $C_7H_6Cl_2NO_2(M+H)^+$: m/z=206.0; found: 206.0.

Step 2. Methyl 2,5-dichloronicotinate 1-oxide

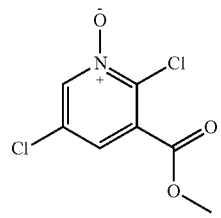

H₂O₂ (30% in water, 19.6 mL, 640 mmol) was added to methyl 2,5-dichloronicotinate (19.4 g, 94.2 mmol, prepared as in Step 1) in TFA (118 mL). The reaction mixture was heated to 70° C. for 1 hour. Solvent was removed in vacuo and the product was purified by flash chromatography, eluting with a gradient from 0-100% ethyl acetate in hexanes to afford a white solid. Yield: 17.4 g, 83%. LCMS calculated for $C_7H_6Cl_2NO_3(M+H)^+$: m/z=222.0; found: 222.0.

Step 3. Methyl 2,5-dichloro-6-cyanonicotinate

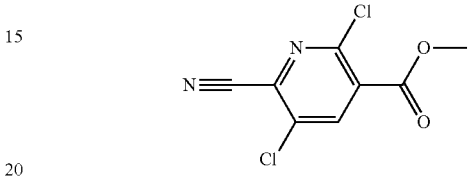

Triethylamine (16.6 mL, 119 mmol) and trimethylsilyl cyanide (25.9 mL, 194 mmol) were added to a solution of methyl 2,5-dichloronicotinate 1-oxide (17.4 g, 78.4 mmol, from Step 2) in acetonitrile (150 mL). The reaction mixture was heated to 70° C. for 20 minutes. Upon cooling to room temperature, the reaction mixture was diluted with EtOAc, and the solution was quenched by slow addition to a cold solution of aqueous K₂CO₃ (500 mL). The resulting aqueous mixture was extracted with DCM. The combined organic extracts were washed with water, followed by brine, dried over Na₂SO₄, filtered, and concentrated. The product was purified by flash chromatography, eluting with a gradient from 0-50% EtOAc/hexanes. Yield: 16.3 g, 90%. LCMS calculated for $C_8H_4Cl_2N_2O_2(M+H)^+$: m/z=231.0; found: 231.0.

Step 4. Methyl 5-chloro-6-cyano-2-(3-fluorophenyl)nicotinate

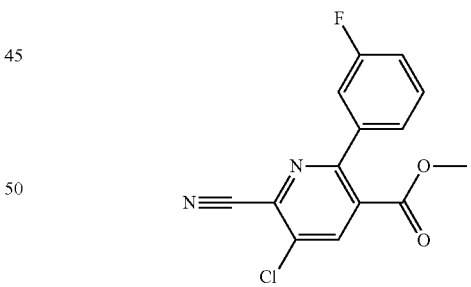

A degassed mixture of methyl 2,5-dichloro-6-cyanonicotinate (5.0 g, 22 mmol, from Step 3), (3-fluorophenyl)boronic acid (3.33 g, 23.8 mmol, Aldrich), bis(triphenylphosphine)palladium(II) chloride (1.05 g, 1.50 mmol), K₂CO₃ (6.52 g, 47.2 mmol) in water (39.0 mL), and 1,4-dioxane (101 mL) was heated at 80° C. for 1 hour. The reaction mixture was diluted with EtOAc and water. The aqueous layer was separated and extracted with additional EtOAc. The combined organic extracts were washed with water, followed by brine, dried over Na₂SO₄, filtered, and concentrated. The product was purified by flash chromatography, eluting with a gradient from 0-30% EtOAc in hexanes Step 5. Methyl 6-(aminomethyl)-5-chloro-2-(3-fluorophenyl)nicotinate acetate salt

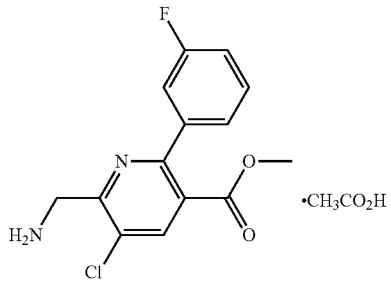

A solution of methyl 5-chloro-6-cyano-2-(3-fluorophenyl)nicotinate (5.5 g, 19 mmol, from Step 4) in acetic acid (55 mL) was degassed and then stirred under 1 atm of $H_2$ over Pd on C (5%, 2.4 g, 1.1 mmol) for 3 hours. The mixture was filtered through Celite® and solvent was removed in vacuo to afford a crystalline solid. The solid was slurried in water and filtered, and the solids were washed with water to give the desired compound as the acetate salt, contaminated with a small amount of the des-chloro byproduct, the bulk of which remained in the filtrate. Yield: 1.9 g, 26%. LCMS calculated for $C_{14}H_{13}ClFN_2O_2$ (M+H)$^+$: m/z=295.1; found: 295.0.

Step 6. Methyl 6-[(acetylamino)methyl]-5-chloro-2-(3-fluorophenyl)nicotinate

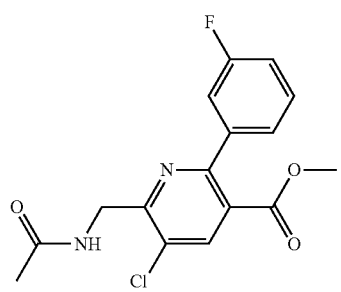 [SMILES: COC(=O)c1cc(Cl)c(CNC(C)=O)nc1-c1cccc(F)c1]

To methyl 6-(aminomethyl)-5-chloro-2-(3-fluorophenyl)nicotinate acetate (0.90 g, 2.5 mmol, from Step 5) and N,N-diisopropylethylamine (0.88 mL, 5.1 mmol) in N,N-dimethylformamide (7.4 mL) was added acetic anhydride (0.26 mL, 2.8 mmol). After 30 minutes, the mixture was quenched with saturated NaHCO$_3$ solution and diluted with water. The aqueous mixture was extracted with EtOAc. The combined organic extracts were washed sequentially with water and brine, dried over Na$_2$SO$_4$, and concentrated to give product that was used without further purification. Yield: 0.85 g, 100%. LCMS calculated for $C_{16}H_{15}ClFN_2O_3$ (M+H)$^+$: m/z=337.1; found: 337.1.

Step 7. Methyl 8-chloro-5-(3-fluorophenyl)-3-methylimidazo[1,5-a]pyridine-6-carboxylate

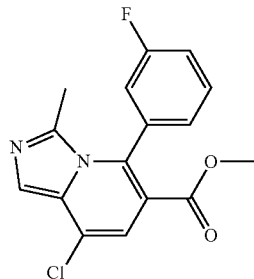 [SMILES: COC(=O)c1cc(Cl)c2cnc(C)n2c1-c1cccc(F)c1]

Methyl 6-[(acetylamino)methyl]-5-chloro-2-(3-fluorophenyl)nicotinate (0.85 g, 2.5 mmol, from Step 6) in POCl$_3$ (10 mL, 110 mmol) was heated to 90° C. for 35 minutes. The mixture was then evaporated to remove POCl$_3$. The product was purified by flash chromatography, eluting with a gradient from 0-100% EtOAc (containing 1% MeOH and 1% NH$_4$OH) in hexanes. Yield: 0.70 g, 78%. LCMS calculated for $C_{16}H_{13}ClFN_2O_2$(M+H)$^+$: m/z=319.1; found: 319.1.

Step 8. 8-Chloro-5-(3-fluorophenyl)-3-methylimidazo[1,5-a]pyridine-6-carboxylic acid

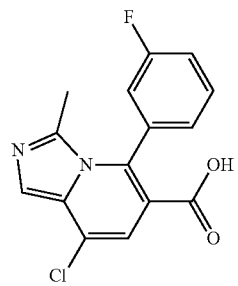 [SMILES: Cc1ncc2c(Cl)cc(C(=O)O)c(-c3cccc(F)c3)n12]

Methyl 8-chloro-5-(3-fluorophenyl)-3-methylimidazo[1,5-a]pyridine-6-carboxylate (230 mg, 0.72 mmol, from Step 7) in MeOH (5 mL) was treated with 3.0 M NaOH in water (0.96 mL, 2.9 mmol) and stirred for 5 hours. The mixture was acidified with acetic acid and the solvents were removed in vacuo. Trituration with water gave the desired compound as a light yellow solid, which was isolated by filtration and air dried. Yield: 0.20 g, 91%. LCMS calculated for $C_{15}H_{11}ClFN_2O_2$ (M+H)$^+$: m/z=305.0; found: 305.0.

Step 9. 8-Chloro-5-(3-fluorophenyl)-N-methoxy-N,3-dimethylimidazo[1,5-a]pyridine-6-carboxamide

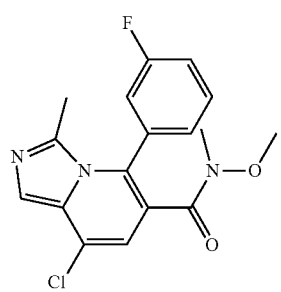 [SMILES: CON(C)C(=O)c1cc(Cl)c2cnc(C)n2c1-c1cccc(F)c1]

To a suspension of 8-chloro-5-(3-fluorophenyl)-3-methylimidazo[1,5-a]pyridine-6-carboxylic acid (0.20 g, 0.66 mmol, from Step 8) in DMF (1.8 mL) was added N,N-diisopropylethylamine (0.572 mL, 3.28 mmol), N O-dimethylhydroxylamine hydrochloride (0.192 g, 1.97 mmol), 0.6 M 1-hydroxy-7-azabenzotriazole in DMF (0.219 mL, 0.131 mmol), and N-(3-dimethylaminopropyl)-N-ethylcarbodiimide hydrochloride (0.189 g, 0.984 mmol). The precipitate slowly dissolved, and the resulting solution was stirred overnight. Saturated NaHCO$_3$ was added, and the mixture was extracted with three portions of EtOAc. The combined organic extracts were washed sequentially with water and brine, dried over Na$_2$SO$_4$, filtered and concentrated. The product was purified by flash chromatography, eluting with a gradient of 0-80% EtOAc in hexanes to afford product as a yellow solid. Yield: 0.18 g, 79%. LCMS calculated for C$_{17}$H$_{16}$ClFN$_3$O$_2$(M+H)$^+$: m/z=348.1; found: 348.0.

Step 10. 1-[8-Chloro-5-(3-fluorophenyl)-3-methylimidazo[1,5-a]pyridin-6-yl]ethanone

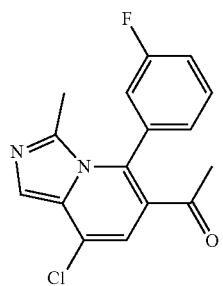 [SMILES: CC(=O)c1cc(Cl)c2cnc(C)n2c1-c1cccc(F)c1]

3.0 M Methylmagnesium bromide in THF (0.78 mL, 2.3 mmol) was added dropwise to a 0° C. solution of 8-chloro-5-(3-fluorophenyl)-N-methoxy-N,3-dimethylimidazo[1,5-a]pyridine-6-carboxamide (0.18 g, 0.52 mmol, from Step 9) in anhydrous THF (5.0 mL, 62 mmol) under N$_2$. The solution was stirred at 0° C. for 1.5 hours. The reaction was quenched at 0° C. by the addition of 1.0 M HCl in water (2.6 mL, 2.6 mmol). The mixture was then made basic by the addition of saturated NaHCO$_3$ solution. The mixture was extracted with EtOAc (75 mL). The organic extract was washed with water, followed by brine, dried over Na$_2$SO$_4$, filtered, and concentrated to afford the product as a yellow solid, which was used without further purification. Yield: 0.14 g, 89%. LCMS calculated for Cl$_6$H$_{13}$ClFN$_2$O (M+H)$^+$: m/z=303.1; found: 303.0.

Step 11. 1-[8-Chloro-5-(3-fluorophenyl)-3-methylimidazo[1,5-a]pyridin-6-yl]ethanamine (Mixture of Diastereomers Prepared)

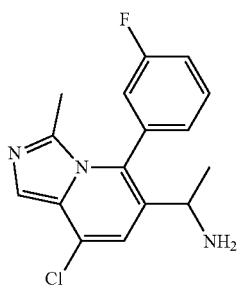 [SMILES: Cc1ncc2c(Cl)cc(C(C)N)c(-c3cccc(F)c3)n12]

A mixture of 1-[8-chloro-5-(3-fluorophenyl)-3-methylimidazo[1,5-a]pyridin-6-yl]ethanone (0.14 g, 0.46 mmol, from Step 10) and ammonium acetate (0.356 g, 4.62 mmol) in methanol (5.2 mL) was heated at 65° C. for 1 hour. Sodium cyanoborohydride (87 mg, 1.4 mmol) was then added and heating was continued for 1 hour. Additional ammonium acetate (0.356 g, 4.62 mmol) and sodium cyanoborohydride (0.087 g, 1.4 mmol) were added and heating was continued for a total of 22 hours. Upon cooling to room temperature, saturated NaHCO$_3$ solution was added and the mixture was extracted with two portions of EtOAc. The combined organic extracts were dried over Na$_2$SO$_4$, filtered, and concentrated. To remove further impurities, the residue was dissolved in 1N HCl and washed with EtOAc. The aqueous layer was made basic again by the addition of NaHCO$_3$ solution, and was extracted with EtOAc. The extract was again dried over Na$_2$SO$_4$, filtered, and concentrated. The product was purified by preparative HPLC-MS (pH 10). Yield: 61 mg, 43%. LCMS calculated for C$_{16}$H$_{16}$ClFN$_3$(M+H)$^+$: m/z=304.1; found: 304.1.

Step 12. 2-Amino-N-{1-[8-chloro-5-(3-fluorophenyl)-3-methylimidazo[1,5-a]pyridin-6-yl]ethyl}pyrazolo[1,5-a]pyrimidine-3-carboxamide trifluoroacetate salt (Mixture of Diastereomers Prepared)

1-[8-Chloro-5-(3-fluorophenyl)-3-methylimidazo[1,5-a]pyridin-6-yl]ethanamine (20. mg, 0.066 mmol, from Step 11) in DMF (0.45 mL) was added to a mixture of 2-[(tert-butoxycarbonyl)amino]pyrazolo[1,5-a]pyrimidine-3-carboxylic acid (18 mg, 0.066 mmol, J&W Pharmlab), N,N,N',N'-tetramethyl-O-(7-azabenzotriazol-1-yl)uronium hexafluorophosphate (30. mg, 0.079 mmol) and N,N-diisopropylethylamine (23 μL, 0.13 mmol) in DMF (0.4 mL). After stirring for 40 minutes, water was added and the precipitated product was isolated by filtration and air dried. The white solid so obtained was stirred with TFA (0.2 mL) in DCM (0.5 mL) for 30 minutes. Solvent was removed in vacuo and the residue was reconstituted in acetonitrile and purified by preparative HPLC-MS (pH 2). Yield: 20 mg. $^1$H NMR (400 MHz, DMSO-d$_6$, mixture of diastereomers) δ 8.95-8.88 (m, 2H), 8.60-8.50 (m, 2H), 8.09-7.95 (m, 2H), 7.87 (s, 2H), 7.76-7.59 (m, 4H), 7.59-7.42 (m, 4H), 7.35 (s, 1H), 7.34 (s, 1H), 7.05-6.99 (m, 2H), 6.43 (br s, 4H), 4.68-4.38 (m, 2H), 1.88 (s, 3H), 1.88 (s, 3H), 1.41 (d, J=6.9 Hz, 3H), 1.40 (d, J=6.9 Hz, 3H); LCMS calculated for C$_{23}$H$_{20}$ClFN$_7$O (M+H)$^+$: m/z=464.1; found: 464.1.

Example 27. 2-Amino-N-(1-(8-chloro-5-phenylimidazo[1,5-a]pyridin-6-yl)ethyl)pyrazolo[1,5-a]pyrimidine-3-carboxamide trifluoroacetate salt (Single Enantiomer Prepared)

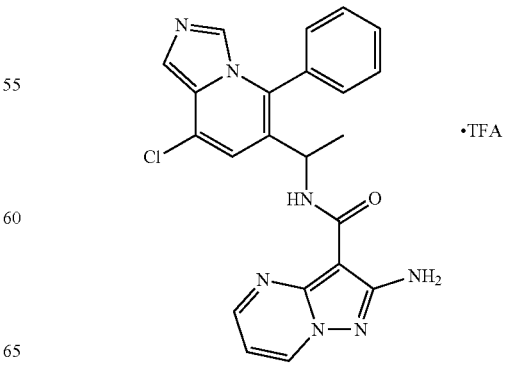

Step 1. Methyl 5-chloro-6-cyano-2-phenylnicotinate

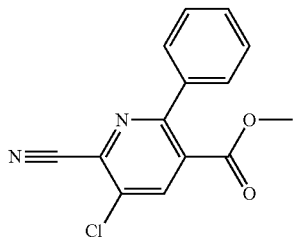 [SMILES: COC(=O)c1cc(Cl)c(C#N)nc1-c1ccccc1]

The title compound was prepared as in Example 26, Step 4, using 2,5-dichloro-6-cyanonicotinate (5.80 g, 25.1 mmol, prepared as in Example 26, Step 3) and phenylboronic acid (3.67 g, 30.1 mmol, Aldrich). Yield: 6.33 g, 93%. NMR (400 MHz, DMSO-$d_6$) δ 8.63 (s, 1H), 7.57-7.48 (m, 5H), 3.74 (s, 3H); LCMS calculated for $C_{14}H_{20}ClN_2O_2(M+H)^+$: m/z=273.0; found: 273.0.

Step 2. Methyl 6-(aminomethyl)-5-chloro-2-phenylnicotinate

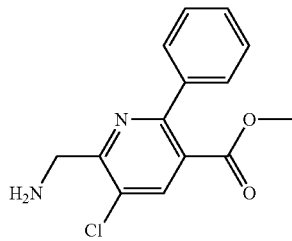 [SMILES: COC(=O)c1cc(Cl)c(CN)nc1-c1ccccc1]

To methyl 5-chloro-6-cyano-2-phenylnicotinate (1.01 g, 3.70 mmol, from Step 1) in methanol (50. mL) was added Raney Ni (1.0 mL of Raney® Nickel suspension in water). The mixture was degassed and stirred under $H_2$ (1 atm) for 2 hours. The mixture was filtered through Celite®, and the Celite® was washed with methanol. Solvent was removed from the filtrate to afford product, which was used without further purification in Step 3. Yield: 1.0 g, 97%. LCMS calculated for $C_{14}H_{14}ClN_2O_2(M+H)^+$: m/z=277.1; found: 277.1.

Step 3. Methyl 5-chloro-6-[(formylamino)methyl]-2-phenylnicotinate

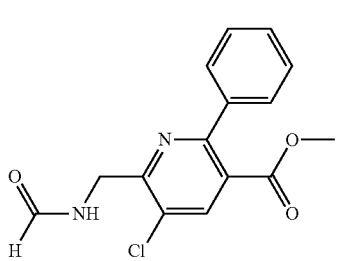 [SMILES: COC(=O)c1cc(Cl)c(CNC=O)nc1-c1ccccc1]

Formic acid (6.7 mL, 180 mmol) and acetic anhydride (1.7 mL, 18 mmol) were combined and stirred for 40 minutes, then the mixture was added dropwise into a 0° C. solution of methyl 6-(aminomethyl)-5-chloro-2-phenylnicotinate (1.0 g, 3.6 mmol, from Step 2) in DCM (20 mL). After stirring for 50 minutes at 0° C., the solution was warmed to room temperature and stirred overnight. Solvent was removed in vacuo to afford 1.34 g of crude product which was used without further purification in Step 4. LCMS calculated for $C_{15}H_{14}ClN_2O_3(M+H)^+$: m/z=305.1; found: 305.0.

Step 4. Methyl 8-chloro-5-phenylimidazo[1,5-a]pyridine-6-carboxylate

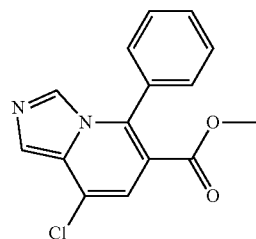 [SMILES: COC(=O)c1cc(Cl)c2cncn2c1-c1ccccc1]

Methyl 5-chloro-6-[(formylamino)methyl]-2-phenylnicotinate (1.13 g, 3.71 mmol, from Step 3) in $POCl_3$ (5.5 mL, 59 mmol) was heated to 75° C. for 35 minutes. Upon cooling to room temperature, the mixture was poured slowly onto crushed ice, and the ice-cold mixture was neutralized by the addition of solid $Na_2CO_3$. The aqueous mixture was extracted with DCM. The organic phase was dried over $Na_2SO_4$, filtered, and concentrated. The product was purified by flash chromatography, eluting with a gradient from 0-30% EtOAc in hexanes. Yield: 0.76 g, 71%. $^1$H NMR (400 MHz, DMSO-$d_6$) δ 7.77 (s, 1H), 7.65 (s, 1H), 7.63-7.57 (m, 3H), 7.56-7.49 (m, 2H), 7.41 (s, 1H), 3.57 (s, 3H); LCMS calculated for $C_{15}H_{12}ClN_2O_2$ $(M+H)^+$: m/z=287.1; found: 287.1.

Step 5. 8-Chloro-5-phenylimidazo[1,5-a]pyridine-6-carboxylic acid

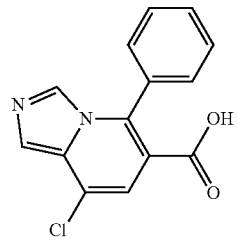 [SMILES: O=C(O)c1cc(Cl)c2cncn2c1-c1ccccc1]

The title compounds was prepared as in Example 26, Step 8, using methyl 8-chloro-5-phenylimidazo[1,5-a]pyridine-6-carboxylate (0.75 g, 2.6 mmol, from Step 4). Yield: 0.70 g, 98%. LCMS calculated for $C_{14}H_{10}ClN_2O_2(M+H)^+$: m/z=273.0; found: 273.0.

Step 6. 8-Chloro-N-methoxy-N-methyl-5-phenylimidazo[1,5-a]pyridine-6-carboxamide

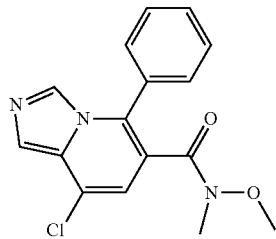 [SMILES: CON(C)C(=O)c1cc(Cl)c2cncn2c1-c1ccccc1]

The title compound was prepared as in Example 26, Step 9, using 8-chloro-5-phenylimidazo[1,5-a]pyridine-6-carboxylic acid (0.70 g, 2.6 mmol, from Step 5). Yield: 0.62 g, 76%. $^1$H NMR (400 MHz, DMSO-$d_6$) δ 8.02 (s, 1H), 7.64 (s, 1H), 7.60 (s, 5H), 7.22 (s, 1H), 3.49 (br s, 3H), 3.00 (br s, 3H); LCMS calculated for $C_{16}H_{15}ClN_3O_2$(M+H)$^+$: m/z=316.1; found: 316.0.

Step 7. 1-(8-Chloro-5-phenylimidazo[1,5-a]pyridin-6-yl)ethanone

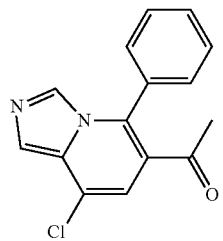 [SMILES: CC(=O)c1cc(Cl)c2cncn2c1-c1ccccc1]

The title compound was prepared from 8-chloro-N-methoxy-N-methyl-5-phenylimidazo[1,5-a]pyridine-6-carboxamide (0.62 g, 2.0 mmol, from Step 6) by the procedure of Example 26, Step 10. The product was used without further purification in Step 8. $^1$H NMR (400 MHz, CDCl$_3$) δ 8.03 (s, 1H), 7.75 (s, 1H), 7.71-7.61 (m, 3H), 7.53-7.42 (m, 2H), 7.37 (s, 1H), 1.96 (s, 3H); LCMS calculated for $C_{15}H_{12}ClN_2O$ (M+H)$^+$: m/z=271.1; found: 271.1.

Step 8. 1-(8-Chloro-5-phenylimidazo[1,5-a]pyridin-6-yl)ethanamine (Scalemic Mixture Prepared)

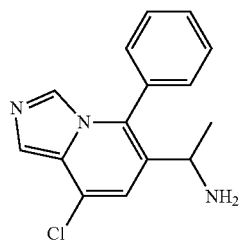 [SMILES: CC(N)c1cc(Cl)c2cncn2c1-c1ccccc1]

A solution of 1-(8-chloro-5-phenylimidazo[1,5-a]pyridin-6-yl)ethanone (0.28 g, 0.83 mmol, from Step 7) and (R)-2-methylpropane-2-sulfinamide (0.22 g, 1.8 mmol, Combi-Blocks) in THF (3.0 mL) was treated with titanium(IV) ethoxide (380 μL, 1.8 mmol, Strem), and was heated to 70° C. in a sealed reaction vessel overnight. The reaction mixture was cooled to −44° C. and 1.0 M L-Selectride® in THF (2.9 mL, 2.9 mmol) was added dropwise. The reaction mixture was warmed to room temperature over 1 hour. The reaction mixture was then cooled to 0° C. and was quenched by the addition of MeOH (0.50 mL). Upon warming to room temperature, the mixture was diluted with EtOAc (25 mL) and brine (0.20 mL) and was stirred for 5 minutes. The slurry was filtered through Celite®, and the filter cake was washed with EtOAc. The filtrate was concentrated to give a residue. LCMS indicated a mixture of diastereomers, a major and a minor isomer, which were not separated. The residue was dissolved in methanol (7.5 mL) and treated with 4.0 N HCl in dioxane (6.2 mL, 25 mmol) for 1 hour. Solvent was removed in vacuo and the residue was reconstituted in MeOH and purified via preparative HPLC-MS (pH=2). The fractions containing product were evaporated to remove most of the acetonitrile. The aqueous mixture was made basic (pH 10) by the addition of sodium carbonate. The basic aqueous mixture was saturated with NaCl and extracted twice with DCM. The combined organic extracts were dried over Na$_2$SO$_4$, filtered, and concentrated to afford product as a white solid. Yield: 91 mg, 40%. $^1$H NMR (400 MHz, DMSO-$d_6$) δ 7.69-7.56 (m, 4H), 7.54 (s, 1H), 7.52-7.47 (m, 2H), 7.38 (s, 1H), 3.65 (q, J=6.5 Hz, 1H), 1.90 (br s, 2H), 1.16 (d, J=6.6 Hz, 3H); LCMS calculated for $C_{15}H_{15}ClN_3$ (M+H)$^+$: m/z=272.1; found: 272.1.

Step 9. tert-Butyl [3-({[1-(8-chloro-5-phenylimidazo[1,5-a]pyridin-6-yl)ethyl]amino}carbonyl)pyrazolo[1,5-a]pyrimidin-2-yl]carbamate (Single Enantiomer Isolated)

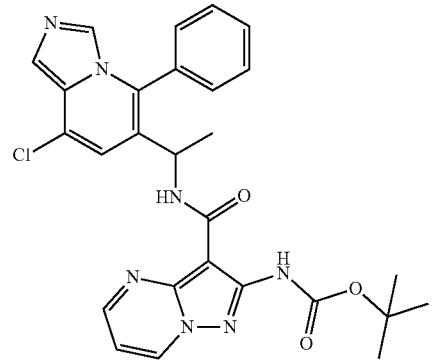 [SMILES: CC(NC(=O)c1c(NC(=O)OC(C)(C)C)nn2cccnc12)c1cc(Cl)c2cncn2c1-c1ccccc1]

A solution of 1-(8-chloro-5-phenylimidazo[1,5-a]pyridin-6-yl)ethanamine (84 mg, 0.31 mmol, from Step 8) in DMF (2.1 mL) was added to a mixture of 2-[(tert-butoxycarbonyl)amino]pyrazolo[1,5-a]pyrimidine-3-carboxylic acid (95 mg, 0.34 mmol, J&W Pharmlab), N,N,N',N'-tetramethyl-O-(7-azabenzotriazol-1-yl)uronium hexafluorophosphate (130 mg, 0.34 mmol) and N,N-diisopropylethylamine (110 μL, 0.62 mmol) in DMF (2 mL). After 30 minutes, saturated NaHCO$_3$ was added. Dilution with water resulted in a precipitate, which was isolated by filtration. The solid product was washed with water, and was air dried. The solid was then dissolved in DCM, and the solution was filtered to remove insoluble impurities. The filtrate was concentrated to afford the product as a light yellow solid. Yield: 0.15 g, 91%. LCMS calculated for $C_{27}H_{27}ClN_7O_3$ (M+H)$^+$: m/z=532.2; found: 532.2. The scalemic mixture was separated by HPLC (Phenomenex Lux Cellulose C-1, 5 μm, 21.2×250 mm, 9 mg/900 μL loading, eluting with 20% EtOH in hexanes at 18 mL/min over 13 min). This provided Enantiomer 1 (first to elute, major component, retention time 8.3 min, Yield: 76 mg), and Enantiomer 2 (second to elute, minor component, retention time 10.9 min, Yield: 10 mg).

Step 10. 2-Amino-N-[1-(8-chloro-5-phenylimidazo[1,5-a]pyridin-6-yl)ethyl]pyrazolo[1,5-a]pyrimidine-3-carboxamide trifluoroacetate salt (Single Enantiomer)

tert-Butyl[3-({[1-(8-chloro-5-phenylimidazo[1,5-a]pyridin-6-yl)ethyl]amino}carbonyl)pyrazolo[1,5-a]pyrimidin-2-yl]carbamate (76 mg, 0.14 mmol, Enantiomer 1 from Step 9) was stirred with TFA (0.5 mL) in DCM (2.0 mL) for 30 minutes. The solvents were removed in vacuo, and the product was reconstituted in acetonitrile and purified by preparative HPLC-MS (pH 2). Yield: 69 mg, 83%, (1.4× TFA salt). $^1$H NMR (500 MHz, DMSO-$d_6$) δ 8.90 (dd, J=6.7, 1.6 Hz, 1H), 8.54 (dd, J=4.5, 1.6 Hz, 1H), 8.02 (d, J=6.4 Hz, 1H), 7.96 (s, 1H), 7.84-7.78 (m, 1H), 7.76 (s, 1H), 7.72-7.66 (m, 1H), 7.66-7.60 (m, 2H), 7.60-7.54 (m, 1H), 7.35 (s, 1H), 6.99 (dd, J=6.7, 4.5 Hz, 1H), 4.75 (p, J=7.0 Hz, 1H), 1.41 (d, J=7.0 Hz, 3H); LCMS calculated for $C_{22}H_{19}ClN_7O$ (M+H)$^+$: m/z=432.1; found: 432.1.

Example 28. 2-Amino-N-[1-(8-chloro-5-phenylimidazo[1,5-a]pyridin-6-yl)ethyl]pyrazolo[1,5-a]pyrimidine-3-carboxamide trifluoroacetate salt (Single Enantiomer)

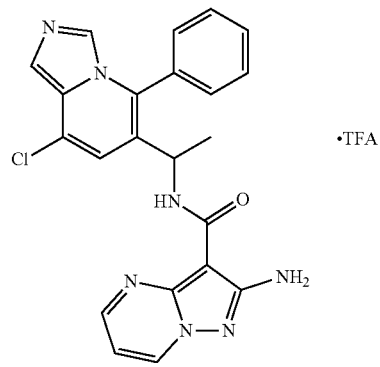 [SMILES: CC(NC(=O)c1c(N)nn2cccnc12)c1cc(Cl)c2cncn2c1-c1ccccc1]

tert-Butyl [3-({[1-(8-chloro-5-phenylimidazo[1,5-a]pyridin-6-yl)ethyl]amino}carbonyl)pyrazolo[1,5-a]pyrimidin-2-yl]carbamate (10 mg, 0.019 mmol, Enantiomer 2 from Example 27, Step 9) was stirred with TFA (0.2 mL) in DCM (1.0 mL) for 30 minutes. The solvents were removed in vacuo, and the product was reconstituted in acetonitrile and purified by preparative HPLC-MS (pH=2). Yield: 4.9 mg, 45%. $^1$H NMR (400 MHz, DMSO-$d_6$) δ 8.92 (dd, J=6.7, 1.5 Hz, 1H), 8.56 (dd, J=4.5, 1.5 Hz, 1H), 8.04 (d, J=6.4 Hz, 1H), 7.87-7.77 (m, 2H), 7.77-7.52 (m, 5H), 7.32 (s, 1H), 7.01 (dd, J=6.7, 4.5 Hz, 1H), 4.76 (p, J=6.8 Hz, 1H), 1.43 (d, J=7.0 Hz, 3H); LCMS calculated for $C_{22}H_{19}ClN_7O$ (M+H)$^+$: m/z=432.1; found: 432.1.

Example 29. 2-Amino-N-{1-[5-(3-fluorophenyl)-3,8-dimethylimidazo[1,5-a]pyridin-6-yl]ethyl}pyrazolo[1,5-a]pyrimidine-3-carboxamide trifluoroacetate salt (Mixture of Diastereomers Prepared)

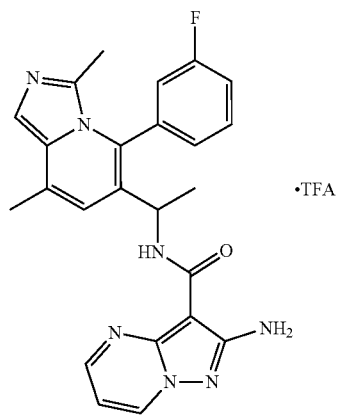 [SMILES: Cc1cc(C(C)NC(=O)c2c(N)nn3cccnc23)c(-c2cccc(F)c2)n2c(C)ncc12]

Step 1. 1-[5-(3-Fluorophenyl)-3,8-dimethylimidazo[1,5-a]pyridin-6-yl]ethanone

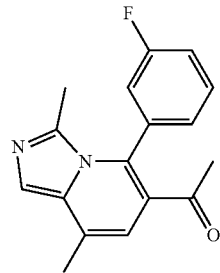

A solution of 1-[8-chloro-5-(3-fluorophenyl)-3-methylimidazo[1,5-a]pyridin-6-yl]ethanone (0.046 g, 0.15 mmol, from Example 26, Step 10) and 1.0 M dimethylzinc in heptane (0.30 mL, 0.30 mmol) in 1,4-dioxane (2 mL) was degassed and [1,1'-bis(diphenylphosphino)ferrocene]dichloropalladium (II) (0.011 g, 0.015 mmol) was added. The reaction mixture was heated to 100° C. for 2 hours in a sealed reaction vial. The reaction mixture was then poured into saturated NaHCO$_3$ and the aqueous mixture was extracted with three portions of EtOAc. The combined organic extracts were washed with brine, dried over Na$_2$SO$_4$, filtered, and concentrated. The product was purified by flash chromatography, eluting with a gradient from 0-100% EtOAc/hexanes. LCMS calculated for $C_{17}H_{16}FNO_2$ (M+H)$^+$: m/z=283.1; found: 283.1.

Step 2. 1-[5-(3-Fluorophenyl)-3,8-dimethylimidazo[1,5-a]pyridin-6-yl]ethanamine (Mixture of Diastereomers Prepared)

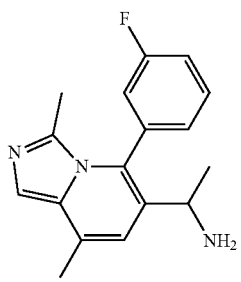 [SMILES: Cc1cc(C(C)N)c(-c2cccc(F)c2)n2c(C)ncc12]

Titanium tetraisopropoxide (0.052 mL, 0.18 mmol) was added to a mixture of 1-[5-(3-fluorophenyl)-3,8-dimethyl-imidazo[1,5-a]pyridin-6-yl]ethanone (0.025 g, 0.088 mmol, prepared as in Step 1) in 2.0 M ammonia in ethanol (0.22 mL, 0.44 mmol). The reaction was heated to 60° C. for 2 hours. The reaction mixture was then cooled to 0° C., and NaBH$_4$ (0.0050 g, 0.13 mmol) was added. After 30 minutes, the reaction mixture was quenched with water and insoluble material was removed by filtration. The solids were washed with acetonitrile. The filtrate was concentrated and the product was used without further purification in Step 3. LCMS calculated for $C_{17}H_{19}FN_3(M+H)^+$: m/z=284.1; found: 284.1.

Step 3. 2-Amino-N-{1-[5-(3-fluorophenyl)-3,8-dimethylimidazo[1,5-a]pyridin-6-yl]ethyl}pyrazolo[1,5-a]pyrimidine-3-carboxamide trifluoroacetate salt (Mixture of Diastereomers Prepared)

A solution of 1-[5-(3-fluorophenyl)-3,8-dimethylimidazo[1,5-a]pyridin-6-yl]ethanamine (0.025 g, 0.088 mmol, as a mixture of diastereomers from Step 2) in DMF (2 mL) was treated with 2-[tert-butoxycarbonyl)amino]pyrazolo[1,5-a]pyrimidine-3-carboxylic acid (0.039 g, 0.14 mmol, J&W Pharmlab), N,N-diisopropylethylamine (0.046 mL, 0.26 mmol) and N,N,N',N'-tetramethyl-O-(7-azabenzotriazol-1-yl)uronium hexafluorophosphate (0.074 g, 0.19 mmol). After stirring for 2 hours, the reaction mixture was diluted with water and extracted with EtOAc. The combined organic extracts were dried over Na$_2$SO$_4$, filtered, and concentrated. The crude product was deprotected by stirring with TFA (1 mL) in DCM (1 mL) for 1 hour. The solvents were removed in vacuo and the residue was reconstituted in MeCN and purified via preparative HPLC-MS (pH 2). Yield: 8 mg. $^1$H NMR (400 MHz, CD$_3$OD, mixture of diastereomers) δ 8.74-8.68 (m, 2H), 8.58-8.53 (m, 2H), 8.00 (s, 2H), 7.77-7.58 (m, 4H), 7.50-7.35 (m, 4H), 7.17 (s, 2H), 7.04-6.95 (m, 2H), 4.82-4.69 (m, 2H), 2.53 (s, 6H), 2.09 (s, 6H), 1.51 (d, J=6.9 Hz, 3H), 1.50 (d, J=6.9 Hz, 3H); LCMS calculated for $C_{24}H_{23}FN_7O$ (M+H)$^+$: m/z=444.1; found: 444.1.

Example 30. 2-Amino-N-[1-(8-cyano-5-phenylimidazo[1,5-a]pyridin-6-yl)ethyl]pyrazolo[1,5-a]pyrimidine-3-carboxamide trifluoroacetate salt

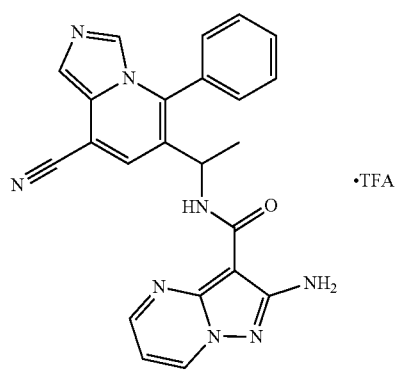 [SMILES: CC(NC(=O)c1c(N)nn2cccnc12)c1cc(C#N)c2cncn2c1-c1ccccc1]

Step 1. 6-Acetyl-5-phenylimidazo[1,5-a]pyridine-8-carbonitrile

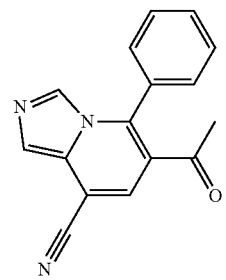

A microwavable vial was charged with 1-(8-chloro-5-phenylimidazo[1,5-a]pyridin-6-yl)ethanone (50. mg, 0.18 mmol, from Example 27, Step 7), Zn(CN)$_2$ (24 mg, 0.20 mmol), tris(dibenzylideneacetone)dipalladium(0) chloroform adduct (11 mg, 0.011 mmol), and 2-(dicyclohexylphosphino)-2',6'-dimethoxy-1,1'-biphenyl (7.6 mg, 0.018 mmol). DMF (3.35 mL) and water (17 µL, 0.92 mmol) were added. The mixture was degassed and the reaction was heated in the microwave to 150° C. for 30 minutes. The reaction mixture was poured into saturated NaHCO$_3$ and extracted with three portions of EtOAc. The combined organic extracts were washed with water, then brine, dried over Na$_2$SO$_4$, filtered and concentrated. The product was purified by flash chromatography, eluting with a gradient from 0-40% EtOAc/hexanes, to afford a yellow solid. Yield: 37 mg, 77%. LCMS calculated for $C_{16}H_{11}N_3O$ (M+H)$^+$: m/z=262.1; found: 262.2.

Step 2. 6-(1-Aminoethyl)-5-phenylimidazo[1,5-a]pyridine-8-carbonitrile (Racemic Mixture Prepared)

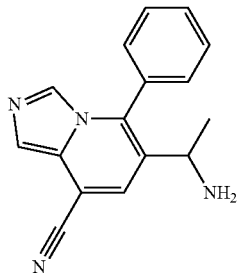 [SMILES: CC(N)c1cc(C#N)c2cncn2c1-c1ccccc1]

6-Acetyl-5-phenylimidazo[1,5-a]pyridine-8-carbonitrile (36 mg, 0.14 mmol, from Step 1) was dissolved in MeOH (1.5 mL) and ammonium acetate (106 mg, 1.38 mmol) was added. The resulting mixture was heated at 65° C. for 1 hour. Sodium cyanoborohydride (26 mg, 0.41 mmol) was added and the solution was heated at 65° C. overnight. Upon cooling to room temperature, the reaction was quenched by the addition of water was added. The mixture was diluted with acetonitrile and the product was purified by preparative HPLC-MS (pH 10; eluting with a gradient from 19.4-37.4% MeCN in water in 12 minutes), which afforded two peaks with the desired mass. The desired product was Peak 1, the minor isomer (eluting at a retention time of 7.0 min), which on evaporation, afforded a yellow solid that was used in Step 3. Yield: 2.8 mg, 8%. LCMS calculated for $C_{16}H_{15}N_4$(M+H)$^+$: m/z=263.1; found: 263.1.

Step 3. 2-Amino-N-[1-(8-cyano-5-phenylimidazo[1,5-a]pyridin-6-yl)ethyl]pyrazolo[1,5-a]pyrimidine-3-carboxamide trifluoroacetate salt (Racemic Mixture Prepared)

A mixture of 2-[(tert-butoxycarbonyl)amino]pyrazolo[1,5-a]pyrimidine-3-carboxylic acid (3.3 mg, 0.012 mmol), N,N,N',N'-tetramethyl-O-(7-azabenzotriazol-1-yl)uronium hexafluorophosphate (4.5 mg, 0.012 mmol) and N,N-diisopropylethylamine (3.7 µL, 0.021 mmol) in DMF (0.20 mL) was stirred for 5 minutes, and 6-(1-aminoethyl)-5-phenylimidazo[1,5-a]pyridine-8-carbonitrile (2.8 mg, 0.011 mmol, Peak 1 from Step 2) in DMF (0.22 mL) was then added. After 30 minutes, the reaction was diluted with saturated NaHCO$_3$, followed by water. The aqueous mixture was extracted with EtOAc and the solvent was removed in vacuo. The crude product was stirred with TFA (0.10 mL) in DCM (0.50 mL) for 1 hour and the solvents were evaporated. The residue was dissolved in acetonitrile and purified by preparative HPLC-MS (pH=2). Yield: 2.5 mg.

$^1$H NMR (400 MHz, DMSO-d$_6$) δ 8.92 (dd, J=6.7, 1.5 Hz, 1H), 8.56 (dd, J=4.5, 1.6 Hz, 1H), 8.05 (d, J=6.2 Hz, 1H), 7.93 (s, 1H), 7.85 (d, J=7.6 Hz, 1H), 7.78-7.57 (m, 6H), 7.01 (dd, J=6.7, 4.5 Hz, 1H), 6.44 (br s, 2H), 4.74 (p, J=6.7 Hz, 1H), 1.44 (d, J=7.0 Hz, 3H); LCMS calculated for $C_{23}H_{19}N_8O$ (M+H)$^+$: m/z=423.1; found: 423.1.

Examples 31A-31B. 2-Amino-N-((1S)-1-(8-chloro-5-(2-methyl-1,1-dioxidothiomorpholino)imidazo[1,5-a]pyridin-6-yl)ethyl)pyrazolo[1,5-a]pyrimidine-3-carboxamide trifluoroacetate salt (Isomers 1-2, Scalemic Mixture Prepared)

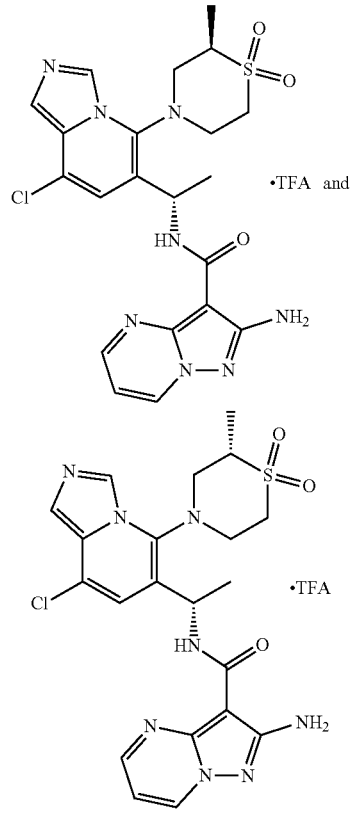

Step 1. Benzyl 2-methylthiomorpholine-4-carboxylate 1,1-dioxide (Single Isomers)

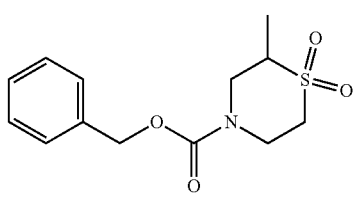 [SMILES: CC1CN(C(=O)OCc2ccccc2)CCS1(=O)=O]

To the suspension of 2-methylthiomorpholine 1,1-dioxide hydrochloride (0.25 g, 1.4 mmol) (racemic mixture, Enamine Building Blocks, EN300-137734) in dichloromethane (4.5 mL) was added triethylamine (0.75 mL, 3.5 mmol). The mixture was cooled to 0° C. Benzyl chloroformate (0.29 mL, 2.0 mmol) was added dropwise. White suspension was observed. The reaction mixture was warmed to room temperature and stirred for 2 h before the solvent was removed under vacuum. The crude product was purified by flash column chromatography (0.35 g, 93% yield). The purified product was submitted for chiral HPLC purification (Phenomenex Lux Amylose 1 column) to afford the two enantiopure isomers.

Step 2. 2-Methylthiomorpholine 1,1-dioxide (Single Isomers)

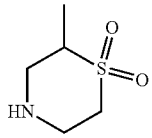

A solution of benzyl 2-methylthiomorpholine-4-carboxylate 1,1-dioxide (0.12 g, 0.42 mmol, peak 2, step 1) in ethyl acetate (2 ml) was degassed with nitrogen gas for 3 minutes before palladium (10% on carbon, 0.045 g, 0.04 mmol) was added. After degassing for another 3 min, the mixture was put under vacuum and hydrogen (1 atm) was then charged into the reaction vessel. The mixture was stirred at room temperature for 12 h. After filtration through Celite, the resulting solution was concentrated under vacuum to afford 2-methylthiomorpholine 1,1-dioxide (single isomer 1, 0.06 g, 0.402 mmol, 95% yield). Single isomer 2 was synthesized according to the above procedure, using peak 1 from step 1 as the starting material.

Step 3. 1-(8-fluoro-5-(2-methyl-1,1-dioxidothiomorpholino)imidazo[1,5-a]pyridin-6-yl)ethan-1-one (Single Isomer)

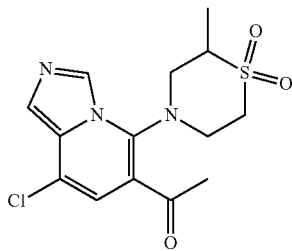 [SMILES: CC(=O)c1cc(Cl)c2cncn2c1N1CCS(=O)(=O)C(C)C1]

A solution of 1-(5,8-dichloroimidazo[1,5-a]pyridin-6-yl)ethan-1-one (0.64 g, 2.8 mmol) (Example 130, Step 7), 2-methylthiomorpholine 1,1-dioxide (single isomer 1, step 2, 0.54 g, 3.6 mmol) and N,N-diethylpropan-2-amine (1.3 mL, 8.4 mmol) in acetonitrile (9 mL) was heated at 140° C. in a microwave reactor and stirred for 5 h. After cooling to room temperature, the solvents were removed under vacuum and the resulting residue was purified by flash column chromatography (0-100% ethyl acetate in hexane to 0-35% methanol in ethyl acetate) to afford 1-(8-chloro-5-(2-methyl-1,1-dioxidothiomorpholino)imidazo[1,5-a]pyridin-6-yl)ethan-1-one (0.9 g, 94% yield) LCMS calculated for $C_{14}H_{17}O_3N_3SCl$ (M+H)$^+$: m/z=342.1; found 342.0.

Step 4. (S)—N-((1S)-1-(8-Chloro-5-(2-methyl-1,1-dioxidothiomorpholino)imidazo[1,5-a]pyridin-6-yl)ethyl)-2-methylpropane-2-sulfinamide (Single Isomer, Scalemic Mixture)

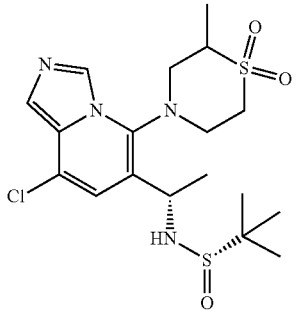 [SMILES: CC1CN(c2c([C@H](C)N[S@@](=O)C(C)(C)C)cc(Cl)c3cncn23)CCS1(=O)=O]

To a suspension of 1-(8-chloro-5-(2-methyl-1,1-dioxidothiomorpholino)imidazo[1,5-a]pyridin-6-yl)ethan-1-one (1.9 g, 5.6 mmol) and (S)-2-methylpropane-2-sulfinamide (6.7 g, 55.6 mmol) in cyclopentyl methyl ether (4 mL) was added titanium tetraisopropoxide (4.9 mL, 16.6 mmol). The reaction mixture was heated to 100° C. and stirred for 36 h. The reaction mixture was cooled to 0° C. and sodium tetrahydroborate (1.05 g, 27.8 mmol) was added in one portion. The mixture was warmed to room temperature and stirred for 8 h. The reaction mixture was cooled to 0° C. and was quenched by the dropwise addition of methanol (1 mL). The resulting solution was poured into brine. The suspension was filtered through celite. The filtrate was diluted with ethyl acetate and the layers were separated. The organic layer was dried over sodium sulfate, filtered, and concentrated, and the residue was purified by flash column chromatography to afford the desired product (1.9 g, 77% yield). LCMS calculated for $C_{18}H_{28}O_3N_4S_2Cl$ (M+H)$^+$: m/z=447.1; found 447.2.

Step 5. (1S)-1-[1,8-Dichloro-5-(1,1-dioxido-1,2,5-thiadiazepan-5-yl)imidazo[1,5-a]pyridin-6-yl]ethanamine hydrogen chloride salt (Single Diasteromer, Scalemic Mixture)

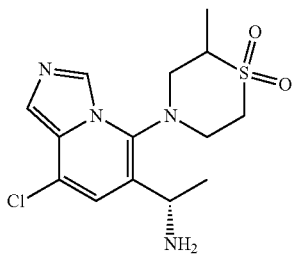 [SMILES: CC1CN(c2c([C@H](C)N)cc(Cl)c3cncn23)CCS1(=O)=O]

To the solution of (S)—N-(1-(8-chloro-5-(2-methyl-1,1-dioxidothiomorpholino)imidazo[1,5-a]pyridin-6-yl)ethyl)-2-methylpropane-2-sulfinamide (1.9 g, 4.2 mmol) in methanol (10 mL) was added hydrogen chloride (4M in dioxane, 10 mL) at 0° C. The mixture was warmed to room temperature and stirred for 1 h. Volatiles were removed under vacuum to afford the crude product as a HCl salt, which was used without further purification. LCMS calculated for $C_{14}H_{20}ClN_4O_2S$ (M+H)$^+$: m/z=343.1; found 343.1.

Step 6. 2-Amino-N-(1-[8-chloro-5-(2-methyl-1,1-dioxidothiomorpholin-4-yl)imidazo[1,5-a]pyridin-6-yl]ethyl}pyrazolo[1,5-a]pyrimidine-3-carboxamide trifluoroacetate salt (Single Diasteromer, Scalemic Mixture)

N,N-Diethylpropan-2-amine (2.45 ml, 15.8 mmol) was added to 2-((tert-butoxycarbonyl)amino)pyrazolo[1,5-a]pyrimidine-3-carboxylic acid (1.32 g, 4.7 mmol) and N,N,N',N'-tetramethyl-O-(7-azabenzotriazol-1-yl)uronium hexafluorophosphate (1.65 g, 4.3 mmol) in N,N-dimethylformamide (8 mL). After stirring for 10 minutes a suspension of (1S)-1-[1,8-dichloro-5-(1,1-dioxido-1,2,5-thiadiazepan-5-yl)imidazo[1,5-a]pyridin-6-yl]ethanamine hydrogen chloride salt (step 5, 1.5 g, 3.9 mmol) in N,N-dimethylformamide (3 mL) was added dropwise. The reaction was stirred for 1 h at room temperature. The reaction was diluted with water (100 mL) and filtered. The cake was washed with water (10 mL) and air-dried for 2 h. Trifluoroacetic acid (10 mL) was added to a solution of the crude product in dichoromethane (10 mL). After stirring for 1 h at room temperature, volatiles were removed in vacuo and the product was purified by preparative LCMS (pH 2) to afford 2-amino-N-(1-[8-chloro-5-(2-methyl-1,1-dioxidothiomorpholin-4-yl)imidazo[1,5-a]pyridin-6-yl]ethyl)pyrazolo[1,5-a]pyrimidine-3-carboxamide trifluoroacetate salt (Isomer 1, 0.2 g, 8.2% yield). LCMS calculated for Isomer 1: $C_{21}H_{24}O_3N_8SCl$ $(M+H)^+$: m/z=503.1; found 503.1. $^1H$ NMR (600 MHz, DMSO, mixture of scalemic isomers): δ 9.31 (s, 0.6H), 8.94-8.86 (m, 1H), 8.82 (s, 0.4H), 8.62-8.48 (m, 1H), 8.16-8.01 (m, 1H), 7.88 (s, 0.6H), 7.73 (s, 0.4H), 7.26 (m, 1H), 7.06-6.91 (m, 1H), 5.54 (p, J=7.0 Hz, 0.4H), 5.20 (p, J=6.9 Hz, 0.6H), 3.89-3.77 (m, 0.6H), 3.77-3.51 (m, 4H), 3.50-3.36 (m, 0.4H), 3.34-3.17 (m, 2H), 1.56 (m, 3H), 1.27 (d, J=6.9 Hz, 1H), 1.17 (d, J=6.8 Hz, 2H).

Isomer 2 was synthesized according to steps 3-6, using single isomer 2 from step 2 as starting material for step 3. LCMS calculated for Isomer 2: $C_{21}H_{24}O_3N_8SCl$ $(M+H)^+$: m/z=503.1; found 503.1.

Examples 32-40

The following Examples 32-40 in Table 3 were prepared by the method of Example 149. NMR data for representative compounds of Table 3 are provided in Table 3a.

TABLE 3

| Ex. No. | Name | R = | LCMS |
|---|---|---|---|
| 32 | 2-Amino-N-(1-(8-chloro-5-(3-cyanopyrrolidin-1-yl)imidazo-[1,5-a]pyridin-6-yl)ethyl)-pyrazolo[1,5-a]pyrimidine-3-carboxamide trifluoroacetate salt (diastereomeric mixture prepared) | (3-cyanopyrrolidin-1-yl) | Calculated for $C_{21}H_{21}ClN_9O$ $(M + H)^+$: m/z = 450.2; found: 450.2 |
| 33 | 2-amino-N-(1-(8-chloro-5-(3-cyano-3-methylpyrrolidin-1-yl)imidazo[1,5-a]pyridin-6-yl)ethyl)pyrazolo[1,5-a]pyrimidine-3-carboxamide trifluoroacetate salt (diastereomeric mixture prepared) | (3-cyano-3-methylpyrrolidin-1-yl) | Calculated for $C_{22}H_{23}ClN_9O$ $(M + H)^+$: m/z = 464.2; found: 464.3 |
| 34 | 2-Amino-N-(1-(8-chloro-5-((3S,4S)-3,4-dihydroxy-pyrrolidin-1-yl)imidazo[1,5-a]pyridin-6-yl)ethyl)pyrazolo-[1,5-a]pyrimidine-3-carboxamide trifluoroacetate salt (diastereomeric mixture prepared) | (3S,4S)-3,4-dihydroxypyrrolidin-1-yl | Calculated for $C_{20}H_{22}ClN_8O_3$ $(M + H)^+$: m/z = 457.2; found: 457.2 |

TABLE 3-continued

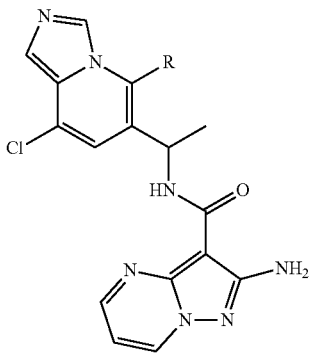

| Ex. No. | Name | R = | LCMS |
|---|---|---|---|
| 35 | 2-Amino-N-(1-(8-chloro-5-((3S,4S)-3-fluoro-4-hydroxy-pyrrolidin-1-yl)imidazo[1,5-a]pyridin-6-yl)ethyl)pyrazolo-[1,5-a]pyrimidine-3-carboxamide trifluoroacetate salt (diastereomeric mixture prepared) | | Calculated for $C_{20}H_{21}ClFN_8O_2$ $(M + H)^+$: m/z = 459.1; found: 459.2 |
| 36 | 2-Amino-N-(1-[8-chloro-5-(1,1-dioxidothiomorpholin-4-yl)imidazo[1,5-a]pyridin-6-yl]ethyl)pyrazolo[1,5-a]-pyrimidine-3-carboxamide trifluoroacetate salt (diastereomeric mixture prepared) | | Calculated for $C_{20}H_{22}ClN_8O_3S$ $(M + H)^+$: m/z = 489.1; found: 489.1 |
| 36A | 2-Amino-N-(1-[8-chloro-5-(1,1-dioxidothiomorpholin-4-yl)imidazo[1,5-a]pyridin-6-yl]ethyl)pyrazolo[1,5-a]-pyrimidine-3-carboxamide (isomer 1) | | Calculated for $C_{20}H_{22}ClN_8O_3S$ $(M + H)^+$: m/z = 489.1; found: 489.1 |
| 37 | 2-Amino-N-(1-[8-chloro-5-(1-oxidothiomorpholin-4-yl)-imidazo[1,5-a]pyridin-6-yl]-ethyl)pyrazolo[1,5-a]pyrimidine-3-carboxamide trifluoroacetate salt (diastereomeric mixture prepared) | | Calculated for $C_{20}H_{22}ClN_8O_2S$ $(M + H)^+$: m/z = 473.1; found: 473.1 |
| 38A | 2-Amino-N-(1-[8-chloro-5-(3-methyl-1,1-dioxidothiomorpholin-4-yl)imidazo-[1,5-a]pyridin-6-yl]ethyl)-pyrazolo[1,5-a]pyrimidine-3-carboxamide trifluoroacetate salt (diastereomeric mixture prepared) (Isomer 1) | | Calculated for $C_{21}H_{24}ClN_8O_3S$ $(M + H)^+$: m/z = 503.1; found: 503.1 |
| 38B | 2-Amino-N(1-[8-chloro-5-(3-methyl-1,1-dioxidothiomorpholin-4-yl)imidazo[1,5-a]pyridin-6-yl]ethyl)pyrazolo-[1,5-a]pyrimidine-3-carboxamide trifluoroacetate salt (diastereomeric mixture prepared) (Isomer 2) | | Calculated for $C_{21}H_{24}ClN_8O_3S$ $(M + H)^+$: m/z = 503.1; found: 503.1 |
| 39 | 2-Amino-N-(1-[8-chloro-5-(1-imino-1-oxidothiomorpholin-4-yl)imidazo[1,5-a]pyridin-6-yl]ethyl)pyrazolo-[1,5-a]pyrimidine-3-carboxamide (diastereomeric mixture prepared) | | Calculated for $C_{20}H_{23}ClN_9O_2S$ $(M + H)^+$: m/z = 488.1; found: 488.1 |

TABLE 3-continued

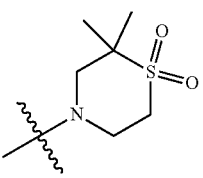 [SMILES: *N1CCS(=O)(=O)C(C)(C)C1]

| Ex. No. | Name | R = | LCMS |
|---|---|---|---|
| 40 | 2-Amino-N-(1-[8-chloro-5-(2,2-dimethyl-1,1-dioxidothio-morpholin-4-yl)imidazo[1,5-a]pyridin-6-yl]ethyl)pyrazolo-[1,5-a]pyrimidine-3-carbox-amide trifluoroacetate salt (scalemic mixture prepared) | | Calculated for $C_{22}H_{26}ClN_8O_3S$ $(M + H)^+$: m/z = 517.2; found: 517.2 |

TABLE 3a

| Ex. No. | $^1$H NMR Data |
|---|---|
| 32 | $^1$H NMR (400 MHz, MeOD) δ 9.31 (m, 1H), 8.72 (d, J = 6.8,, 1H), 8.59 (d, J = 4.5, 1H), 8.10 (s, 1H), 7.44 (s, 1H), 7.02 (dd, J = 6.8, 4.5 Hz, 1H), 5.59-5.30 (m, 1H), 3.88 (m, 1H), 3.71-3.45 (m, 4H), 2.72-2.58 (m, 1H), 2.58-2.42 (m, 1H), 1.67 (dd, J = 7.0, 1.7 Hz, 3H). |
| 33 | $^1$H NMR (400 MHz, MeOD) δ 9.16 (s, 1H), 8.73 (d, J = 6.7 Hz, 1H), 8.60 (d, J = 4.5 Hz, 1H), 8.03 (s, 1H), 7.39 (s, 1H), 7.10-6.94 (m, 1H), 5.51 (s, 1H), 3.78 (m, 4H), 2.69 (m, 1H), 2.41 (m, 1H), 1.79-1.56 (m, 6H). |
| 36 | $^1$H NMR (400 MHz, MeOD) δ 9.53 (s, 1H), 8.70 (dd, J = 6.8, 1.6 Hz, 1H), 8.57 (dd, J = 4.5, 1.6 Hz, 1H), 8.09 (s, 1H), 7.43 (s, 1H), 6.99 (dd, J = 6.8, 4.5 Hz, 1H), 5.51 (q, J = 7.0 Hz, 1H), 4.32-4.06 (m, 1H), 4.01-3.73 (m, 3H), 3.68-3.41 (m, 3H), 3.41-3.34 (m, 1H), 1.68 (d, J = 7.0 Hz, 3H). |

Example 41. 2-Amino-N-(1-(4-chloro-7-ethoxy-1H-indazol-6-yl)ethyl)-5-(5-methoxypyridin-3-yl)pyrazolo[1,5-a]pyrimidine-3-carboxamide

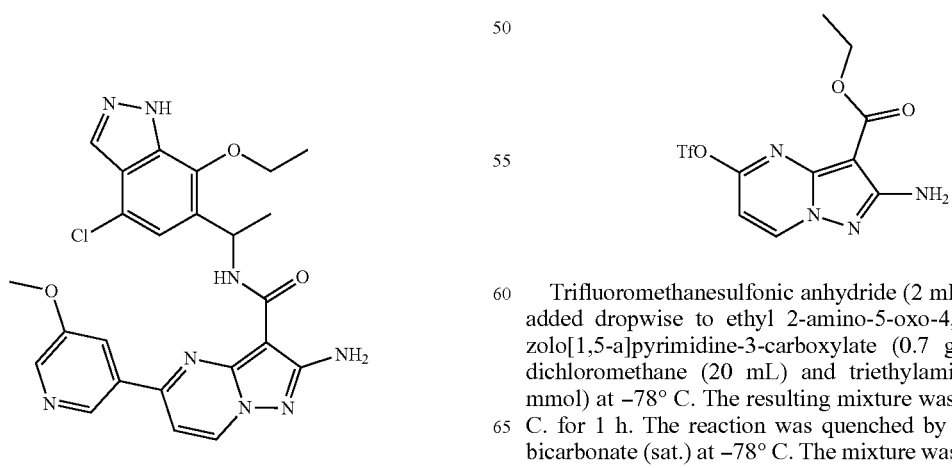

Step 1. Ethyl 2-amino-5-(trifluoromethylsulfonyloxy)pyrazolo[1,5-a]pyrimidine-3-carboxylate Trifluoromethanesulfonic anhydride (2 mL, 9 mmol) was added dropwise to ethyl 2-amino-5-oxo-4,5-dihydropyrazolo[1,5-a]pyrimidine-3-carboxylate (0.7 g, 3 mmol) in dichloromethane (20 mL) and triethylamine (3 mL, 20 mmol) at −78° C. The resulting mixture was stirred at −78° C. for 1 h. The reaction was quenched by adding sodium bicarbonate (sat.) at −78° C. The mixture was further diluted with dichloromethane (10 mL) and stirred from −78° C. to room temperature. After aqueous workup, the combined organic layer was dried over sodium sulfate, filtered, and concentrated under vacuum. Purification by flash column chromatography (0-20% methanol in dichloromethane) afforded the desired product (0.09 g, 8%). LCMS calculated for $C_{10}H_{10}F_3N_4O_5S$ (M+H)$^+$: m/z=355.0; found: 355.0.

Step 2. Ethyl 2-amino-5-(5-methoxypyridin-3-yl)pyrazolo[1,5-a]pyrimidine-3-carboxylate

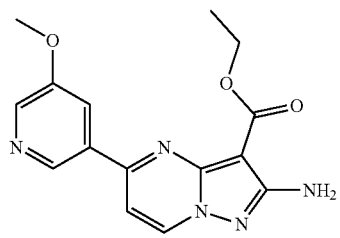 [SMILES: CCOC(=O)c1c(N)nn2ccc(-c3cncc(OC)c3)nc12]

A suspension of ethyl 2-amino-5-(trifluoromethylsulfonyloxy)pyrazolo[1,5-a]pyrimidine-3-carboxylate (0.02 g, 0.06 mmol), 3-methoxy-5-(4,4,5,5-tetramethyl-1,3,2-dioxaborolan-2-yl)pyridine (0.017 g, 0.073 mmol) (676624, Aldrich), dichloro(bis{di-tert-butyl[4-(dimethylamino)phenyl]phosphoranyl})palladium (0.004 g, 0.006 mmol), sodium carbonate (0.01 g, 0.1 mmol) in 1,4-dioxane (2 mL) and water (0.5 mL) was degassed with nitrogen gas and then heated at 80° C. for 1 h. The mixture was cooled to room temperature, diluted with methanol, filtered through Celite, and concentrated under vacuum. The residue was purified by flash column chromatography to afford the desired product (0.020 g, 100%). LCMS calculated for $C_{15}H_{16}N_5O_3$ (M+H)$^+$: m/z=314.1; found: 314.0.

Step 3. 2-Amino-5-(5-methoxypyridin-3-yl)pyrazolo[1,5-a]pyrimidine-3-carboxylic acid

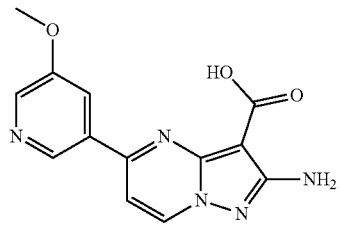 [SMILES: COc1cncc(-c2ccn3nc(N)c(C(=O)O)c3n2)c1]

Lithium hydroxide (14 mg, 0.42 mmol) was added to a solution of ethyl 2-amino-5-(5-methoxypyridin-3-yl)pyrazolo[1,5-a]pyrimidine-3-carboxylate (0.014 g, 0.042 mmol) in methanol (1 mL). The mixture was heated to 80° C. for 2 h. The solvent was evaporated under vacuum. The residue was used in the next step without purification. LCMS calculated for $C_{13}H_{12}N_5O_3$ (M+H)$^+$: m/z=286.1; found: 286.1.

Step 4. 2-Amino-N-(1-(4-chloro-7-ethoxy-1H-indazol-6-yl)ethyl)-5-(5-methoxypyridin-3-yl)pyrazolo[1,5-a]pyrimidine-3-carboxamide To the mixture of crude 2-amino-5-(5-methoxypyridin-3-yl)pyrazolo[1,5-a]pyrimidine-3-carboxylic acid (from step 3), 1-(4-chloro-7-ethoxy-1H-indazol-6-yl)ethanamine (Examples 3a-3b, Step 1, 0.010 g, 0.042 mmol) and N,N-diisopropylethylamine (20 μL, 0.1 mmol) in anhydrous N,N-dimethylformamide (1 mL) was added N,N,N',N'-tetramethyl-O-(7-azabenzotriazol-1-yl)uronium hexafluorophosphate (0.016 g, 0.042 mmol) and the resultant mixture was stirred at room temperature for 1 h. Ice-water (0.2 mL) was added to the reaction mixture and then stirred for 10 min. The mixture was diluted with methanol (4 mL). Purification by preparative LCMS (pH 10) afforded the desired product (9 mg, 20% over two steps). LCMS calculated for $C_{24}H_{24}ClN_8O_3$ (M+H)$^+$: m/z=507.2; found: 507.1.

Example 42. 2-Amino-N-(1-(4-chloro-7-ethoxy-1H-indazol-6-yl)ethyl)-5-(5-(hydroxymethyl)pyridin-3-yl)pyrazolo[1,5-a]pyrimidine-3-carboxamide

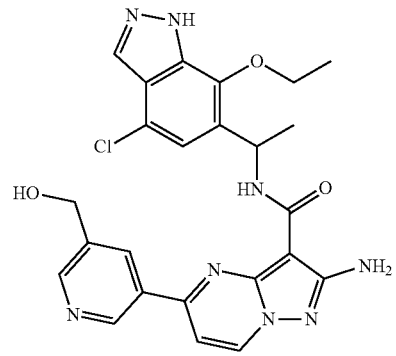 [SMILES: CCOc1c(C(C)NC(=O)c2c(N)nn3ccc(-c4cncc(CO)c4)nc23)cc(Cl)c2cn[nH]c12]

This compound was synthesized according to the procedure of Example 41, using [5-(hydroxymethyl)pyridin-3-yl] boronic acid (BB-3541, Combi-Blocks) to replace 3-methoxy-5-(4,4,5,5-tetramethyl-1,3,2-dioxaborolan-2-yl)pyridine as one of the starting materials in step 2. LCMS calculated for $C_{24}H_{24}ClN_8O_3$ (M+H)$^+$: m/z=507.2; found: 507.2.

Example 43. 2-Amino-N-(1-(3,4-dichloro-7-ethoxy-1H-indazol-6-yl)ethyl)-5-(5-methoxypyridin-3-yl)pyrazolo[1,5-a]pyrimidine-3-carboxamide trifluoroacetate salt

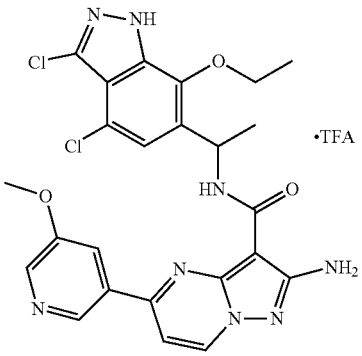 [SMILES: CCOc1c(C(C)NC(=O)c2c(N)nn3ccc(-c4cncc(OC)c4)nc23)cc(Cl)c2c(Cl)n[nH]c12]

Step 1.
1-(3,4-dichloro-7-ethoxy-1H-indazol-6-yl)ethanone

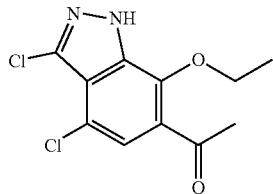 [SMILES: CCOc1c(C(C)=O)cc(Cl)c2c(Cl)n[nH]c12]

To a solution of 1-(4-chloro-7-ethoxy-1H-indazol-6-yl)ethanone (90 mg, 0.4 mmol) in N,N-dimethylformamide (2 mL) was added N-chlorosuccinimide (76 mg, 0.56 mmol) at room temperature. After stirring for 4 h, the reaction mixture was diluted with EtOAc, washed with sodium carbonate (sat.), dried over sodium sulfate and concentrated under vacuum. Purification by flash column chromatography afforded the desired product. LCMS calculated for $C_{11}H_{11}Cl_2N_2O_2$ (M+H)$^+$: m/z=273.0; found: 273.0.

Step 2. 1-(3,4-Dichloro-7-ethoxy-1H-indazol-6-yl)ethanamine

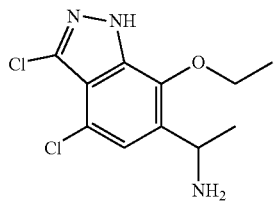 [SMILES: CCOc1c(C(C)N)cc(Cl)c2c(Cl)n[nH]c12]

To a solution of 1-(3,4-dichloro-7-ethoxy-1H-indazol-6-yl)ethanone (0.10 g, 0.37 mmol) in 2.0 M ammonia in ethanol (4 mL, 8 mmol) was added titanium tetraisopropoxide (300 µL, 1 mmol). The reaction mixture was heated at 80° C. for 3 h and then cooled to 0° C. Sodium tetrahydroborate (40 mg, 1 mmol) was added to the mixture. After stirring for 0.5 h, the reaction was quenched with ammonium hydroxide (1 M), filtered, and the solid was washed with acetonitrile. The volatiles were removed in vacuo, and the residue dissolved in EtOAc and washed with water and brine. The organic layer was dried over sodium sulfate, filtered, and concentrated under vacuum. The crude product was used directly in the next step without purification. LCMS calculated for $C_{11}H_{14}Cl_2N_3O$ (M+H)$^+$: m/z=274.1; found: 274.0.

Step 3. 2-Amino-5-(5-methoxypyridin-3-yl)pyrazolo[1,5-a]pyrimidine-3-carboxylic acid This compound was synthesized according to the procedure of Example 41, using 1-(3,4-dichloro-7-ethoxy-1H-indazol-6-yl)ethanamine to replace 1-(4-chloro-7-ethoxy-1H-indazol-6-yl)ethanamine as the starting material in step 4. LCMS calculated for $C_{24}H_{23}Cl_2N_8O_3$ (M+H)$^+$: m/z=541.1; found: 541.1 $^1$H NMR (400 MHz, DMSO) δ 13.76 (s, 1H), 9.12-8.98 (m, 2H), 8.49 (d, J=2.7 Hz, 1H), 8.25 (d, J=6.9 Hz, 1H), 8.15 (s, 1H), 7.74 (d, J=7.1 Hz, 1H), 7.29 (s, 1H), 5.68-5.23 (m, 1H), 4.45-4.02 (m, 2H), 3.95 (s, 3H), 1.59 (d, J=6.9 Hz, 2H), 1.40 (t, J=7.0 Hz, 3H).

Example 44. 2-Amino-N-(1-(4-chloro-7-ethoxy-1H-indazol-6-yl)ethyl)-5-(piperidin-1-yl)pyrazolo[1,5-a]pyrimidine-3-carboxamide trifluoroacetate salt

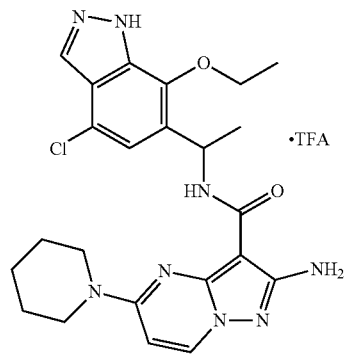 [SMILES: CCOc1c(C(C)NC(=O)c2c(N)nn3ccc(N4CCCCC4)nc23)cc(Cl)c2cn[nH]c12]

Step 1. 2-Amino-5-(piperidin-1-yl)pyrazolo[1,5-a]pyrimidine-3-carboxylic acid

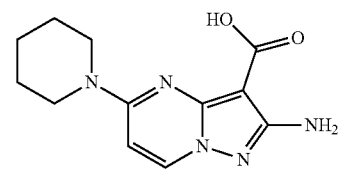 [SMILES: Nc1nn2ccc(N3CCCCC3)nc2c1C(=O)O]

To a solution of ethyl 2-amino-5-{[(trifluoromethyl)sulfonyl]oxy}pyrazolo[1,5-a]pyrimidine-3-carboxylate (Example 43, Step 1, 20 mg, 0.056 mmol) in acetonitrile (0.6 mL) was added piperidine (0.017 mL, 0.17 mmol) and N,N-diisopropylethylamine (0.1 mL, 0.6 mmol). The resultant mixture was stirred at 80° C. for 1 h. To the mixture was added lithium hydroxide in water (4.0 M, 0.1 mL, 0.6 mmol). The resultant mixture was heated at 80° C. for 1 h. The solvent was removed and the residue was purified by preparative LCMS (pH 10) to afford the desired product (14 mg, 95% yield). LCMS calculated for $C_{12}H_{16}N_5O_2$ (M+H)$^+$: m/z=262.1; found: 262.0.

Step 2. 2-Amino-N-(1-(4-chloro-7-ethoxy-1H-indazol-6-yl)ethyl)-5-(piperidin-1-yl)pyrazolo[1,5-a]pyrimidine-3-carboxamide trifluoroacetate salt To a vial containing 1-(4-chloro-7-ethoxy-1H-indazol-6-yl)ethanamine trifluoroacetic acid (5.4 mg, 0.015 mmol), 2-amino-5-(piperidin-1-yl)pyrazolo[1,5-a]pyrimidine-3-carboxylic acid (4.0 mg, 0.015 mmol) and N,N,N',N'-tetramethyl-O-(7-azabenzotriazol-1-yl)uronium hexafluorophosphate (5.8 mg, 0.015 mmol) was added N,N-dimethylformamide (0.7 mL), followed by dropwise addition f N,N-diisopropylethylamine (10 µL, 0.08 mmol) at room temperature. After stirring for 1 h, ice-water (0.2 mL) was added to the reaction mixture and stirred for 10 min. The mixture was diluted with methanol (4 mL). Purification by preparative LCMS (pH 2) afforded the desired product. LCMS calculated for $C_{23}H_{28}ClN_8O_2$ (M+H)$^+$: m/z=483.2; found: 483.2.

Example 45. 2-Amino-6-chloro-N-(1-(4-chloro-7-ethoxy-1H-indazol-6-yl)ethyl)imidazo[1,2-b]pyridazine-3-carboxamide

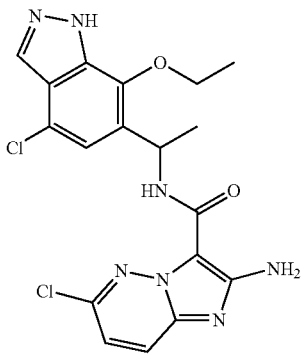 [SMILES: CCOc1c(C(C)NC(=O)c2c(N)nc3ccc(Cl)nn23)cc(Cl)c2cn[nH]c12]

Step 1. 6-chloro-3-iodoimidazo[1,2-b]pyridazin-2-amine

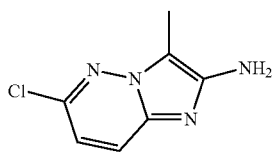

To a solution of 6-chloroimidazo[1,2-b]pyridazin-2-amine (0.50 g, 2.96 mmol) (32325, Affinity Research Chemicals) in N,N-Dimethylformamide (20 mL) at 0° C. was added N-iodosuccinimide (0.80 g, 3.6 mmol). The resulting solution was stirred at room temperature for 1 h. Water (20 mL) was added to quench the reaction. After aqueous work up, the combined organic layers were dried over sodium sulfate, filtered, and concentrated under vacuum. Purification with flash column chromatography afforded the desired product (0.87 g, 62% yield). LCMS calculated for $C_6H_5ClIN_4$ $(M+H)^+$: m/z=294.9; found: 294.8.

Step 2. Methyl 2-amino-6-chloroimidazo[1,2-b]pyridazine-3-carboxylate

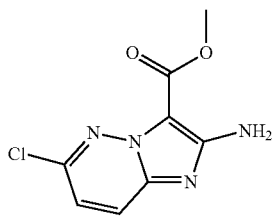

In a 40 mL vial, 6-chloro-3-iodoimidazo[1,2-b]pyridazin-2-amine (300 mg, 1.0 mmol) in methanol (20 mL) and triethylamine (0.52 mL, 3.8 mmol) was degassed with a stream of nitrogen for 5 min. To the solution was added [1,1'-bis(diphenylphosphino)ferrocene]dichloropalladium(II), complex with dichloromethane (1:1) (40 mg, 0.05 mmol). The solution was saturated with carbon monoxide by bubbling the carbon monoxide gas through the reaction subsurface for 3 min. The vessel was sealed and heated to 55° C. for 12 h. The reaction was cooled to room temperature and the solvents were removed under vacuum. Purification by flash column chromatography afforded the desired product (0.12 g, 52% yield). LCMS calculated for $C_8H_8ClN_4O_2$ $(M+H)^+$: m/z=227.0; found: 227.0.

Step 3. 2-Amino-6-chloroimidazo[1,2-b]pyridazine-3-carboxylic acid

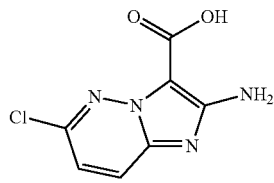 [SMILES: Nc1nc2ccc(Cl)nn2c1C(=O)O]

A mixture of methyl 2-amino-6-chloroimidazo[1,2-b]pyridazine-3-carboxylate (15 mg, 0.066 mmol) and lithium hydroxide (8 mg, 0.3 mmol) in tetrahydrofuran (1 mL) and water (0.050 mL) was heated at 80° C. for 3 h. The reaction mixture was cooled to room temperature and diluted with methanol (4 mL). Purification by preparative LCMS (pH 10) afforded the desired product (14 mg, 60% yield). LCMS calculated for $C_7H_6ClN_4O_2$ $(M+H)^+$: m/z=213.0; found: 213.0.

Step 4. 2-Amino-6-chloro-N-(1-(4-chloro-7-ethoxy-1H-indazol-6-yl)ethyl)imidazo[1,2-b]pyridazine-3-carboxamide To a mixture of 2-amino-6-chloroimidazo[1,2-b]pyridazine-3-carboxylic acid (20 mg, 0.09 mmol), 1-(4-chloro-7-ethoxy-1H-indazol-6-yl)ethanamine (Examples 3a-3b, Step 1, 32 mg, 0.13 mmol) and N,N,N',N'-tetramethyl-O-(7-azabenzotriazol-1-yl)uronium hexafluorophosphate (43 mg, 0.11 mmol) in N,N-dimethylformamide (2.4 mL) was added N,N-diisopropylethylamine (50 μL, 0.3 mmol) and the resultant mixture was stirred at room temperature for 1 h. Ice-water was added to the reaction mixture and then stirred for 10 min. The mixture was further diluted with methanol (4 mL). Purification by preparative LCMS (pH10) afforded the desired product. (14 mg, 60% yield). LCMS calculated for $C_{18}H_{18}Cl_2N_7O_2$ $(M+H)^+$: m/z=434.1; found: 434.2.

Example 46. 2-Amino-N-(1-(4-chloro-7-ethoxy-1H-indazol-6-yl)ethyl)-6-methylimidazo[1,2-b]pyridazine-3-carboxamide

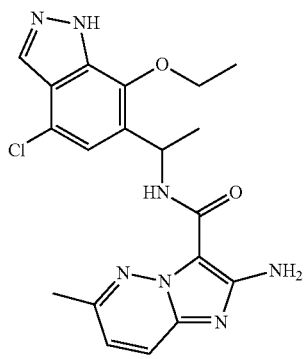 [SMILES: CCOc1c(C(C)NC(=O)c2c(N)nc3ccc(C)nn23)cc(Cl)c2cn[nH]c12]

Step 1. Methyl 2-amino-6-methylimidazo[1,2-b]pyridazine-3-carboxylate

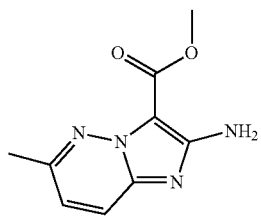

To a vial containing the mixture of trimethylboroxine (25 μL, 0.18 mmol), dicyclohexyl(2',4',6'-triisopropylbiphenyl-2-yl)phosphine-(2'-aminobiphenyl-2-yl)(chloro)palladium (1:1) (6 mg, 0.008 mmol), and potassium phosphate (56 mg, 0.26 mmol) was added a solution of methyl 2-amino-6-chloroimidazo[1,2-b]pyridazine-3-carboxylate (Example 45, Step 2, 0.020 g, 0.088 mmol) in 1,4-dioxane (1 mL) and water (100 μL). The reaction was degassed with nitrogen and stirred at 50° C. for 5 h. After cooling to room temperature, the mixture was diluted with methanol (4 mL) and purified by preparative LCMS (pH 10) to afford the desired product (12.0 mg, 67% yield). LCMS calculated for $C_9H_{11}N_4O_2$ (M+H)$^+$: m/z=207.1; found: 207.1

Step 2. 2-Amino-6-methylimidazo[1,2-b]pyridazine-3-carboxylic acid

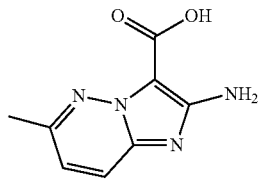

This compound was synthesized according to the procedure of Example 45, step 3, using methyl 2-amino-6-methylimidazo[1,2-b]pyridazine-3-carboxylate to replace methyl 2-amino-6-chloroimidazo[1,2-b]pyridazine-3-carboxylate as the starting material. LCMS calculated for $C_8H_9N_4O_2$ (M+H)$^+$: m/z=193.1; found: 193.1.

Step 3. 2-Amino-N-(1-(4-chloro-7-ethoxy-1H-indazol-6-yl)ethyl)-6-methylimidazo[1,2-b]pyridazine-3-carboxamide This compound was synthesized according to the procedure of Example 45, step 4, using 2-amino-6-methylimidazo[1,2-b]pyridazine-3-carboxylic acid to replace 2-amino-6-chloroimidazo[1,2-b]pyridazine-3-carboxylic acid as the starting material. LCMS calculated for $C_{19}H_{21}ClN_7O_2$ (M+H)$^+$: m/z=414.1; found: 414.1.

Example 47. 2-Amino-N-(1-(4-chloro-7-ethoxy-1H-indazol-6-yl)ethyl)-6-(piperidin-1-yl)imidazo[1,2-b]pyridazine-3-carboxamide

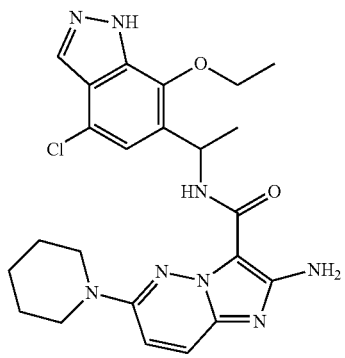 [SMILES: CCOc1c(C(C)NC(=O)c2c(N)nc3ccc(N4CCCCC4)nn23)cc(Cl)c2cn[nH]c12]

This compound was synthesized according to the procedure of Example 44, using methyl 2-amino-6-chloroimidazo[1,2-b]pyridazine-3-carboxylate (Example 45, Step 2) to replace ethyl 2-amino-5-{[(trifluoromethyl)sulfonyl]oxy}pyrazolo[1,5-a]pyrimidine-3-carboxylate as one of the starting materials in step 1. LCMS calculated for $C_{23}H_{28}ClN_8O_2$(M+H)$^+$: m/z=483.2; found: 483.2.

Example 48. 2-Amino-N-(1-(4-chloro-7-ethoxy-1H-indazol-6-yl)ethyl)-6-(5-(hydroxymethyl)pyridin-3-yl)imidazo[1,2-b]pyridazine-3-carboxamide

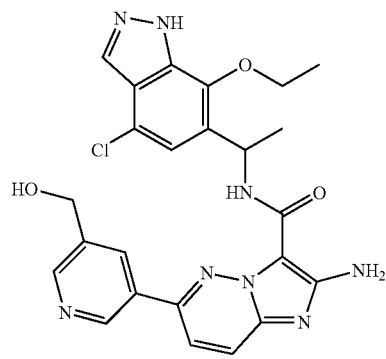 [SMILES: CCOc1c(C(C)NC(=O)c2c(N)nc3ccc(-c4cncc(CO)c4)nn23)cc(Cl)c2cn[nH]c12]

Step 1. Methyl 2-amino-6-(5-(hydroxymethyl)pyridin-3-yl)imidazo[1,2-b]pyridazine-3-carboxylate

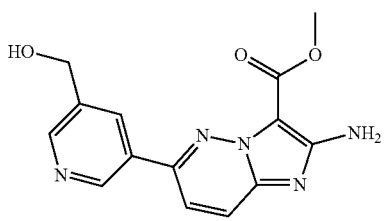 [SMILES: COC(=O)c1c(N)nc2ccc(-c3cncc(CO)c3)nn12]

A suspension of methyl 2-amino-6-chloroimidazo[1,2-b]pyridazine-3-carboxylate (Example 45, Step 2, 0.02 g, 0.09 mmol), [5-(hydroxymethyl)pyridin-3-yl]boronic acid (0.018 g, 0.11 mmol), [1,1'-bis(diphenylphosphino)ferrocene]dichloropalladium (II) (0.003 g, 0.004 mmol), sodium carbonate (0.028 g, 0.26 mmol) in 1,4-dioxane (1 mL) and water (0.2 mL) was degassed by bubbling nitrogen. The mixture was heated to 80° C. and stirred for 1 h. After cooling to room temperature, the mixture was diluted with methanol (8 mL), filtered through Celite, and concentrated under vacuum. Purification by flash column chromatography afforded the desired product. (20.0 mg, 80% yield). LCMS calculated for $C_{14}H_{14}N_5O_3$ (M+H)$^+$: m/z=300.1; found: 300.1.

Step 2. 2-Amino-6-methylimidazo[1,2-b]pyridazine-3-carboxylic acid

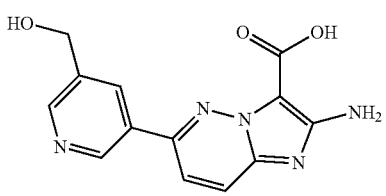 [SMILES: Nc1nc2ccc(-c3cncc(CO)c3)nn2c1C(=O)O]

This compound was synthesized according to the procedure of Example 45, step 3, using methyl 2-amino-6-(5-(hydroxymethyl)pyridin-3-yl)imidazo[1,2-b]pyridazine-3-carboxylate to replace methyl 2-amino-6-chloroimidazo[1,2-b]pyridazine-3-carboxylate as the starting material. LCMS calculated for $C_{13}H_{12}N_5O_3$ (M+H)$^+$: m/z=286.1; found: 286.1.

Step 3. 2-Amino-N-(1-(4-chloro-7-ethoxy-1H-indazol-6-yl)ethyl)-6-methylimidazo[1,2-b]pyridazine-3-carboxamide This compound was synthesized according to the procedure of Example 45, step 4, using 2-amino-6-methylimidazo[1,2-b]pyridazine-3-carboxylic acid to replace 2-amino-6-chloroimidazo[1,2-b]pyridazine-3-carboxylic acid as the starting material. LCMS calculated for $C_{24}H_{24}ClN_8O_3$ (M+H)$^+$: m/z=507.2; found: 507.1.

Example 49. 2-Amino-N-(1-(3,4-dichloro-7-ethoxy-1H-indazol-6-yl)ethyl)-6-(5-(hydroxymethyl)pyridin-3-yl)imidazo[1,2-b]pyridazine-3-carboxamide

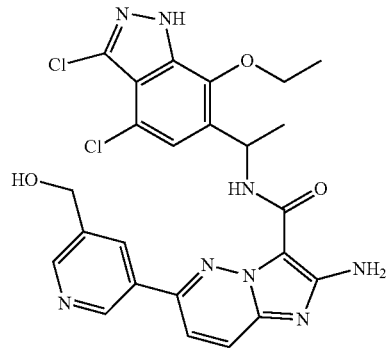 [SMILES: CCOc1c(C(C)NC(=O)c2c(N)nc3ccc(-c4cncc(CO)c4)nn23)cc(Cl)c2c(Cl)n[nH]c12]

This compound was synthesized according to the procedure of Example 48, using 1-(3,4-dichloro-7-ethoxy-1H-indazol-6-yl)ethanamine (Example 43, Step 2) to replace 1-(4-chloro-7-ethoxy-1H-indazol-6-yl)ethanamine as the starting material in step 3. LCMS calculated for $C_{24}H_{23}Cl_2N_8O_3$ (M+H)$^+$: m/z=541.1; found: 541.1.

Example 50. 2-Amino-N-[1-(4-chloro-7-ethoxy-1H-indazol-6-yl)ethyl]-5-pyridin-3-ylpyrazolo[1,5-a]pyrimidine-3-carboxamide bis(trifluoroacetate)

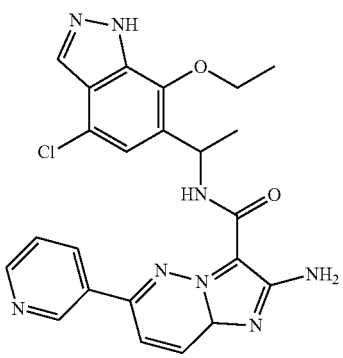

This compound was synthesized according to the procedure of Example 41, using 3-pyridylboronic acid to replace 3-methoxy-5-(4,4,5,5-tetramethyl-1,3,2-dioxaborolan-2-yl)pyridine as one of the starting materials in step 2. LCMS calculated for $C_{23}H_{22}ClN_8O_2$ (M+H)$^+$: m/z=477.2; found: 477.2.

Example 51. 2-Amino-N-(1-(4-chloro-3-ethyl-7-phenyl-1H-indazol-6-yl)ethyl)pyrazolo[1,5-a]pyrimidine-3-carboxamide trifluoroacetate

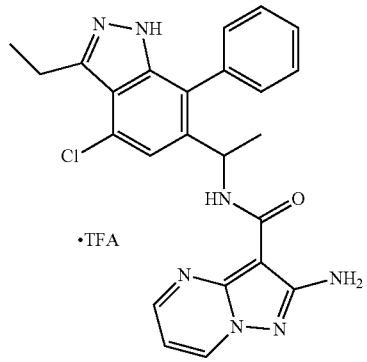 [SMILES: CCc1n[nH]c2c(-c3ccccc3)c(C(C)NC(=O)c3c(N)nn4cccnc34)cc(Cl)c12]

Step 1. 1-(4-chloro-3-ethyl-7-phenyl-JH-indazol-6-yl)ethanone

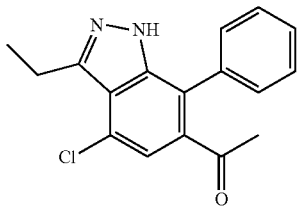 [SMILES: CCc1n[nH]c2c(-c3ccccc3)c(C(C)=O)cc(Cl)c12]

To a solution of 1-(3-bromo-4-chloro-7-phenyl-1H-indazol-6-yl)ethanone (60.0 mg, 0.172 mmol, from Example 23, Step 1) and [1,1'-bis(diphenylphosphino)ferrocene]dichloropalladium (II) (6 mg, 0.008 mmol) in dioxane (1 mL) was added 1.0 M diethyl zinc in hexanes (0.26 mL, 0.26 mmol) at room temperature and the reaction mixture was heated to 80° C. for 2 h. After cooling to room temperature, the volatiles were evaporated in vacuo and the residue was purified by flash chromatography (0-30% EtOAc/hexanes) to afford the title compound as a white solid (27 mg, 53%), contaminated with a minor amount of the bis-ethylated product (from Cl coupling). LCMS calculated for $C_{17}H_{16}ClN_2O$ (M+H)$^+$: m/z=299.1; found: 299.1.

Step 2. 1-(4-chloro-3-ethyl-7-phenyl-1H-indazol-6-yl)ethanamine

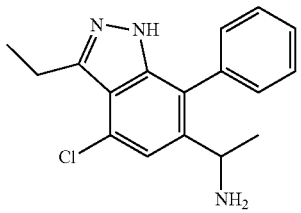 [SMILES: CCc1n[nH]c2c(-c3ccccc3)c(C(C)N)cc(Cl)c12]

This compound was synthesized according to the procedure described in Example 23, Step 2, starting from 1-(4-chloro-3-ethyl-7-phenyl-1H-indazol-6-yl)ethanone (27 mg, 0.090 mmol). The product was used without purification (theoretical yield assumed). LCMS calculated for $C_{17}H_{16}ClN_2$ (M–NH$_2$)$^+$: m/z=283.1; found: 283.1.

Step 3. 2-amino-N-(1-(4-chloro-3-ethyl-7-phenyl-1H-indazol-6-yl)ethyl)pyrazolo[1,5-a]pyrimidine-3-carboxamide trifluoroacetate To a vial containing 1-(4-chloro-3-ethyl-7-phenyl-1H-indazol-6-yl)ethanamine (27 mg, 0.090 mmol), 2-[(tert-butoxycarbonyl)amino]pyrazolo[1,5-a]pyrimidine-3-carboxylic acid (28 mg, 0.099 mmol, from J&W Pharmlab), and N,N,N',N'-tetramethyl-O-(7-azabenzotriazol-1-yl)uronium hexafluorophosphate (38 mg, 0.099 mmol) was added DMF (2 mL), followed by dropwise addition of N,N-diisopropylethylamine (0.047 mL, 0.27 mmol) at room temperature. After stirring for 1 h, the reaction mixture was diluted with EtOAc (10 mL) and quenched with water (5 mL). The layers were separated, and the organic layer was dried over MgSO$_4$, filtered, and concentrated. The residue was stirred with TFA (1 mL) in CH$_2$Cl$_2$ (2 mL) for 0.5 h. The volatiles were removed in vacuo and the residue was dissolved in MeOH and purified by preparative HPLC (pH 2). $^1$H NMR (600 MHz, DMSO) δ 8.92 (dd, J=6.7, 1.6 Hz, 1H), 8.56 (dd, J=4.5, 1.6 Hz, 1H), 8.11 (d, J=6.8 Hz, 1H), 7.62 (br s, 1H), 7.57 (br s, 2H), 7.53-7.47 (m, 1H), 7.39 (br s, 1H), 7.21 (s, 1H), 7.01 (dd, J=6.7, 4.5 Hz, 1H), 5.07 (p, J=6.9 Hz, 1H), 3.08 (q, J=7.5 Hz, 2H), 1.36 (d, J=6.9 Hz, 3H), 1.30 (t, J=7.5 Hz, 3H). LCMS calculated for $C_{24}H_{23}ClN_7O$ (M+H)$^+$: m/z=460.2; found: 460.1.

Example 52. 2-Amino-N-(1-(3-bromo-4-chloro-7-ethoxy-1H-indazol-6-yl)ethyl)pyrazolo[1,5-a]pyrimidine-3-carboxamide trifluoroacetate

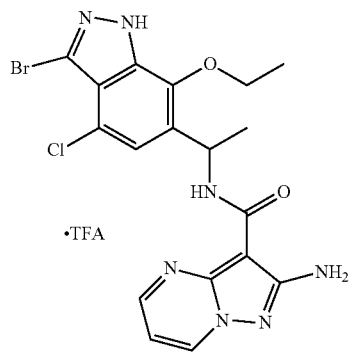 [SMILES: CCOc1c(C(C)NC(=O)c2c(N)nn3cccnc23)cc(Cl)c2c(Br)n[nH]c12]

Step 1. 1-(3-bromo-4-chloro-7-ethoxy-1H-indazol-6-yl)ethanone

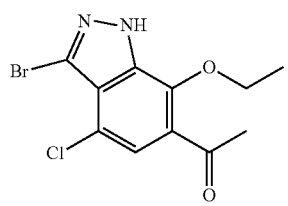 [SMILES: CCOc1c(C(C)=O)cc(Cl)c2c(Br)n[nH]c12]

To a solution of 1-(4-chloro-7-ethoxy-1H-indazol-6-yl)ethanone (100 mg, 0.419 mmol, from Example 1, Step 3) in DMF (2 mL) was added N-bromosuccinimide (89 mg, 0.50 mmol) at room temperature. After stirring for 2 h, the reaction mixture was quenched with saturated aqueous NaHCO$_3$ and extracted with EtOAc. The organic layer was dried over MgSO$_4$, filtered, and concentrated to afford an orange solid that was used without purification. LCMS calculated for $C_{11}H_{11}BrClN_2O_2 (M+H)^+$: m/z=317.0; found: 316.9.

Step 2. 1-(3-bromo-4-chloro-7-ethoxy-1H-indazol-6-yl)ethanamine

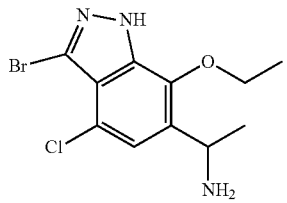

This compound was synthesized according to the procedure described in Example 23, Step 2, starting from 1-(3-bromo-4-chloro-7-ethoxy-1H-indazol-6-yl)ethanone (120 mg, 0.380 mmol). The product was used without purification (theoretical yield assumed). LCMS calculated for $C_{11}H_{11}BrClN_2O (M-NH_2)^+$: m/z=301.0; found: 300.9.

Step 3. tert-butyl 3-(1-(3-bromo-4-chloro-7-ethoxy-1H-indazol-6-yl)ethylcarbamoyl)pyrazolo[1,5-a]pyrimidin-2-ylcarbamate

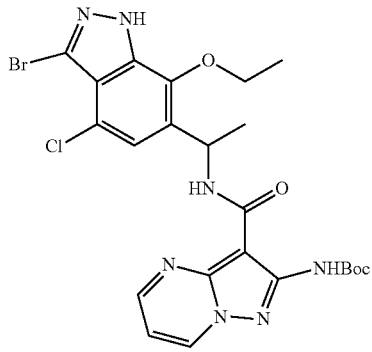 [SMILES: CCOc1c(C(C)NC(=O)c2c(NC(=O)OC(C)(C)C)nn3cccnc23)cc(Cl)c2c(Br)n[nH]c12]

This compound was synthesized according to the procedure described in Example 1, Step 6, starting from 1-(3-bromo-4-chloro-7-ethoxy-1H-indazol-6-yl)ethanamine (120 mg, 0.380 mmol). The residue was purified by flash chromatography (0-100% EtOAc/hexanes) to afford the product as an off white solid. LCMS calculated for $C_{23}H_{26}BrClN_7O_4 (M+H)^+$: m/z=578.1; found: 578.0.

Step 4. 2-amino-N-(1-(3-bromo-4-chloro-7-ethoxy-1H-indazol-6-yl)ethyl)pyrazolo[1,5-a]pyrimidine-3-carboxamide trifluoroacetate This compound was synthesized according to the procedure described in Example 1, Step 7, starting from tert-butyl 3-(1-(3-bromo-4-chloro-7-ethoxy-1H-indazol-6-yl)ethylcarbamoyl)pyrazolo[1,5-a]pyrimidin-2-ylcarbamate (10 mg, 0.02 mmol). The residue was purified by preparative HPLC (pH 2) to afford the product as a white solid. $^1$H NMR (600 MHz, DMSO) δ 13.92 (s, 1H), 8.92 (dd, J=6.7, 1.6 Hz, 1H), 8.56 (dd, J=4.5, 1.6 Hz, 1H), 8.18 (d, J=7.5 Hz, 1H), 7.18 (s, 1H), 7.01 (dd, J=6.7, 4.5 Hz, 1H), 6.45 (br s, 2H), 5.51 (p, J=7.0 Hz, 1H), 4.28-4.19 (m, 2H), 1.52 (d, J=7.0 Hz, 3H), 1.45 (t, J=7.0 Hz, 3H). LCMS calculated for $C_{18}H_{18}BrClN_7O_2 (M+H)^+$: m/z=478.1; found: 478.0.

Examples 53-54. 2-Amino-N-(1-(3-bromo-4-chloro-7-ethoxy-2-(2-hydroxyethyl)-2H-indazol-6-yl)ethyl)pyrazolo[1,5-a]pyrimidine-3-carboxamide (Example 53) & 2-Amino-N-(1-(3-bromo-4-chloro-7-ethoxy-1-(2-hydroxyethyl)-1H-indazol-6-yl)ethyl)pyrazolo[1,5-a]pyrimidine-3-carboxamide trifluoroacetate (Example 54)

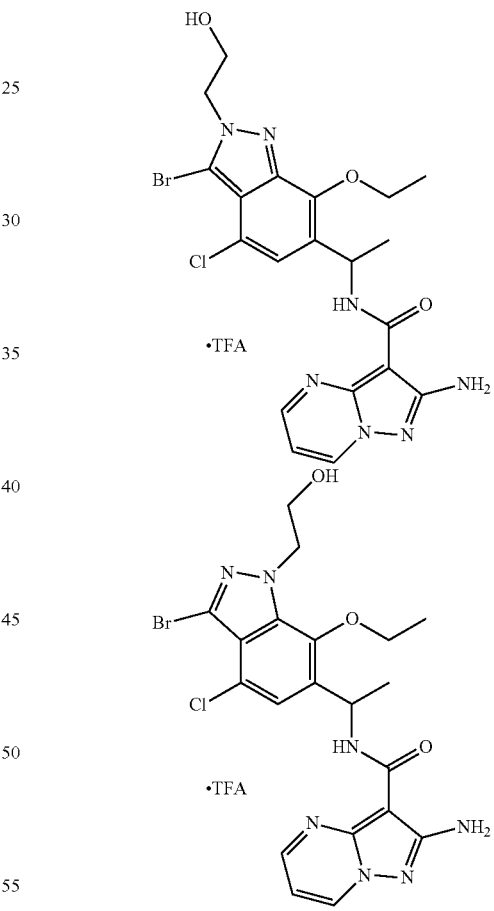

To a solution of tert-butyl 3-(1-(3-bromo-4-chloro-7-ethoxy-1H-indazol-6-yl)ethylcarbamoyl)pyrazolo[1,5-a]pyrimidin-2-ylcarbamate (35 mg, 0.060 mmol, from Example 52, Step 3) in DMF (1 mL) was added potassium carbonate (40 mg, 0.3 mmol), followed by 2-iodoethanol (50 μL, 0.60 mmol) and the reaction mixture was heated to 70° C. overnight. After cooling to room temperature, the mixture was diluted with EtOAc and washed with water. The organic layer was washed with brine, dried over MgSO$_4$, filtered, and concentrated. The residue was dissolved in DCM (2 mL), and TFA (1 mL) was added. After stirring for 0.5 h, the volatiles were removed in vacuo and the residue was purified by preparative HPLC (pH 2) to afford the title compounds, which were readily separable (36.1-56.1% MeCN/water gradient). Peak 1 (Example 53): Retention time=5.05. LCMS calculated for $C_{20}H_{22}BrClN_7O_3$ $(M+H)^+$: m/z=522.1; found: 522.1. Peak 2 (Example 54): Retention time=5.68. LCMS calculated for $C_{20}H_{22}BrClN_7O_3$ $(M+H)^+$: m/z=522.1; found: 522.1.

Example 55. 2-Amino-N-(1-(4-chloro-3-cyano-7-phenyl-1H-indazol-6-yl)ethyl)pyrazolo[1,5-a]pyrimidine-3-carboxamide trifluoroacetate

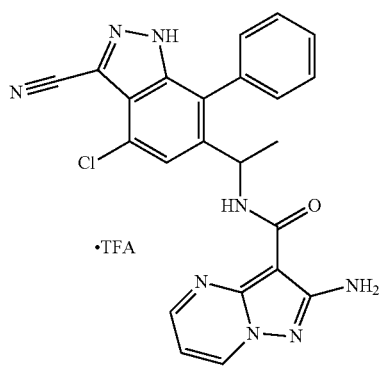 [SMILES: CC(NC(=O)c1c(N)nn2cccnc12)c1cc(Cl)c2c(C#N)n[nH]c2c1-c1ccccc1]

Step 1. 1-(4-chloro-3-iodo-7-phenyl-1H-indazol-6-yl)ethanone

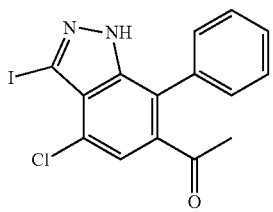 [SMILES: CC(=O)c1cc(Cl)c2c(I)n[nH]c2c1-c1ccccc1]

To a solution of 1-(4-chloro-7-phenyl-1H-indazol-6-yl)ethanone (Example 14, Step 4, 500 mg, 1.85 mmol) in DMF (9 mL) was added N-iodosuccinimide (540 mg, 2.4 mmol) and the reaction mixture was stirred overnight. The reaction was quenched with saturated NaHCO$_3$ and extracted with EtOAc. The organic layer was washed with brine, dried over MgSO$_4$, filtered, and concentrated. The residue was purified by flash chromatography (0-35% EtOAc/hexanes) to afford the title compound (640 mg, 87%) as an off white solid. LCMS calculated for $C_{15}H_{11}ClIN_2O$ $(M+H)^+$: m/z=397.0; found: 396.9.

Step 2. methyl 6-acetyl-4-chloro-7-phenyl-1H-indazole-3-carboxylate

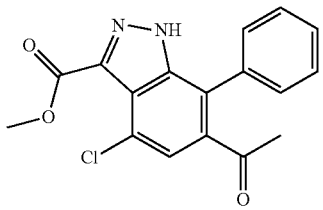 [SMILES: COC(=O)c1n[nH]c2c(-c3ccccc3)c(C(C)=O)cc(Cl)c12]

A solution of 1-(4-chloro-3-iodo-7-phenyl-1H-indazol-6-yl)ethanone (40 mg, 0.101 mmol), Pd(dppf)Cl$_2$ (4 mg, 0.005 mmol), and triethylamine (42 µL, 0.30 mmol) in DMF (1.6 mL) and MeOH (0.4 mL) was saturated with CO for 10 min. The reaction mixture was then heated at 90° C. under balloon pressure of CO overnight. The volatiles were evaporated and the residue was purified by flash chromatography (0-40% EtOAc/hexanes) to afford the title compound (33 mg, quant.) as a yellow oil. LCMS calculated for $C_{17}H_{14}ClN_2O_3$ $(M+H)^+$: m/z=329.1; found: 329.0.

Step 3. 6-acetyl-4-chloro-7-phenyl-1H-indazole-3-carboxylic acid

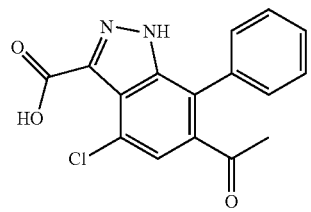

To a solution of methyl 6-acetyl-4-chloro-7-phenyl-1H-indazole-3-carboxylate (33.0 mg, 0.100 mmol) in THF/methanol/water (1:1:1) was added sodium hydroxide (40 mg, 1 mmol) and the reaction mixture was heated at 65° C. for 4 h. After cooling to room temperature, the volatiles were evaporated in vacuo and the residue was treated with 1M HCl, forming a precipitate, which was solubilized by addition of EtOAc. The solution was diluted with additional EtOAc and 1M HCl, and the layers were separated. The organic layer was washed with brine, dried over MgSO$_4$, filtered and concentrated to afford the title compound (31 mg, 98%) that was used without purification. LCMS calculated for $C_{16}H_{12}ClN_2O_3$ $(M+H)^+$: m/z=315.1; found: 315.0.

Step 4. 6-acetyl-4-chloro-7-phenyl-1H-indazole-3-carboxamide

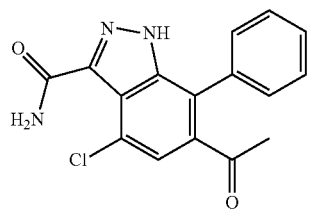 [SMILES: CC(=O)c1cc(Cl)c2c(C(=O)O)n[nH]c2c1-c1ccccc1]

To a mixture of 6-acetyl-4-chloro-7-phenyl-1H-indazole-3-carboxylic acid (31.0 mg, 0.0985 mmol), ammonium chloride (10 mg, 0.20 mmol), and HATU (75 mg, 0.20 mmol) in DMF (3 mL) was added N,N-diisopropylethylamine (86 µL, 0.49 mmol) at room temperature. After stirring overnight, the reaction mixture was diluted with EtOAc and quenched with water. The layers were separated and the aqueous layer was extracted with EtOAc. The combined organic layers were washed with brine, dried over MgSO$_4$ and concentrated. The residue was purified by flash chromatography (0-100% EtOAc/hexanes) to afford the product as a white solid, still containing residual DMF. Quantitative yield was assumed. LCMS calculated for C$_{16}$H$_{13}$ClN$_3$O$_2$ (M+H)$^+$: m/z=314.1; found: 314.0.

Step 5. 6-acetyl-4-chloro-7-phenyl-1H-indazole-3-carbonitrile

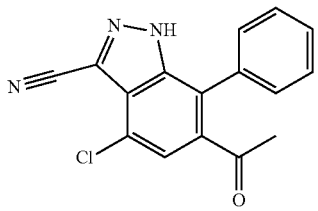 [SMILES: CC(=O)c1cc(Cl)c2c(C#N)n[nH]c2c1-c1ccccc1]

To a suspension of 6-acetyl-4-chloro-7-phenyl-1H-indazole-3-carboxamide (30.0 mg, 0.0956 mmol) in CH$_2$Cl$_2$ (39 mmol) at 0° C. was added Et$_3$N (40 µL, 0.29 mmol), followed by dropwise addition of 1.0 M trifluoromethanesulfonic anhydride (1M/CH$_2$Cl$_2$, 0.29 mL, 0.29 mmol). During the addition, the white suspension gradually became a yellow, then deep red solution. After the addition was complete, the ice bath was removed and the solution was stirred at room temperature for 1 h. The reaction was quenched with saturated NaHCO$_3$ and the resulting mixture was extracted with DCM. The organic layer was dried over MgSO$_4$, filtered, and concentrated. The residue was purified by flash chromatography (0-45% EtOAc/hexanes) to afford the title compound (8.2 mg, 29%) as a reddish solid. LCMS calculated for C$_{16}$H$_{11}$ClN$_3$O (M+H)$^+$: m/z=296.0; found: 296.0.

Step 6. 6-(1-aminoethyl)-4-chloro-7-phenyl-1H-indazole-3-carbonitrile

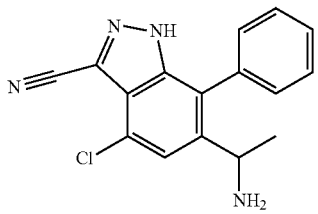 [SMILES: CC(N)c1cc(Cl)c2c(C#N)n[nH]c2c1-c1ccccc1]

This compound was synthesized according to the procedure described in Example 23, Step 2, starting from 6-acetyl-4-chloro-7-phenyl-1H-indazole-3-carbonitrile (8.0 mg, 0.027 mmol). The product was used without purification (theoretical yield assumed). LCMS calculated for C$_{16}$H$_{11}$ClN$_3$ (M−NH$_2$)$^+$: m/z=280.0; found: 280.0.

Step 7. 2-amino-N-(1-(4-chloro-3-cyano-7-phenyl-1H-indazol-6-yl)ethyl)pyrazolo[1,5-a]pyrimidine-3-carboxamide trifluoroacetate This compound was synthesized according to the procedure described in Example 26, Step 3, starting from 6-(1-aminoethyl)-4-chloro-7-phenyl-1H-indazole-3-carbonitrile (8.0 mg, 0.027 mmol). The residue was purified by preparative HPLC (pH 2) to afford the title compound as a white solid (2.5 mg, 20%). LCMS calculated for C$_{23}$H$_{18}$ClN$_8$O (M+H)$^+$: m/z=457.1; found: 457.1.

Example 56. 2-Amino-N-(1-(4-chloro-7-(4-cyanopiperidin-1-yl)pyrazolo[1,5-a]pyridin-6-yl)ethyl)pyrazolo[1,5-a]pyrimidine-3-carboxamide trifluoroacetate

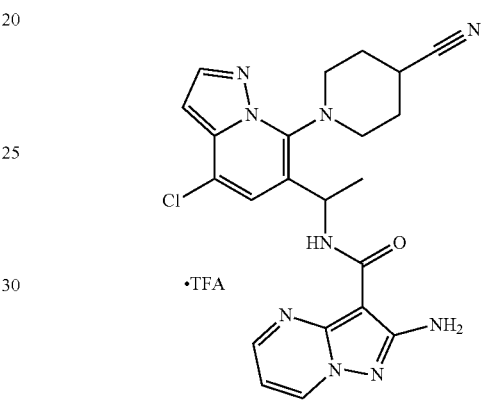

Step 1. 1-amino-2-methoxypyridinium 2,4-dinitrobenzenolate

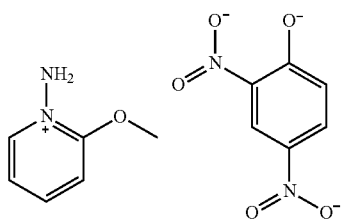

To a solution of O-(2,4-dinitrophenyl)hydroxylamine (9.1 g, 46 mmol) in acetonitrile (30 mL, 600 mmol) was added 2-methoxypyridine (4.8 mL, 46 mmol) and the reaction mixture was heated to 40° C. over the weekend. The solvent was removed in vacuo and the solid was filtered, washed with diethyl ether (20 mL), and dried to yield the title compound (9.17 g, 65%) as a light orange solid. $^1$H NMR (400 MHz, DMSO) δ 8.61 (d, J=3.1 Hz, 1H), 8.56 (dd, J=6.5, 1.4 Hz, 1H), 8.32-8.22 (m, 1H), 7.85 (dd, J=9.7, 3.1 Hz, 1H), 7.74-7.71 (m, 3H), 7.55-7.44 (m, 1H), 6.43 (d, J=9.7 Hz, 1H), 4.27 (s, 3H). LCMS calculated for C$_6$H$_9$N$_2$O (M)$^+$: m/z=125.1; found 125.1.

Step 2. ethyl 7-methoxypyrazolo[1,5-a]pyridine-3-carboxylate

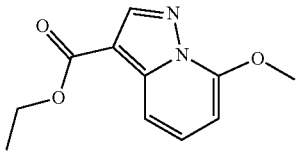 [SMILES: CCOC(=O)c1cnn2c(OC)cccc12]

To a suspension of 1-amino-2-methoxypyridinium 2,4-dinitrobenzenolate (9.17 g, 29.7 mmol) in DMF (79 mL) was added potassium carbonate (6.2 g, 45 mmol), followed by dropwise addition of ethyl propiolate (4.5 mL, 45 mmol) at room temperature. After stirring for 2 h the reaction mixture was poured into water and diluted with EtOAc. The layers were separated and the aqueous layer was extracted with EtOAc. The combined organic layers were washed with brine, dried over MgSO$_4$, filtered, and concentrated. The residue was purified by flash chromatography (0-60% EtOAc/hexanes) to afford the title compound (3.1 g, 47%) as a beige solid. $^1$H NMR (400 MHz, DMSO) δ 8.42 (s, 1H), 7.69 (dd, J=8.7, 1.0 Hz, 1H), 7.65-7.57 (m, 1H), 6.70-6.63 (m, 1H), 4.30 (q, J=7.1 Hz, 2H), 4.15 (s, 3H), 1.34 (t, J=7.1 Hz, 3H). LCMS calculated for C$_{11}$H$_{13}$N$_2$O$_3$ (M+H)$^+$: m/z=221.1; found 221.1.

Step 3. ethyl 6-chloro-7-methoxypyrazolo[1,5-a]pyridine-3-carboxylate

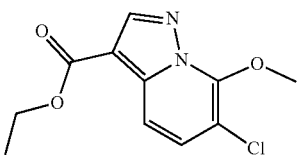 [SMILES: CCOC(=O)c1cnn2c(OC)c(Cl)ccc12]

To a solution of ethyl 7-methoxypyrazolo[1,5-a]pyridine-3-carboxylate (294 mg, 1.34 mmol) in DMF (6.0 mL) was added N-chlorosuccinimide (187 mg, 1.40 mmol) and the reaction mixture was stirred at room temperature overnight. The reaction mixture was diluted with EtOAc and washed with water and brine. The organic layer was dried over MgSO$_4$ and concentrated, and the residue was purified by flash chromatography (0-15% EtOAc/hexanes) to afford the title compound (237 mg, 70%) as an off white solid. $^1$H NMR (400 MHz, DMSO) δ 8.51 (s, 1H), 7.83 (d, J=9.4 Hz, 1H), 7.70 (d, J=9.4 Hz, 1H), 4.32 (q, J=7.1 Hz, 2H), 4.22 (s, 3H), 1.34 (t, J=7.1 Hz, 4H). LCMS calculated for C$_{11}$H$_{12}$ClN$_2$O$_3$ (M+H)$^+$: m/z=255.1; found 255.1.

Step 4. ethyl 6-acetyl-7-methoxypyrazolo[1,5-a]pyridine-3-carboxylate

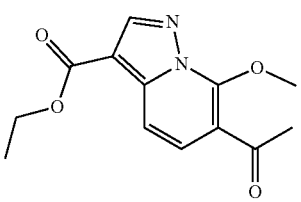 [SMILES: CCOC(=O)c1cnn2c(OC)c(C(C)=O)ccc12]

To a mixture of ethyl 6-chloro-7-methoxypyrazolo[1,5-a]pyridine-3-carboxylate (237.0 mg, 0.93 mmol), cesium fluoride (280 mg, 1.9 mmol), and XPhos Pd G2 (70 mg, 0.09 mmol) in 1,4-dioxane (5.0 mL) was added tributyl(1-ethoxyvinyl)tin (0.38 mL, 1.1 mmol) and the reaction mixture was heated to reflux for 4 h. After cooling to room temp, 1M HCl was added and the reaction mixture was stirred for 1 h. The reaction mixture was partitioned between water and EtOAc, and the layers were separated. The organic layer was washed with brine, dried over MgSO$_4$, filtered, and concentrated. The residue was purified by flash chromatography (0-30% EtOAc/hexanes) to afford the title compound (621 mg, 91%) as a white solid. LCMS calculated for C$_{13}$H$_{15}$N$_2$O$_4$ (M+H)$^+$: m/z=263.1; found 263.1.

Step 5. ethyl 6-acetyl-7-amino-4-chloropyrazolo[1,5-a]pyridine-3-carboxylate

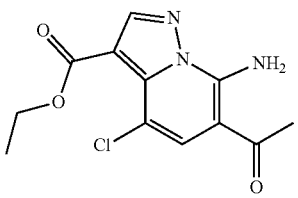 [SMILES: CCOC(=O)c1cnn2c(N)c(C(C)=O)cc(Cl)c12]

A solution of ethyl 6-acetyl-7-methoxypyrazolo[1,5-a]pyridine-3-carboxylate (300.0 mg, 1.144 mmol) in 2.0 M ammonia in ethanol (7.0 mL, 14 mmol) was heated to 60° C. for 2 h. The volatiles were removed in vacuo, the resulting solid was suspended in acetic acid (9.0 mL, 160 mmol) and N-chlorosuccinimide (460 mg, 3.4 mmol) was added. The reaction mixture was heated to 45° C. for 3 h. The reaction mixture was partitioned between water and EtOAc, and the layers were separated. The aqueous layer was extracted with EtOAc and the combined organic layers were washed with brine, dried over MgSO$_4$, filtered, and concentrated. The residue was purified by flash chromatography (0-25% EtOAc/hexanes) to afford the title compound (208 mg, 65%). LCMS calculated for C$_{12}$H$_{13}$ClN$_3$O$_3$ (M+H)$^+$: m/z=282.1; found 282.1.

Step 6. ethyl 6-acetyl-4,7-dichloropyrazolo[1,5-a]pyridine-3-carboxylate

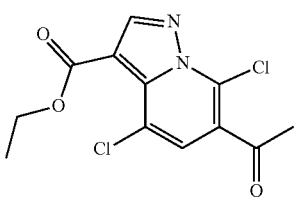 [SMILES: CCOC(=O)c1cnn2c(Cl)c(C(C)=O)cc(Cl)c12]

Ethyl 6-acetyl-7-amino-4-chloropyrazolo[1,5-a]pyridine-3-carboxylate (413 mg, 1.47 mmol) was dissolved in conc. HCl (6.0 mL) and acetic acid (6.0 mL) and cooled to 0° C. A solution of sodium nitrite (300 mg, 4.4 mmol) in water (1.0 mL) was added dropwise, and the solution changed from yellow to dark green. After 0.5 h, the reaction mixture was diluted with water and EtOAc, and the layers were separated. The organic layer was washed with brine, dried over MgSO$_4$, and concentrated. The resulting dark brown solid was washed with hexanes, filtered, and air dried to afford the title compound (410 mg, 93%) as a light brown solid. LCMS calculated for $C_{12}H_{11}Cl_2N_2O_3$ (M+H)$^+$: m/z=301.0; found 301.0.

Step 7. 1-(4,7-dichloropyrazolo[1,5-a]pyridin-6-yl)ethanone

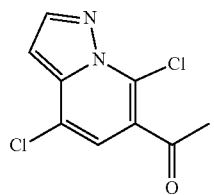

Ethyl 6-acetyl-4,7-dichloropyrazolo[1,5-a]pyridine-3-carboxylate (410 mg, 1.4 mmol) was taken up in 6M HCl (6.0 mL) and acetic acid (6.0 mL), and heated to 100° C. overnight. After cooling to room temp, the reaction mixture was partitioned between water and EtOAc, and the layers were separated. The organic layer was washed with brine, dried over MgSO$_4$, and concentrated. The residue was purified by flash chromatography (0-20% EtOAc/hexanes) to afford the title compound (296 mg, 95%) as a yellow solid. LCMS calculated for $C_9H_7Cl_2N_2O$ (M+H)$^+$: m/z=229.0; found 229.0.

Step 8. 1-(6-acetyl-4-chloropyrazolo[1,5-a]pyridin-7-yl)piperidine-4-carbonitrile

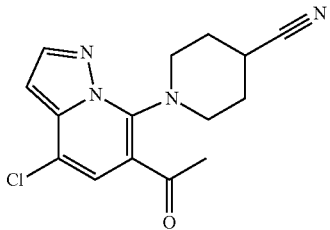 [SMILES: CC(=O)c1cc(Cl)c2ccnn2c1N1CCC(C#N)CC1]

A mixture of 1-(4,7-dichloropyrazolo[1,5-a]pyridin-6-yl)ethanone (15.0 mg, 0.065 mmol), piperidine-4-carbonitrile (11 μL, 0.098 mmol), and cesium carbonate (43 mg, 0.13 mmol) was taken up in acetonitrile (2.0 mL, 38 mmol) and heated to 70° C. for 1.5 h. The reaction mixture was partitioned between EtOAc and water, and the layers were separated. The organic layer was washed with brine, dried over MgSO$_4$ and concentrated. The residue was used without purification (theoretical yield assumed). LCMS calculated for $C_{15}H_{16}ClN_4O$ (M+H)$^+$: m/z=303.1; found 303.1.

Step 9. 2-amino-N-(1-(4-chloro-7-(4-cyanopiperidin-1-yl)pyrazolo[1,5-a]pyridin-6-yl)ethyl)pyrazolo[1,5-a]pyrimidine-3-carboxamide trifluoroacetate To a solution of 1-(6-acetyl-4-chloropyrazolo[1,5-a]pyridin-7-yl)piperidine-4-carbonitrile (19.0 mg, 0.0628 mmol) in 2.0 M ammonia in ethanol (3.0 mL, 6.0 mmol) was added titanium tetraisopropoxide (56 ηL, 0.19 mmol) and the reaction mixture was heated at 60° C. overnight. The resulting solution was cooled to room temperature, then 0° C., and sodium borohydride (7.1 mg, 0.19 mmol) was added. After stirring for 0.5 h, the reaction was quenched with 1M NH$_4$OH, filtered, and the solid was washed with EtOAc. The filtrate was washed with water, brine, dried over MgSO$_4$, and concentrated. The product was used without purification. To a vial containing the crude amine, 2-[(tert-butoxycarbonyl)amino]pyrazolo[1,5-a]pyrimidine-3-carboxylic acid (21 mg, 0.075 mmol), and HATU (29 mg, 0.075 mmol) was added DMF (3 mL), followed by dropwise addition of N,N-diisopropylethylamine (33 μL, 0.19 mmol) at room temperature. After stirring for 1 h, the reaction was quenched with water and extracted with EtOAc. The organic layer was washed with brine, dried over MgSO$_4$, filtered and concentrated. The residue was dissolved in DCM (2 mL) and TFA (1.0 mL, 13 mmol) was added at room temp. After stirring for 1 h, the volatiles were evaporated in vacuo and the residue was purified by prep HPLC (pH 2) to afford the title compound (11.2 mg, 39%) as a white solid. LCMS calculated for $C_{22}H_{23}ClN_9O$ (M+H)$^+$: m/z=464.2; found 464.2.

Example 57-58. (S)-2-Amino-N-(1-(4-chloro-7-(1,1-dioxidothiomorpholino)pyrazolo[1,5-a]pyridin-6-yl)ethyl)pyrazolo[1,5-a]pyrimidine-3-carboxamide trifluoroacetate (Example 57) & (S)-2-Amino-N-(1-(4-chloro-7-(1,1-dioxidothiomorpholino)-3-fluoropyrazolo[1,5-a]pyridin-6-yl)ethyl)pyrazolo[1,5-a]pyrimidine-3-carboxamide trifluoroacetate (Example 58)

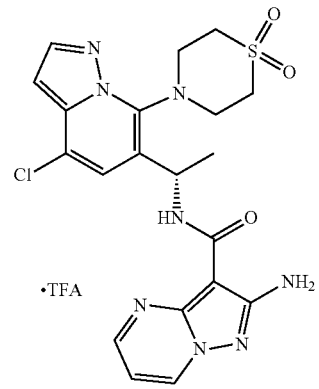

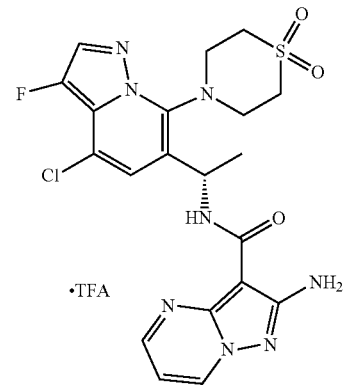

189

Step 1. 1-(4,7-dichloropyrazolo[1,5-a]pyridin-6-yl)ethanone & 1-(4,7-dichloro-3-fluoropyrazolo[1,5-a]pyridin-6-yl)ethanone

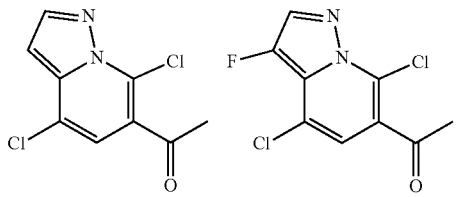

To a solution of 1-(4,7-dichloropyrazolo[1,5-a]pyridin-6-yl)ethan-1-one (820 mg, 3.58 mmol, from Example 56, Step 7) in acetonitrile (7.0 ml) was added Selectfluor (2.54 g, 7.16 mmol) and the reaction mixture was stirred at room temperature for 8.5 h. The reaction mixture was diluted with EtOAc and washed with water and brine. The organic layer was dried over MgSO$_4$, filtered, and concentrated. The residue was purified by flash chromatography (0-10% EtOAc/hexanes) to afford a 1:1 mixture of the title compounds (701 mg, 79%). Peak 1: LCMS calculated for $C_9H_7Cl_2N_2O$ (M+H)$^+$: m/z=229.0; found 229.0. Peak 2: LCMS calculated for $C_9H_6Cl_2FN_2O$ (M+H)$^+$: m/z=247.0; found 247.0.

Step 2. 1-(4-chloro-7-(1,1-dioxidothiomorpholino)pyrazolo[1,5-a]pyridin-6-yl)ethan-1-one & 1-(4-chloro-7-(1,1-dioxidothiomorpholino)-3-fluoropyrazolo[1,5-a]pyridin-6-yl)ethan-1-one

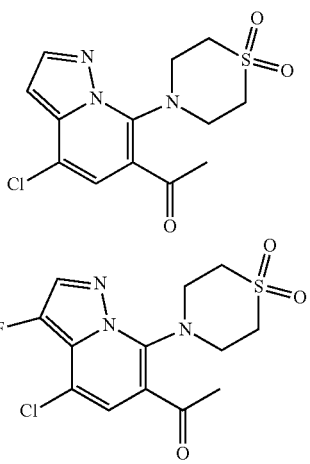

A 1:1 mixture of 1-(4,7-dichloropyrazolo[1,5-a]pyridin-6-yl)ethan-1-one and 1-(4,7-dichloro-3-fluoropyrazolo[1,5-a]pyridin-6-yl)ethan-1-one (701 mg, ~3.06 mmol), thiomorpholine dioxide (827 mg, 6.12 mmol), and DIPEA (1.069 ml, 6.12 mmol) was heated to 140° C. in the microwave for 1 h. LCMS indicated complete conversion to the desired product. The reaction mixture was diluted with EtOAc, washed with water and brine, dried over MgSO$_4$ and concentrated. The residue was used without purification. Peak 1: LCMS calculated for $C_{13}H_{15}ClN_3O_3S$ (M+H)$^+$: m/z=328.0; found 328.0. Peak 2: LCMS calculated for $C_{13}H_{14}ClFN_3O_3S$ (M+H)$^+$: m/z=346.0; found 346.0.

190

Step 3. N—((S)-1-(4-chloro-7-(1,1-dioxidothiomorpholino)pyrazolo[1,5-a]pyridin-6-yl)ethyl)-2-methylpropane-2-sulfinamide & N—((S)-1-(4-chloro-7-(1,1-dioxidothiomorpholino)-3-fluoropyrazolo[1,5-a]pyridin-6-yl)ethyl)-2-methylpropane-2-sulfinamide

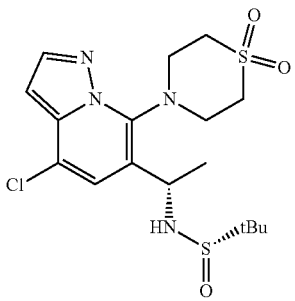

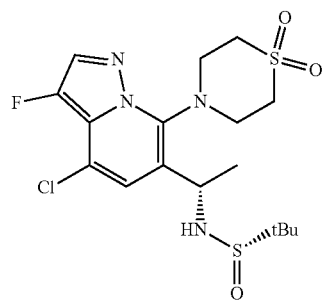

To a solution of 1-(4-chloro-7-(1,1-dioxidothiomorpholino)pyrazolo[1,5-a]pyridin-6-yl)ethan-1-one and 1-(4-chloro-7-(1,1-dioxidothiomorpholino)-3-fluoropyrazolo[1,5-a]pyridin-6-yl)ethan-1-one (1.03 g, ~3.14 mmol), and (S)-2-methylpropane-2-sulfinamide (3.81 g, 31.4 mmol) in cyclopentyl methyl ether (20 ml) was added titanium(IV) isopropoxide (2.76 ml, 9.43 mmol) and the reaction mixture was heated to 100° C. overnight. The resulting mixture of sulfinimines was cooled to 0° C. and sodium borohydride (1.189 g, 31.4 mmol) was added in several portions. The reaction mixture was allowed to warm to room temperature and a small amount of EtOH (~0.5 mL) was added dropwise. After stirring for 0.5 h, LCMS indicated complete conversion (6:1 d.r. for both compounds). The reaction mixture was cooled to 0° C., quenched by the dropwise addition of MeOH, and vigorously stirred until no more gas evolution was observed. The solution was poured into brine and the resulting suspension was filtered through celite. The filtrate was diluted with EtOAc and water, and the layers were separated. The organic layer was dried over MgSO$_4$, filtered, and concentrated. The residue was purified by flash chromatography (0-70-100% EtOAc/hexanes). Both of the undesired diastereomers were separated, affording an inseparable 1:1 mixture of the title compounds (842 mg, 62%) as single diastereomers. Peak 1: LCMS calculated for $C_{17}H_{26}ClN_4O_3S_2$ (M+H)$^+$: m/z=433.1; found 433.1. Peak 2: LCMS calculated for $C_{17}H_{25}ClFN_4O_3S_2$ (M+H)$^+$: m/z=451.1; found 451.1.

Step 4. (S)-4-(6-(1-aminoethyl)-4-chloropyrazolo[1,5-a]pyridin-7-yl)thiomorpholine 1,1-dioxide hydrochloride & (S)-4-(6-(1-aminoethyl)-4-chloro-3-fluoropyrazolo[1,5-a]pyridin-7-yl)thiomorpholine 1,1-dioxide hydrochloride

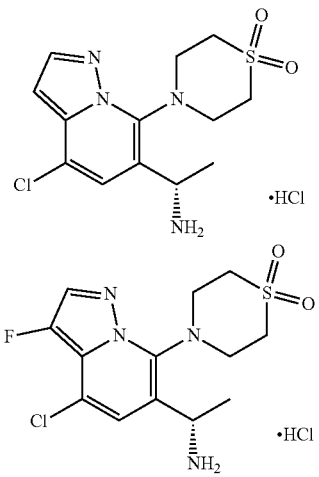

To a solution of N—((S)-1-(4-chloro-7-(1,1-dioxidothiomorpholino)pyrazolo[1,5-a]pyridin-6-yl)ethyl)-2-methylpropane-2-sulfinamide and N—((S)-1-(4-chloro-7-(1,1-dioxidothiomorpholino)-3-fluoropyrazolo[1,5-a]pyridin-6-yl)ethyl)-2-methylpropane-2-sulfinamide (1:1 mixture, 842 mg, ~1.945 mmol) in MeOH (10 ml) was added HCl (4.0M in dioxane) (10 mL, 40 mmol) and the reaction mixture was stirred at room temperature for 0.5 h. LCMS indicated the reaction was complete, and the volatiles were removed in vacuo. The residue was used without purification. Peak 1: LCMS calculated for $C_{13}H_{15}ClN_3O_2S$ $(M-NH_2)^+$: m/z=312.1; found 312.0. Peak 2: LCMS calculated for $C_{13}H_{14}ClFN_3O_2S$ $(M-NH_2)^+$: m/z=330.1; found 330.0.

Step 5. (S)-2-amino-N-(1-(4-chloro-7-(1,1-dioxidothiomorpholino)pyrazolo[1,5-a]pyridin-6-yl)ethyl)pyrazolo[1,5-a]pyrimidine-3-carboxamide trifluoroacetate & (S)-2-amino-N-(1-(4-chloro-7-(1,1-dioxidothiomorpholino)-3-fluoropyrazolo[1,5-a]pyridin-6-yl)ethyl)pyrazolo[1,5-a]pyrimidine-3-carboxamide trifluoroacetate To a vial containing (S)-4-(6-(1-aminoethyl)-4-chloropyrazolo[1,5-a]pyridin-7-yl)thiomorpholine 1,1-dioxide hydrochloride and (S)-4-(6-(1-aminoethyl)-4-chloro-3-fluoropyrazolo[1,5-a]pyridin-7-yl)thiomorpholine 1,1-dioxide hydrochloride (1:1 mixture, 710 mg, 1.944 mmol), 2-((tert-butoxycarbonyl)amino)pyrazolo[1,5-a]pyrimidine-3-carboxylic acid (649 mg, 2.333 mmol), and HATU (887 mg, 2.333 mmol) was added DMF (12 ml), followed by dropwise addition of DIPEA (1.018 ml, 5.83 mmol) at room temp. After stirring for 0.5 h, the reaction was quenched with water and extracted with EtOAc. The organic layer was washed with brine, dried over MgSO$_4$, and concentrated. The residue was dissolved in DCM (6.0 ml) and TFA (6 ml, 78 mmol) was added at room temp. After stirring for 0.5 h, the volatiles were evaporated in vacuo and the products were purified by prep HPLC (pH 2). Peak 1 (Example 57): $^1$H NMR (600 MHz, DMSO) δ 8.92 (dd, J=6.7, 1.6 Hz, 1H), 8.57 (dd, J=4.5, 1.6 Hz, 1H), 8.14 (d, J=2.3 Hz, 1H), 8.10 (d, J=6.9 Hz, 1H), 7.50 (s, 1H), 7.01 (dd, J=6.7, 4.5 Hz, 1H), 6.72 (d, J=2.3 Hz, 1H), 5.73 (p, J=7.0 Hz, 1H), 4.28-4.24 (m, 1H), 4.17-4.12 (m, 1H), 3.59-3.46 (m, 3H), 3.37-3.21 (m, 3H), 1.56 (d, J=7.0 Hz, 3H). LCMS calculated for $C_{20}H_{22}ClN_8O_3S$ $(M+H)^+$: m/z=489.1; found 489.0. Peak 2 (Example 58): $^1$H NMR (600 MHz, DMSO) δ 8.92 (dd, J=6.7, 1.6 Hz, 1H), 8.57 (dd, J=4.5, 1.6 Hz, 1H), 8.26 (d, J=3.7 Hz, 1H), 8.09 (d, J=6.9 Hz, 1H), 7.46 (d, J=1.9 Hz, 1H), 7.02 (dd, J=6.7, 4.5 Hz, 1H), 5.68 (p, J=7.0 Hz, 1H), 4.22-4.15 (m, 1H), 4.13-4.05 (m, 1H), 3.60-3.45 (m, 3H), 3.35 (d, J=13.3 Hz, 1H), 3.26 (m, 2H), 1.55 (d, J=7.0 Hz, 3H). LCMS calculated for $C_{20}H_{21}ClFN_8O_3S$ $(M+H)^+$: m/z=507.1; found 507.1.

Example 59. 2-Amino-N-(1-(4-chloro-7-(pyridin-3-yl)pyrazolo[1,5-a]pyridin-6-yl)ethyl)pyrazolo[1,5-a]pyrimidine-3-carboxamide trifluoroacetate

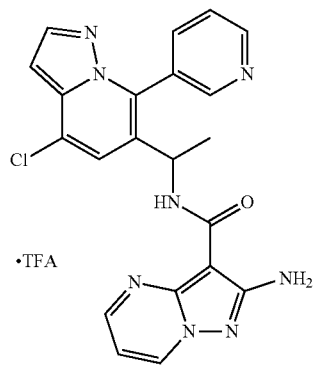 [SMILES: CC(NC(=O)c1c(N)nn2cccnc12)c1cc(Cl)c2ccnn2c1-c1cccnc1 ; "·TFA"]

Step 1. 1-(4-chloro-7-(pyridin-3-yl)pyrazolo[1,5-a]pyridin-6-yl)ethanone

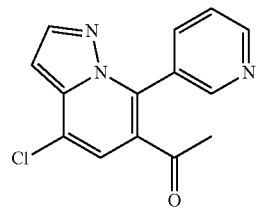 [SMILES: CC(=O)c1cc(Cl)c2ccnn2c1-c1cccnc1]

A mixture of 1-(4,7-dichloropyrazolo[1,5-a]pyridin-6-yl)ethanone (19.0 mg, 0.0829 mmol, from Example 56, Step 7), 3-(4,4,5,5-tetramethyl-1,3,2-dioxaborolan-2-yl)pyridine (26 mg, 0.12 mmol), tetrakis(triphenylphosphine)palladium(O) (10 mg, 0.008 mmol), and sodium carbonate (18 mg, 0.16 mmol) was taken up in 1,4-dioxane (2.5 mL, 32 mmol) and water (0.5 mL, 30 mmol) and heated to 100° C. for 2 h. The reaction mixture was cooled to room temperature, partitioned between EtOAc and water, and the layers were separated. The organic layer was washed with brine, dried over MgSO$_4$, and concentrated. The residue was purified by flash chromatography (0-100% EtOAc/hexanes) to afford the title compound as a white solid (16.4 mg, 73%). LCMS calculated for $C_{14}H_{11}ClN_3O$ $(M+H)^+$: m/z=272.1; found 272.1.

Step 2. 2-amino-N-(1-(4-chloro-7-(pyridin-3-yl)pyrazolo[1,5-a]pyridin-6-yl)ethyl)pyrazolo[1,5-a]pyrimidine-3-carboxamide trifluoroacetate

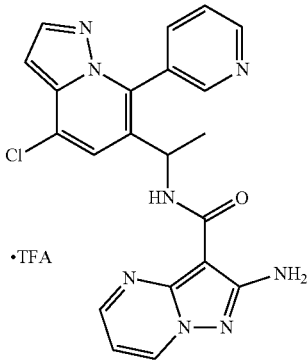 [SMILES: CC(NC(=O)c1c(N)nn2cccnc12)c1cc(Cl)c2ccnn2c1-c1cccnc1 ; "·TFA"]

This compound was prepared according to the procedure described in Example 56, Step 9, starting from 1-(4-chloro-7-(pyridin-3-yl)pyrazolo[1,5-a]pyridin-6-yl)ethanone instead of 1-(6-acetyl-4-chloropyrazolo[1,5-a]pyridin-7-yl)piperidine-4-carbonitrile. The residue was purified by preparative HPLC (pH 2) to afford the title compound (4.3 mg, 16%) as a white solid. LCMS calculated for $C_{21}H_{18}ClN_8O$ $(M+H)^+$: m/z=433.1; found 433.0.

Example 60. 2-Amino-N-(1-(4-chloro-3-cyano-7-(1,1-dioxidothiomorpholino)pyrazolo[1,5-a]pyridin-6-yl)ethyl)pyrazolo[1,5-a]pyrimidine-3-carboxamide trifluoroacetate

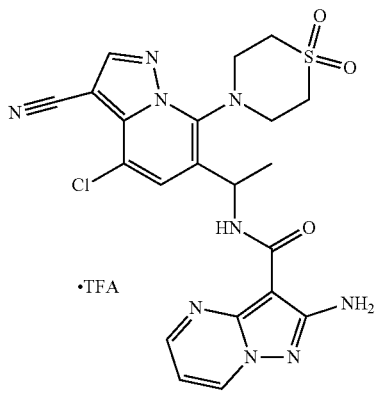 [SMILES: CC(NC(=O)c1c(N)nn2cccnc12)c1cc(Cl)c2c(C#N)cnn2c1N1CCS(=O)(=O)CC1 ; "·TFA"]

Step 1. 6-acetyl-4,7-dichloropyrazolo[1,5-a]pyridine-3-carbonitrile

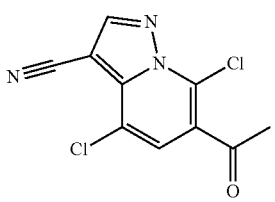 [SMILES: CC(=O)c1cc(Cl)c2c(C#N)cnn2c1Cl]

To a solution of 1-(4,7-dichloropyrazolo[1,5-a]pyridin-6-yl)ethan-1-one (110 mg, 0.480 mmol, from Example 56, Step 7) in acetonitrile (3.0 ml) was added chlorosulfonyl isocyanate (0.13 ml, 1.44 mmol) at room temperature. After stirring for 1 h, the reaction mixture was cooled to 0° C. and DMF (0.11 ml, 1.44 mmol) was added dropwise. The ice bath was removed and the reaction mixture was stirred at room temperature for 0.5 h. The reaction mixture was diluted with EtOAc and quenched with ice chips, and the layers were separated. The aqueous layer was extracted with EtOAc. The combined organic layers were washed with brine, dried over $MgSO_4$, filtered, and concentrated. The residue was purified by flash chromatography (0-30% EtOAc/hexanes) to afford the title compound (103 mg, 84%) as a light yellow solid. LCMS calculated for $C_{10}H_6Cl_2N_3O$ $(M+H)^+$: m/z=254.0; found 253.8.

Step 2. 6-acetyl-4-chloro-7-(1,1-dioxidothiomorpholino)pyrazolo[1,5-a]pyridine-3-carbonitrile

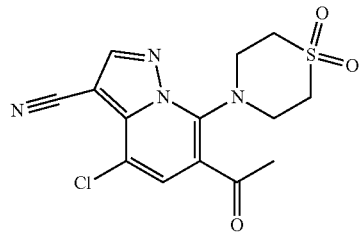 [SMILES: CC(=O)c1cc(Cl)c2c(C#N)cnn2c1N1CCS(=O)(=O)CC1]

A mixture of 6-acetyl-4,7-dichloropyrazolo[1,5-a]pyridine-3-carbonitrile (20 mg, 0.079 mmol), thiomorpholine 1,1-dioxide (21.3 mg, 0.157 mmol), and DIPEA (0.027 ml, 0.157 mmol) was heated to 140° C. in a microwave reactor for 1 h. LCMS indicated complete conversion to the desired product. The reaction mixture was diluted with EtOAc, washed with water and brine, dried over $MgSO_4$, and concentrated. The product was used without purification. LCMS calculated for $C_{14}H_{14}ClN_4O_3S$ $(M+H)^+$: m/z=353.0; found 353.0.

Step 3. 6-(1-aminoethyl)-4-chloro-7-(1,1-dioxidothiomorpholino)pyrazolo[1,5-a]pyridine-3-carbonitrile hydrochloride

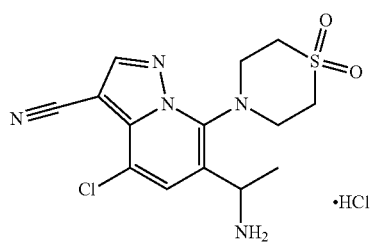 [SMILES: CC(N)c1cc(Cl)c2c(C#N)cnn2c1N1CCS(=O)(=O)CC1 ; Cl]

This compound was prepared according to the procedure described in Examples 57-58, Steps 3-4, starting from 6-acetyl-4-chloro-7-(1,1-dioxidothiomorpholino)pyrazolo[1,5-a]pyridine-3-carbonitrile, with the exception that the diastereomers from the reductive amination step were not separated. The product was used without purification. LCMS calculated for $C_{14}H_{14}ClN_4O_2S$ $(M-NH_2)^+$: m/z=337.1; found 337.1.

Step 4. 2-amino-N-(1-(4-chloro-3-cyano-7-(1,1-dioxidothiomorpholino)pyrazolo[1,5-a]pyridin-6-yl)ethyl)pyrazolo[1,5-a]pyrimidine-3-carboxamide trifluoroacetate This compound was prepared according to the procedure described in Example 57-58, Step 5, starting from 6-(1-aminoethyl)-4-chloro-7-(1,1-dioxidothiomorpholino)pyrazolo[1,5-a]pyridine-3-carbonitrile hydrochloride. The product was purified by preparative HPLC (pH 2) to afford the title compound as a white solid. LCMS calculated for $C_{21}H_{21}ClN_9O_3S$ (M+H)$^+$: m/z=514.1; found 514.1.

Example 61. 2-Amino-N-(1-(4-chloro-3-cyano-7-((S)-3-hydroxypiperidin-1-yl)pyrazolo[1,5-a]pyridin-6-yl)ethyl)pyrazolo[1,5-a]pyrimidine-3-carboxamide trifluoroacetate

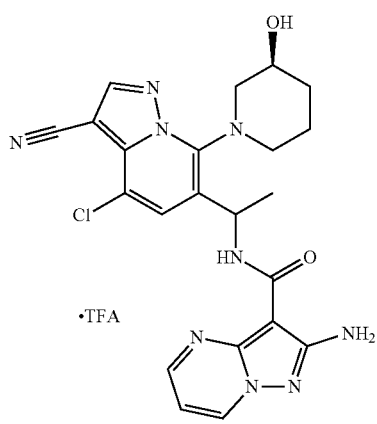 [SMILES: CC(NC(=O)c1c(N)nn2cccnc12)c1cc(Cl)c2c(C#N)cnn2c1N1CCC[C@H](O)C1 ; "·TFA"]

Step 1. (S)-6-acetyl-4-chloro-7-(3-hydroxypiperidin-1-yl)pyrazolo[1,5-a]pyridine-3-carbonitrile

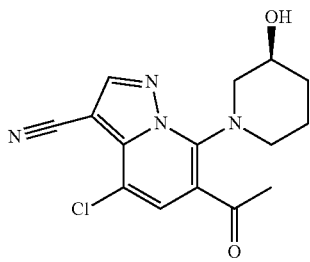 [SMILES: CC(=O)c1cc(Cl)c2c(C#N)cnn2c1N1CCC[C@H](O)C1]

This compound was prepared according to the procedure described in Example 60, Step 2, utilizing (S)-piperidin-3-ol instead of thiomorpholine 1,1-dioxide. LCMS calculated for $C_{15}H_{16}ClN_4O_2$ (M+H)$^+$: m/z=319.1; found 319.0.

Step 2. 2-amino-N-(1-(4-chloro-3-cyano-7-((S)-3-hydroxypiperidin-1-yl)pyrazolo[1,5-a]pyridin-6-yl)ethyl)pyrazolo[1,5-a]pyrimidine-3-carboxamide trifluoroacetate (Mixture of Diastereomers Prepared)

This compound was prepared according to the procedure described in Example 56, Step 9, starting from (S)-6-acetyl-4-chloro-7-(3-hydroxypiperidin-1-yl)pyrazolo[1,5-a]pyridine-3-carbonitrile. The product was purified by preparative HPLC (pH 2). LCMS calculated for $C_{22}H_{23}ClN_9O_2$ (M+H)$^+$: m/z=480.2; found 480.0.

Example 62. 2-amino-N-(1-(8-chloro-5-cyclopentylimidazo[1,5-a]pyridin-6-yl)ethyl)pyrazolo[1,5-a]pyrimidine-3-carboxamide trifluoroacetate

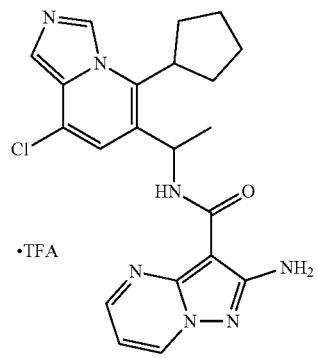 [SMILES: CC(NC(=O)c1c(N)nn2cccnc12)c1cc(Cl)c2cncn2c1C1CCCC1 ; "·TFA"]

Step 1. 1-(8-chloro-5-cyclopentylimidazo[1,5-a]pyridin-6-yl)ethanone

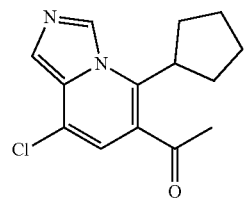 [SMILES: CC(=O)c1cc(Cl)c2cncn2c1C1CCCC1]

To a suspension of copper cyanide (39 mg, 0.44 mmol) in THF (0.8 mL) and HMPA (0.2 mL) at −78° C. was added cyclopentylmagnesium bromide (2M/Et$_2$O, 0.22 mL, 0.44 mmol) dropwise. After stirring at this temperature for 15 min, a solution of 1-(5,8-dichloroimidazo[1,5-a]pyridin-6-yl)ethanone (20.0 mg, 0.0873 mmol, from Example 130, Step 7) in THF (0.5 mL) was added dropwise, and the reaction mixture was allowed to warm to room temperature overnight. The reaction was quenched with 1M HCl and extracted with EtOAc. The organic layer was washed with brine, dried over MgSO$_4$, and concentrated. The residue was purified by flash chromatography (0-40% EtOAc/hexanes) to afford the title compound (11 mg, 48%). LCMS calculated for $C_{14}H_{16}ClN_2O$ (M+H)$^+$: m/z=263.1; found 263.1.

Step 2. 2-amino-N-(1-(8-chloro-5-cyclopentylimidazo[1,5-a]pyridin-6-yl)ethyl)pyrazolo[1,5-a]pyrimidine-3-carboxamide trifluoroacetate This compound was prepared according to the procedure described in Example 56, Step 9, starting from 1-(8-chloro-5-cyclopentylimidazo[1,5-a]pyridin-6-yl)ethanone. The product was purified by preparative HPLC (pH 2) to afford the title compound as a white solid. $^1$H NMR (600 MHz, DMSO) δ 8.92 (dd, J=6.7, 1.6 Hz, 1H), 8.56 (dd, J=4.5, 1.6 Hz, 1H), 8.51 (s, 1H), 8.12 (d, J=6.8 Hz, 1H), 7.64 (s, 1H), 7.17 (s, 1H), 7.01 (dd, J=6.7, 4.5 Hz, 1H), 5.45 (p, J=6.9 Hz, 1H), 4.10 (p, J=6.0 Hz, 1H), 2.16-1.98 (m, 4H), 1.93-1.85

(m, 2H), 1.84-1.79 (m, 2H), 1.54 (d, J=7.0 Hz, 3H). LCMS calculated for $C_{21}H_{23}ClN_7O$ (M+H)$^+$: m/z=424.2; found 424.2.

Example 63. 2-Amino-N-(1-(4-chloro-7-phenyl-[1,2,3]triazolo[1,5-a]pyridin-6-yl)ethyl)pyrazolo[1,5-a]pyrimidine-3-carboxamide trifluoroacetate

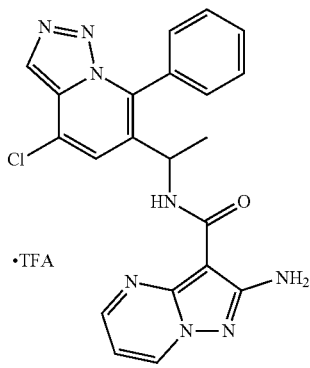

Step 1. methyl 5-chloro-2-phenylnicotinate

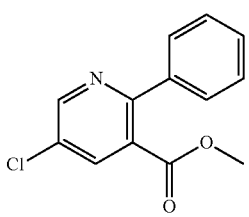 [SMILES: COC(=O)c1cc(Cl)cnc1-c1ccccc1]

A solution of methyl 2,5-dichloronicotinate (10.7 g, 51.9 mmol, from WO 2011/130342, Example 1, Step A, the disclosure of which is incorporated herein in its entirety), phenylboronic acid (6.65 g, 54.5 mmol), and potassium carbonate (15.6 g, 113 mmol) in water (50 mL) and 1,4-Dioxane (200 mL) was degassed with nitrogen (10 min). The reaction mixture was treated with bis(triphenylphosphine)palladium(II) chloride (2 g, 2 mmol), degassed with nitrogen (10 min), and heated at 80° C. for 3 hours. The reaction mixture was diluted with EtOAc and water. The aqueous layer was separated and extracted with EtOAc. The combined organic layers were washed with water and brine, dried with magnesium sulfate, filtered, and concentrated. The residue was purified by flash chromatography (0-40% EtOAc/hexanes) to afford the title compound (11.3 g, 88%) as a yellow oil, which solidified upon standing. LCMS calculated for $C_{13}H_{11}ClNO_2$ (M+H)$^+$: m/z=248.0; found 248.0.

Step 2.
5-chloro-3-(methoxycarbonyl)-2-phenylpyridine 1-oxide

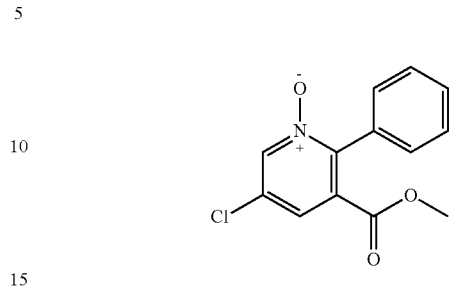

Methyl 5-chloro-2-phenylnicotinate (400.0 mg, 1.615 mmol) was stirred in ethaneperoxoic acid (14 mmol, 3 mL) at 90° C. for 1.5 h. The volatiles were removed in vacuo and the residue was purified by flash chromatography (0-100% EtOAc/hexanes) to afford the title compound (283 mg, 66%) as a viscous oil. LCMS calculated for $C_{13}H_{11}ClNO_3$ (M+H)$^+$: m/z=264.0; found 264.0.

Step 3. methyl 5,6-dichloro-2-phenylnicotinate

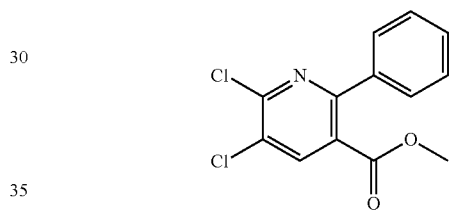

Methyl 5-chloro-2-phenylnicotinate 1-oxide (243.0 mg, 0.9216 mmol) was stirred in phosphoryl chloride (32 mmol, 3 mL) at 90° C. for 1 h. The black reaction mixture was cooled to room temperature and the volatiles were evaporated. The residue was purified by flash chromatography (0-20% EtOAc/hexanes) to afford the title compound (193 mg, 74%) as a white powder. LCMS calculated for $C_{15}H_{13}ClNO_2$ (M+H)$^+$: m/z=282.0; found 282.0.

Step 4. methyl 5-chloro-2-phenyl-6-vinylnicotinate

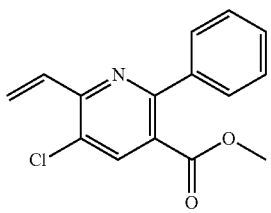 [SMILES: C=Cc1nc(-c2ccccc2)c(C(=O)OC)cc1Cl]

A mixture of methyl 5,6-dichloro-2-phenylnicotinate (54.0 mg, 0.191 mmol), tetrakis(triphenylphosphine)palladium(0) (10 mg, 0.01 mmol), pyridine-trivinylboroxin (1:1) (55 mg, 0.23 mmol), and potassium carbonate (79 mg, 0.57 mmol) in dioxane (2 mL) and water (0.5 mL) was purged with N$_2$ for 5 minutes and heated to 100° C. for 1 h. The reaction mixture was diluted with EtOAc, washed with water and brine, dried over MgSO$_4$, filtered, and concentrated. The residue was purified by flash chromatography (0-20% EtOAc/hexanes) to afford the title compound (37 mg, 71%) as a colorless oil. LCMS calculated for $C_{15}H_{13}ClNO_2$ (M+H)$^+$: m/z=274.1; found 274.0.

Step 5. methyl 5-chloro-6-formyl-2-phenylnicotinate

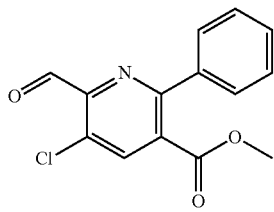 [SMILES: COC(=O)c1cc(Cl)c(C=O)nc1-c1ccccc1]

To a solution of methyl 5-chloro-2-phenyl-6-vinylnicotinate (254 mg, 0.928 mmol) in THF (4 mL) was added sodium periodate (0.60 g, 2.8 mmol), followed by osmium tetroxide (4%/H$_2$O, 60 µL, 0.009 mmol) and the reaction mixture was stirred at room temperature overnight. The reaction mixture was diluted with EtOAc and filtered. The organic layer was washed with brine, dried over MgSO$_4$, filtered and concentrated. The residue was used without purification. LCMS calculated for $C_{14}H_{11}ClNO_3$ (M+H)$^+$: m/z=276.0; found 276.0.

Step 6. methyl 5-chloro-6-(hydrazonomethyl)-2-phenylnicotinate

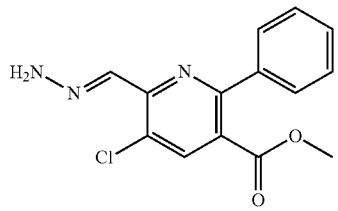 [SMILES: COC(=O)c1cc(Cl)c(/C=N/N)nc1-c1ccccc1]

To a solution of methyl 5-chloro-6-formyl-2-phenylnicotinate (254 mg, 0.921 mmol) in methanol (120 mmol) was added hydrazine (58 µL, 1.8 mmol) and the reaction mixture was heated to 55° C. for 0.5 h. The reaction mixture was filtered and the volatiles were evaporated. The residue was used without purification. LCMS calculated for $C_{14}H_{13}ClN_3O_2$ (M+H)$^+$: m/z=290.1; found 290.0.

Step 7. 1-(4-chloro-7-phenyl-[1,2,3]triazolo[1,5-a]pyridin-6-yl)ethanone

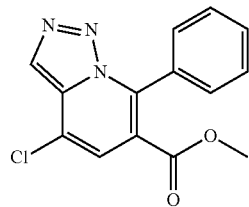 [SMILES: COC(=O)c1cc(Cl)c2cnnn2c1-c1ccccc1]

To a solution of methyl 5-chloro-6-(hydrazonomethyl)-2-phenylnicotinate (267 mg, 0.922 mmol) in DCM (6 mL) was added iodobenzene diacetate (440 mg, 1.4 mmol) and the reaction mixture was stirred at room temperature for 2 h. The volatiles were evaporated in vacuo and the residue was purified by flash chromatography (0-25% EtOAc/hexanes) to afford the title compound (165 mg, 62% over 3 steps). LCMS calculated for $C_{14}H_{11}ClN_3O_2$ (M+H)$^+$: m/z=288.1; found 288.0.

Step 8. 4-chloro-7-phenyl-[1,2,3]triazolo[1,5-a]pyridine-6-carboxylic acid

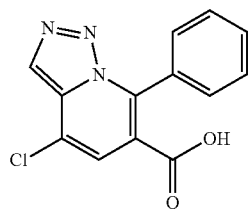 [SMILES: O=C(O)c1cc(Cl)c2cnnn2c1-c1ccccc1]

To a solution of methyl 4-chloro-7-phenyl[1,2,3]triazolo[1,5-a]pyridine-6-carboxylate (165 mg, 0.574 mmol) in methanol (74 mmol) was added 3.0 M sodium hydroxide in water (1.91 mL, 5.74 mmol) and the reaction mixture was stirred at room temperature for 1 h. The volatiles were evaporated in vacuo and the residue was treated with 1M HCl, forming a precipitate, which was solubilized by addition of EtOAc. The solution was diluted with additional EtOAc and 1M HCl, and the layers were separated. The organic layer was washed with brine, dried over MgSO$_4$, filtered, and concentrated, providing a white solid that was used without purification. LCMS calculated for $C_{13}H_9ClN_3O_2$ (M+H)$^+$: m/z=274.0; found 274.0.

Step 9. 4-chloro-N-methoxy-N-methyl-7-phenyl-[1,2,3]triazolo[1,5-a]pyridine-6-carboxamide

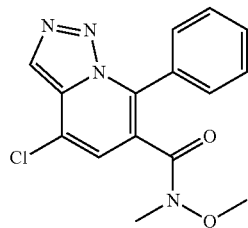 [SMILES: CON(C)C(=O)c1cc(Cl)c2cnnn2c1-c1ccccc1]

To a solution of 4-chloro-7-phenyl[1,2,3]triazolo[1,5-a]pyridine-6-carboxylic acid (157 mg, 0.574 mmol), N,O-dimethylhydroxylamine hydrochloride (110 mg, 1.1 mmol), and HATU (440 mg, 1.1 mmol) in DMF (4 mL) was added N,N-diisopropylamine (0.40 mL, 2.9 mmol) and the reaction mixture was stirred at room temperature overnight. After diluting with EtOAc, the reaction mixture was quenched with water and extracted with EtOAc. The organic layer was dried over MgSO$_4$, filtered, and concentrated. The residue was purified by flash chromatography (0-40% EtOAc/hexanes) to afford the title compound (127 mg, 70%). LCMS calculated for $C_{15}H_{14}ClN_4O_2$ (M+H)$^+$: m/z=317.1; found 317.1.

Step 10. 1-(4-chloro-7-phenyl-[1,2,3]triazolo[1,5-a]pyridin-6-yl)ethanone

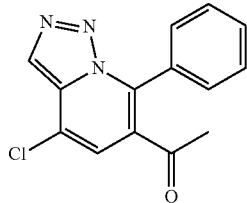 [SMILES: CC(=O)c1cc(Cl)c2cnnn2c1-c1ccccc1]

To a solution of 4-chloro-N-methoxy-N-methyl-7-phenyl[1,2,3]triazolo[1,5-a]pyridine-6-carboxamide (127 mg, 0.401 mmol) in THF (3 mL) at 0° C. was added methylmagnesium bromide (3M/THF, 0.53 mL, 1.6 mmol) dropwise. After stirring for 1 h, the reaction was quenched with 1M HCl and warmed to room temperature. The reaction mixture was diluted with EtOAc and poured into saturated aqueous NaHCO$_3$. The layers were separated and the organic layer was dried over MgSO$_4$, filtered, and concentrated. The residue was purified by flash chromatography (0-25% EtOAc/hexanes) to afford the title compound (31 mg, 28%) as a white solid. LCMS calculated for C$_{14}$H$_{11}$ClN$_3$O (M+H)$^+$: m/z=272.1; found 271.9.

Step 11. 2-amino-N-(1-(4-chloro-7-phenyl-[1,2,3]triazolo[1,5-a]pyridin-6-yl)ethyl)pyrazolo[1,5-a]pyrimidine-3-carboxamide trifluoroacetate This compound was prepared according to the procedure described in Example 56, Step 9, starting from 1-(4-chloro-7-phenyl-[1,2,3]triazolo[1,5-a]pyridin-6-yl)ethanone. The product was purified by preparative HPLC (pH 2). $^1$H NMR (600 MHz, DMSO) δ 8.92 (dd, J=6.7, 1.6 Hz, 1H), 8.57 (dd, J=4.5, 1.6 Hz, 1H), 8.35 (s, 1H), 8.15-8.10 (m, 1H), 7.83 (s, 1H), 7.70-7.57 (m, 4H), 7.56-7.46 (m, 1H), 7.02 (dd, J=6.7, 4.5 Hz, 1H), 4.91 (p, J=6.9 Hz, 1H), 1.48 (d, J=7.0 Hz, 3H). LCMS calculated for C$_{21}$H$_{18}$ClN$_8$O (M+H)$^+$: m/z=433.1; found 433.1.

Example 64. 2-Amino-N-{1-[7-(3-aminopropoxy)-4-chloro-1H-indazol-6-yl]ethyl}pyrazolo[1,5-a]pyrimidine-3-carboxamide bis(trifluoroacetate)

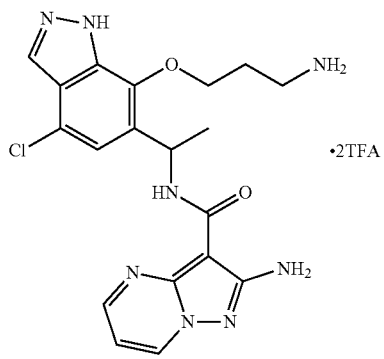 [SMILES: CC(NC(=O)c1c(N)nn2cccnc12)c1cc(Cl)c2cn[nH]c2c1OCCCN]

Step 1. tert-Butyl [3-(6-acetyl-4-chloro-3-methyl-2-nitrophenoxy)propyl]carbamate

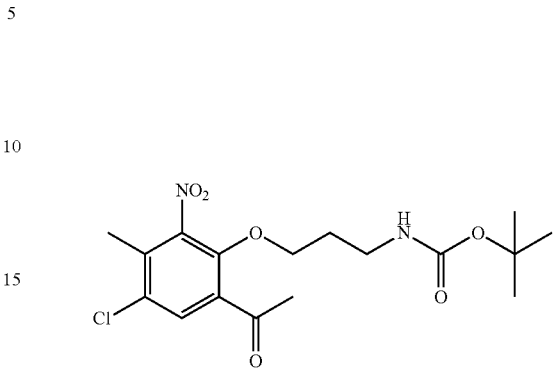

To a mixture of 1-(5-chloro-2-hydroxy-4-methyl-3-nitrophenyl)ethanone (0.50 g, 2.2 mmol), tert-butyl (3-hydroxypropyl)carbamate (0.74 mL, 4.4 mmol), and triphenylphosphine (1.3 g, 4.9 mmol) in tetrahydrofuran (5.0 mL) at 0° C. was added dropwise diisopropyl azodicarboxylate (0.86 mL, 4.4 mmol). The 0° C. bath was removed, and the reaction mixture was stirred overnight. The reaction mixture was partioned between water and EtOAc. The organic layer was separated, washed with brine, dried over sodium sulfate, filtered, and concentrated. Purification via silica gel chromatography (5-40% EtOAc in hexanes) afforded the title compound 0.81 g, 97%) as a white solid. LCMS for C$_{17}$H$_{23}$ClN$_2$NaO$_6$ (M+Na)$^+$: calculated m/z=409.1; found 409.1.

Step 2: tert-Butyl [3-(6-acetyl-2-amino-4-chloro-3-methylphenoxy)propyl]carbamate

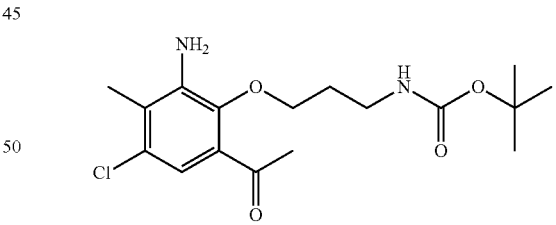

To a solution of tert-butyl [3-(6-acetyl-4-chloro-3-methyl-2-nitrophenoxy)propyl]carbamate (760 mg, 2.0 mmol) in methanol (10.0 mL) and acetic acid (2.4 mL) was added zinc (604.7 mg, 9.248 mmol). The reaction mixture was stirred rapidly for 1 hour at room temperature. The reaction mixture was filtered through celite, and the filter cake was rinsed with MeOH. The filtrate was concentrated. The resulting residue was dissolved in EtOAc and washed with sat. NaHCO$_3$ and then brine. The organic layer was dried over Na$_2$SO$_4$, filtered, and concentrated to afford the title compound (0.75 g, 106%) which was used without further purification. LCMS for C$_{17}$H$_{25}$ClN$_2$NaO$_4$ (M+Na)$^+$: calculated m/z=379.1; found 379.1.

Step 3: tert-Butyl {3-[(6-acetyl-4-chloro-1H-indazol-7-yl)oxy]propyl}carbamate

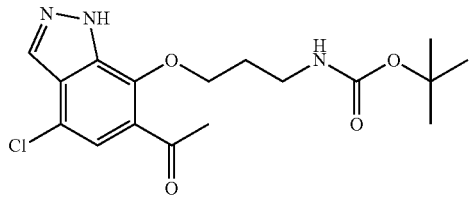 [SMILES: CC(=O)c1cc(Cl)c2cn[nH]c2c1OCCCNC(=O)OC(C)(C)C]

To a solution of tert-butyl [3-(6-acetyl-2-amino-4-chloro-3-methylphenoxy)propyl]carbamate (750.0 mg, 2.1 mmol) in acetic acid (10.0 mL) was added dropwise a solution of sodium nitrite (140 mg, 2.1 mmol) in water (11 mL). The reaction mixture was stirred at room temperature overnight. The reaction mixture was diluted with EtOAc, and the reaction was quenched with sat. NaHCO$_3$ until the aqueous layer reached pH 8. The organic layer was removed, and the aqueous layer was extracted with EtOAc. The combined organic layers were dried over Mg$_2$SO$_4$, filtered, and concentrated. Purification on silica gel column using EtOAc/hexane as the eluent gave the title compound (0.60 g, 78%). LCMS for C$_{17}$H$_{22}$ClN$_3$NaO$_4$ (M+Na)$^+$: calculated m/z=390.1; found 390.1

Step 4: tert-Butyl (3-{[6-(1-aminoethyl)-4-chloro-1H-indazol-7-yl]oxy}propyl)carbamate

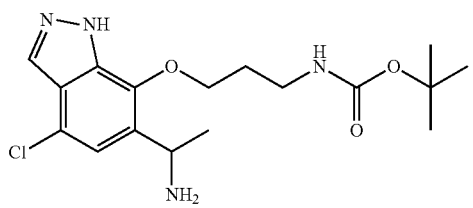 [SMILES: CC(N)c1cc(Cl)c2cn[nH]c2c1OCCCNC(=O)OC(C)(C)C]

To a solution of tert-butyl {3-[(6-acetyl-4-chloro-1H-indazol-7-yl)oxy]propyl}carbamate (300 mg, 0.82 mmol) in 2.0 M ammonia in ethanol (15 mL, 30. mmol) was added titanium tetraisopropoxide (0.72 mL, 2.4 mmol), and the reaction mixture was heated at 60° C. for 5 hours. The reaction mixture was cooled to room temperature and then 0° C., and sodium tetrahydroborate (92 mg, 2.4 mmol) was added. The reaction mixture was stirred at 0° C. for 45 min. The mixture was quenched with 1 M NH$_4$OH (5.0 mL), filtered, and the solid was washed with acetonitrile. Volatiles were removed in vacuo. The resulting residue was dissolved in EtOAc and washed with water and brine, sequentially. The organic layer dried over Na$_2$SO$_4$ and concentrated to afford the title compound (0.30 g, 100%), which used in the next step without purification. LCMS for C$_{17}$H$_{25}$ClN$_4$NaO$_3$ (M+Na)$^+$: calculated m/z=391.2; found 391.1

Step 5: tert-Butyl [3-({[1-(7-{3-[(tert-butoxycarbonyl)amino]propoxy}-4-chloro-1H-indazol-6-yl)ethyl]amino}carbonyl)pyrazolo[1,5-a]pyrimidin-2-yl]arbamate

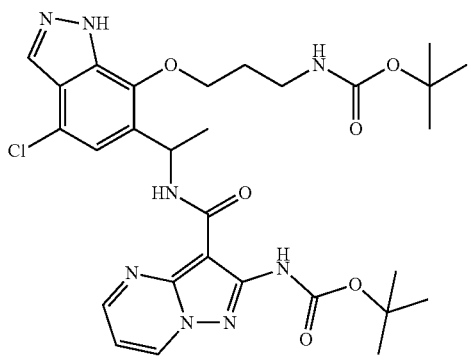 [SMILES: CC(NC(=O)c1c(NC(=O)OC(C)(C)C)nn2cccnc12)c1cc(Cl)c2cn[nH]c2c1OCCCNC(=O)OC(C)(C)C]

To a flask containing 2-[(tert-butoxycarbonyl)amino]pyrazolo[1,5-a]pyrimidine-3-carboxylic acid (270 mg, 0.98 mmol), tert-butyl (3-{[6-(1-aminoethyl)-4-chloro-1H-indazol-7-yl]oxy}propyl)carbamate (0.30 g, 0.82 mmol) and N,N,N',N'-tetramethyl-O-(7-azabenzotriazol-1-yl)uronium hexafluorophosphate (370 mg, 0.98 mmol) was added N,N-dimethylformamide (60 mL). N,N-diisopropylethylamine (1.4 mL, 8.2 mmol) was added dropwise. After stirring for 5 min, the reaction mixture was partioned between EtOAc and sat. NaHCO$_3$. The organic layer was removed, dried over Na$_2$SO$_4$, and concentrated. The crude was purified on silica gel column to give the title compound (340 mg, 66%). LCMS for C$_{29}$H$_{37}$ClN$_8$NaO$_6$ (M+Na)$^+$: calculated m/z=651.1; found 651.1

Step 6: 2-Amino-N-{1-[7-(3-aminopropoxy)-4-chloro-1H-indazol-6-yl]ethyl}pyrazolo[1,5-a]pyrimidine-3-carboxamide bis(trifluoroacetate)

A solution of tert-butyl [3-({[1-(7-{3-[(tert-butoxycarbonyl)amino]propoxy}-4-chloro-1H-indazol-6-yl)ethyl]amino}carbonyl)pyrazolo[1,5-a]pyrimidin-2-yl]carbamate (76 mg, 0.12 mmol) in trifluoroacetic acid (0.5 mL) and dichloromethane (1.0 mL) was stirred for 1 h at room temperature. The reaction mixture was concentrated to give the title compound (78 mg, 99%). LCMS for C$_{19}$H$_{22}$ClN$_8$O$_2$ (M+H)$^+$: calculated m/z=429.1; found 429.1.

Examples 65-80

The following Examples 65-80 in Table 4 were prepared by the method of Example 143. NMR data for representative compounds of Table 4 are provided in Table 4a.

TABLE 4

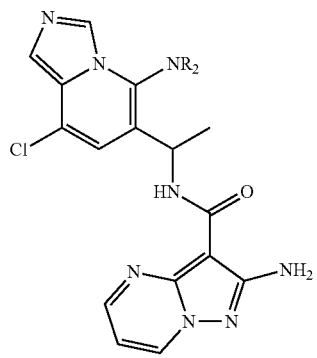

| Ex. No. | Name | NR₂ | LCMS [M + H]⁺ |
|---|---|---|---|
| 65 | 2-Amino-N-{1-[8-chloro-5-(4,4-difluoropiperidin-1-yl)imidazo[1,5-a]pyridin-6-yl]ethyl}pyrazolo[1,5-a]-pyrimidine-3-carboxamide bistrifluoroacetate | 4,4-difluoropiperidinyl | 475.1 |
| 66 | 2-Amino-N-{1-[8-chloro-5-(4-fluoro-piperidin-1-yl)imidazo[1,5-a]pyridin-6-yl]ethyl}pyrazolo[1,5-]pyrimidine-3-carboxamide bistrifluoroacetate | 4-fluoropiperidinyl | 457.2 |
| 67 | 2-Amino-N-{1-[8-chloro-5-(3,3-difluoropiperidin-1-yl)imidazo[1,5-a]pyridin-6-yl]ethyl}pyrazolo[1,5-a]-pyrimidine-3-carboxamide bis trifluoroacetate | 3,3-difluoropiperidinyl | 475.2 |
| 68 | 2-Amino-N-{1-[8-chloro-5-(3,3-difluoropyrrolidin-1-yl)imidazo[1,5-a]pyridin-6-yl]ethyl}pyrazolo[1,5-a]-pyrimidine-3-carboxamide bistrifluoroacetate | 3,3-difluoropyrrolidinyl | 461.2 |
| 69 | 2-Amino-N-{1-[8-chloro-5-(4-methyl-piperidin-1-yl)imidazo[1,5-a]pyridin-6-yl]ethyl}pyrazolo[1,5-a]pyrimidine-3-carboxamide bistrifluoroacetate | 4-methylpiperidinyl | 453.2 |
| 70 | 2-Amino-N-{1-[8-chloro-5-(2,2-dimethylpyrrolidin-1-yl)imidazo[1,5-a]-pyridin-6-yl]ethyl}pyrazolo[1,5-a]-pyrimidine-3-carboxamide bistrifluoroacetate | 2,2-dimethylpyrrolidinyl | 453.2 |
| 71A | 2-Amino-N-(1-{8-chloro-5-[(2R)-2-methylpyrrolidin-1-yl]imidazo[1,5-a]-pyridin-6-yl}ethyl)pyrazolo[1,5-a]-pyrimidine-3-carboxamide bistrifluoroacetate | (2R)-2-methylpyrrolidinyl | 439.2 |

TABLE 4-continued

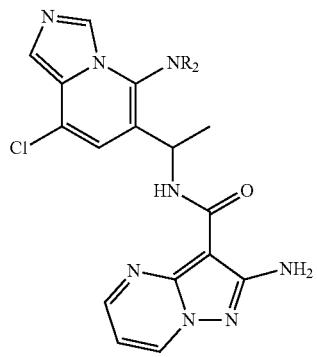

| Ex. No. | Name | NR₂ | LCMS [M + H]⁺ |
|---|---|---|---|
| 71B | 2-Amino-N-(1-{8-chloro-5-[(2S)-2-methylpyrrolidin-1-yl]imidazo[1,5-a]-pyridin-6-yl}ethyl)pyrazolo[1,5-a]-pyrimidine-3-carboxamide bistrifluoro-acetate | | 439.2 |
| 72A | 2-Amino-N-{1-[8-chloro-5-[(2R)-2-methylpiperidin-1-yl]imidazo[1,5-a]-pyridin-6-yl]ethyl}pyrazolo[1,5-a]-pyrimidine-3-carboxamide bistrifluoro-acetate | | 453.2 |
| 72B | 2-Amino-N-{1-[8-chloro-5-[(2S)-2-methylpiperidin-1-yl]imidazo[1,5-a]-pyridin-6-yl]ethyl}pyrazolo[1,5-a]-pyrimidine-3-carboxamide bistrifluoro-acetate | | 453.2 |
| 73A | 2-Amino-N-{1-[8-chloro-5-(3-fluoro-piperidin-1-yl)imidazo[1,5-a]pyridin-6-yl]ethyl}pyrazolo[1,5-a]pyrimidine-3-carboxamide | | 457.2 |
| 73B | 2-Amino-N-{1-[8-chloro-5-(3-fluoro-piperidin-1-yl)imidazo[1,5-a]pyridin-6-yl]ethyl}pyrazolo[1,5-a]pyrimidine-3-carboxamide | | 457.2 |
| 73C-73D | 2-Amino-N-{1-[8-chloro-5-(3-fluoro-piperidin-1-yl)imidazo[1,5-a]pyridin-6-yl]ethyl}pyrazolo[1,5-a]pyrimidine-3-carboxamide | | 457.2 |
| 74 | 2-Amino-N-{1-[8-chloro-5-(3,3-dimethylpyrrolidin-1-yl)imidazo[1,5-a]pyridin-6-yl]ethyl}pyrazolo[1,5-a]-pyrimidine-3-carboxamide bistrifluoro-acetate | | 453.2 |

TABLE 4-continued

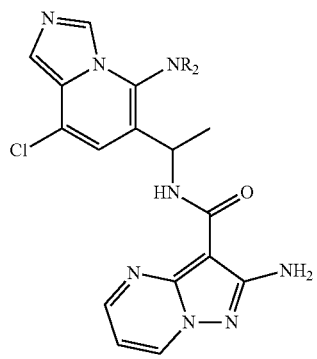

| Ex. No. | Name | NR₂ | LCMS [M + H]⁺ |
|---|---|---|---|
| 75A | 2-Amino-N-(1-{8-chloro-5-[(3R)-3-fluoropyrrolidin-1-yl]imidazo[1,5-a]-pyridin-6-yl}ethyl)pyrazolo[1,5-a]-pyrimidine-3-carboxamide bistrifluoro-acetate | (3R)-3-fluoropyrrolidin-1-yl | 443.2 |
| 75B | 2-Amino-N-(1-{8-chloro-5-[(3S)-3-fluoropyrrolidin-1-yl]imidazo[1,5-a]-pyridin-6-yl}ethyl)pyrazolo[1,5-a]-pyrimidine-3-carboxamide bistrifluoro-acetate | (3S)-3-fluoropyrrolidin-1-yl | 443.2 |
| 76A | 2-Amino-N-{1-[8-chloro-5-(3-hydroxy-3-methylpiperidin-1-yl)imidazo[1,5-a]-pyridin-6-yl]ethyl}pyrazolo[1,5-a]-pyrimidine-3-carboxamide trifluoro-acetate | 3-hydroxy-3-methylpiperidin-1-yl | 469.2 |
| 76B | 2-Amino-N-{1-[8-chloro-5-(3-hydroxy-3-methylpiperidin-1-yl)imidazo[1,5-a]-pyridin-6-yl]ethyl}pyrazolo[1,5-a]-pyrimidine-3-carboxamide trifluoro-acetate | 3-hydroxy-3-methylpiperidin-1-yl | 469.2 |
| 77A | 2-Amino-N-{1-[8-chloro-5-(3-cyano-3-methylpiperidin-1-yl)imidazo[1,5-a]-pyridin-6-yl]ethyl}pyrazolo[1,5-a]-pyrimidine-3-carboxamide trifluoro-acetate | 3-cyano-3-methylpiperidin-1-yl | 478.2 |
| 77B | 2-Amino-N-{1-[8-chloro-5-(3-cyano-3-methylpiperidin-1-yl)imidazo[1,5-a]-pyridin-6-yl]ethyl}pyrazolo[1,5-a]-pyrimidine-3-carboxamide trifluoro-acetate | 3-cyano-3-methylpiperidin-1-yl | 478.2 |

TABLE 4-continued

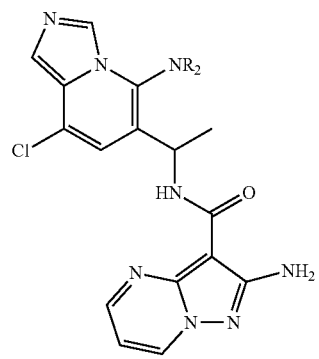

| Ex. No. | Name | NR₂ | LCMS [M + H]⁺ |
|---|---|---|---|
| 78A | 2-Amino-N-(1-{8-chloro-5-[3-hydroxy-3-(trifluoromethyl)piperidin-1-yl]-imidazo[1,5-a]pyridin-6-yl}ethyl)-pyrazolo[1,5-a]pyrimidine-3-carbox-amide trifluoroacetate | | 523.2 |
| 78B | 2-Amino-N-(1-{8-chloro-5-[3-hydroxy-3-(trifluoromethyl)piperidin-1-yl]-imidazo[1,5-a]pyridin-6-yl}ethyl)-pyrazolo[1,5-a]pyrimidine-3-carbox-amide trifluoroacetate | | 523.2 |
| 79 | 2-Amino-N-{1-[8-chloro-5-(2-oxo-3-oxa-1,8-diazaspiro[4.5]dec-8-yl)-imidazo[1,5-a]pyridin-6-yl]ethyl}-pyrazolo[1,5-a]pyrimidine-3-carbox-amide trifluoroacetate | | 510.2 |
| 80 | 2-Amino-N-{1-[8-chloro-5-(2-oxo-1-oxa-3,8-diazaspiro[4.5]dec-8-yl)-imidazo[1,5-a]pyridin-6-yl]ethyl}-pyrazolo[1,5-a]pyrimidine-3-carbox-amide trifluoroacetate | | 510.2 |

TABLE 4a

| Ex. No. | ¹H NMR Data |
|---|---|
| 73B | ¹H NMR (DMSO) δ: 8.90 (d, J = 6.7 Hz, 1H), 8.59-8.54 (m, 1H), 8.53 (s, 1H), 8.04 (d, J = 6.5 Hz, 1H), 7.46 (s, 1H), 7.00 (m, 2H), 6.40 (d, J = 6.5 Hz, 2H), 5.40 (dt, J = 24.6, 6.8 Hz, 1H), 5.02-4.75 (m, 1H), 3.64 (dd, J = 21.2, 10.9 Hz, 1H), 3.53-3.44 (m, 2H), 3.44-3.33 (m, 2H), 1.97-1.88 (m, 2H), 1.56-1.47 (m, 3H), 1.30-1.13 (m, 2H) |
| 75A | ¹H NMR (DMSO) δ: 8.91 (dt, J = 6.7, 1.9 Hz, 1H), 8.56 (dt, J = 3.5, 1.7 Hz, 1H), 8.48 (s, 1H), 8.09 (dd, J = 10.3, 6.9 Hz, 1H), 7.66 (s, 1H), 7.13 (d, J = 11.9 Hz, 1H), 7.00 (ddd, J = 6.8, 4.5, 2.3 Hz, 1H), 5.51 (m, 1H), 5.37 (dt, J = 22.4, 7.0 Hz, 1H), 3.85 (dd, J = 36.4, 13.3 Hz, 2H), 3.73 (d, J = 16.3 Hz, 1H), 3.67-3.54 (m, 2H), 2.42-2.23 (m, 1H), 1.52 (d, J = 7.0 Hz, 3H) |

Example 81. 2-Amino-N-(1-(4-chloro-7-(2-methoxyethoxy)-1H-indazol-6-yl)ethyl)pyrazolo[1,5-a]pyrimidine-3-carboxamide trifluoroacetate

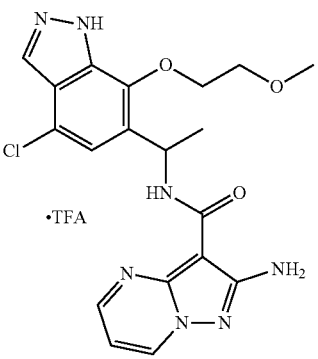 [SMILES: COCCOc1c(C(C)NC(=O)c2c(N)nn3cccnc23)cc(Cl)c2cn[nH]c12]

Step 1. 1-(5-Chloro-2-(2-methoxyethoxy)-4-methyl-3-nitrophenyl)ethanone

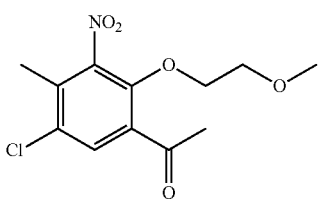

1-Bromo-2-methoxyethane (62 μL, 0.65 mmol) was added to a mixture of 1-(5-chloro-2-hydroxy-4-methyl-3-nitrophenyl)ethanone (0.10 g, 0.44 mmol, from Biogene Organics, BG-C1031) and K₂CO₃ (0.12 g, 0.87 mmol) in DMF (1.0 mL). The reaction mixture was then heated at 60° C. for 1.5 h. An additional portion of the 1-bromo-2-methoxyethane (62 μL, 0.65 mmol) was added, and the reaction mixture was stirred for 1.5 days at 80° C. After cooling to room temperature, the reaction mixture was diluted with EtOAc (2 mL) and washed with water (2×2 mL) and then brine (2 mL). The organic layer was dried over Na₂SO₄, filtered, and concentrated. Purification via silica gel chromatography (100% DCM) afforded the title compound as a red-orange oil (0.077 g, 61%). ¹H NMR (400 MHz, CDCl₃) δ 7.72 (s, 1H), 4.18-4.02 (m, 2H), 3.67-3.55 (m, 2H), 3.36 (s, 3H), 2.65 (s, 3H), 2.34 (s, 3H).

Step 2. 1-(3-Amino-5-chloro-2-(2-methoxyethoxy)-4-methylphenyl)ethanone

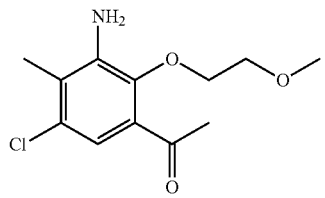

To a solution of 1-(5-chloro-2-(2-methoxyethoxy)-4-methyl-3-nitrophenyl)ethanone (76 mg, 0.26 mmol) in MeOH (5.2 mL) and acetic acid (AcOH, 1.3 mL) was added zinc powder (0.10 g, 1.6 mmol). The reaction mixture was stirred rapidly for 25 min at room temperature. The reaction mixture was filtered through Celite, rinsing with MeOH. The filtrate was concentrated. The resulting residue was dissolved in EtOAc and washed with sat. NaHCO₃ and then brine. The organic layer was dried over Na₂SO₄, filtered, and concentrated to afford the title compound as a yellow-brown solid (69.7 mg, >99%). LCMS for C₁₂H₁₇ClNO₃ (M+H)⁺: calculated m/z=258.1; found 258.0.

Step 3. 1-(4-Chloro-7-(2-methoxyethoxy)-1H-indazol-6-yl)ethanone

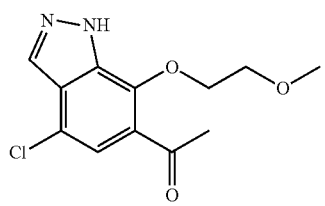 [SMILES: COCCOc1c(C(C)=O)cc(Cl)c2cn[nH]c12]

The title compound was synthesized according to an experimental procedure analogous to the synthesis of Example 1, Step 3, substituting 1-(3-amino-5-chloro-2-(2-methoxyethoxy)-4-methylphenyl)ethanone for 1-(3-amino-5-chloro-2-ethoxy-4-methylphenyl)ethanone. LCMS for C₁₂H₁₂ClN₂O₃ (M+H)⁺: calculated m/z=269.1; found 269.0.

Step 4. 2-Amino-N-(1-(4-chloro-7-(2-methoxyethoxy)-1H-indazol-6-yl)ethyl)pyrazolo[1,5-a]pyrimidine-3-carboxamide trifluoroacetate To a solution of 1-(4-chloro-7-(2-methoxyethoxy)-1H-indazol-6-yl)ethanone (10 mg, 0.037 mmol) and racemic 2-methylpropane-2-sulfinamide (12 mg, 0.099 mmol) in THF (0.090 mL) was added titanium(IV) ethoxide (0.02 mL, 0.07 mmol). The reaction mixture was stirred at 70° C. in a sealed vial for 7 h. The reaction mixture was then cooled to −44° C. L-Selectride (0.11 mL, 0.11 mmol, 1.0 M in THF) was then added dropwise, and the reaction mixture was warmed to room temperature while stirring overnight. The reaction mixture was then cooled to 0° C., and sodium borohydride (6 mg, 0.1 mmol) was added. The reaction mixture was stirred overnight after coming to room temperature. The reaction mixture was again cooled to 0° C., and the reaction was quenched with MeOH (0.1 mL). The mixture was warmed to room temperature and diluted with EtOAC (0.25 mL). Brine (10 µL) was then added, and the resulting slurry was stirred for 5 min. The slurry was filtered through Celite, and the filter cake was washed with EtOAc. The filtrate was concentrated. The resulting residue was dissolved in MeOH (1.1 mL), and HCl (0.05 mL, 0.2 mmol, 4.0 M in 1,4-dioxane) was added dropwise while the reaction flask was in a room temperature water bath. The bath was removed, and after stirring 1 h at room temperature, the reaction mixture was concentrated. To a mixture of the resulting residue, 2-[(tert-butoxycarbonyl)amino]pyrazolo[1,5-a]pyrimidine-3-carboxylic acid (14 mg, 0.050 mmol, from J&W PharmLab, 68R0546), and N,N,N',N'-tetramethyl-O-(7-azabenzotriazol-1-yl)uronium hexafluorophosphate (21 mg, 0.055 mmol) in DMF was added dropwise N,N-diisopropylethylamine (0.05 mL, 0.3 mmol). The reaction mixture was stirred 2 h at room temperature. The reaction mixture was then partitioned between EtOAc and sat. NaHCO$_3$. The organic layer was removed, filtered through a plug of Na$_2$SO$_4$, and concentrated. The resulting residue was dissolved in DCM (2.3 mL) and TFA (0.2 mL). The reaction mixture was then stirred for 1 h. Purification via preparative HPLC on a C-18 column (pH 2, 36-51% MeCN/0.1% TFA (aq) over 5 min, 60 mL/min) afforded the title compound as a white solid (7.7 mg, 38%). $^1$H NMR (600 MHz, d$_6$-DMSO) δ 13.53 (s, 1H), 8.91 (dd, J=6.7, 1.6 Hz, 1H), 8.56 (dd, J=4.5, 1.6 Hz, 1H), 8.14 (d, J=7.3 Hz, 1H), 8.09 (d, J=1.3 Hz, 1H), 7.11 (s, 1H), 7.00 (dd, J=6.7, 4.5 Hz, 1H), 6.44 (s, 2H), 5.69-5.40 (m, 1H), 4.43-4.36 (m, 1H), 4.36-4.29 (m, 1H), 3.86-3.62 (m, 2H), 3.36 (s, 3H), 1.51 (d, J=7.0 Hz, 3H). LCMS for C$_{19}$H$_{20}$ClN$_7$NaO$_3$ (M+Na)$^+$: calculated m/z=452.1; found 452.1.

Example 82. 2-Amino-N-(1-(4-chloro-7-methoxy-1H-indazol-6-yl)ethyl)pyrazolo[1,5-a]pyrimidine-3-carboxamide trifluoroacetate

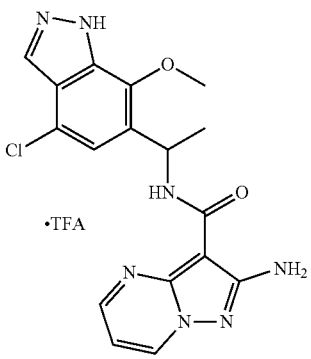 [SMILES: COc1c(C(C)NC(=O)c2c(N)nn3cccnc23)cc(Cl)c2cn[nH]c12]

The title compound was synthesized according to an experimental procedure analogous to the synthesis of Example 81, Steps 2-4, substituting 1-(5-chloro-2-methoxy-4-methyl-3-nitrophenyl)ethanone for 1-[5-chloro-2-(2-methoxyethoxy)-4-methyl-3-nitrophenyl]ethanone in Step 2. $^1$H NMR (600 MHz, d$_6$-DMSO) δ 13.64 (br s, 1H), 8.91 (dd, J=6.7, 1.6 Hz, 1H), 8.57 (dd, J=4.5, 1.7 Hz, 1H), 8.21 (d, J=7.7 Hz, 1H), 8.11 (s, 1H), 7.12 (s, 1H), 7.00 (dd, J=6.7, 4.5 Hz, 1H), 6.45 (br s, 2H), 5.52 (apparent p, J=7.0 Hz, 1H), 4.05 (s, 3H), 1.51 (d, J=7.0 Hz, 3H). LCMS for C$_{17}$H$_{16}$ClN$_7$NaO$_2$ (M+Na)$^+$: calculated m/z=408.1; found 408.1.

Example 83. 2-Amino-N-(1-(4-chloro-7-(difluoromethoxy)-1H-indazol-6-yl)ethyl)pyrazolo[1,5-a]pyrimidine-3-carboxamide trifluoroacetate

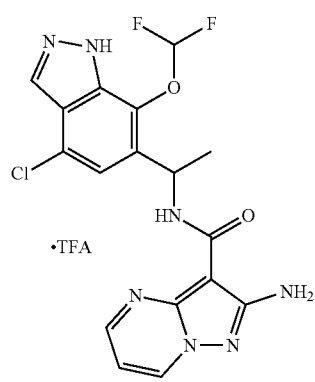 [SMILES: CC(NC(=O)c1c(N)nn2cccnc12)c1cc(Cl)c2cn[nH]c2c1OC(F)F]

Step 1. 1-(5-Chloro-2-(difluoromethoxy)-4-methyl-3-nitrophenyl)ethanone

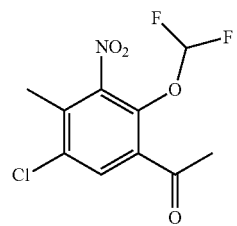 [SMILES: CC(=O)c1cc(Cl)c(C)c([N+](=O)[O-])c1OC(F)F]

To a mixture of 1-(5-chloro-2-hydroxy-4-methyl-3-nitrophenyl)ethanone (50. mg, 0.22 mmol, from Biogene Organics, BG-C1031) in 1:1 MeCN/H$_2$O (2.2 mL) at −78° C. was added KOH (0.24 g, 4.4 mmol) and then diethyl [bromo(difluoro)methyl]phosphonate (80 µL, 0.4 mmol, from Matrix Scientific, 007430). The reaction mixture was warmed to room temperature. After stirring for 30 min, the reaction mixture was cooled to −78° C., and an additional portion of diethyl [bromo(difluoro)methyl]phosphonate (80 µL, 0.4 mmol) was added. The reaction mixture was stirred 30 min during which time it came to room temperature. The reaction mixture was then extracted with Et$_2$O (3×3 mL). The combined organic layers were dried over Na$_2$SO$_4$, filtered, and concentrated. Purification via silica gel chromatography (1-20% EtOAc in hexanes) afforded the title compound as a light yellow oil (26 mg, 43%). $^1$H NMR (400

MHz, CDCl₃) δ 7.80 (s, 1H), 6.55 (t, J=73.6 Hz, 1H), 2.61 (s, 3H), 2.40 (s, 3H). $^1$H NMR (376 MHz, CDCl₃) δ −81.80.

Step 2. 2-Amino-N-(1-(4-chloro-7-(difluoromethoxy)-1H-indazol-6-yl)ethyl)pyrazolo[1,5-a]pyrimidine-3-carboxamide trifluoroacetate The title compound was synthesized according to experimental procedures analogous to Example 81, Steps 2-4, substituting 1-(5-chloro-2-(difluoromethoxy)-4-methyl-3-nitrophenyl)ethanone for 1-[5-chloro-2-(2-methoxyethoxy)-4-methyl-3-nitrophenyl]ethanone in Step 2. LCMS for C₁₇H₁₅ClF₂N₇O₂ (M+H)⁺: calculated m/z=422.1; found 422.1.

Example 84. 2-Amino-N-(1-(4-chloro-7-(2-hydroxyethoxy)-1H-indazol-6-yl)ethyl)pyrazolo[1,5-a]pyrimidine-3-carboxamide trifluoroacetate

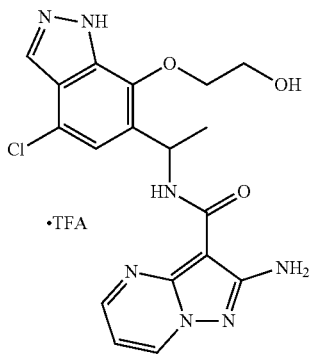 [SMILES: CC(NC(=O)c1c(N)nn2cccnc12)c1cc(Cl)c2cn[nH]c2c1OCCO]

Step 1. 1-(2-(2-(tert-Butyldimethylsilyloxy)ethoxy)-5-chloro-4-methyl-3-nitrophenyl)ethanone

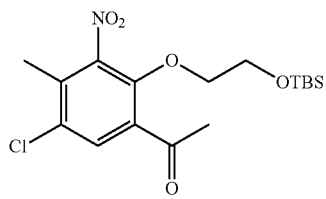 [SMILES: CC(=O)c1cc(Cl)c(C)c([N+](=O)[O-])c1OCCO[Si](C)(C)C(C)(C)C]

Diisopropyl azodicarboxylate (0.26 mL, 1.3 mmol) was added dropwise to a mixture of 1-(5-chloro-2-hydroxy-4-methyl-3-nitrophenyl)ethanone (0.15 g, 0.65 mmol, from Biogene Organics, BG-C1031), 2-{[tert-butyl(dimethyl)silyl]oxy}ethanol (0.26 mL, 1.3 mmol), and triphenylphosphine (0.39 g, 1.5 mmol) in THF at 0° C. The 0° C. bath was removed, and the reaction mixture was stirred for 6 h at room temperature. The reaction mixture was partitioned between water and EtOAc. The organic layer was separated, washed with brine, dried over Na₂SO₄, filtered, and concentrated. Purification via silica gel chromatography (1-12% EtOAc in hexanes) afforded the title compound as a clear oil (0.17 g, 67%). $^1$H NMR (400 MHz, CDCl₃) δ 7.73 (s, 1H), 4.03-3.97 (m, 2H), 3.90-3.83 (m, 2H), 2.68 (s, 3H), 2.34 (s, 3H), 0.88 (s, 9H), 0.06 (s, 6H).

Step 2. 1-(3-Amino-2-(2-(tert-butyldimethylsilyloxy)ethoxy)-5-chloro-4-methylphenyl)ethanone

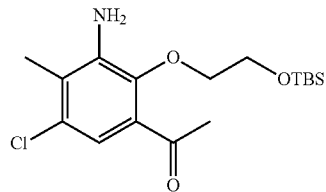 [SMILES: CC(=O)c1cc(Cl)c(C)c(N)c1OCCO[Si](C)(C)C(C)(C)C]

The title compound was synthesized according to an experimental procedure analogous to the synthesis of Example 81, Step 2 substituting 1-(2-(2-(tert-butyldimethylsilyloxy)ethoxy)-5-chloro-4-methyl-3-nitrophenyl)ethanone for 1-[5-chloro-2-(2-methoxyethoxy)-4-methyl-3-nitrophenyl]ethanone. LCMS for C₁₇H₂₉ClNO₃Si (M+H)⁺: calculated m/z=358.2; found 358.1.

Step 3. 1-[7-(2-{[tert-Butyl(dimethyl)silyl]oxy}ethoxy)-4-chloro-1H-indazol-6-yl]ethanone

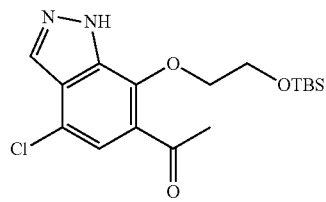 [SMILES: CC(=O)c1cc(Cl)c2cn[nH]c2c1OCCO[Si](C)(C)C(C)(C)C]

To a solution of 1-(3-amino-2-(2-(tert-butyldimethylsilyloxy)ethoxy)-5-chloro-4-methylphenyl)ethanone (0.13 g, 0.37 mmol) in AcOH (3.8 mL) was added dropwise a solution of sodium nitrite (26 mg, 0.38 mmol) in H₂O (1.9 mL). The reaction mixture was stirred at room temperature for 1.5 h and then concentrated. The resulting orange oil was dissolved in DCM, and the resulting organic solution was washed with sat. NaHCO₃ and then brine. The organic layer was dried over Mg₂SO₄, filtered, and concentrated. Purification via silica gel chromatography (5-40% EtOAc in hexanes [1% DCM]) afforded the title compound as a yellow orange solid (0.070 g, 52%). LCMS for C₁₇H₂₆ClN₂O₃Si (M+H)⁺: calculated m/z=369.1; found 369.1.

Step 4. 1-[7-(2-{[tert-Butyl(dimethyl)silyl]oxy}ethoxy)-4-chloro-1H-indazol-6-yl]ethanamine

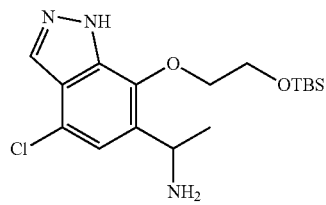 [SMILES: CC(N)c1cc(Cl)c2cn[nH]c2c1OCCO[Si](C)(C)C(C)(C)C]

The title compound was synthesized according to an experimental procedure analogous to the synthesis of Example 23, Step 2 substituting 1-[7-(2-{[tert-butyl(dimethyl)silyl]oxy}ethoxy)-4-chloro-1H-indazol-6-yl]ethanone for 1-(3-bromo-4-chloro-7-phenyl-1H-indazol-6-yl)ethanone LCMS for $C_{17}H_{26}ClN_2O_2Si$ $(M-NH_2)^+$: calculated m/z=353.1; found 353.1.

Step 5. 2-Amino-N-(1-(4-chloro-7-(2-hydroxyethoxy)-1H-indazol-6-yl)ethyl)pyrazolo[1,5-a]pyrimidine-3-carboxamide trifluoroacetate To a mixture of 1-[7-(2-{[tert-butyl(dimethyl)silyl]oxy}ethoxy)-4-chloro-1H-indazol-6-yl]ethanamine, 2-[(tert-butoxycarbonyl)amino]pyrazolo[1,5-a]pyrimidine-3-carboxylic acid (11 mg, 0.039 mmol, from J&W PharmLab, 68R0546), and N,N,N',N'-tetramethyl-O-(7-azabenzotriazol-1-yl)uronium hexafluorophosphate (16 mg, 0.043 mmol) in DMF (0.82 mL) was added dropwise N,N-diisopropylethylamine (30 µL, 0.1 mmol). The reaction mixture was stirred overnight at room temperature. The reaction mixture was then partitioned between EtOAc and sat. NaHCO$_3$. The organic layer was removed, dried over Na$_2$SO$_4$, filtered, and concentrated. The resulting residue was dissolved in MeOH (2.2 mL), and conc. HCl (0.15 mL) was added. The reaction mixture was stirred at room temperature for 1 h and then concentrated. The resulting residue was dissolved in DCM (1.8 mL) and TFA (0.2 mL). The reaction mixture was stirred for 1 h and then concentrated. Purification via preparative HPLC on a C-18 column (pH 2, 26-46% MeCN/0.1% TFA (aq) over 5 min, 60 mL/min) afforded the title compound as a white to tan solid (6.7 mg). LCMS for $C_{18}H_{19}ClN_7O_3$ $(M+H)^+$: calculated m/z=416.1; found 416.0.

Example 85. 2-Amino-N-(1-(4-chloro-7-(2,3-dihydroxypropoxy)-1H-indazol-6-yl)ethyl)pyrazolo[1,5-a]pyrimidine-3-carboxamide trifluoroacetate

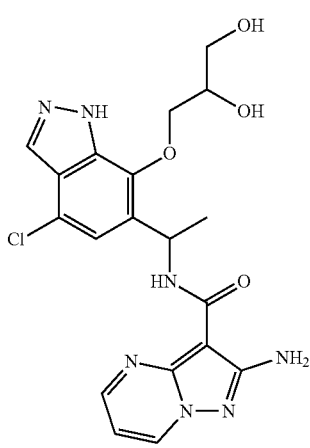 [SMILES: CC(NC(=O)c1c(N)nn2cccnc12)c1cc(Cl)c2cn[nH]c2c1OCC(O)CO]

Step 1. 1-(5-Chloro-2-((2,2-dimethyl-1,3-dioxolan-4-yl)methoxy)-4-methyl-3-nitrophenyl)ethanone

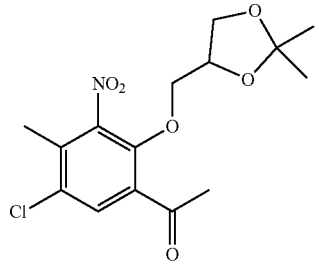 [SMILES: CC(=O)c1cc(Cl)c(C)c([N+](=O)[O-])c1OCC1COC(C)(C)O1]

The title compound was synthesized according to an experimental procedure analogous to the synthesis of Example 84, Step 1 substituting 2,2-dimethyl-1,3-dioxolane-4-methanol for 2-{[tert-butyl(dimethyl)silyl]oxy}ethanol. $^1$H NMR (400 MHz, CDCl$_3$) δ 7.73 (s, 1H), 4.38 (apparent p, J=5.8 Hz, 1H), 4.10 (dd, J=8.6, 6.6 Hz, 1H), 4.02-3.88 (m, 2H), 3.78 (dd, J=8.6, 5.9 Hz, 1H), 2.66 (s, 3H), 2.35 (s, 3H), 1.41 (s, 3H), 1.37 (s, 3H). LCMS for $C_{15}H_{19}ClNO_6$ $(M+H)^+$: calculated m/z=344.1; found 344.0.

Step 2. 1-(3-Amino-5-chloro-((2,2-dimethyl-1,3-dioxolan-4-yl)methoxy)-4-methylphenyl)ethanone

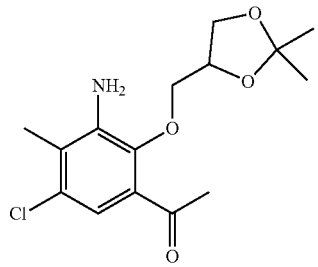

The title compound was synthesized according to an experimental procedure analogous to the synthesis of Example 81, Step 2 substituting 1-(5-chloro-2-((2,2-dimethyl-1,3-dioxolan-4-yl)methoxy)-4-methyl-3-nitrophenyl)ethanone for 1-[5-chloro-2-(2-methoxyethoxy)-4-methyl-3-nitrophenyl]ethanone. LCMS for $C_{15}H_{20}ClNNaO_4$ $(M+Na)^+$: calculated m/z=336.1; found 336.0.

Step 3. 1-(4-Chloro-7-((2,2-dimethyl-1,3-dioxolan-4-yl)methoxy)-1H-indazol-6-yl)ethanone

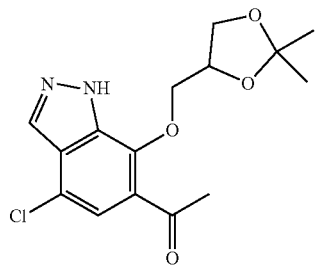 [SMILES: CC(=O)c1cc(Cl)c2cn[nH]c2c1OCC1COC(C)(C)O1]

The title compound was synthesized according to an experimental procedure analogous to the synthesis of Example 84, Step 3 substituting 1-(3-amino-5-chloro-2-((2,2-dimethyl-1,3-dioxolan-4-yl)methoxy)-4-methylphenyl)ethanone for 1-[3-amino-2-(2-{[tert-butyl(dimethyl)silyl]oxy}ethoxy)-5-chloro-4-methylphenyl]ethanone LCMS for $C_{15}H_{18}ClN_2O_4$ (M+H)$^+$: calculated m/z=325.1; found 325.0.

Step 4. 3-(6-(1-Aminoethyl)-4-chloro-1H-indazol-7-yloxy)propane-1,2-diol hydrochloride

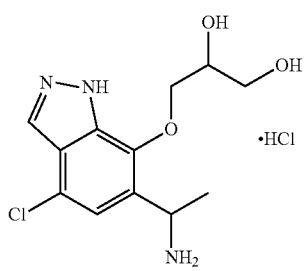 [SMILES: CC(N)c1cc(Cl)c2cn[nH]c2c1OCC(O)CO ; Cl]

To a solution of 1-(4-chloro-7-((2,2-dimethyl-1,3-dioxolan-4-yl)methoxy)-1H-indazol-6-yl)ethanone (61 mg, 0.19 mmol) in 2.0 M $NH_3$ in EtOH (3.5 mL, 7.0 mmol) was added titanium(IV) isopropoxide (0.16 mL, 0.55 mmol), and the reaction mixture was heated at 60° C. for 2 h. The reaction mixture was cooled to room temperature and then 0° C. $NaBH_4$ (21 mg, 0.55 mmol) was added, and the reaction mixture was stirred at 0° C. for 30 min. The reaction was quenched with 1 M $NH_4OH$ (1 mL) and diluted with MeCN. The resulting suspension was stirred at room temperature for 5 min. The mixture was then filtered through Celite, and the filter cake was washed with MeCN. Volatiles were removed in vacuo. The resulting residue was dissolved in acetone (0.60 mL), and 1.0 M HCl (0.18 mL, 0.18 mmol) was added. The reaction mixture was stirred at room temperature for 1.5 h. An additional portion of 1.0 M HCl (0.18 mL, 0.18 mmol) was added, and the reaction mixture was heated at 50° C. for 2 h. The reaction mixture was concentrated. The resulting residue was dissolved in 4.0 M HCl in 1,4-dioxane (4 mL, 20 mmol) while the reaction flask was in a room temperature water bath. $H_2O$ (14 μL, 0.75 mmol) was added, and after removal of the water bath, the reaction mixture was stirred at room temperature for 45 min. MeOH (1 mL, 20 mmol) was added, and the reaction mixture was stirred at room temperature for 1.5 h. The reaction mixture was concentrated, and the product was used without purification (theoretical yield assumed). LCMS for $C_{12}H_{16}ClN_3NaO_3$ (M+Na)$^+$: calculated m/z=308.1; found 308.0.

Step 5. tert-Butyl 1-(4-chloro-7-(2,3-dihydroxypropoxy)-1H-indazol-6-yl)ethylcarbamate

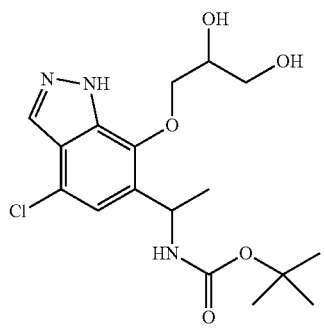 [SMILES: CC(NC(=O)OC(C)(C)C)c1cc(Cl)c2cn[nH]c2c1OCC(O)CO]

Triethylamine (50 μL, 0.36 mmol) was added to a mixture of 3-(6-(1-aminoethyl)-4-chloro-1H-indazol-7-yloxy)propane-1,2-diol hydrochloride (0.061 g, 0.19 mmol) and di-tert-butyl dicarbonate (64 μL, 0.28 mmol) in 1,4-dioxane (1.2 mL)/$H_2O$ (58 μL). The reaction mixture was stirred at room temperature for 1.5 h. DCM (1.0 mL, 16 mmol) was added, and the reaction mixture was stirred for an additional 2 h. An additional portion of di-tert-butyl dicarbonate (64 μL, 0.28 mmol) and triethylamine (50 μL, 0.36 mmol) were added, and the reaction mixture was stirred at room temperature overnight. The reaction mixture was concentrated. Purification via silica gel chromatography (1-15% MeOH in DCM) afforded the title compound (25 mg). LCMS for $C_{17}H_{24}ClN_3NaO_5$ (M+Na)$^+$: calculated m/z=408.1; found 408.0.

Step 6. 3-(6-(1-Aminoethyl)-4-chloro-1H-indazol-7-yloxy)propane-1,2-diol trifluoroacetate

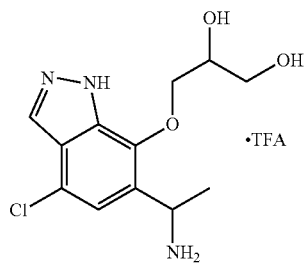 [SMILES: CC(N)c1cc(Cl)c2cn[nH]c2c1OCC(O)CO]

tert-Butyl 1-(4-chloro-7-(2,3-dihydroxypropoxy)-1H-indazol-6-yl)ethylcarbamate (12.5 mg, 0.0324 mmol) was dissolved in DCM (2.0 mL) and TFA (0.2 mL). After stirring at room temperature for 1 h, the reaction mixture was then concentrated to afford the title compound. The product was used without purification (theoretical yield assumed). LCMS for $C_{12}H_{16}ClN_3NaO_3$ (M+Na)$^+$: calculated m/z=308.1; found 308.0.

Step 7. 2-Amino-N-(1-(4-chloro-7-(2,3-dihydroxypropoxy)-1H-indazol-6-yl)ethyl)pyrazolo[1,5-a]pyrimidine-3-carboxamide trifluoroacetate To a mixture of 3-(6-(1-aminoethyl)-4-chloro-1H-indazol-7-yloxy)propane-1,2-diol trifluoroacetate (0.0130 g, 0.0324 mmol), 2-[(tert-butoxycarbonyl)amino]pyrazolo[1, 5-a]pyrimidine-3-carboxylic acid (12 mg, 0.043 mmol), and N,N,N',N'-tetramethyl-O-(7-azabenzotriazol-1-yl)uronium hexafluorophosphate (18 mg, 0.047 mmol) in DMF (0.9 mL) was added dropwise N,N-diisopropylethylamine (40 µL, 0.2 mmol). The reaction mixture was stirred 1 h at room temperature. The reaction mixture was then partitioned between EtOAc and sat. NaHCO₃. The organic layer was removed, filtered through a plug of Na₂SO₄, and concentrated. The resulting residue was dissolved in DCM (2 mL) and TFA (0.2 mL). The reaction mixture was then stirred for 1 h and then concentrated. Purification via preparative HPLC on a C-18 column (pH 2, 25-45% MeCN/0.1% TFA (aq) over 5 min, 60 mL/min) afforded the title compound a white solid (4 mg). LCMS for $C_{19}H_{20}ClN_7NaO_4$ (M+Na)⁺: calculated m/z=468.1; found 468.1.

Example 86. 2-Amino-N-(1-(4-chloro-3-cyano-7-ethoxy-1H-indazol-6-yl)ethyl)pyrazolo[1,5-a]pyrimidine-3-carboxamide trifluoroacetate

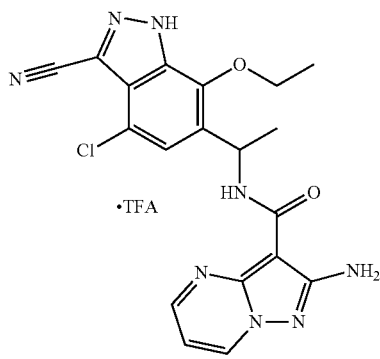 [SMILES: CCOc1c(C(C)NC(=O)c2c(N)nn3cccnc23)cc(Cl)c2c(C#N)n[nH]c12]

Step 1. 1-(4-chloro-7-ethoxy-3-iodo-1H-indazol-6-yl)ethanone

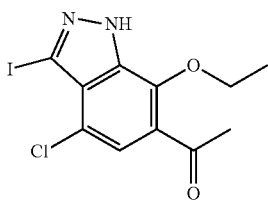 [SMILES: CCOc1c(C(C)=O)cc(Cl)c2c(I)n[nH]c12]

To a solution 1-(4-chloro-7-ethoxy-1H-indazol-6-yl)ethanone (0.266 g, 1.11 mmol, from Example 1, Step 3) in DMF (5 mL) was added N-iodosuccinimide (0.29 g, 1.3 mmol). After stirring overnight at room temperature, the reaction mixture was diluted with sat. NaHCO₃ and extracted with EtOAc. The organic layer was washed with saturated sodium thiosulfate, dried over Na₂SO₄, and concentrated in vacuo. The crude product was passed through a plug of silica gel eluting with 1:1 DCM/EtOAc. The filtrate was concentrated, taken up into a mixture of DCM and hexanes, and concentrated to afford the title compound as a tan solid (0.175 g, 43%). ¹H NMR (400 MHz, d₆-DMSO) δ 7.32 (s, 1H), 4.24 (br s, 2H), 2.64 (s, 3H), 1.39 (t, J=7.0 Hz, 3H). LCMS for $C_{11}H_{11}ClIN_2O_2$ (M+H)⁺: calculated m/z=365.0; found 364.8.

Step 2. Methyl 6-acetyl-4-chloro-7-ethoxy-1H-indazole-3-carboxylate

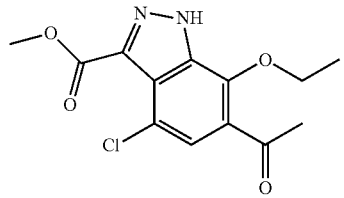 [SMILES: CCOc1c(C(C)=O)cc(Cl)c2c(C(=O)OC)n[nH]c12]

A mixture of 1-(4-chloro-7-ethoxy-3-iodo-1H-indazol-6-yl)ethanone (50 mg, 0.14 mmol) and triethylamine (53 µL, 0.38 mmol) in 4:1 DMF/MeOH (2.5 mL) was degassed with N₂ for 5 min. [1,1'-Bis(diphenylphosphino)ferrocene]dichloropalladium(II), complex with dichloromethane (6 mg, 0.007 mmol) was added, and carbon monoxide was bubbled through the reaction mixture for 10 min. The reaction mixture was then heated at 90° C. in sealed vial overnight. The reaction mixture was concentrated. Purification via silica gel chromatography (1-40% EtOAc/hexanes) afforded the title compound as a brown solid. LCMS for $C_{13}H_{14}ClN_2O_4$ (M+H)⁺: calculated m/z=297.1; found 297.0.

Step 3. 6-Acetyl-4-chloro-7-ethoxy-1H-indazole-3-carboxylic acid

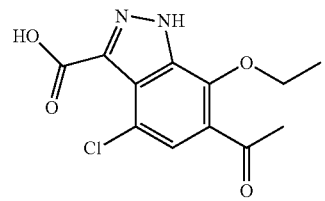 [SMILES: CCOc1c(C(C)=O)cc(Cl)c2c(C(=O)O)n[nH]c12]

A solution of methyl 6-acetyl-4-chloro-7-ethoxy-1H-indazole-3-carboxylate (53 mg, 0.18 mmol) in a mixture of THF (1.8 mL), MeOH (1.8 mL), and 1.0 M NaOH (1.8 mL, 1.8 mmol) was heated at 65° C. for 4 h. After cooling to room temperature, the reaction mixture was concentrated by approximately half and then diluted with EtOAc. 1M HCl was added and the layers were separated. The organic layer was washed with brine, dried over Na₂SO₄, filtered, and concentrated, providing the title compound as a tan solid (39 mg, 77%). LCMS for $C_{12}H_{12}ClN_2O_4$ (M+H)⁺: calculated m/z=283.0; found 283.1.

Step 4. 6-Acetyl-4-chloro-7-ethoxy-1H-indazole-3-carboxamide

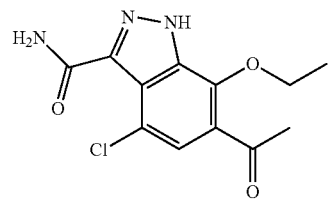 [SMILES: CCOc1c(C(C)=O)cc(Cl)c2c(C(N)=O)n[nH]c12]

To a mixture of 6-acetyl-4-chloro-7-ethoxy-1H-indazole-3-carboxylic acid (39 mg, 0.14 mmol), NH₄Cl (16 mg, 0.30 mmol), and N,N,N',N'-tetramethyl-O-(7-azabenzotriazol-1-yl)uronium hexafluorophosphate (0.10 g, 0.28 mmol) in DMF (1.7 mL) was added N,N-diisopropylethylamine (0.12 mL, 0.69 mmol) at room temperature. After stirring 1.5 h, the reaction mixture was partitioned between EtOAc and sat. NaHCO₃. The layers were separated, and the organic layer was dried over Na₂SO₄, filtered, and concentrated to afford a brown solid. This crude product was used without purification (theoretical yield assumed). LCMS for $C_{12}H_{13}ClN_3O_3$ (M+H)⁺: calculated m/z=282.1; found 281.9.

Step 5. 6-Acetyl-4-chloro-7-ethoxy-1H-indazole-3-carbonitrile

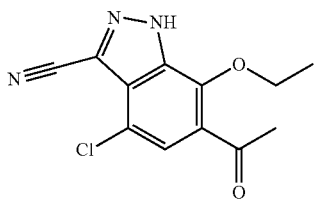 [SMILES: CCOc1c(C(C)=O)cc(Cl)c2c(C#N)n[nH]c12]

To a suspension of 6-acetyl-4-chloro-7-ethoxy-1H-indazole-3-carboxamide (0.039 g, 0.14 mmol) in DCM (3.9 mL) at 0° C. was added triethylamine (58 µL, 0.42 mmol). Trifluoromethanesulfonic anhydride in DCM (0.42 mL, 0.42 mmol, 1.0 M) was then added dropwise. After the addition was complete, the reaction mixture was stirred at room temperature for 1 h. The reaction vial was placed in a room temperature water bath, and the reaction was quenched with saturated NaHCO₃. The organic layer was removed, and the aqueous layer was extracted with DCM (2×). The combined organic layers were dried over MgSO₄, filtered, and concentrated. Purification by silica gel chromatography (15-50% EtOAc/hexanes) afforded the title compound a light brown solid (6.7 mg, 18%). LCMS for $C_{12}H_{11}ClN_3O_2$ (M+H)⁺: calculated m/z=264.1; found 264.0.

Step 6. 6-(1-Aminoethyl)-4-chloro-7-ethoxy-1H-indazole-3-carbonitrile

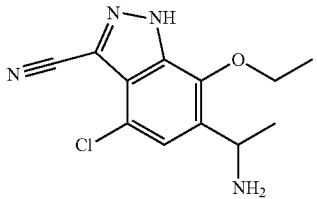 [SMILES: CCOc1c(C(C)N)cc(Cl)c2c(C#N)n[nH]c12]

The title compound was synthesized according to an experimental procedure analogous to the synthesis of Example 23, Step 2 substituting 6-acetyl-4-chloro-7-ethoxy-1H-indazole-3-carbonitrile for 1-(3-bromo-4-chloro-7-phenyl-1H-indazol-6-yl)ethanone. LCMS for $C_{12}H_{11}ClN_3O$ (M–NH₂)⁺: calculated m/z=248.1; found 248.0.

Step 7. 2-Amino-N-(1-(4-chloro-3-cyano-7-ethoxy-1H-indazol-6-yl)ethyl)pyrazolo[1,5-a]pyrimidine-3-carboxamide trifluoroacetate The title compound was synthesized according to an experimental procedure analogous to the synthesis of Example 85, Step 7 substituting 6-(1-aminoethyl)-4-chloro-7-ethoxy-1H-indazole-3-carbonitrile for 3-(6-(1-aminoethyl)-4-chloro-1H-indazol-7-yloxy)propane-1,2-diol trifluoroacetate. ¹H NMR (400 MHz, CD₃OD) δ 8.70 (dd, J=6.8, 1.6 Hz, 1H), 8.55 (dd, J=4.5, 1.6 Hz, 1H), 8.47 (d, J=7.5 Hz, 1H), 7.35 (s, 1H), 6.98 (dd, J=6.8, 4.5 Hz, 1H), 5.82-5.51 (m, 1H), 4.57 (s, 1H), 4.43-4.20 (m, 1H), 1.60 (d, J=7.0 Hz, 3H), 1.55 (t, J=7.0 Hz, 3H). LCMS for $C_{19}H_{18}ClN_8O_2$ (M+H)⁺: calculated m/z=425.1; found 425.1.

Examples 87-89

The following Examples 87-89 in Table 5 were prepared by the method of Example 143.

TABLE 5

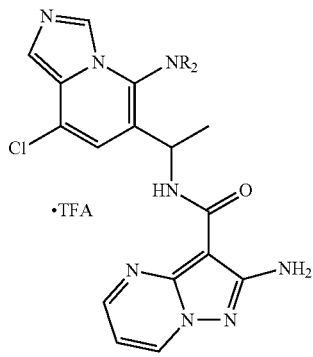

| Ex. No. | Name | NR₂ | LCMS [M + H]⁺ |
|---|---|---|---|
| 87 | 2-Amino-N-(1-(8-chloro-5-(4-hydroxy-4-methylpiperidin-1-yl)imidazo[1,5-a]pyridin-6-yl)ethyl)pyrazolo[1,5-a]pyrimidine-3-carboxamide trifluoroacetate | 4-hydroxy-4-methylpiperidin-1-yl | 469.1 |

TABLE 5-continued

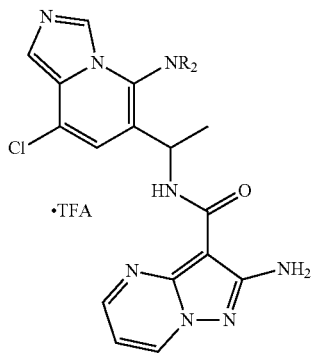

| Ex. No. | Name | NR₂ | LCMS [M + H]⁺ |
|---|---|---|---|
| 88 | 2-Amino-N-(1-(8-chloro-5-(4-cyano-4-methylpiperidin-1-yl)imidazo[1,5-a]-pyridin-6-yl)ethyl)pyrazolo[1,5-a]-pyrimidine-3-carboxamide trifluoroacetate | 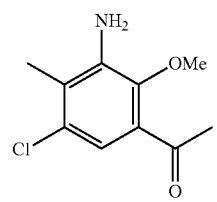 | 478.2 |
| 89 | 2-Amino-N-(1-(8-chloro-5-(4-hydroxy-4-(trifluoromethyl)piperidin-1-yl)imidazo-[1,5-a]pyridin-6-yl)ethyl)pyrazolo[1,5-a]-pyrimidine-3-carboxamide trifluoroacetate | | 523.1 |

Examples 90A-90B. 2-Amino-N-{1-[4-chloro-7-(3-hydroxypyrrolidin-1-yl)-2H-indazol-6-yl]ethyl}pyrazolo[1,5-a]pyrimidine-3-carboxamide bis(trifluoroacetate)

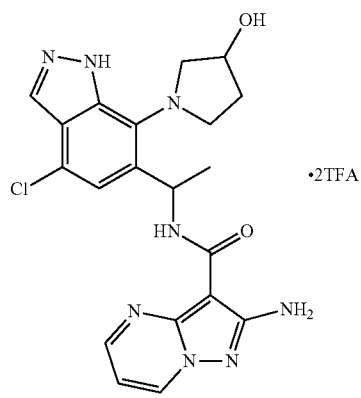 [SMILES: CC(NC(=O)c1c(N)nn2cccnc12)c1cc(Cl)c2cn[nH]c2c1N1CCC(O)C1]

Step 1. 1-(3-Amino-5-chloro-2-methoxy-4-methylphenyl)ethanone

A solution of 1-(5-chloro-2-methoxy-4-methyl-3-nitrophenyl)ethanone (15.0 g, 61.6 mmol) [Oakwood, 019298] in methanol (1.20 L) and acetic acid (310 mL) was treated with zinc (24.2 g, 369 mmol) and stirred at 20° C. for 15 min. The reaction mixture was decanted to leave behind the zinc. The solution was concentrated to a light brown solid that was azeotroped with toluene (2×). The solid was diluted with methanol and the insoluble white solid was filtered. The filtrate was concentrated, rediluted with ethyl acetate, and washed with water and brine. The organic layer was separated, dried with magnesium sulfate, filtered, and concentrated to give the desired product (13.3 g, 101%) as a brown solid that was used without further purification. LCMS for $C_{10}H_{13}ClNO_2$ (M+H)⁺: m/z=214.1; Found: 214.1.

Step 2. 1-(4-Chloro-7-methoxy-1H-indazol-6-yl)ethanone

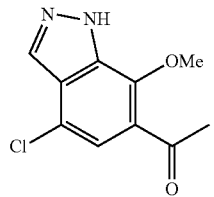

A solution of 1-(3-amino-5-chloro-2-methoxy-4-methylphenyl)ethanone (13.2 g, 61.6 mmol) in acetic acid (300 mL) was treated with amyl nitrite (9.1 mL, 68 mmol) dropwise and stirred at 110° C. for 30 min. The reaction mixture was concentrated and the resulting residue was azeotroped with toluene (2×). The crude solid was diluted with diethyl ether and the heterogenous mixture was filtered to give the desired product (9.95 g, 72%) as an orange-brown solid that was used without further purification. LCMS for $C_{10}H_{10}ClN_2O_2$ (M+H)$^+$: m/z=225.0; Found: 225.1.

Step 3. 1-(4-Chloro-7-hydroxy-1H-indazol-6-yl)ethanone

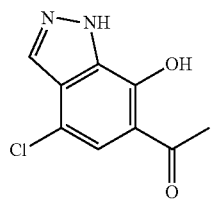

A solution of 1-(4-chloro-7-methoxy-1H-indazol-6-yl)ethanone (11.4 g, 50.6 mmol) in hydrogen bromide (57.2 mL, 506 mmol) in a round bottom flask equipped with a condenser was stirred at 80° C. for 15 h. The reaction mixture was quenched with ice and diluted with water. The solid that precipitated was filtered and washed with water to give the desired product (9.21 g, 87%) as a brown solid that was used without further purification. LCMS for $C_9H_8ClN_2O_2$ (M+H)$^+$: m/z=211.0; Found: 211.0.

Step 4. 6-Acetyl-4-chloro-1H-indazol-7-yl trifluoromethanesulfonate

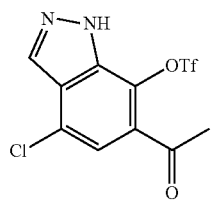 [SMILES: CC(=O)c1cc(Cl)c2cn[nH]c2c1OS(=O)(=O)C(F)(F)F]

A solution of 1-(4-chloro-7-hydroxy-1H-indazol-6-yl)ethanone (1.00 g, 4.75 mmol) in tetrahydrofuran (40.0 mL) was treated with triethylamine (2.3 mL, 17 mmol), cooled to −78° C., treated with a solution of 1.0 M trifluoromethanesulfonic anhydride in dichloromethane (10.0 mL), and stirred at −78° C. for 1 h. The reaction mixture was diluted with ethyl acetate and washed with saturated sodium bicarbonate. The organic layer was separated, dried with magnesium sulfate, filtered, and concentrated to give a black oil. Purification by flash column chromatography using ethyl acetate in hexanes (0%-20%) gave the desired product (912 mg, 56%) as a brown solid. LCMS for $C_{10}H_7ClF_3N_2O_4S$ (M+H)$^+$: m/z=343.0; Found: 342.9.

Step 5. 6-Acetyl-4-chloro-2-{[2-(trimethylsilyl)ethoxy]methyl}-2H-indazol-7-yl trifluoromethanesulfonate

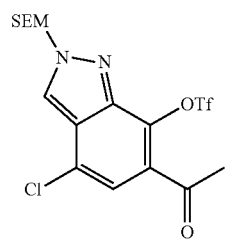 [SMILES: CC(=O)c1cc(Cl)c2cn(COCC[Si](C)(C)C)nc2c1OS(=O)(=O)C(F)(F)F]

A stirred solution of 6-acetyl-4-chloro-1H-indazol-7-yl trifluoromethanesulfonate (0.8940 g, 2.609 mmol) and N-cyclohexyl-N-methyl-cyclohexanamine (1.00 mL, 4.70 mmol) in tetrahydrofuran (25.5 mL) at −78° C. was treated with [β-(trimethylsilyl)ethoxy]methyl chloride (0.785 mL, 4.44 mmol) dropwise. The reaction mixture was warmed slowly to room temperature and was stirred overnight. The reaction mixture was cooled to 0° C., quenched with water (100 mL), and extracted with ethyl acetate (100 mL). The organic layer was separated, washed with brine (40 mL), dried over sodium sulfate, filtered and concentrated to give a yellow oil. Purification by flash column chromatography using diethyl ether in hexanes (0%-30%) gave two separate isomers. The second peak that eluted was the desired product (594 mg, 48%). LCMS for $C_{16}H_{20}ClF_3N_2O_5SSiNa$ (M+Na)$^+$: m/z=495.0; Found: 495.0.

Step 6. 1-(4-Chloro-7-(3-hydroxypyrrolidin-1-yl)-2-{[2-(trimethylsilyl)ethoxy]methyl}-2H-indazol-6-yl)ethanone

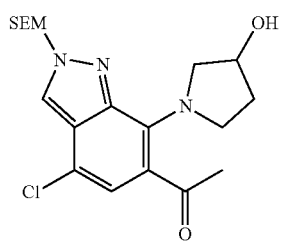 [SMILES: CC(=O)c1cc(Cl)c2cn(COCC[Si](C)(C)C)nc2c1N1CCC(O)C1]

A stirred suspension of 6-acetyl-4-chloro-2-{[2-(trimethylsilyl)ethoxy]methyl}-2H-indazol-7-yl trifluoromethanesulfonate (0.0687 g, 0.145 mmol) and sodium bicarbonate (0.0488 g, 0.581 mmol) in acetonitrile (0.578 mL) was treated with a solution of 3-pyrrolidinol (0.0316 g, 0.363 mmol) in acetonitrile (1.02 mL). The suspension was stirred at ambient temperature for 2 h and at 50° C. for 15 min. The reaction mixture was poured into a saturated sodium bicarbonate solution (15 mL) and extracted with ethyl acetate (30 mL). The organic layer was washed with brine, dried over sodium sulfate, filtered, and concentrated to give a yellow residue. Purification by flash column chromatography using ethyl acetate in hexanes (0%-80%) gave the desired product (56 mg, 94%) as a green yellow foam. LCMS for $C_{19}H_{29}ClN_3O_3Si$ (M+H)$^+$: m/z=410.2; Found: 410.1.

Step 7. 1-(6-(1-Aminoethyl)-4-chloro-2-{[2-(trimethylsilyl)ethoxy]methyl}-2H-indazol-7-yl)pyrrolidin-3-ol

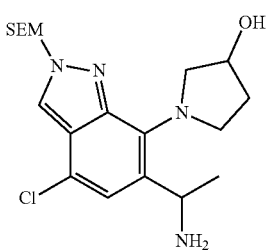 [SMILES: CC(N)c1cc(Cl)c2cn(COCC[Si](C)(C)C)nc2c1N1CCC(O)C1]

A solution of 1-(4-chloro-7-(3-hydroxypyrrolidin-1-yl)-2-{[2-(trimethylsilyl)ethoxy]methyl}-2H-indazol-6-yl)ethanone (56.4 mg, 0.138 mmol) in 2.0 M ammonia in ethanol (2.92 mL, 5.83 mmol) was treated with titanium tetraisopropoxide (102 µL, 0.344 mmol) and heated in a sealed tube at 60° C. for 14 h. The reaction mixture was cooled to 0° C., treated with sodium tetrahydroborate (13.0 mg, 0.344 mmol), stirred at 0° C. for 30 mins, and at room temperature for 30 min. The reaction mixture was quenched with a few drops of water, filtered over Celite, and the Celite was washed with acetonitrile. The filtrate was concentrated to a residue, diluted with saturated sodium bicarbonate, and extracted with dichloromethane (2×20 mL). The combined organic extracts were dried over sodium sulfate, filtered, and concentrated to give the desired product (55 mg, 96%) as a tan foam that was used without further purification. LCMS for $C_{19}H_{32}ClN_4O_2Si$ (M+H)$^+$: m/z=411.2; Found: 411.2.

Step 8. tert-Butyl [3-({[1-(4-chloro-7-(3-hydroxypyrrolidin-1-yl)-2-{[2-(trimethylsilyl)ethoxy]methyl}-2H-indazol-6-yl)ethyl]amino}carbonyl)pyrazolo[1,5-a]pyrimidin-2-yl]carbamate

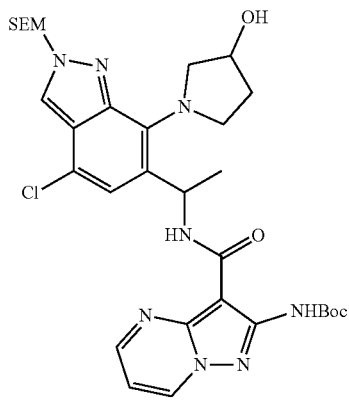 [SMILES: CC(NC(=O)c1c(NC(=O)OC(C)(C)C)nn2cccnc12)c1cc(Cl)c2cn(COCC[Si](C)(C)C)nc2c1N1CCC(O)C1]

The desired compound was prepared according to the procedure of Example 1, step 6, using 1-(6-(1-aminoethyl)-4-chloro-2-{[2-(trimethylsilyl)ethoxy]methyl}-2H-indazol-7-yl)pyrrolidin-3-ol as the starting material. LCMS for $C_{31}H_{44}ClN_8O_5Si$ (M+H)$^+$: m/z=671.3; Found: 671.3.

Step 9. 2-Amino-N-{1-[4-chloro-7-(3-hydroxypyrrolidin-1-yl)-2H-indazol-6-yl]ethyl}pyrazolo[1,5-a]pyrimidine-3-carboxamide bis(trifluoroacetate)

A solution of tert-butyl [3-({[1-(4-chloro-7-(3-hydroxypyrrolidin-1-yl)-2-{[2-(trimethylsilyl)ethoxy]methyl}-2H-indazol-6-yl)ethyl]amino}carbonyl)pyrazolo[1,5-a]pyrimidin-2-yl]carbamate (21.3 mg, 0.0317 mmol) in 4.0 M hydrogen chloride in dioxane (1.0 mL) and methanol (0.5 mL) was stirred for 2 h. The volatiles were evaporated and the crude residue was purified by preparative LCMS (XBridge C18 Column, eluting with a gradient of acetonitrile in water with 0.1% trifluoroacetic acid, at flow rate of 60 mL/min) to give two sets of diastereoisomers with each set containing mixtures of enantiomers. The first peak that eluted (Example 90A, 5.5 mg, 26%) and the second peak that eluted (Example 90B, 6.1 mg, 29%) were both white solids. Example 90A: $^1$H NMR (400 MHz, DMSO) δ 13.22 (s, 1H), 8.89 (dd, J=6.7, 1.4 Hz, 1H), 8.71 (s, 1H), 8.54 (dd, J=4.5, 1.4 Hz, 1H), 8.26 (d, J=8.0 Hz, 1H), 8.11 (s, 1H), 7.12 (s, 1H), 6.98 (dd, J=6.7, 4.5 Hz, 1H), 6.48 (s, 2H), 5.74-5.56 (m, 1H), 4.63-4.44 (m, 1H), 3.36-3.24 (m, 1H), 3.21-3.10 (m, 1H), 3.05 (d, J=10.7 Hz, 1H), 2.24-2.07 (m, 1H), 2.01-1.92 (m, 1H), 1.60-1.40 (m, 3H). LCMS for $C_{20}H_{22}ClN_8O_2$ (M+H)$^+$: m/z=441.2; Found: 441.1. Example 90B: $^1$H NMR (400 MHz, DMSO) δ 13.22 (s, 1H), 8.90 (dd, J=6.7, 1.3 Hz, 1H), 8.78-8.64 (m, 1H), 8.54 (dd, 1H), 8.32 (d, J=7.9 Hz, 1H), 8.11 (s, 1H), 7.11 (s, 1H), 6.99 (dd, J=6.6, 4.6 Hz, 1H), 5.78-5.59 (m, 1H), 4.52 (s, 1H), 3.31-3.18 (m, 1H), 3.11 (d, J=10.6 Hz, 1H), 2.26-2.09 (m, 1H), 2.09-1.93 (m, 1H), 1.50 (d, J=6.9 Hz, 3H). LCMS for $C_{20}H_{22}ClN_8O_2$ (M+H)$^+$: m/z=441.2; Found: 441.1.

Examples 91-94

The following Examples 91-94 of Table 6 were synthesized according to the procedure of Examples 90A-90B. NMR data for the compounds of Table 6 are provided in Table 6a.

TABLE 6

| Ex. No. | Name | R | LCMS |
|---|---|---|---|
| 91 | 2-Amino-N-{1-[4-chloro-7-(3-methoxy-pyrrolidin-1-yl)-2H-indazol-6-yl]ethyl}-pyrazolo[1,5-a]pyrimidine-3-carboxamide bis(trifluoroacetate) | 3-methoxy-pyrrolidin-1-yl | for $C_{21}H_{24}ClN_8O_2$ (M + H)$^+$: m/z = 455.2; Found: 455.1 |
| 92 | 2-Amino-N-[1-(4-chloro-7-{3-[(methyl-amino)sulfonyl]pyrrolidin-1-yl}-2H-indazol-6-yl)ethyl]pyrazolo[1,5-a]-pyrimidine-3-carboxamide | 3-[(methylamino)sulfonyl]pyrrolidin-1-yl | for $C_{21}H_{25}ClN_9O_3S$ (M + H)$^+$: m/z = 518.1; Found: 518.2 |
| 93 | 2-Amino-N-[1-(4-chloro-7-{4-[(dimethylamino)sulfonyl]piperidin-1-yl}-2H-indazol-6-yl)ethyl]pyrazolo[1,5-a]-pyrimidine-3-carboxamide | 4-[(dimethylamino)sulfonyl]piperidin-1-yl | for $C_{23}H_{29}ClN_9O_3S$ (M + H)$^+$: m/z = 546.2; Found: 546.3 |
| 94 | 2-Amino-N-{1-[4-chloro-7-(1,1-dioxido-thiomorpholin-4-yl)-2H-indazol-6-yl]-ethyl}pyrazolo[1,5-a]pyrimidine-3-carboxamide trifluoroacetate | 1,1-dioxido-thiomorpholin-4-yl | for $C_{20}H_{22}ClN_8O_3S$ (M + H)$^+$: m/z = 489.1; Found: 489.1 |

TABLE 6a

| Ex. No. | $^1$H NMR Data |
|---|---|
| 91 | $^1$H NMR (400 MHz, DMSO) δ 13.05 (s, 1H), 8.90 (dd, J = 6.7, 1.5 Hz, 1H), 8.55 (dd, J = 4.5, 1.5 Hz, 1H), 8.19 (d, J = 7.7 Hz, 1H), 8.11 (s, 1H), 7.12 (s, 1H), 6.99 (dd, J = 6.7, 4.5 Hz, 1H), 6.42 (s, 2H), 5.78-5.48 (m, 1H), 4.35-4.11 (m, 1H), 3.31 (s, 3H), 3.21-3.07 (m, 2H), 2.32-2.18 (m, 1H), 2.14-1.92 (m, 1H), 1.49 (d, J = 6.9 Hz, 3H). |
| 92 | $^1$H NMR (400 MHz, DMSO) δ 13.22 (s, 0.5H), 8.90 (d, J = 6.4 Hz, 1H), 8.68-8.47 (m, 1H), 8.29-8.03 (m, 2H), 7.13 (s, 2H), 7.04-6.90 (m, 1H), 6.53-6.30 (m, 2H), 5.85-5.66 (m, 0.5H), 5.66-5.51 (m, 0.5H), 4.33-4.12 (m, 1H), 3.78-3.54 (m, 1H), 3.56-3.35 (m, 2H), 3.24-3.10 (m, 0.5H), 2.67 (s, 3H), 2.42-2.25 (m, 2H), 1.62-1.39 (m, 3H). |
| 93 | $^1$H NMR (400 MHz, DMSO) δ 13.34 (s, 1H), 9.08-8.71 (m, 1H), 8.54 (d, J = 3.0 Hz, 1H), 8.34-7.93 (m, 2H), 7.13 (s, 1H), 7.00 (dd, J = 6.6, 4.6 Hz, 1H), 6.42 (s, 2H), 5.76-5.54 (m, 1H), 3.60-3.46 (m, 1H), 3.46-3.34 (m, 2H), 3.21-3.04 (m, 1H), 2.90 (s, 6H), 2.15-1.81 (m, 4H), 1.52 (d, J = 6.9 Hz, 3H). |

TABLE 6a-continued

| Ex. No. | $^1$H NMR Data |
|---|---|
| 94 | $^1$H NMR (400 MHz, DMSO) δ 13.49 (s, 0.5H), 8.90 (dd, J = 6.7, 1.5 Hz, 1H), 8.55 (dd, J = 4.5, 1.5 Hz, 1H), 8.12 (d, J = 7.1 Hz, 2H), 7.15 (s, 1H), 6.99 (dd, J = 6.7, 4.5 Hz, 1H), 5.83-5.60 (m, 1H), 4.05-3.86 (m, 2H), 3.85-3.52 (m, 2H), 3.49-3.22 (m, 5H), 1.53 (d, J = 6.9 Hz, 3H). |

Example 95. N-(1-{7-[(3S)-3-(Acetylamino)pyrrolidin-1-yl]-4-chloro-2H-indazol-6-yl}ethyl)-2-aminopyrazolo[1,5-a]pyrimidine-3-carboxamide trifluoroacetate

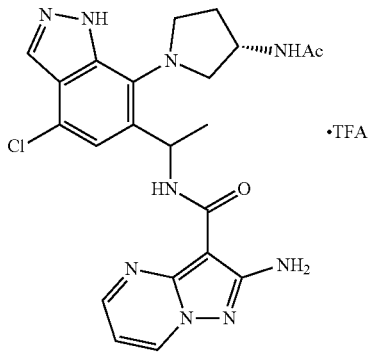 [SMILES: CC(=O)N[C@H]1CCN(c2c(C(C)NC(=O)c3c(N)nn4cccnc34)cc(Cl)c3cn[nH]c23)C1]

Step 1. Benzyl [(3S)-1-(6-{1-[({2-[(tert-butoxycarbonyl)amino]pyrazolo[1,5-a]pyrimidin-3-yl}carbonyl)amino]ethyl}-4-chloro-2-{[2-(trimethylsilyl)ethoxy]methyl}-2H-indazol-7-yl)pyrrolidin-3-yl]carbamate

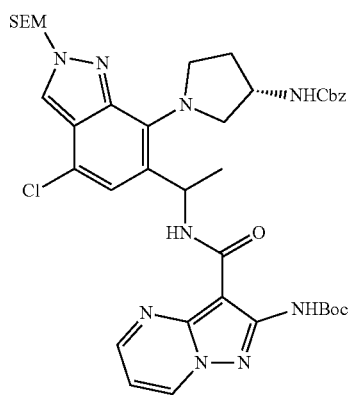 [SMILES: CC(NC(=O)c1c(NC(=O)OC(C)(C)C)nn2cccnc12)c1cc(Cl)c2cn(COCC[Si](C)(C)C)nc2c1N1CC[C@H](NC(=O)OCc2ccccc2)C1]

The desired compound was prepared according to the procedure of Examples 90A-90B, steps 1-8, using benzyl (3S)-pyrrolidin-3-ylcarbamate in step 6 instead of 3-pyrrolidinol. LCMS for $C_{39}H_{51}ClN_9O_6Si$ (M+H)$^+$: m/z=804.3; Found: 804.5.

Step 2. tert-Butyl [3-({[1-(7-[(3S)-3-aminopyrrolidin-1-yl]-4-chloro-2-{[2-(trimethylsilyl)ethoxy]methyl}-2H-indazol-6-yl)ethyl]amino}carbonyl)pyrazolo[1,5-a]pyrimidin-2-yl]carbamate

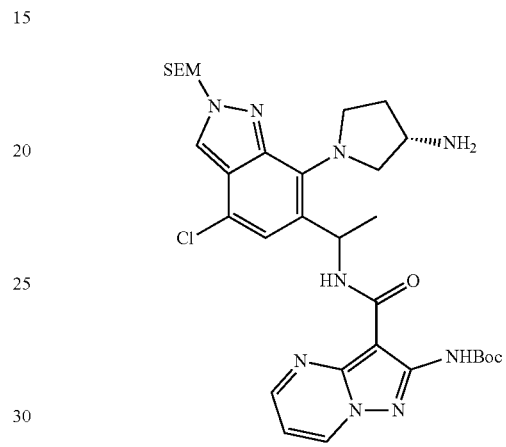

A solution of benzyl [(3S)-1-(6-{1-[({2-[(tert-butoxycarbonyl)amino]pyrazolo[1,5-a]pyrimidin-3-yl}carbonyl)amino]ethyl}-4-chloro-2-{[2-(trimethylsilyl)ethoxy]methyl}-2H-indazol-7-yl)pyrrolidin-3-yl]carbamate (0.101 g, 0.126 mmol) in methanol (3.0 mL) was degassed with nitrogen, treated with 30 mg of 10% Pd on carbon (Degussa type), and hydrogenated with a balloon of hydrogen for 2 h. The reaction mixture was filtered over a disposable fritted cartridge, rinsed with methanol, and concentrated to give the desired product (77.8 mg, 92%) as a tan solid that was used without further purification. LCMS for $C_{31}H_{45}ClN_9O_4Si$ (M+H)$^+$: m/z=670.3; Found: 670.5.

Step 3. N-(1-{7-[(3S)-3-(Acetylamino)pyrrolidin-1-yl]-4-chloro-2H-indazol-6-yl}ethyl)-2-aminopyrazolo[1,5-a]pyrimidine-3-carboxamide trifluoroacetate A solution of tert-butyl [3-({[1-(7-[(3S)-3-aminopyrrolidin-1-yl]-4-chloro-2-{[2-(trimethylsilyl)ethoxy]methyl}-2H-indazol-6-yl)ethyl]amino}carbonyl)pyrazolo[1,5-a]pyrimidin-2-yl]carbamate (38.9 mg, 0.0580 mmol) in dichloromethane (1.1 mL) at 0° C. was treated with triethylamine (0.0243 mL, 0.174 mmol) followed by dropwise additon of 0.2 M acetic anhydride in DMF (0.377 mL, 0.0754 mmol). The ice bath was removed and the reaction mixture was stirred for 30 min. The reaction mixture was diluted with water (20 mL) and extracted with ethyl acetate (30 mL). The organic layer was separated, washed with brine, dried over sodium sulfate, filtered, and concentrated to give the intermediate acetate that still contained the SEM and Boc protecting groups. This intermediate was dissolved in methanol (0.5 mL), treated with 4.0 M hydrogen chloride in dioxane (1.0 mL, 4.0 mmol), and stirred for 1 h at room temperature and heated at 60° C. for 15 min. The volatiles were evaporated to give a crude residue that was purified by preparative LCMS (XBridge C18 Column, eluting with a gradient of acetonitrile in water with 0.1% trifluoroacetic acid, at flow rate of 60 mL/min) to give two peaks. The second peak that eluted was the desired product (3 mg, 42%). $^1$H NMR (400 MHz, DMSO) δ 13.31 (s, 1H), 8.90 (dd, J=6.7, 1.5 Hz, 1H), 8.55 (dd, J=4.5, 1.6 Hz, 1H), 8.29-7.99 (m, 2H), 7.15 (s, 1H), 6.99 (dd, J=6.7, 4.5 Hz, 1H), 6.45 (s, 2H), 5.76-5.63 (m, 1H), 4.64-4.46 (m, 1H), 3.27-3.19 (m, 1H), 3.10-2.94 (m, 1H), 2.41-2.27 (m, 1H), 2.00-1.89 (m, 1H), 1.87 (s, 3H), 1.52 (d, J=7.0 Hz, 3H). LCMS for $C_{22}H_{25}ClN_9O_2$ (M+H)$^+$: m/z=482.2; Found: 482.1.

Example 96A. 2-Amino-N-[1-(4-chloro-7-{(3S)-3-[(methylsulfonyl)amino]pyrrolidin-1-yl}-2H-indazol-6-yl)ethyl]pyrazolo[1,5-a]pyrimidine-3-carboxamide trifluoroacetate

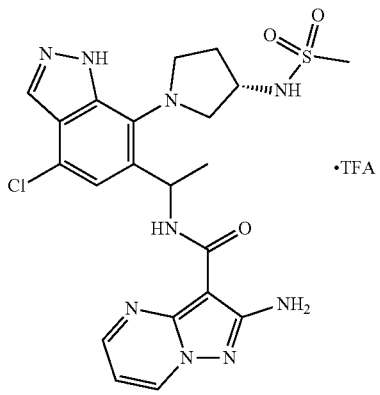 [SMILES: CC(NC(=O)c1c(N)nn2cccnc12)c1cc(Cl)c2cn[nH]c2c1N1CC[C@H](NS(C)(=O)=O)C1]

The desired compound was prepared according to the procedure of Example 95, step 3, using 0.2 M methanesulfonyl chloride in DMF instead of 0.2 M acetic anhydride in DMF. $^1$H NMR (400 MHz, DMSO) δ 13.28 (s, 1H), 8.89 (dd, J=6.7, 1.6 Hz, 1H), 8.56 (dd, J=4.5, 1.6 Hz, 1H), 8.17 (d, J=7.9 Hz, 1H), 8.12 (s, 1H), 7.37 (d, J=8.0 Hz, 1H), 7.15 (s, 1H), 6.99 (dd, J=6.7, 4.5 Hz, 1H), 6.44 (s, 2H), 5.79-5.59 (m, 1H), 4.38-4.14 (m, 1H), 3.58-3.42 (m, 1H), 3.22-3.11 (m, 1H), 2.95 (s, 3H), 2.45-2.36 (m, 1H), 2.14-1.94 (m, 1H), 1.52 (d, J=7.0 Hz, 3H). LCMS for $C_{21}H_{25}ClN_9O_3S$ (M+H)$^+$: m/z=518.1; Found: 518.1.

Example 96B. 2-Amino-N-[1-(4-chloro-7-{(3R)-3-[(methylsulfonyl)amino]pyrrolidin-1-yl}-2H-indazol-6-yl)ethyl]pyrazolo[1,5-a]pyrimidine-3-carboxamide trifluoroacetate

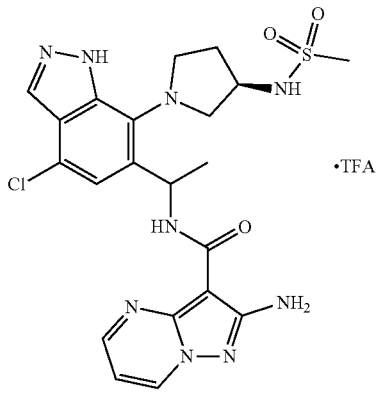 [SMILES: CC(NC(=O)c1c(N)nn2cccnc12)c1cc(Cl)c2cn[nH]c2c1N1CC[C@@H](NS(C)(=O)=O)C1]

Step 1. tert-Butyl [(3R)-1-(6-{1-[({2-[(tert-butoxycarbonyl)amino]pyrazolo[1,5-a]pyrimidin-3-yl}carbonyl)amino]ethyl}-4-chloro-2-{[2-(trimethylsilyl)ethoxy]methyl}-2H-indazol-7-yl]pyrrolidin-3-yl]carbamate

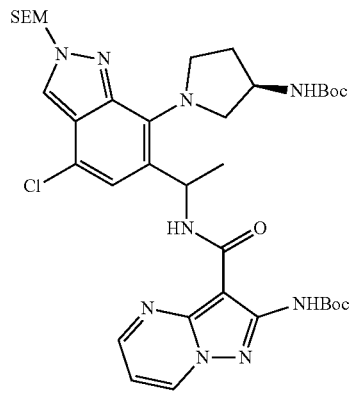 [SMILES: CC(NC(=O)c1c(NC(=O)OC(C)(C)C)nn2cccnc12)c1cc(Cl)c2cn(COCC[Si](C)(C)C)nc2c1N1CC[C@@H](NC(=O)OC(C)(C)C)C1]

The desired compound was prepared according to the procedure of Examples 90A-90B, steps 1-8, using tert-butyl (3R)-pyrrolidin-3-ylcarbamate in step 6 instead of 3-pyrrolidinol. LCMS for $C_{36}H_{53}ClN_9O_6Si$ (M+H)$^+$: m/z=770.4; Found: 770.5.

Step 2. 2-Amino-N-(1-{7-[(3R)-3-aminopyrrolidin-1-yl]-4-chloro-2H-indazol-6-yl}ethyl)pyrazolo[1,5-a]pyrimidine-3-carboxamide

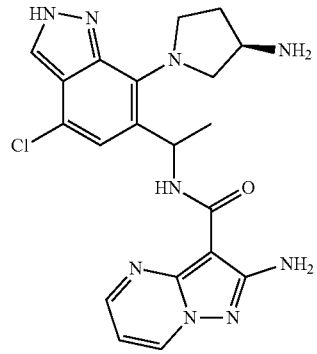 [SMILES: CC(NC(=O)c1c(N)nn2cccnc12)c1cc(Cl)c2c[nH]nc2c1N1CC[C@@H](N)C1]

The desired compound was prepared according to the procedure of Examples 90A, step 9, using tert-butyl [(3R)-1-(6-{1-[({2-[(tert-butoxycarbonyl)amino]pyrazolo[1,5-a]pyrimidin-3-yl}carbonyl)amino]ethyl}-4-chloro-2-{[2-(trimethylsilyl)ethoxy]methyl}-2H-indazol-7-yl)pyrrolidin-3-yl]carbamate as the starting material. LCMS for $C_{20}H_{23}ClN_9O$ (M+H)$^+$: m/z=440.2; Found: 440.2.

Step 3. 2-Amino-N-[1-(4-chloro-7-{(3R)-3-[(methylsulfonyl)amino]pyrrolidin-1-yl}-2H-indazol-6-yl)ethyl]pyrazolo[1,5-a]pyrimidine-3-carboxamide trifluoroacetate The desired compound was prepared according to the procedure of Example 95, step 3, using 2-amino-N-(1-{7-[(3R)-3-aminopyrrolidin-1-yl]-4-chloro-2H-indazol-6- yl}ethyl)pyrazolo[1,5-a]pyrimidine-3-carboxamide and 0.2 M methanesulfonyl chloride in DMF instead of 0.2 M acetic anhydride in DMF. ¹H NMR (400 MHz, DMSO) δ 13.30 (s, 1H), 8.90 (dd, J=6.7, 1.6 Hz, 1H), 8.55 (dd, J=4.5, 1.6 Hz, 1H), 8.26-7.97 (m, 2H), 7.36 (d, J=7.8 Hz, 1H), 7.13 (s, 1H), 6.99 (dd, J=6.7, 4.5 Hz, 1H), 6.43 (s, 2H), 5.84-5.54 (m, 1H), 4.43-4.09 (m, 1H), 3.76-3.55 (m, 1H), 3.20-3.01 (m, 2H), 2.96 (s, 3H), 2.43-2.29 (m, 1H), 2.16-1.87 (m, 1H), 1.50 (d, J=6.9 Hz, 3H). LCMS for $C_{21}H_{25}ClN_9O_3S$ (M+H)⁺: m/z=518.1; Found: 518.3.

Example 97. Ethyl 4-[6-(1-{[(2-aminopyrazolo[1,5-a]pyrimidin-3-yl)carbonyl]amino}ethyl)-4-chloro-2H-indazol-7-yl]cyclohex-3-ene-1-carboxylate bis-trifluoroacetate

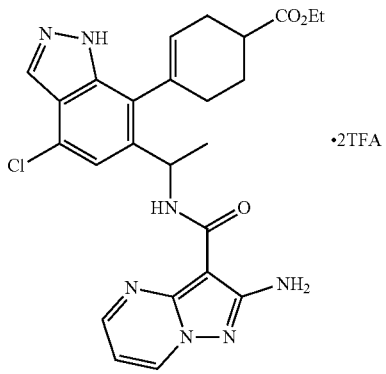 [SMILES: CCOC(=O)C1CC=C(c2c(C(C)NC(=O)c3c(N)nn4cccnc34)cc(Cl)c3cn[nH]c23)CC1 ; "·2TFA"]

Step 1. Ethyl 4-(6-acetyl-4-chloro-2-{[2-(trimethylsilyl)ethoxy]methyl}-2H-indazol-7-yl)cyclohex-3-ene-1-carboxylate

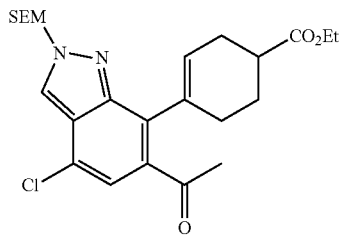 [SMILES: CCOC(=O)C1CC=C(c2c(C(C)=O)cc(Cl)c3cn(COCC[Si](C)(C)C)nc23)CC1]

A solution of 6-acetyl-4-chloro-2-{[2-(trimethylsilyl)ethoxy]methyl}-2H-indazol-7-yl trifluoromethanesulfonate (Examples 90A-90B, Step 5, 0.0950 g, 0.201 mmol) in toluene (0.712 mL) was added a solution of sodium bicarbonate (0.0321 g, 0.382 mmol) in water (0.475 mL, 26.4 mmol), followed by ethyl 4-(4,4,5,5-tetramethyl-1,3,2-dioxaborolan-2-yl)cyclohex-3-ene-1-carboxylate (0.0732 g, 0.261 mmol) and the mixture was bubbled with nitrogen for 5 min. Added tetrakis(triphenylphosphine)palladium(0) (0.012 g, 0.010 mmol), bubbled with nitrogen for another 5 min, and heated at 80° C. for 4.5 h. The reaction mixture was poured into saturated sodium bicarbonate solution (20 mL) and extracted with ethyl acetate (30 mL). The organic extract was washed with brine, dried over sodium sulfate, filtered, and concentrated to give a brown gum. Purification by flash column chromatography using ethyl acetate in hexanes (0%-30%) gave the desired product (78.8 mg, 82%) as a colorless oil. LCMS for $C_{24}H_{34}ClN_2O_4Si$ (M+H)⁺: m/z=477.2; Found: 477.1.

Step 2. Ethyl 4-(6-(1-aminoethyl)-4-chloro-2-{[2-(trimethylsilyl)ethoxy]methyl}-2H-indazol-7-yl)cyclohex-3-ene-1-carboxylate

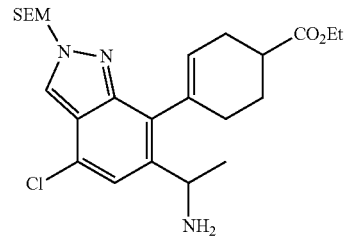 [SMILES: CCOC(=O)C1CC=C(c2c(C(C)N)cc(Cl)c3cn(COCC[Si](C)(C)C)nc23)CC1]

The desired compound was prepared according to the procedure of Example 1, step 5, using ethyl 4-(6-acetyl-4-chloro-2-{[2-(trimethylsilyl)ethoxy]methyl}-2H-indazol-7-yl)cyclohex-3-ene-1-carboxylate as the starting material. LCMS for $C_{24}H_{37}ClN_3O_3Si$ (M+H)⁺: m/z=478.2; Found: 478.2.

Step 3. Ethyl 4-(6-{1-[({2-[(tert-butoxycarbonyl)amino]pyrazolo[1,5-a]pyrimidin-3-yl}carbonyl)amino]ethyl}-4-chloro-2-{[2-(trimethylsilyl)ethoxy]methyl}-2H-indazol-7-yl)cyclohex-3-ene-1-carboxylate

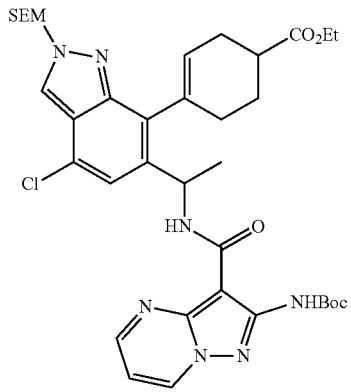 [SMILES: CCOC(=O)C1CC=C(c2c(C(C)NC(=O)c3c(NC(=O)OC(C)(C)C)nn4cccnc34)cc(Cl)c3cn(COCC[Si](C)(C)C)nc23)CC1]

The desired compound was prepared according to the procedure of Example 1, step 6, using ethyl 4-(6-(1-aminoethyl)-4-chloro-2-{[2-(trimethylsilyl)ethoxy]methyl}-2H-indazol-7-yl)cyclohex-3-ene-1-carboxylate as the starting material. LCMS for $C_{36}H_{49}ClN_7O_6Si$ (M+H)⁺: m/z=738.3; Found: 738.3.

Step 4. Ethyl 4-[6-(1-{[(2-aminopyrazolo[1,5-a]pyrimidin-3-yl)carbonyl]amino}ethyl)-4-chloro-2H-indazol-7-yl]cyclohex-3-ene-1-carboxylate bistrifluoroacetate The desired compound was prepared according to the procedure of Examples 90A-90B, step 9, using ethyl 4-(6-{1-[({2-[(tert-butoxycarbonyl)amino]pyrazolo[1,5-a]pyrimidin-3-yl}carbonyl)amino]ethyl}-4-chloro-2-{[2-(trimethylsilyl)ethoxy]methyl}-2H-indazol-7-yl)cyclohex-3-ene-1-carboxylate as the starting material. $^1$H NMR (400 MHz, DMSO) δ 13.25 (s, 1H), 8.90 (d, J=6.7 Hz, 1H), 8.54 (s, 1H), 8.11 (s, 1H), 8.05 (d, J=3.5 Hz, 1H), 7.22-7.13 (m, 1H), 7.03-6.94 (m, 1H), 6.38 (s, 2H), 5.99-5.58 (m, 1H), 5.44-5.01 (m, 1H), 4.12 (q, J=7.1 Hz, 2H), 2.95 (s, 1H), 2.75-2.56 (m, 1H), 2.19-1.96 (m, 2H), 1.91-1.77 (m, 1H), 1.47 (d, J=6.7 Hz, 3H), 1.22 (t, J=7.1 Hz, 3H). LCMS for $C_{25}H_{27}ClN_7O_3$ (M+H)$^+$: m/z=508.2; Found: 508.2.

Example 98. Benzyl 4-[6-(1-{[(2-aminopyrazolo[1,5-a]pyrimidin-3-yl)carbonyl]amino}ethyl)-4-chloro-2H-indazol-7-yl]-3,6-dihydropyridine-1(2H)-carboxylate bis(trifluoroacetate)

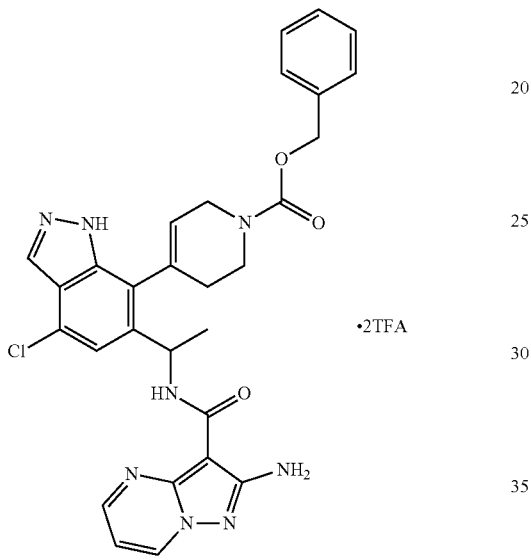

The desired compound was prepared according to the procedure of Example 97, using benzyl 4-(4,4,5,5-tetramethyl-1,3,2-dioxaborolan-2-yl)-3,6-dihydropyridine-1(2H)-carboxylate as the starting material. LCMS for $C_{29}H_{28}ClN_8O_3$ (M+H)$^+$: m/z=571.2; Found: 571.2.

Example 99. 2-Amino-N-{1-[4-chloro-7-(1,2,3,6-tetrahydropyridin-4-yl)-2H-indazol-6-yl]ethyl}pyrazolo[1,5-a]pyrimidine-3-carboxamide bis(trifluoroacetate)

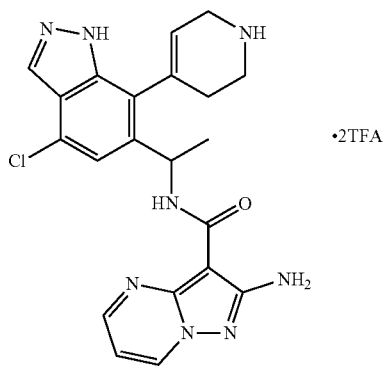 [SMILES: CC(NC(=O)c1c(N)nn2cccnc12)c1cc(Cl)c2cn[nH]c2c1C1=CCNCC1 ; "·2TFA"]

A solution of benzyl 4-[6-(1-{[(2-aminopyrazolo[1,5-a]pyrimidin-3-yl)carbonyl]amino}ethyl)-4-chloro-2H-indazol-7-yl]-3,6-dihydropyridine-1(2H)-carboxylate trifluoroacetate (Example 98, 20.1 mg, 0.0293 mmol) in methanol (2.5 mL) was treated with 1.0 M hydrogen chloride in water (0.0734 mL, 0.0734 mmol), degassed with nitrogen, and treated with 20.1 mg of 10% Pd/C (Degussa type), and hydrogenated with a balloon of hydrogen for 1.5 h. The reaction mixture was filtered over a disposable fritted cartridge, rinsed with methanol, and concentrated to give a crude residue. Purification by preparative LCMS (XBridge C18 Column, eluting with a gradient of acetonitrile in water with 0.1% trifluoroacetic acid, at flow rate of 60 mL/min) gave desired product (3 mg, 10%) as a white solid. $^1$H NMR (400 MHz, DMSO) δ 13.39-13.10 (m, 1H), 8.92 (d, J=6.7 Hz, 1H), 8.58 (d, J=3.3 Hz, 1H), 8.18 (s, 1H), 8.10 (s, 1H), 7.20 (s, 1H), 7.01 (dd, J=6.6, 4.7 Hz, 1H), 6.51 (s, 1H), 6.39 (s, 2H), 6.12-5.71 (m, 1H), 5.49-5.09 (m, 1H), 4.01-3.61 (m, 2H), 3.49 (s, 2H), 1.49 (d, J=6.9 Hz, 3H). LCMS for $C_{21}H_{22}ClN_8O$ (M+H)$^+$: m/z=437.2; Found: 437.1.

Example 100. 2-Amino-N-{1-[4-chloro-7-(4-methoxycyclohex-1-en-1-yl)-2H-indazol-6-yl]ethyl}pyrazolo[1,5-a]pyrimidine-3-carboxamide trifluoroacetate

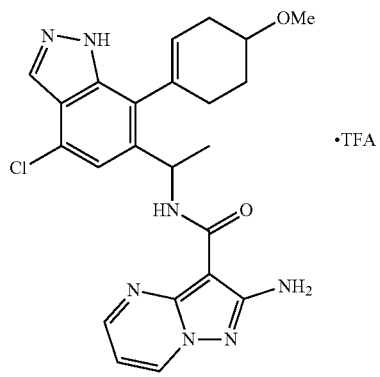 [SMILES: COC1CC=C(c2c(C(C)NC(=O)c3c(N)nn4cccnc34)cc(Cl)c3cn[nH]c23)CC1]

The desired compound was prepared according to the procedure of Example 97, using 2-(4-methoxycyclohex-1-en-1-yl)-4,4,5,5-tetramethyl-1,3,2-dioxaborolane as the starting material. $^1$H NMR (400 MHz, DMSO) δ 13.24 (s, 1H), 8.90 (d, J=6.3 Hz, 1H), 8.54 (s, 1H), 8.24-7.92 (m, 2H), 7.36-7.05 (m, 1H), 7.03-6.95 (m, 1H), 6.41 (s, 2H), 5.83-5.56 (m, 1H), 5.48-5.09 (m, 1H), 3.89-3.64 (m, 1H), 3.33 (s, 3H), 2.21-1.97 (m, 2H), 1.96-1.56 (m, 1H), 1.47 (d, J=6.8 Hz, 3H). LCMS for $C_{23}H_{25}ClN_7O_2$ (M+H)$^+$: m/z=466.2; Found: 466.2.

243

Example 101. 2-Amino-N-{1-[4-chloro-7-(4-cyano-cyclohex-1-en-1-yl)-2H-indazol-6-yl]ethyl}pyrazolo[1,5-a]pyrimidine-3-carboxamide trifluoroacetate

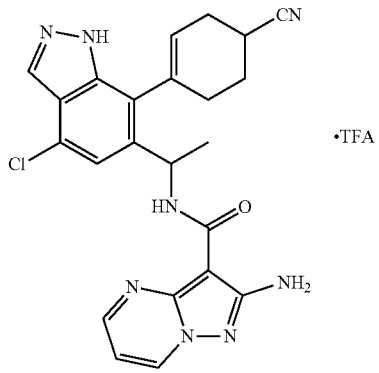 [SMILES: CC(NC(=O)c1c(N)nn2cccnc12)c1cc(Cl)c2cn[nH]c2c1C1=CCC(C#N)CC1]

The desired compound was prepared according to the procedure of Example 97, using 4-(4,4,5,5-tetramethyl-1,3,2-dioxaborolan-2-yl)cyclohex-3-ene-1-carbonitrile as the starting material. LCMS for $C_{23}H_{22}ClN_8O$ (M+H)+: m/z=466.2; Found: 461.1.

Example 102. Methyl 1-[6-(1-{[(2-aminopyrazolo[1,5-a]pyrimidin-3-yl)carbonyl]amino}ethyl)-4-chloro-2H-indazol-7-yl]pyrrolidine-3-carboxylate trifluoroacetate

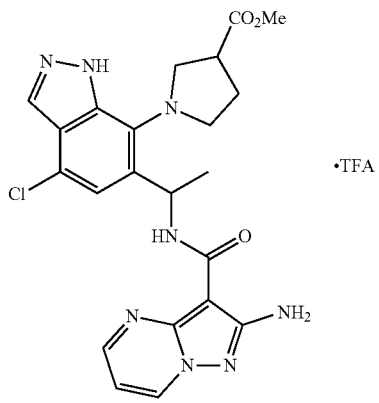 [SMILES: COC(=O)C1CCN(c2c(C(C)NC(=O)c3c(N)nn4cccnc34)cc(Cl)c3cn[nH]c23)C1]

Step 1. Methyl 1-(6-{1-[({2-[(tert-butoxycarbonyl)amino]pyrazolo[1,5-a]pyrimidin-3-yl}carbonyl)amino]ethyl}-4-chloro-2-{[2-(trimethylsilyl)ethoxy]methyl}-2H-indazol-7-yl)pyrrolidine-3-carboxylate

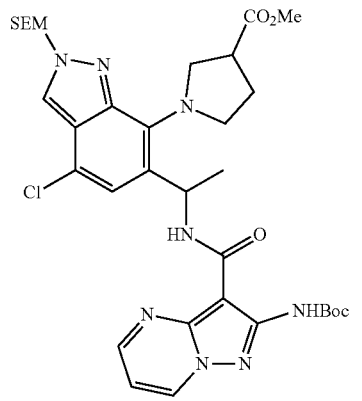 [SMILES: COC(=O)C1CCN(c2c(C(C)NC(=O)c3c(NC(=O)OC(C)(C)C)nn4cccnc34)cc(Cl)c3cn(COCC[Si](C)(C)C)nc23)C1]

244

The desired compound was prepared according to the procedure of Examples 90A-90B, steps 1-8, using methyl pyrrolidine-3-carboxylate hydrochloride in step 6 instead of 3-pyrrolidinol. LCMS for $C_{33}H_{46}ClN_8O_6Si$ (M+H)+: m/z=713.3; Found: 713.4.

Step 2. Methyl 1-[6-(1-{[(2-aminopyrazolo[1,5-a]pyrimidin-3-yl)carbonyl]amino}ethyl)-4-chloro-2H-indazol-7-yl]pyrrolidine-3-carboxylate trifluoroacetate The desired compound was prepared according to the procedure of Examples 90A-90B, step 9, using methyl 1-(6-{1-[({2-[(tert-butoxycarbonyl)amino]pyrazolo[1,5-a]pyrimidin-3-yl}carbonyl)amino]ethyl}-4-chloro-2-{[2-(trimethylsilyl)ethoxy]methyl}-2H-indazol-7-yl)pyrrolidine-3-carboxylate as the starting material. $^1$H NMR (400 MHz, DMSO) δ 13.34 (s, 1H), 8.89 (d, J=6.9 Hz, 1H), 8.53 (d, J=5.1 Hz, 1H), 8.34-7.93 (m, 2H), 7.11 (d, J=3.1 Hz, 1H), 7.04-6.94 (m, 1H), 6.41 (br s, 1H), 5.71-5.46 (m, 1H), 3.49-3.30 (m, 2H), 3.27-3.08 (m, 2H), 2.39-2.22 (m, 2H), 1.61-1.37 (m, 3H). LCMS for $C_{22}H_{24}ClN_8O_3$ (M+H)+: m/z=483.2; Found: 483.2.

Examples 103A-103B. 2-Amino-N-[1-(4-chloro-7-{3-[(methylamino)carbonyl]pyrrolidin-1-yl}-2H-indazol-6-yl)ethyl]pyrazolo[1,5-a]pyrimidine-3-carboxamide trifluoroacetate (Isomers 1-2)

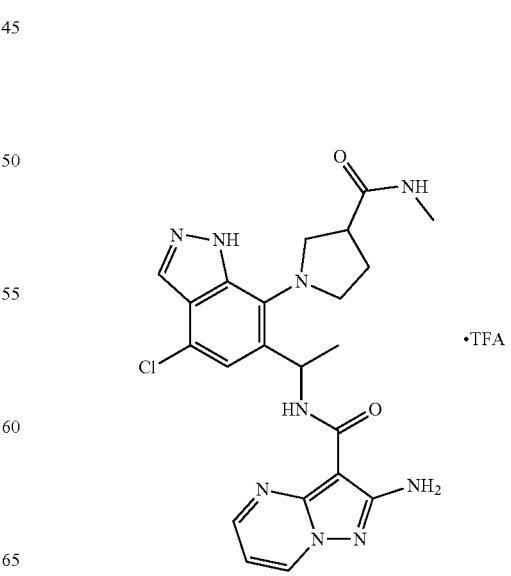

Step 1. 1-(6-{1-[({2-[(tert-Butoxycarbonyl)amino]pyrazolo[1,5-a]pyrimidin-3-yl}carbonyl)amino]ethyl}-4-chloro-2-{[2-(trimethylsilyl)ethoxy]methyl}-2H-indazol-7-yl)pyrrolidine-3-carboxylic acid

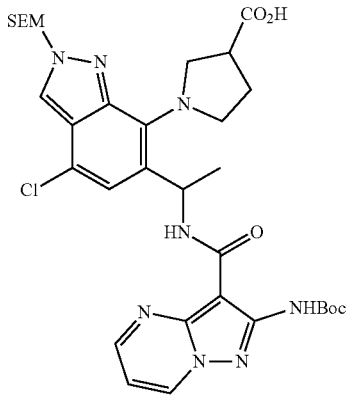 [SMILES: CC(NC(=O)c1c(NC(=O)OC(C)(C)C)nn2cccnc12)c1cc(Cl)c2cn(COCC[Si](C)(C)C)nc2c1N1CCC(C(=O)O)C1]

A solution of methyl 1-(6-{1-[({2-[(tert-butoxycarbonyl)amino]pyrazolo[1,5-a]pyrimidin-3-yl}carbonyl)amino]ethyl}-4-chloro-2-{[2-(trimethylsilyl)ethoxy]methyl}-2H-indazol-7-yl)pyrrolidine-3-carboxylate (Example 102, Step 1, 71.8 mg, 0.101 mmol) in tetrahydrofuran (0.50 mL) and methanol (0.50 mL) was treated with 2.0 M lithium hydroxide in water (0.151 mL, 0.302 mmol) and stirred for 16 h. The reaction mixture was cooled at 0° C., diluted with water (5 mL) and 1.0 M hydrogen chloride in water (0.453 mL, 0.453 mmol) dropwise until the pH was acidic, and extracted with ethyl acetate (25 mL). The organic layer was washed with brine, dried over sodium sulfate, filtered, and concentrated to give the desired product (65.4 mg, 93%) as a tan solid that was used without further purification. LCMS for $C_{32}H_{44}ClN_8O_6Si$ (M+H)$^+$: m/z=699.3; Found: 699.4.

Step 2. 2-Amino-N-[1-(4-chloro-7-{3-[(methylamino)carbonyl]pyrrolidin-1-yl}-2H-indazol-6-yl)ethyl]pyrazolo[1,5-a]pyrimidine-3-carboxamide trifluoroacetate A solution of 1-(6-{1-[({2-[(tert-butoxycarbonyl)amino]pyrazolo[1,5-a]pyrimidin-3-yl}carbonyl)amino]ethyl}-4-chloro-2-{[2-(trimethylsilyl)ethoxy]methyl}-2H-indazol-7-yl)pyrrolidine-3-carboxylic acid (32.5 mg, 0.0465 mmol) in N,N-dimethylformamide (0.50 mL, 6.46 mmol) was treated with 2.0 M methylamine in THF (69.7 µL, 0.139 mmol) followed by N,N-diisopropylethylamine (32.4 µL, 0.186 mmol). The reaction mixture was stirred for a few minutes, treated with benzotriazol-1-yloxytris(dimethylamino)phosphonium hexafluorophosphate (28.8 mg, 0.0651 mmol), and stirred at room temperature for 1 h. The reaction mixture was poured into water (10 mL) and saturated sodium bicarbonate solution (10 mL) and extracted with ethyl acetate (30 mL). The organic layer was washed with brine, dried over sodium sulfate, filtered, and concentrated to give the intermediate acetate that still contained the SEM and Boc protecting groups. This intermediate was dissolved in methanol (0.50 mL), treated with 4.0 M hydrogen chloride in dioxane (1.0 mL, 4.0 mmol), and stirred for 2 h. The volatiles were evaporated to give a crude residue that was purified by preparative LCMS (XBridge C18 Column, eluting with a gradient of acetonitrile in water with 0.1% trifluoroacetic acid, at flow rate of 60 mL/min) to give two sets of diastereoisomers with each set containing mixtures of enantiomers. The first peak that eluted (Example 103A, 6 mg, 22%) and the second peak that eluted (Example 103B, 7.3 mg, 26%) were both white solids.

Example 103A: $^1$H NMR (400 MHz, DMSO) δ 8.89 (dd, J=6.7, 1.5 Hz, 1H), 8.54 (dd, J=4.5, 1.5 Hz, 1H), 8.40-8.26 (m, 1H), 8.20 (d, J=7.9 Hz, 1H), 8.11 (s, 1H), 7.12 (s, 1H), 6.98 (dd, J=6.7, 4.5 Hz, 1H), 6.45 (br s, 2H), 5.77-5.50 (m, 1H), 3.39-3.20 (m, 4H), 3.15-2.99 (m, 1H), 2.69 (d, J=4.5 Hz, 3H), 2.39-2.24 (m, 1H), 2.18-1.94 (m, 1H), 1.52 (d, J=7.0 Hz, 3H). LCMS for $C_{22}H_{25}ClN_9O_2$ (M+H)$^+$: m/z=482.2; Found: 482.3. Example 103B: $^1$H NMR (400 MHz, DMSO) δ 8.90 (d, J=6.5 Hz, 1H), 8.54 (d, J=3.3 Hz, 1H), 8.37 (d, J=7.5 Hz, 2H), 8.11 (s, 1H), 7.11 (s, 1H), 7.00 (dd, J=6.5, 4.6 Hz, 1H), 6.44 (br s, 1H), 5.64 (dd, J=7.4 Hz, 1H), 3.41-3.23 (m, 6H), 3.23-3.11 (m, 1H), 2.70 (d, J=4.4 Hz, 3H), 2.44-2.27 (m, 1H), 2.16-2.01 (m, 1H), 1.50 (d, J=7.0 Hz, 3H). LCMS for $C_{22}H_{25}ClN_9O_2$ (M+H)$^+$: m/z=482.2; Found: 482.3.

Example 104. N-(1-(7-((S)-3-Acetamidopiperidin-1-yl)-4-chloro-1H-indazol-6-yl)ethyl)-2-aminopyrazolo[1,5-a]pyrimidine-3-carboxamide trifluoroacetate

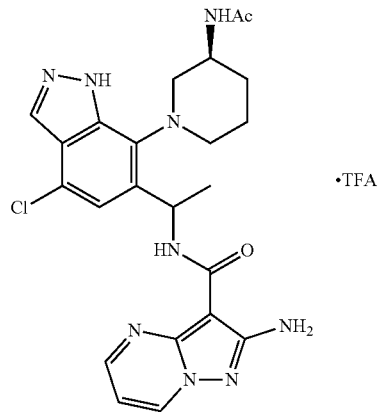 [SMILES: CC(=O)N[C@H]1CCCN(c2c(C(C)NC(=O)c3c(N)nn4cccnc34)cc(Cl)c3cn[nH]c23)C1]

Step 1. tert-Butyl [3-({[1-(7-[(3S)-3-aminopiperidin-1-yl]-4-chloro-2-{[2-(trimethylsilyl)ethoxy]methyl}-2H-indazol-6-yl)ethyl]amino}carbonyl)pyrazolo[1,5-a]pyrimidin-2-yl]carbamate

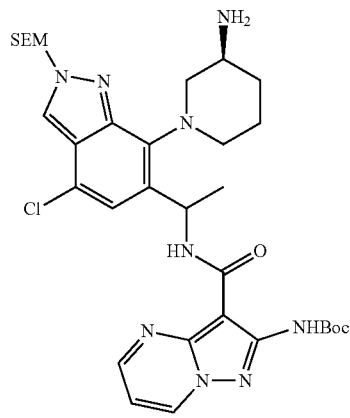 [SMILES: CC(NC(=O)c1c(NC(=O)OC(C)(C)C)nn2cccnc12)c1cc(Cl)c2cn(COCC[Si](C)(C)C)nc2c1N1CCC[C@H](N)C1]

The desired compound was prepared according to the procedure of Example 95, steps 1-2 using benzyl (3S)-piperidin-3-ylcarbamate. LCMS for C$_{32}$H$_{47}$ClN$_9$O$_4$Si (M+H)$^+$: m/z=684.3; Found: 684.5.

Step 2. N-(1-(7-((S)-3-Acetamidopiperidin-1-yl)-4-chloro-1H-indazol-6-yl)ethyl)-2-aminopyrazolo[1,5-a]pyrimidine-3-carboxamide trifluoroacetate The desired compound was prepared according to the procedure of Example 95, step 3 using tert-butyl [3-({[1-(7-[(3S)-3-aminopiperidin-1-yl]-4-chloro-2-{[2-(trimethyl)ethoxy]methyl}-2H-indazol-6-yl)ethyl]amino}carbonyl)pyrazolo[1,5-a]pyrimidin-2-yl]carbamate as the starting material. LCMS for C$_{23}$H$_{27}$ClN$_9$O$_2$ (M+H)$^+$: m/z=496.2; Found: 496.3.

Example 105. 2-Amino-N-[1-(4-chloro-7-{(3S)-3-[(methylsulfonyl)amino]piperidin-1-yl}-2H-indazol-6-yl)ethyl]pyrazolo[1,5-a]pyrimidine-3-carboxamide trifluoroacetate

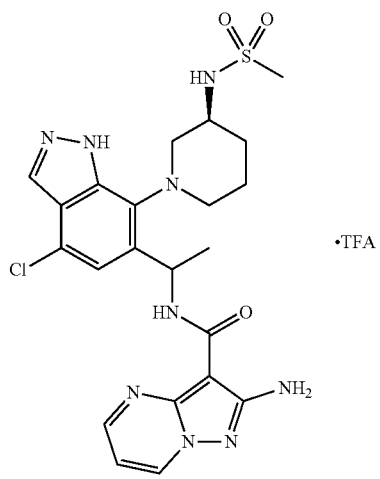 [SMILES: CC(NC(=O)c1c(N)nn2cccnc12)c1cc(Cl)c2cn[nH]c2c1N1CCC[C@H](NS(C)(=O)=O)C1]

The desired compound was prepared according to the procedure of Example 95, step 3, using tert-butyl [3-({[1-(7-[(3S)-3-aminopiperidin-1-yl]-4-chloro-2-{[2-(trimethylsilyl)ethoxy]methyl}-2H-indazol-6-yl)ethyl]amino}carbonyl)pyrazolo[1,5-a]pyrimidin-2-yl]carbamate and 0.2 M methanesulfonyl chloride in DMF instead of 0.2 M acetic anhydride in DMF. LCMS for C$_{22}$H$_{27}$ClN$_9$O$_3$S (M+H)$^+$: m/z=532.2; Found: 532.3.

Example 106. Ethyl 1-[6-(1-{[(2-aminopyrazolo[1,5-a]pyrimidin-3-yl)carbonyl]amino}ethyl)-4-chloro-2H-indazol-7-yl]piperidine-4-carboxylate trifluoroacetate

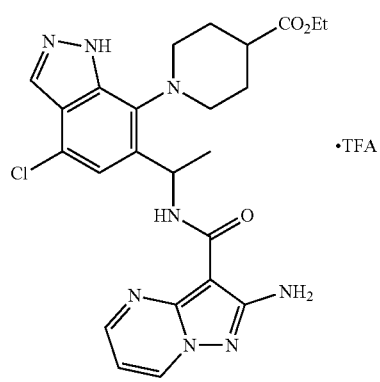 [SMILES: CCOC(=O)C1CCN(c2c(C(C)NC(=O)c3c(N)nn4cccnc34)cc(Cl)c3cn[nH]c23)CC1]

Step 1. Ethyl 1-(6-{1-[({2-[(tert-butoxycarbonyl)amino]pyrazolo[1,5-a]pyrimidin-3-yl}carbonyl)amino]ethyl}-4-chloro-2-{[2-(trimethylsilyl)ethoxy]methyl}-2H-indazol-7-yl)piperidine-4-carboxylate

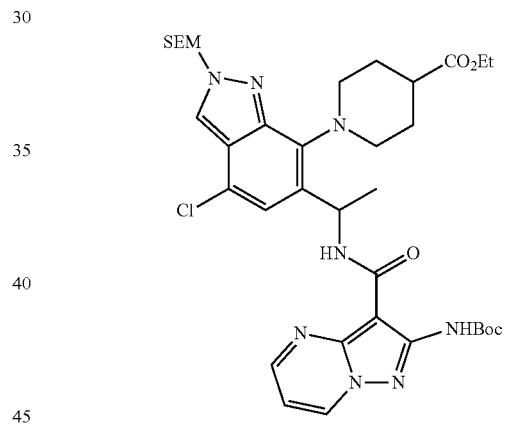

The desired compound was prepared according to the procedure of Examples 90A-90B, steps 1-8, using ethyl piperidine-4-carboxylate in step 6 instead of 3-pyrrolidinol. LCMS for C$_{35}$H$_{50}$ClN$_8$O$_6$Si (M+H)$^+$: m/z=741.3; Found: 741.5.

Step 2. Ethyl 1-[6-(1-{[(2-aminopyrazolo[1,5-a]pyrimidin-3-yl)carbonyl]amino}ethyl)-4-chloro-2H-indazol-7-yl]piperidine-4-carboxylate trifluoroacetate The desired compound was prepared according to the procedure of Examples 90A-90B, step 9, using ethyl 1-(6-{1-[({2-[(tert-butoxycarbonyl)amino]pyrazolo[1,5-a]pyrimidin-3-yl}carbonyl)amino]ethyl}-4-chloro-2-{[2-(trimethylsilyl)ethoxy]methyl}-2H-indazol-7-yl)piperidine-4-carboxylate as the starting material. $^1$H NMR (400 MHz, DMSO) δ 13.38 (s, 1H), 8.90 (d, J=6.7 Hz, 1H), 8.52 (d, J=3.2 Hz, 1H), 8.23-8.00 (m, 2H), 7.11 (s, 1H), 6.99 (dd, J=6.7, 4.6 Hz, 1H), 6.42 (s, 2H), 5.79-5.58 (m, 1H), 4.12 (q, J=7.0 Hz, 2H), 3.59-3.43 (m, 1H), 3.15-2.99 (m, 1H), 2.88-2.74 (m, 1H), 2.70-2.54 (m, 1H), 2.03-1.89 (m, 2H), 1.89-1.71 (m, 2H), 1.50 (d, J=6.9 Hz, 3H), 1.22 (t, J=7.1 Hz, 3H). LCMS for C$_{24}$H$_{28}$ClN$_8$O$_3$ (M+H)$^+$: m/z=511.2; Found: 511.3.

Example 107. 2-Amino-N-[1-(4-chloro-7-{4-[(methylamino)carbonyl]piperidin-1-yl}-2H-indazol-6-yl)ethyl]pyrazolo[1,5-a]pyrimidine-3-carboxamide trifluoroacetate

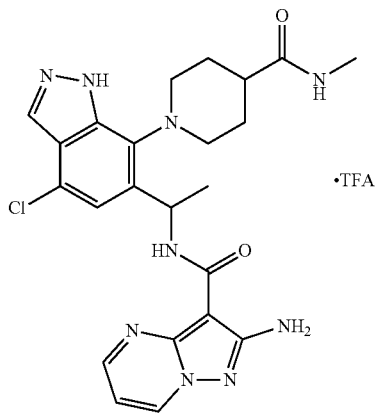 [SMILES: CNC(=O)C1CCN(c2c(C(C)NC(=O)c3c(N)nn4cccnc34)cc(Cl)c3cn[nH]c23)CC1]

Step 1. 1-(6-{1-[({2-[(tert-Butoxycarbonyl)amino]pyrazolo[1,5-a]pyrimidin-3-yl}carbonyl)amino]ethyl}-4-chloro-2-{[2-(trimethylsilyl)ethoxy]methyl}-2H-indazol-7-yl)piperidine-4-carboxylic acid

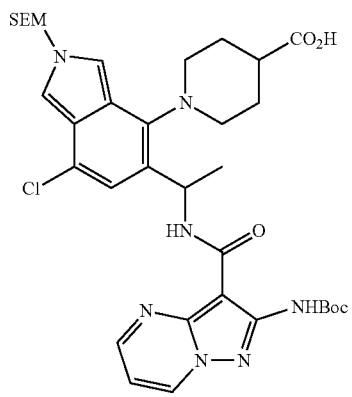 [SMILES: CC(NC(=O)c1c(NC(=O)OC(C)(C)C)nn2cccnc12)c1cc(Cl)c2cn(COCC[Si](C)(C)C)cc2c1N1CCC(C(=O)O)CC1]

The desired compound was prepared according to the procedure of Examples 103A-103B, step 1, using ethyl 1-(6-{1-[({2-[(tert-butoxycarbonyl)amino]pyrazolo[1,5-a]pyrimidin-3-yl}carbonyl)amino]ethyl}-4-chloro-2-{[2-(trimethylsilyl)ethoxy]methyl}-2H-indazol-7-yl)piperidine-4-carboxylate as the starting material. LCMS for C$_{33}$H$_{46}$ClN$_8$O$_6$Si (M+H)$^+$: m/z=713.3; Found: 713.4.

Step 2. 2-Amino-N-[1-(4-chloro-7-{4-[(methylamino)carbonyl]piperidin-1-yl}-2H-indazol-6-yl)ethyl]pyrazolo[1,5-a]pyrimidine-3-carboxamide trifluoroacetate The desired compound was prepared according to the procedure of Examples 103A-103B, step 2, using 1-(6-{1-[({2-[(tert-butoxycarbonyl)amino]pyrazolo[1,5-a]pyrimidin-3-yl}carbonyl)amino]ethyl}-4-chloro-2-{[2-(trimethylsilyl)ethoxy]methyl}-2H-indazol-7-yl)piperidine-4-carboxylic acid as the starting material. $^1$H NMR (400 MHz, DMSO) δ 13.41 (br s, 0.5H), 8.90 (dd, J=6.7, 1.5 Hz, 1H), 8.55 (dd, J=4.5, 1.5 Hz, 1H), 8.23-8.01 (m, 2H), 7.77 (d, J=4.6 Hz, 1H), 7.09 (s, 1H), 6.99 (dd, J=6.7, 4.5 Hz, 1H), 5.81-5.63 (m, 1H), 3.61-3.44 (m, 1H), 3.38-3.22 (m, 1H), 3.16-2.98 (m, 1H), 2.90-2.73 (m, 1H), 2.60 (d, J=4.5 Hz, 3H), 2.44-2.28 (m, 2H), 1.98-1.67 (m, 4H), 1.50 (d, J=6.9 Hz, 3H). LCMS for C$_{23}$H$_{27}$ClN$_9$O$_2$ (M+H)$^+$: m/z=496.2; Found: 496.3.

Example 108. 2-Amino-N-[1-(4-chloro-7-{4-[(dimethylamino)carbonyl]piperidin-1-yl}-2H-indazol-6-yl)ethyl]pyrazolo[1,5-a]pyrimidine-3-carboxamide trifluoroacetate

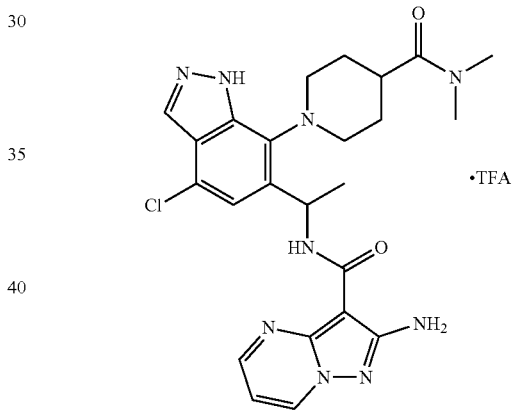

The desired compound was prepared according to the procedure of Examples 103A-103B using 1-(6-{1-[({2-[(tert-butoxycarbonyl)amino]pyrazolo[1,5-a]pyrimidin-3-yl}carbonyl)amino]ethyl}-4-chloro-2-{[2-(trimethylsilyl)ethoxy]methyl}-2H-indazol-7-yl)piperidine-4-carboxylic acid and 2.0 M dimethylamine in THF instead of 2.0 M methylamine in THF. $^1$H NMR (400 MHz, DMSO) δ 13.38 (s, 0.5H), 8.89 (dd, J=6.7, 1.5 Hz, 1H), 8.55 (dd, J=4.5, 1.5 Hz, 1H), 8.23-8.02 (m, 2H), 7.10 (s, 1H), 6.99 (dd, J=6.7, 4.5 Hz, 1H), 5.81-5.57 (m, 1H), 3.65-3.47 (m, 1H), 3.46-3.31 (m, 1H), 3.16-3.00 (m, 4H), 3.01-2.91 (m, 1H), 2.86 (s, 3H), 2.83-2.74 (m, 1H), 2.01-1.63 (m, 4H), 1.51 (d, J=6.9 Hz, 3H). LCMS for C$_{24}$H$_{29}$ClN$_9$O$_2$ (M+H)$^+$: m/z=510.2; Found: 510.3.

Examples 109-111

The following Examples 109-111 of Table 7 were synthesized according to the procedure of Example 56. NMR data for the compounds of Table 7 are provided in Table 7a.

TABLE 7

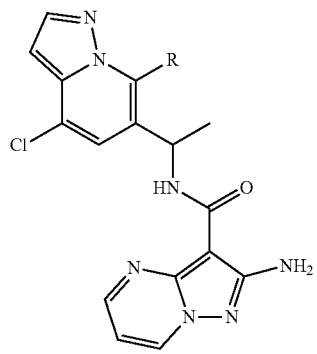

| Ex. No. | Name | R | LCMS |
|---|---|---|---|
| 109 | 2-Amino-N-{1-[4-chloro-7-(1,1-dioxido-1,4-thiazepan-4-yl)pyrazolo[1,5-a]pyridin-6-yl]-ethyl}pyrazolo[1,5-a]pyrimidine-3-carboxamide trifluoroacetate | (thiazepane-1,1-dioxide) | for $C_{21}H_{24}ClN_8O_3S$ (M + H)⁺: m/z = 503.1; Found: 503.2 |
| 110 | 2-Amino-N-{1-[4-chloro-7-(1,1-dioxido-1,2,5-thiadiazepan-5-yl)pyrazolo[1,5-a]-pyridin-6-yl]ethyl}pyrazolo[1,5-a]-pyrimidine-3-carboxamide trifluoroacetate | (thiadiazepane-1,1-dioxide with NH) | for $C_{20}H_{23}ClN_9O_3S$ (M + H)⁺: m/z = 504.1; Found: 504.3 |
| 111 | 2-Amino-N-{1-[4-chloro-7-(2,2-dimethyl-1,1-dioxidothiomorpholin-4-yl)pyrazolo[1,5-a]pyridin-6-yl]ethyl}pyrazolo[1,5-a]-pyrimidine-3-carboxamide trifluoroacetate | (2,2-dimethylthiomorpholine-1,1-dioxide) | for $C_{22}H_{26}ClN_8O_3S$ (M + H)⁺: m/z = 517.2; Found: 517.1 |

TABLE 7a

| Ex. No. | ¹H NMR Data |
|---|---|
| 109 | ¹H NMR (400 MHz, DMSO) δ 8.91 (d, J = 6.4 Hz, 1H), 8.65-8.50 (m, 1H), 8.24-7.96 (m, 2H), 7.48 (s, 1H), 7.08-6.90 (m, 1H), 6.72 (d, J = 2.2 Hz, 1H), 6.39 (br s, 2H), 5.95-5.56 (m, 1H), 4.00-3.67 (m, 3H), 3.66-3.40 (m, 3H), 3.16-3.02 (m, 1H), 2.38-2.25 (m, 0.5H), 2.20-2.08 (m, 1H), 1.54 (d, J = 6.8 Hz, 3H). |
| 110 | ¹H NMR (400 MHz, DMSO) δ 8.91 (dd, J = 6.7, 1.5 Hz, 1H), 8.71-8.43 (m, 1H), 8.18-8.04 (m, 2H), 7.76-7.64 (m, 0.5H), 7.64-7.55 (m, 0.5H), 7.44 (s, 1H), 7.01 (dd, J = 6.6, 4.7 Hz, 1H), 6.71 (d, J = 2.2 Hz, 1H), 5.90-5.68 (m, 1H), 3.48-3.26 (m, 3H), 3.25-3.04 (m, 2H), 1.52 (t, J = 6.8 Hz, 3H). |
| 111 | ¹H NMR (400 MHz, DMSO) δ 9.12-8.75 (m, 1H), 8.65-8.45 (m, 1H), 8.25-8.01 (m, 2H), 7.53 (s, 0.66H), 7.43 (s, 0.33H), 7.08-6.94 (m, 1H), 6.71 (d, J = 2.2 Hz, 1H), 6.41 (s, 2H), 5.97-5.79 (m, 0.66H), 5.78-5.58 (m, 0.33H), 4.41-4.26 (m, 0.33H), 4.27-4.15 (m, 1H), 4.14-3.96 (m, 0.66H), 3.81-3.55 (m, 2H), 3.28-3.15 (m, 1H), 3.08 (d, J = 12.7 Hz, 1H), 1.68 (s, 1H), 1.64 (s, 2H), 1.59-1.47 (m, 3H), 1.21 (d, J = 6.8 Hz, 3H). |

Examples 112A-112B. 2-Amino-N-{1-[3,4-dichloro-7-(2-methyl-1,1-dioxidothiomorpholin-4-yl)pyrazolo[1,5-a]pyridin-6-yl]ethyl}pyrazolo[1,5-a]pyrimidine-3-carboxamide trifluoroacetate (Isomers 1-2)

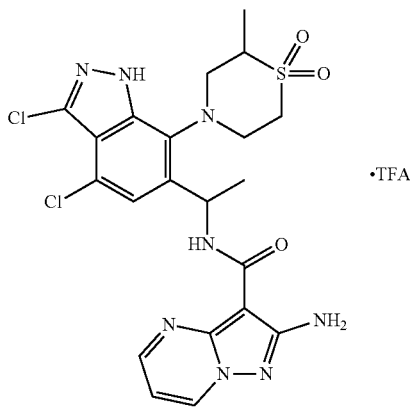 [SMILES: CC(NC(=O)c1c(N)nn2cccnc12)c1cc(Cl)c2c(Cl)n[nH]c2c1N1CCS(=O)(=O)C(C)C1]

Step 1. 1-(3,4,7-Trichloropyrazolo[1,5-a]pyridin-6-yl)ethanone

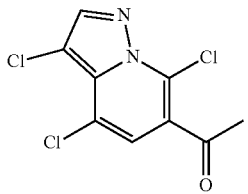

A solution of 1-(4,7-dichloropyrazolo[1,5-a]pyridin-6-yl)(ethanone (Example 56, Step 7, 38.0 mg, 0.166 mmol) in N,N-dimethylformamide (1.14 mL) was treated with N-chlorosuccinimide (33.2 mg, 0.249 mmol) and stirred at 50° C. for 2 h. The reaction mixture was diluted with water (15 mL) and saturated sodium bicarbonate solution (15 mL) and extracted with ethyl acetate (30 mL). The organic layer was separated, washed with brine, dried over sodium sulfate, filtered, and concentrated to give the desired product (46.6 mg, >100%) as a yellow solid that was used without further purification. LCMS for $C_9H_6Cl_3N_2O$ $(M+H)^+$: m/z=263.0, 264.9; Found: 263.0, 264.9.

Step 2. 1-[3,4-Dichloro-7-(2-methyl-1,1-dioxidothiomorpholin-4-yl)pyrazolo[1,5-a]pyridin-6-yl]ethanone

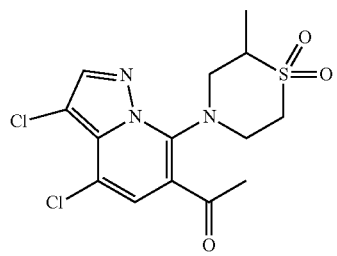 [SMILES: CC(=O)c1cc(Cl)c2c(Cl)cnn2c1N1CCS(=O)(=O)C(C)C1]

A mixture of 1-(3,4,7-trichloropyrazolo[1,5-a]pyridin-6-yl)ethanone (16.0 mg, 0.0607 mmol), 2-methylthiomorpholine 1,1-dioxide hydrochloride (28.2 mg, 0.152 mmol), and N,N-diisopropylethylamine (52.9 μL, 0.304 mmol) was heated at 140° C. in the microwave for 1 h. The reaction mixture was diluted with ethyl acetate (30 mL), washed with water (20 mL) and brine (10 mL), dried over sodium sulfate, filtered, and concentrated to give the desired product (25.6 mg, >100%) as a brown solid that was used without further purification. LCMS for $C_{14}H_{16}Cl_2N_3O_3S$ $(M+H)^+$: m/z=376.0, 378.0; Found: 376.0, 378.0.

Step 3. 2-Amino-N-{1-[3,4-dichloro-7-(2-methyl-1,1-dioxidothiomorpholin-4-yl)pyrazolo[1,5-a]pyridin-6-yl]ethyl}pyrazolo[1,5-a]pyrimidine-3-carboxamide trifluoroacetate The desired compound was prepared according to the procedure of Example 56, step 9, using 1-[3,4-dichloro-7-(2-methyl-1,1-dioxidothiomorpholin-4-yl)pyrazolo[1,5-a]pyridin-6-yl]ethanone as the starting material. The crude reaction mixture was evaporated and the crude residue was purified by preparative LCMS (XBridge C18 Column, eluting with a gradient of acetonitrile in water with 0.1% trifluoroacetic acid, at flow rate of 60 mL/min) to give two sets of diastereoisomers with each set containing mixtures of enantiomers. The first peak that eluted (Example 112A, 4.3 mg, 11%) and the second peak that eluted (Example 112B, 3.9 mg, 10%) were both white solids. Example 112A: $^1$H NMR (400 MHz, DMSO) δ 9.06-8.75 (m, 1H), 8.54 (d, J=3.0 Hz, 1H), 8.25 (d, J=5.5 Hz, 1H), 8.17-7.99 (m, 1H), 7.55 (s, 1H), 7.00 (dd, J=6.7, 4.6 Hz, 1H), 6.50 (s, 0.66H), 6.42 (s, 1.33H), 5.80-5.58 (m, 1H), 4.34-4.13 (m, 1H), 4.06-3.89 (m, 0.5H), 3.82-3.72 (m, 1H), 3.72-3.59 (m, 1H), 3.59-3.38 (m, 2H), 1.54 (d, J=7.0 Hz, 3H), 1.48 (d, J=6.9 Hz, 1H), 1.11 (d, J=6.7 Hz, 2H). LCMS for $C_{21}H_{23}Cl_2N_8O_3S$ $(M+H)^+$: m/z=537.1; Found: 537.1. Example 112B: $^1$H NMR (400 MHz, DMSO) δ 8.90 (dd, J=6.7, 1.5 Hz, 1H), 8.62-8.49 (m, 1H), 8.31-8.21 (m, 1H), 8.08 (d, J=6.7 Hz, 1H), 7.53 (s, 0.75H), 7.47 (s, 0.25H), 7.00 (dd, J=6.7, 4.5 Hz, 1H), 6.50 (s, 0.5H), 6.41 (s, 1.5H), 5.77-5.60 (m, 0.75H), 5.58-5.42 (m, 0.25H), 4.26-4.15 (m, 0.25H), 4.15-3.98 (m, 1H), 3.96-3.82 (m, 1H), 3.63-3.48 (m, 2.5H), 3.47-3.38 (m, 0.5H), 3.22 (d, J=12.7 Hz, 1H), 1.54 (d, J=7.0 Hz, 3H), 1.47 (d, J=6.2 Hz, 0.5H), 1.11 (d, J=6.8 Hz, 2.5H). LCMS for $C_{21}H_{23}Cl_2N_8O_3S$ $(M+H)^+$: m/z=537.1; Found: 537.1.

Examples 113-116

The following Examples 113-116 of Table 8 were synthesized according to the procedure of Examples 112A-112B. NMR data for the compounds of Table 8 are provided in Table 8a.

TABLE 8

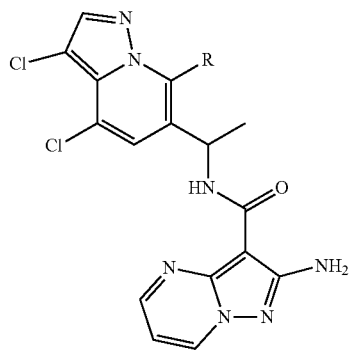

| Ex. No. | Name | R | LCMS |
|---|---|---|---|
| 113 | 2-Amino-N-{1-[3,4-dichloro-7-(1,1-dioxido-thiomorpholin-4-yl)pyrazolo[1,5-a]pyridin-6-yl]ethyl}pyrazolo[1,5-a]pyrimidine-3-carboxamide trifluoroacetate | (1,1-dioxothiomorpholin-4-yl) | for C$_{20}$H$_{21}$Cl$_2$N$_8$O$_3$S (M + H)$^+$: m/z = 523.1; Found: 523.2 |
| 114 | 2-Amino-N-{1-[3,4-dichloro-7-(1,1-dioxido-1,4-thiazepan-4-yl)pyrazolo[1,5-a]pyridin-6-yl]ethyl}pyrazolo[1,5-a]pyrimidine-3-carboxamide trifluoroacetate | (1,1-dioxo-1,4-thiazepan-4-yl) | for C$_{21}$H$_{23}$Cl$_2$N$_8$O$_3$S (M + H)$^+$: m/z = 537.1; Found: 537.1 |
| 115 | 2-Amino-N-{1-[3,4-dichloro-7-(1,1-dioxido-1,2,5-thiadiazepan-5-yl)pyrazolo[1,5-a]-pyridin-6-yl]ethyl}pyrazolo[1,5-a]pyrimidine-3-carboxamide trifluoroacetate | (1,1-dioxo-1,2,5-thiadiazepan-5-yl) | for C$_{20}$H$_{22}$Cl$_2$N$_9$O$_3$S (M + H)$^+$: m/z = 538.1; Found: 538.1 |
| 116 | 2-Amino-N-{1-13,4-dichloro-7-(2,2-dimethyl-1,1-dioxidothiomorpholin-4-yl)pyrazolo-[1,5-a]pyridin-6-yl]ethyl}pyrazolo[1,5-a]-pyrimidine-3-carboxamide trifluoroacetate | (2,2-dimethyl-1,1-dioxothiomorpholin-4-yl) | for C$_{22}$H$_{25}$Cl$_2$N$_8$O$_3$S (M + H)$^+$: m/z = 551.1; Found: 551.1 |

TABLE 8a

| Ex. No. | $^1$H NMR Data |
|---|---|
| 113 | $^1$H NMR (400 MHz, DMSO) δ 8.90 (d, J = 6.7 Hz, 1H), 8.55 (d, J = 4.4 Hz, 1H), 8.25 (s, 1H), 8.08 (d, J = 6.8 Hz, 1H), 7.52 (s, 1H), 7.00 (dd, J = 6.6, 4.6 Hz, 1H), 6.40 (br s, 2H), 5.88-5.47 (m, 1H), 4.26-3.97 (m, 2H), 1.53 (d, J = 6.9 Hz, 3H). |
| 114 | $^1$H NMR (400 MHz, DMSO) δ 8.91 (d, J = 6.6 Hz, 1H), 8.65-8.50 (m, 1H), 8.24 (s, 1H), 8.16-8.02 (m, 1H), 7.51 (s, 1H), 7.08-6.93 (m, 1H), 6.40 (br s, 2H), 5.86-5.55 (m, 1H), 3.95-3.83 (m, 0.5H), 3.83-3.62 (m, 2H), 3.62-3.40 (m, 3H), 3.19-3.02 (m, 0.5H), 2.41-2.22 (m, 0.5H), 2.19-1.99 (m, 3H), 1.53 (d, J = 6.8 Hz, 3H). |
| 115 | $^1$H NMR (400 MHz, DMSO) δ 8.91 (d, J = 6.8 Hz, 1H), 8.65-8.51 (m, 1H), 8.23 (s, 1H), 8.17-8.03 (m, 1H), 7.74-7.63 (m, 0.66H), 7.63-7.54 (m, 0.33H), 7.49 (s, 1H), 7.10-6.93 (m, 1H), 6.50 (s, 0.5H), 6.39 (s, 2H), 5.87-5.63 (m, 1H), 4.08-3.91 (m, 1H), 3.89-3.66 (m, 2H), 3.62-3.47 (m, 1H), 3.21-3.07 (m, 2H), 1.58-1.42 (m, 3H). |
| 116 | $^1$H NMR (400 MHz, DMSO) δ 9.08-8.76 (m, 1H), 8.64-8.47 (m, 1H), 8.27 (s, 1H), 8.10 (d, J = 6.5 Hz, 1H), 7.57 (s, 0.75H), 7.46 (s, 0.25H), 7.07-6.94 (m, 1H), 6.52 (s, 0.5H), 6.41 (s, 2H), 5.92-5.73 (m, 0.75H), 5.71-5.53 (m, 0.25H), 4.31-4.19 (m, 0.33H), 4.19-4.08 (m, 1H), 4.08-3.94 (m, 0.66H), 3.82-3.58 (m, 2H), 3.10 (d, J = 12.4 Hz, 0.75H), 1.66 (s, 1H), 1.62 (s, 2H), 1.58-1.47 (m, 3H), 1.21 (d, J = 8.2 Hz, 3H). |

Example 117. 2-Amino-N-[1-(8-cyclopropyl-5-phenylimidazo[1,5-a]pyridin-6-yl)ethyl]pyrazolo[1,5-a]pyrimidine-3-carboxamide trifluoroacetate salt (Racemic Mixture Prepared)

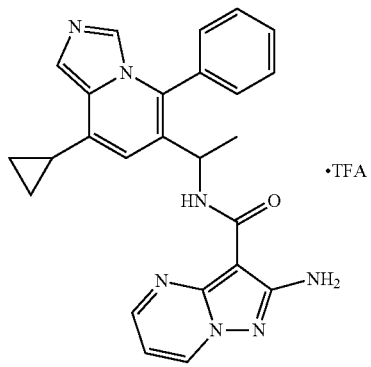 [SMILES: CC(NC(=O)c1c(N)nn2cccnc12)c1cc(C2CC2)c2cncn2c1-c1ccccc1]

Step 1. 1-(8-Cyclopropyl-5-phenylimidazo[1,5-a]pyridin-6-yl)ethanone

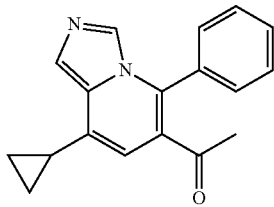 [SMILES: CC(=O)c1cc(C2CC2)c2cncn2c1-c1ccccc1]

A degassed mixture of 1-(8-chloro-5-phenylimidazo[1,5-a]pyridin-6-yl)ethanone (30. mg, 0.11 mmol, from Example 27, Step 7), cyclopropylboronic acid (14 mg, 0.17 mmol, Aldrich), Cs$_2$CO$_3$ (180 mg, 0.55 mmol) and tetrakis(triphenylphosphine)palladium(0) (6.4 mg, 0.0055 mmol) in 1,4-dioxane (1.2 mL) and water (0.30 mL) was heated to 80° C. for 1 hour. Additional tetrakis(triphenylphosphine)palladium(0) (13 mg, 0.011 mmol) and cyclopropylboronic acid (28 mg, 0.33 mmol) were added. The mixture was degassed, sealed and heated to 80° C. overnight. Additional cyclopropylboronic acid (19 mg, 0.22 mmol), Cs$_2$CO$_3$ (72 mg, 0.22 mmol) and tetrakis(triphenylphosphine)palladium(0) (13 mg, 0.011 mmol) were added. The mixture was again degassed and heated to 100° C. for 3 hours. Upon cooling to room temperature, the reaction mixture was partitioned between EtOAc and water. The organic layer was dried over Na$_2$SO$_4$, filtered and concentrated. The product was purified by preparative HPLC/MS (pH=10). Yield: 15 mg, 57%. LCMS calculated for C$_{18}$H$_{17}$N$_2$O monoisotopic (M+H)$^+$: m/z=277.1; found 277.1.

Step 2. 2-Amino-N-[1-(8-cyclopropyl-5-phenylimidazo[1,5-a]pyridin-6-yl)ethyl]pyrazolo[1,5-a]pyrimidine-3-carboxamide trifluoroacetate salt (Racemic Mixture Prepared)

Using 1-(8-cyclopropyl-5-phenylimidazo[1,5-a]pyridin-6-yl)ethanone (15 mg, 0.054 mmol), Steps 11 and 12 of Example 26 were followed to afford the title compound. Yield: 5.2 mg. LCMS calculated for C$_{25}$H$_{24}$N$_7$O monoisotopic (M+H)$^+$: m/z=438.2; found 438.2. $^1$H NMR (400 MHz, d$_6$-DMSO) δ 8.93 (dd, J=6.7, 1.4 Hz, 1H), 8.55 (dd, J=4.4, 1.4 Hz, 1H), 8.40 (s, 1H), 8.15 (s, 1H), 8.07 (d, J=6.9 Hz, 1H), 7.78 (d, J=7.6 Hz, 1H), 7.74-7.53 (m, 4H), 7.02 (dd, J=6.7, 4.5 Hz, 1H), 6.93 (s, 1H), 6.40 (br s, 2H), 4.81 (p, J=6.9 Hz, 1H), 2.24 (tt, J=8.4, 5.2 Hz, 1H), 1.42 (d, J=6.9 Hz, 3H), 1.16-1.01 (m, 2H), 1.01-0.91 (m, 1H), 0.91-0.79 (m, 1H).

Example 118. 2-Amino-N-{1-[8-chloro-3-methyl-5-(1H-pyrazol-4-yl)imidazo[1,5-a]pyridin-6-yl]ethyl}pyrazolo[1,5-a]pyrimidine-3-carboxamide trifluoroacetate salt (Racemic Mixture Prepared)

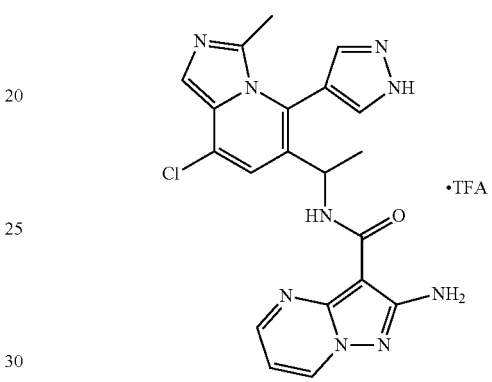

Step 1. Methyl 5-chloro-6-cyano-2-(1H-pyrazol-4-yl)nicotinate

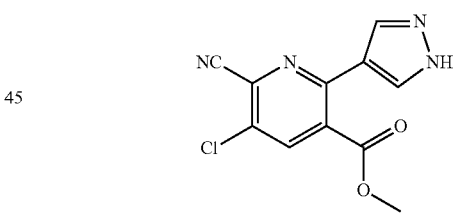

To a solution of methyl 2,5-dichloro-6-cyanonicotinate (0.80 g, 3.5 mmol, Example 26, Step 3), tert-butyl 4-(4,4,5,5-tetramethyl-1,3,2-dioxaborolan-2-yl)-1H-pyrazole-1-carboxylate (2.0 g, 6.9 mmol, Aldrich), and cesium fluoride (1.6 g, 10. mmol) in water (6.08 mL) and 1,4-dioxane (15.8 mL) was added bis(triphenylphosphine)palladium(II) chloride (0.14 g, 0.21 mmol). The mixture was degassed by sparging the solution with nitrogen for 10 minutes. The reaction was heated to 80° C. for 2 hours and 20 minutes. Upon cooling to room temperature, saturated NaHCO$_3$ was added, and the mixture was extracted with EtOAc. The organic extract was dried over Na$_2$SO$_4$, filtered, and concentrated. The product was purified by flash chromatography (0-50% EtOAc in hexanes). Yield: 0.76 g, 90%. LCMS calculated for C$_{11}$H$_8$ClN$_4$O$_2$ monoisotopic (M+H)$^+$: m/z=263.0; found 263.0.

Step 2. Methyl 8-chloro-3-methyl-5-(1H-pyrazol-4-yl)imidazo[1,5-a]pyridine-6-carboxylate

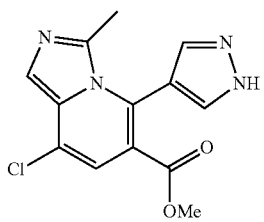 [SMILES: COC(=O)c1cc(Cl)c2cnc(C)n2c1-c1cn[nH]c1]

A degassed solution of methyl 5-chloro-6-cyano-2-(1H-pyrazol-4-yl)nicotinate (0.79 g, 2.7 mmol) in MeOH (44. mL) was treated with Raney® Nickel 2800 (0.030 mL of a slurry in water). The mixture was stirred under 1 atm of $H_2$ (provided by a balloon) for 2 hours. An additional portion of Raney® Nickel 2800 (0.030 mL) was added, and the mixture stirred under an atmosphere of $H_2$ for 2 additional hours. The reaction mixture was filtered through Celite® and the filter aid was washed with MeOH. The filtrate was concentrated. The crude product was dissolved in DMF (6.0 mL), and N,N-diisopropylethylamine (1.2 mL, 6.8 mmol) and acetic anhydride (0.28 mL, 3.0 mmol) were added. After 30 minutes, the reaction was quenched by the addition of saturated $NaHCO_3$ solution, and the aqueous mixture was extracted with EtOAc. The combined organic extracts were washed with water and brine, dried over $Na_2SO_4$, filtered, and concentrated to afford the crude product as a solid. The crude solid was suspended in phosphoryl chloride (5.0 mL, 54 mmol) and stirred at room temperature for 4 hours. The reaction mixture was poured slowly onto crushed ice, then treated with solid $K_2CO_3$ to achieve pH=10. The aqueous mixture was extracted with three portions of DCM. The combined organic extracts were dried over $Na_2SO_4$, filtered and concentrated. The product was purified by flash chromatography (0-5% MeOH in DCM). Yield: 0.40 g, 51%. LCMS calculated for $C_{13}H_{12}ClN_4O_2$ monoisotopic $(M+H)^+$: m/z=291.0; found 291.0.

Step 3. 2-Amino-N-{1-[8-chloro-3-methyl-5-(1H-pyrazol-4-yl)imidazo[1,5-a]pyridin-6-yl]ethyl}pyrazolo[1,5-a]pyrimidine-3-carboxamide trifluoroacetate salt (Racemic Mixture Prepared)

Using methyl 8-chloro-3-methyl-5-(1H-pyrazol-4-yl)imidazo[1,5-a]pyridine-6-carboxylate, Steps 8-12 of Example 26 were followed to afford the title compound. LCMS calculated for $C_{20}H_{19}ClN_9O$ monoisotopic $(M+H)^+$: m/z=436.1; found 436.2. $^1$H NMR (400 MHz, $d_6$-DMSO) δ 8.92 (dd, J=6.7, 1.6 Hz, 1H), 8.56 (dd, J=4.5, 1.5 Hz, 1H), 8.07-7.95 (m, 3H), 7.90 (s, 1H), 7.33 (s, 1H), 7.02 (dd, J=6.7, 4.5 Hz, 1H), 4.73 (p, J=6.4 Hz, 1H), 2.03 (s, 3H), 1.41 (d, J=7.0 Hz, 3H).

Examples 119-121

Examples 119-121 in Table 9 were prepared by the method of Example 118. NMR data for the compounds of Table 9 are provided in Table 9a.

TABLE 9

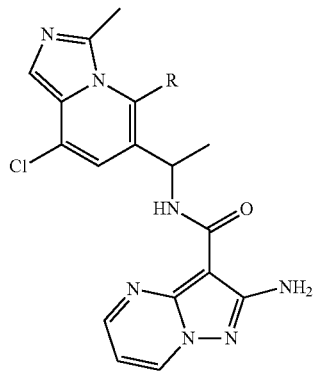

| Ex. No. | Name | R = | LCMS |
|---|---|---|---|
| 119 | 2-Amino-N-{1-[8-chloro-3-methyl-5-(1-methyl-1H-pyrazol-4-yl)imidazo[1,5-a]-pyridin-6-yl]ethyl}pyrazolo[1,5-a]-pyrimidine-3-carboxamide trifluoroacetate salt (racemic mixture prepared) | 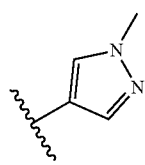 [SMILES: *c1cnn(C)c1] | Calculated for $C_{21}H_{21}ClN_9O$ monoisotopic $(M + H)^+$: m/z = 450.1; found: 450.1 |

TABLE 9-continued

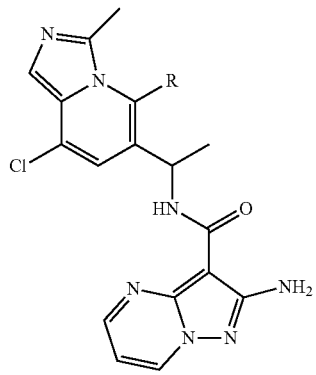

| Ex. No. | Name | R = | LCMS |
|---|---|---|---|
| 120 | 2-Amino-N-[1-(8-chloro-3-methyl-5-pyridin-3-ylimidazo[1,5-a]pyridin-6-yl)-ethyl]pyrazolo[1,5-a]pyrimidine-3-carboxamide trifluoroacetate salt (racemic mixture prepared) | 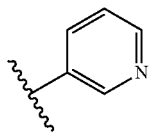 [SMILES: *c1cccnc1] | Calculated for $C_{22}H_{20}ClN_8O$ monoisotopic $(M + H)^+$: m/z = 447.1; found: 447.1 |
| 121 | 2-Amino-N-[1-(8-chloro-3-methyl-5-phenylimidazo[1,5-a]pyridin-6-yl)ethyl]-pyrazolo[1,5-a]pyrimidine-3-carboxamide trifluoroacetate salt (racemic mixture prepared) | 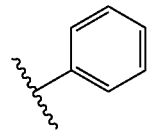 [SMILES: *c1ccccc1] | Calculated for $C_{23}H_{21}ClN_7O$ monoisotopic $(M + H)^+$: m/z = 446.2; found: 446.1 |

TABLE 9a

| Ex. No. | $^1$H NMR |
|---|---|
| 119 | $^1$H NMR (400 MHz, $d_6$-DMSO) δ 8.92 (dd, J = 6.7, 1.5 Hz, 1H), 8.57 (dd, J = 4.5, 1.0 Hz, 1H), 8.11 (s, 0.5H), 8.09 (s, 0.5H), 8.03 (d, J = 6.4 Hz, 1H), 7.91 (s, 1H), 7.81 (s, 0.5H), 7.75 (s, 0.5H), 7.33 (s, 1H), 7.02 (dd, J = 6.7, 4.6 Hz, 1H), 4.76 (p, J = 6.4 Hz, 1H), 4.01 (s, 1.5H), 3.98 (s, 1.5H), 2.08 (s, 3H), 1.41 (d, J = 7.0 Hz, 3H). |
| 120 | $^1$H NMR (400 MHz, $d_6$-DMSO) δ 9.05 (d, J = 1.5 Hz, 0.5H), 8.95-8.90 (m, 1H), 8.85 (dd, J = 4.9, 1.3 Hz, 1H), 8.83 (d, J = 1.6 Hz, 0.5H), 8.56 (dd, J = 4.5, 1.6 Hz, 1H), 8.32 (dt, J = 8.1, 1.9 Hz, 0.5H), 8.12 (dt, J = 7.8, 1.8 Hz, 0.5H), 8.05 (d, J = 6.3 Hz 0.5H), 8.05 (d, J = 6.2 Hz 0.5H), 7.95 (s, 1H), 7.72 (dd, J = 7.8, 5.0 Hz, 0.5H), 7.67 (dd, J = 7.7, 4.9 Hz, 0.5H), 7.42 (s, 0.5H), 7.42 (s, 0.5H), 7.02 (dd, J = 6.7, 4.5 Hz, 1H), 4.49 (p, J = 7.3, 6.7 Hz, 1H), 1.85 (s, 3H), 1.43 (d, J = 7.5 Hz, 1.5H), 1.41 (d, J = 7.3 Hz, 1.5H) |
| 121 | $^1$H NMR (400 MHz, $d_6$-DMSO) δ 8.91 (dd, J = 6.7, 1.5 Hz, 1H), 8.55 (dd, J = 4.5, 1.5 Hz, 1H), 8.03 (d, J = 6.3 Hz, 1H), 7.97 (s, 1H), 7.86-7.78 (m, 1H), 7.70-7.53 (m, 4H), 7.38 (s, 1H), 7.01 (dd, J = 6.7, 4.5 Hz, 1H), 4.59 (p, J = 6.7 Hz, 1H), 1.83 (s, 3H), 1.38 (d, J = 7.0 Hz, 3H) |

Example 122. 2-Amino-N-{1-[1,8-dichloro-3-methyl-5-(1H-pyrazol-4-yl)imidazo[1,5-a]pyridin-6-yl]ethyl}pyrazolo[1,5-a]pyrimidine-3-carboxamide trifluoroacetate salt (Racemic Mixture Prepared)

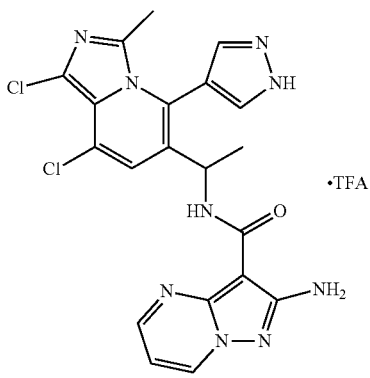 [SMILES: Cc1nc(Cl)c2c(Cl)cc(C(C)NC(=O)c3c(N)nn4cccnc34)c(-c3cn[nH]c3)n12]

Step 1. 1-[1,8-Dichloro-3-methyl-5-(1H-pyrazol-4-yl)imidazo[1,5-a]pyridin-6-yl]ethanone

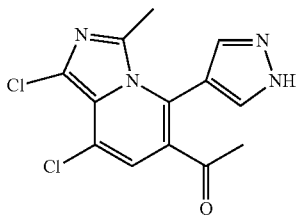 [SMILES: CC(=O)c1cc(Cl)c2c(Cl)nc(C)n2c1-c1cn[nH]c1]

1-[8-Chloro-3-methyl-5-(1H-pyrazol-4-yl)imidazo[1,5-a]pyridin-6-yl]ethanone was prepared by treating the product of Example 118, Step 2 with the methods of Example 26, Steps 8 through 10 to provide 1-[8-chloro-3-methyl-5-(1H-pyrazol-4-yl)imidazo[1,5-a]pyridin-6-yl]ethanone. To a solution of 1-[8-chloro-3-methyl-5-(1H-pyrazol-4-yl)imidazo[1,5-a]pyridin-6-yl]ethanone (15.0 mg, 0.0546 mmol) in DMF (0.20 mL) was added N-chlorosuccinimide (8.7 mg, 0.066 mmol) in DMF (0.20 mL). The mixture was stirred at ambient temperature for 22 hours. Saturated $NaHCO_3$ was added, and the mixture was extracted with EtOAc. The organic layer was washed with brine, dried over $Na_2SO_4$, filtered and concentrated. The product was purified by flash chromatography (0-100% EtOAc in hexanes). Yield: 5.6 mg, 33%. LCMS calculated for $C_{13}H_{11}Cl_2N_4O$ monoisotopic $(M+H)^+$: m/z=309.0; found 309.1.

Step 2. 2-Amino-N-{1-[1,8-dichloro-3-methyl-5-(1I-pyrazol-4-yl)imidazo[1,5-a]pyridin-6-yl]ethyl}pyrazolo[1,5-a]pyrimidine-3-carboxamide trifluoroacetate salt (Racemic Mixture Prepared)

Using 1-[1,8-dichloro-3-methyl-5-(1H-pyrazol-4-yl)imidazo[1,5-a]pyridin-6-yl]ethanone (5.0 mg, 0.016 mmol), Steps 11 and 12 of Example 26 were followed to afford the title compound. Yield: 2.4 mg. LCMS calculated for $C_{20}H_{18}Cl_2N_9O$ monoisotopic $(M+H)^+$: m/z=470.1; found 470.2. $^1H$ NMR (400 MHz, $d_6$-DMSO) δ 8.91 (dd, J=6.7, 1.6 Hz, 1H), 8.56 (dd, J=4.5, 1.6 Hz, 1H), 8.05-7.92 (m, 3H), 7.03 (s, 1H), 7.01 (dd, J=6.8, 4.5 Hz, 1H), 4.67 (p, J=7.3, 6.8 Hz, 1H), 1.88 (s, 3H), 1.37 (d, J=7.0 Hz, 3H).

Example 123. 2-Amino-N-{1-[8-chloro-1-fluoro-3-methyl-5-(1H-pyrazol-4-yl)imidazo[1,5-a]pyridin-6-yl]ethyl}pyrazolo[1,5-a]pyrimidine-3-carboxamide trifluoroacetate salt (Racemic Mixture Prepared)

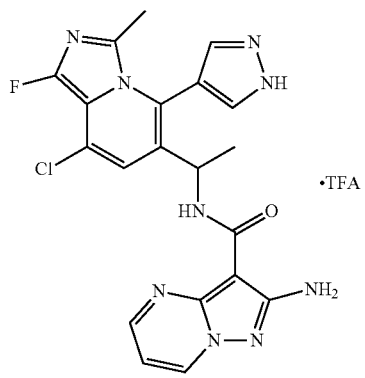 [SMILES: Cc1nc(F)c2c(Cl)cc(C(C)NC(=O)c3c(N)nn4cccnc34)c(-c3cn[nH]c3)n12]

Step 1. 1-[8-Chloro-1-fluoro-3-methyl-5-(1H-pyrazol-4-yl)imidazo[1,5-a]pyridin-6-yl]ethanone

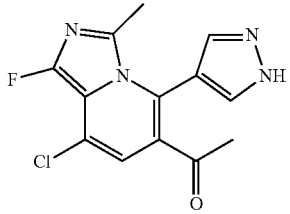 [SMILES: CC(=O)c1cc(Cl)c2c(F)nc(C)n2c1-c1cn[nH]c1]

To a solution of 1-[8-chloro-3-methyl-5-(1H-pyrazol-4-yl)imidazo[1,5-a]pyridin-6-yl]ethanone (45 mg, 0.16 mmol, prepared by treating the product of Example 118, Step 2 with the methods of Example 26, Steps 8 through 10) in DMF (1.8 mL) was added 1-fluoro-2,4,6-trimethylpyridinium tetrafluoroborate (254 mg, 1.15 mmol, Aldrich). The reaction was heated to 60° C. for 3 hours. Upon cooling, 1N NaOH was added, and the mixture was extracted with three portions of DCM. The combined organic extracts were washed with brine, dried over $Na_2SO_4$, filtered and concentrated. The product was purified by preparative HPLC/MS (pH=2). Acetonitrile was evaporated from the eluent and the aqueous mixture was basified to pH=8 by the addition of solid $NaHCO_3$. The basic aqueous mixture was extracted with two portions of DCM and the extracts were dried over $Na_2SO_4$, filtered and concentrated. Yield: 10. mg, 14%. LCMS calculated for $C_{13}H_{11}ClFN_4O$ monoisotopic $(M+H)^+$: m/z=293.1; found 293.0.

Step 2. 2-Amino-N-{1-[8-chloro-1-fluoro-3-methyl-5-(1H-pyrazol-4-yl)imidazo[1,5-a]pyridin-6-yl]ethyl}pyrazolo[1,5-a]pyrimidine-3-carboxamide (Racemic Mixture Prepared)

Using 1-[8-chloro-1-fluoro-3-methyl-5-(1H-pyrazol-4-yl)imidazo[1,5-a]pyridin-6-yl]ethanone (10.0 mg, 0.024 mmol), Steps 11 and 12 of Example 26 were followed to afford the title compound. The product was purified by preparative HPLC/MS (pH=10). Yield: 2.5 mg. LCMS calculated for $C_{20}H_{18}ClFN_9O$ monoisotopic (M+H)$^+$: m/z=454.1; found 454.1. $^1$H NMR (400 MHz, d$_6$-DMSO) δ 8.91 (dd, J=6.7, 1.6 Hz, 1H), 8.56 (dd, J=4.5, 1.5 Hz, 1H), 7.99 (d, J=6.6 Hz, 1H), 7.99 (br s, 2H), 7.01 (dd, J=6.7, 4.5 Hz, 1H), 6.89 (s, 1H), 6.44 (s, 2H), 4.67 (p, J=7.1 Hz, 1H), 1.84 (s, 3H), 1.37 (d, J=7.0 Hz, 3H).

Example 124. 2-Amino-N-{1-[8-chloro-3-methyl-5-phenyl-1-(trifluoromethyl)imidazo[1,5-a]pyridin-6-yl]ethyl}pyrazolo[1,5-a]pyrimidine-3-carboxamide trifluoroacetate salt (Racemic Mixture Prepared)

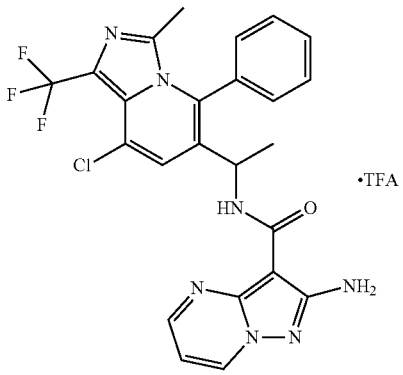 [SMILES: Cc1nc(C(F)(F)F)c2c(Cl)cc(C(C)NC(=O)c3c(N)nn4cccnc34)c(-c3ccccc3)n12]

Step 1. 1-(8-Chloro-1-iodo-3-methyl-5-phenylimidazo[1,5-a]pyridin-6-yl)ethanone

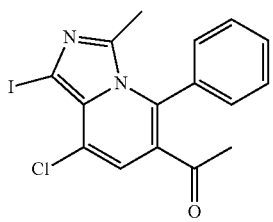 [SMILES: CC(=O)c1cc(Cl)c2c(I)nc(C)n2c1-c1ccccc1]

1-(8-Chloro-3-methyl-5-phenylimidazo[1,5-a]pyridin-6-yl)ethanone was prepared by the method of Example 26, Steps 1-10 substituting phenylboronic acid (Aldrich) for (3-fluorophenyl)boronic acid in Step 4. To a solution of 1-(8-chloro-3-methyl-5-phenylimidazo[1,5-a]pyridin-6-yl)ethanone (0.28 g, 0.98 mmol) in DMF (5.3 mL) was added N-iodosuccinimide (0.24 g, 1.1 mmol). After stirring for 70 minutes, the reaction was quenched by the addition of saturated NaHCO$_3$ solution. The mixture was extracted with EtOAc, and the combined organic extracts were dried over Na$_2$SO$_4$, filtered and concentrated. The product was purified by flash chromatography (0-20% EtOAc in hexanes). Yield: 0.40 g, 99%. LCMS calculated for $C_{16}H_{13}ClIN_2O$ monoisotopic (M+H)$^+$: m/z=411.0; found 411.0.

Step 2. 1-[8-Chloro-3-methyl-5-phenyl-1-(trifluoromethyl)imidazo[1,5-a]pyridin-6-yl]ethanone

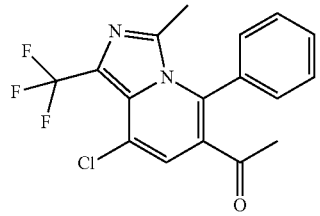 [SMILES: CC(=O)c1cc(Cl)c2c(C(F)(F)F)nc(C)n2c1-c1ccccc1]

To a solution of 1-(8-chloro-1-iodo-3-methyl-5-phenylimidazo[1,5-a]pyridin-6-yl)ethanone (40. mg, 0.097 mmol) in DMF (2.0 mL) was added copper(I) iodide (93 mg, 0.49 mmol), hexamethylphosphoramide (169 μL, 0.974 mmol), and methyl difluoro(fluorosulfonyl)acetate (80. μL, 0.63 mmol, Aldrich). The mixture was heated to 80° C. under nitrogen for 2 hours. Upon cooling to room temperature, water was added. The mixture was extracted with Et$_2$O. The combined organic extracts were washed with water and diluted with EtOAc. The organic layer was washed with saturated NaHCO$_3$ solution, then with brine, dried over Na$_2$SO$_4$, filtered and concentrated. The product was purified by flash chromatography (0-20% EtOAc in hexanes). Yield: 0.030 g, 87%. LCMS calculated for $C_{17}H_{13}ClF_3N_2O$ monoisotopic (M+H)$^+$: m/z=353.1; found 353.0.

Step 3. 2-Amino-N-{1-[8-chloro-3-methyl-5-phenyl-1-(trifluoromethyl)imidazo[1,5-a]pyridin-6-yl]ethyl}pyrazolo[1,5-a]pyrimidine-3-carboxamide trifluoroacetate salt (Racemic Mixture Prepared)

Using 1 [8-chloro-3-methyl-5-phenyl-1-(trifluoromethyl)imidazo[1,5-a]pyridin-6-yl]ethanone (7.3 mg, 0.021 mmol), Steps 11 and 12 of Example 26 were followed to afford the title compound. Yield: 6.1 mg. LCMS calculated for $C_{24}H_{20}ClF_3N_7O$ monoisotopic (M+H)$^+$: m/z=514.1; found 514.1. $^1$H NMR (400 MHz, d$_6$-DMSO) δ 8.92 (dd, J=6.7, 1.5 Hz, 1H), 8.56 (dd, J=4.5, 1.5 Hz, 1H), 8.05 (d, J=6.3 Hz, 1H), 7.84-7.79 (m, 1H), 7.71-7.54 (m, 4H), 7.47 (s, 1H), 7.01 (dd, J=6.7, 4.5 Hz, 1H), 4.59 (p, J=6.8 Hz, 1H), 1.76 (s, 3H), 1.37 (d, J=7.0 Hz, 3H).

Example 125. 2-Amino-N-[1-(8-chloro-1-cyano-3-methyl-5-phenylimidazo[1,5-a]pyridin-6-yl)ethyl]pyrazolo[1,5-a]pyrimidine-3-carboxamide trifluoroacetate salt (Racemic Mixture Prepared)

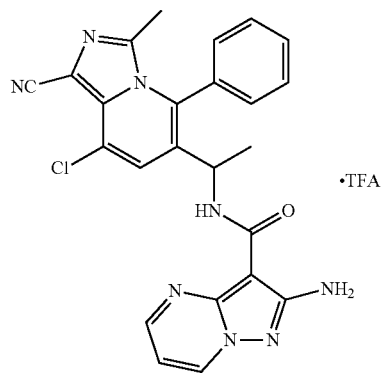 [SMILES: Cc1nc(C#N)c2c(Cl)cc(C(C)NC(=O)c3c(N)nn4cccnc34)c(-c3ccccc3)n12]

Step 1. 6-Acetyl-8-chloro-3-methyl-5-phenylimidazo[1,5-a]pyridine-1-carbonitrile trifluoroacetate salt

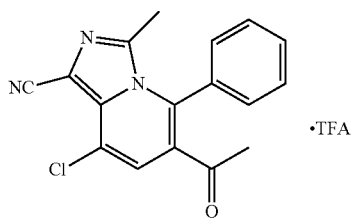 [SMILES: CC(=O)c1cc(Cl)c2c(C#N)nc(C)n2c1-c1ccccc1]

A degassed mixture of 1-(8-chloro-1-iodo-3-methyl-5-phenylimidazo[1,5-a]pyridin-6-yl)ethanone (125 mg, 0.304 mmol, from Example 124, Step 1), zinc cyanide (180 mg, 1.5 mmol), tris(dibenzylideneacetone)dipalladium(0) chloroform adduct (32 mg, 0.030 mmol), and 2-(dicyclohexylphosphino)-2',6'-dimethoxy-1,1'-biphenyl (25 mg, 0.061 mmol) in DMF (5.5 mL) and water (27 μL) was heated in the microwave to 160° C. for 45 minutes. The mixture was diluted with acetonitrile and filtered. The product was purified by preparative HPLC/MS (pH=2). Yield: 0.020 g, 21%. LCMS calculated for $C_{17}H_{13}ClN_3O$ monoisotopic (M+H)$^+$: m/z=310.1; found. 310.0.

Step 2. 2-Amino-N-[1-(8-chloro-1-cyano-3-methyl-5-phenylimidazo[1,5-a]pyridin-6-yl)ethyl]pyrazolo[1,5-a]pyrimidine-3-carboxamide trifluoroacetate salt (Racemic Mixture Prepared)

Using 6-acetyl-8-chloro-3-methyl-5-phenylimidazo[1,5-a]pyridine-1-carbonitrile trifluoroacetate salt, Steps 11 and 12 of Example 26 were followed to afford the title compound. Yield: 4.3 mg. LCMS calculated for $C_{24}H_{20}ClN_8O$ monoisotopic (M+H)$^+$: m/z=471.1; found. 471.1. $^1$H NMR (400 MHz, d$_6$-DMSO) δ 8.91 (dd, J=6.7, 1.5 Hz, 1H), 8.55 (dd, J=4.5, 1.5 Hz, 1H), 8.04 (d, J=6.3 Hz, 1H), 7.84-7.74 (m, 1H), 7.68-7.53 (m, 4H), 7.58 (s, 1H), 7.01 (dd, J=6.7, 4.5 Hz, 1H), 4.58 (p, J=6.8 Hz, 1H), 1.73 (s, 3H), 1.37 (d, J=7.0 Hz, 3H).

Example 126. 2-Amino-N-[1-(8-chloro-1-ethynyl-3-methyl-5-phenylimidazo[1,5-a]pyridin-6-yl)ethyl]pyrazolo[1,5-a]pyrimidine-3-carboxamide (Racemic Mixture Prepared)

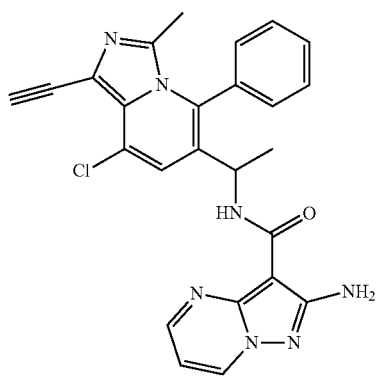 [SMILES: C#Cc1nc(C)n2c(-c3ccccc3)c(C(C)NC(=O)c3c(N)nn4cccnc34)cc(Cl)c12]

Step 1. 1-(8-Chloro-1-ethynyl-3-methyl-5-phenylimidazo[1,5-a]pyridin-6-yl)ethanamine

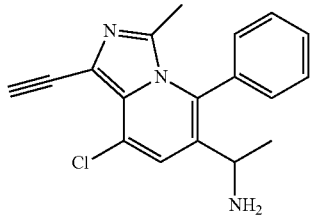 [SMILES: C#Cc1nc(C)n2c(-c3ccccc3)c(C(C)N)cc(Cl)c12]

(Trimethylsilyl)acetylene (72 μL, 0.51 mmol, Aldrich) and triethylamine (92 μL, 0.66 mmol) were added to a degassed mixture of 1-(8-chloro-1-iodo-3-methyl-5-phenylimidazo[1,5-a]pyridin-6-yl)ethanone (30. mg, 0.073 mmol, from Example 124, Step 1), tetrakis(triphenylphosphine)palladium(0) (5.1 mg, 0.0044 mmol) and copper(I) iodide (1.4 mg, 0.0073 mmol) in DMF (1.0 mL). The reaction mixture was heated in the microwave to 100° C. for 30 minutes. Upon cooling, saturated NaHCO$_3$ solution was added. The mixture was diluted with water and extracted with EtOAc. The organic extract was washed with water, followed by brine, dried over Na$_2$SO$_4$, filtered and concentrated. The residue was dissolved in methanol (2.0 mL), and ammonium acetate (84.5 mg, 1.10 mmol) and sodium cyanoborohydride (23 mg, 0.36 mmol) were added. The reaction vessel was sealed and heated to 65° C. overnight. The product was purified by preparative HPLC/MS (pH=10). Yield: 5.0 mg 22%. LCMS calculated for $C_{18}H_{17}ClN_3$ monoisotopic (M+H)$^+$: m/z=310.1; found. 310.1.

Step 2. 2-Amino-N-[1-(8-chloro-1-ethynyl-3-methyl-5-phenylimidazo[1,5-a]pyridin-6-yl)ethyl]pyrazolo[1,5-a]pyrimidine-3-carboxamide (Racemic Mixture Prepared)

Using 1-(8-chloro-1-ethynyl-3-methyl-5-phenylimidazo[1,5-a]pyridin-6-yl)ethanamine (5.0 mg, 0.016 mmol), Step 12 of Example 26 was followed to provide the title compound. Yield: 0.8 mg. LCMS calculated for $C_{25}H_{21}ClN_7O$ monoisotopic (M+H)$^+$: m/z=470.1; found. 470.1. $^1$H NMR (400 MHz, d$_6$-DMSO) δ 8.92 (dd, J=6.7, 1.6 Hz, 1H), 8.55 (dd, J=4.3, 1.6 Hz, 1H), 8.01 (d, J=6.6 Hz, 1H), 7.80-7.73 (m, 1H), 7.65-7.53 (m, 4H), 7.16 (s, 1H), 7.01 (dd, J=6.6, 4.6 Hz, 1H), 6.42 (s, 2H), 4.55 (p, J=7.5 Hz, 1H), 2.08 (s, 1H), 1.69 (s, 3H), 1.35 (d, J=6.9 Hz, 3H).

Example 127. 2-Amino-N-[1-(8-chloro-5-pyridin-3-ylimidazo[1,5-a]pyridin-6-yl)ethyl]pyrazolo[1,5-a]pyrimidine-3-carboxamide trifluoroacetate salt (Racemic Mixture Prepared)

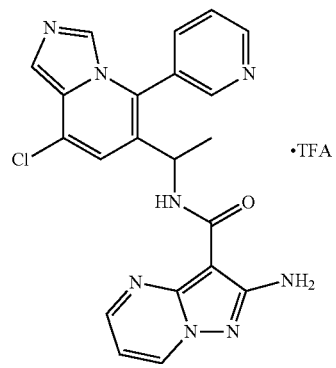 [SMILES: CC(NC(=O)c1c(N)nn2cccnc12)c1cc(Cl)c2cncn2c1-c1cccnc1]

Step 1. Methyl 5-chloro-6-cyano-2,3'-bipyridine-3-carboxylate

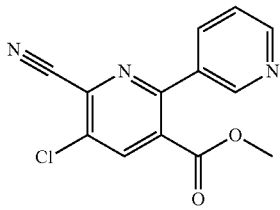 [SMILES: COC(=O)c1cc(Cl)c(C#N)nc1-c1cccnc1]

The product was prepared by the method of Example 118, Step 1, using 3-(4,4,5,5-tetramethyl-1,3,2-dioxaborolan-2-yl)pyridine (4.0 g, 19 mmol, Aldrich) and methyl 2,5-dichloro-6-cyanonicotinate (3.0 g, 13 mmol, from Example 26, Step 3). Yield: 3.6 g, 93%. LCMS calculated for $C_{13}H_9ClN_3O_2$ monoisotopic $(M+H)^+$: m/z=274.1; found 274.0.

Step 2. Methyl 6-(aminomethyl)-5-chloro-2,3'-bipyridine-3-carboxylate

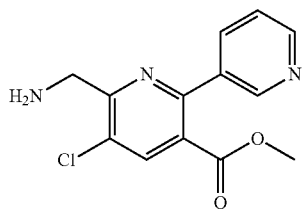 [SMILES: COC(=O)c1cc(Cl)c(CN)nc1-c1cccnc1]

A degassed solution of methyl 5-chloro-6-cyano-2,3'-bipyridine-3-carboxylate (3.3 g, 12 mmol) in MeOH (200 mL) was treated with Raney® Nickel 2800 (1.0 mL of a slurry in water, Aldrich) and stirred under 1 atm $H_2$ (provided by a balloon) overnight. The reaction mixture was filtered through Celite® and the filtrate was concentrated in vacuo. The product was used without further purification. Yield: 3.2 g, 86%. LCMS calculated for $C_{13}H_{13}ClN_3O_2$ monoisotopic $(M+H)^+$: m/z=278.1; found 278.0.

Step 3. Methyl 8-chloro-5-pyridin-3-ylimidazo[1,5-a]pyridine-6-carboxylate

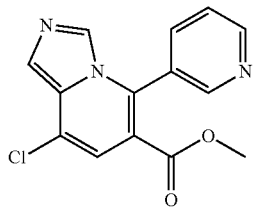 [SMILES: COC(=O)c1cc(Cl)c2cncn2c1-c1cccnc1]

Formic acid (19 mL) and acetic anhydride (5.0 mL) were combined and stirred for 40 minutes at room temperature, then the mixture was added dropwise into a 0° C. solution of methyl 6-(aminomethyl)-5-chloro-2,3'-bipyridine-3-carboxylate (3.2 g, 10. mmol) in DCM (57 mL). The cooling bath was removed, and the mixture was warmed to room temperature and stirred for 30 minutes after reaching room temperature. Volatiles were removed in vacuo. The residue was dissolved in phosphoryl chloride (12 mL, 130 mmol). After stirring for 1 hour at room temperature, the mixture was poured slowly onto crushed ice and the aqueous solution was neutralized by the addition of $Na_2CO_3$. The aqueous mixture was extracted twice with DCM. The combined organic extracts were dried over $Na_2SO_4$, filtered and concentrated. The product was purified by flash chromatography (0-5% MeOH in DCM). Yield: 1.92 g, 64%. LCMS calculated for $C_{14}H_{11}ClN_3O_2$ monoisotopic $(M+H)^+$: m/z=288.1; found 288.1.

Step 4. 2-Amino-N-[1-(8-chloro-5-pyridin-3-ylimidazo[1,5-a]pyridin-6-yl)ethyl]pyrazolo[1,5-a]pyrimidine-3-carboxamide trifluoroacetate salt (Racemic Mixture Prepared)

Using methyl 8-chloro-5-pyridin-3-ylimidazo[1,5-a]pyridine-6-carboxylate, Steps 8-12 of Example 26 were followed to afford the title compound. LCMS calculated for $C_{21}H_{18}ClN_8O$ monoisotopic $(M+H)^+$: m/z=433.1; found 433.1. $^1$H NMR (400 MHz, $d_6$-DMSO) δ 9.13-9.08 (m, 0.5H), 8.95-8.85 (m, 2.5H), 8.58-8.54 (m, 1H), 8.42-8.37 (m, 0.5H), 8.26-8.21 (m, 0.5H), 8.19 (s, 1H), 8.07-8.02 (m, 1H), 7.85 (dd, J=7.8, 5.1 Hz, 0.5H), 7.83 (s, 1H), 7.80 (dd, J=7.7, 5.2 Hz, 0.5H), 7.44 (s, 0.5H), 7.44 (s, 0.5H), 7.04-6.99 (m, 1H), 4.65 (h, J=6.9 Hz, 1H), 1.49 (d, J=7.0 Hz, 1.5H), 1.45 (d, J=7.0 Hz, 1.5H).

Example 128. 2-Amino-N-[1-(8-chloro-1-cyano-5-pyridin-3-ylimidazo[1,5-a]pyridin-6-yl)ethyl]pyrazolo[1,5-a]pyrimidine-3-carboxamide trifluoroacetate salt (Racemic Mixture Prepared)

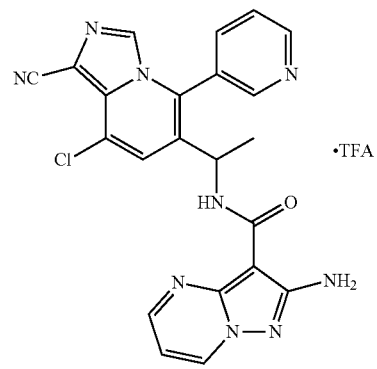 [SMILES: CC(NC(=O)c1c(N)nn2cccnc12)c1cc(Cl)c2c(C#N)ncn2c1-c1cccnc1]

Step 1. 1-(8-Chloro-1-iodo-5-pyridin-3-ylimidazo[1,5-a]pyridin-6-yl)ethanone

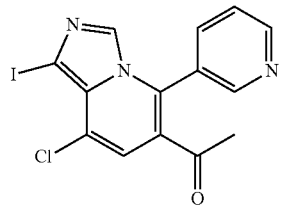 [SMILES: CC(=O)c1cc(Cl)c2c(I)ncn2c1-c1cccnc1]

1-(8-Chloro-5-(pyridin-3-yl)imidazo[1,5-a]pyridin-6-yl)ethanone was prepared by treating methyl 8-chloro-5-pyridin-3-ylimidazo[1,5-a]pyridine-6-carboxylate (Example 127, Step 3) with the methods of Example 26, Steps 8 through 10 to afford 1-(8-chloro-5-(pyridin-3-yl)imidazo[1,5-a]pyridin-6-yl)ethanone. 1-(8-Chloro-5-(pyridin-3-yl)imidazo[1,5-a]pyridin-6-yl)ethanone (0.300 g, 1.10 mmol) was iodinated by the method of Example 124, Step 1 to provide the title compound. Yield: 0.44 g, 100%. LCMS calculated for $C_H H_{10}ClIN_3O$ monoisotopic $(M+H)^+$: m/z=398.0; found 397.9.

Step 2. 6-Acetyl-8-chloro-5-(pyridin-3-yl)imidazo[1,5-a]pyridine-1-carbonitrile

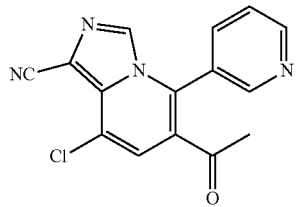 [SMILES: CC(=O)c1cc(Cl)c2c(C#N)ncn2c1-c1cccnc1]

Using 1-(8-chloro-1-iodo-5-pyridin-3-ylimidazo[1,5-a]pyridin-6-yl)ethanone, the method of Example 164, Steps 2 through 5 were followed to afford the title compound. LCMS calculated for $C_{15}H_{10}ClN_4O$ monoisotopic $(M+H)^+$: m/z=297.1; found 297.0.

Step 3. 2-Amino-N-[1-(8-chloro-1-cyano-5-pyridin-3-ylimidazo[1,5-a]pyridin-6-yl)ethyl]pyrazolo[1,5-a]pyrimidine-3-carboxamide trifluoroacetate salt (Racemic Mixture Prepared)

Starting with 6-acetyl-8-chloro-5-(pyridin-3-yl)imidazo[1,5-a]pyridine-1-carbonitrile (19 mg, 0.064 mmol), the methods of Steps 11 and 12 of Example 26 were followed to afford the title compound. Yield: 3.5 mg. LCMS calculated for $C_{22}H_{17}ClN_9O$ monoisotopic $(M+H)^+$: m/z=458.1; found 458.1. $^1$H NMR (400 MHz, $d_6$-DMSO) δ 9.05-9.03 (m, 0.5H), 8.93 (dd, J=2.7, 1.6 Hz, 0.5H), 8.91 (dd, J=2.7, 1.7 Hz, 0.5H), 8.86 (dd, J=4.9, 1.5 Hz, 1H), 8.82-8.80 (m, 0.5H), 8.57-8.54 (m, 1H), 8.33-8.27 (m, 0.5H), 8.17-8.10 (m, 0.5H), 8.07 (d, J=6.2 Hz, 0.5H), 8.06 (d, J=6.1 Hz, 0.5H), 7.97 (s, 1H), 7.80 (s, 0.5H), 7.78 (s, 0.5H), 7.76 (dd, J=7.8, 4.9 Hz, 0.5H), 7.70 (dd, J=7.6, 5.2 Hz, 0.5H), 7.04-7.00 (m, 1H), 4.73-4.59 (m, 1H), 1.49 (d, J=7.0 Hz, 1.5H), 1.44 (d, J=7.1 Hz, 1.5H).

Example 129. 2-Amino-N-[1-(8-chloro-1-methyl-5-pyridin-3-ylimidazo[1,5-a]pyridin-6-yl)ethyl]pyrazolo[1,5-a]pyrimidine-3-carboxamide trifluoroacetate salt (Racemic Mixture Prepared)

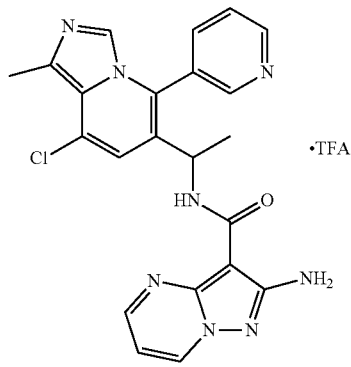 [SMILES: Cc1ncn2c(-c3cccnc3)c(C(C)NC(=O)c3c(N)nn4cccnc34)cc(Cl)c12]

Step 1. 1-(8-Chloro-1-methyl-5-pyridin-3-ylimidazo[1,5-a]pyridin-6-yl)ethanone

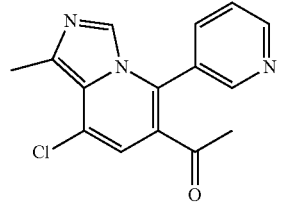 [SMILES: CC(=O)c1cc(Cl)c2c(C)ncn2c1-c1cccnc1]

A degassed mixture of 1-(8-chloro-1-iodo-5-pyridin-3-ylimidazo[1,5-a]pyridin-6-yl)ethanone (25 mg, 0.063 mmol, Example 128, Step 1), trimethylboroxine (11 μL, 0.078 mmol, Aldrich), $K_2CO_3$ (35 mg, 0.25 mmol) and [1,1'-bis(diphenylphosphino)ferrocene]dichloropalladium(II), complex with dichloromethane (1:1), (5.1 mg, 0.0063 mmol) in DMF (1.0 mL) was heated to 140° C. in the microwave for 30 minutes. Upon cooling to room temperature, the mixture was diluted with MeCN, filtered and purified by preparative HPLC/MS (pH=10). Yield: 2.6 mg, 14%. LCMS calculated for $C_{15}H_{13}ClN_3O$ monoisotopic $(M+H)^+$: m/z=286.1; found 286.1.

Step 2. 2-Amino-N-[1-(8-chloro-1-methyl-5-pyridin-3-ylimidazo[1,5-a]pyridin-6-yl)ethyl]pyrazolo[1,5-a]pyrimidine-3-carboxamide trifluoroacetate salt (Racemic Mixture Prepared)

Using 1-(8-chloro-1-methyl-5-pyridin-3-ylimidazo[1,5-a]pyridin-6-yl)ethanone (2.6 mg, 0.0091 mmol), the procedures in Example 26, Steps 11 and 12 were followed to afford the title compound. Yield: 2.7 mg. LCMS calculated for $C_{22}H_{20}ClN_8O$ monoisotopic $(M+H)^+$: m/z=447.1; found 447.2. $^1$H NMR (400 MHz, $CD_3OD$) δ 9.19-9.14 (m, 0.5H), 8.93-8.85 (m, 1H), 8.82-8.77 (m, 1.5H), 8.69 (dd, J=6.7, 1.4 Hz, 1H), 8.53 (dd, J=4.4, 1.5 Hz, 1H), 8.51-8.48 (m, 0.5H), 8.23 (d, J=8.0 Hz, 0.5H), 7.91-7.81 (m, 1H), 7.48 (s, 1H), 6.98 (dd, J=6.7, 4.7 Hz, 1H), 4.76-4.65 (m, 1H), 2.87 (s, 3H), 2.02 (s, 3H), 1.55 (d, J=7.2 Hz, 1.5H), 1.53 (d, J=7.2 Hz, 1.5H).

Example 130. 2-Amino-N-{1-[8-chloro-5-(1H-pyrazol-3-yl)imidazo[1,5-a]pyridin-6-yl]ethyl}pyrazolo[1,5-a]pyrimidine-3-carboxamide trifluoroacetate salt (Racemic Mixture Prepared)

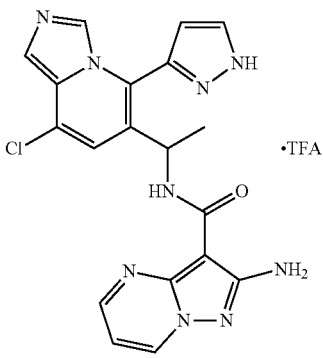 [SMILES: CC(NC(=O)c1c(N)nn2cccnc12)c1cc(Cl)c2cncn2c1-c1cc[nH]n1]

Step 1.
2,5-Dichloro-N-methoxy-N-methylnicotinamide

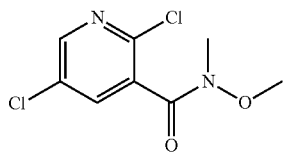

2,5-Dichloronicotinic acid (25.0 g, 120 mmol, Combi-Blocks) in DMF (500 mL) was treated with N,N-diisopropylethylamine (110 mL, 630 mmol), N-(3-dimethylaminopropyl)-N'-ethylcarbodiimide hydrochloride (30. g, 160 mmol), 1-hydroxy-7-azabenzotriazole (5 g, 40 mmol) and N,O-dimethylhydroxylamine hydrochloride (19 g, 200 mmol). The reaction was stirred for 60 hours. Water was added and the mixture was extracted with two portions of EtOAc. The combined organic extracts were washed with water, followed by brine, dried over $Na_2SO_4$, filtered and concentrated. The product was used without further purification. Yield: 30.6 g, 81%. LCMS calculated for $C_8H_9Cl_2N_2O_2$ monoisotopic (M+H)$^+$: m/z=235.0; found 234.9.

Step 2.
2,5-Dichloro-N-methoxy-N-methylnicotinamide 1-oxide

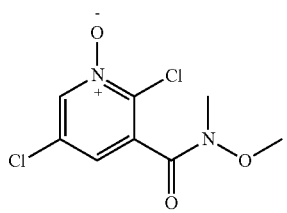

Urea hydrogen peroxide addition compound (21 g, 220 mmol) was added to 2,5-dichloro-N-methoxy-N-methylnicotinamide (24.7 g, 105 mmol) in DCM (200 mL) at 0° C. This was followed by the dropwise addition of trifluoroacetic anhydride (30 mL, 210 mmol). The reaction mixture was allowed to slowly warm to room temperature and stir overnight. A $Na_2S_2O_3$ solution was added and the mixture was stirred for 10 minutes. Saturated $NaHCO_3$ solution (200 mL) was then carefully added. Additional solid $Na_2CO_3$ was added to achieve pH=8. The layers were separated and the aqueous layer was extracted with DCM. The combined organic extracts were washed with brine, dried over $Na_2SO_4$, filtered and concentrated. The product was purified by flash chromatography (0-70% EtOAc in hexanes). Yield: 14.9 g, 57%. LCMS calculated for $C_8H_9Cl_2N_2O_3$ monoisotopic (M+H)$^+$: m/z=251.0; found 250.9.

Step 3. 2,5-Dichloro-6-cyano-N-methoxy-N-methylnicotinamide

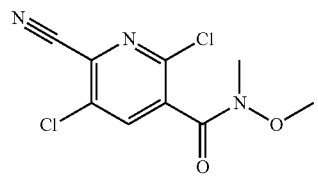 [SMILES: CON(C)C(=O)c1cc(Cl)c(C#N)nc1Cl]

2,5-Dichloro-N-methoxy-N-methylnicotinamide 1-oxide (14.9 g, 59.3 mmol) in MeCN (250 mL) and triethylamine (26 mL, 190 mmol) was treated with trimethylsilyl cyanide (20. mL, 150 mmol) dropwise at room temperature. The mixture was then heated to 70° C. for 6.5 hours. The reaction was cooled to room temperature and poured into $K_2CO_3$ solution. After stirring for 20 minutes, the layers were separated and the aqueous layer was extracted with two portions of EtOAc. The combined organic extracts were dried over $Na_2SO_4$, filtered and concentrated. The product was purified by flash chromatography (25-65% EtOAc in hexanes). Yield: 13.4 g, 87%. LCMS calculated for $C_9H_8Cl_2N_3O_2$ monoisotopic (M+H)$^+$: m/z=260.0; found 259.9.

Step 4. 6-(Aminomethyl)-2,5-dichloro-N-methoxy-N-methylnicotinamide

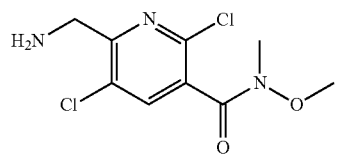 [SMILES: CON(C)C(=O)c1cc(Cl)c(CN)nc1Cl]

To a degassed solution of 2,5-dichloro-6-cyano-N-methoxy-N-methylnicotinamide (4000. mg, 15.38 mmol) in formic acid (120 mL) was rapidly added Raney® Nickel 2800 (28 mL of a slurry in water). The reaction mixture was stirred at room temperature for 5 minutes. The reaction mixture was filtered through Celite® and the filter aid was then washed with MeOH and water, and all solvents were removed in vacuo from the filtrate. To the residue was added water, and the mixture was washed once with EtOAc to remove impurities. A 6N sodium hydroxide solution was added to the aqueous layer to achieve pH=10. Formed solids were again removed by filtration through Celite®, and the filter aid was washed with excess EtOAc. The layers of the biphasic filtrate were separated, and the aqueous layer was saturated with NaCl and extracted with three additional portions of EtOAc. The combined organic extracts were dried over Na$_2$SO$_4$, filtered, and concentrated. The product was used without further purification. Yield: 2.6 g (64%). LCMS calculated for C$_9$H$_{12}$Cl$_2$N$_3$O$_2$ monoisotopic (M+H)$^+$: m/z=264.0; found 264.0.

Step 5. 2,5-Dichloro-6-[(formylamino)methyl]-N-methoxy-N-methylnicotinamide

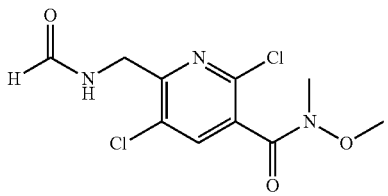 [SMILES: CON(C)C(=O)c1cc(Cl)c(CNC=O)nc1Cl]

Formic acid (24 mL, 630 mmol) and acetic anhydride (6.2 mL, 65 mmol) were stirred together for 40 minutes at room temperature, and the mixture was added dropwise into a solution of 6-(aminomethyl)-2,5-dichloro-N-methoxy-N-methylnicotinamide (5.37 g, 20.3 mmol) in DCM (130 mL) at 0° C. The mixture was stirred at 0° C. for 30 minutes, then allowed to slowly warm to room temperature overnight. Volatiles were removed in vacuo at ambient temperature, and the product was used without further purification. LCMS calculated for C$_{10}$H$_{12}$Cl$_2$N$_3$O$_3$ monoisotopic (M+H)$^+$: m/z=292.0; found 292.0.

Step 6. 5,8-Dichloro-N-methoxy-N-methylimidazo[1,5-a]pyridine-6-carboxamide

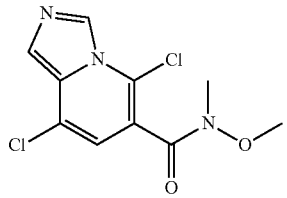 [SMILES: CON(C)C(=O)c1cc(Cl)c2cncn2c1Cl]

2,5-Dichloro-6-[(formylamino)methyl]-N-methoxy-N-methylnicotinamide (5.94 g, 20.3 mmol) in THF (300 mL) was treated with phosphoryl chloride (13 mL, 140 mmol) at room temperature for 7 hours. The reaction mixture was poured slowly onto crushed ice and the pH of the cold aqueous mixture was adjusted to pH=8 by the addition of solid K$_2$CO$_3$. Some of the THF was removed in vacuo. The organic layer was then separated and solid NaCl was added to saturate the aqueous layer. The aqueous layer was then extracted with DCM (3×). All organic extracts were combined, washed with brine, dried over Na$_2$SO$_4$, filtered and concentrated. The product was purified by flash chromatography (0-100% EtOAc/hexanes). Yield: 4.35 g, 78.0%. LCMS calculated for C$_{10}$H$_{10}$Cl$_2$N$_3$O$_2$ monoisotopic (M+H)$^+$: m/z=274.0; found 274.0.

Step 7. 1-(5,8-Dichloroimidazo[1,5-a]pyridin-6-yl)ethanone

3.0 M Methylmagnesium chloride in THF (8 mL, 20 mmol) was added to a solution of 5,8-dichloro-N-methoxy-N-methylimidazo[1,5-a]pyridine-6-carboxamide (2.1 g, 7.7 mmol) in THF (40 mL) at 0° C. The reaction was stirred for 2 hours, and then allowed to gradually warm to room temperature. The reaction was then cooled to 0° C. and was quenched by the addition of 1.0 N HCl (8 mL, 8 mmol). The mixture was diluted with water, and extracted twice with EtOAc. The combined organic extracts were washed with brine, dried over MgSO$_4$, filtered, and concentrated. The product was purified by flash chromatography (0-80% EtOAc in hexanes). Yield: 1.45 g, 81%. LCMS calculated for C$_9$H$_7$Cl$_2$N$_2$O monoisotopic (M+H)$^+$: m/z=229.0; found 229.1.

Step 8. 1-{8-Chloro-5-[1-(tetrahydro-2H-pyran-2-yl)-1H-pyrazol-5-yl]imidazo[1,5-a]pyridin-6-yl}ethanone

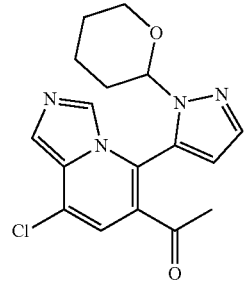 [SMILES: CC(=O)c1cc(Cl)c2cncn2c1-c1ccnn1C1CCCCO1]

A degassed mixture of 1-(5,8-dichloroimidazo[1,5-a]pyridin-6-yl)ethanone (20 mg, 0.086 mmol), 1-(tetrahydro-2H-pyran-2-yl)-5-(4,4,5,5-tetramethyl-1,3,2-dioxaborolan-2-yl)-1H-pyrazole (36 mg, 0.13 mmol, Aldrich), cesium fluoride (39 mg, 0.26 mmol) and bis(triphenylphosphine)palladium(II) chloride (6.1 mg, 0.0086 mmol) in water (0.15 mL) and 1,4-dioxane (0.4 mL) was heated to 80° C. for 3 hours, then at 70° C. overnight. Additional 1-(tetrahydro-2H-pyran-2-yl)-5-(4,4,5,5-tetramethyl-1,3,2-dioxaborolan-2-yl)-1H-pyrazole (24 mg, 0.086 mmol), cesium fluoride (39 mg, 0.26 mmol) and bis(triphenylphosphine)palladium(II) chloride (6.1 mg, 0.0086 mmol) were added and heating was continued at 85° C. for 3 hours. The mixture was cooled to room temperature and saturated NaHCO$_3$ solution was added. The mixture was extracted with EtOAc (3×). The combined organic extracts were dried over Na$_2$SO$_4$, filtered and concentrated. The product was purified by flash chromatography (0-80% EtOAc in hexanes). Yield: 14 mg, 47%. LCMS calculated for C$_{17}$H$_{18}$ClN$_4$O$_2$ monoisotopic (M+H)$^+$: m/z=345.1; found 345.1.

Step 9. 2-Amino-N-{1-[8-chloro-5-(1H-pyrazol-3-yl)imidazo[1,5-a]pyridin-6-yl]ethyl}pyrazolo[1,5-a]pyrimidine-3-carboxamide trifluoroacetate salt (Racemic Mixture Prepared)

Using 1-{8-chloro-5-[1-(tetrahydro-2H-pyran-2-yl)-1H-pyrazol-5-yl]imidazo[1,5-a]pyridin-6-yl}ethanone (14 mg, 0.041 mmol), Steps 11 and 12 of Example 26 were followed to provide the title compound. Yield: 3.9 mg. LCMS calculated for $C_{19}H_{17}ClN_9O$ monoisotopic $(M+H)^+$: m/z=422.1; found 422.1. $^1$H NMR (400 MHz, $d_6$-DMSO) δ 8.91 (dd, J=6.7, 1.5 Hz, 1H), 8.57 (dd, J=4.5, 1.5 Hz, 1H), 8.29 (s, 1H), 8.11-8.01 (m, 2H), 7.64 (s, 1H), 7.27 (s, 1H), 7.01 (dd, J=6.7, 4.5 Hz, 1H), 6.88 (d, J=2.3 Hz, 1H), 5.11 (p, J=7.1 Hz, 1H), 1.52 (d, J=7.0 Hz, 3H).

Examples 131-138

The following Examples of Table 10 were prepared as in Example 130, using appropriately substituted boronic esters, boronic acids or stannanes as starting materials in Step 8. NMR data for the compounds of Table 10 are provided in Table 10a.

TABLE 10

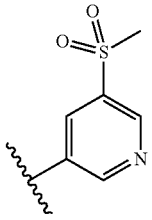 [SMILES: *c1cncc(S(C)(=O)=O)c1]

| Ex. No. | Name | R = | LCMS |
|---|---|---|---|
| 131 | 2-Amino-N-(1-{8-chloro-5-[5-(methylsulfonyl)pyridin-3-yl]imidazo[1,5-a]pyridin-6-yl}-ethyl)pyrazolo[1,5-a]pyrimidine-3-carboxamide trifluoroacetate salt (racemic mixture prepared) | 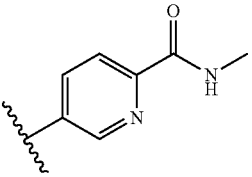 [SMILES: *c1ccc(C(=O)NC)nc1] | Calculated for $C_{22}H_{20}ClN_8O_3S$ monoisotopic $(M + H)^+$: m/z = 511.1; found: 511.1 |
| 132 | 2-Amino-N-(8-chloro-5-{6-[(methylamino)carbonyl]pyridin-3-yl}imidazo-[1,5-a]pyridin-6-yl)ethyl]pyrazolo[1,5-a]pyrimidine-3-carboxamide trifluoroacetate salt (racemic mixture prepared) | 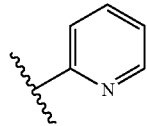 | Calculated for $C_{23}H_{21}ClN_9O_2$ monoisotopic $(M + H)^+$: m/z = 490.1; found: 490.1 |
| 133 | 2-Amino-N-[1-(8-chloro-5-pyridin-2-ylimidazo[1,5-a]pyridin-6-yl)ethyl]-pyrazolo[1,5-a]pyrimidine-3-carboxamide trifluoroacetate salt (racemic mixture prepared) | 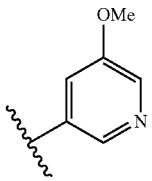 [SMILES: *c1cncc(OC)c1] | Calculated for $C_{21}H_{18}ClN_8O$ monoisotopic $(M + H)^+$: m/z = 433/1; found 433.1 |
| 134 | 2-Amino-N-{1-[8-chloro-5-(5-methoxypyridin-3-yl)imidazo[1,5-a]pyridin-6-yl]ethyl}pyrazolo[1,5-a]pyrimidine-3-carboxamide trifluoroacetate salt (racemic mixture prepared) | OMe | Calculated for $C_{22}H_{20}ClN_8O_2$ monoisotopic $(M + H)^+$: m/z = 463.1; found: 463.1 |

TABLE 10-continued

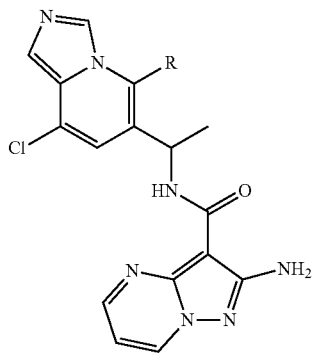

| Ex. No. | Name | R = | LCMS |
|---|---|---|---|
| 135 | 2-Amino-N-[1-(8-chloro-5-{4-[(methyl-amino)sulfonyl]phenyl}imidazo[1,5-a]pyridin-6-yl)ethyl]pyrazolo[1,5-a]-pyrimidine-3-carboxamide trifluoroacetate salt (racemic mixture prepared) | | Calculated for $C_{23}H_{22}ClN_8O_3S$ isotopic $(M + H)^+$: m/z = 525.1; found: 525.1 |
| 136 | 2-Amino-N-(1-{8-chloro-5-[4-(methyl-sulfonyl)phenyl]imidazo[1,5-a]pyridin-6-yl}ethyl)pyrazolo[1,5-a]pyrimidine-3-carboxamide trifluoroacetate salt (racemic mixture prepared) | | Calculated for $C_{23}H_{21}ClN_7O_3S$ monoisotopic $(M + H)^+$: m/z = 510.1; found: 510.1 |
| 137 | 2-Amino-N-{1-[8-chloro-5-(5-cyano-pyridin-3-yl)imidazo[1,5-a]pyridin-6-yl]ethyl}pyrazolo[1,5-a]pyrimidine-3-carboxamide trifluoroacetate salt (racemic mixture prepared) | | Calculated for $C_{22}H_{17}ClN_9O$ monoisotopic $(M + H)^+$: m/z = 458.1; found: 458.1 |
| 138 | 2-Amino-N-[1-(8-chloro-5-pyrazin-2-ylimidazo[1,5-a]pyridin-6-yl)ethyl]-pyrazolo[1,5-a]pyrimidine-3-carbox-amide trifluoroacetate salt (racemic mixture prepared) | | Calculated for $C_{20}H_{17}ClN_9O$ monoisotopic $(M + H)^+$: m/z = 434.1; found: 434.1 |

TABLE 10a

| Ex. No. | $^1$H NMR |
|---|---|
| 131 | $^1$H NMR (400 MHz, $d_6$-DMSO) δ 9.33 (d, J = 1.9 Hz, 0.5H), 9.31 (d, J = 2.2 Hz, 0.5H), 9.29 (d, J = 2.2 Hz, 0.5H), 9.12 (d, J = 1.9 Hz, 0.5H), 8.93-8.88 (m, 1H), 8.76 (t, J = 2.0 Hz, 0.5H), 8.64 (t, J = 2.0 Hz, 0.5H), 8.57-8.53 (m, 1H), 8.14 (s, 0.5H), 8.13 (s, 0.5H), 8.03 (d, J = 6.6 Hz, 0.5H), 8.01 (d, J = 6.9 Hz, 0.5H), 7.74 (s, 0.5H), 7.73 (s, 0.5H), 7.45 (s, 0.5H), 7.38 (s, 0.5H), 7.01 (dd, J = 6.5, 4.8 Hz, 1H), 4.63 (p, J = 6.8 Hz, 0.5H), 4.58 (p, J = 6.9 Hz, 0.5H), 3.42 (s, 1.5H), 3.42 (s, 1.5H), 1.51 (d, J = 7.0 Hz, 1.5H), 1.46 (d, J = 7.0 Hz, 1.5H) |
| 132 | $^1$H NMR (400 MHz, $d_6$-DMSO) δ 9.11-9.06 (m, 0.5H), 9.05-9.00 (m, 0.5H), 8.93-8.86 (m, 1.5H), 8.80-8.78 (m, 0.5H), 8.56-8.53 (m, 0.5H), 8.51-8.49 (m, 0.5H), 8.43-8.38 (m, 0.5H), 8.32-8.18 (m, 1.5H), 8.00 (d, J = 6.3 Hz, 0.5H), 7.94 (d, J = 6.5 Hz, 0.5H), 7.90 (s, 0.5H), 7.89 (s, 0.5H), 7.63 (s, 1H), 7.33 (s, 0.5H), 7.32 (s, 0.5H), 7.04-6.97 (m, 1H), 6.41 (br s, 2H), 4.65 (p, J = 7.0 Hz, 1H), 2.88 (d, J = 4.0 Hz, 1.5H), 2.87 (d, J = 4.0 Hz, 1.5H), 1.50 (d, J = 7.0 Hz, 1.5H), 1.45 (d, J = 7.0 Hz, 1.5H). |
| 133 | $^1$H NMR (400 MHz, $d_6$-DMSO) δ 8.91 (dd, J = 6.7, 1.5 Hz, 1H), 8.87-8.85 (m, 1H), 8.56 (dd, J = 4.5, 1.5 Hz, 1H), 8.13 (td, J = 7.7, 1.6 Hz, 1H), 8.03 (d, J = 6.5 Hz, 1H), 8.00 (d, 1H), 7.99 (s, 1H), 7.67 (s, 1H), 7.65-7.61 (m, 1H), 7.33 (s, 1H), 7.01 (dd, J = 6.7, 4.5 Hz, 1H), 4.88 (p, J = 6.8 Hz, 1H), 1.47 (d, J = 7.0 Hz, 3H) |

TABLE 10a-continued

| Ex. No. | ¹H NMR |
|---|---|
| 134 | ¹H NMR (400 MHz, CD$_3$OD) δ 8.69 (dd, J = 6.8, 1.2 Hz, 1H), 8.65-8.62 (m, 1H), 8.60-8.57 (m, 0.5H), 8.56-8.51 (m, 1H), 8.50-8.47 (m, 0.5H), 8.47-8.43 (m, 0.5H), 8.36-8.34 (m, 0.5H), 8.07-8.04 (m, 0.5H), 8.03 (s, 1H), 7.70-7.64 (m, 0.5H), 7.52 (s, 0.5H), 7.51 (s, 0.5H), 7.00-6.96 (m, 1H), 4.93-4.87 (m, 1H), 4.00 (s, 1.5H), 3.84 (s, 1.5H), 1.57 (d, J = 7.0 Hz, 1.5H), 1.56 (d, J = 7.1 Hz, 1.5H) |
| 135 | ¹H NMR (400 MHz, d$_6$-DMSO) δ 8.92 (dd, J = 6.7, 1.6 Hz, 1H), 8.55 (dd, J = 4.5, 1.6 Hz, 1H), 8.09-7.99 (m, 4H), 7.97 (s, 1H), 7.85 (d, J = 8.1 Hz, 1H), 7.73 (s, 1H), 7.66 (q, J = 4.9 Hz, 1H), 7.36 (s, 1H), 7.01 (dd, J = 6.7, 4.5 Hz, 1H), 4.68 (p, J = 7.1 Hz, 1H), 2.54 (d, J = 4.9 Hz, 3H), 1.45 (d, J = 7.0 Hz, 3H) |
| 136 | ¹H NMR (400 MHz, d$_6$-DMSO) δ 8.92 (dd, J = 6.7, 1.5 Hz, 1H), 8.56 (dd, J = 4.5, 1.5 Hz, 1H), 8.25 (dd, J = 8.1, 1.8 Hz, 1H), 8.17 (dd, J = 8.1, 1.7 Hz, 1H), 8.12 (dd, J = 8.0, 1.2 Hz, 1H), 8.04 (d, J = 6.3 Hz, 1H), 7.95 (s, 1H), 7.90 (dd, J = 8.1, 1.3 Hz, 1H), 7.73 (s, 1H), 7.36 (s, 1H), 7.01 (dd, J = 6.7, 4.5 Hz, 1H), 4.67 (p, J = 6.6 Hz, 1H), 3.36 (s, 3H), 1.46 (d, J = 7.0 Hz, 3H) |
| 137 | ¹H NMR (400 MHz, d$_6$-DMSO) δ 9.28-9.24 (m, 1.5H), 9.06 (d, J = 2.1 Hz, 0.5H), 8.93 (dd, J = 2.9, 1.8 Hz, 0.5H), 8.91 (dd, J = 3.0, 1.7 Hz, 0.5H), 8.76 (t, J = 2.0 Hz, 0.5H), 8.67 (t, J = 2.0 Hz, 0.5H), 8.55 (dd, J = 4.4, 1.6 Hz, 1H), 7.99 (d, J = 6.2 Hz, 1H), 7.97 (s, 1H), 7.62 (s, 1H), 7.35 (s, 0.5H), 7.31 (s, 0.5H), 7.03-6.99 (m, 1H), 4.64-4.53 (m, 1H), 1.51 (d, J = 7.0 Hz, 1.5H), 1.45 (d, J = 7.0 Hz, 1.5H) |
| 138 | ¹H NMR (400 MHz, d$_6$-DMSO) δ 9.20 (s, 1H), 8.94 (dd, J = 2.3, 1.6 Hz, 1H), 8.91 (dd, J = 6.8, 1.6 Hz, 1H), 8.88 (d, J = 2.5 Hz, 1H), 8.55 (dd, J = 4.5, 1.5 Hz, 1H), 8.08 (s, 1H), 8.01 (d, J = 6.4 Hz, 1H), 7.65 (s, 1H), 7.35 (s, 1H), 7.01 (dd, J = 6.7, 4.5 Hz, 1H), 4.80 (p, J = 6.8 Hz, 1H), 1.50 (d, J = 7.0 Hz, 3H) |

Example 139. 2-Amino-N-{1-[8-chloro-5-(1H-pyrazol-4-yl)imidazo[1,5-a]pyridin-6-yl]ethyl}pyrazolo[1,5-a]pyrimidine-3-carboxamide trifluoroacetate salt (Racemic Mixture Prepared)

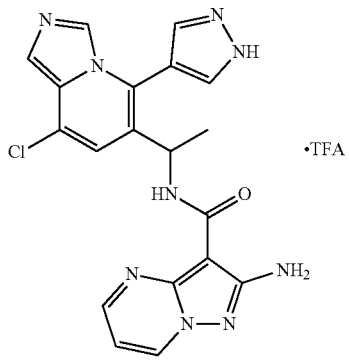 [SMILES: CC(NC(=O)c1c(N)nn2cccnc12)c1cc(Cl)c2cncn2c1-c1cn[nH]c1]

Step 1. Methyl 5-chloro-6-cyano-2-(1H-pyrazol-4-yl)nicotinate

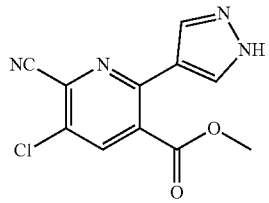 [SMILES: COC(=O)c1cc(Cl)c(C#N)nc1-c1cn[nH]c1]

A degassed mixture of methyl 2,5-dichloro-6-cyanonicotinate (1.5 g, 6.5 mmol, Example 26, Step 3), tert-butyl 4-(4,4,5,5-tetramethyl-1,3,2-dioxaborolan-2-yl)-1H-pyrazole-1-carboxylate (3.8 g, 13 mmol, Aldrich), cesium fluoride (3.0 g, 19 mmol) and bis(triphenylphosphine)palladium (II) chloride (0.27 g, 0.39 mmol) in water (11.4 mL) and 1,4-dioxane (29.6 mL) was heated to 80° C. for 3 hours, then overnight at 70° C. Only the Boc-deprotected product was observed. Upon cooling to room temperature, saturated NaHCO$_3$ was added, and the mixture was extracted with EtOAc. The EtOAc extract was dried over Na$_2$SO$_4$, filtered and concentrated. The product was purified by flash chromatography (0-50% EtOAc in hexanes). Yield: 1.4 g, 82%. LCMS calculated for C$_{11}$H$_8$ClN$_4$O$_2$ monoisotopic (M+H)$^+$: m/z=263.0; found: 263.1.

Step 2. tert-Butyl {3-[({1-[8-chloro-5-(1H-pyrazol-4-yl)imidazo[1,5-a]pyridin-6-yl]ethyl}amino)carbonyl]pyrazolo[1,5-a]pyrimidin-2-yl}carbamate

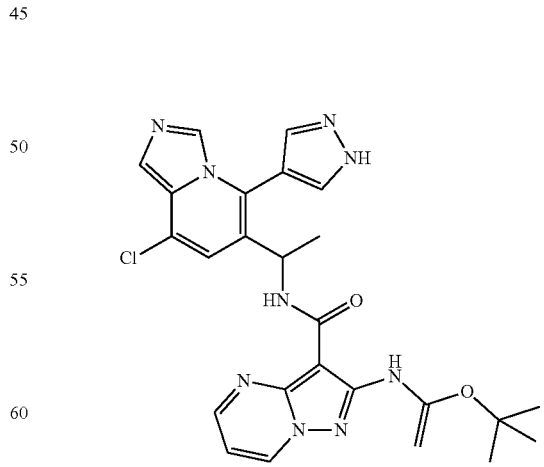

Using methyl 5-chloro-6-cyano-2-(1H-pyrazol-4-yl)nicotinate, Example 27, Steps 2-9 were followed to afford the title compound. LCMS calculated for C$_{24}$H$_{25}$ClN$_9$O$_3$ monoisotopic (M+H)$^+$: m/z=522.2; found: 522.1.

Step 3. 2-Amino-N-{1-[8-chloro-5-(1H-pyrazol-4-yl)imidazo[1,5-a]pyridin-6-yl]ethyl}pyrazolo[1,5-a]pyrimidine-3-carboxamide trifluoroacetate salt (Racemic Mixture Prepared)

The method of Example 27, Step 10 was followed, starting with tert-butyl {3-[({1-[8-chloro-5-(1H-pyrazol-4-yl)imidazo[1,5-a]pyridin-6-yl]ethyl}amino)carbonyl]pyrazolo[1,5-a]pyrimidin-2-yl}carbamate (10. mg, 0.019 mmol) to afford the title compound. Yield: 8.5 mg. LCMS calculated for $C_{19}H_{17}ClN_9O$ monoisotopic (M+H)$^+$: m/z=422.1; found: 422.1. $^1$H NMR (400 MHz, d$_6$-DMSO) δ 8.91 (dd, J=6.7, 1.5 Hz, 1H), 8.56 (dd, J=4.5, 1.6 Hz, 1H), 8.32 (s, 1H), 8.16 (s, 1H), 8.07 (d, J=6.6 Hz, 1H), 7.73 (s, 1H), 7.31 (s, 1H), 7.01 (dd, J=6.7, 4.5 Hz, 1H), 4.98 (p, J=6.8 Hz, 1H), 1.46 (d, J=7.0 Hz, 3H).

Example 140. 2-Amino-N-{1-[8-chloro-5-(1-methyl-1H-pyrazol-4-yl)imidazo[1,5-a]pyridin-6-yl]ethyl}pyrazolo[1,5-a]pyrimidine-3-carboxamide trifluoroacetate salt (Racemic Mixture Prepared)

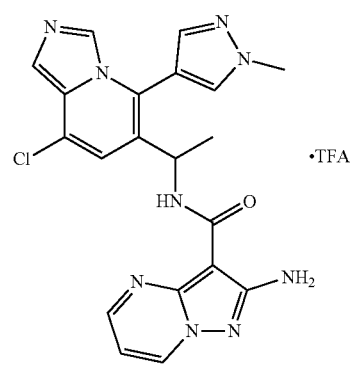 [SMILES: CC(NC(=O)c1c(N)nn2cccnc12)c1cc(Cl)c2cncn2c1-c1cnn(C)c1]

tert-Butyl{3[({1-[8-chloro-5-1H-pyrazol-4-yl)imidazo[1,5-a]pyridin-6-yl]ethyl}amino)carbonyl]pyrazolo[1,5-a]pyrimidin-2-yl}carbamate (12 mg, 0.023 mmol, Example 139, Step 2) in DMF (0.20 mL) was treated with Cs$_2$CO$_3$ (15 mg, 0.046 mmol) and MeI (0.10 mL of a stock solution prepared from adding 0.16 mL MeI to 10 mL of DMF). The reaction was stirred for 15 minutes, then was diluted with DCM, filtered, and concentrated. The residue was stirred with TFA (0.1 mL) in DCM (0.7 mL) for 2 hours. Volatiles were removed in vacuo and the product was purified by preparative HPLC/MS (pH=2). Yield: 5.9 mg. LCMS calculated for $C_{20}H_{19}ClN_9O$ monoisotopic (M+H)$^+$: m/z=436.1; found: 436.1. $^1$H NMR (400 MHz, d$_6$-DMSO) δ 8.92 (dd, J=6.7, 1.4 Hz, 1H), 8.57 (dd, J=4.5, 1.4 Hz, 1H), 8.38 (s, 1H), 8.28 (s, 1H), 8.07 (d, J=6.5 Hz, 1H), 7.92 (s, 1H), 7.72 (s, 1H), 7.29 (s, 1H), 7.02 (dd, J=6.7, 4.6 Hz, 1H), 5.00 (p, J=6.6 Hz, 1H), 4.00 (s, 3H), 1.47 (d, J=7.0 Hz, 3H).

Example 141. 2-Amino-N-(1-{8-chloro-5-[4-(methylsulfonyl)piperazin-1-yl]imidazo[1,5-a]pyridin-6-yl}ethyl)pyrazolo[1,5-a]pyrimidine-3-carboxamide trifluoroacetate salt (Racemic Mixture Prepared)

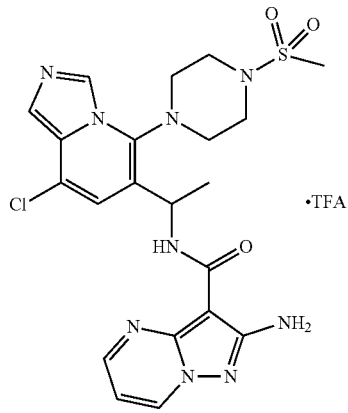 [SMILES: CC(NC(=O)c1c(N)nn2cccnc12)c1cc(Cl)c2cncn2c1N1CCN(S(C)(=O)=O)CC1]

Step 1. tert-Butyl 4-[5-chloro-6-cyano-3-(methoxycarbonyl)pyridin-2-yl]piperazine-1-carboxylate

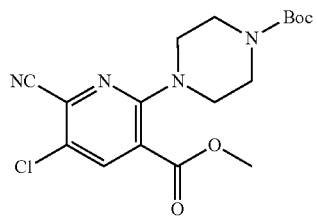 [SMILES: COC(=O)c1cc(Cl)c(C#N)nc1N1CCN(C(=O)OC(C)(C)C)CC1]

A mixture of methyl 2,5-dichloro-6-cyanonicotinate (370 mg, 1.6 mmol, Example 26, Step 3), tert-butyl piperazine-1-carboxylate (300 mg, 2 mmol, Aldrich) and Cs$_2$CO$_3$ (1 g, 3 mmol) in acetonitrile (3 mL) was heated to 70° C. for 1 hour. Upon cooling, the reaction mixture was partitioned between EtOAc and water. The organic layer was washed with brine, dried over MgSO$_4$, filtered and concentrated. The product was purified by flash chromatography (0-50% EtOAc in hexanes). Yield: 0.45 g, 74%. LCMS calculated for $C_{17}H_{22}ClN_4O_4$ monoisotopic (M+H)$^+$: m/z=381.1; found 381.1.

Step 2. tert-Butyl 4-[6-(aminomethyl)-5-chloro-3-(methoxycarbonyl)pyridin-2-yl]piperazine-1-carboxylate

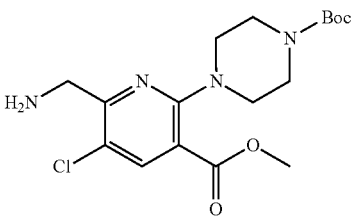 [SMILES: COC(=O)c1cc(Cl)c(CN)nc1N1CCN(C(=O)OC(C)(C)C)CC1]

tert-Butyl 4-[5-chloro-6-cyano-3-(methoxycarbonyl)pyridin-2-yl]piperazine-1-carboxylate (450 mg, 1.2 mmol) in methanol (10 mL) was treated with Raney® Nickel 2800 (200 µL of a slurry in water) and stirred under H₂ at 20 psi for 2 hours. The reaction mixture was filtered and solvent was removed in vacuo. The product was used without further purification. Yield: 0.40 g, 90%. LCMS calculated for $C_{17}H_{26}ClN_4O_4$ monoisotopic (M+H)⁺: m/z=385.2; found 385.1.

Step 3. Methyl 8-chloro-5-piperazin-1-ylimidazo[1,5-a]pyridine-6-carboxylate

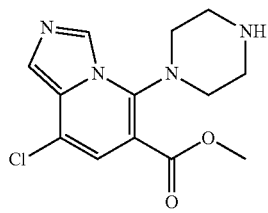 [SMILES: COC(=O)c1cc(Cl)c2cncn2c1N1CCNCC1]

Formic acid (3.5 mL) and acetic anhydride (0.90 mL) were stirred for 40 minutes at room temperature, then the mixture was added dropwise into a 0° C. solution of tert-butyl 4-[6-(aminomethyl)-5-chloro-3-(methoxycarbonyl)pyridin-2-yl]piperazine-1-carboxylate (720 mg, 1.9 mmol) in DCM (10. mL). The mixture was stirred for 50 minutes at 0° C., then warmed to room temperature and stirred overnight. Solvents were removed in vacuo and the residue was dissolved in phosphoryl chloride (6 mL, 60 mmol) and heated to 75° C. for 1 hour. Upon cooling to room temperature, the mixture was poured into ice and saturated NaHCO₃ was added to neutralize to pH=7. The mixture was extracted with DCM. The combined organic extracts were washed with brine, dried over MgSO₄, filtered and concentrated. The product was used without further purification. Yield: 0.22 g, 40%. LCMS calculated for $C_{13}H_{16}ClN_4O_2$ monoisotopic (M+H)⁺: m/z=295.1; found 295.0.

Step 4. Methyl 5-[4-(tert-butoxycarbonyl)piperazin-1-yl]-8-chloroimidazo[1,5-a]pyridine-6-carboxylate

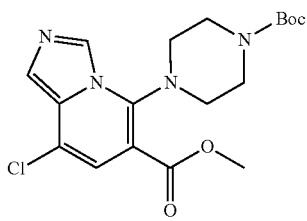 [SMILES: COC(=O)c1cc(Cl)c2cncn2c1N1CCN(C(=O)OC(C)(C)C)CC1]

di-tert-Butyldicarbonate (380 mg, 1.7 mmol) was added to a mixture of methyl 8-chloro-5-piperazin-1-ylimidazo[1,5-a]pyridine-6-carboxylate (220 mg, 0.75 mmol) and NaHCO₃ (380 mg, 4.5 mmol) in THF (9 mL) and water (6 mL). The reaction was stirred overnight, then concentrated in vacuo. The residue was partitioned between EtOAc and water. The organic layer was washed with brine, dried over MgSO₄, filtered and concentrated. The product was purified by flash chromatography (0-100% EtOAc in hexanes). Yield: 0.20 g, 70%. LCMS calculated for $C_{18}H_{24}ClN_4O_4$ monoisotopic (M+H)⁺: m/z=395.1; found 395.2.

Step 5. tert-Butyl 4-(6-acetyl-8-chloroimidazo[1,5-a]pyridin-5-yl)piperazine-1-carboxylate

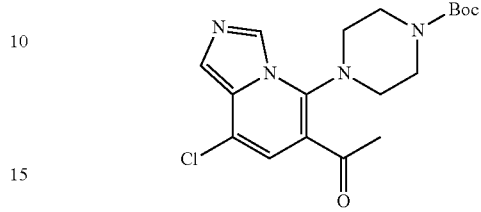

Using methyl 5-[4-(tert-butoxycarbonyl)piperazin-1-yl]-8-chloroimidazo[1,5-a]pyridine-6-carboxylate, Steps 8-10 of Example 26 were followed to afford the title compound. LCMS calculated for $C_{18}H_{24}ClN_4O_3$ monoisotopic (M+H)⁺: m/z=379.2; found 379.2.

Step 6. 1-(8-Chloro-5-piperazin-1-ylimidazo[1,5-a]pyridin-6-yl)ethanone hydrochloride salt

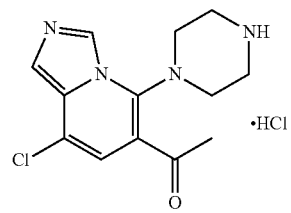 [SMILES: CC(=O)c1cc(Cl)c2cncn2c1N1CCNCC1 ; Cl]

4.0 M Hydrogen chloride in dioxane (2 mL, 8 mmol) was added to a solution of tert-butyl 4-(6-acetyl-8-chloroimidazo[1,5-a]pyridin-5-yl)piperazine-1-carboxylate (70 mg, 0.2 mmol) in 1,4-dioxane (2 mL). The reaction was stirred for 30 minutes, and the volatiles were removed in vacuo. The product was used without further purification. Yield: 0.060 g, 100%. LCMS calculated for $C_{13}H_{16}ClN_4O$ monoisotopic (M+H)⁺: m/z=279.1; found 279.2.

Step 7. 1-{8-Chloro-5-[4-(methylsulfonyl)piperazin-1-yl]imidazo[1,5-a]pyridin-6-yl}ethanone

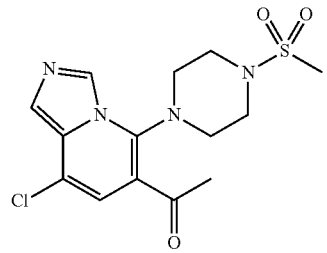 [SMILES: CC(=O)c1cc(Cl)c2cncn2c1N1CCN(S(C)(=O)=O)CC1]

Methanesulfonyl chloride (11 µL, 0.14 mmol) was added to a solution of 1-(8-chloro-5-piperazin-1-ylimidazo[1,5-a]pyridin-6-yl)ethanone hydrochloride salt (30 mg, 0.1 mmol) and N,N-diisopropylethylamine (80 µL, 0.5 mmol) in DCM (2 mL). The reaction was stirred for 30 minutes and volatiles were removed in vacuo. The product was used without further purification. Yield: 0.030 g, 90%. LCMS calculated for $C_{14}H_{18}ClN_4O_3S$ monoisotopic $(M+H)^+$: m/z=357.1; found 357.1.

Step 8. 2-Amino-N-(1-{8-chloro-5-[4-(methylsulfonyl)piperazin-1-yl]imidazo[1,5-a]pyridin-6-yl}ethyl)pyrazolo[1,5-a]pyrimidine-3-carboxamide trifluoroacetate salt (Racemic Mixture Prepared)

Using 1-{8-chloro-5-[4-(methylsulfonyl)piperazin-1-yl]imidazo[1,5-a]pyridin-6-yl}ethanone (30. mg, 0.08 mmol), Steps 11 and 12 of Example 26 were followed to afford the title compound. Yield: 3.0 mg. LCMS calculated for $C_{21}H_{25}ClN_9O_3S$ monoisotopic $(M+H)^+$: m/z=518.1; found 518.1. $^1H$ NMR (600 MHz, $d_6$-DMSO) δ 8.91 (dd, J=6.7, 1.6 Hz, 1H), 8.79 (s, 1H), 8.56 (dd, J=4.5, 1.6 Hz, 1H), 8.09 (d, J=6.9 Hz, 1H), 7.63 (s, 1H), 7.15 (s, 1H), 7.01 (dd, J=6.7, 4.5 Hz, 1H), 6.45 (br s, 2H), 5.48 (p, J=6.9 Hz, 1H), 3.59-3.26 (m, 8H), 2.99 (s, 3H), 1.54 (d, J=7.0 Hz, 3H).

Example 142. 2-Amino-N-[1-(8-chloro-5-pyrrolidin-1-ylimidazo[1,5-a]pyridin-6-yl)ethyl]pyrazolo[1,5-a]pyrimidine-3-carboxamide trifluoroacetate salt (Racemic Mixture Prepared)

Step 1. Methyl 5-chloro-6-cyano-2-pyrrolidin-1-ylnicotinate

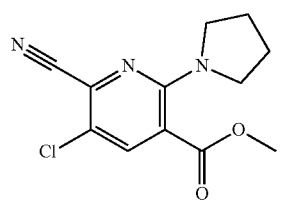 [SMILES: COC(=O)c1cc(Cl)c(C#N)nc1N1CCCC1]

A mixture of methyl 2,5-dichloro-6-cyanonicotinate (300 mg, 1 mmol, Example 26, Step 3), pyrrolidine (90 mg, 1 mmol), and $Cs_2CO_3$ (800 mg, 2 mmol) in acetonitrile (2 mL) was heated to 70° C. for 1 hour. Upon cooling, the reaction mixture was partitioned between EtOAc and water, and the organic layer was washed with brine, dried over $MgSO_4$, filtered and concentrated. The product was purified by flash chromatography (0-100% EtOAc in hexanes). Yield: 300 mg, 90%. LCMS calculated for $C_{12}H_{13}ClN_3O_2$ monoisotopic $(M+H)^+$: m/z=266.1; found: 266.1.

Step 2. 1-(8-Chloro-5-pyrrolidin-1-ylimidazo[1,5-a]pyridin-6-yl)ethanone

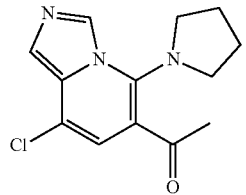 [SMILES: CC(=O)c1cc(Cl)c2cncn2c1N1CCCC1]

Using methyl 5-chloro-6-cyano-2-pyrrolidin-1-ylnicotinate, Steps 2 through 7 of Example 27 were followed to afford the title compound. LCMS calculated for $C_{13}H_{15}ClN_3O$ monoisotopic $(M+H)^+$: m/z=264.1; found: 264.1.

Step 3. 1-(8-Chloro-5-pyrrolidin-1-ylimidazo[1,5-a]pyridin-6-yl)ethanamine (Racemic Mixture Prepared)

A mixture of 1-(8-chloro-5-pyrrolidin-1-ylimidazo[1,5-a]pyridin-6-yl)ethanone (80 mg, 0.3 mmol), ammonium acetate (440 mg, 5.7 mmol), and sodium cyanoborohydride (120 mg, 1.9 mmol) in methanol (12 mL) was heated to 65° C. overnight in a sealed reaction vessel. Upon cooling, water and methanol were added and the mixture was filtered and purified by preparative HPLC/MS (pH=10). Yield: 8.0 mg, 10%. LCMS calculated for $C_{13}H_{18}ClN_4$ monoisotopic $(M+H)^+$: m/z=265.1; found: 265.1.

Step 4. 2-Amino-N-[1-(8-chloro-5-pyrrolidin-1-ylimidazo[1,5-a]pyridin-6-yl)ethyl]pyrazolo[1,5-a]pyrimidine-3-carboxamide trifluoroacetate salt (Racemic Mixture Prepared)

Using 1-(8-chloro-5-pyrrolidin-1-ylimidazo[1,5-a]pyridin-6-yl)ethanamine (racemic) (6.0 mg, 0.02 mmol), the method of Example 26, Step 12 was followed to afford the title compound. Yield: 3.0 mg. LCMS calculated for $C_{20}H_{22}ClN_8O$ monoisotopic $(M+H)^+$: m/z=425.2; found: 425.3. $^1H$ NMR (400 MHz, $CD_3OD$) δ 9.20 (s, 1H), 8.69 (dd, J=6.8, 1.5 Hz, 1H), 8.55 (dd, J=4.5, 1.5 Hz, 1H), 8.03 (s, 1H), 7.40 (s, 1H), 6.98 (dd, J=6.8, 4.5 Hz, 1H), 5.43 (q, J=6.9 Hz, 1H), 3.69-3.54 (m, 2H), 3.49-3.38 (m, 2H), 2.25-2.16 (m, 4H), 1.63 (d, J=7.0 Hz, 3H).

Example 143. 2-Amino-N-{1-[8-chloro-5-(4-methoxypiperidin-1-yl)imidazo[1,5-a]pyridin-6-yl]ethyl}pyrazolo[1,5-a]pyrimidine-3-carboxamide (Racemic Mixture Prepared)

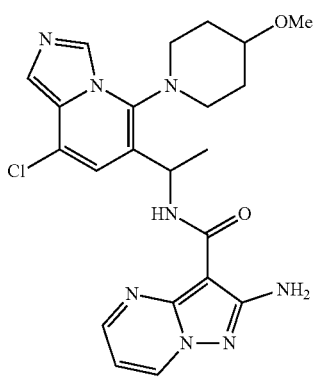 [SMILES: COC1CCN(c2c(C(C)NC(=O)c3c(N)nn4cccnc34)cc(Cl)c3cncn23)CC1]

Step 1. 1-[8-Chloro-5-(4-methoxypiperidin-1-yl)imidazo[1,5-a]pyridin-6-yl]ethanamine (Racemic Mixture Prepared)

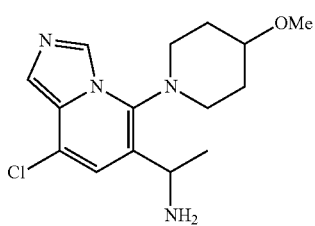 [SMILES: COC1CCN(c2c(C(C)N)cc(Cl)c3cncn23)CC1]

Titanium tetraisopropoxide (300 μL, 1 mmol) was added to 1-[8-chloro-5-(4-methoxypiperidin-1-yl)imidazo[1,5-a]pyridin-6-yl]ethanone (50 mg, 0.2 mmol, prepared by the method of Example 142, Steps 1 and 2, using 4-methoxy piperidine in Step 1) in 2.0 M ammonia in ethanol (800 μL, 2 mmol) and the reaction mixture was heated to 65° C. in a sealed vial overnight. The reaction mixture was then cooled to 0° C. and sodium borohydride (9.6 mg, 0.26 mmol) was added. After stirring for 1 hour, the reaction was quenched by the addition of 1N NH$_4$OH. Formed solids were removed by filtration and washed with acetonitrile. The filtrate was evaporated to dryness, reconstituted with EtOAc, dried using MgSO$_4$, filtered and concentrated. The product was used without further purification. Yield: 40 mg, 30%. LCMS calculated for C$_{15}$H$_{22}$ClN$_4$O monoisotopic (M+H)$^+$: m/z=309.1; found: 309.1.

Step 2. tert-Butyl {3-[({1-[8-chloro-5-(4-methoxypiperidin-1-yl)imidazo[1,5-a]pyridin-6-yl]ethyl}amino)carbonyl]pyrazolo[1,5-a]pyrimidin-2-yl}carbamate (Racemic Mixture Prepared)

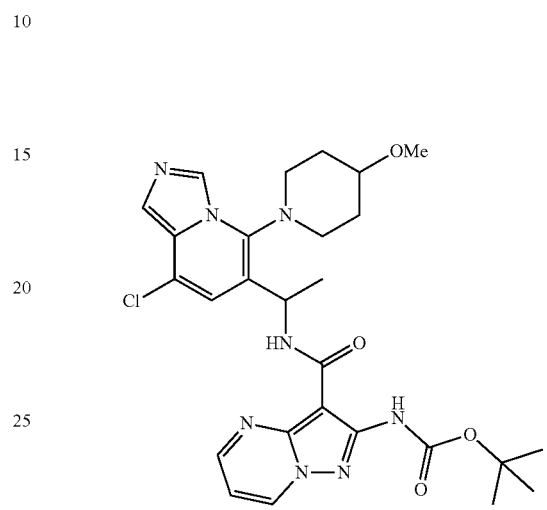

Using 1-[8-chloro-5-(4-methoxypiperidin-1-yl)imidazo[1,5-a]pyridin-6-yl]ethanamine (20 mg, 0.06 mmol), the method of Example 27, Step 9 was followed to afford the title compound. The racemic product was used without further purification. LCMS calculated for C$_{27}$H$_{34}$ClN$_8$O$_4$ monoisotopic (M+H)$^+$: m/z=569.2; found: 569.2.

Step 3. 2-Amino-N-{1-[8-chloro-5-(4-methoxypiperidin-1-yl)imidazo[1,5-a]pyridin-6-yl]ethyl}pyrazolo[1,5-a]pyrimidine-3-carboxamide (Racemic Mixture Prepared)

Using tert-butyl {3-[({1-[8-chloro-5-(4-methoxypiperidin-1-yl)imidazo[1,5-a]pyridin-6-yl]ethyl}amino)carbonyl]pyrazolo[1,5-a]pyrimidin-2-yl}carbamate (racemic), the method of Example 27, Step 10 was used to afford the title compound. The product was purified using the pH=10 method. Yield: 7 mg over the two steps. LCMS calculated for C$_{22}$H$_{26}$ClN$_8$O$_2$ monoisotopic (M+H)$^+$: m/z=469.2; found: 469.2. $^1$H NMR (400 MHz, d$_6$-DMSO) δ 8.92 (dd, J=6.7, 1.4 Hz, 1H), 8.58-8.55 (m, 1H), 8.52 (s, 0.6H), 8.32 (s, 0.4H), 8.10-8.03 (m, 1H), 7.46 (s, 1H), 7.05 (s, 0.4H), 7.03-6.99 (m, 1.6H), 6.42 (s, 2H), 5.53-5.44 (m, 0.6H), 5.45-5.35 (m, 0.4H), 3.55-3.09 (m, 8H), 2.11-1.96 (m, 2H), 1.80-1.60 (m, 2H), 1.54 (d, J=7.0 Hz, 1.2H), 1.52 (d, J=7.0 Hz, 1.8H).

Examples 144-145

Examples 144-145 in Table 11 were prepared according to the method of Example 143. NMR data for the compounds of Table 11 are provided in Table 11a.

TABLE 11

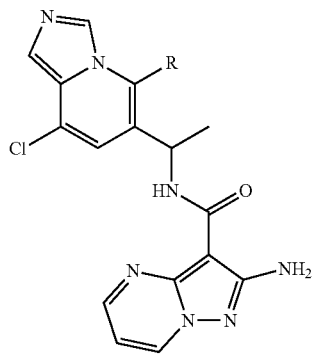

| Ex. No. | Name | R = | LCMS |
|---|---|---|---|
| 144 | 2-Amino-N-{1-[8-chloro-5-(3-methoxy-pyrrolidin-1-yl)imidazo[1,5-a]pyridin-6-yl]ethyl}pyrazolo[1,5-a]pyrimidine-3-carboxamide trifluoroacetate salt (mixture of diastereomers prepared) | 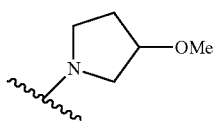 [SMILES: *N1CCC(OC)C1] | Calculated for $C_{21}H_{24}ClN_8O_2$ monoisotopic (M + H)+: m/z = 455.2; found: 455.2 |
| 145 | 2-Amino-N-[1-(8-chloro-5-morpholin-4-ylimidazo[1,5-a]pyridin-6-yl)ethyl]-pyrazolo[1,5-a]pyrimidine-3-carbox-amide trifluoroacetate salt (racemic mixture prepared) | 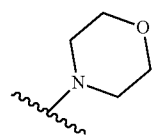 [SMILES: *N1CCOCC1] | Calculated for $C_{20}H_{22}ClN_8O_2$ monoisotopic (M + H)+: m/z = 441.2; found: 441.2 |

TABLE 11a

| Ex. No. | $^1$H NMR |
|---|---|
| 144 | $^1$H NMR (400 MHz, CD$_3$OD) δ 9.33-9.24 (m, 2H), 8.72-8.64 (m, 2H), 8.58-8.53 (m, 2H), 7.99 (s, 2H), 7.35 (s, 1H), 7.33 (s, 1H), 7.01-6.94 (m, 2H), 5.58-5.47 (m, 2H), 4.26-4.16 (m, 2H), 3.81-3.39 (m, 8H), 3.47 (s, 3H), 3.46 (s, 3H), 2.39-2.12 (m, 4H), 1.62 (d, J = 7.0 Hz, 3H), 1.60 (d, J = 6.9 Hz, 3H) |
| 145 | $^1$H NMR (400 MHz, d$_6$-DMSO) δ 8.91 (dd, J = 6.7, 1.6 Hz, 1H), 8.88 (s, 1H), 8.56 (dd, J = 4.5, 1.6 Hz, 1H), 8.09 (d, J = 6.8 Hz, 1H), 7.72 (s, 1H), 7.20 (s, 1H), 7.01 (dd, J = 6.7, 4.5 Hz, 1H), 5.53 (p, J = 6.4 Hz, 1H), 3.99-3.68 (m, 4H), 3.55-3.38 (m, 2H), 3.33 (d, J = 13.1 Hz, 1H), 3.26-3.09 (m, 1H), 1.55 (d, J = 6.9 Hz, 3H) |

Example 146. 2-Amino-N-{1-[8-chloro-5-(4-hydroxypiperidin-1-yl)imidazo[1,5-a]pyridin-6-yl]ethyl}pyrazolo[1,5-a]pyrimidine-3-carboxamide trifluoroacetate salt (Racemic Mixture Prepared)

Example 147. 2-Amino-N-{1-[5-(4-bromopiperidin-1-yl)-8-chloroimidazo[1,5-a]pyridin-6-yl]ethyl}pyrazolo[1,5-a]pyrimidine-3-carboxamide trifluoroacetate salt (Racemic Mixture Prepared)

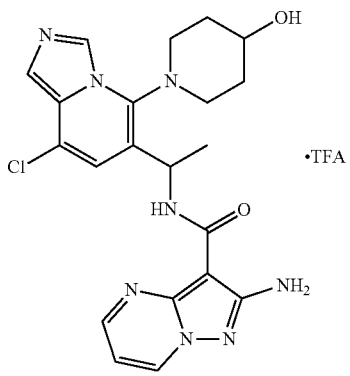 [SMILES: CC(NC(=O)c1c(N)nn2cccnc12)c1cc(Cl)c2cncn2c1N1CCC(O)CC1]

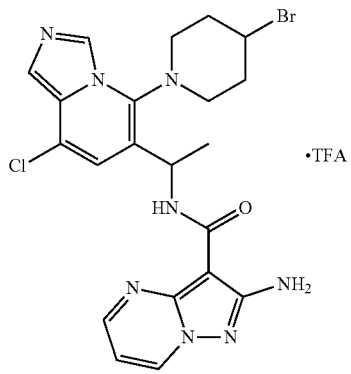 [SMILES: CC(NC(=O)c1c(N)nn2cccnc12)c1cc(Cl)c2cncn2c1N1CCC(Br)CC1]

1.0 M Boron tribromide in DCM (188 µL, 0.188 mmol) was added portionwise to a solution of tert-butyl {3-[({1-[8-chloro-5-(4-methoxypiperidin-1-yl)imidazo[1,5-a]pyridin-6-yl]ethyl}amino)carbonyl]pyrazolo[1,5-a]pyrimidin-2-yl}carbamate (25 mg, 0.044 mmol, Example 143, Step 2) in DCM (2 mL) at −78° C. The reaction was warmed to room temperature and was quenched by the addition of saturated NaHCO$_3$. The mixture was extracted with EtOAc. The combined organic extracts were dried over MgSO$_4$, filtered, and concentrated. Removal of the Boc protecting group occurred under conditions of the reaction. The product was purified by preparative HPLC/MS (pH=2). Yield: 2 mg. LCMS calculated for $C_{21}H_{24}ClN_8O_2$ monoisotopic (M+H)$^+$: m/z=455.2; found: 455.2.

The title compound was isolated as a byproduct of the reaction described in Example 146. Yield: 3 mg. LCMS calculated for $C_{21}H_{23}BrClN_8O$ monoisotopic (M+H)$^+$: m/z=517.1; found: 517.1. $^1$H NMR (400 MHz, d$_6$-DMSO) δ 8.94-8.90 (m, 1H), 8.72 (s, 0.6H), 8.65 (s, 0.4H), 8.57 (dd, J=4.5, 1.6 Hz, 1H), 8.11-8.05 (m, 1H), 7.67 (s, 0.4H), 7.60 (s, 0.6H), 7.16 (s, 0.4H), 7.11 (s, 0.6H), 7.02 (dd, J=6.7, 4.4 Hz, 1H), 5.56-5.48 (m, 0.6H), 5.43-5.34 (m, 0.4H), 4.73-4.57 (m, 1H), 3.56-3.12 (m, 4H), 2.43-2.05 (m, 4H), 1.56 (d, J=3.7 Hz, 1.2H), 1.54 (d, J=3.4 Hz, 1.8H).

Example 148

Example 148 in Table 12 was prepared by the method of Example 146, using Example 144 as the starting material (Boc-Deprotected).

TABLE 12

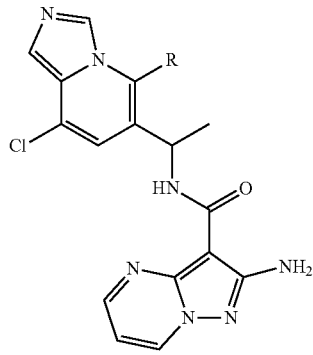

| Ex. No. | Name | R = | LCMS |
|---|---|---|---|
| 148 | 2-Amino-N-{1-[8-chloro-5-(3-hydroxypyrrolidin-1-yl)imidazo[1,5-a]pyridin-6-yl]ethyl}pyrazolo[1,5-a]pyrimidine-3-carboxamide trifluoroacetate salt (mixture of diastereomers prepared) | 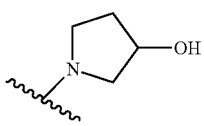 | Calculated for $C_{20}H_{22}ClN_8O_2$ monoisotopic (M + H)$^+$: m/z = 441.2; found: 441.1 |

Example 149. 2-Amino-N-{1-[8-chloro-5-(1,1-di-oxido-1,2,5-thiadiazepan-5-yl)imidazo[1,5-a]pyridin-6-yl]ethyl}pyrazolo[1,5-a]pyrimidine-3-carboxamide trifluoroacetate salt (Racemic Mixture Prepared)

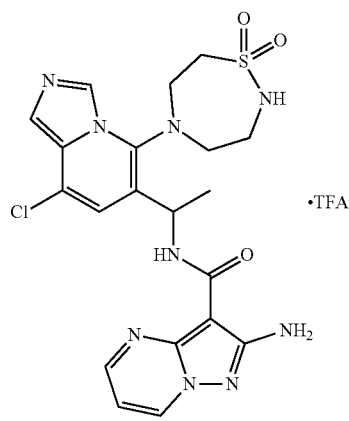 [SMILES: CC(NC(=O)c1c(N)nn2cccnc12)c1cc(Cl)c2cncn2c1N1CCNS(=O)(=O)CC1]

Step 1. 1-[8-Chloro-5-(1,1-dioxido-1,2,5-thiadiazepan-5-yl)imidazo[1,5-a]pyridin-6-yl]ethanone

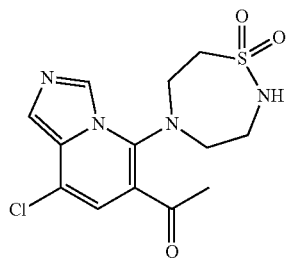 [SMILES: CC(=O)c1cc(Cl)c2cncn2c1N1CCNS(=O)(=O)CC1]

A mixture of 1-(5,8-dichloroimidazo[1,5-a]pyridin-6-yl)ethanone (30.0 mg, 0.131 mmol, Example 130, Step 7), 1,2,5-thiadiazepane 1,1-dioxide (0.051 g, 0.17 mmol, 1:1 by weight with TEA prepared as described in WO 2014/009295) and N,N-diisopropylethylamine (0.068 mL, 0.39 mmol) in MeCN (1.0 mL) was heated to 70° C. for 1 hour. Additional 1,2,5-thiadiazepane 1,1-dioxide (0.051 g, 0.17 mmol) was added and heating was continued for 16 hours. Volatiles were removed in vacuo and the product was purified by flash chromatography (0-100% EtOAc/hexanes). Yield: 0.022 g, 49%. LCMS calculated for $C_{13}H_{16}O_3N_4SCl$ monoisotopic (M+H)$^+$: m/z=343.1; found 343.0.

Step 2. 1-[8-Chloro-5-(1,1-dioxido-1,2,5-thiadiazepan-5-yl)imidazo[1,5-a]pyridin-6-yl]ethanamine (Racemic Mixture Prepared)

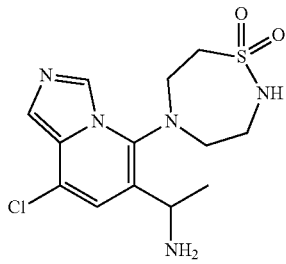 [SMILES: CC(N)c1cc(Cl)c2cncn2c1N1CCNS(=O)(=O)CC1]

A mixture of 1-[8-chloro-5-(1,1-dioxido-1,2,5-thiadiazepan-5-yl)imidazo[1,5-a]pyridin-6-yl]ethanone (22 mg, 0.064 mmol) in 2.0 M NH$_3$ in EtOH (3 mL, 6 mmol) was treated with titanium tetraisopropoxide (100 μL, 0.4 mmol) and the reaction mixture was heated to 65° C. overnight. The reaction mixture was cooled to 0° C. and sodium borohydride (7 mg, 0.2 mmol) was added. The reaction was stirred at 0° C. for 1 hour. Additional sodium borohydride (4 mg, 1 mmol) was added and the reaction mixture was stirred for 4 hours. A dilute solution of NH$_4$OH was added (0.2 mL). The mixture was filtered through a PTFE syringe filter and the filter was rinsed with MeCN (10 mL). The filtrate was concentrated. The residue was partitioned between EtOAc and water and the layers were separated. The aqueous portion was extracted with two additional portions of EtOAc. The combined organic extracts were washed with brine, dried over Na$_2$SO$_4$, filtered and concentrated. The product was used without further purification and theoretical yield was assumed. LCMS calculated for $C_{13}H_{19}O_2N_5SCl$ monoisotopic (M+H)$^+$: m/z=344.1; found 344.0.

Step 3. tert-Butyl {3-[({1-[8-chloro-5-(1,1-dioxido-1,2,5-thiadiazepan-5-yl)imidazo[1,5-a]pyridin-6-yl]ethyl}amino)carbonyl]pyrazolo[1,5-a]pyrimidin-2-yl}carbamate (Racemic Mixture Prepared)

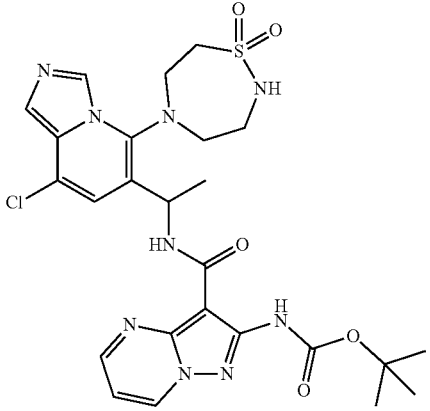 [SMILES: CC(NC(=O)c1c(NC(=O)OC(C)(C)C)nn2cccnc12)c1cc(Cl)c2cncn2c1N1CCNS(=O)(=O)CC1]

N,N-Diisopropylethylamine (30 μL, 0.2 mmol) was added to a mixture of 1-[8-chloro-5-(1,1-dioxido-1,2,5-thiadiazepan-5-yl)imidazo[1,5-a]pyridin-6-yl]ethanamine (22 mg, 0.064 mmol), 2-[(tert-butoxycarbonyl)amino]pyrazolo[1,5-a]pyrimidine-3-carboxylic acid (21 mg, 0.077 mmol, J&W Pharmlab) and N,N,N',N'-tetramethyl-O-(7-azabenzotriazol-1-yl)uronium hexafluorophosphate (36 mg, 0.096 mmol) in DMF (2.5 mL). After stirring for 1 hour, the reaction was diluted with water and extracted with EtOAc. The organic layer was washed with brine, dried over $Na_2SO_4$, filtered and concentrated to afford product which was used without further purification. Theoretical yield was assumed. LCMS calculated for $C_{25}H_{31}ClN_9O_5S$ monoisotopic (M+H)$^+$: m/z=604.2, found 604.3.

Step 4. 2-Amino-N-{1-[8-chloro-5-(1,1-dioxido-1,2,5-thiadiazepan-5-yl)imidazo[1,5-a]pyridin-6-yl]ethyl}pyrazolo[1,5-a]pyrimidine-3-carboxamide (Racemic Mixture Prepared)

To tert-butyl {3-[({1-[8-chloro-5-(1,1-dioxido-1,2,5-thiadiazepan-5-yl)imidazo[1,5-a]pyridin-6-yl]ethyl}amino)carbonyl]pyrazolo[1,5-a]pyrimidin-2-yl}carbamate (0.039 g, 0.064 mmol) in DCM (2 mL) was added TFA (2 mL). The solution was stirred for 1 hour. Volatiles were removed in vacuo. The residue was dissolved in MeOH/$H_2$O/MeCN and purified by preparative HPLC/MS (pH=2) to afford product as the trifluoroacetate salt. Yield: 30 mg. LCMS calculated for $C_{20}H_{23}O_3N_9SCl$ monoisotopic (M+H)$^+$: m/z=504.1; found 504.1. $^1$H NMR (400 MHz, CD$_3$OD) δ 9.43 (s, 0.5H), 9.34 (s, 0.5H), 8.69 (dd, J=6.8, 1.6 Hz, 1H), 8.58-8.53 (m, 1H), 7.98 (s, 0.5H), 7.97 (s, 0.5H), 7.37 (s, 0.5H), 7.35 (s, 0.5H), 6.98 (dd, J=6.7, 4.6 Hz, 1H), 5.63 (q, J=7.0, 6.2 Hz, 0.5H), 5.54 (q, J=7.1, 6.0 Hz, 0.5H), 4.14-3.32 (m, 8H), 1.65 (d, J=3.6 Hz, 1.5H), 1.63 (d, J=3.6 Hz, 1.5H).

Examples 150-153

Examples 150-153 in Table 13 were prepared by the method of Example 149, using appropriately substituted commercially available amines in Step 1. NMR data for representative compounds of Table 13 are provided in Table 13a.

TABLE 13

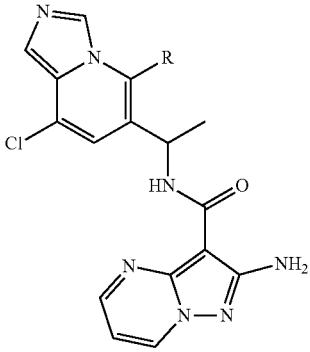

| Ex. No. | Name | R = | LCMS |
|---|---|---|---|
| 150 | 2-Amino-N-(1-{8-chloro-5-[(3S,5S)-3,5-dihydroxypiperidin-1-yl]imidazo[1,5-a]pyridin-6-yl}ethyl)pyrazolo[1,5-a]pyrimidine-3-carboxamide trifluoroacetate salt (single isomer prepared via separation of diastereomers- peak2, second to elute during preparative HPLC/MS at pH = 2) | 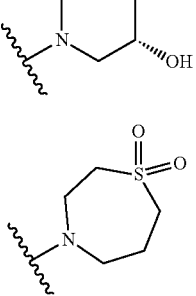 | Calculated for $C_{21}H_{24}ClN_8O_3$, monoisotopic (M + H)$^+$: m/z = 471.2; found: 471.1 |
| 151 | 2-Amino-N-{1-[8-chloro-5-(1,1-dioxido-1,4-thiazepan-4-yl)imidazo[1,5-a]pyridin-6-yl]ethyl}pyrazolo[1,5-a]pyrimidine-3-carboxamide trifluoroacetate salt (racemic mixture prepared) | 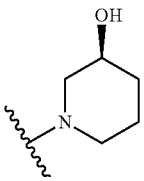 [SMILES: *N1CCC[C@H](O)C1] | Calculated for $C_{21}H_{24}ClN_8O_3S$ monoisotopic (M + H)$^+$: m/z = 503.1: found: 503.2 |
| 152 | 2-Amino-N-(1-{8-chloro-5-[(3S)-3-hydroxypiperidin-1-yl]imidazo[1,5-a]pyridin-6-yl}ethyl)pyrazolo[1,5-a]pyrimidine-3-carboxamide trifluoroacetate salt (mixture of two diastereomers prepared) | 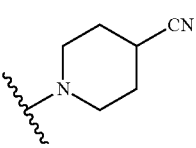 [SMILES: *N1CCC(C#N)CC1] | Calculated for $C_{21}H_{24}ClN_8O_2$: monoisotopic (M + H)$^+$: m/z = 455.2; found: 455.2 |
| 153 | 2-Amino-N-{1-[8-chloro-5-(4-cyanopiperidin-1-yl)imidazo[1,5-a]pyridin-6-yl]ethyl}pyrazolo[1,5-a]pyrimidine-3-carboxamide trifluoroacetate salt (racemic mixture prepared) | | Calculated for $C_{22}H_{23}ClN_9O$ monoisotopic (M + H)$^+$: m/z = 464.2; found: 464.2 |

TABLE 13a

| Ex. No. | $^1$H NMR |
|---|---|
| 150 | $^1$H NMR (400 MHz, d$_6$-DMSO) δ 9.00 (s, 1H), 8.92 (dd, J = 6.7, 1.4 Hz, 1H), 8.57 (dd, J = 4.5, 1.4 Hz, 1H), 8.08 (d, J = 6.6 Hz, 1H), 7.59 (s, 1H), 7.10 (s, 1H), 7.01 (dd, J = 6.7, 4.5 Hz, 1H), 5.43 (p, J = 6.7 Hz, 1H), 4.10-3.98 (m, 1H), 3.48-3.41 (m, 1H), 3.16-3.05 (m, 4H), 2.00-1.87 (m, 1H), 1.68-1.58 (m, 1H), 1.51 (d, J = 6.8 Hz, 3H) |
| 151 | $^1$H NMR (400 MHz, CD$_3$OD) δ 9.46 (s, 1H), 8.74-8.69 (m, 1H), 8.60-8.56 (m, 1H), 7.99 (s, 1H), 7.38 (s, 1H), 7.01 (dd, J = 6.8, 4.5 Hz, 1H), 5.56 (p, J = 6.9 Hz, 1H), 4.10-3.36 (m, 8H), 2.42-2.16 (m, 2H), 1.68 (d, J = 6.8 Hz, 1.5H), 1.66 (d, J = 6.7 Hz, 1.5H) |

Example 154. 2-Amino-N-{1-[8-chloro-5-(4-methyl-3-oxopiperazin-1-yl)imidazo[1,5-a]pyridin-6-yl]ethyl}pyrazolo[1,5-a]pyrimidine-3-carboxamide trifluoroacetate salt (Racemic Mixture Prepared)

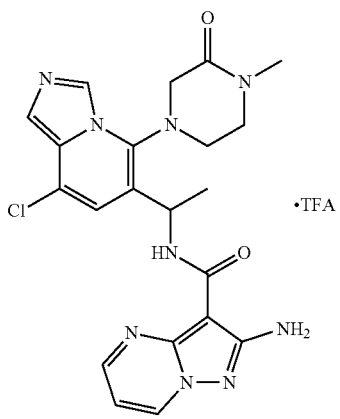 [SMILES: CC(NC(=O)c1c(N)nn2cccnc12)c1cc(Cl)c2cncn2c1N1CCN(C)C(=O)C1]

Step 1. 4-[6-(1-Aminoethyl)-8-chloroimidazo[1,5-a]pyridin-5-yl]-1-methylpiperazin-2-one A mixture of 4-(6-acetyl-8-chloroimidazo[1,5-a]pyridin-5-yl)-1-methylpiperazin-2-one (7.0 mg, 0.016 mmol, prepared as in Example 149, Step 1 using 1-methylpiperazin-2-one instead of 1,2,5-thiadiazepane 1,1-dioxide), ammonium acetate (26 mg, 0.34 mmol) and sodium cyanoborohydride (7.2 mg, 0.11 mmol) was heated to 70° C. overnight. Upon cooling to room temperature, saturated NaHCO$_3$ (5 mL) was added. The mixture was then extracted twice with 10% iPrOH in DCM. The combined organic extracts were dried over Na$_2$SO$_4$, filtered and concentrated. The product was used without further purification, and theoretical yield was assumed. LCMS calculated for C$_{14}$H$_{19}$ClN$_5$O monoisotopic (M+H)$^+$: m/z=308.1; found: 308.1.

Step 2. 2-Amino-N-{1-[8-chloro-5-(4-methyl-3-oxopiperazin-1-yl)imidazo[1,5-a]pyridin-6-yl]ethyl}pyrazolo[1,5-a]pyrimidine-3-carboxamide trifluoroacetate salt (Racemic Mixture Prepared)

Using 4-[6-(1-aminoethyl)-8-chloroimidazo[1,5-a]pyridin-5-yl]-1-methylpiperazin-2-one, the method of Example 26, Step 12 was followed to afford the title compound. Yield: 4.0 mg. LCMS calculated for C$_{21}$H$_{23}$ClN$_9$O$_2$ monoisotopic (M+H)$^+$: m/z=468.2; found: 468.2. $^1$H NMR (400 MHz, d$_6$-DMSO) δ 9.05 (s, 0.5H), 8.98 (s, 0.5H), 8.95-8.87 (m, 1H), 8.60-8.53 (m, 1H), 8.14-8.05 (m, 1H), 7.79 (s, 0.5H), 7.76 (s, 0.5H), 7.24 (s, 0.5H), 7.23 (s, 0.5H), 7.06-6.99 (m, 1H), 5.49-5.33 (m, 1H), 4.34-3.39 (m, 6H), 2.98 (s, 3H), 1.55 (d, J=6.5 Hz, 1.5H), 1.54 (d, J=6.5 Hz, 1.5H).

Examples 155A-157

Examples 155A-157 in Table 14 were prepared by the method of Example 154, using amines prepared as described in Tetrahedron Letters, 36(4), 549-52; 1995, or derived therefrom using methods known to one skilled in the art. NMR data for representative compounds of Table 14 are provided in Table 14a.

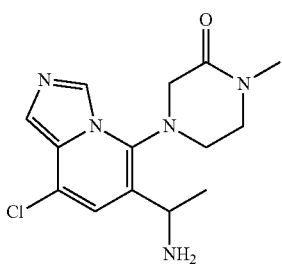 [SMILES: CC(N)c1cc(Cl)c2cncn2c1N1CCN(C)C(=O)C1]

TABLE 14

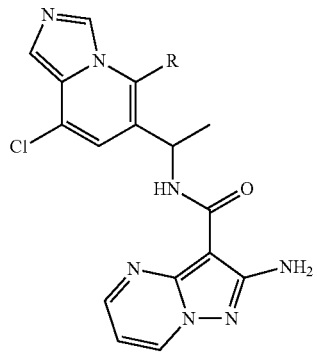

| Ex. No. | Name | R = | LCMS |
|---|---|---|---|
| 155A | 2-Amino-N-(1-{8-chloro-5-[(3R,5R)-3,5-dihydroxypiperidin-1-yl]imidazo-[1,5-a]pyridin-6-yl}ethyl)pyrazolo-[1,5-a]pyrimidine-3-carboxamide trifluoroacetate salt (mixture of two diastereomers prepared) | 3,5-dihydroxypiperidinyl (OH ''', OH) | Calculated for $C_{21}H_{24}ClN_8O_3$ monoisotopic $(M + H)^+$: m/z = 471.2: found: 471.1 |
| 155B | 2-Amino-N-(1-{8-chloro-5-[(3R,5S)-3,5-dihydroxypiperidin-1-yl]imidazo-[1,5-a]pyridin-6-yl}ethyl)pyrazolo-[1,5-a]pyrimidine-3-carboxamide trifluoroacetate salt (mixture of two diastereomers prepared) | 3,5-dihydroxypiperidinyl (OH, OH) | Calculated for $C_{21}H_{24}ClN_8O_3$ monoisotopic $(M + H)^+$: m/z = 471 2: found: 471.2 |
| 156 | 2-Amino-N-(1-{8-chloro-5-[(3R,5R)-3-fluoro-5-hydroxypiperidin-1-yl]-imidazo[1,5-a]pyridin-6-yl}ethyl)-pyrazolo[1,5-a]pyrimidine-3-carbox-amide trifluoroacetate salt (mixture of two diastereomers prepared) | 3-fluoro-5-hydroxypiperidinyl (OH ''', F) | Calculated for $C_{21}H_{23}ClFN_8O_2$ monoisotopic $(M + H)^+$: m/z = 473.2; found: 473.1 |
| 157 | 2-Amino-N-(1-{8-chloro-5-[(3S,5R)-3-cyano-5-hydroxypiperidin-1-yl]-imidazo[1,5-a]pyridin-6-yl}ethyl)-pyrazolo[1,5-a]pyrimidine-3-carbox-amide trifluoroacetate salt (mixture of two diastereomers prepared) | 3-cyano-5-hydroxypiperidinyl (OH ''', CN) | Calculated for $C_{22}H_{23}ClN_9O_2$ monoisotopic $(M + H)^+$: m/z = 480.2: found: 480.1 |

TABLE 14a

| Ex. No. | $^1$H NMR |
|---|---|
| 156 | $^1$H NMR (400 MHz, CD$_3$OD) δ 9.90-9.72 (m, 0.5H), 9.29-9.13 (m, 0.5H), 8.71-8.65 (m, 1H), 8.57-8.51 (m, 1H), 7.41 (s, 0.5H), 7.39 (s, 0.5H), 7.02-6.93 (m, 1H), 5.51-5.41 (m, 1H), 5.18-5.07 (m, 0.5H), 5.06-4.97 (m, 0.5H), 4.27-4.15 (m, 1H), 3.88-3.21 (m, 4H), 2.50-1.69 (m, 2H), 1.63 (d, J = 7.0 Hz, 1.5H), 1.60 (d, J = 7.0 Hz, 1.5H) |

Example 158. 2-Amino-N-(1-(8-chloro-5-(1,1-dioxido-1,4-thiazepan-4-yl)-3-methylimidazo[1,5-a]pyridin-6-yl)ethyl)pyrazolo[1,5-a]pyrimidine-3-carboxamide trifluoroacetate salt (Racemic Mixture Prepared)

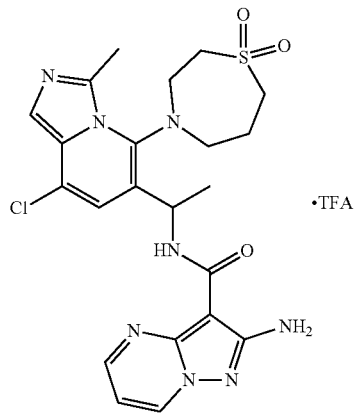 [SMILES: Cc1ncc2c(Cl)cc(C(C)NC(=O)c3c(N)nn4cccnc34)c(N3CCCS(=O)(=O)CC3)n12]

Step 1. 5,8-Dichloro-N-methoxy-N,3-dimethylimidazo[1,5-a]pyridine-6-carboxamide

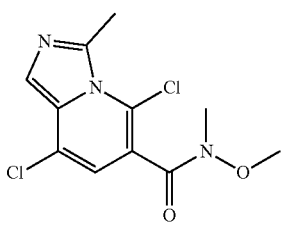 [SMILES: CON(C)C(=O)c1cc(Cl)c2cnc(C)n2c1Cl]

To 6-(aminomethyl)-2,5-dichloro-N-methoxy-N-methylnicotinamide (700 mg, 3 mmol, from Example 130, Step 4) and N,N-diisopropylethylamine (1.2 mL, 6.6 mmol) in DMF (6.4 mL) was added acetic anhydride (380 µL, 4.0 mmol). After 30 minutes, saturated NaHCO$_3$ solution was added and the mixture was extracted with EtOAc. The combined organic extracts were washed with water, then brine, dried over Na$_2$SO$_4$, filtered and concentrated. The crude product was stirred at room temperature with phosphoryl chloride (7.1 mL, 76 mmol) for one hour. Phosphoryl chloride was removed on the rotovap and crushed ice was added to the flask. Solid Na$_2$CO$_3$ was added to achieve pH=7. The mixture was extracted with EtOAc. The organic extract was dried over Na$_2$SO$_4$, filtered and concentrated. The product was used without further purification. Yield: 550 mg, 70%. LCMS calculated for C$_{11}$H$_{12}$Cl$_2$N$_3$O$_2$ monoisotopic (M+H)$^+$: m/z=288.0; found 288.1.

Step 2. 1-(5,8-Dichloro-3-methylimidazo[1,5-a]pyridin-6-yl)ethanone

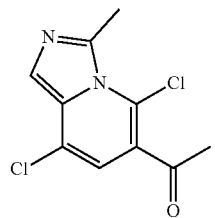

3.0 M Methylmagnesium chloride in THF (4 mL, 10 mmol) was added to a solution of 5,8-dichloro-N-methoxy-N,3-dimethylimidazo[1,5-a]pyridine-6-carboxamide (1.1 g, 3.8 mmol) in THF (20 mL) at 0° C. After 2 hours, the bath was removed and the mixture was warmed to room temperature. The reaction mixture was re-cooled to 0° C. and 3.0 M Methylmagnesium chloride in THF (1.26 mL, 3.8 mmol) was added. The cooling bath was removed and the mixture was stirred at room temperature for 1 hour. The mixture was re-cooled to 0° C. and 1.0 N HCl (2 mL, 2 mmol) was added. The mixture was diluted with water and extracted with EtOAc. The organic extract was washed with brine, dried over MgSO$_4$, filtered and concentrated. The product was purified by flash chromatography (0-100% EtOAc in hexanes). Yield: 0.80 g, 90%. LCMS calculated for C$_{10}$H$_9$Cl$_2$N$_2$O monoisotopic (M+H)$^+$: m/z=243.0; found 243.1.

Step 3. 1-(8-Chloro-5-(1,1-dioxido-1,4-thiazepan-4-yl)-3-methylimidazo[1,5-a]pyridin-6-yl)ethan-1-one

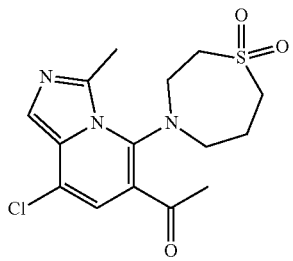 [SMILES: CC(=O)c1cc(Cl)c2cnc(C)n2c1N1CCCS(=O)(=O)CC1]

1-(5,8-Dichloro-3-methylimidazo[1,5-a]pyridin-6-yl)ethanone (20 mg, 0.09 mmol), 1,4-thiazepane 1,1-dioxide HCl salt (30 mg, 0.2 mmol, Enamine) and N,N-diisopropylethylamine (40 µL, 0.3 mmol) in MeCN (1 mL) was heated to 150° C. in the microwave for 3 hours. Upon cooling, the reaction mixture was partitioned between EtOAc and water. The organic layer was dried over MgSO$_4$, filtered and concentrated. The product was purified by flash chromatography (0-100% EtOAc in hexanes). Yield: 25 mg, 80%. LCMS calculated for C$_{15}$H$_{19}$ClN$_3$O$_3$S monoisotopic (M+H)$^+$: m/z=356.1; found 356.1.

Step 4. 1-[8-Chloro-5-(1,1-dioxido-1,4-thiazepan-4-yl)-3-methylimidazo[1,5-a]pyridin-6-yl]ethanamine (Racemic Mixture Prepared)

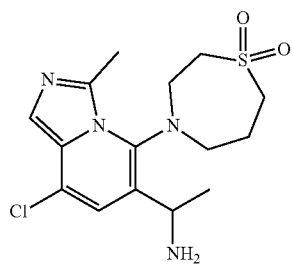 [SMILES: Cc1ncc2c(Cl)cc(C(C)N)c(N3CCCS(=O)(=O)CC3)n12]

Titanium tetraisopropoxide (200 μL, 0.5 mmol) was added to a mixture of 1-[8-chloro-5-(1,1-dioxido-1,4-thiazepan-4-yl)-3-methylimidazo[1,5-a]pyridin-6-yl]ethanone (30 mg, 0.09 mmol) in 2.0 M ammonia in ethanol (3 mL, 6 mmol). The reaction was stirred at 65° C. in a sealed tube overnight. Sodium borohydride (10 mg, 0.3 mmol) was added and the mixture was stirred for 1 hour. A 1N ammonium hydroxide solution was added and a precipitate formed that was filtered off and rinsed with acetonitrile. The crude product obtained on evaporation of the filtrate was partitioned between water and EtOAc. The organic layer was washed with brine, dried over MgSO$_4$, filtered and concentrated to afford product which was used without further purification. Yield: 20 mg, 60%. LCMS calculated for $C_{15}H_{22}ClN_4O_2S$ monoisotopic (M+H)$^+$: m/z=357.1; found 357.1.

Step 5. 2-Amino-N-(1-(8-chloro-5-(1,1-dioxido-1,4-thiazepan-4-yl)-3-methylimidazo[1,5-a]pyridin-6-yl)ethyl)pyrazolo[1,5-a]pyrimidine-3-carboxamide trifluoroacetate salt (Racemic Mixture Prepared)

Starting with 1-[8-chloro-5-(1,1-dioxido-1,4-thiazepan-4-yl)-3-methylimidazo[1,5-a]pyridin-6-yl]ethanamine (racemic) (20 mg, 0.06 mmol), the method of Example 26, Step 12 was used to provide the title compound. Yield: 5 mg. LCMS calculated for $C_{22}H_{26}ClN_8O_3S$ monoisotopic (M+H)$^+$: m/z=517.2; found 517.1. $^1$H NMR (400 MHz, CD$_3$OD) δ 8.69 (dd, J=6.8, 1.3 Hz, 1H), 8.58-8.54 (m, 1H), 8.00 (s, 1H), 7.36 (s, 0.4H), 7.33 (s, 0.6H), 6.98 (dd, J=6.4, 4.7 Hz, 1H), 5.59 (q, J=6.6 Hz, 0.4H), 5.51 (q, J=7.0 Hz, 0.6H), 4.18-3.34 (m, 8H), 3.07 (s, 1.8H), 3.05 (s, 1.2H), 2.60-2.20 (m, 2H), 1.66 (d, J=6.8 Hz, 3H).

Example 159. 2-Amino-N-{1-[8-chloro-5-(1,1-dioxido-1,2,5-thiadiazepan-5-yl)-1-(trifluoromethyl)imidazo[1,5-a]pyridin-6-yl]ethyl}pyrazolo[1,5-a]pyrimidine-3-carboxamide trifluoroacetate salt (Racemic Mixture Prepared)

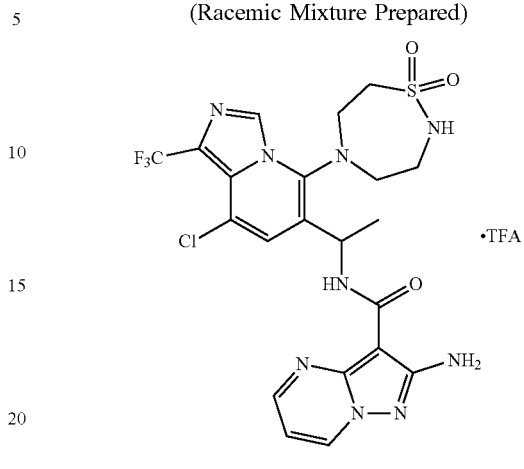

To 2-amino-N-{1-[8-chloro-5-(1,1-dioxido-1,2,5-thiadiazepan-5-yl)imidazo[1,5-a]pyridin-6-yl]ethyl}pyrazolo[1,5-a]pyrimidine-3-carboxamide trifluoroacetate salt (0.023 g, 0.037 mmol, from Example 149) and zinc bis(trifluoromethanesulfinate) (0.037 g, 0.11 mmol, Aldrich) in CHCl$_3$ (0.6 mL) and H$_2$O (0.150 mL) at 0° C. was added tert-butyl hydroperoxide (0.025 mL, 0.19 mmol). The reaction mixture was warmed to room temperature and stirred overnight. The reaction was worked up by partition between EtOAc and water. The aqueous layer was extracted with two further portions of EtOAc. The combined organic extracts were dried over Na$_2$SO$_4$, filtered and concentrated. DMF and MeOH were used to reconstitute the residue, which was purified by preparative HPLC/MS (pH=2). Yield: 2 mg. LCMS calculated for $C_{21}H_{22}ClF_3N_9O_3S$ monoisotopic (M+H)$^+$: m/z=572.1; found 572.2. $^1$H NMR (400 MHz, CD$_3$OD) δ 8.68 (dd, J=6.8, 1.4 Hz, 1H), 8.66 (s, 0.5H), 8.63 (s, 0.5H), 8.57-8.54 (m, 1H), 7.38 (s, 0.5H), 7.34 (s, 0.5H), 6.98 (dd, J=6.8, 4.7 Hz, 1H), 5.70 (q, J=6.8 Hz, 0.5H), 5.63 (q, J=6.9 Hz, 0.5H), 4.17-3.34 (m, 8H), 1.63 (d, J=7.4 Hz, 1.5H), 1.61 (d, J=7.3 Hz, 1.5H).

Example 160. 2-Amino-N-{(1S)-1-[1,8-dichloro-5-(1,1-dioxido-1,2,5-thiadiazepan-5-yl)imidazo[1,5-a]pyridin-6-yl]ethyl}pyrazolo[1,5-a]pyrimidine-3-carboxamide trifluoroacetate salt (Scalemic Mixture Prepared)

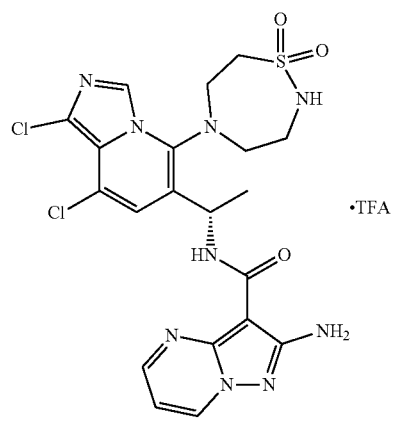 [SMILES: C[C@H](NC(=O)c1c(N)nn2cccnc12)c1cc(Cl)c2c(Cl)ncn2c1N1CCNS(=O)(=O)CC1]

Step 1. 1-(1,5,8-Trichloroimidazo[1,5-a]pyridin-6-yl)ethanone

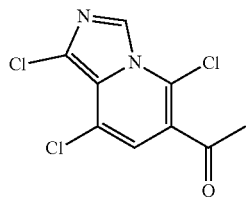

1-(5,8-Dichloroimidazo[1,5-a]pyridin-6-yl)ethanone (0.300 g, 1.31 mmol, from Example 130, Step 7) in DMF (10 mL) was treated with N-chlorosuccinimide (0.19 g, 1.4 mmol). The reaction was stirred overnight. An additional portion of N-chlorosuccinimide (0.040 g, 0.29 mmol) was added and the reaction was stirred for 1 hour. The reaction mixture was diluted with water and extracted with three portions of EtOAc. The combined organic extracts were washed with water, dried over $Na_2SO_4$, filtered and concentrated. The crude product was purified by flash chromatography (0-75% EtOAc/hexanes). Yield: 0.24 g, 70%. LCMS calculated for $C_9H_6ON_2Cl_3$ monoisotopic $(M+H)^+$: m/z=263.0; found 262.9.

Step 2. 1-[1,8-Dichloro-5-(1,1-dioxido-1,2,5-thiadiazepan-5-yl)imidazo[1,5-a]pyridin-6-yl]ethanone

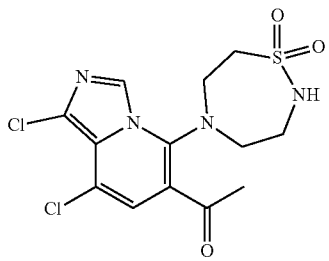 [SMILES: CC(=O)c1cc(Cl)c2c(Cl)ncn2c1N1CCNS(=O)(=O)CC1]

A mixture of 1-(1,5,8-trichloroimidazo[1,5-a]pyridin-6-yl)ethanone (50.0 mg, 0.190 mmol), 1,2,5-thiadiazepane 1,1-dioxide (0.074 g, 0.25 mmol, 1:1 by weight with TEA, prepared as described in WO2014/009295) and N,N-diisopropylethylamine (0.10 mL, 0.57 mmol) in acetonitrile (1.4 mL) was heated to 70° C. for 2.5 hours. Additional 1,2,5-thiadiazepane 1,1-dioxide (0.074 g, 0.25 mmol) was added and heating was continued for 2 hours. The reaction was diluted with water and extracted with three portions of EtOAc. The combined organic extracts were dried over $Na_2SO_4$, filtered and concentrated. The product was triturated with MeOH to afford a yellow powder. Yield: 0.055 g, 77%. LCMS calculated for $C_{13}H_{15}O_3N_4SCl_2$ monoisotopic $(M+H)^+$: m/z=377.0; found 377.0.

Step 3. (1S)-1-[1,8-Dichloro-5-(1,1-dioxido-1,2,5-thiadiazepan-5-yl)imidazo[1,5-a]pyridin-6-yl]ethanamine hydrochloride salt (Scalemic Mixture Prepared)

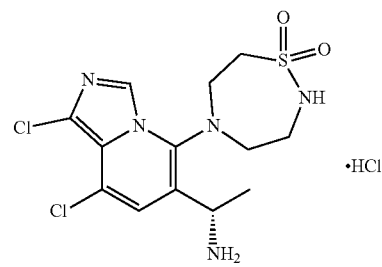 [SMILES: C[C@H](N)c1cc(Cl)c2c(Cl)ncn2c1N1CCNS(=O)(=O)CC1 ; Cl]

To a solution of 1-[1,8-dichloro-5-(1,1-dioxido-1,2,5-thiadiazepan-5-yl)imidazo[1,5-a]pyridin-6-yl]ethanone (27 mg, 0.072 mmol) and (S)-2-methylpropane-2-sulfinamide (87 mg, 0.72 mmol, Aldrich) in 1.1 mL cyclopentyl methyl ether (CPME) was added titanium tetraisopropoxide (0.063 mL, 0.21 mmol) and the reaction mixture was heated to 100° C. for 6 hours. Additional CPME (1.5 mL), (S)-2-methylpropane-2-sulfinamide (20 mg, 0.17 mmol) and $Ti(OiPr)_4$ (30 µL, 0.1 mmol) were added and the reaction was heated overnight. A third portion of (S)-2-methylpropane-2-sulfinamide (20 mg, 0.17 mmol) and $Ti(OiPr)_4$ (30 µL, 0.1 mmol) were added and heating was continued for 6 hours. The reaction mixture was cooled to 0° C. and ethanol (0.5 mL, 8 mmol) and sodium borohydride (15 mg, 0.40 mmol, powdered, in one portion) were added. After 15 minutes, the bath was removed and the reaction mixture was rapidly warmed to ambient temperature. The reaction was quenched by the dropwise addition of water. The mixture was diluted with water and was extracted with three portions of EtOAc. The combined organic extracts were dried over $Na_2SO_4$, filtered and concentrated. The product was purified by preparative HPLC/MS (pH=2) and eluent evaporated. The sulfinamide obtained (0.020 g, 0.034 mmol) was dissolved in MeOH (1.0 mL) and treated with 4.0 M HCl in dioxane (1.0 mL, 4.0 mmol). After stirring for 45 minutes, volatiles were removed in vacuo to afford the crude product as the HCl salt, which was used without further purification. Yield: 16 mg. LCMS calculated for $C_{13}H_{18}Cl_2N_5O_2S$ monoisotopic $(M+H)^+$: m/z=378.1; found 378.1.

Step 4. 2-Amino-N-{(1S)-1-[1,8-dichloro-5-(1,1-dioxido-1,2,5-thiadiazepan-5-yl)imidazo[1,5-a]pyridin-6-yl]ethyl}pyrazolo[1,5-a]pyrimidine-3-carboxamide trifluoroacetate salt (Scalemic Mixture Prepared)

N,N-Diisopropylethylamine (20 µL, 0.1 mmol) was added to 2-[(tert-butoxycarbonyl)amino]pyrazolo[1,5-a]pyrimidine-3-carboxylic acid (15 mg, 0.055 mmol, J&W Pharmlab) and N,N,N',N'-tetramethyl-O-(7-azabenzotriazol-1-yl)uronium hexafluorophosphate (24 mg, 0.063 mmol) in DMF (1 mL). After stirring for 10 minutes, (1S)-1-[1,8-dichloro-5-(1,1-dioxido-1,2,5-thiadiazepan-5-yl)imidazo[1,5-a]pyridin-6-yl]ethanamine (16 mg, 0.042 mmol) in DMF (1 mL) was added dropwise. The reaction was stirred for 1 hour. The reaction was diluted with water and extracted with EtOAc. The organic layer was washed with brine, dried over Na$_2$SO$_4$, filtered and concentrated. Trifluoroacetic Acid (1 mL) was added to a solution of the crude product in DCM (1 mL). After stirring for 1 hour, volatiles were removed in vacuo and the product was purified by preparative HPLC/MS (pH=2). Yield: 6 mg. LCMS calculated for C$_{20}$H$_{22}$O$_3$N$_9$SCl$_2$ (M+H)$^+$: m/z=538.1; found 538.0. $^1$H NMR (400 MHz, CD$_3$OD) δ 8.67 (dd, J=6.8, 1.6 Hz, 1H), 8.55 (dd, J=4.5, 1.3 Hz, 1H), 8.45 (s, 0.5H), 8.42 (s, 0.5H), 7.04 (s, 0.5H), 6.99 (s, 0.5H), 6.97 (dd, J=6.8, 4.5 Hz, 1H), 5.68 (q, J=6.9 Hz, 0.5H), 5.60 (q, J=6.9 Hz, 0.5H), 4.04-3.32 (m, 8H), 1.60 (d, J=7.5 Hz, 1.5H), 1.58 (d, J=7.3 Hz, 1.5H).

Example 161

Example 161 of Table 15 were prepared by the method of Example 160, using an appropriately substituted amine in Step 2. NMR data for the compound of Table 15 is provided in Table 15a.

TABLE 15

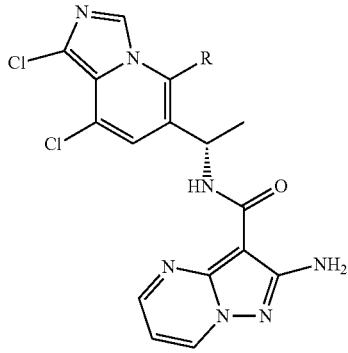

| Ex. No. | Name | R = | LCMS |
|---|---|---|---|
| 161 | 2-Amino-N-{(1S)-1-[1,8-dichloro-5-(5-oxo-1,4-diazepan-1-yl)imidazo-[1,5-a]pyridin-6-yl]ethyl}pyrazolo-[1,5-a]pyrimidine-3-carboxamide trifluoroacetate salt (scalemic mixture prepared) | | Calculated for C$_{21}$H$_{22}$Cl$_2$N$_9$O$_2$ monoisotopic (M + H)$^+$: m/z = 502.1; found: 502.1 |

TABLE 15a

| Ex. No. | $^1$H NMR |
|---|---|
| 161 | $^1$H NMR (400 MHz, CD$_3$OD) δ 8.69-8.65 (m, 1H), 8.54 (m, J = 3.3 Hz, 1H), 8.44 (s, 0.5H), 8.43 (s, 0.5H), 7.00 (s, 0.5H), 6.99 (s, 0.5H), 6.98-6.93 (m, 1H), 5.58-5.50 (m, 1H), 3.71-3.32 (m, 6H), 2.96-2.78 (m, 2H), 1.58 (d, J = 6.9 Hz, 3H) |

Example 162. 2-Amino-N-{1-[1,8-dichloro-5-(1,1-dioxidothiomorpholin-4-yl)imidazo[1,5-a]pyridin-6-yl]ethyl}pyrazolo[1,5-a]pyrimidine-3-carboxamide trifluoroacetate salt (Racemic Mixture Prepared)

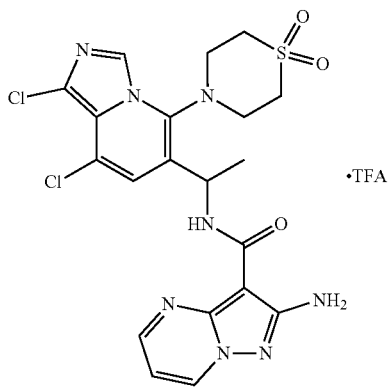 [SMILES: CC(NC(=O)c1c(N)nn2cccnc12)c1cc(Cl)c2c(Cl)ncn2c1N1CCS(=O)(=O)CC1]

Step 1. 1-[8-Chloro-5-(1,1-dioxidothiomorpholin-4-yl)imidazo[1,5-a]pyridin-6-yl]ethanone

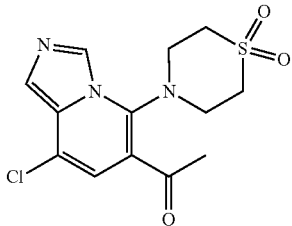 [SMILES: CC(=O)c1cc(Cl)c2cncn2c1N1CCS(=O)(=O)CC1]

A mixture of 1-(5,8-dichloroimidazo[1,5-a]pyridin-6-yl)ethanone (30 mg, 0.1 mmol, Example 130, Step 7), N,N-diisopropylethylamine (70 µL, 0.4 mmol) and thiomorpholine 1,1-dioxide (40 mg, 0.3 mmol, TCI) in MeCN (1 mL) was heated in the microwave to 150° C. for 2 hours. The reaction mixture was partitioned between EtOAc and water and the layers were separated. The organic layer was washed with brine, dried over MgSO$_4$, filtered and concentrated. The product was purified by flash chromatography (0-100% EtOAc in hexanes). Yield: 30 mg, 70%. LCMS calculated for C$_{13}$H$_{15}$ClN$_3$O$_3$S monoisotopic (M+H)$^+$: m/z=328.0; found 328.1.

Step 2. 1-[1,8-Dichloro-5-(1,1-dioxidothiomorpholin-4-yl)imidazo[1,5-a]pyridin-6-yl]ethanone

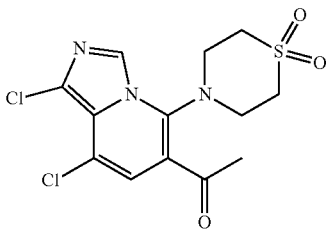 [SMILES: CC(=O)c1cc(Cl)c2c(Cl)ncn2c1N1CCS(=O)(=O)CC1]

N-Chlorosuccinimide (18 mg, 0.13 mmol) was added to 1-[8-chloro-5-(1,1-dioxidothiomorpholin-4-yl)imidazo[1,5-a]pyridin-6-yl]ethanone (40 mg, 0.1 mmol) in DMF (1 mL). The reaction was heated to 70° C. for 2 hours. Upon cooling to room temperature, the reaction was diluted with EtOAc and water, and the layers were separated. The organic layer was washed with brine, dried over MgSO$_4$, filtered and concentrated. The product was purified by flash chromatography (0-100% EtOAc in hexanes). Yield: 30 mg, 80%. LCMS calculated for C$_{13}$H$_{14}$Cl$_2$N$_3$O$_3$S monoisotopic (M+H)$^+$: m/z=362.0; found 362.1.

Step 3. 1-[1,8-Dichloro-5-(1,1-dioxidothiomorpholin-4-yl)imidazo[1,5-a]pyridin-6-yl]ethanamine (Racemic Mixture Prepared)

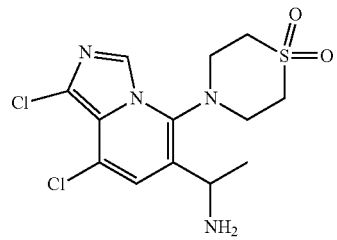 [SMILES: CC(N)c1cc(Cl)c2c(Cl)ncn2c1N1CCS(=O)(=O)CC1]

Titanium tetraisopropoxide (100 µL, 0.4 mmol) was added to a mixture of 1-[1,8-dichloro-5-(1,1-dioxidothiomorpholin-4-yl)imidazo[1,5-a]pyridin-6-yl]ethanone (20 mg, 0.06 mmol) in 2.0 M ammonia in ethanol (3 mL, 5 mmol). The reaction was stirred at 65° C. in a sealed vessel overnight. The reaction mixture was cooled to 0° C. and sodium borohydride (7 mg, 0.2 mmol) was added. When complete, the reaction was quenched by the addition of 1N NH$_4$OH solution. The reaction mixture was filtered and the solid was washed with MeCN. The filtrate was concentrated in vacuo and the residue was partitioned between water and EtOAc. The organic layer was washed with brine, dried over MgSO$_4$, filtered and concentrated to afford product which was used without further purification. Yield: 20 mg, 90%. LCMS calculated for C$_{13}$H$_{17}$Cl$_2$N$_4$O$_2$S monoisotopic (M+H)$^+$: m/z=363.0; found 363.1.

Step 4. 2-Amino-N-{1-[1,8-dichloro-5-(1,1-dioxidothiomorpholin-4-yl)imidazo[1,5-a]pyridin-6-yl]ethyl}pyrazolo[1,5-a]pyrimidine-3-carboxamide trifluoroacetate salt (Racemic Mixture Prepared)

N,N-Diisopropylethylamine (30 µL, 0.2 mmol) was added to a mixture of 1-[1,8-dichloro-5-(1,1-dioxidothiomorpholin-4-yl)imidazo[1,5-a]pyridin-6-yl]ethanamine (20 mg, 0.06 mmol), 2-[(tert-butoxycarbonyl)amino]pyrazolo[1,5-a]pyrimidine-3-carboxylic acid (20 mg, 0.07 mmol), and N,N,N',N'-tetramethyl-O-(7-azabenzotriazol-1-yl)uronium hexafluorophosphate (34 mg, 0.090 mmol) in DMF (2 mL). After stirring for 1 hour, the reaction was diluted with water and extracted with EtOAc. The combined organic extracts were washed with brine, dried over MgSO$_4$, filtered and concentrated. The residue was dissolved in DCM (1 mL) and TFA (1 mL) was added. The reaction was stirred for 1 hour and volatiles were removed in vacuo. The product was purified by preparative HPLC/MS (pH=2). Yield: 5 mg. LCMS calculated for C$_{20}$H$_{21}$Cl$_2$N$_8$O$_3$S monoisotopic (M+H)$^+$: m/z=523.1; found 523.1. $^1$H NMR (400 MHz, d$_6$-DMSO) δ 8.92 (dd, J=6.7, 1.4 Hz, 1H), 8.67 (s, 1H), 8.57 (dd, J=4.5, 1.5 Hz, 1H), 8.09 (d, J=6.8 Hz, 1H), 7.08 (s, 1H), 7.01 (dd, J=6.7, 4.6 Hz, 1H), 6.42 (s, 2H), 5.30 (p, J=6.8 Hz, 1H), 4.07-3.19 (m, 8H), 1.55 (d, J=6.9 Hz, 3H).

Example 163. 2-Amino-N-{1-[1,8-dichloro-5-(4-cyanopiperidin-1-yl)imidazo[1,5-a]pyridin-6-yl]ethyl}pyrazolo[1,5-a]pyrimidine-3-carboxamide trifluoroacetate salt (Racemic Mixture Prepared)

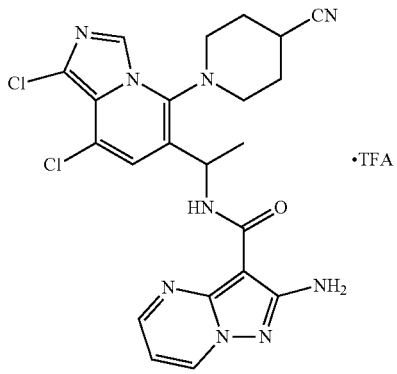 [SMILES: CC(NC(=O)c1c(N)nn2cccnc12)c1cc(Cl)c2c(Cl)ncn2c1N1CCC(C#N)CC1]

The title compound was prepared by the method of Example 162, substituting piperidine-4-carbonitrile (29 mg, 0.26 mmol, Aldrich) for the amine and Cs$_2$CO$_3$ (100 mg, 0.4 mmol) for the base in Step 1 and performing the reaction of Step 1 at 70° C. in the microwave for 1 hour. LCMS calculated for C$_{22}$H$_{22}$Cl$_2$N$_9$O monoisotopic (M+H)$^+$: m/z=498.1; found 498.1. $^1$H NMR (400 MHz, d$_6$-DMSO) δ 8.94-8.87 (m, 1H), 8.58-8.53 (m, 1H), 8.47 (s, 0.5H), 8.42 (s, 0.5H), 8.10-8.01 (m, 1H), 7.05 (s, 1H), 7.03-6.98 (m, 1H), 6.42 (br s, 2H), 5.45-5.37 (m, 0.5H), 5.32-5.24 (m, 0.5H), 3.59-2.96 (m, 5H), 2.20-1.85 (m, 4H), 1.52 (d, J=7.0 Hz, 3H).

Example 164. 2-Amino-N-{1-[8-chloro-1-cyano-5-(1,1-dioxidothiomorpholin-4-yl)imidazo[1,5-a]pyridin-6-yl]ethyl}pyrazolo[1,5-a]pyrimidine-3-carboxamide trifluoroacetate salt (Racemic Mixture Prepared)

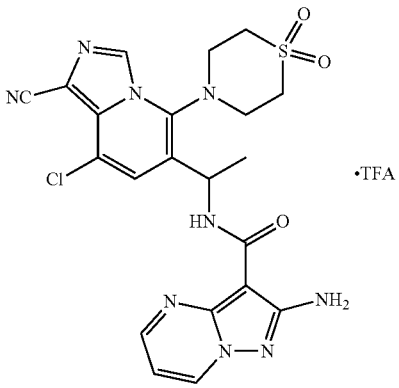 [SMILES: CC(NC(=O)c1c(N)nn2cccnc12)c1cc(Cl)c2c(C#N)ncn2c1N1CCS(=O)(=O)CC1]

Step 1. 1-[8-Chloro-5-(1,1-dioxidothiomorpholin-4-yl)-1-iodoimidazo[1,5-a]pyridin-6-yl]ethanone

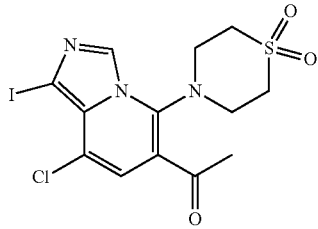 [SMILES: CC(=O)c1cc(Cl)c2c(I)ncn2c1N1CCS(=O)(=O)CC1]

To a solution of 1-[8-chloro-5-(1,1-dioxidothiomorpholin-4-yl)imidazo[1,5-a]pyridin-6-yl]ethanone (200 mg, 0.6 mmol, Example 162, Step 1) in DMF (1.6 mL) was added N-iodosuccinimide (151 mg, 0.671 mmol) and the reaction was stirred for 1 hour. The reaction was quenched by the addition of saturated NaHCO$_3$ solution. The mixture was diluted with water and extracted with EtOAc. The extract was washed with water, followed by brine, dried over Na$_2$SO$_4$, filtered and concentrated. The product was used without further purification. Yield: 300 mg, 100%. LCMS calculated for C$_{13}$H$_{14}$ClIN$_3$O$_3$S monoisotopic (M+H)$^+$: m/z=453.9; found 453.9.

Step 2. Methyl 6-acetyl-8-chloro-5-(1,1-dioxidothiomorpholin-4-yl)imidazo[1,5-a]pyridine-1-carboxylate

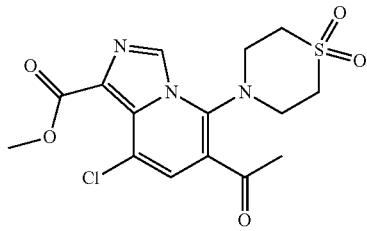 [SMILES: COC(=O)c1ncn2c(N3CCS(=O)(=O)CC3)c(C(C)=O)cc(Cl)c12]

To a mixture of 1-[8-chloro-5-(1,1-dioxidothiomorpholin-4-yl)-1-iodoimidazo[1,5-a]pyridin-6-yl]ethanone (300 mg, 0.7 mmol) in MeOH (8 mL) and DMF (5 mL) was added triethylamine (0.24 mL, 1.7 mmol) and the mixture was degassed with a stream of nitrogen for 5 minutes. [1,1'-Bis(diphenylphosphino)ferrocene]dichloropalladium(II), complex with dichloromethane (1:1) (60 mg, 0.07 mmol) was added. The solution was saturated with carbon monoxide by bubbling the gas through the reaction subsurface using a CO balloon. The flask was heated to 60° C. for 2 hours under an atmosphere of CO provided by the balloon. The reaction was cooled to room temperature and stirred overnight. The mixture was partitioned between water and EtOAc. The aqueous layer was extracted with a further portion of EtOAc. The combined organic extracts were dried over Na$_2$SO$_4$, filtered, and concentrated. The product was purified by flash chromatography (0-100% EtOAc in hexanes). Yield: 0.18 g, 70%. LCMS calculated for C$_{15}$H$_{17}$ClN$_3$O$_5$S monoisotopic (M+H)$^+$: m/z=386.1; found 386.1.

Step 3. 6-Acetyl-8-chloro-5-(1,1-dioxidothiomorpholin-4-yl)imidazo[1,5-a]pyridine-1-carboxylic acid

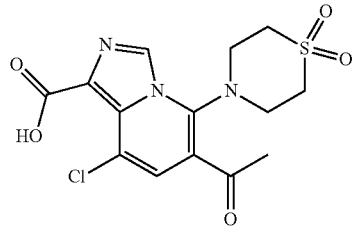 [SMILES: CC(=O)c1cc(Cl)c2c(C(=O)O)ncn2c1N1CCS(=O)(=O)CC1]

To methyl 6-acetyl-8-chloro-5-(1,1-dioxidothiomorpholin-4-yl)imidazo[1,5-a]pyridine-1-carboxylate (200 mg, 0.5 mmol) in MeOH (10 mL) and THF (10 mL) was added lithium hydroxide (50 mg, 2 mmol) in water (3 mL). After stirring for 1 hour, additional lithium hydroxide (25 mg, 1.0 mmol) in water (2 mL) was added and the reaction was stirred for 3 hours. The mixture was concentrated in vacuo to half the original volume. Water was then added and the basic aqueous mixture was washed with EtOAc to remove impurities. The aqueous layer was then acidified to pH=4 by the addition of 1N HCl. The acidic aqueous mixture was extracted once with EtOAc, and three times with 5% iPrOH in DCM to obtain the desired product. The combined extracts were washed with brine, dried over MgSO$_4$, filtered and concentrated. The product was used without further purification. Yield: 60 mg, 30%. LCMS calculated for $C_{14}H_{15}ClN_3O_5S$ monoisotopic (M+H)$^+$: m/z=372.0; found 372.1.

Step 4. 6-Acetyl-8-chloro-5-(1,1-dioxidothiomorpholin-4-yl)imidazo[1,5-a]pyridine-1-carboxamide

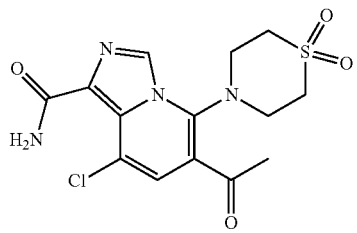

To a mixture of 6-acetyl-8-chloro-5-(1,1-dioxidothiomorpholin-4-yl)imidazo[1,5-a]pyridine-1-carboxylic acid (60 mg, 0.2 mmol), ammonium chloride (20 mg, 0.3 mmol) and N,N,N',N'-tetramethyl-O-(7-azabenzotriazol-1-yl)uronium hexafluorophosphate (100 mg, 0.3 mmol) in DMF (3 mL) was added N,N-diisopropylethylamine (100 µL, 0.6 mmol). After stirring overnight, the reaction mixture was diluted with EtOAc and washed with water. The layers were separated and the aqueous layer was extracted with EtOAc. The combined organic extracts were washed with brine, dried over MgSO$_4$, filtered and concentrated. The product was purified by flash chromatography (0-5% MeOH/DCM). Yield: 50 mg, 80%. LCMS calculated for $C_{14}H_{16}ClN_4O_4S$ monoisotopic (M+H)$^+$: m/z=371.1; found 371.2.

Step 5. 6-Acetyl-8-chloro-5-(1,1-dioxidothiomorpholin-4-yl)imidazo[1,5-a]pyridine-1-carbonitrile

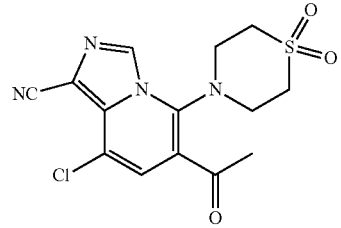 [SMILES: CC(=O)c1cc(Cl)c2c(C#N)ncn2c1N1CCS(=O)(=O)CC1]

A mixture of 6-acetyl-8-chloro-5-(1,1-dioxidothiomorpholin-4-yl)imidazo[1,5-a]pyridine-1-carboxamide (50 mg, 0.1 mmol) and TEA (200 µL, 1 mmol) in DCM (2 mL) at 0° C. was treated with trichloroacetyl chloride (60 µL, 0.5 mmol). After 15 minutes, the reaction was quenched by the addition of saturated NaHCO$_3$ solution and extracted with DCM. The organic layer was dried over MgSO$_4$, filtered and concentrated. The product was purified by flash chromatography (0-100% EtOAc in hexanes). Yield: 15 mg, 30%. LCMS calculated for $C_{14}H_{14}ClN_4O_3S$ monoisotopic (M+H)$^+$: m/z=353.0; found 353.1.

Step 6. 6-(1-Aminoethyl)-8-chloro-5-(1,1-dioxidothiomorpholin-4-yl)imidazo[1,5-a]pyridine-1-carbonitrile (Racemic Mixture Prepared)

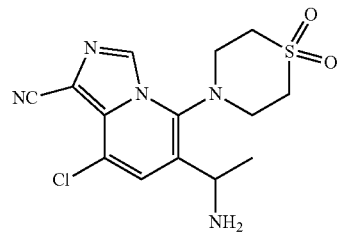 [SMILES: CC(N)c1cc(Cl)c2c(C#N)ncn2c1N1CCS(=O)(=O)CC1]

Titanium tetraisopropoxide (40 µL, 0.1 mmol) was added to 6-acetyl-8-chloro-5-(1,1-dioxidothiomorpholin-4-yl)imidazo[1,5-a]pyridine-1-carbonitrile (15 mg, 0.042 mmol) in 2.0 M ammonia in ethanol (2 mL, 4 mmol). The reaction was heated to 65° C. in a sealed reaction vessel overnight. The reaction mixture was cooled to 0° C. and sodium borohydride (5 mg, 0.1 mmol) was added. After 1 hour, an additional portion of NaBH$_4$ was added and the reaction was stirred for another 1 hour. The reaction was quenched by the addition of 1N NH$_4$OH, and the solids formed were removed by filtration and washed with acetonitrile. The residue obtained on evaporation of solvent from the filtrate was then partitioned between water and EtOAc. The organic layer was washed with brine, dried over MgSO$_4$, filtered and concentrated. The product was used without further purification. Yield: 10 mg, 67%. LCMS calculated for $C_{14}H_{17}ClN_5O_2S$ monoisotopic (M+H)$^+$: m/z=354.1; found 354.1.

Step 7. 2-Amino-N-{1-[8-chloro-1-cyano-5-(1,1-dioxidothiomorpholin-4-yl)imidazo[1,5-a]pyridin-6-yl]ethyl}pyrazolo[1,5-a]pyrimidine-3-carboxamide trifluoroacetate salt (Racemic Mixture Prepared)

Using 6-(1-aminoethyl)-8-chloro-5-(1,1-dioxidothiomorpholin-4-yl)imidazo[1,5-a]pyridine-1-carbonitrile (10 mg, 0.03 mmol), the method of Example 26, Step 12 was followed to afford the title compound. Yield: 2 mg. LCMS calculated for $C_{21}H_{21}ClN_9O_3S$ monoisotopic $(M+H)^+$: m/z=514.1; found 514.1. $^1$H NMR (500 MHz, $d_6$-DMSO) δ 8.92 (d, J=1.6 Hz, 1H), 8.91 (s, 1H), 8.57 (dd, J=4.5, 1.6 Hz, 1H), 8.14 (d, J=6.7 Hz, 1H), 7.59 (s, 1H), 7.02 (dd, J=6.7, 4.5 Hz, 1H), 5.34 (p, J=6.7 Hz, 1H), 3.99 (m, 1H), 3.87-3.78 (m, 1H), 3.74-3.65 (m, 3H), 3.61-3.53 (m, 1H), 1.58 (d, J=7.0 Hz, 3H).

Example 165. 2-Amino-N-(1-(8-chloro-1-cyano-5-(2-methyl-1,1-dioxidothiomorpholino)imidazo[1,5-a]pyridin-6-yl)ethyl)pyrazolo[1,5-a]pyrimidine-3-carboxamide trifluoroacetate salt (Mixture of Four Diastereomers Prepared)

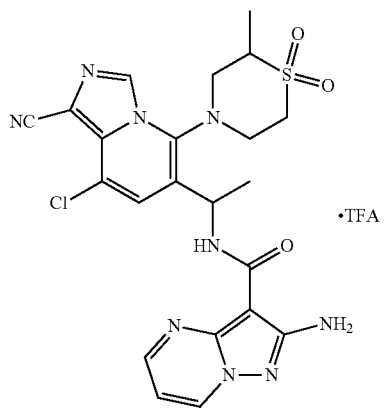 [SMILES: CC(NC(=O)c1c(N)nn2cccnc12)c1cc(Cl)c2c(C#N)ncn2c1N1CCS(=O)(=O)C(C)C1]

Step 1. 6-Acetyl-8-chloro-5-(2-methyl-1,1-dioxidothiomorpholino)imidazo[1,5-a]pyridine-1-carbonitrile (Racemic Mixture Prepared)

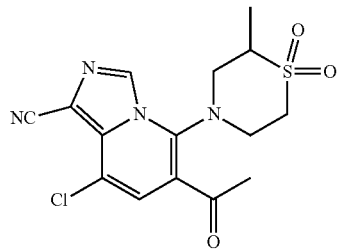 [SMILES: CC(=O)c1cc(Cl)c2c(C#N)ncn2c1N1CCS(=O)(=O)C(C)C1]

1-[8-Chloro-1-iodo-5-(2-methyl-1,1-dioxidothiomorpholino)imidazo[1,5-a]pyridin-6-yl]ethanone was prepared from 1-(5,8-dichloroimidazo[1,5-a]pyridin-6-yl)ethanone (Example 130, Step 7) and 2-methylthiomorpholine 1,1-dioxide (Enamine) by the method of Example 162, Step 1 followed by iodination as described in Example 164, Step 1. A mixture of 1-[8-chloro-1-iodo-5-(2-methyl-1,1-dioxidothiomorpholino)imidazo[1,5-a]pyridin-6-yl]ethanone (0.050 g, 0.107 mmol) and copper(I) cyanide (0.029 g, 0.321 mmol) in DMF (2 mL) was heated to 130° C. in the microwave for 80 minutes. Upon cooling, water was added and the mixture was extracted with DCM (2×). The combined organic extracts were dried over MgSO$_4$, filtered and concentrated. The product was purified by flash chromatography (0-100% EtOAc in hexanes). Yield: 20 mg, 51%. LCMS calculated for $C_{15}H_{16}ClN_4O_3S$ monoisotopic $(M+H)^+$: m/z=367.1; found 367.1.

Step 2. 6-(1-Aminoethyl)-8-chloro-5-)2-methyl-1,1-dioxidothiomorpholino)imidazo[1,5-a]pyridine-1-carbonitrile, HCl salt (Mixture of Four Diastereomers Prepared)

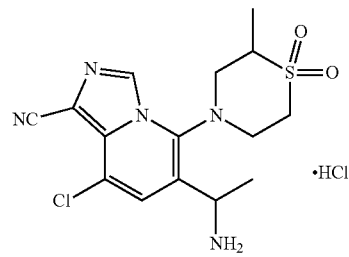 [SMILES: CC(N)c1cc(Cl)c2c(C#N)ncn2c1N1CCS(=O)(=O)C(C)C1 ; Cl]

Titanium(IV) isopropoxide (0.073 mL, 0.245 mmol) was added to a mixture of 6-acetyl-8-chloro-5-(2-methyl-1,1-dioxidothiomorpholino)imidazo[1,5-a]pyridine-1-carbonitrile (0.030 g, 0.082 mmol) and racemic 2-methylpropane-2-sulfinamide (0.099 g, 0.818 mmol) in cyclopentyl methyl ether (1.90 mL). The mixture was heated overnight at 100° C. in a sealed vial. Upon cooling, the mixture was diluted with EtOH (1 mL) and treated with sodium borohydride (9.3 mg, 0.25 mmol). After stirring for 1 hour, the reaction mixture was poured into brine, and solids were filtered off. The solids were washed with EtOAc. Layers of the filtrate were separated, and the organic layer was dried over MgSO$_4$, filtered, and concentrated. The product was used without further purification. LCMS calculated for $C_{19}H_{27}ClN_5O_3S_2$ monoisotopic $(M+H)^+$: m/z=472.1; found 472.1. 4N HCl in dioxane (2 mL) was added to N-(1-(8-chloro-1-cyano-5-(2-methyl-1,1-dioxidothiomorpholino)imidazo[1,5-a]pyridin-6-yl)ethyl-2-methypropane-2-sulfinamide. The mixture was stirred for 1 hour and volatiles were removed in vacuo to afford product as the HCl salt. Yield: 26 mg, 79%. LCMS calculated for $C_{15}H_{19}ClN_5O_2S$ monoisotopic $(M+H)^+$: m/z=368.1; found 368.1.

Step 3. 2-Amino-N-(1-(8-chloro-1-cyano-5-(2-methyl-1,1-dioxidothiomorpholino)imidazo[1,5-a]pyridin-6-yl)ethyl)pyrazolo[1,5-a]pyrimidine-3-carboxamide trifluoroacetate salt (Mixture of Four Diastereomers Prepared)

Using 6-(1-aminoethyl)-8-chloro-5-)2-methyl-1,1-dioxidothiomorpholino)imidazo[1,5-a]pyridine-1-carbonitrile, HCl salt (15 mg, 0.037 mmol), Example 26, Step 12 was followed to afford the title compound. Yield: 4 mg. LCMS calculated for $C_{22}H_{23}ClN_9O_3S$ monoisotopic $(M+H)^+$: m/z=528.1; found 528.1.

Example 166. 2-Amino-N-{[8-chloro-5-(1,1-dioxi-dothiomorpholin-4-yl)imidazo[1,5-a]pyridin-6-yl]methyl}pyrazolo[1,5-a]pyrimidine-3-carboxamide trifluoroacetate salt

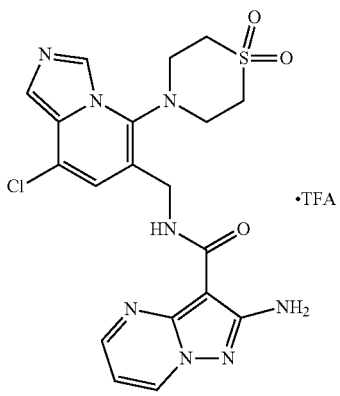 [SMILES: Nc1nn2cccnc2c1C(=O)NCc1cc(Cl)c2cncn2c1N1CCS(=O)(=O)CC1]

Step 1. 8-Chloro-N-methoxy-N-methyl-5-thiomorpholin-4-ylimidazo[1,5-a]pyridine-6-carboxamide

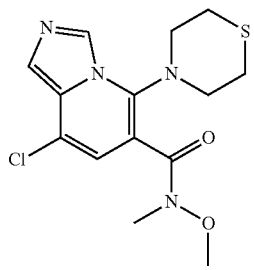 [SMILES: CON(C)C(=O)c1cc(Cl)c2cncn2c1N1CCSCC1]

A mixture of 5,8-dichloro-N-methoxy-N-methylimidazo[1,5-a]pyridine-6-carboxamide (0.20 g, 0.73 mmol, Example 130, Step 6), thiomorpholine (0.28 mL, 2.9 mmol, Aldrich) and N,N-diisopropylethylamine (0.45 mL, 2.6 mmol) in acetonitrile (7 mL) was heated to 120° C. in the microwave for 1.5 hours. Volatiles were removed in vacuo and the product was purified by flash chromatography (0-50% EtOAc/hexanes). Yield: 0.23 g, 92%. LCMS calculated for $C_{14}H_{28}ClN_4O_2S$ monoisotopic (M+H)⁺: m/z=341.1; found 341.0.

Step 2. 8-Chloro-5-thiomorpholin-4-ylimidazo[1,5-a]pyridine-6-carbaldehyde

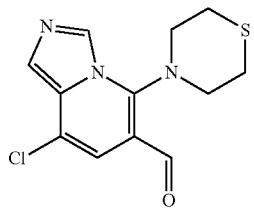 [SMILES: O=Cc1cc(Cl)c2cncn2c1N1CCSCC1]

To 8-chloro-N-methoxy-N-methyl-5-thiomorpholin-4-ylimidazo[1,5-a]pyridine-6-carboxamide (0.18 g, 0.53 mmol) in THF (12 mL) at −78° C. was added 1.0 M diisobutylaluminum hydride in hexanes (2.1 mL, 2.1 mmol). The mixture was stirred for 1.5 hours at −78° C., and further 1.0 M diisobutylaluminum hydride in hexanes (2.1 mL, 2.1 mmol) was added and the reaction was continued for 2 hours. The reaction was then quenched at −78° C. by the dropwise addition of MeOH. Saturated Rochelle salt solution was added and the mixture was stirred for 30 minutes at room temperature. The mixture was then extracted with EtOAc. The extract was dried over $Na_2SO_4$, filtered, and concentrated. The product was purified by flash chromatography (0-50% EtOAc in hexanes). Yield: 0.091 g, 49%. LCMS calculated for $C_{12}H_{13}ClN_3OS$ monoisotopic (M+H)⁺: m/z=282.0; found 282.1.

Step 3. 8-Chloro-5-(1,1-dioxidothiomorpholin-4-yl)imidazo[1,5-a]pyridine-6-carbaldehyde

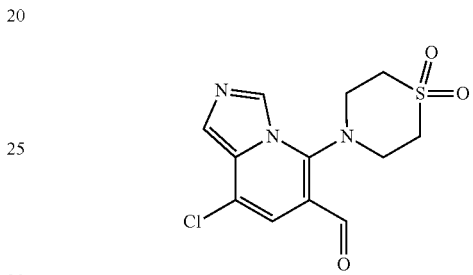

8-Chloro-5-thiomorpholin-4-ylimidazo[1,5-a]pyridine-6-carbaldehyde (91 mg, 0.26 mmol) in ethyl acetate (7 mL) was treated with m-chloroperbenzoic acid (89 mg, 0.52 mmol). After stirring for 1 hour, solvent was removed in vacuo. The crude product was dissolved in a mixture of MeCN and MeOH and purified by preparative HPLC/MS (pH=10). Yield: 34 mg, 42%. LCMS calculated for $C_{12}H_{13}ClN_3O_3S$ monoisotopic (M+H)⁺: m/z=314.0; found 314.0.

Step 4. 1-[8-Chloro-5-(1,1-dioxidothiomorpholin-4-yl)imidazo[1,5-a]pyridin-6-yl]methanamine

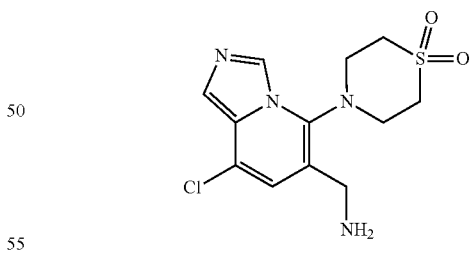

Titanium tetraisopropoxide (30 µL, 0.1 mmol) was added to a mixture of 8-chloro-5-(1,1-dioxidothiomorpholin-4-yl)imidazo[1,5-a]pyridine-6-carbaldehyde (8.0 mg, 0.025 mmol) in 2.0M ammonia in ethanol (1 mL, 2 mmol). The reaction was stirred at 65° C. in a sealed reaction vessel for 70 minutes. The reaction mixture was cooled to 0° C., and sodium borohydride (3 mg, 0.08 mmol) was added and the reaction stirred at 0° C. for 30 minutes. A small amount of 1N $NH_4OH$ solution was added, followed by acetonitrile (5 mL). Precipitated solids were removed by filtration and washed with acetonitrile. The filtrate was concentrated to afford crude product as a solid that was slurried in 10% IPA in DCM (50 mL). The solid product was obtained by filtration. Yield: 7.9 mg, 98%. LCMS calculated for $C_{12}H_{16}ClN_4O_2S$ monoisotopic (M+H)$^+$: m/z=315.1; found 315.0.

Step 5. 2-Amino-N-{[8-chloro-5-(1,1-dioxidothiomorpholin-4-yl)imidazo[1,5-a]pyridin-6-yl]methyl}pyrazolo[1,5-a]pyrimidine-3-carboxamide trifluoroacetate salt Using 1-[8-chloro-5-(1,1-dioxidothiomorpholin-4-yl)imidazo[1,5-a]pyridin-6-yl]methanamine (7.9 mg, 0.025 mmol), the procedure of Example 26, Step 12 was followed to afford the title compound. Yield: 5.1 mg. LCMS calculated for $C_{19}H_{20}ClN_8O_3S$ monoisotopic (M+H)$^+$: m/z=475.1; found 475.1. $^1$H NMR (400 MHz, d$_6$-DMSO) δ 9.09 (s, 1H), 8.92 (dd, J=6.7, 1.5 Hz, 1H), 8.52 (dd, J=4.5, 1.5 Hz, 1H), 8.29 (t, J=6.0 Hz, 1H), 7.81 (s, 1H), 7.15 (s, 1H), 7.01 (dd, J=6.7, 4.5 Hz, 1H), 4.58 (d, J=6.0 Hz, 2H), 3.83-3.67 (m, 4H), 3.67-3.53 (m, 2H), 3.40-3.28 (m, 2H).

Example 167. 2-Amino-N-((8-chloro-5-(2-methyl-1,1-dioxidothiomorpholino)imidazo[1,5-a]pyridin-6-yl)methyl)pyrazolo[1,5-a]pyrimidine-3-carboxamide trifluoroacetate salt (Racemic Mixture Prepared)

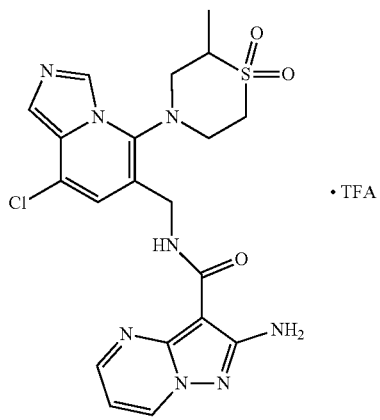 [SMILES: CC1CN(c2c(CNC(=O)c3c(N)nn4cccnc34)cc(Cl)c3cncn23)CCS1(=O)=O]

Step 1. 8-Chloro-N-methoxy-N-methyl-5-(2-methyl-1,1-dioxidothiomorpholino)imidazo[1,5-a]pyridine-6-carboxamide (Racemic Mixture Prepared)

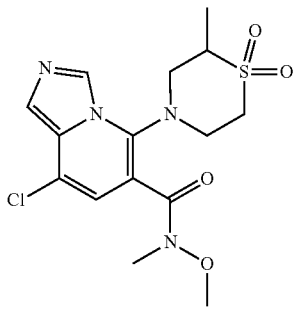 [SMILES: CON(C)C(=O)c1cc(Cl)c2cncn2c1N1CCS(=O)(=O)C(C)C1]

A mixture of 5,8-dichloro-N-methoxy-N-methylimidazo[1,5-a]pyridine-6-carboxamide (150. mg, 0.547 mmol, Example 130, Step 6), 2-methylthiomorpholine 1,1-dioxide HCl salt (203 mg, 1.09 mmol, Enamine) and N,N-diisopropylethylamine (0.191 mL, 1.094 mmol) in acetonitrile (3.0 mL) was heated in the microwave to 170° C. for 12 hours. Solvent was removed in vacuo and the product was purified by flash chromatography (0-80-100% EtOAc in hexanes). Yield: 91 mg, 43%. LCMS calculated for $C_{15}H_{20}ClN_4O_4S$ monoisotopic (M+H)$^+$: m/z=387.1; found 387.1.

Step 2. 8-Chloro-5-(2-methyl-1,1-dioxidothiomorpholino)imidazo[1,5-a]pyridine-6-carbaldehyde (Racemic Mixture Prepared)

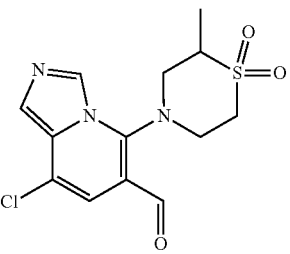 [SMILES: CC1CN(c2c(C=O)cc(Cl)c3cncn23)CCS1(=O)=O]

8-Chloro-N-methoxy-N-methyl-5-(2-methyl-1,1-dioxidothiomorpholino)imidazo[1,5-a]pyridine-6-carboxamide (20. mg, 0.052 mmol) in THF (1.0 mL) at −78° C. was treated with DIBAL-H (1.0 M in hexanes, 0.310 mL, 0.310 mmol). After 50 minutes at −78° C., the reaction was quenched by the dropwise addition of water and one gram of Rochelle salt was added. The reaction was warmed to room temperature and DCM (5 mL) was added. The mixture was stirred for 30 minutes and was dried by the addition of anhydrous MgSO$_4$. Acetonitrile was added (5 mL) and the mixture was filtered through Celite®. The filtrate was concentrated to afford product which was used without further purification. Yield: 13.3 mg, 78%. LCMS calculated for $C_{13}H_{15}ClN_3O_3S$ monoisotopic (M+H)$^+$: m/z=328.0; found 328.1.

Step 3. 2-Amino-N-((8-chloro-5-(2-methyl-1,1-dioxidothiomorpholino)imidazo[1,5-a]pyridin-6-yl)methyl)pyrazolo[1,5-a]pyrimidine-3-carboxamide trifluoroacetate salt (Racemic Mixture Prepared)

Using 8-chloro-5-(2-methyl-1,1-dioxidothiomorpholino)imidazo[1,5-a]pyridine-6-carbaldehyde (13 mg, 0.040 mmol), Example 166, Steps 4 and 5 were followed to afford the title compound. Yield: 4.8 mg. LCMS calculated for $C_{20}H_{22}ClN_8O_3S$ monoisotopic (M+H)$^+$: m/z=489.1; found 489.2.

Example 168

Example 168 in Table 16 was prepared by the method of Example 167. NMR data of the compound of Table 16 is provided in Table 16a.

TABLE 16

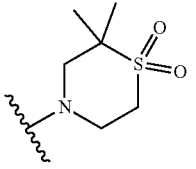 [SMILES: *N1CCS(=O)(=O)C(C)(C)C1]

| Ex. No. | Name | R = | LCMS |
|---|---|---|---|
| 168 | 2-Amino-N-((8-chloro-5-(2,2-dimethyl-1,1-dioxidothiomorpholino)imidazo-[1,5-a]pyridin-6-yl)methyl)pyrazolo-[1,5-a]pyrimidine-3-carboxamide trifluoroacetate salt | | Calculated for $C_{21}H_{24}ClN_8O_3S$ monoisotopic $(M + H)^+$: m/z = 503.1; found: 503.1 |

TABLE 16a

| Ex. No. | $^1$H NMR |
|---|---|
| 168 | $^1$H NMR (400 MHz, $d_6$-DMSO) δ 9.00-8.83 (m, 1H), 8.50 (dd, J = 4.5, 1.5 Hz, 1H), 8.28 (t, J = 5.9 Hz, 1H), 7.77 (s, 1H), 7.13 (s, 1H), 7.01 (dd, J = 6.7, 4.5 Hz, 1H), 4.70 (dd, J = 14.9, 6.2 Hz, 1H), 4.53 (dd, J = 14.9, 5.8 Hz, 1H), 4.02-3.90 (m, 1H), 3.81-3.62 (m, 3H), 3.58-3.48 (m, 1H), 3.41-3.28 (m, 1H), 1.52 (s, 3H), 1.35 (s, 3H) |

Example 169. 2-Amino-N-((1,8-dichloro-5-(2-methyl-1,1-dioxidothiomorpholino)imidazo[1,5-a]pyridin-6-yl)methyl)pyrazolo[1,5-a]pyrimidine-3-carboxamide trifluoroacetate salt (Racemic Mixture Prepared)

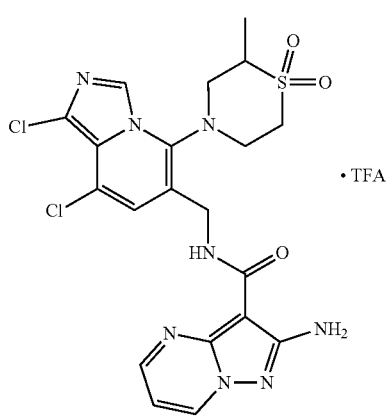 [SMILES: CC1CN(c2c(CNC(=O)c3c(N)nn4cccnc34)cc(Cl)c3c(Cl)ncn23)CCS1(=O)=O]

Step 1. 1,8-Dichloro-5-(2-methyl-1,1-dioxidothiomorpholino)imidazo[1,5-a]pyridine-6-carbaldehyde (Racemic Mixture Prepared)

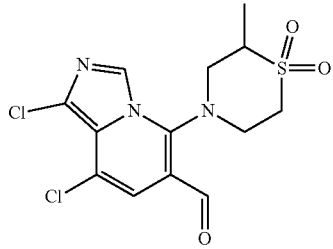 [SMILES: CC1CN(c2c(C=O)cc(Cl)c3c(Cl)ncn23)CCS1(=O)=O]

8-Chloro-5-(2-methyl-1,1-dioxidothiomorpholino)imidazo[1,5-a]pyridine-6-carbaldehyde (27 mg, 0.082 mmol, Example 167, Step 2) in DMF (1.0 mL) was treated with N-chlorosuccinimide (12. mg, 0.091 mmol) at 60° C. for 20 minutes. Upon cooling to room temperature, water was added and the solution was made basic by the addition of saturated NaHCO$_3$ solution (1 mL). Solid NaCl was added and stirred for 10 minutes. The precipitated product, a yellow solid, was isolated by filtration. The product was used without further purification. Yield: 14 mg, 47%. LCMS calculated for $C_{13}H_{14}Cl_2N_3O_3S$ monoisotopic $(M+H)^+$: m/z=362.0; found 362.0.

Step 2. 2-Amino-N-((1,8-dichloro-5-(2-methyl-1,1-dioxidothiomorpholino)imidazo[1,5-a]pyridin-6-yl)methyl)pyrazolo[1,5-a]pyrimidine-3-carboxamide trifluoroacetate salt (Racemic Mixture Prepared)

Using 1,8-dichloro-5-(2-methyl-1,1-dioxidothiomorpholino)imidazo[1,5-a]pyridine-6-carbaldehyde (racemic) (20 mg, 0.039 mmol), Example 166, Steps 4 and 5 were followed to afford the title compound. Yield: 6.3 mg. LCMS calculated for $C_{20}H_{21}Cl_2N_8O_3S$ monoisotopic $(M+H)^+$: m/z=523.1; found 523.0.

Example 170

Example 170 in Table 17 was prepared by the method of Example 169. NMR data of the compound of Table 17 is shown in Table 17a.

TABLE 17

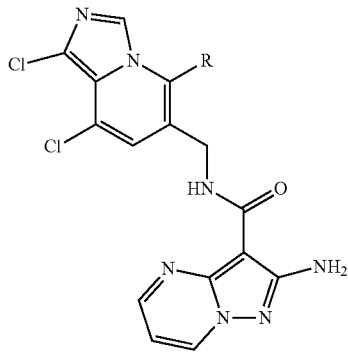

| Ex. No. | Name | R = | LCMS |
|---|---|---|---|
| 170 | 2-Amino-N-((1,8-dichloro-5-(2,2-dimethyl-1,1-dioxidothiomorph-olino)imidazo[1,5-a]pyridin-6-yl)-methyl)pyrazolo[1,5-a]pyrimidine-3-carboxamide trifluoroacetate salt | | Calculated for $C_{21}H_{23}Cl_2N_8O_3S$ monoisotopic $(M + H)^+$: m/z = 537.1: found: 537.1 |

TABLE 17a

| Ex. No. | $^1$H NMR |
|---|---|
| 170 | $^1$H NMR (400 MHz, $d_6$-DMSO) δ 8.95-8.87 (m, 1H), 8.59 (s, 1H), 8.54-8.45 (m, 1H), 8.25 (t, J = 5.9 Hz, 1H), 7.02 (s, 1H), 7.01-6.98 (m, 1H), 6.52 (br s, 2H), 4.63 (dd, J = 14.9, 6.3 Hz, 1H), 4.48 (dd, J = 15.0, 5.7 Hz, 1H), 4.04-3.94 (m, 1H), 3.79-3.46 (m, 5H), 1.52 (s, 3H), 1.31 (s, 3H) |

Example 171. 2-Amino-N-((8-chloro-5-(pyrrolidin-1-yl)imidazo[1,5-a]pyridin-6-yl)methyl)pyrazolo[1,5-a]pyrimidine-3-carboxamide trifluoroacetate salt

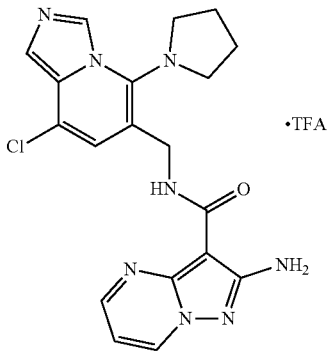 [SMILES: Nc1nn2cccnc2c1C(=O)NCc1cc(Cl)c2cncn2c1N1CCCC1]

Step 1. 8-Chloro-N-methoxy-N-methyl-5-(pyrrolidin-1-yl)imidazo[1,5-a]pyridine-6-carboxamide

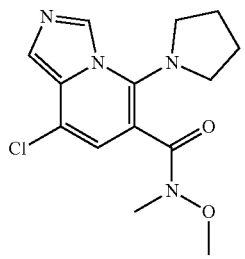 [SMILES: CON(C)C(=O)c1cc(Cl)c2cncn2c1N1CCCC1]

To 5,8-dichloro-N-methoxy-N-methylimidazo[1,5-a]pyridine-6-carboxamide (50 mg, 0.182 mmol, Example 130, Step 6) and cesium carbonate (178 mg, 0.547 mmol) in acetonitrile (5 mL) was added pyrrolidine (14.27 mg, 0.201 mmol). The reaction was heated to 70° C. for 2 hours. Upon cooling to room temperature, the reaction mixture was partitioned between water and EtOAc. The layers were separated and the organic layer was washed with brine, dried over MgSO₄, filtered, and concentrated. The product was purified by flash chromatography (0-100% EtOAc in hexanes). Yield: 45 mg, 80%. LCMS calculated for $C_{14}H_{18}ClN_4O_2$ monoisotopic (M+H)⁺: m/z=309.1; found 309.1.

Step 2. 8-Chloro-5-(pyrrolidin-1-yl)imidazo[1,5-a]pyridine-6-carbaldehyde

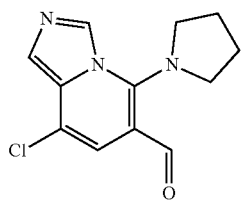 [SMILES: O=Cc1cc(Cl)c2cncn2c1N1CCCC1]

To 8-chloro-N-methoxy-N-methyl-5-(pyrrolidin-1-yl)imidazo[1,5-a]pyridine-6-carboxamide (45 mg, 0.146 mmol) in THF (1.0 mL) at −78° C. was added DIBAL-H (1.0M in hexanes, 0.874 mL, 0.874 mmol). After stirring for 50 minutes at −78° C., the reaction was quenched by the dropwise addition of water and one gram of Rochelle salt was added. The cooling bath was removed and DCM (5 mL) was added. The mixture was stirred for 30 minutes, anhydrous MgSO₄ was added. The mixture was diluted with acetonitrile (5 mL) and filtered through Celite®. The filtrate was concentrated and the product was used without further purification. Theoretical yield was assumed. LCMS calculated for $C_{12}H_{13}ClN_3O$ monoisotopic (M+H)⁺: m/z=250.1; found 250.1.

Step 3. (8-Chloro-5-(pyrrolidin-1-yl)imidazo[1,5-a]pyridin-6-yl)methanamine Titanium(IV) isopropoxide (0.213 mL, 0.721 mmol) was added to a solution of 8-chloro-5-(pyrrolidin-1-yl)imidazo[1,5-a]pyridine-6-carbaldehyde (0.036 g, 0.146 mmol) in 2.0 M ammonia in ethanol (2 mL, 4.00 mmol). The mixture was heated to 65° C. in a sealed vial for 40 minutes. The reaction mixture was cooled to 0° C. and sodium borohydride (0.020 g, 0.541 mmol) was added. After 30 minutes at 0° C., the reaction was quenched by the addition of 1N NH₄OH solution. Acetonitrile (5 mL) was added and solids were removed by filtration. The product (contained in the filtrate) was purified by preparative HPLC/MS (pH=10). Yield: 20 mg, 48%. LCMS calculated for $C_{12}H_{16}ClN_4$ monoisotopic (M+H)⁺: m/z=251.1; found 251.1.

Step 4. 2-Amino-N-((8-chloro-5-(pyrrolidin-1-yl)imidazo[1,5-a]pyridin-6-yl)methyl)pyrazolo[1,5-a]pyrimidine-3-carboxamide trifluoroacetate salt Using (8-chloro-5-(pyrrolidin-1-yl)imidazo[1,5-a]pyridin-6-yl)methanamine (20 mg, 0.07 mmol), the method of Example 26, Step 12 was used to afford the title product. Yield: 5 mg. LCMS calculated for $C_{19}H_{20}ClN_8O$ monoisotopic (M+H)⁺: m/z=411.1; found 411.1. ¹H NMR (400 MHz, d₆-DMSO) δ 8.90 (dd, J=6.7, 1.5 Hz, 1H), 8.55 (s, 1H), 8.48 (dd, J=4.5, 1.6 Hz, 1H), 8.17 (t, J=5.9 Hz, 1H), 7.65 (s, 1H), 7.07 (s, 1H), 6.98 (dd, J=6.7, 4.5 Hz, 1H), 4.51 (d, J=6.0 Hz, 2H), 3.36 (t, J=6.2 Hz, 4H), 2.08 (t, J=6.2 Hz, 4H).

Example 172. 2-Amino-N-((1,8-dichloro-5-(pyrrolidin-1-yl)imidazo[1,5-a]pyridin-6-yl)methyl)pyrazolo[1,5-a]pyrimidine-3-carboxamidetrifluoroacetate salt

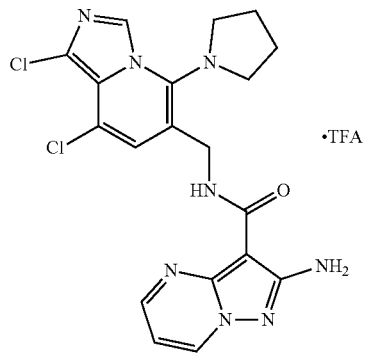 [SMILES: Nc1nn2cccnc2c1C(=O)NCc1cc(Cl)c2c(Cl)ncn2c1N1CCCC1]

Step 1. 1,8-Dichloro-5-(pyrrolidin-1-yl)imidazo[1,5-a]pyridine-6-carbaldehyde

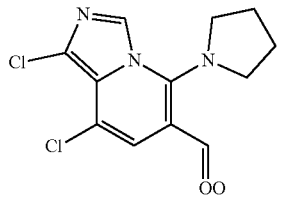

A mixture of 8-chloro-5-(pyrrolidin-1-yl)imidazo[1,5-a]pyridine-6-carbaldehyde (0.050 g, 0.200 mmol, Example 171, Step 2) in DMF (3 mL) was treated with N-chlorosuccinimide (0.027 g, 0.200 mmol) at 60° C. for 3 hours. Upon cooling, the reaction mixture was partitioned between water and EtOAc. The organic extract was washed with brine, dried over MgSO$_4$, filtered and concentrated. The product was purified by flash chromatography (0-100% EtOAc in hexanes). Yield: 40 mg, 70%. LCMS calculated for $C_{12}H_{12}Cl_2N_3O$ monoisotopic (M+H)$^+$: m/z=284.0; found 284.1.

Step 2. N-((1,8-Dichloro-5-(pyrrolidin-1-yl)imidazo[1,5-a]pyridin-6-yl)methyl)-2-methylpropane-2-sulfinamide

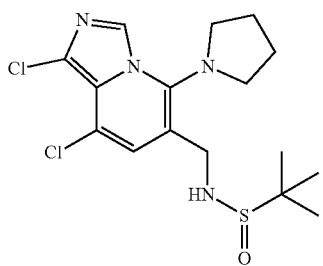 [SMILES: CC(C)(C)S(=O)NCc1cc(Cl)c2c(Cl)ncn2c1N1CCCC1]

Titanium(IV) isopropoxide (0.063 mL, 0.211 mmol) was added to a mixture of 1,8-dichloro-5-(pyrrolidin-1-yl)imidazo[1,5-a]pyridine-6-carbaldehyde (0.020 g, 0.070 mmol) and (racemic) 2-methylpropane-2-sulfinamide (0.085 g, 0.704 mmol) in cyclopentyl methyl ether (3 mL) and the reaction was heated to 60° C. for 1 hour in a sealed vial. Upon cooling to room temperature, ethanol (1.0 mL) and sodium borohydride (8.0 mg, 0.21 mmol) were added and the reaction was stirred for 30 minutes. The reaction mixture was poured into saturated NaCl solution and the mixture was then filtered. The filter was washed with EtOAc. The layers of the filtrate were separated and the aqueous layer was extracted with EtOAc. The combined organic solutions were dried over MgSO$_4$, filtered and concentrated. The product was purified by flash chromatography (0-100% EtOAc in hexanes). Yield: 20. mg, 73%. LCMS calculated for $C_{16}H_{23}Cl_2N_4OS$ monoisotopic (M+H)$^+$: m/z=389.1; found 389.1.

Step 3. (1,8-Dichloro-5-(pyrrolidin-1-yl)imidazo[1,5-a]pyridin-6-yl)methanamine, HCl salt

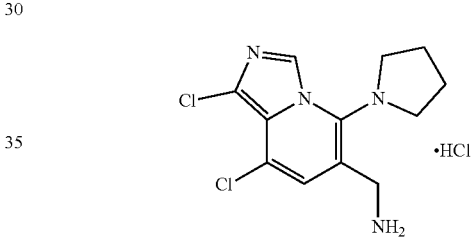

4N HCl in dioxane (1 mL, 4.0 mmol) was added to a mixture of N-((1,8-dichloro-5-(pyrrolidin-1-yl)imidazo[1,5-a]pyridin-6-yl)methyl)-2-methylpropane-2-sulfinamide (30 mg, 0.077 mmol) in MeOH (1 mL). After 1 hour, solvents were removed in vacuo and the residue was purified by preparative HPLC/MS (pH=10). Yield: 20 mg, 81% yield. LCMS calculated for $C_{12}H_{15}Cl_2N_4$ monoisotopic (M+H)$^+$: m/z=285.1; found 285.1.

Step 4. 2-Amino-N-((8-chloro-5-(pyrrolidin-1-yl)imidazo[1,5-a]pyridin-6-yl)methyl)pyrazolo[1,5-a]pyrimidine-3-carboxamide trifluoroacetate salt Using (1,8-dichloro-5-(pyrrolidin-1-yl)imidazo[1,5-a]pyridin-6-yl)methanamine, HCl salt (20 mg, 0.06 mmol), Example 26, Step 12 was followed to afford the title compound. Yield: 10 mg. LCMS calculated for $C_{19}H_{19}Cl_2N_8O$ monoisotopic (M+H)$^+$: m/z=445.1; found 445.1. $^1$H NMR (400 MHz, d$_6$-DMSO) δ 8.93-8.86 (m, 1H), 8.52-8.42 (m, 1H), 8.27 (s, 1H), 8.16 (t, J=5.8 Hz, 1H), 7.00 (s, 1H), 6.98 (dd, J=6.1, 4.1 Hz, 1H), 4.47 (d, J=5.9 Hz, 2H), 3.50-3.18 (m, 4H), 2.12-1.94 (m, 4H).

Example 173. 2-Amino-N-((8-chloro-1-cyano-5-(pyrrolidin-1-yl)imidazo[1,5-a]pyridin-6-yl)methyl)pyrazolo[1,5-a]pyrimidine-3-carboxamide trifluoroacetate salt

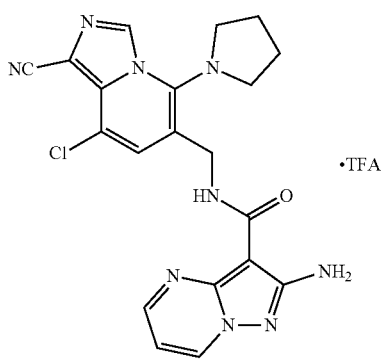 [SMILES: N#Cc1ncn2c(N3CCCC3)c(CNC(=O)c3c(N)nn4cccnc34)cc(Cl)c12]

Step 1. 8-Chloro-1-iodo-5-(pyrrolidin-1-yl)imidazo[1,5-a]pyridine-6-carbaldehyde

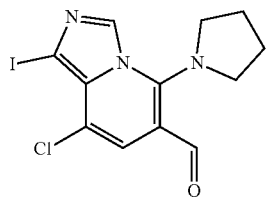 [SMILES: O=Cc1cc(Cl)c2c(I)ncn2c1N1CCCC1]

A mixture of 8-chloro-5-(pyrrolidin-1-yl)imidazo[1,5-a]pyridine-6-carbaldehyde (0.050 g, 0.200 mmol, from Example 171, Step 2) and N-iodosuccinimide (0.050 g, 0.220 mmol) in DMF (3 mL) was stirred for 3 hours at room temperature. The reaction mixture was partitioned between water and EtOAc. The organic layer was washed with brine, dried over MgSO$_4$, filtered, and concentrated. The product was purified by flash chromatography (0-100% EtOAc in hexanes). Yield: 50. mg, 67%. LCMS calculated for C$_{12}$H$_{12}$ClIN$_3$O monoisotopic (M+H)$^+$: m/z=376.0; found 376.0.

Step 2. 8-Chloro-6-formyl-5-(pyrrolidin-1-yl)imidazo[1,5-a]pyridine-1-carbonitrile

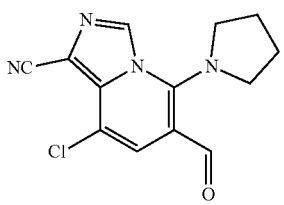 [SMILES: N#Cc1ncn2c(N3CCCC3)c(C=O)cc(Cl)c12]

A mixture of 8-chloro-1-iodo-5-(pyrrolidin-1-yl)imidazo[1,5-a]pyridine-6-carbaldehyde (0.050 g, 0.13 mmol) and copper(I) cyanide (0.036 g, 0.399 mmol) in DMF (2 mL) was heated to 130° C. in the microwave for 80 minutes. Upon cooling, water was added and the mixture was extracted with DCM twice. The combined organic extracts were dried over MgSO$_4$, filtered, and concentrated. The product was used without further purification. LCMS calculated for C$_{13}$H$_{12}$ClN$_4$O monoisotopic (M+H)$^+$: m/z=275.1; found 275.1.

Step 3. 2-Amino-N-((8-chloro-1-cyano-5-(pyrrolidin-1-yl)imidazo[1,5-a]pyridin-6-yl)methyl)pyrazolo[1,5-a]pyrimidine-3-carboxamide trifluoroacetate salt Starting with 8-chloro-6-formyl-5-(pyrrolidin-1-yl)imidazo[1,5-a]pyridine-1-carbonitrile (0.02 g, 0.073 mmol), Steps 2 through 4 of Example 172 were followed to afford the title compound. Yield: 5 mg. LCMS calculated for C$_{20}$H$_{19}$ClN$_9$O monoisotopic (M+H)$^+$: m/z=436.1; found 436.1.

Example 174. 2-Amino-N-((8-chloro-1-cyano-5-(2-methyl-1,1-dioxidothiomorpholino)imidazo[1,5-a]pyridin-6-yl)methyl)pyrazolo[1,5-a]pyrimidine-3-carboxamide trifluoroacetate salt (Racemic Mixture Prepared)

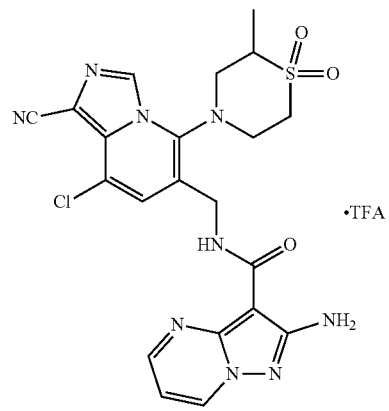 [SMILES: CC1CN(c2c(CNC(=O)c3c(N)nn4cccnc34)cc(Cl)c3c(C#N)ncn23)CCS1(=O)=O]

Step 1. 8-Chloro-6-formyl-5-(2-methyl-1,1-dioxidothiomorpholino)imidazo[1,5-a]pyridine-1-carbonitrile (Racemic Mixture Prepared)

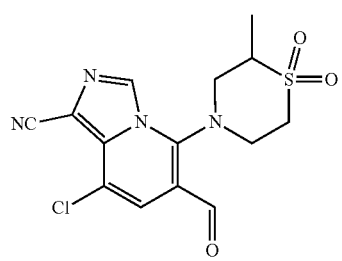 [SMILES: CC1CN(c2c(C=O)cc(Cl)c3c(C#N)ncn23)CCS1(=O)=O]

Using 8-chloro-5-(2-methyl-1,1-dioxidothiomorpholino)imidazo[1,5-a]pyridine-6-carbaldehyde (racemic, Example 167, Step 2), Steps 1 and 2 of Example 173 were followed to afford the title compound. LCMS calculated for C$_{14}$H$_{14}$ClN$_4$O$_3$S monoisotopic (M+H)$^+$: m/z=353.0; found 353.0.

Step 2. 2-Amino-N-((8-chloro-1-cyano-5-(2-methyl-1,1-dioxidothiomorpholino)imidazo[1,5-a]pyridin-6-yl)methyl)pyrazolo[1,5-a]pyrimidine-3-carboxamide trifluoroacetate salt (Racemic Mixture Prepared)

Using 8-chloro-6-formyl-5-(2-methyl-1,1-dioxidothiomorpholino)imidazo[1,5-a]pyridine-1-carbonitrile (28 mg, 0.079 mmol), Steps 2 through 4 of Example 172 were followed to afford the title compound. LCMS calculated for $C_{21}H_{21}ClN_9O_3S$ monoisotopic $(M+H)^+$: m/z=514.1; found 514.2.

Example 175. 2-Amino-N-(1-(8-chloro-1-cyano-5-(2-methyl-1,1-dioxidothiomorpholino)imidazo[1,5-a]pyridin-6-yl)propyl)pyrazolo[1,5-a]pyrimidine-3-carboxamide trifluoroacetate salt (Mixture of Four Diastereomers Prepared)

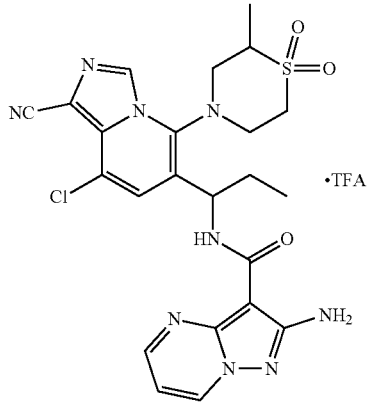 [SMILES: CCC(NC(=O)c1c(N)nn2cccnc12)c1cc(Cl)c2c(C#N)ncn2c1N1CCS(=O)(=O)C(C)C1]

Step 1. N-((8-Chloro-1-cyano-5-(2-methyl-1,1-dioxidothiomorpholino)imidazo[1,5-a]pyridin-6-yl)methylene)-2-methylpropane-2-sulfinamide (Mixture of Diastereomers Prepared)

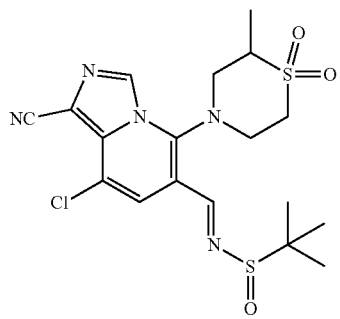 [SMILES: CC1CN(c2c(/C=N/S(=O)C(C)(C)C)cc(Cl)c3c(C#N)ncn23)CCS1(=O)=O]

To a mixture of 8-chloro-6-formyl-5-(2-methyl-1,1-dioxidothiomorpholino)imidazo[1,5-a]pyridine-1-carbonitrile (28 mg, 0.079 mmol, Example 174, Step 1) and 2-methylpropane-2-sulfinamide (19.24 mg, 0.159 mmol, racemic) in THF (2.0 mL) was added titanium(IV) isopropoxide (0.070 mL, 0.24 mmol). The mixture was stirred at 70° C. in a sealed vial for 50 minutes. The mixture was cooled to 0° C. and was treated with water (0.50 mL). The mixture was then diluted with 5 mL each of acetonitrile and EtOAc. After stirring for 10 minutes, $Na_2SO_4$ was added. The mixture was stirred for 5 minutes and was filtered through Celite®. The filter aid was washed with additional EtOAc and the filtrate was concentrated to afford crude product. The product was purified by flash chromatography (0-100% EtOAc in hexanes). Yield: 32 mg, 88%. LCMS calculated for $C_{18}H_{23}ClN_5O_3S_2$ monoisotopic $(M+H)^+$: m/z=456.1; found 456.0.

Step 2. 6-(1-Aminopropyl)-8-chloro-5-(2-methyl-1,1-dioxidothiomorpholino)imidazo[1,5-a]pyridine-1-carbonitrile (Mixture of Four Diastereomers Prepared)

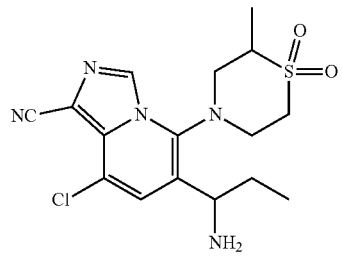 [SMILES: CCC(N)c1cc(Cl)c2c(C#N)ncn2c1N1CCS(=O)(=O)C(C)C1]

N-((8-Chloro-1-cyano-5-(2-methyl-1,1-dioxidothiomorpholino)imidazo[1,5-a]pyridin-6-yl)methylene)-2-methylpropane-2-sulfinamide (20 mg, 0.044 mmol) in THF (2.0 mL) at 0° C. was treated with ethylmagnesium chloride (2.0 M in ether, 0.175 mL, 0.351 mmol). The cooling bath was removed and the reaction was allowed to warm to room temperature and stir for 10 minutes at room temperature. The reaction mixture was then re-cooled to 0° C. and MeOH (0.5 mL) was added. 4.0 M HCl in dioxane (0.44 mL, 1.8 mmol) was introduced. The reaction mixture was warmed to room temperature and stirred for 30 minutes. Solvent was removed in vacuo and the product was purified by preparative HPLC/MS (pH=10). Yield: 12.6 mg, 75%. LCMS calculated for $C_{16}H_{21}ClN_5O_2S$ monoisotopic $(M+H)^+$: m/z=382.1; found 382.1.

Step 3. 2-Amino-N-(1-(8-chloro-1-cyano-5-(2-methyl-1,1-dioxidothiomorpholino)imidazo[1,5-a]pyridin-6-yl)propyl)pyrazolo[1,5-a]pyrimidine-3-carboxamide trifluoroacetate salt (Mixture of Four Diastereomers Prepared)

Using 6-(1-aminopropyl)-8-chloro-5-(2-methyl-1,1-dioxidothiomorpholino)imidazo[1,5-a]pyridine-1-carbonitrile (mixture of diastereomers) (12.6 mg, 0.033 mmol), the method of Example 26, Step 12 was followed to afford the title compound. Yield: 13.7 mg. LCMS calculated for $C_{23}H_{25}ClN_9O_3S$ monoisotopic $(M+H)^+$: m/z=542.1, found 542.2.

Example 176

Example 176 in Table 18 was prepared by the method of Example 175, using cyclopropylmagnesium bromide in Step 2.

TABLE 18

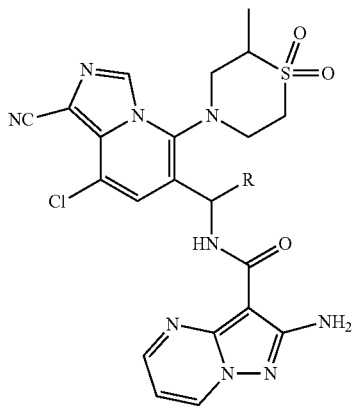

| Ex. No. | Name | R = | LCMS |
|---|---|---|---|
| 176 | 2-Amino-N-{(8-chloro-1-cyano-5-(2-methyl-1,1-dioxido-thiomorpholino)imidazo[1,5-a]pyridin-6-yl)(cyclopropyl)-methyl)pyrazolo[1,5-a]pyrimidine-3-carboxamide trifluoro-acetate salt (mixture of four diastereomers prepared) | 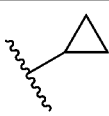 | Calculated for $C_{24}H_{25}ClN_9O_3S$ monoisotopic $(M + H)^+$: m/z = 554.1; found: 554.1 |

Example 177. 2-Amino-N-(1-(8-chloro-1-cyano-5-(2-methyl-1,1-dioxidothiomorpholino)imidazo[1,5-a]pyridin-6-yl)-2,2,2-trifluoroethyl)pyrazolo[1,5-a]pyrimidine-3-carboxamide trifluoroacetate salt (Mixture of Four Diastereomers Prepared)

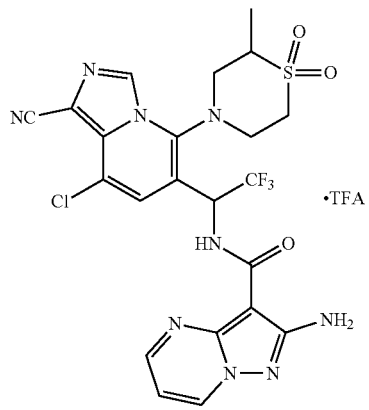 [SMILES: CC1CN(c2c(C(NC(=O)c3c(N)nn4cccnc34)C(F)(F)F)cc(Cl)c3c(C#N)ncn23)CCS1(=O)=O]

Step 1. 6-(1-Amino-2,2,2-trifluoroethyl)-8-chloro-5-(2-methyl-1,1-dioxidothiomorpholino)imidazo[1,5-a]pyridine-1-carbonitrile (Mixture of Four Diastereomers Prepared)

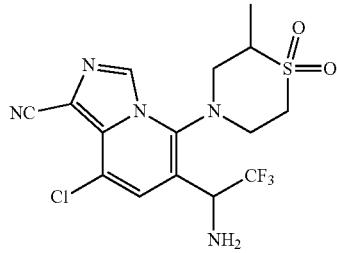 [SMILES: CC1CN(c2c(C(N)C(F)(F)F)cc(Cl)c3c(C#N)ncn23)CCS1(=O)=O]

To N-((8-chloro-1-cyano-5-(2-methyl-1,1-dioxidothiomorpholino)imidazo[1,5-a]pyridin-6-yl)methylene)-2-methylpropane-2-sulfinamide (22. mg, 0.048 mmol, Example 175, Step 1) and tetramethylammonium fluoride (5.39 mg, 0.058 mmol, Aldrich) in DMF (1.0 mL) at 0° C. was added trimethyl(trifluoromethyl)silane (0.018 mL, 0.121 mmol, Aldrich). The mixture was stirred at 0° C. for 2 hours. Additional trimethyl(trifluoromethyl)silane (23 mg, 0.18 mmol) was added portionwise as the reaction stirred for a further 1 hour and 20 minutes at 0° C. Saturated $NH_4Cl$ solution was added and the mixture was extracted with EtOAc. The combined extracts were washed with brine, dried over $Na_2SO_4$, filtered, and concentrated. The residue was dissolved in MeOH (1.0 mL), cooled to 0° C. and 4.0 M HCl in dioxane (0.36 mL, 1.4 mmol) was added. After 15 minutes, volatiles were removed in vacuo. The residue was dissolved in MeOH and triethylamine was added to neutralize. Volatiles were again removed in vacuo. The product was then purified by flash chromatography (0-5% MeOH in DCM). Yield: 5.7 mg, 28%. LCMS calculated for $C_{15}H_{16}ClF_3N_5O_2S$ monoisotopic $(M+H)^+$: m/z=422.1; found 422.1.

Step 2. 2-Amino-N-(1-(8-chloro-1-cyano-5-(2-methyl-1,1-dioxidothiomorpholino)imidazo[1,5-a]pyridin-6-yl)-2,2,2-trifluoroethyl)pyrazolo[1,5-a]pyrimidine-3-carboxamide trifluoroacetate salt (Mixture of Four Diastereomers Prepared)

Using 6-(1-amino-2,2,2-trifluoroethyl)-8-chloro-5-(2-methyl-1,1-dioxidothiomorpholino)imidazo[1,5-a]pyridine-1-carbonitrile (5.7 mg, 0.014 mmol), the method of Example 26, Step 12 was followed to afford the title compound. Yield: 3.8 mg. LCMS calculated for $C_{22}H_{20}ClF_3N_9O_3S$ monoisotopic $(M+H)^+$: m/z=582.1; found 582.1.

Example 178. 2-Amino-N-{1-[8-chloro-5-(1,1-di-oxidothiomorpholin-4-yl)imidazo[1,5-a]pyridin-6-yl]propyl}pyrazolo[1,5-a]pyrimidine-3-carboxamide trifluoroacetate salt (Racemic Mixture Prepared)

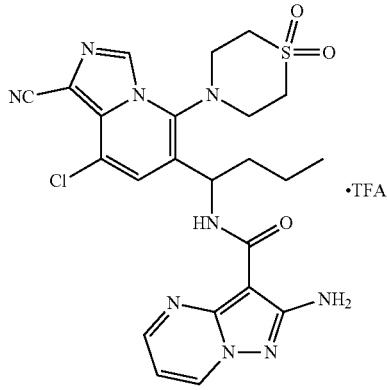 [SMILES: CCCC(NC(=O)c1c(N)nn2cccnc12)c1cc(Cl)c2c(C#N)ncn2c1N1CCS(=O)(=O)CC1]

Step 1. 1-(8-Chloro-5-thiomorpholin-4-ylimidazo[1,5-a]pyridin-6-yl)butan-1-one

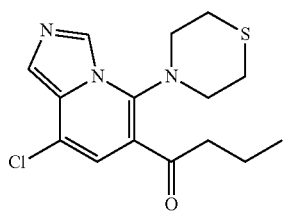 [SMILES: CCCC(=O)c1cc(Cl)c2cncn2c1N1CCSCC1]

2.0 M Propylmagnesium chloride in diethyl ether (0.14 mL, 0.29 mmol) was added to a solution of 8-chloro-N-methoxy-N-methyl-5-thiomorpholin-4-ylimidazo[1,5-a]pyridine-6-carboxamide (33 mg, 0.097 mmol, Example 166, Step 1) in THF at 0° C. The reaction was stirred for one hour at 0° C. and then allowed to stir with warming to room temperature for 2 hours. The reaction was re-cooled to 0° C. and quenched by the addition of 1.0 M HCl (0.3 mL). The solution was stirred for 15 minutes. Saturated NaHCO₃ was added to ensure basicity, and the mixture was extracted with EtOAc three times. The combined organic extracts were washed with brine, dried over Na₂SO₄, filtered and concentrated. The product was purified by flash chromatography (0-50% EtOAc in hexanes). Yield: 12 mg, 38%. LCMS calculated for $C_{15}H_{19}ClN_3OS$ monoisotopic (M+H)⁺: m/z=324.1; found 324.1.

Step 2. 1-[8-Chloro-5-(1,1-dioxidothiomorpholin-4-yl)imidazo[1,5-a]pyridin-6-yl]butan-1-one

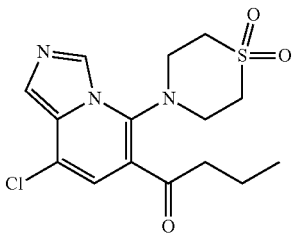 [SMILES: CCCC(=O)c1cc(Cl)c2cncn2c1N1CCS(=O)(=O)CC1]

1-(8-Chloro-5-thiomorpholin-4-ylimidazo[1,5-a]pyridin-6-yl)butan-1-one (11 mg, 0.035 mmol) in ethyl acetate (1 mL) was treated with m-chloroperbenzoic acid (18 mg, 0.11 mmol). The reaction was stirred for 1 hour and solvent was removed in vacuo. The product was purified by preparative HPLC/MS (pH=10) and eluent evaporated. Yield: 6.0 mg, 48%. LCMS calculated for $C_{15}H_{19}ClN_3O_3S$ monoisotopic (M+H)⁺: m/z=356.1, found 356.1.

Step 3. 1-[8-Chloro-5-(1,1-dioxidothiomorpholin-4-yl)imidazo[1,5-a]pyridin-6-yl]butan-1-amine (Racemic Mixture Prepared)

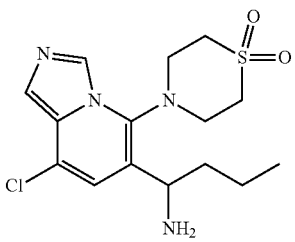 [SMILES: CCCC(N)c1cc(Cl)c2cncn2c1N1CCS(=O)(=O)CC1]

Sodium cyanoborohydride (7.6 mg, 0.12 mmol) was added to a mixture of 1-[8-chloro-5-(1,1-dioxidothiomorpholin-4-yl)imidazo[1,5-a]pyridin-6-yl]butan-1-one (6.0 mg, 0.017 mmol) and ammonium acetate (28 mg, 0.36 mmol) in MeOH (0.75 mL). The mixture was sealed and heated to 70° C. for 2 days. Additional ammonium acetate (28 mg, 0.36 mmol) and sodium cyanoborohydride (7.6 mg, 0.12 mmol) were added and heating was continued for 2 days. Upon cooling to room temperature, saturated NaHCO₃ was added. The mixture was diluted with water and the aqueous mixture was saturated with NaCl. The aqueous mixture was extracted with 10% iPrOH in DCM three times. The combined extracts were dried over Na₂SO₄, filtered and concentrated. The product was used without further purification. LCMS calculated for $C_{15}H_{22}ClN_4O_2S$ monoisotopic (M+H)⁺: m/z=357.1, found 357.1.

Step 4. 2-Amino-N-{1-[8-chloro-5-(1,1-dioxidothiomorpholin-4-yl)imidazo[1,5-a]pyridin-6-yl]propyl}pyrazolo[1,5-a]pyrimidine-3-carboxamide trifluoroacetate salt (Racemic Mixture Prepared)

Using 1-[8-chloro-5-(1,1-dioxidothiomorpholin-4-yl)imidazo[1,5-a]pyridin-6-yl]butan-1-amine, the method of Example 26, Step 12 was followed to provide the title compound. Yield: 3.1 mg. LCMS calculated for $C_{22}H_{26}ClN_8O_3S$ monoisotopic (M+H)$^+$: m/z=517.2, found 517.1. $^1$H NMR (400 MHz, $d_6$-DMSO) δ 9.01 (s, 1H), 8.91 (dd, J=6.7, 1.5 Hz, 1H), 8.57 (dd, J=4.5, 1.5 Hz, 1H), 8.10 (d, J=7.4 Hz, 1H), 7.74 (s, 1H), 7.21 (s, 1H), 7.01 (dd, J=6.7, 4.6 Hz, 1H), 5.34-5.26 (m, 1H), 4.01-3.21 (m, 8H), 2.07-1.91 (m, 1H), 1.79-1.68 (m, 1H), 1.58-1.44 (m, 1H), 1.43-1.27 (m, 1H), 0.96 (t, J=7.2 Hz, 3H).

Example 179

Example 179 in Table 19 was prepared by the method of Example 178, using ethylmagnesium chloride in Step 1. NMR data for the compounds of Table 19 is shown in Table 19a.

TABLE 19

| Ex. No. | Name | R = | LCMS |
|---|---|---|---|
| 179 | 2-Amino-N-{1-[8-chloro-5-(1,1-dioxido-thiomorpholin-4-yl)imidazo[1,5-a]-pyridin-6-yl]propyl}pyrazolo[1,5-a]-pyrimidine-3-carboxamide trifluoro-acetate salt (racemic mixture prepared) | 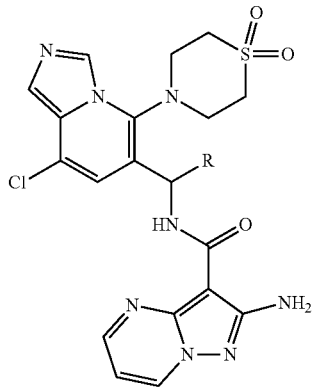 | Calculated for $C_{21}H_{24}ClN_8O_3S$ monoisotopic (M + H)$^+$: m/z = 503.1: found: 503.1 |

TABLE 19a

| Ex. No. | $^1$H NMR |
|---|---|
| 179 | $^1$H NMR (400 MHz, CD$_3$OD) δ 9.50 (s, 1H), 8.69 (dd, J = 6.8, 1.6 Hz, 1H), 8.56 (dd, J = 4.5, 1.6 Hz, 1H), 8.09 (s, 1H), 7.40 (s, 1H), 6.98 (dd, J = 6.8, 4.5 Hz, 1H), 5.35 (dd, J = 8.9, 6.1 Hz, 1H), 4.21-4.09 (m, 1H), 3.99-3.81 (m, 2H), 3.81-3.69 (m, 1H), 3.67-3.31 (m, 4H), 2.14-2.02 (m, 1H), 1.99-1.86 (m, 1H), 1.14 (t, J = 7.4 Hz, 3H) |

Example 180. 2-Amino-N-{1-[8-chloro-5-(1,1-dioxidothiomorpholin-4-yl)imidazo[1,5-a]pyridin-6-yl]-2,2,2-trifluoroethyl}pyrazolo[1,5-a]pyrimidine-3-carboxamide trifluoroacetate salt (Racemic Mixture Prepared)

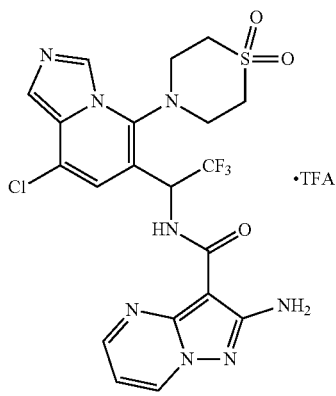 [SMILES: Nc1nn2cccnc2c1C(=O)NC(c1cc(Cl)c2cncn2c1N1CCS(=O)(=O)CC1)C(F)(F)F]

Step 1. N-{(1E)-[8-Chloro-5-(1,1-dioxidothiomorpholin-4-yl)imidazo[1,5-a]pyridin-6-yl]methylene}-2-methylpropane-2-sulfinamide

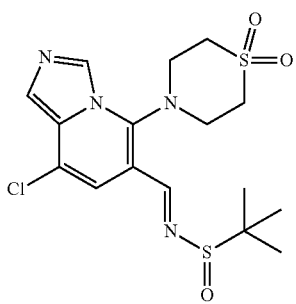 [SMILES: CC(C)(C)S(=O)/N=C/c1cc(Cl)c2cncn2c1N1CCS(=O)(=O)CC1]

The method of Example 175, Step 1 was used, starting with 8-chloro-5-(1,1-dioxidothiomorpholin-4-yl)imidazo[1,5-a]pyridine-6-carbaldehyde (20 mg, 0.064 mmol, Example 166, Step 3) to afford the title compound. Yield: 20 mg, 75%. LCMS calculated for $C_{16}H_{22}ClN_4O_3S_2$ monoisotopic $(M+H)^+$: m/z=417.1; found 417.1.

Step 2. 1-[8-Chloro-5-(1,1-dioxidothiomorpholin-4-yl)imidazo[1,5-a]pyridin-6-yl]-2,2,2-trifluoroethanamine (Racemic Mixture Prepared)

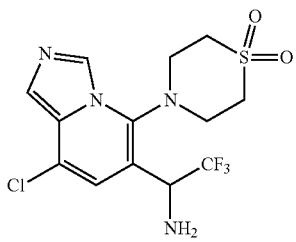 [SMILES: NC(c1cc(Cl)c2cncn2c1N1CCS(=O)(=O)CC1)C(F)(F)F]

N-{(1E)-[8-Chloro-5-(1,1-dioxidothiomorpholin-4-yl)imidazo[1,5-a]pyridin-6-yl]methylene}-2-methylpropane-2-sulfinamide (10. mg, 0.024 mmol) in THF (1.5 mL) at −45° C., was treated with tetramethylammonium fluoride (2.4 mg, 0.026 mmol, Aldrich), followed by (trifluoromethyl)trimethylsilane (4.6 µL, 0.031 mmol, Aldrich) in THF (0.10 mL). The mixture was then allowed to warm to −20° C., and additional (trifluoromethyl)trimethylsilane (4.6 µL, 0.031 mmol) in THF (0.1 mL) was added. The solution was warmed to 0° C. and further (trifluoromethyl)trimethylsilane (4.6 µL, 0.031 mmol) and tetramethylammonium fluoride (2.4 mg, 0.026 mmol), were added. After 30 minutes of stirring at 0° C., 1N HCl (0.5 mL) was added. Volatiles were removed in vacuo. The residue was dissolved in MeOH (1.0 mL) and treated with 4.0 M HCl in dioxane (0.18 mL, 0.72 mmol) at 0° C. for 15 minutes. Volatiles were removed in vacuo and the product was purified by preparative HPLC/MS (pH=10). Yield: 2.0 mg, 22%. LCMS calculated for $C_{13}H_{15}ClF_3N_4O_2S$ monoisotopic $(M+H)^+$: m/z=383.1; found 383.0.

Step 3. 2-Amino-N-{1-[8-chloro-5-(1,1-dioxidothiomorpholin-4-yl)imidazo[1,5-a]pyridin-6-yl]-2,2,2-trifluoroethyl}pyrazolo[1,5-a]pyrimidine-3-carboxamide trifluoroacetate salt (Racemic Mixture Prepared)

1-[8-Chloro-5-(1,1-dioxidothiomorpholin-4-yl)imidazo[1,5-a]pyridin-6-yl]-2,2,2-trifluoroethanamine (2.0 mg, 0.0052 mmol) was treated according to the method of Example 26, Step 12 to afford the title compound. Yield: 1.2 mg. LCMS calculated for $C_{20}H_{19}ClF_3N_8O_3S$ monoisotopic $(M+H)^+$: m/z=543.1; found 543.1. $^1$H NMR (400 MHz, CD$_3$OD) δ 9.46 (s, 1H), 8.93 (d, J=8.7 Hz, 1H), 8.73 (dd, J=6.8, 1.5 Hz, 1H), 8.60 (dd, J=4.5, 1.5 Hz, 1H), 8.12 (s, 1H), 7.36 (s, 1H), 7.02 (dd, J=6.8, 4.6 Hz, 1H), 6.70-6.54 (m, 1H), 4.13-3.31 (m, 8H).

Example 181. 2-Amino-N-(1-(8-chloro-5-(1,1-dioxidothiomorpholino)imidazo[1,5-a]pyridin-6-yl)-2-methylpropyl)pyrazolo[1,5-a]pyrimidine-3-carboxamide trifluoroacetate salt (Racemic Mixture Prepared)

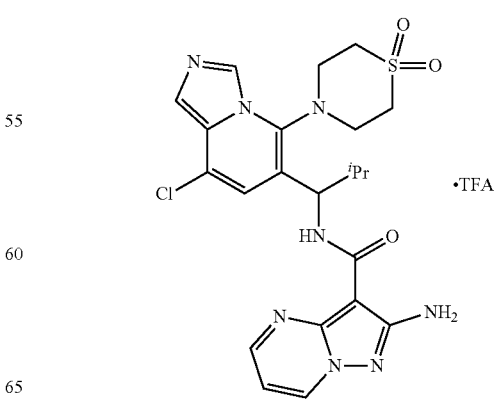

Step 1. 4-(6-(1-Amino-2-methylpropyl)-8-chloro-imidazo[1,5-a]pyridin-5-yl)thiomorpholine 1,1-dioxide

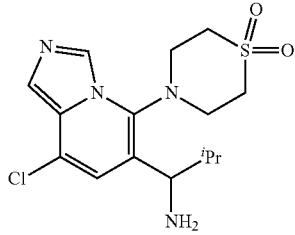 [SMILES: CC(C)C(N)c1cc(Cl)c2cncn2c1N1CCS(=O)(=O)CC1]

Using (E)-N-((8-chloro-5-(1,1-dioxidothiomorpholino)imidazo[1,5-a]pyridin-6-yl)methylene)-2-methylpropane-2-sulfinamide (45 mg, 0.11 mmol, Example 180, Step 1), the method of Example 175, Step 2 was followed, using isopropylmagnesium chloride (2.0 M in THF, 0.43 mL, 0.86 mmol) to afford the title compound. Yield: 4.0 mg, 10%. LCMS calculated for $C_{15}H_{22}ClN_4O_2$ monoisotopic $(M+H)^+$: m/z=357.1; found 357.1.

Step 2. 2-Amino-N-(1-(8-chloro-5-(1,1-dioxidothiomorpholino)imidazo[1,5-a]pyridin-6-yl)-2-methylpropyl)pyrazolo[1,5-a]pyrimidine-3-carboxamidetrifluoroacetate salt (Racemic Mixture Prepared)

Using 4-(6-(1-amino-2-methylpropyl)-8-chloroimidazo[1,5-a]pyridin-5-yl)thiomorpholine 1,1-dioxide (4.0 mg, 0.011 mmol), the method of Example 26, Step 12 was followed to afford the title compound. Yield: 3.6 mg. LCMS calculated for $C_{22}H_{26}ClN_8O_3S$ monoisotopic $(M+H)^+$: m/z=517.2; found 517.2. $^1$H NMR (400 MHz, $d_6$-DMSO) δ 8.92 (dd, J=6.7, 1.5 Hz, 1H), 8.86 (s, 1H), 8.57 (dd, J=4.5, 1.5 Hz, 1H), 8.17 (d, J=8.0 Hz, 1H), 7.71 (s, 1H), 7.16 (s, 1H), 7.01 (dd, J=6.7, 4.5 Hz, 1H), 5.12 (t, J=8.6 Hz, 1H), 3.94-3.25 (m, 8H), 2.27-2.14 (m, 1H), 1.15 (d, J=6.4 Hz, 3H), 0.87 (d, J=6.7 Hz, 3H).

Example 182

Example 182 in Table 20 was prepared by the method of Example 181, using cyclopropylmagnesium bromide in Step 1. NMR data for the compound of Table 20 is shown in Table 20a.

TABLE 20

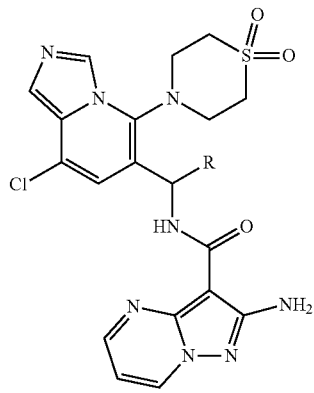

| Ex. No. | Name | R = | LCMS |
|---|---|---|---|
| 182 | 2-Amino-N-((8-chloro-5-(1,1-dioxido-thiomorpholino)imidazo[1,5-a]pyridin-6-yl)(cyclopropyl)methyl)pyrazolo[1,5-a]-pyrimidine-3-carboxamide trifluoro-acetate salt (racemic mixture prepared) | cyclopropyl | Calculated for $C_{22}H_{24}ClN_8O_3S$ monoisotopic $(M + H)^+$: m/z = 515.1; found:515.1 |

TABLE 20a

| Ex. No. | $^1$H NMR |
|---|---|
| 182 | $^1$H NMR (400 MHz, $d_6$-DMSO) δ 8.95 (s, 1H), 8.93 (dd, J = 6.7, 1.5 Hz, 1H), 8.57 (dd, J = 4.5, 1.5 Hz, 1H), 8.20 (d, J = 7.2 Hz, 1H), 7.77 (s, 1H), 7.31 (s, 1H), 7.02 (dd, J = 6.7, 4.5 Hz, 1H), 4.91 (t, J = 7.7 Hz, 1H), 3.95-3.66 (m, 3H), 3.62-3.38 (m, 4H), 3.38-3.21 (m, 1H), 1.56-1.43 (m, 1H), 0.74-0.61 (m, 2H), 0.60-0.45 (m, 1H), 0.37-0.22 (m, 1H) |

Example 183. 2-Amino-N-[1-(8-chloro-5-cyclohexylimidazo[1,5-a]pyridin-6-yl)ethyl]pyrazolo[1,5-a]pyrimidine-3-carboxamide trifluoroacetate salt (Racemic Mixture Prepared)

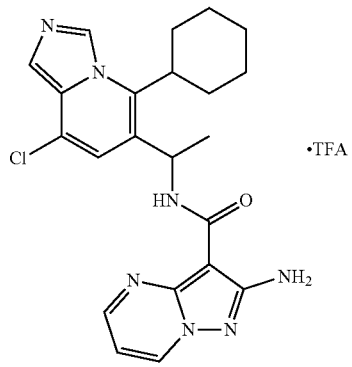 [SMILES: CC(NC(=O)c1c(N)nn2cccnc12)c1cc(Cl)c2cncn2c1C1CCCCC1]

Step 1. 1-(8-Chloro-5-cyclohexylimidazo[1,5-a]pyridin-6-yl)ethanone

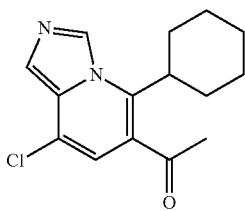 [SMILES: CC(=O)c1cc(Cl)c2cncn2c1C1CCCCC1]

To a degassed solution of 1-(5,8-dichloroimidazo[1,5-a]pyridin-6-yl)ethanone (10.0 mg, 0.0436 mmol, Example 130, Step 7) in 1,4-dioxane (2 mL) was added [1,1'-bis(diphenylphosphino)ferrocene]dichloropalladium(II), complex with dichloromethane (1:1) (2 mg, 0.002 mmol) and 0.4 M dicyclohexylzinc in ether (0.2 mL, 0.08 mmol). The resulting mixture was heated to 50° C. for 1 hour. Additional [1,1'-bis(diphenylphosphino)ferrocene]dichloropalladium (II), complex with dichloromethane (1:1) (2 mg) and 0.4 M dicyclohexylzinc in ether (0.2 mL) were added and the reaction was heated to 60° C. overnight. Upon cooling, water was added and the mixture was extracted with EtOAc. The organic extract was washed with brine, dried over MgSO$_4$, filtered and concentrated. The product was purified by flash chromatography (0-60% EtOAc in hexanes). Yield: 10 mg, 80%. LCMS calculated for C$_{15}$H$_{18}$ClN$_2$O monoisotopic (M+H)$^+$: m/z=277.1; found 277.1.

Step 2. 1-(8-Chloro-5-cyclohexylimidazo[1,5-a]pyridin-6-yl)ethanamine trifluoroacetate salt (Racemic Mixture Prepared)

2.0 M Ammonia in ethanol (2 mL, 4 mmol) and titanium tetraisopropoxide (50 µL, 0.2 mmol) were added to 1-(8-chloro-5-cyclohexylimidazo[1,5-a]pyridin-6-yl)ethanone (12 mg, 0.043 mmol). The mixture heated to 65° C. overnight in a sealed vial. After cooling to room temperature, sodium borohydride (3 mg, 0.07 mmol) was added and the reaction was stirred for 1 hour. 1N NH$_4$OH was introduced and the mixture was diluted with acetonitrile. The precipitate that formed was removed by filtration. The filtrate was collected and acetonitrile was removed in vacuo. The residue was partitioned between water and EtOAc. The aqueous layer was extracted again with EtOAc. The combined organic extracts were washed with brine, dried over MgSO$_4$, filtered, and concentrated. The product was purified by preparative HPLC/MS (pH=2). Yield: 5 mg. LCMS calculated for C$_{15}$H$_{21}$ClN$_3$ monoisotopic (M+H)$^+$: m/z=278.1; found 278.1.

Step 3. 2-Amino-N-[1-(8-chloro-5-cyclohexylimidazo[1,5-a]pyridin-6-yl)ethyl]pyrazolo[1,5-a]pyrimidine-3-carboxamide trifluoroacetate salt (Racemic Mixture Prepared)

1-(8-Chloro-5-cyclohexylimidazo[1,5-a]pyridin-6-yl)ethanamine trifluoroacetate salt (5 mg, 0.02 mmol) was treated by the method of Example 26, Step 12 to afford the title compound. Yield: 3 mg. LCMS calculated for C$_{22}$H$_{25}$ClN$_7$O monoisotopic (M+H)$^+$: m/z=438.2; found 438.1.

Example 184. 2-Amino-N-[1-(8-chloro-3-methyl-5-phenyl[1,2,4]triazolo[4,3-a]pyridin-6-yl)ethyl]pyrazolo[1,5-a]pyrimidine-3-carboxamide trifluoroacetate salt (Racemic Mixture Prepared)

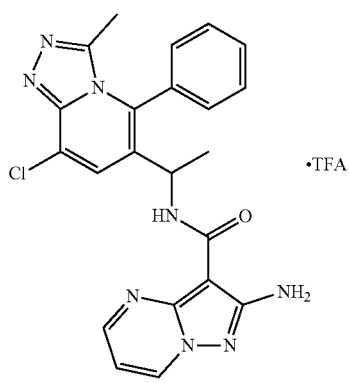 [SMILES: Cc1nnc2c(Cl)cc(C(C)NC(=O)c3c(N)nn4cccnc34)c(-c3ccccc3)n12]

Step 1. Methyl 5-chloro-2-phenylnicotinate

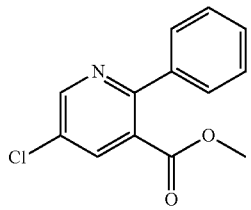 [SMILES: COC(=O)c1cc(Cl)cnc1-c1ccccc1]

A degassed mixture of methyl 2,5-dichloronicotinate (4.25 g, 20.6 mmol), phenylboronic acid (2.77 g, 22.7 mmol, Aldrich), $K_2CO_3$ (6.13 g, 44.4 mmol) and bis(triphenylphosphine)palladium(II) chloride (1.6 g, 2.3 mmol) in water (15 mL) and 1,4-dioxane (40 mL) was heated to 80° C. overnight. Upon cooling, the reaction mixture was diluted with EtOAc and water and filtered through Celite®. The aqueous layer was separated and extracted with two further portions of EtOAc. The combined organic extracts were washed with water and brine, dried over $Na_2SO_4$, filtered and concentrated. The product was purified by flash chromatography (0-80% EtOAc in hexanes). Yield: 3.9 g, 76%. LCMS calculated for $C_{13}H_{11}ClNO_2$ monoisotopic $(M+H)^+$: m/z=248.0; found 248.0.

Step 2. Methyl 5-chloro-2-phenylnicotinate 1-oxide

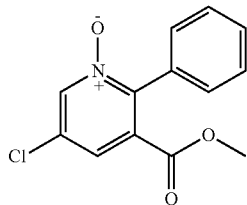

Methyl 5-chloro-2-phenylnicotinate (3.9 g, 16 mmol) in ethaneperoxoic acid (8.1 mL, 38 mmol) was heated to 90° C. for 3.5 hours. Additional ethaneperoxoic acid (16.0 mL, 76 mmol) was added portionwise at 1 hour increments over 4 hours. Solvent was removed in vacuo and the product was purified by flash chromatography (0-50% EtOAc/hexanes). Yield: 2.74 g, 66%. LCMS calculated for $C_{13}H_{11}ClNO_3$ monoisotopic $(M+H)^+$: m/z=264.0; found 264.0.

Step 3. Methyl 5,6-dichloro-2-phenylnicotinate

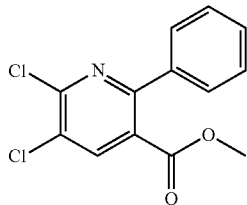 [SMILES: COC(=O)c1cc(Cl)c(Cl)nc1-c1ccccc1]

Methyl 5-chloro-2-phenylnicotinate 1-oxide (2.74 g, 10.4 mmol) in phosphoryl chloride (27 mL, 290 mmol) was heated to 90° C. for 1.5 hours. The POCl3 was evaporated on the rotovap and the residue was subjected to flash chromatography (0-30% EtOAc/hexanes). Yield: 2.20 g, 75.0%. LCMS calculated for $C_{13}H_{10}Cl_2NO_2$ monoisotopic $(M+H)^+$: m/z=282.0; found 282.0.

Step 4. Methyl 8-chloro-3-methyl-5-phenyl[1,2,4]triazolo[4,3-a]pyridine-6-carboxylate

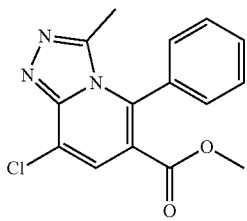 [SMILES: COC(=O)c1cc(Cl)c2nnc(C)n2c1-c1ccccc1]

A mixture of methyl 5,6-dichloro-2-phenylnicotinate (0.500 g, 1.77 mmol) and hydrazine hydrate (0.10 mL, 2.0 mmol) in ethanol (5 mL) was heated to 75° C. for 1 hour. Further hydrazine hydrate (0.10 mL, 2.0 mmol) was added and heating was continued for 3.5 hours. Additional hydrazine hydrate (0.1 mL) was added and the heating was continued for 45 minutes, then discontinued and the reaction mixture was stirred at room temperature overnight. Volatiles were removed in vacuo and the product was used without further purification in triazole form. Triethyl orthoacetate (5 mL, 30 mmol) was added to the residue and the reaction was heated to 85° C. for 1 hour. Volatiles were again removed in vacuo to afford a solid that was used without further purification. Theoretical yield assumed. LCMS calculated for $C_{15}H_{13}ClN_3O_2$ monoisotopic $(M+H)^+$: m/z=302.1; found 302.1.

Step 5. 8-Chloro-3-methyl-5-phenyl[1,2,4]triazolo[4,3-a]pyridine-6-carboxylic acid

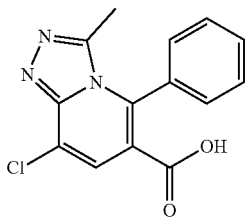 [SMILES: Cc1nnc2c(Cl)cc(C(=O)O)c(-c3ccccc3)n12]

Methyl 8-chloro-3-methyl-5-phenyl[1,2,4]triazolo[4,3-a]pyridine-6-carboxylate (0.524 g, 1.74 mmol) in methanol (10 mL) was treated with 3.0 M NaOH (2.3 mL, 7.0 mmol). After stirring for 20 minutes, 1N HCl was added to achieve pH=4. The solid white product precipitated and was isolated by filtration and air dried. Yield: 0.36 g, 72%. LCMS calculated for $C_{14}H_{11}ClN_3O_2$ monoisotopic $(M+H)^+$: m/z=288.1; found 288.0.

Step 6. 2-Amino-N-[1-(8-chloro-3-methyl-5-phenyl[1,2,4]triazolo[4,3-a]pyridin-6-yl)ethyl]pyrazolo[1,5-a]pyrimidine-3-carboxamide trifluoroacetate salt (Racemic Mixture Prepared)

Using 8-chloro-3-methyl-5-phenyl[1,2,4]triazolo[4,3-a]pyridine-6-carboxylic acid, the methods described in Steps 9-12 of Example 26 were followed to afford the title compound. LCMS calculated for $C_{22}H_{20}ClN_8O$ monoisotopic (M+H)$^+$: m/z=447.1; found 447.1. $^1$H NMR (400 MHz, CD$_3$OD) δ 8.68 (dd, J=6.8, 1.6 Hz, 1H), 8.53 (dd, J=4.5, 1.6 Hz, 1H), 7.89-7.84 (m, 1H), 7.83 (s, 1H), 7.71-7.47 (m, 4H), 6.97 (dd, J=6.8, 4.5 Hz, 1H), 4.79 (q, J=7.2 Hz, 1H), 1.93 (s, 3H), 1.48 (d, J=7.0 Hz, 3H).

Example 185. 2-Amino-N-[1-(8-chloro-5-phenyl[1,2,4]triazolo[4,3-a]pyridin-6-yl)ethyl]pyrazolo[1,5-a]pyrimidine-3-carboxamide trifluoroacetate salt (Racemic Mixture Prepared)

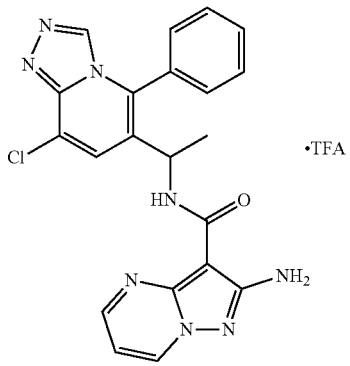 [SMILES: CC(NC(=O)c1c(N)nn2cccnc12)c1cc(Cl)c2nncn2c1-c1ccccc1]

The title compound was prepared by the method of Example 184, substituting trimethyl orthoformate for triethyl orthoacetate in Step 4. LCMS calculated for $C_{21}H_{18}ClN_8O$ monoisotopic (M+H)$^+$: m/z=433.1; found 433.1. $^1$H NMR (400 MHz, CD$_3$OD) δ 8.68 (dd, J=6.8, 1.6 Hz, 1H), 8.57 (s, 1H), 8.53 (dd, J=4.5, 1.6 Hz, 1H), 7.92-7.86 (m, 1H), 7.85 (s, 1H), 7.73-7.51 (m, 4H), 6.97 (dd, J=6.8, 4.5 Hz, 1H), 4.97 (q, J=6.9 Hz, 1H), 1.52 (d, J=7.0 Hz, 3H).

Example A. THP-1 RPS6 ELISA Assay

To measure the Phosphorylated Ribosomal Protein S6 (RPS6) in cell lysates, THP-1 cells (Human Acute Monocytic Leukemia) are purchased from ATCC (Manassas, VA) and maintained in RPMI with 10% FBS (Gibco/Life Technologies, Carlsbad, CA). For the assay, THP-1 cells are serum starved overnight in RPMI, then plated in RPMI (2×10$^5$ cells/well in 90 μL) into 96-well flat-bottom tissue culture treated plates (Corning, Corning, NY), in the presence or absence of a concentration range of test compounds. Covered plates are incubated for 2 hours at 37° C., 5% CO$_2$ then treated with or without 10 nM MCP-1 (MYBioSource, San Diego, CA) for 15 minutes at 37° C., 5% CO$_2$. Plates are centrifuged at 1600 RPM and supernatants are removed. Cells are lysed in Lysis Buffer (Cell Signaling, Danvers, MA) with Protease Inhibitor (Calbiochem/EMD, Germany), PMSF (Sigma, St Louis MO), HALTS (Thermo Fisher, Rockford, IL) for 30 min on wet ice. Cell lysates are frozen at −80° C. before testing. The lysates are tested in the Human/Mouse/Rat Phospho-RPS6 ELISA (R&D Systems, Inc. Minn, MN). The plate is measured using a microplate reader (SpectraMax M5-Molecular Devices, LLC Sunnyvale, CA) set to 450 nm with a wavelength correction of 540. IC$_{50}$ determination is performed by fitting the curve of inhibitor percent inhibition versus the log of the inhibitor concentration using the GraphPad Prism 5.0 software.

Example B. PI3K-γ Scintillation Proximity Assay

Materials

[γ-$^{33}$P]ATP (10 mCi/mL) and Wheat Germ Agglutinin (WGA) YSi SPA Scintillation Beads was purchased from Perkin-Elmer (Waltham, MA). Lipid kinase substrate, D-myo-Phosphatidylinositol 4,5-bisphosphate (PtdIns(4,5) P2)D (+)-sn-1,2-di-O-octanoylglyceryl, 3-O-phospho linked (PIP2), CAS 204858-53-7, was purchased from Echelon Biosciences (Salt Lake City, UT). PI3Kγ (p110γ) Recombinant Human Protein was purchased from Life technology (Grand Island, NY). ATP, MgCl$_2$, DTT, EDTA, MOPS and CHAPS were purchased from Sigma-Aldrich (St. Louis, MO).

The kinase reaction was conducted in polystyrene 384-well Greiner Bio-one white plate from Thermo Fisher Scientific in a final volume of 25 μL. Inhibitors were first diluted serially in DMSO and added to the plate wells before the addition of other reaction components. The final concentration of DMSO in the assay was 2%. The PI3Kγ assay was carried out at room temperature in 20 mM MOPS, pH 6.7, 10 mM MgCl$_2$, 5 mM DTT and CHAPS 0.03%. Reactions were initiated by the addition of ATP, the final reaction mixture consisted of 20 μM PIP2, 2 μM ATP, 0.5 μCi [γ-$^{33}$P] ATP, 13 nM PI3Kγ. Reactions were incubated for 120 min and terminated by the addition of 40 μL SPA beads suspended in quench buffer: 163 mM potassium phosphate pH 7.8, 20% glycerol, 25 mM EDTA. The final concentration of SPA beads is 1.0 mg/mL. After the plate sealing, plates were shaken overnight at room temperature and centrifuged at 1500 rpm for 10 min, the radioactivity of the product was determined by scintillation counting on Topcount (Perkin-Elmer). IC$_{50}$ determination was performed by fitting the curve of percent of the solvent control activity versus the log of the inhibitor concentration using the GraphPad Prism 6.0 software. Data for the Examples, obtained using the methods described in Example B, are provided in Table B.

Example C. PI3Kδ Scintillation Proximity Assay

Materials

[γ-$^{33}$P]ATP (10 mCi/mL) and Wheat Germ Agglutinin (WGA) YSi SPA Scintillation Beads was purchased from Perkin-Elmer (Waltham, MA). Lipid kinase substrate, D-myo-Phosphatidylinositol 4,5-bisphosphate (PtdIns(4,5) P2)D (+)-sn-1,2-di-O-octanoylglyceryl, 3-O-phospho linked (PIP2), CAS 204858-53-7, was purchased from Echelon Biosciences (Salt Lake City, UT). PI3Kδ (p110δ/p85α) Recombinant Human Protein was purchased from Eurofins (St Charles, MO). ATP, MgCl$_2$, DTT, EDTA, MOPS and CHAPS were purchased from Sigma-Aldrich (St. Louis, MO).

The kinase reaction was conducted in polystyrene 384-well Greiner Bio-one white plate from Thermo Fisher Scientific in a final volume of 25 μL. Inhibitors were first diluted serially in DMSO and added to the plate wells before the addition of other reaction components. The final concentration of DMSO in the assay was 2%. The PI3Kδ assay was carried out at room temperature in 20 mM MOPS, pH 6.7, 10 mM MgCl$_2$, 5 mM DTT and CHAPS 0.03%. Reactions were initiated by the addition of ATP, the final reaction mixture consisted of 20 μM PIP2, 2 μM ATP, 0.5 μCi [γ-$^{33}$P] ATP, 3.4 nM PI3Kδ. Reactions were incubated for 120 min and terminated by the addition of 40 μL SPA beads suspended in quench buffer: 163 mM potassium phosphate pH 7.8, 20% glycerol, 25 mM EDTA. The final concentration of SPA beads is 1.0 mg/mL. After the plate sealing, plates were shaken overnight at room temperature and centrifuged at 1500 rpm for 10 min, the radioactivity of the product was determined by scintillation counting on Topcount (Perkin-Elmer). $IC_{50}$ determination was performed by fitting the curve of percent of the solvent control activity versus the log of the inhibitor concentration using the GraphPad Prism 6.0 software.

Data for the Examples, obtained using the methods described in Examples A, B and C, are provided in Table 21.

TABLE 21

| Ex. No. | PI3Kγ $IC_{50}$ (nM) | PI3Kδ $IC_{50}$ (nM) | PI3Kγ_THP1_RPS6_ELISA $IC_{50}$ (nM) |
|---|---|---|---|
| 1 | ++ | ++ | |
| 2 | ++ | +++ | |
| 3a | + | + | # |
| 3b | ++++ | ++++ | |
| 4 | + | + | # |
| 5 | + | + | # |
| 6 | + | + | # |
| 7 | + | + | # |
| 8 | +++ | +++ | |
| 9 | ++ | ++ | |
| 10 | ++ | +++ | |
| 11 | ++ | ++ | |
| 5a | +++ | +++ | |
| 6a | +++ | +++ | |
| 7a | ++++ | ++++ | |
| 8a | +++ | ++++ | |
| 9a | +++ | ++++ | |
| 10a | +++ | ++++ | |
| 11a | +++ | ++++ | |
| 12 | ++ | ++ | |
| 13 | ++ | ++ | |
| 14 | + | ++ | ## |
| 15 | + | ++ | ### |
| 16 | ++ | +++ | |
| 17 | ++ | +++ | |
| 18 | ++ | +++ | |
| 19 | + | + | # |
| 20 | ++ | ++ | |
| 21 | +++ | ++++ | |
| 22 | ++ | ++ | |
| 23 | + | +++ | ## |
| 24 | + | ++ | |
| 25 | ++ | +++ | |
| 26 | + | + | # |
| 27 | + | + | |
| 28 | ++ | +++ | |
| 29 | + | +++ | |
| 30 | ++ | ++ | |
| 31A | + | + | # |
| 31B | + | + | # |
| 32 | + | + | # |
| 33 | + | + | # |
| 34 | + | + | # |
| 35 | + | + | # |
| 36 | + | + | # |
| 36A | + | + | # |
| 37 | + | ++ | # |
| 38A | + | + | # |
| 38B | + | + | # |
| 39 | + | + | # |
| 40 | + | + | # |
| 41 | + | + | # |
| 42 | + | + | # |
| 43 | + | + | # |
| 44 | ++ | +++ | ### |
| 45 | + | + | # |
| 46 | ++ | ++ | |
| 47 | ++ | ++ | |
| 48 | + | + | # |
| 49 | + | + | # |
| 50 | + | + | # |
| 51 | +++ | ++++ | NT |
| 52 | + | ++ | # |
| 53 | + | +++ | ### |
| 54 | + | + | ### |
| 55 | + | +++ | ### |
| 56 | + | + | # |
| 57 | + | + | # |
| 58 | + | + | # |
| 59 | + | + | # |
| 60 | + | ++ | # |
| 61 | + | +++ | ## |
| 62 | + | ++ | # |
| 63 | ++ | ++ | # |
| 64 | ++ | ++ | |
| 65 | + | + | # |
| 66 | + | + | # |
| 67 | + | + | # |
| 68 | + | + | # |
| 69 | + | ++ | ## |
| 70 | + | + | # |
| 71A | + | ++ | ## |
| 71B | + | + | # |
| 72A | + | + | # |
| 72B | + | + | # |
| 73A | + | + | # |
| 73B | + | + | # |
| 73C-73D | ++ | ++++ | |
| 74 | + | + | # |
| 75A | + | ++ | # |
| 75B | + | + | # |
| 76A | + | + | # |
| 76B | + | ++ | # |
| 77A | + | ++ | # |
| 77B | + | + | # |
| 78A | + | ++ | # |
| 78B | + | + | # |
| 79 | + | ++ | ### |
| 80 | + | ++ | # |
| 81 | + | + | # |
| 82 | + | + | # |
| 83 | + | + | # |
| 84 | + | + | # |
| 85 | + | + | # |
| 86 | + | ++ | ### |
| 87 | + | ++ | # |
| 88 | + | + | # |
| 89 | + | ++ | # |
| 90A | + | ++ | # |
| 90B | + | ++ | # |
| 91 | + | + | ## |
| 92 | + | ++ | # |
| 93 | + | +++ | ### |
| 94 | + | ++ | # |
| 95 | + | + | ## |
| 96A | + | + | ## |
| 96B | + | + | ### |
| 97 | + | ++ | ## |
| 98 | ++ | +++ | NA |
| 99 | ++ | + | NA |
| 100 | + | ++ | ### |
| 101 | + | ++ | # |
| 102 | + | ++ | ### |
| 103A | + | ++ | ## |
| 103B | + | ++ | # |
| 104 | + | + | # |
| 105 | + | + | # |
| 106 | + | ++ | ### |
| 107 | + | ++ | # |
| 108 | + | ++ | NA |
| 109 | + | + | # |
| 110 | + | + | # |
| 111 | + | + | # |
| 112A | + | + | # |
| 112B | + | + | # |
| 113 | + | + | # |

TABLE 21-continued

| Ex. No. | PI3Kγ IC$_{50}$ (nM) | PI3Kδ IC$_{50}$ (nM) | PI3Kγ_THP1_RPS6_ELISA IC$_{50}$ (nM) |
|---|---|---|---|
| 114 | + | + | # |
| 115 | + | + | # |
| 116 | + | + | # |
| 117 | ++ | +++ | NT |
| 118 | + | + | # |
| 119 | + | ++ | # |
| 120 | + | + | # |
| 121 | + | ++ | # |
| 122 | + | + | # |
| 123 | + | + | # |
| 124 | ++ | ++++ | ### |
| 125 | + | ++ | # |
| 126 | + | +++ | # |
| 127 | + | + | # |
| 128 | + | +++ | ### |
| 129 | + | +++ | ## |
| 130 | + | ++ | # |
| 131 | + | + | # |
| 132 | ++ | ++ | NT |
| 133 | + | ++ | # |
| 134 | + | ++ | ### |
| 135 | + | ++ | ### |
| 136 | + | ++ | ### |
| 137 | + | + | # |
| 138 | + | ++ | ## |
| 139 | + | + | # |
| 140 | + | + | # |
| 141 | + | ++ | # |
| 142 | + | + | # |
| 143 | + | ++ | ## |
| 144 | + | ++ | # |
| 145 | + | + | ### |
| 146 | + | + | # |
| 147 | + | ++ | # |
| 148 | ++ | ++ | # |
| 149 | + | + | # |
| 150 | + | + | # |
| 151 | + | + | # |
| 152 | + | + | # |
| 153 | + | + | # |
| 154 | ++ | ++ | ## |
| 155A | + | ++ | # |
| 155B | + | + | # |
| 156 | + | +++ | ## |
| 157 | + | ++ | ## |
| 158 | + | ++ | # |
| 159 | ++ | +++ | NT |
| 160 | + | + | NT |
| 161 | + | + | NT |
| 162 | + | ++ | # |
| 163 | + | + | # |
| 164 | + | +++ | ### |
| 165 | + | +++ | # |
| 166 | + | +++ | ## |
| 167 | + | ++ | # |
| 168 | + | +++ | ### |
| 169 | + | ++ | # |
| 170 | + | +++ | ### |
| 171 | + | ++ | ### |
| 172 | + | ++ | ## |
| 173 | ++ | +++ | ### |
| 174 | + | +++ | ### |
| 175 | + | +++ | # |
| 176 | + | +++ | # |
| 177 | + | ++++ | ## |
| 178 | + | + | # |
| 179 | + | + | # |
| 180 | + | + | # |
| 181 | + | + | # |
| 182 | + | + | # |
| 183 | ++ | +++ | NT |
| 184 | ++ | ++++ | NT |
| 185 | ++ | ++++ | NT |

+ refers to IC$_{50}$ of <100 nM;
++ refers to IC$_{50}$ of <500 nM;
+++ refers to an IC$_{50}$ of <2000 nM;
++++ refers to an IC$_{50}$ of ≥2000 nM.
# refers to IC$_{50}$ of <500 nM;
## refers to IC$_{50}$ of <1000 nM;
### refers to an IC$_{50}$ of ≥1000 nM.

Example D: In Vitro JAK Kinase Assay

Compounds herein were tested for inhibitory activity of JAK targets according to the following in vitro assay described in Park et al., *Analytical Biochemistry* 1999, 269, 94-104. The catalytic domains of human JAK1 (a.a. 837-1142), JAK2 (a.a. 828-1132) and JAK3 (a.a. 781-1124) were expressed using baculovirus in insect cells and purified. The catalytic activity of JAK1, JAK2 or JAK3 was assayed by measuring the phosphorylation of a biotinylated peptide. The phosphorylated peptide was detected by homogenous time resolved fluorescence (HTRF). IC$_{50}$s of compounds were measured for each kinase in the 40 μL reactions that contain the enzyme, ATP and 500 nM peptide in 50 mM Tris (pH 7.8) buffer with 100 mM NaCl, 5 mM DTT, and 0.1 mg/mL (0.01%) BSA. For the 1 mM IC$_{50}$ measurements, ATP concentration in the reactions was 1 mM. Reactions were carried out at room temperature for 1 hour and then stopped with 20 μL 45 mM EDTA, 300 nM SA-APC, 6 nM Eu-Py20 in assay buffer (Perkin Elmer, Boston, MA). Binding to the Europium labeled antibody took place for 40 minutes and HTRF signal was measured on a PHERA star plate reader (BMG, Cary, NC).

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A method of treating a disease or disorder associated with overexpression of PI3Kγ kinase, wherein the disease or disorder is selected from the group consisting of tumors, sarcomas, lymphomas, leukemias, lung cancer, melanoma, pancreatic cancer, breast cancer, prostate cancer, liver cancer, colon cancer, endometrial cancer, bladder cancer, skin cancer, cancer of the uterus, renal cancer, gastric cancer, myeloma, rheumatoid arthritis, multiple sclerosis, asthma, allergy, pancreatitis, psoriasis, anaphylaxis, glomerulonephritis, inflammatory bowel disease, thrombosis, meningitis, encephalitis, diabetic retinopathy, benign prostatic hypertrophy, myasthenia gravis, Sjögren's syndrome, osteoarthritis, restenosis, atherosclerosis, autoimmune hemolytic anemia, systemic lupus erythematosus, lupus nephritis, pemphigus, and inflammation, the method comprising administering to a patient in need thereof a therapeutically effective amount of a compound selected from:

2-amino-N-(1-[8-chloro-5-(2-methyl-1,1-dioxidothiomorpholin-4-yl)imidazo[1,5-a]pyridin-6-yl]ethyl)pyrazolo[1,5-a]pyrimidine-3-carboxamide;

2-amino-N-{1-[8-chloro-1-cyano-5-(1,1-dioxidothiomorpholin-4-yl)imidazo[1,5-a]pyridin-6-yl]ethyl}pyrazolo[1,5-a]pyrimidine-3-carboxamide;

2-amino-N-(1-(8-chloro-1-cyano-5-(2-methyl-1,1-dioxidothiomorpholino)imidazo[1,5-a]pyridin-6-yl)ethyl)pyrazolo[1,5-a]pyrimidine-3-carboxamide; and 2-amino-N-(1-(8-chloro-1-cyano-5-(2-methyl-1,1-dioxi-dothiomorpholino)imidazo[1,5-a]pyridin-6-yl)propyl)pyrazolo[1,5-a]pyrimidine-3-carboxamide;

or a pharmaceutically acceptable salt thereof.

2. The method of claim 1, wherein the disease or disorder is lung cancer, melanoma, pancreatic cancer, breast cancer, prostate cancer, liver cancer, colon cancer, endometrial cancer, bladder cancer, skin cancer, cancer of the uterus, renal cancer, gastric cancer, or sarcoma.

3. The method of claim 2, wherein the sarcoma is Askin's tumor, sarcoma botryoides, chondrosarcoma, Ewing's sarcoma, malignant hemangioendothelioma, malignant schwannoma, osteosarcoma, alveolar soft part sarcoma, angiosarcoma, cystosarcoma phyllodes, dermatofibrosarcoma protuberans, desmoid tumor, desmoplastic small round cell tumor, epithelioid sarcoma, extraskeletal chondrosarcoma, extraskeletal osteosarcoma, fibrosarcoma, gastrointestinal stromal tumor, hemangiopericytoma, hemangiosarcoma, Kaposi's sarcoma, leiomyosarcoma, liposarcoma, lymphangiosarcoma, lymphosarcoma, malignant peripheral nerve sheath tumor, neurofibrosarcoma, rhabdomyosarcoma, synovial sarcoma, or undifferentiated pleomorphic sarcoma.

4. The method of claim 1, wherein the disease or disorder is acute myeloid leukemia, acute monocytic leukemia, small lymphocytic lymphoma, chronic lymphocytic leukemia, chronic myelogenous leukemia, multiple myeloma, T-cell acute lymphoblastic leukemia, cutaneous T-cell lymphoma, large granular lymphocytic leukemia, mature peripheral t-cell neoplasm, anaplastic large cell lymphoma, or lymphoblastic lymphoma.

5. The method of claim 4, wherein the mature peripheral t-cell neoplasm is T-cell prolymphocytic leukemia, T-cell granular lymphocytic leukemia, aggressive NK-cell leukemia, mycosis fungoides, Sezary syndrome, anaplastic large cell lymphoma, enteropathy type T-cell lymphoma, adult T-cell leukemia, adult T-cell lymphoma, or angioimmunoblastic T-cell lymphoma.

6. The method of claim 4, wherein the anaplastic large cell lymphoma is systemic anaplastic large cell lymphoma or primary cutaneous anaplastic large cell lymphoma.

7. The method of claim 1, wherein the disease or disorder is Burkitt's lymphoma, acute myeloblastic leukemia, chronic myeloid leukemia, non-Hodgkin's lymphoma, Hodgkin's lymphoma, hairy cell leukemia, Mantle cell lymphoma, small lymphocytic lymphoma, follicular lymphoma, lymphoplasmacytic lymphoma, extranodal marginal zone lymphoma, Waldenstrom's macroglobulinemia, prolymphocytic leukemia, acute lymphoblastic leukemia, myelofibrosis, mucosa-associated lymphatic tissue lymphoma, mediastinal (thymic) large B-cell lymphoma, lymphomatoid granulomatosis, splenic marginal zone lymphoma, primary effusion lymphoma, intravascular large B-cell lymphoma, plasma cell leukemia, extramedullary plasmacytoma, smouldering myeloma, monoclonal gammopathy of undetermined significance, or diffuse large B cell lymphoma.

8. The method of claim 7, wherein the non-Hodgkin's lymphoma is relapsed non-Hodgkin's lymphoma, refractory non-Hodgkin's lymphoma, recurrent follicular non-Hodgkin's lymphoma, indolent non-Hodgkin's lymphoma, or aggressive non-Hodgkin's lymphoma.

9. The method of claim 7, wherein the diffuse large B cell lymphoma is activated B-cell like diffuse large B cell lymphoma, or germinal center B cell diffuse large B cell lymphoma.

10. The method of claim 7, wherein the Burkitt's lymphoma is endemic Burkitt's lymphoma, sporadic Burkitt's lymphoma, or Burkitt's-like lymphoma.

11. The method of claim 1, wherein the disease or disorder is rheumatoid arthritis, multiple sclerosis, systemic lupus erythematosus, asthma, allergy, pancreatitis, psoriasis, anaphylaxis, glomerulonephritis, inflammatory bowel disease, thrombosis, meningitis, encephalitis, diabetic retinopathy, benign prostatic hypertrophy, myasthenia gravis, Sjögren's syndrome, osteoarthritis, or atherosclerosis.

12. The method of claim 1, wherein the disease or disorder is autoimmune hemolytic anemia, systemic lupus erythematosus, lupus nephritis, or pemphigus.

13. The method of claim 1, wherein the disease or disorder is vasculitis that is Behcet's disease, Cogan's syndrome, giant cell arteritis, polymyalgia rheumatica, Takayasu's arteritis, Buerger's disease, central nervous system vasculitis, Kawasaki disease, polyarteritis nodosa, Churg-Strauss syndrome, mixed cryoglobulinemia vasculitis, Henoch-Schonlein purpura, hypersensitivity vasculitis, microscopic polyangiitis, Wegener's granulomatosis, or anti-neutrophil cytoplasm antibody associated systemic vasculitis.

14. The method of claim 1, further comprising administering an inhibitor of JAK1, an inhibitor of JAK2, an inhibitor of JAK1 and JAK2, or an inhibitor of PI3Kδ, to said patient.

15. The method of claim 1, wherein disease or disorder is lung cancer, melanoma, breast cancer, acute myeloid leukemia, acute monocytic leukemia, chronic myelogenous leukemia, multiple myeloma, acute myeloblastic leukemia, chronic myeloid leukemia, or smoldering myeloma.

16. The method of claim 1, wherein the disease or disorder is lung cancer.

17. The method of claim 16, wherein the lung cancer is non-small cell lung cancer.

18. The method of claim 1, wherein the disease or disorder is melanoma.

19. The method of claim 1, wherein the disease or disorder is breast cancer.

20. The method of claim 1, wherein the disease or disorder is acute myeloid leukemia, chronic myelogenous leukemia, multiple myeloma, myelofibrosis, or smoldering myeloma.

21. The method of claim 1, wherein the compound is 2-amino-N-(1-[8-chloro-5-(2-methyl-1,1-dioxidothiomorpholin-4-yl)imidazo[1,5-a]pyridin-6-yl]ethyl)pyrazolo[1,5-a]pyrimidine-3-carboxamide, or a pharmaceutically acceptable salt thereof.

22. The method of claim 21, wherein the compound is 2-amino-N-((1S)-1-(8-chloro-5-(2-methyl-1,1-dioxidothiomorpholino)imidazo[1,5-a]pyridin-6-yl)ethyl)pyrazolo[1,5-a]pyrimidine-3-carboxamide, or a pharmaceutically acceptable salt thereof.

23. The method of claim 21, wherein the compound is 2-amino-N—((S)-1-(8-chloro-5-((R)-2-methyl-1,1-dioxidothiomorpholino)imidazo[1,5-a]pyridin-6-yl)ethyl)pyrazolo[1,5-a]pyrimidine-3-carboxamide, or a pharmaceutically acceptable salt thereof.

24. The method of claim 21, wherein the compound is 2-amino-N—((S)-1-(8-chloro-5-((S)-2-methyl-1,1-dioxidothiomorpholino)imidazo[1,5-a]pyridin-6-yl)ethyl)pyrazolo[1,5-a]pyrimidine-3-carboxamide, or a pharmaceutically acceptable salt thereof.

25. The method of claim 1, wherein the compound is 2-amino-N-{1-[8-chloro-1-cyano-5-(1,1-dioxidothiomorpholin-4-yl)imidazo[1,5-a]pyridin-6-yl]ethyl}pyrazolo[1,5-a]pyrimidine-3-carboxamide, or a pharmaceutically acceptable salt thereof.

26. The method of claim 1, wherein the compound is 2-amino-N-(1-(8-chloro-1-cyano-5-(2-methyl-1,1-dioxido-thiomorpholino)imidazo[1,5-a]pyridin-6-yl)ethyl)pyrazolo[1,5-a]pyrimidine-3-carboxamide, or a pharmaceutically acceptable salt thereof.

27. The method of claim 1, wherein the compound is 2-amino-N-(1-(8-chloro-1-cyano-5-(2-methyl-1,1-dioxido-thiomorpholino)imidazo[1,5-a]pyridin-6-yl)propyl)pyrazolo[1,5-a]pyrimidine-3-carboxamide, or a pharmaceutically acceptable salt thereof.

\* \* \* \* \*